United States Patent
Fotouhi et al.

(10) Patent No.: US 7,579,368 B2
(45) Date of Patent: *Aug. 25, 2009

(54) CIS-IMIDAZOLINES

(75) Inventors: Nader Fotouhi, Basking Ridge, NJ (US); Gregory Jay Haley, San Diego, CA (US); Klaus B. Simonsen, Frederiksberg (DK); Binh Thanh Vu, North Caldwell, NJ (US); Stephen Evan Webber, San Diego, CA (US)

(73) Assignee: Hoffman-La Roche Inc., Nutley, NJ (US)

( * ) Notice: Subject to any disclaimer, the term of this patent is extended or adjusted under 35 U.S.C. 154(b) by 513 days.

This patent is subject to a terminal disclaimer.

(21) Appl. No.: 11/374,407

(22) Filed: Mar. 13, 2006

(65) Prior Publication Data

US 2006/0211693 A1 Sep. 21, 2006

Related U.S. Application Data

(60) Provisional application No. 60/662,516, filed on Mar. 16, 2005.

(51) Int. Cl.
*A61K 31/4164* (2006.01)
*C07D 233/08* (2006.01)

(52) U.S. Cl. .................... 514/385; 548/311.1
(58) Field of Classification Search ............. 514/385; 548/311.1
See application file for complete search history.

(56) References Cited

U.S. PATENT DOCUMENTS 6,734,302 B2 * 5/2004 Kong et al. ............... 544/139
7,425,638 B2 * 9/2008 Haley et al. ............... 548/334.1

FOREIGN PATENT DOCUMENTS

| WO | WO 03/051359   | * | 6/2003 |
| WO | WO 03/051359 A |   | 6/2003 |
| WO | WO 2005/110996 A |   | 11/2005 |
| WO | WO 2005/123691 A |   | 12/2005 |

OTHER PUBLICATIONS

Vassilev, et. al., Science, V.303, N.5659, p. 844-848 (2004).

* cited by examiner

*Primary Examiner*—Joseph K. McKane
*Assistant Examiner*—Janet L Coppins
(74) *Attorney, Agent, or Firm*—George W. Johnston; Patricia S. Rocha-Tramaloni

(57) ABSTRACT

There are presented compounds of the formula

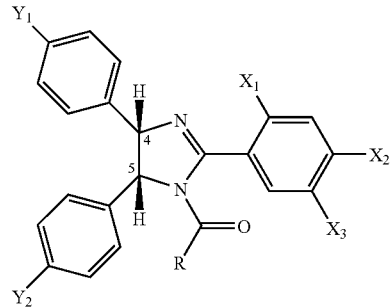

or pharmaceutically acceptable salts thereof,
wherein $Y_1$, $Y_2$, $X_1$, $X_2$, $X_3$ and R are as described in this application. These compounds are believed to inhibit MDM2-p53 interaction and as such the compounds will have anti-hyperproliferative cellular activity.

42 Claims, No Drawings

CIS-IMIDAZOLINES

PRIORITY TO RELATED APPLICATIONS

This application claims the benefit of U.S. Provisional Application No. 60/662,516, filed Mar. 16, 2005, which is hereby incorporated by reference in its entirety.

BACKGROUND OF THE INVENTION

The present invention provides chiral cis-imidazolines which are small molecule inhibitors of the MDM2-p53 interaction. In cell-free and cell-based assays, compounds of the present invention are shown to inhibit the interaction of MDM2 protein with a p53-like peptide with a potency that is approximately 100 fold greater than a p53-derived peptide. In cell-based assays, these compounds demonstrate mechanistic activity. Incubation of cancer cells with wild-type p53 leads to accumulation of p53 protein, induction of p53-regulated p21 gene, and cell cycle arrest in G1 and G2 phase, resulting in potent antiproliferative activity against wild-type p53 cells in vitro. In contrast, these activities were not observed in cancer cells with mutant p53 at comparable compound concentrations. Therefore, the activity of MDM2 antagonists is likely linked to its mechanism of action. These compounds can be potent and selective anticancer agents.

SUMMARY OF THE INVENTION

This invention relates to at least one compound of the formula I

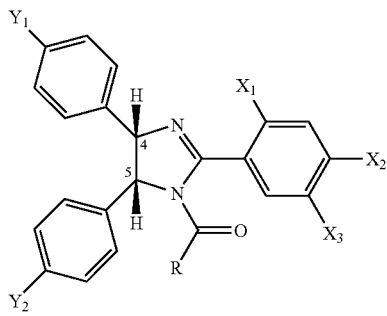

I or pharmaceutically acceptable salts thereof, wherein $Y_1$, $Y_2$, $X_1$, $X_2$, $X_3$ and R are as described in this application. These compounds are believed to inhibit MDM2-p53 interaction and as such the compounds will have anti-hyperproliferative cellular activity.

DETAILED DESCRIPTION OF THE INVENTION

The present invention provides at least one compound of formula I

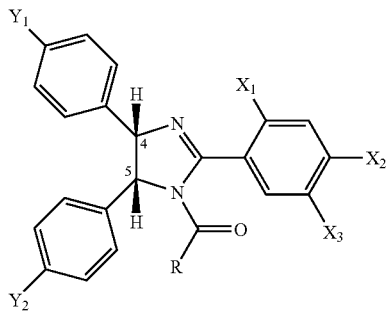

I and the pharmaceutically acceptable salts and esters thereof, wherein $X_1$ is selected from the group consisting of:
lower alkoxy,
lower alkoxy substituted by trifluoromethyl or fluorine;

$X_2$ and $X_3$ are independently selected from the group consisting of:
hydrogen,
halogen,
cyano,
lower alkyl,
lower alkoxy,
—$NX_4X_5$,
—$SO_2NX_4X_5$,
—$C(O)NX_4X_5$,
—$C(O)X_6$,
—$SOX_6$, —$SO_2X_6$,
—NC(O)-lower alkoxy
—C≡C—$X_7$,
with the proviso that $X_2$ and $X_3$ are both not hydrogen, lower alkyl, or lower alkoxy,
with the proviso that when $X_2$ or $X_3$ is hydrogen, the other is not lower alkyl, lower alkoxy, or halogen, $X_2$ and $X_3$ can be taken together to form a ring selected from 5 to 7 membered unsaturated rings, and 5 to 7 membered usaturated rings that contain at least one hetero atom selected from S, N, and O;

$X_4$ and $X_5$ are independently selected from the group consisting of:
hydrogen,
lower alkyl,
cycloalkyl,
lower alkoxy,
lower alkyl substituted with lower alkoxy,
—$C(O)X_6$,
—$SO_2X_6$, $X_4$ and $X_5$ can be taken together to form a ring selected from 5 to 7 membered unsaturated rings, and 5 to 7 membered usaturated rings that contain at least one hetero atom selected from S, N, and O;

$X_6$ is selected from the group consisting of:
lower alkyl,
morpholine,
piperidine,
piperazine,
2-piperazinone,
pyrrolidine;

$X_7$ is selected from the group consisting of:
hydrogen,
lower alkyl,
trifluoromethyl;

$Y_1$ and $Y_2$ are independently selectect from the group consisting of:
halogen,
acetylene;

R is selected from the group consisting of:
lower alkoxy,
piperidinyl substituted by five or six membered heterocycle,
piperidinyl substituted by hydroxy, —$CH_2OH$, or —$C(O)NH_2$,
piperazinyl substituted by $R_1$,
[1,4]diazepanyl substituted by $R_1$,
$R_1$ can be one or two substituents selected from the group consisting of:
hydrogen,
oxo, lower alkyl substituted by R$_2$,
—C(O)R$_3$,
—SO$_2$—R$_3$;
R$_2$ is selected from the group consisting of:
—SO$_2$-lower alkyl,
hydroxy,
lower alkoxy,
trifluoromethyl,
—NH—SO$_2$-lower alkyl,
—NH—C(O)-lower alkyl,
—C(O)-lower alkyl,
-cyano,
—C(O)R$_4$;
R$_3$ is selected from the group consisting of:
five membered heterocycle,
lower alkyl,
cycloalkyl,
lower alkyl substituted by lower alkoxy,
lower alkyl substituted by piperazinyl substituted by R$_1$,
—N-cycloalkyl,
lower alkoxy;
R$_4$ is selected from the group consisting of:
hydroxy,
lower alkoxy,
morpholine,
piperidine,
pyrrolidine,
piperazinyl substituted by R$_1$,
aziridine,
—NR$_5$R$_6$;
R$_5$ and R$_6$ are independently selected from the group consisting of:
hydrogen,
lower alkyl,
lower alkyl substituted by lower alkoxy or cyano,
lower alkoxy.

Preferred compounds are compounds of formula I wherein Y$_1$ and Y$_2$ are each independently selected from —Cl and —Br.

Further preferred compounds are compounds of formula I wherein R is piperazinyl substituted by oxo or lower alkyl substituted by R$_2$.

Also preferred compounds are compounds in which the two hydrogen atoms of the imidazoline ring are in a cis configuration to each other. The compounds may be in a racemic form and may be optically active. The preferred absolute stereochemistry at the 4 and 5 position of the imidazoline ring are S and R, respectively.

Especially preferred compounds are:
4-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-3-ethoxy-benzonitrile;
5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-2-chloro-4-ethoxy-N-methyl-benzenesulfonamide;
5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-2-chloro-4-ethoxy-N,N-dimethyl-benzenesulfonamide;
5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-2-chloro-4-ethoxy-benzenesulfonamide;
4-[4,5-Bis-(4-chloro-phenyl)-1-(3-oxo-piperazine-1-carbonyl)-4,5-dihydro-1H-imidazol-2-yl]-3-ethoxy-benzonitrile;
4-{4,5-Bis-(4-chloro-phenyl)-1-[4-(2-hydroxy-ethyl)-piperazine-1-carbonyl]-4,5-dihydro-1H-imidazol-2-yl}-3-ethoxy-benzonitrile;
4-[4,5-Bis-(4-chloro-phenyl)-1-(4-pyrrolidin-1-yl-piperidine-1-carbonyl)-4,5-dihydro-1H-imidazol-2-yl]-3-ethoxy-benzonitrile;
3-[4,5-Bis-(4-chloro-phenyl)-1-(3-oxo-piperazine-1-carbonyl)-4,5-dihydro-1H-imidazol-2-yl]-4-ethoxy-N,N-dimethyl-benzenesulfonamide;
3-{4,5-Bis-(4-chloro-phenyl)-1-[4-(2-hydroxy-ethyl)-piperazine-1-carbonyl]-4,5-dihydro-1H-imidazol-2-yl}-4-ethoxy-N,N-dimethyl-benzenesulfonamide;
3-[4,5-Bis-(4-chloro-phenyl)-1-(4-pyrrolidin-1-yl-piperidine-1-carbonyl)-4,5-dihydro-1H-imidazol-2-yl]-4-ethoxy-N,N-dimethyl-benzenesulfonamide;
5-[4,5-Bis-(4-chloro-phenyl)-1-(3-oxo-piperazine-1-carbonyl)-4,5-dihydro-1H-imidazol-2-yl]-2-chloro-4-ethoxy-N,N-dimethyl-benzenesulfonamide;
5-{4,5-Bis-(4-chloro-phenyl)-1-[4-(2-morpholin-4-yl-2-oxo-ethyl)-piperazine-1-carbonyl]-4,5-dihydro-1H-imidazol-2-yl}-2-chloro-4-ethoxy-N,N-dimethyl-benzenesulfonamide;
5-{4,5-Bis-(4-chloro-phenyl)-1-[4-(2-hydroxy-ethyl)-3-oxo-piperazine-1-carbonyl]-4,5-dihydro-1H-imidazol-2-yl}-2-chloro-4-ethoxy-N,N-dimethyl-benzenesulfonamide;
5-[4,5-Bis-(4-chloro-phenyl)-1-(3-oxo-piperazine-1-carbonyl)-4,5-dihydro-1H-imidazol-2-yl]-4-ethoxy-2-methoxy-N,N-dimethyl-benzenesulfonamide;
5-{4,5-Bis-(4-chloro-phenyl)-1-[4-(2-hydroxy-ethyl)-piperazine-1-carbonyl]-4,5-dihydro-1H-imidazol-2-yl}-4-ethoxy-2-methoxy-N,N-dimethyl-benzenesulfonamide;
2-{4-[4,5-Bis-(4-chloro-phenyl)-2-(5-dimethylsulfamoyl-2-ethoxy-4-methoxy-phenyl)-4,5-dihydro-imidazole-1-carbonyl]-piperazin-1-yl}-N,N-dimethyl-acetamide;
5-{4,5-Bis-(4-chloro-phenyl)-1-[4-(2-methanesulfonyl-ethyl)-piperazine-1-carbonyl]-4,5-dihydro-1H-imidazol-2-yl}-4-ethoxy-2-methoxy-N,N-dimethyl-benzenesulfonamide;
4-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-3-ethoxy-benzonitrile;
5-{(4S,5R)-4,5-Bis-(4-chloro-phenyl)-1-[4-(2-hydroxy-ethyl)-piperazine-1-carbonyl]-4,5-dihydro-1H-imidazol-2-yl}-2-chloro-4-ethoxy-N,N-dimethyl-benzenesulfonamide;
4-[4,5-Bis-(4-chloro-phenyl)-2-(2-ethoxy-4-methanesulfinyl-phenyl)-4,5-dihydro-imidazole-1-carbonyl]-piperazin-2-one;
4-[4,5-Bis-(4-chloro-phenyl)-2-(2-ethoxy-4-methanesulfonyl-phenyl)-4,5-dihydro-imidazole-1-carbonyl]-piperazin-2-one;
2-{4-[4,5-Bis-(4-chloro-phenyl)-2-(2-ethoxy-4-methanesulfinyl-phenyl)-4,5-dihydro-imidazole-1-carbonyl]-piperazin-1-yl}-N,N-dimethyl-acetamide;
2-{4-[4,5-Bis-(4-chloro-phenyl)-2-(2-ethoxy-4-methanesulfonyl-phenyl)-4,5-dihydro-imidazole-1-carbonyl]-piperazin-1-yl}-N,N-dimethyl-acetamide;
[4,5-Bis-(4-chloro-phenyl)-2-(2-ethoxy-4-methanesulfinyl-phenyl)-4,5-dihydro-imidazol-1-yl]-[4-(2-methanesulfonyl-ethyl)-piperazin-1-yl]-methanone;
[4,5-Bis-(4-chloro-phenyl)-2-(2-ethoxy-4-methanesulfonyl-phenyl)-4,5-dihydro-imidazol-1-yl]-[4-(2-methanesulfonyl-ethyl)-piperazin-1-yl]-methanone;
[4,5-Bis-(4-chloro-phenyl)-2-(2-ethoxy-4-methanesulfinyl-phenyl)-4,5-dihydro-imidazol-1-yl]-[4-(2-hydroxy-ethyl)-piperazin-1-yl]-methanone;

[4,5-Bis-(4-chloro-phenyl)-2-(2-ethoxy-4-methanesulfonyl-phenyl)-4,5-dihydro-imidazol-1-yl]-[4-(2-hydroxy-ethyl)-piperazin-1-yl]-methanone;

1-[(4S,5R)-4,5-Bis-(4-chloro-phenyl)-2-(4-cyano-2-ethoxy-phenyl)-4,5-dihydro-imidazole-1-carbonyl]-piperidine-4-carboxylic acid amide;

4-{(4S,5R)-4,5-Bis-(4-chloro-phenyl)-1-[4-(3,5-dimethyl-isoxazole-4-carbonyl)-piperazine-1-carbonyl]-4,5-dihydro-1H-imidazol-2-yl}-3-ethoxy-benzonitrile;

4-[(4S,5R)-4,5-Bis-(4-chloro-phenyl)-1-(4-cyclopropanecarbonyl-piperazine-1-carbonyl)-4,5-dihydro-1H-imidazol-2-yl]-3-ethoxy-benzonitrile;

4-{(4S,5R)-4,5-Bis-(4-chloro-phenyl)-1-[4-(3-methyl-but-2-enoyl)-piperazine-1-carbonyl]-4,5-dihydro-1H-imidazol-2-yl}-3-ethoxy-benzonitrile;

4-{(4S,5R)-4,5-Bis-(4-chloro-phenyl)-1-[4-(3,5-dimethyl-isoxazole-4-sulfonyl)-piperazine-1-carbonyl]-4,5-dihydro-1H-imidazol-2-yl}-3-ethoxy-benzonitrile;

4-{(4S,5R)-4,5-Bis-(4-chloro-phenyl)-1-[4-(2-hydroxy-ethyl)-piperazine-1-carbonyl]-4,5-dihydro-1H-imidazol-2-yl}-3-ethoxy-benzonitrile;

4-{(4S,5R)-4,5-Bis-(4-chloro-phenyl)-1-[4-(2-cyano-ethyl)-piperazine-1-carbonyl]-4,5-dihydro-1H-imidazol-2-yl}-3-ethoxy-benzonitrile;

4-{(4S,5R)-4,5-Bis-(4-chloro-phenyl)-1-[4-(2-methoxy-ethyl)-piperazine-1-carbonyl]-4,5-dihydro-1H-imidazol-2-yl}-3-ethoxy-benzonitrile;

4-((4S,5R)-4,5-Bis-(4-chloro-phenyl)-1-{4-[2-(3-oxo-piperazin-1-yl)-acetyl]-piperazine-1-carbonyl}-4,5-dihydro-1H-imidazol-2-yl)-3-ethoxy-benzonitrile;

1-[(4S,5R)-4,5-Bis-(4-chloro-phenyl)-2-(4-cyano-2-ethoxy-phenyl)-4,5-dihydro-imidazole-1-carbonyl]-piperidine-3-carboxylic acid amide;

4-[(4S,5R)-1-{4-[2-(4-Acetyl-piperazin-1-yl)-2-oxo-ethyl]-piperazine-1-carbonyl}-4,5-bis-(4-chloro-phenyl)-4,5-dihydro-1H-imidazol-2-yl]-3-ethoxy-benzonitrile;

2-{4-[(4S,5R)-4,5-Bis-(4-chloro-phenyl)-2-(4-cyano-2-ethoxy-phenyl)-4,5-dihydro-imidazole-1-carbonyl]-piperazin-1-yl}-N-(2-methoxy-1-methyl-ethyl)-acetamide;

4-[(4S,5R)-4,5-Bis-(4-chloro-phenyl)-1-(4-hydroxymethyl-piperidine-1-carbonyl)-4,5-dihydro-1H-imidazol-2-yl]-3-ethoxy-benzonitrile;

4-[(4S,5R)-4,5-Bis-(4-chloro-phenyl)-1-(3-hydroxy-piperidine-1-carbonyl)-4,5-dihydro-1H-imidazol-2-yl]-3-ethoxy-benzonitrile;

4-[(4S,5R)-4,5-Bis-(4-chloro-phenyl)-1-(3-oxo-piperazine-1-carbonyl)-4,5-dihydro-1H-imidazol-2-yl]-3-ethoxy-benzonitrile;

2-{4-[(4S,5R)-4,5-Bis-(4-chloro-phenyl)-2-(4-cyano-2-ethoxy-phenyl)-4,5-dihydro-imidazole-1-carbonyl]-piperazin-1-yl}-N,N-dimethyl-acetamide;

4-{(4S,5R)-4,5-Bis-(4-chloro-phenyl)-1-[4-(2-oxo-2-piperidin-1-yl-ethyl)-piperazine-1-carbonyl]-4,5-dihydro-1H-imidazol-2-yl}-3-ethoxy-benzonitrile;

4-[(4S,5R)-4,5-Bis-(4-chloro-phenyl)-1-(4-ethanesulfonyl-piperazine-1-carbonyl)-4,5-dihydro-1H-imidazol-2-yl]-3-ethoxy-benzonitrile;

1-[4,5-Bis-(4-chloro-phenyl)-2-(5-dimethylsulfamoyl-2-ethoxy-phenyl)-4,5-dihydro-imidazole-1-carbonyl]-piperidine-4-carboxylic acid amide;

3-{4,5-Bis-(4-chloro-phenyl)-1-[4-(3,5-dimethyl-isoxazole-4-carbonyl)-piperazine-1-carbonyl]-4,5-dihydro-1H-imidazol-2-yl}-4-ethoxy-N,N-dimethyl-benzenesulfonamide;

3-[4,5-Bis-(4-chloro-phenyl)-1-(4-cyclopropanecarbonyl-piperazine-1-carbonyl)-4,5-dihydro-1H-imidazol-2-yl]-4-ethoxy-N,N-dimethyl-benzenesulfonamide;

3-{4,5-Bis-(4-chloro-phenyl)-1-[4-(3-methyl-but-2-enoyl)-piperazine-1-carbonyl]-4,5-dihydro-1H-imidazol-2-yl}-4-ethoxy-N,N-dimethyl-benzenesulfonamide;

3-{4,5-Bis-(4-chloro-phenyl)-1-[4-(3,5-dimethyl-isoxazole-4-sulfonyl)-piperazine-1-carbonyl]-4,5-dihydro-1H-imidazol-2-yl}-4-ethoxy-N,N-dimethyl-benzenesulfonamide;

3-{4,5-Bis-(4-chloro-phenyl)-1-[4-(2-cyano-ethyl)-piperazine-1-carbonyl]-4,5-dihydro-1H-imidazol-2-yl}-4-ethoxy-N,N-dimethyl-benzenesulfonamide;

3-{4,5-Bis-(4-chloro-phenyl)-1-[4-(2-methoxy-ethyl)-piperazine-1-carbonyl]-4,5-dihydro-1H-imidazol-2-yl}-4-ethoxy-N,N-dimethyl-benzenesulfonamide;

3-(4,5-Bis-(4-chloro-phenyl)-1-{4-[2-(3-oxo-piperazin-1-yl)-acetyl]-piperazine-1-carbonyl}-4,5-dihydro-1H-imidazol-2-yl)-4-ethoxy-N,N-dimethyl-benzenesulfonamide;

2-{4-[4,5-Bis-(4-chloro-phenyl)-2-(5-dimethylsulfamoyl-2-ethoxy-phenyl)-4,5-dihydro-imidazole-1-carbonyl]-piperazin-1-yl}-N-methyl-acetamide;

1-[4,5-Bis-(4-chloro-phenyl)-2-(5-dimethylsulfamoyl-2-ethoxy-phenyl)-4,5-dihydro-imidazole-1-carbonyl]-piperidine-3-carboxylic acid amide;

3-[1-{4-[2-(4-Acetyl-piperazin-1-yl)-2-oxo-ethyl]-piperazine-1-carbonyl}-4,5-bis-(4-chloro-phenyl)-4,5-dihydro-1H-imidazol-2-yl]-4-ethoxy-N,N-dimethyl-benzenesulfonamide;

2-{4-[4,5-Bis-(4-chloro-phenyl)-2-(5-dimethylsulfamoyl-2-ethoxy-phenyl)-4,5-dihydro-imidazole-1-carbonyl]-piperazin-1-yl}-N-(2-methoxy-1-methyl-ethyl)-acetamide;

3-[4,5-Bis-(4-chloro-phenyl)-1-(4-hydroxymethyl-piperidine-1-carbonyl)-4,5-dihydro-1H-imidazol-2-yl]-4-ethoxy-N,N-dimethyl-benzenesulfonamide;

3-[4,5-Bis-(4-chloro-phenyl)-1-(3-hydroxy-piperidine-1-carbonyl)-4,5-dihydro-1H-imidazol-2-yl]-4-ethoxy-N,N-dimethyl-benzenesulfonamide;

2-{4-[4,5-Bis-(4-chloro-phenyl)-2-(5-dimethylsulfamoyl-2-ethoxy-phenyl)-4,5-dihydro-imidazole-1-carbonyl]-piperazin-1-yl}-N,N-dimethyl-acetamide;

3-{4,5-Bis-(4-chloro-phenyl)-1-[4-(2-morpholin-4-yl-2-oxo-ethyl)-piperazine-1-carbonyl]-4,5-dihydro-1H-imidazol-2-yl}-4-ethoxy-N,N-dimethyl-benzenesulfonamide;

3-{4,5-Bis-(4-chloro-phenyl)-1-[4-(2-oxo-2-piperidin-1-yl-ethyl)-piperazine-1-carbonyl]-4,5-dihydro-1H-imidazol-2-yl}-4-ethoxy-N,N-dimethyl-benzenesulfonamide;

3-[4,5-Bis-(4-chloro-phenyl)-1-(4-ethanesulfonyl-piperazine-1-carbonyl)-4,5-dihydro-1H-imidazol-2-yl]-4-ethoxy-N,N-dimethyl-benzenesulfonamide;

3-[4,5-Bis-(4-chloro-phenyl)-1-(3-oxo-piperazine-1-carbonyl)-4,5-dihydro-1H-imidazol-2-yl]-4-ethoxy-N-isobutyl-N-methyl-benzenesulfonamide;

3-{4,5-Bis-(4-chloro-phenyl)-1-[4-(2-methanesulfonyl-ethyl)-piperazine-1-carbonyl]-4,5-dihydro-1H-imidazol-2-yl}-4-ethoxy-N-isobutyl-N-methyl-benzenesulfonamide;

2-(4-{4,5-Bis-(4-chloro-phenyl)-2-[2-ethoxy-5-(isobutyl-methyl-sulfamoyl)-phenyl]-4,5-dihydro-imidazole-1-carbonyl}-piperazin-1-yl)-N,N-dimethyl-acetamide;

3-[4,5-Bis-(4-chloro-phenyl)-1-(4-ethanesulfonyl-piperazine-1-carbonyl)-4,5-dihydro-1H-imidazol-2-yl]-4-ethoxy-N-isobutyl-N-methyl-benzenesulfonamide;

3-(4,5-Bis-(4-chloro-phenyl)-1-{4-[2-(3-oxo-piperazin-1-yl)-acetyl]-piperazine-1-carbonyl}-4,5-dihydro-1H-imidazol-2-yl)-4-ethoxy-N-isobutyl-N-methyl-benzenesulfonamide;

2-(4-{4,5-Bis-(4-chloro-phenyl)-2-[2-ethoxy-5-(isobutyl-methyl-sulfamoyl)-phenyl]-4,5-dihydro-imidazole-1-carbonyl}-piperazin-1-yl)-N-(2-methoxy-1-methyl-ethyl)-acetamide;

3-{4,5-Bis-(4-chloro-phenyl)-1-[4-(2-hydroxy-ethyl)-piperazine-1-carbonyl]-4,5-dihydro-1H-imidazol-2-yl}-4-ethoxy-N-isobutyl-N-methyl-benzenesulfonamide;

2-(4-{4,5-Bis-(4-chloro-phenyl)-2-[2-ethoxy-5-(isobutyl-methyl-sulfamoyl)-phenyl]-4,5-dihydro-imidazole-1-carbonyl}-piperazin-1-yl)-N-methyl-acetamide;

3-{4,5-Bis-(4-chloro-phenyl)-1-[4-(2-morpholin-4-yl-2-oxo-ethyl)-piperazine-1-carbonyl]-4,5-dihydro-1H-imidazol-2-yl}-4-ethoxy-N-isobutyl-N-methyl-benzenesulfonamide;

3-[4,5-Bis-(4-chloro-phenyl)-1-(4-cyclopropanecarbonyl-piperazine-1-carbonyl)-4,5-dihydro-1H-imidazol-2-yl]-4-ethoxy-N-isobutyl-N-methyl-benzenesulfonamide;

3-{4,5-Bis-(4-chloro-phenyl)-1-[4-(2-methoxy-ethyl)-piperazine-1-carbonyl]-4,5-dihydro-1H-imidazol-2-yl}-4-ethoxy-N-isobutyl-N-methyl-benzenesulfonamide;

3-[4,5-Bis-(4-chloro-phenyl)-1-(3-oxo-piperazine-1-carbonyl)-4,5-dihydro-1H-imidazol-2-yl]-4-ethoxy-N,N-bis-(2-methoxy-ethyl)-benzenesulfonamide;

3-{4,5-Bis-(4-chloro-phenyl)-1-[4-(2-methanesulfonyl-ethyl)-piperazine-1-carbonyl]-4,5-dihydro-1H-imidazol-2-yl}-4-ethoxy-N,N-bis-(2-methoxy-ethyl)-benzenesulfonamide;

2-{4-[2-{5-[Bis-(2-methoxy-ethyl)-sulfamoyl]-2-ethoxy-phenyl}-4,5-bis-(4-chloro-phenyl)-4,5-dihydro-imidazole-1-carbonyl]-piperazin-1-yl}-N,N-dimethyl-acetamide;

3-(4,5-Bis-(4-chloro-phenyl)-1-{4-[2-(3-oxo-piperazin-1-yl)-acetyl]-piperazine-1-carbonyl}-4,5-dihydro-1H-imidazol-2-yl)-4-ethoxy-N,N-bis-(2-methoxy-ethyl)-benzenesulfonamide;

2-{4-[2-{5-[Bis-(2-methoxy-ethyl)-sulfamoyl]-2-ethoxy-phenyl}-4,5-bis-(4-chloro-phenyl)-4,5-dihydro-imidazole-1-carbonyl]-piperazin-1-yl}-N-(2-methoxy-1-methyl-ethyl)-acetamide;

2-{4-[2-{5-[Bis-(2-methoxy-ethyl)-sulfamoyl]-2-ethoxy-phenyl}-4,5-bis-(4-chloro-phenyl)-4,5-dihydro-imidazole-1-carbonyl]-piperazin-1-yl}-N-methyl-acetamide;

3-{4,5-Bis-(4-chloro-phenyl)-1-[4-(2-morpholin-4-yl-2-oxo-ethyl)-piperazine-1-carbonyl]-4,5-dihydro-1H-imidazol-2-yl}-4-ethoxy-N,N-bis-(2-methoxy-ethyl)-benzenesulfonamide;

3-[4,5-Bis-(4-chloro-phenyl)-1-(4-cyclopropanecarbonyl-piperazine-1-carbonyl)-4,5-dihydro-1H-imidazol-2-yl]-4-ethoxy-N,N-bis-(2-methoxy-ethyl)-benzenesulfonamide;

4-{4,5-Bis-(4-chloro-phenyl)-2-[2-ethoxy-5-(piperidine-1-sulfonyl)-phenyl]-4,5-dihydro-imidazole-1-carbonyl}-piperazin-2-one;

{4,5-Bis-(4-chloro-phenyl)-2-[2-ethoxy-5-(piperidine-1-sulfonyl)-phenyl]-4,5-dihydro-imidazol-1-yl}[4-(2-methanesulfonyl-ethyl)-piperazin-1-yl]-methanone;

2-(4-{4,5-Bis-(4-chloro-phenyl)-2-[2-ethoxy-5-(piperidine-1-sulfonyl)-phenyl]-4,5-dihydro-imidazole-1-carbonyl}-piperazin-1-yl)-N,N-dimethyl-acetamide;

{4,5-Bis-(4-chloro-phenyl)-2-[2-ethoxy-5-(piperidine-1-sulfonyl)-phenyl]-4,5-dihydro-imidazol-1-yl}-(4-ethanesulfonyl-piperazin-1-yl)-methanone;

4-[2-(4-{4,5-Bis-(4-chloro-phenyl)-2-[2-ethoxy-5-(piperidine-1-sulfonyl)-phenyl]-4,5-dihydro-imidazole-1-carbonyl}-piperazin-1-yl)-2-oxo-ethyl]-piperazin-2-one;

2-(4-{4,5-Bis-(4-chloro-phenyl)-2-[2-ethoxy-5-(piperidine-1-sulfonyl)-phenyl]-4,5-dihydro-imidazole-1-carbonyl}-piperazin-1-yl)-N-(2-methoxy-1-methyl-ethyl)-acetamide;

{4,5-Bis-(4-chloro-phenyl)-2-[2-ethoxy-5-(piperidine-1-sulfonyl)-phenyl]-4,5-dihydro-imidazol-1-yl}-[4-(2-hydroxy-ethyl)-piperazin-1-yl]-methanone;

2-(4-{4,5-Bis-(4-chloro-phenyl)-2-[2-ethoxy-5-(piperidine-1-sulfonyl)-phenyl]-4,5-dihydro-imidazole-1-carbonyl}-piperazin-1-yl)-N-methyl-acetamide;

2-(4-{4,5-Bis-(4-chloro-phenyl)-2-[2-ethoxy-5-(piperidine-1-sulfonyl)-phenyl]-4,5-dihydro-imidazole-1-carbonyl}-piperazin-1-yl)-1-morpholin-4-yl-ethanone;

{4,5-Bis-(4-chloro-phenyl)-2-[2-ethoxy-5-(piperidine-1-sulfonyl)-phenyl]-4,5-dihydro-imidazol-1-yl}-(4-cyclopropanecarbonyl-piperazin-1-yl)-methanone;

3-[4,5-Bis-(4-chloro-phenyl)-1-(3-oxo-piperazine-1-carbonyl)-4,5-dihydro-1H-imidazol-2-yl]-4-ethoxy-N-(2-methoxy-1-methyl-ethyl)-benzenesulfonamide;

3-{4,5-Bis-(4-chloro-phenyl)-1-[4-(2-methanesulfonyl-ethyl)-piperazine-1-carbonyl]-4,5-dihydro-1H-imidazol-2-yl}-4-ethoxy-N-(2-methoxy-1-methyl-ethyl)-benzenesulfonamide;

2-(4-{4,5-Bis-(4-chloro-phenyl)-2-[2-ethoxy-5-(2-methoxy-1-methyl-ethylsulfamoyl)-phenyl]-4,5-dihydro-imidazole-1-carbonyl}-piperazin-1-yl)-N,N-dimethyl-acetamide;

3-[4,5-Bis-(4-chloro-phenyl)-1-(4-ethanesulfonyl-piperazine-1-carbonyl)-4,5-dihydro-1H-imidazol-2-yl]-4-ethoxy-N-(2-methoxy-1-methyl-ethyl)-benzenesulfonamide;

3-(4,5-Bis-(4-chloro-phenyl)-1-{4-[2-(3-oxo-piperazin-1-yl)-acetyl]-piperazine-1-carbonyl}-4,5-dihydro-1H-imidazol-2-yl)-4-ethoxy-N-(2-methoxy-1-methyl-ethyl)-benzenesulfonamide;

2-(4-{4,5-Bis-(4-chloro-phenyl)-2-[2-ethoxy-5-(2-methoxy-1-methyl-ethylsulfamoyl)-phenyl]-4,5-dihydro-imidazole-1-carbonyl}-piperazin-1-yl)-N-(2-methoxy-1-methyl-ethyl)-acetamide;

3-{4,5-Bis-(4-chloro-phenyl)-1-[4-(2-hydroxy-ethyl)-piperazine-1-carbonyl]-4,5-dihydro-1H-imidazol-2-yl}-4-ethoxy-N-(2-methoxy-1-methyl-ethyl)-benzenesulfonamide;

2-(4-{4,5-Bis-(4-chloro-phenyl)-2-[2-ethoxy-5-(2-methoxy-1-methyl-ethylsulfamoyl)-phenyl]-4,5-dihydro-imidazole-1-carbonyl}-piperazin-1-yl)-N-methyl-acetamide;

4-{4,5-Bis-(4-chloro-phenyl)-2-[2-ethoxy-5-(pyrrolidine-1-sulfonyl)-phenyl]-4,5-dihydro-imidazole-1-carbonyl}-piperazin-2-one;

{4,5-Bis-(4-chloro-phenyl)-2-[2-ethoxy-5-(pyrrolidine-1-sulfonyl)-phenyl]-4,5-dihydro-imidazol-1-yl}-[4-(2-methanesulfonyl-ethyl)-piperazin-1-yl]-methanone;

2-(4-{4,5-Bis-(4-chloro-phenyl)-2-[2-ethoxy-5-(pyrrolidine-1-sulfonyl)-phenyl]-4,5-dihydro-imidazole-1-carbonyl}-piperazin-1-yl)-N,N-dimethyl-acetamide;

4-[2-(4-{4,5-Bis-(4-chloro-phenyl)-2-[2-ethoxy-5-(pyrrolidine-1-sulfonyl)-phenyl]-4,5-dihydro-imidazole-1-carbonyl}-piperazin-1-yl)-2-oxo-ethyl]-piperazin-2-one;

2-(4-{4,5-Bis-(4-chloro-phenyl)-2-[2-ethoxy-5-(pyrrolidine-1-sulfonyl)-phenyl]-4,5-dihydro-imidazole-1-carbonyl}-piperazin-1-yl)-N-(2-methoxy-1-methyl-ethyl)-acetamide;

{4,5-Bis-(4-chloro-phenyl)-2-[2-ethoxy-5-(pyrrolidine-1-sulfonyl)-phenyl]-4,5-dihydro-imidazol-1-yl}-[4-(2-hydroxy-ethyl)-piperazin-1-yl]-methanone;

5-[4,5-Bis-(4-chloro-phenyl)-1-(3-oxo-piperazine-1-carbonyl)-4,5-dihydro-1H-imidazol-2-yl]-4-ethoxy-2-fluoro-N,N-dimethyl-benzenesulfonamide;

5-{4,5-Bis-(4-chloro-phenyl)-1-[4-(2-hydroxy-ethyl)-piperazine-1-carbonyl]-4,5-dihydro-1H-imidazol-2-yl}-4-ethoxy-2-fluoro-N,N-dimethyl-benzenesulfonamide;

2-{4-[4,5-Bis-(4-chloro-phenyl)-2-(5-dimethylsulfamoyl-2-ethoxy-4-fluoro-phenyl)-4,5-dihydro-imidazole-1-carbonyl]-piperazin-1-yl}-N,N-dimethyl-acetamide;

5-{4,5-Bis-(4-chloro-phenyl)-1-[4-(2-methanesulfonyl-ethyl)-piperazine-1-carbonyl]-4,5-dihydro-1H-imidazol-2-yl}-4-ethoxy-2-fluoro-N,N-dimethyl-benzenesulfonamide;

4-[4,5-Bis-(4-chloro-phenyl)-2-(7-ethoxy-2-methyl-1,1-dioxo-1,2,3,4-tetrahydro-1$\lambda$6-benzo[b][1,4,5]oxathiazepin-8-yl)-4,5-dihydro-imidazole-1-carbonyl]-piperazin-2-one;

[4,5-Bis-(4-chloro-phenyl)-2-(7-ethoxy-2-methyl-1,1-dioxo-1,2,3,4-tetrahydro-1$\lambda$6-benzo[b][1,4,5]oxathiazepin-8-yl)-4,5-dihydro-imidazol-1-yl]-[4-(2-methanesulfonyl-ethyl)-piperazin-1-yl]-methanone;

2-{4-[4,5-Bis-(4-chloro-phenyl)-2-(7-ethoxy-2-methyl-1,1-dioxo-1,2,3,4-tetrahydro-1$\lambda$6-benzo[b][1,4,5]oxathiazepin-8-yl)-4,5-dihydro-imidazole-1-carbonyl]-piperazin-1-yl}-1-morpholin-4-yl-ethanone;

2-{4-[(4S,5R)-4,5-Bis-(4-chloro-phenyl)-2-(5-dimethylsulfamoyl-2-ethoxy-4-fluoro-phenyl)-4,5-dihydro-imidazole-1-carbonyl]-piperazin-1-yl}-N,N-dimethyl-acetamide hydrochloride;

5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-4-ethoxy-2-fluoro-N,N-dimethyl-benzenesulfonamide hydrochloride;

5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-4-ethoxy-2-fluoro-N,N-dimethyl-benzenesulfonamide hydrochloride;

4-[4,5-Bis-(4-chloro-phenyl)-1-(3-oxo-piperazine-1-carbonyl)-4,5-dihydro-1H-imidazol-2-yl]-3-ethoxy-N,N-dimethyl-benzenesulfonamide hydrochloride;

4-{4,5-Bis-(4-chloro-phenyl)-1-[4-(2-methanesulfonyl-ethyl)-piperazine-1-carbonyl]-4,5-dihydro-1H-imidazol-2-yl}-3-ethoxy-N,N-dimethyl-benzenesulfonamide hydrochloride;

4-{4,5-Bis-(4-chloro-phenyl)-1-[4-(2-morpholin-4-yl-2-oxo-ethyl)-piperazine-1-carbonyl]-4,5-dihydro-1H-imidazol-2-yl}-3-ethoxy-N,N-dimethyl-benzenesulfonamide hydrochloride;

2-{4-[4,5-Bis-(4-chloro-phenyl)-2-(4-dimethylsulfamoyl-2-ethoxy-phenyl)-4,5-dihydro-imidazole-1-carbonyl]-piperazin-1-yl}-N,N-dimethyl-acetamide hydrochloride;

4-[4,5-Bis-(4-chloro-phenyl)-2-(2-ethoxy-5-methanesulfonyl-phenyl)-4,5-dihydro-imidazole-1-carbonyl]-piperazin-2-one;

[4,5-Bis-(4-chloro-phenyl)-2-(2-ethoxy-5-methanesulfonyl-phenyl)-4,5-dihydro-imidazol-1-yl]-[4-(2-methanesulfonyl-ethyl)-piperazin-1-yl]-methanone hydrochloride;

2-{4-[4,5-Bis-(4-chloro-phenyl)-2-(2-ethoxy-5-methanesulfonyl-phenyl)-4,5-dihydro-imidazole-1-carbonyl]-piperazin-1-yl}-1-morpholin-4-yl-ethanone hydrochloride;

5-[(4S,5R)-4,5-Bis-(4-chloro-phenyl)-1-(3-oxo-piperazine-1-carbonyl)-4,5-dihydro-1H-imidazol-2-yl]-2-cyano-4-ethoxy-N,N-dimethyl-benzenesulfonamide;

2-{4-[(4S,5R)-4,5-Bis-(4-chloro-phenyl)-2-(4-cyano-5-dimethylsulfamoyl-2-ethoxy-phenyl)-4,5-dihydro-imidazole-1-carbonyl]-piperazin-1-yl}-N,N-dimethyl-acetamide hydrochloride;

5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-2-cyano-4-ethoxy-N,N-dimethyl-benzenesulfonamide hydrochloride;

5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-2-cyano-4-ethoxy-N,N-dimethyl-benzenesulfonamide hydrochloride;

5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-4-ethoxy-2-methoxy-benzonitrile hydrochloride;

5-[(4S,5R)-4,5-Bis-(4-chloro-phenyl)-1-(3-oxo-piperazine-1-carbonyl)-4,5-dihydro-1H-imidazol-2-yl]-4-ethoxy-2-methoxy-benzonitrile hydrochloride;

5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-4-ethoxy-2-methoxy-benzonitrile hydrochloride;

2-{4-[(4S,5R)-4,5-Bis-(4-chloro-phenyl)-2-(5-dimethylsulfamoyl-2-ethoxy-4-methoxy-phenyl)-4,5-dihydro-imidazole-1-carbonyl]-piperazin-1-yl}-N,N-dimethyl-acetamide hydrochloride;

5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-4-ethoxy-2-methoxy-N,N-dimethyl-benzenesulfonamide hydrochloride;

3-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-4-ethoxy-N,N-dimethyl-benzamide hydrochloride;

3-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-4-ethoxy-N,N-dimethyl-benzamide hydrochloride;

3-[(4S,5R)-4,5-Bis-(4-chloro-phenyl)-1-(3-oxo-piperazine-1-carbonyl)-4,5-dihydro-1H-imidazol-2-yl]-4-ethoxy-N,N-dimethyl-benzamide hydrochloride;

2-(4-{(4S,5R)-4,5-Bis-(4-chloro-phenyl)-2-[2-ethoxy-5-(pyrrolidine-1-carbonyl)-phenyl]-4,5-dihydro-imidazole-1-carbonyl}-piperazin-1-yl)-1-morpholin-4-yl-ethanone hydrochloride;

{(4S,5R)-4,5-Bis-(4-chloro-phenyl)-2-[2-ethoxy-5-(pyrrolidine-1-carbonyl)-phenyl]-4,5-dihydro-imidazol-1-yl}-[4-(2-methanesulfonyl-ethyl)-piperazin-1-yl]-methanone hydrochloride;

2-(4-{(4S,5R)-4,5-Bis-(4-chloro-phenyl)-2-[2-ethoxy-5-(piperidine-1-carbonyl)-phenyl]-4,5-dihydro-imidazole-1-carbonyl}-piperazin-1-yl)-1-morpholin-4-yl-ethanone hydrochloride;

{(4S,5R)-4,5-Bis-(4-chloro-phenyl)-2-[2-ethoxy-5-(piperidine-1-carbonyl)-phenyl]-4,5-dihydro-imidazol-1-yl}-[4-(2-methanesulfonyl-ethyl)-piperazin-1-yl]-methanone hydrochloride;

4-{(4S,5R)-4,5-Bis-(4-chloro-phenyl)-2-[2-ethoxy-5-(piperidine-1-carbonyl)-phenyl]-4,5-dihydro-imidazole-1-carbonyl}-piperazin-2-one hydrochloride;

2-(4-{(4S,5R)-4,5-Bis-(4-chloro-phenyl)-2-[2-ethoxy-5-(morpholine-4-carbonyl)-phenyl]-4,5-dihydro-imidazole-1-carbonyl}-piperazin-1-yl)-1-morpholin-4-yl-ethanone hydrochloride;

5-[(4S,5R)-4,5-Bis-(4-chloro-phenyl)-1-(3-oxo-piperazine-1-carbonyl)-4,5-dihydro-1H-imidazol-2-yl]-4-ethoxy-2-fluoro-N,N-dimethyl-benzenesulfonamide;

2-(4-{(4S,5R)-4,5-Bis-(4-chloro-phenyl)-2-[2-ethoxy-4-methyl-5-(pyrrolidine-1-sulfonyl)-phenyl]-4,5-dihydro-imidazole-1-carbonyl}-piperazin-1-yl)-1-morpholin-4-yl-ethanone hydrochloride;

[(4S,5R)-2-[4-Chloro-2-ethoxy-5-(pyrrolidine-1-sulfonyl)-phenyl]-4,5-bis-(4-chloro-phenyl)-4,5-dihydro-imidazol-1-yl]-[4-(2-methanesulfonyl-ethyl)-piperazin-1-yl]-methanone hydrochloride;

2-{4-[(4S,5R)-2-[4-Chloro-2-ethoxy-5-(piperidine-1-sulfonyl)-phenyl]-4,5-bis-(4-chloro-phenyl)-4,5-dihydro-imidazole-1-carbonyl]-piperazin-1-yl}-1-morpholin-4-yl-ethanone hydrochloride;

[(4S,5R)-2-[4-Chloro-2-ethoxy-5-(piperidine-1-sulfonyl)-phenyl]-4,5-bis-(4-chloro-phenyl)-4,5-dihydro-imidazol-1-yl]-[4-(2-methanesulfonyl-ethyl)-piperazin-1-yl]-methanone hydrochloride;

4-[(4S,5R)-2-[4-Chloro-2-ethoxy-5-(piperidine-1-sulfonyl)-phenyl]-4,5-bis-(4-chloro-phenyl)-4,5-dihydro-imidazole-1-carbonyl]-piperazin-2-one hydrochloride;

2-{4-[(4S,5R)-2-[4-Chloro-2-ethoxy-5-(morpholine-4-sulfonyl)-phenyl]-4,5-bis-(4-chloro-phenyl)-4,5-dihydro-imidazole-1-carbonyl]-piperazin-1-yl}-1-morpholin-4-yl-ethanone hydrochloride;

[(4S,5R)-2-[4-Chloro-2-ethoxy-5-(morpholine-4-sulfonyl)-phenyl]-4,5-bis-(4-chloro-phenyl)-4,5-dihydro-imidazol-1-yl]-[4-(2-methanesulfonyl-ethyl)-piperazin-1-yl]-methanone hydrochloride;

4-[(4S,5R)-2-[4-Chloro-2-ethoxy-5-(morpholine-4-sulfonyl)-phenyl]-4,5-bis-(4-chloro-phenyl)-4,5-dihydro-imidazole-1-carbonyl]-piperazin-2-one hydrochloride;

{(4S,5R)-4,5-Bis-(4-chloro-phenyl)-2-[2-ethoxy-4-methyl-5-(pyrrolidine-1-sulfonyl)-phenyl]-4,5-dihydro-imidazol-1-yl}-[4-(2-methanesulfonyl-ethyl)-piperazin-1-yl]-methanone hydrochloride;

2-(4-{(4S,5R)-4,5-Bis-(4-chloro-phenyl)-2-[2-ethoxy-4-methyl-5-(piperidine-1-sulfonyl)-phenyl]-4,5-dihydro-imidazole-1-carbonyl}-piperazin-1-yl)-1-morpholin-4-yl-ethanone hydrochloride;

{(4S,5R)-4,5-Bis-(4-chloro-phenyl)-2-[2-ethoxy-4-methyl-5-(piperidine-1-sulfonyl)-phenyl]-4,5-dihydro-imidazol-1-yl}-[4-(2-methanesulfonyl-ethyl)-piperazin-1-yl]-methanone hydrochloride;

4-{(4S,5R)-4,5-Bis-(4-chloro-phenyl)-2-[2-ethoxy-4-methyl-5-(piperidine-1-sulfonyl)-phenyl]-4,5-dihydro-imidazole-1-carbonyl}-piperazin-2-one hydrochloride;

2-(4-{(4S,5R)-4,5-Bis-(4-chloro-phenyl)-2-[2-ethoxy-4-methyl-5-(morpholine-4-sulfonyl)-phenyl]-4,5-dihydro-imidazole-1-carbonyl}-piperazin-1-yl)-1-morpholin-4-yl-ethanone hydrochloride;

{(4S,5R)-4,5-Bis-(4-chloro-phenyl)-2-[2-ethoxy-4-methyl-5-(morpholine-4-sulfonyl)-phenyl]-4,5-dihydro-imidazol-1-yl}-[4-(2-methanesulfonyl-ethyl)-piperazin-1-yl]-methanone hydrochloride;

4-{(4S,5R)-4,5-Bis-(4-chloro-phenyl)-2-[2-ethoxy-4-methyl-5-(morpholine-4-sulfonyl)-phenyl]-4,5-dihydro-imidazole-1-carbonyl}piperazin-2-one hydrochloride;

2-{4-[(4S,5R)-2-[4-Chloro-2-ethoxy-5-(pyrrolidine-1-sulfonyl)-phenyl]-4,5-bis-(4-chloro-phenyl)-4,5-dihydro-imidazole-1-carbonyl]-piperazin-1-yl}-1-morpholin-4-yl-ethanone hydrochloride;

4-[(4S,5R)-4,5-Bis-(4-chloro-phenyl)-1-(3-oxo-piperazine-1-carbonyl)-4,5-dihydro-1H-imidazol-2-yl]-3-ethoxy-N,N-dimethyl-benzenesulfonamide hydrochloride;

4-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-3-ethoxy-N,N-dimethyl-benzenesulfonamide hydrochloride;

4-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-3-ethoxy-N,N-dimethyl-benzenesulfonamide hydrochloride;

2-{4-[(4S,5R)-4,5-Bis-(4-chloro-phenyl)-2-(4-dimethylsulfamoyl-2-ethoxy-phenyl)-4,5-dihydro-imidazole-1-carbonyl]-piperazin-1-yl}-N,N-dimethyl-acetamide hydrochloride;

2-{4-[(4S,5R)-4,5-Bis-(4-chloro-phenyl)-2-(4-cyano-2-ethoxy-phenyl)-4,5-dihydro-imidazole-1-carbonyl]-piperazin-1-yl}-N-tert-butyl-acetamide;

2-{4-[(4S,5R)-4,5-Bis-(4-chloro-phenyl)-2-(4-cyano-2-ethoxy-phenyl)-4,5-dihydro-imidazole-1-carbonyl]-piperazin-1-yl}-acetamide;

2-{4-[(4S,5R)-4,5-Bis-(4-chloro-phenyl)-2-(4-cyano-2-ethoxy-phenyl)-4,5-dihydro-imidazole-1-carbonyl]-piperazin-1-yl}-N-cyanomethyl-N-methyl-acetamide;

2-{4-[(4S,5R)-4,5-Bis-(4-chloro-phenyl)-2-(4-cyano-2-ethoxy-phenyl)-4,5-dihydro-imidazole-1-carbonyl]-piperazin-1-yl}-N-cyclopropyl-acetamide;

2-{4-[(4S,5R)-4,5-Bis-(4-chloro-phenyl)-2-(4-cyano-2-ethoxy-phenyl)-4,5-dihydro-imidazole-1-carbonyl]-piperazin-1-yl}-N-(2-methoxy-ethyl)-acetamide;

2-{4-[(4S,5R)-4,5-Bis-(4-chloro-phenyl)-2-(4-cyano-2-ethoxy-phenyl)-4,5-dihydro-imidazole-1-carbonyl]-piperazin-1-yl}-N,N-bis-(2-methoxy-ethyl)-acetamide;

2-{4-[(4S,5R)-4,5-Bis-(4-chloro-phenyl)-2-(4-cyano-2-ethoxy-phenyl)-4,5-dihydro-imidazole-1-carbonyl]-piperazin-1-yl}-N-methoxy-N-methyl-acetamide;

2-{4-[(4S,5R)-4,5-Bis-(4-chloro-phenyl)-2-(4-cyano-2-ethoxy-phenyl)-4,5-dihydro-imidazole-1-carbonyl]-piperazin-1-yl}-N-isopropyl-N-methyl-acetamide;

2-{4-[(4S,5R)-4,5-Bis-(4-chloro-phenyl)-2-(4-cyano-2-ethoxy-phenyl)-4,5-dihydro-imidazole-1-carbonyl]-piperazin-1-yl}-N-(2-cyano-ethyl)-N-methyl-acetamide;

4-[(4S,5R)-4,5-Bis-(4-chloro-phenyl)-1-(3-oxo-[1,4]diazepane-1-carbonyl)-4,5-dihydro-1H-imidazol-2-yl]-3-ethoxy-benzonitrile;

4-{(4S,5R)-4,5-Bis-(4-chloro-phenyl)-2-[2-ethoxy-4-fluoro-5-(morpholine-4-sulfonyl)-phenyl]-4,5-dihydro-imidazole-1-carbonyl}-piperazin-2-one;

1-{(4S,5R)-4,5-Bis-(4-chloro-phenyl)-2-[2-ethoxy-4-fluoro-5-(morpholine-4-sulfonyl)-phenyl]-4,5-dihydro-imidazole-1-carbonyl}-[1,4]diazepan-5-one;

{(4S,5R)-4,5-Bis-(4-chloro-phenyl)-2-[2-ethoxy-4-fluoro-5-(morpholine-4-sulfonyl)-phenyl]-4,5-dihydro-imidazol-1-yl}-[4-(2-methanesulfonyl-ethyl)-piperazin-1-yl]-methanone hydrochloride;

2-(4-{(4S,5R)-4,5-Bis-(4-chloro-phenyl)-2-[2-ethoxy-4-fluoro-5-(morpholine-4-sulfonyl)-phenyl]-4,5-dihydro-imidazole-1-carbonyl}-piperazin-1-yl)-1-morpholin-4-yl-ethanone hydrochloride;

4-{(4S,5R)-4,5-Bis-(4-chloro-phenyl)-2-[2-ethoxy-4-(morpholine-4-sulfonyl)-phenyl]-4,5-dihydro-imidazole-1-carbonyl}-piperazin-2-one hydrochloride;

{(4S,5R)-4,5-Bis-(4-chloro-phenyl)-2-[2-ethoxy-4-(morpholine-4-sulfonyl)-phenyl]-4,5-dihydro-imidazol-1-yl}-[4-(2-methanesulfonyl-ethyl)-piperazin-1-yl]-methanone hydrochloride;

2-(4-{(4S,5R)-4,5-Bis-(4-chloro-phenyl)-2-[2-ethoxy-4-(morpholine-4-sulfonyl)-phenyl]-4,5-dihydro-imidazole-1-carbonyl}-piperazin-1-yl)-1-morpholin-4-yl-ethanone hydrochloride;

4-{(4S,5R)-4,5-Bis-(4-chloro-phenyl)-2-[2-ethoxy-4-(pyrrolidine-1-sulfonyl)-phenyl]-4,5-dihydro-imidazole-1-carbonyl}-piperazin-2-one hydrochloride;

{(4S,5R)-4,5-Bis-(4-chloro-phenyl)-2-[2-ethoxy-4-(pyrrolidine-1-sulfonyl)-phenyl]-4,5-dihydro-imidazol-1-yl}-[4-(2-methanesulfonyl-ethyl)-piperazin-1-yl]-methanone hydrochloride;

2-(4-{(4S,5R)-4,5-Bis-(4-chloro-phenyl)-2-[2-ethoxy-4-(pyrrolidine-1-sulfonyl)-phenyl]-4,5-dihydro-imidazole-1-carbonyl}-piperazin-1-yl)-1-morpholin-4-yl-ethanone hydrochloride;

5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-4-ethoxy-N-methoxy-2,N-dimethyl-benzenesulfonamide;

4-[(4S,5R)-4,5-Bis-(4-chloro-phenyl)-1-(3-oxo-piperazine-1-carbonyl)-4,5-dihydro-1H-imidazol-2-yl]-2,5-diethoxy-benzonitrile;

4-[(4S,5R)-4,5-Bis-(4-chloro-phenyl)-1-(5-oxo-[1,4]diazepane-1-carbonyl)-4,5-dihydro-1H-imidazol-2-yl]-2,5-diethoxy-benzonitrile;

4-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-2,5-diethoxy-benzonitrile hydrochloride;

4-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-2,5-diethoxy-benzonitrile hydrochloride;

4-{(4S,5R)-4,5-Bis-(4-chloro-phenyl)-2-[2-ethoxy-5-(piperidine-1-sulfonyl)-4-piperidin-1-yl-phenyl]-4,5-dihydro-imidazole-1-carbonyl}-piperazin-2-one hydrochloride;

1-{(4S,5R)-4,5-Bis-(4-chloro-phenyl)-2-[2-ethoxy-5-(piperidine-1-sulfonyl)-4-piperidin-1-yl-phenyl]-4,5-dihydro-imidazole-1-carbonyl}-[1,4]diazepan-5-one hydrochloride;

{(4S,5R)-4,5-Bis-(4-chloro-phenyl)-2-[2-ethoxy-5-(piperidine-1-sulfonyl)-4-piperidin-1-yl-phenyl]-4,5-dihydro-imidazol-1-yl}-[4-(2-methanesulfonyl-ethyl)-piperazin-1-yl]-methanone hydrochloride;

2-(4-{(4S,5R)-4,5-Bis-(4-chloro-phenyl)-2-[2-ethoxy-5-(piperidine-1-sulfonyl)-4-piperidin-1-yl-phenyl]-4,5-dihydro-imidazole-1-carbonyl}-piperazin-1-yl)-1-morpholin-4-yl-ethanone hydrochloride;

4,5-Bis-(4-chloro-phenyl)-2-(4-dimethylamino-5-dimethylsulfamoyl-2-ethoxy-phenyl)-4,5-dihydro-imidazole-1-carboxylic acid ethyl ester hydrochloride;

5-[(4S,5R)-4,5-Bis-(4-chloro-phenyl)-1-(3-oxo-piperazine-1-carbonyl)-4,5-dihydro-1H-imidazol-2-yl]-2-dimethylamino-4-ethoxy-N,N-dimethyl-benzenesulfonamide hydrochloride;

5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-2-dimethylamino-4-ethoxy-N,N-dimethyl-benzenesulfonamide hydrochloride;

5-[(4S,5R)-4,5-Bis-(4-chloro-phenyl)-1-(5-oxo-[1,4]diazepane-1-carbonyl)-4,5-dihydro-1H-imidazol-2-yl]-2-dimethylamino-4-ethoxy-N,N-dimethyl-benzenesulfonamide hydrochloride;

5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-2-dimethylamino-4-ethoxy-N,N-dimethyl-benzenesulfonamide hydrochloride;

5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-2-chloro-4-ethoxy-benzonitrile;

5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-4-ethoxy-N-isopropyl-2-methyl-benzenesulfonamide;

5-[(4S,5R)-4,5-Bis-(4-chloro-phenyl)-1-(3-oxo-piperazine-1-carbonyl)-4,5-dihydro-1H-imidazol-2-yl]-4-ethoxy-N-isopropyl-2-methyl-benzenesulfonamide;

5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-4-ethoxy-2,N-dimethyl-benzenesulfonamide;

5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-4-ethoxy-2,N-dimethyl-benzenesulfonamide;

5-[(4S,5R)-4,5-Bis-(4-chloro-phenyl)-1-(3-oxo-piperazine-1-carbonyl)-4,5-dihydro-1H-imidazol-2-yl]-4-ethoxy-2,N-dimethyl-benzenesulfonamide;

5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-2-chloro-4-ethoxy-benzonitrile;

5-[(4S,5R)-4,5-Bis-(4-chloro-phenyl)-1-(3-oxo-piperazine-1-carbonyl)-4,5-dihydro-1H-imidazol-2-yl]-2-chloro-4-ethoxy-benzonitrile;

5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-2-dimethylamino-4-ethoxy-benzonitrile;

5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-2-dimethylamino-4-ethoxy-benzonitrile;

5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-4-ethoxy-N-isopropyl-2-methyl-benzenesulfonamide;

4-[(4S,5R)-4,5-Bis-(4-chloro-phenyl)-2-(2-ethoxy-4-ethynyl-phenyl)-4,5-dihydro-imidazole-1-carbonyl]-piperazin-2-one;

1-[(4S,5R)-4,5-Bis-(4-chloro-phenyl)-2-(2-ethoxy-4-ethynyl-phenyl)-4,5-dihydro-imidazole-1-carbonyl]-[1,4]diazepan-5-one;

[(4S,5R)-4,5-Bis-(4-chloro-phenyl)-2-(2-ethoxy-4-ethynyl-phenyl)-4,5-dihydro-imidazol-1-yl]-[4-(2-methanesulfonyl-ethyl)-piperazin-1-yl]-methanone hydrochloride;

2-{4-[(4S,5R)-4,5-Bis-(4-chloro-phenyl)-2-(2-ethoxy-4-ethynyl-phenyl)-4,5-dihydro-imidazole-1-carbonyl]-piperazin-1-yl}-1-morpholin-4-yl-ethanone hydrochloride;

5-[(4S,5R)-4,5-Bis-(4-chloro-phenyl)-1-(4-ethanesulfonyl-piperazine-1-carbonyl)-4,5-dihydro-1H-imidazol-2-yl]-N-tert-butyl-2-chloro-4-ethoxy-benzenesulfonamide hydrochloride;

5-{(4S,5R)-4,5-Bis-(4-chloro-phenyl)-1-[4-(3,5-dimethyl-isoxazole-4-carbonyl)-piperazine-1-carbonyl]-4,5-dihydro-1H-imidazol-2-yl}-2-chloro-4-ethoxy-benzenesulfonamide;

N-tert-Butyl-2-{4-[(4S,5R)-2-(4-chloro-2-ethoxy-5-sulfamoyl-phenyl)-4,5-bis-(4-chloro-phenyl)-4,5-dihydro-imidazole-1-carbonyl]-piperazin-1-yl}-acetamide;

5-[(4S,5R)-4,5-Bis-(4-chloro-phenyl)-1-(3-oxo-piperazine-1-carbonyl)-4,5-dihydro-1H-imidazol-2-yl]-2-chloro-4-ethoxy-benzenesulfonamide;

5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-2-chloro-4-ethoxy-benzenesulfonamide;

2-{4-[(4S,5R)-2-(4-Chloro-2-ethoxy-5-sulfamoyl-phenyl)-4,5-bis-(4-chloro-phenyl)-4,5-dihydro-imidazole-1-carbonyl]-piperazin-1-yl}-acetamide;

2-{4-[(4S,5R)-2-(4-Chloro-2-ethoxy-5-sulfamoyl-phenyl)-4,5-bis-(4-chloro-phenyl)-4,5-dihydro-imidazole-1-carbonyl]-piperazin-1-yl}-N-isopropyl-N-methyl-acetamide;

5-[(4S,5R)-4,5-Bis-(4-chloro-phenyl)-1-(4-ethanesulfonyl-piperazine-1-carbonyl)-4,5-dihydro-1H-imidazol-2-yl]-2-chloro-4-ethoxy-benzenesulfonamide;

4-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-N-tert-butyl-3-ethoxy-benzamide;

N-tert-Butyl-4-[(4S,5R)-1-(4-carbamoylmethyl-piperazine-1-carbonyl)-4,5-bis-(4-chloro-phenyl)-4,5-dihydro-1H-imidazol-2-yl]-3-ethoxy-benzamide;

{(4S,5R)-4,5-Bis-(4-chloro-phenyl)-2-[2-ethoxy-4-(piperidine-1-carbonyl)-phenyl]-4,5-dihydro-imidazol-1-yl}-[4-(3,5-dimethyl-isoxazole-4-carbonyl)-piperazin-1-yl]-methanone;

2-(4-{(4S,5R)-4,5-Bis-(4-chloro-phenyl)-2-[2-ethoxy-4-(piperidine-1-carbonyl)-phenyl]-4,5-dihydro-imidazole-1-carbonyl}-piperazin-1-yl)-1-morpholin-4-yl-ethanone;

2-(4-{(4S,5R)-4,5-Bis-(4-chloro-phenyl)-2-[2-ethoxy-4-(piperidine-1-carbonyl)-phenyl]-4,5-dihydro-imidazole-1-carbonyl}-piperazin-1-yl)-N-tert-butyl-acetamide;

4-{(4S,5R)-4,5-Bis-(4-chloro-phenyl)-2-[2-ethoxy-4-(piperidine-1-carbonyl)-phenyl]-4,5-dihydro-imidazole-1-carbonyl}-piperazin-2-one;

{(4S,5R)-4,5-Bis-(4-chloro-phenyl)-2-[2-ethoxy-4-(piperidine-1-carbonyl)-phenyl]-4,5-dihydro-imidazol-1-yl}-[4-(2-methanesulfonyl-ethyl)-piperazin-1-yl]-methanone;

2-(4-{(4S,5R)-4,5-Bis-(4-chloro-phenyl)-2-[2-ethoxy-4-(piperidine-1-carbonyl)-phenyl]-4,5-dihydro-imidazole-1-carbonyl}-piperazin-1-yl)-acetamide;

2-(4-{(4S,5R)-4,5-Bis-(4-chloro-phenyl)-2-[2-ethoxy-4-(piperidine-1-carbonyl)-phenyl]-4,5-dihydro-imidazole-1-carbonyl}-piperazin-1-yl)-N-isopropyl-N-methyl-acetamide;

{(4S,5R)-4,5-Bis-(4-chloro-phenyl)-2-[2-ethoxy-4-(piperidine-1-carbonyl)-phenyl]-4,5-dihydro-imidazol-1-yl}(4-ethanesulfonyl-piperazin-1-yl)-methanone;

5-{(4S,5R)-4,5-Bis-(4-chloro-phenyl)-1-[4-(3,5-dimethyl-isoxazole-4-carbonyl)-piperazine-1-carbonyl]-4,5-dihydro-1H-imidazol-2-yl}-2-chloro-4-ethoxy-N-methyl-benzenesulfonamide;

5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-2-chloro-4-ethoxy-N-isopropyl-benzenesulfonamide;

2-{4-[(4S,5R)-2-(4-Chloro-2-ethoxy-5-isopropylsulfamoyl-phenyl)-4,5-bis-(4-chloro-phenyl)-4,5-dihydro-imidazole-1-carbonyl]-piperazin-1-yl}-acetamide;

2-{4-[(4S,5R)-2-(4-Chloro-2-ethoxy-5-isopropylsulfamoyl-phenyl)-4,5-bis-(4-chloro-phenyl)-4,5-dihydro-imidazole-1-carbonyl]-piperazin-1-yl}-N-isopropyl-N-methyl-acetamide;

5-[(4S,5R)-4,5-Bis-(4-chloro-phenyl)-1-(4-ethanesulfonyl-piperazine-1-carbonyl)-4,5-dihydro-1H-imidazol-2-yl]-2-chloro-4-ethoxy-N-isopropyl-benzenesulfonamide;

N-tert-Butyl-2-{4-[(4S,5R)-2-(4-chloro-2-ethoxy-5-methylsulfamoyl-phenyl)-4,5-bis-(4-chloro-phenyl)-4,5-dihydro-imidazole-1-carbonyl]-piperazin-1-yl}-acetamide;

5-[(4S,5R)-4,5-Bis-(4-chloro-phenyl)-1-(3-oxo-piperazine-1-carbonyl)-4,5-dihydro-1H-imidazol-2-yl]-2-chloro-4-ethoxy-N-methyl-benzenesulfonamide;

5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-2-chloro-4-ethoxy-N-methyl-benzenesulfonamide;

2-{4-[(4S,5R)-2-(4-Chloro-2-ethoxy-5-methylsulfamoyl-phenyl)-4,5-bis-(4-chloro-phenyl)-4,5-dihydro-imidazole-1-carbonyl]-piperazin-1-yl}-acetamide;

2-{4-[(4S,5R)-2-(4-Chloro-2-ethoxy-5-methylsulfamoyl-phenyl)-4,5-bis-(4-chloro-phenyl)-4,5-dihydro-imidazole-1-carbonyl]-piperazin-1-yl}-N-isopropyl-N-methyl-acetamide;

5-[(4S,5R)-4,5-Bis-(4-chloro-phenyl)-1-(4-ethanesulfonyl-piperazine-1-carbonyl)-4,5-dihydro-1H-imidazol-2-yl]-2-chloro-4-ethoxy-N-methyl-benzenesulfonamide;

5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-2-chloro-4-ethoxy-N-isopropyl-benzenesulfonamide;

5-{(4S,5R)-4,5-Bis-(4-chloro-phenyl)-1-[4-(3,5-dimethyl-isoxazole-4-carbonyl)-piperazine-1-carbonyl]-4,5-dihydro-1H-imidazol-2-yl}-2-chloro-4-ethoxy-N-isopropyl-benzenesulfonamide;

N-tert-Butyl-2-{4-[(4S,5R)-2-(4-chloro-2-ethoxy-5-isopropylsulfamoyl-phenyl)-4,5-bis-(4-chloro-phenyl)-4,5-dihydro-imidazole-1-carbonyl]-piperazin-1-yl}-acetamide;

5-[(4S,5R)-4,5-Bis-(4-chloro-phenyl)-1-(3-oxo-piperazine-1-carbonyl)-4,5-dihydro-1H-imidazol-2-yl]-2-chloro-4-ethoxy-N-isopropyl-benzenesulfonamide;

N-{4-[(4S,5R)-4,5-Bis-(4-chloro-phenyl)-1-(3-oxo-piperazine-1-carbonyl)-4,5-dihydro-1H-imidazol-2-yl]-3-ethoxy-phenyl}-N-(3-oxo-piperazine-1-carbonyl)-methanesulfonamide;

N-(4-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-3-ethoxy-phenyl)-methanesulfonamide hydrochloride;

N-{4-[(4S,5R)-4,5-Bis-(4-chloro-phenyl)-1-(3-oxo-piperazine-1-carbonyl)-4,5-dihydro-1H-imidazol-2-yl]-3-ethoxy-phenyl}-2,2-dimethyl-propionamide;

5-[(4S,5R)-4,5-Bis-(4-chloro-phenyl)-1-(3-oxo-piperazine-1-carbonyl)-4,5-dihydro-1H-imidazol-2-yl]-4-ethoxy-2-ethynyl-N,N-dimethyl-benzenesulfonamide;

5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-4-ethoxy-2-ethynyl-N,N-dimethyl-benzenesulfonamide hydrochloride;

5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-4-ethoxy-2-ethynyl-N,N-dimethyl-benzenesulfonamide hydrochloride;

2-{4-[(4S,5R)-4,5-Bis-(4-chloro-phenyl)-2-(5-dimethylsulfamoyl-2-ethoxy-4-ethynyl-phenyl)-4,5-dihydro-imidazole-1-carbonyl]-piperazin-1-yl}-N-isopropyl-N-methyl-acetamide hydrochloride;

N-(4{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-3-ethoxy-phenyl)-2,2-dimethyl-propionamide hydrochloride;

N-{4-[(4S,5R)-4,5-Bis-(4-chloro-phenyl)-1-(4-dimethylcarbamoylmethyl-piperazine-1-carbonyl)-4,5-dihydro-1H-imidazol-2-yl]-3-ethoxy-phenyl}-2,2-dimethyl-propionamide hydrochloride;

N-(4-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-3-ethoxy-phenyl)-2,2-dimethyl-propionamide hydrochloride;

2-{4-[(4S,5R)-4,5-Bis-(4-chloro-phenyl)-2-(2-ethoxy-4-ethynyl-phenyl)-4,5-dihydro-imidazole-1-carbonyl]-piperazin-1-yl}-N-tert-butyl-acetamide hydrochloride;

2-{4-[(4S,5R)-4,5-Bis-(4-chloro-phenyl)-2-(2-ethoxy-4-ethynyl-phenyl)-4,5-dihydro-imidazole-1-carbonyl]-piperazin-1-yl}-N-methoxy-N-methyl-acetamide hydrochloride;

N-(2-{4-[(4S,5R)-4,5-Bis-(4-chloro-phenyl)-2-(2-ethoxy-4-ethynyl-phenyl)-4,5-dihydro-imidazole-1-carbonyl]-piperazin-1-yl}-ethyl)-methanesulfonamide hydrochloride;

[(4S,5R)-4,5-Bis-(4-chloro-phenyl)-2-(2-ethoxy-4-ethynyl-phenyl)-4,5-dihydro-imidazol-1-yl]-(4-ethanesulfonyl-piperazin-1-yl)-methanone;

[(4S,5R)-4,5-Bis-(4-chloro-phenyl)-2-(2-ethoxy-4-ethynyl-phenyl)-4,5-dihydro-imidazol-1-yl]-[4-(2-methoxy-ethyl)-piperazin-1-yl]-methanone hydrochloride;

1-{4-[(4S,5R)-4,5-Bis-(4-chloro-phenyl)-2-(2-ethoxy-4-ethynyl-phenyl)-4,5-dihydro-imidazole-1-carbonyl]-piperazin-1-yl}-ethanone;

3-{4-[(4S,5R)-4,5-Bis-(4-chloro-phenyl)-2-(2-ethoxy-4-ethynyl-phenyl)-4,5-dihydro-imidazole-1-carbonyl]-piperazin-1-yl}-propionitrile hydrochloride;

[(4S,5R)-4,5-Bis-(4-chloro-phenyl)-2-(2-ethoxy-4-ethynyl-phenyl)-4,5-dihydro-imidazol-1-yl]-[4-(3-methanesulfonyl-propyl)-piperazin-1-yl]-methanone hydrochloride;

2-{4-[(4S,5R)-4,5-Bis-(4-chloro-phenyl)-2-(2-ethoxy-4-ethynyl-phenyl)-4,5-dihydro-imidazole-1-carbonyl]-piperazin-1-yl}-acetamide hydrochloride;

2-{(4-[(4S,5R)-4,5-Bis-(4-chloro-phenyl)-2-(2-ethoxy-4-ethynyl-phenyl)-4,5-dihydro-imidazole-1-carbonyl]-piperazin-1-yl}-N-isopropyl-N-methyl-acetamide hydrochloride;

3-{4-[(4S,5R)-4,5-Bis-(4-chloro-phenyl)-2-(2-ethoxy-4-ethynyl-phenyl)-4,5-dihydro-imidazole-1-carbonyl]-piperazin-1-yl}-propionic acid hydrochloride;

4-[(4S,5R)-4,5-Bis-(4-chloro-phenyl)-2-(2-ethoxy-4-trifluoroprop-1-ynyl-phenyl)-4,5-dihydro-imidazole-1-carbonyl]-piperazin-2-one;

[(4S,5R)-4,5-Bis-(4-chloro-phenyl)-2-(2-ethoxy-4-trifluoroprop-1-ynyl-phenyl)-4,5-dihydro-imidazol-1-yl]-[4-(2-methanesulfonyl-ethyl)-piperazin-1-yl]-methanone hydrochloride;

2-{4-[(4S,5R)-4,5-Bis-(4-chloro-phenyl)-2-(2-ethoxy-4-trifluoroprop-1-ynyl-phenyl)-4,5-dihydro-imidazole-1-carbonyl]-piperazin-1-yl}-1-morpholin-4-yl-ethanone hydrochloride;

2-{4-[(4S,5R)-4,5-Bis-(4-chloro-phenyl)-2-(2-ethoxy-4-trifluoroprop-1-ynyl-phenyl)-4,5-dihydro-imidazole-1-carbonyl]-piperazin-1-yl}-N-isopropyl-N-methyl-acetamide hydrochloride;

2-(4-{(4S,5R)-4,5-Bis-(4-chloro-phenyl)-2-[2-ethoxy-4-methyl-5-(piperidine-1-sulfonyl)-phenyl]-4,5-dihydro-imidazole-1-carbonyl}-piperazin-1-yl)-N-tert-butyl-acetamide;

2-(4-{(4S,5R)-4,5-Bis-(4-chloro-phenyl)-2-[2-ethoxy-4-methyl-5-(piperidine-1-sulfonyl)-phenyl]-4,5-dihydro-imidazole-1-carbonyl}-piperazin-1-yl)-acetamide;

2-(4-{(4S,5R)-4,5-Bis-(4-chloro-phenyl)-2-[2-ethoxy-4-methyl-5-(piperidine-1-sulfonyl)-phenyl]-4,5-dihydro-imidazole-1-carbonyl}-piperazin-1-yl)-N,N-bis-(2-methoxy-ethyl)-acetamide;

2-(4-{(4S,5R)-4,5-Bis-(4-chloro-phenyl)-2-[2-ethoxy-4-methyl-5-(piperidine-1-sulfonyl)-phenyl]-4,5-dihydro-imidazole-1-carbonyl}-piperazin-1-yl)-N-methoxy-N-methyl-acetamide;

2-(4-{(4S,5R)-4,5-Bis-(4-chloro-phenyl)-2-[2-ethoxy-4-methyl-5-(piperidine-1-sulfonyl)-phenyl]-4,5-dihydro-imidazole-1-carbonyl}-piperazin-1-yl)-N-isopropyl-N-methyl-acetamide;

2-(4-{(4S,5R)-4,5-Bis-(4-chloro-phenyl)-2-[2-ethoxy-4-methyl-5-(piperidine-1-sulfonyl)-phenyl]-4,5-dihydro-imidazole-1-carbonyl}-piperazin-1-yl)-N-(2-cyano-ethyl)-N-methyl-acetamide;

2-(4-{(4S,5R)-4,5-Bis-(4-chloro-phenyl)-2-[2-ethoxy-4-methyl-5-(piperidine-1-sulfonyl)-phenyl]-4,5-dihydro-imidazole-1-carbonyl}-piperazin-1-yl)-N-(2-methoxy-1-methyl-ethyl)-acetamide;

{(4S,5R)-4,5-Bis-(4-chloro-phenyl)-2-[2-ethoxy-4-methyl-5-(piperidine-1-sulfonyl)-phenyl]-4,5-dihydro-imidazol-1-yl}-[4-(3,5-dimethyl-isoxazole-4-carbonyl)-piperazin-1-yl]-methanone;

{(4S,5R)-4,5-Bis-(4-chloro-phenyl)-2-[2-ethoxy-4-methyl-5-(piperidine-1-sulfonyl)-phenyl]-4,5-dihydro-imidazol-1-yl}-(4-ethanesulfonyl-piperazin-1-yl)-methanone;

N-[2-(4{(4S,5R)-4,5-Bis-(4-chloro-phenyl)-2-[2-ethoxy-4-methyl-5-(piperidine-1-sulfonyl)-phenyl]-4,5-dihydro-imidazole-1-carbonyl}-piperazin-1-yl)-ethyl]-methanesulfonamide;

{(4S,5R)-4,5-Bis-(4-chloro-phenyl)-2-[2-ethoxy-4-methyl-5-(piperidine-1-sulfonyl)-phenyl]-4,5-dihydro-imidazol-1-yl}-[4-(3-methanesulfonyl-propyl)-piperazin-1-yl]-methanone;

N-tert-Butyl-2-{4-[(4S,5R)-2-(5-tert-butylsulfamoyl-2-ethoxy-4-methyl-phenyl)-4,5-bis-(4-chloro-phenyl)-4,5-dihydro-imidazole-1-carbonyl]-piperazin-1-yl}-acetamide;

2-{4-[(4S,5R)-2-(5-tert-Butylsulfamoyl-2-ethoxy-4-methyl-phenyl)-4,5-bis-(4-chloro-phenyl)-4,5-dihydro-imidazole-1-carbonyl]-piperazin-1-yl}-acetamide;

2-{4-[(4S,5R)-2-(5-tert-Butylsulfamoyl-2-ethoxy-4-methyl-phenyl)-4,5-bis-(4-chloro-phenyl)-4,5-dihydro-imidazole-1-carbonyl]-piperazin-1-yl}-N,N-bis-(2-methoxy-ethyl)-acetamide;

2-{4-[(4S,5R)-2-(5-tert-Butylsulfamoyl-2-ethoxy-4-methyl-phenyl)-4,5-bis-(4-chloro-phenyl)-4,5-dihydro-imidazole-1-carbonyl]-piperazin-1-yl}-N-methoxy-N-methyl-acetamide;

2-{4-[(4S,5R)-2-(5-tert-Butylsulfamoyl-2-ethoxy-4-methyl-phenyl)-4,5-bis-(4-chloro-phenyl)-4,5-dihydro-imidazole-1-carbonyl]-piperazin-1-yl}-N-isopropyl-N-methyl-acetamide;

2-{4-[(4S,5R)-2-(5-tert-Butylsulfamoyl-2-ethoxy-4-methyl-phenyl)-4,5-bis-(4-chloro-phenyl)-4,5-dihydro-imidazole-1-carbonyl]-piperazin-1-yl}-N-(2-cyano-ethyl)-N-methyl-acetamide;

2-{4-[(4S,5R)-2-(5-tert-Butylsulfamoyl-2-ethoxy-4-methyl-phenyl)-4,5-bis-(4-chloro-phenyl)-4,5-dihydro-imidazole-1-carbonyl]-piperazin-1-yl}-N-(2-methoxy-1-methyl-ethyl)-acetamide;

5-{(4S,5R)-4,5-Bis-(4-chloro-phenyl)-1-[4-(3,5-dimethyl-isoxazole-4-carbonyl)-piperazine-1-carbonyl]-4,5-dihydro-1H-imidazol-2-yl}-N-tert-butyl-4-ethoxy-2-methyl-benzenesulfonamide;

5-[(4S,5R)-4,5-Bis-(4-chloro-phenyl)-1-(4-ethanesulfonyl-piperazine-1-carbonyl)-4,5-dihydro-1H-imidazol-2-yl]-N-tert-butyl-4-ethoxy-2-methyl-benzenesulfonamide;

5-{(4S,5R)-4,5-Bis-(4-chloro-phenyl)-1-[4-(2-methanesulfonylamino-ethyl)-piperazine-1-carbonyl]-4,5-dihydro-1H-imidazol-2-yl}-N-tert-butyl-4-ethoxy-2-methyl-benzenesulfonamide;

5-{(4S,5R)-4,5-Bis-(4-chloro-phenyl)-1-[4-(3-methanesulfonyl-propyl)-piperazine-1-carbonyl]-4,5-dihydro-1H-imidazol-2-yl}-N-tert-butyl-4-ethoxy-2-methyl-benzenesulfonamide;

5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-N-tert-butyl-4-ethoxy-2-methyl-benzenesulfonamide;

5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-N-tert-butyl-4-ethoxy-2-methyl-benzenesulfonamide;

2-(4-{(4S,5R)-4,5-Bis-(4-chloro-phenyl)-2-[2-ethoxy-5-(methoxy-methyl-sulfamoyl)-4-methyl-phenyl]-4,5-dihydro-imidazole-1-carbonyl}-piperazin-1-yl)-N-tert-butyl-acetamide;

2-(4-{(4S,5R)-4,5-Bis-(4-chloro-phenyl)-2-[2-ethoxy-5-(methoxy-methyl-sulfamoyl)-4-methyl-phenyl]-4,5-dihydro-imidazole-1-carbonyl}-piperazin-1-yl)-acetamide;

2-(4-{(4S,5R)-4,5-Bis-(4-chloro-phenyl)-2-[2-ethoxy-5-(methoxy-methyl-sulfamoyl)-4-methyl-phenyl]-4,5-dihydro-imidazole-1-carbonyl}-piperazin-1-yl)-N,N-bis-(2-methoxy-ethyl)-acetamide;

2-(4-{(4S,5R)-4,5-Bis-(4-chloro-phenyl)-2-[2-ethoxy-5-(methoxy-methyl-sulfamoyl)-4-methyl-phenyl]-4,5-dihydro-imidazole-1-carbonyl}-piperazin-1-yl)-N-methoxy-N-methyl-acetamide;

2-(4-{(4S,5R)-4,5-Bis-(4-chloro-phenyl)-2-[2-ethoxy-5-(methoxy-methyl-sulfamoyl)-4-methyl-phenyl]-4,5-dihydro-imidazole-1-carbonyl}-piperazin-1-yl)-N-isopropyl-N-methyl-acetamide;

2-(4-{(4S,5R)-4,5-Bis-(4-chloro-phenyl)-2-[2-ethoxy-5-(methoxy-methyl-sulfamoyl)-4-methyl-phenyl]-4,5-dihydro-imidazole-1-carbonyl}-piperazin-1-yl)-N-(2-methoxy-1-methyl-ethyl)-acetamide;

5-{(4S,5R)-4,5-Bis-(4-chloro-phenyl)-1-[4-(3,5-dimethyl-isoxazole-4-carbonyl)-piperazine-1-carbonyl]-4,5-dihydro-1H-imidazol-2-yl}-4-ethoxy-N-methoxy-2,N-dimethyl-benzenesulfonamide;

5-[(4S,5R)-4,5-Bis-(4-chloro-phenyl)-1-(4-ethanesulfonyl-piperazine-1-carbonyl)-4,5-dihydro-1H-imidazol-2-yl]-4-ethoxy-N-methoxy-2,N-dimethyl-benzenesulfonamide;

5-{(4S,5R)-4,5-Bis-(4-chloro-phenyl)-1-[4-(3-methanesulfonyl-propyl)-piperazine-1-carbonyl]-4,5-dihydro-1H-imidazol-2-yl}-4-ethoxy-N-methoxy-2,N-dimethyl-benzenesulfonamide;

5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-4-ethoxy-N-methoxy-2,N-dimethyl-benzenesulfonamide;

2-(4-{(4S,5R)-4,5-Bis-(4-chloro-phenyl)-2-[2-ethoxy-4-methoxy-5-(piperidine-1-sulfonyl)-phenyl]-4,5-dihydro-imidazole-1-carbonyl}-piperazin-1-yl)-N-tert-butyl-acetamide;

2-(4-{(4S,5R)-4,5-Bis-(4-chloro-phenyl)-2-[2-ethoxy-4-methoxy-5-(piperidine-1-sulfonyl)-phenyl]-4,5-dihydro-imidazole-1-carbonyl}-piperazin-1-yl)-acetamide;

2-(4-{(4S,5R)-4,5-Bis-(4-chloro-phenyl)-2-[2-ethoxy-4-methoxy-5-(piperidine-1-sulfonyl)-phenyl]-4,5-dihydro-imidazole-1-carbonyl}-piperazin-1-yl)-N,N-bis-(2-methoxy-ethyl)-acetamide;

2-(4-{(4S,5R)-4,5-Bis-(4-chloro-phenyl)-2-[2-ethoxy-4-methoxy-5-(piperidine-1-sulfonyl)-phenyl]-4,5-dihydro-imidazole-1-carbonyl}-piperazin-1-yl)-N-methoxy-N-methyl-acetamide;

2-(4-{(4S,5R)-4,5-Bis-(4-chloro-phenyl)-2-[2-ethoxy-4-methoxy-5-(piperidine-1-sulfonyl)-phenyl]-4,5-dihydro-imidazole-1-carbonyl}-piperazin-1-yl)-N-isopropyl-N-methyl-acetamide;

2-(4-{(4S,5R)-4,5-Bis-(4-chloro-phenyl)-2-[2-ethoxy-4-methoxy-5-(piperidine-1-sulfonyl)-phenyl]-4,5-dihydro-imidazole-1-carbonyl}-piperazin-1-yl)-N-(2-cyano-ethyl)-N-methyl-acetamide;

2-(4-{(4S,5R)-4,5-Bis-(4-chloro-phenyl)-2-[2-ethoxy-4-methoxy-5-(piperidine-1-sulfonyl)-phenyl]-4,5-dihydro-imidazole-1-carbonyl}-piperazin-1-yl)-N-(2-methoxy-1-methyl-ethyl)-acetamide;

{(4S,5R)-4,5-Bis-(4-chloro-phenyl)-2-[2-ethoxy-4-methoxy-5-(piperidine-1-sulfonyl)-phenyl]-4,5-dihydro-imidazol-1-yl}-[4-(3,5-dimethyl-isoxazole-4-carbonyl)-piperazin-1-yl]-methanone;

{(4S,5R)-4,5-Bis-(4-chloro-phenyl)-2-[2-ethoxy-4-methoxy-5-(piperidine-1-sulfonyl)-phenyl]-4,5-dihydro-imidazol-1-yl}-(4-ethanesulfonyl-piperazin-1-yl)-methanone;

N-[2-(4-{(4S,5R)-4,5-Bis-(4-chloro-phenyl)-2-[2-ethoxy-4-methoxy-5-(piperidine-1-sulfonyl)-phenyl]-4,5-dihydro-imidazole-1-carbonyl}-piperazin-1-yl)-ethyl]-methanesulfonamide;

{(4S,5R)-4,5-Bis-(4-chloro-phenyl)-2-[2-ethoxy-4-methoxy-5-(piperidine-1-sulfonyl)-phenyl]-4,5-dihydro-imidazol-1-yl}-[4-(3-methanesulfonyl-propyl)-piperazin-1-yl]-methanone;

{(4S,5R)-4,5-Bis-(4-chloro-phenyl)-2-[2-ethoxy-4-methoxy-5-(piperidine-1-sulfonyl)-phenyl]-4,5-dihydro-imidazol-1-yl}-[4-(2-methanesulfonyl-ethyl)-piperazin-1-yl]-methanone;

2-(4-{(4S,5R)-4,5-Bis-(4-chloro-phenyl)-2-[2-ethoxy-4-methoxy-5-(piperidine-1-sulfonyl)-phenyl]-4,5-dihydro-imidazole-1-carbonyl}-piperazin-1-yl)-1-morpholin-4-yl-ethanone;

2-(4-{(4S,5R)-4,5-Bis-(4-chloro-phenyl)-2-[2-ethoxy-4-methoxy-5-(methoxy-methyl-sulfamoyl)-phenyl]-4,5-dihydro-imidazole-1-carbonyl}-piperazin-1-yl)-N-tert-butyl-acetamide;

2-(4-{(4S,5R)-4,5-Bis-(4-chloro-phenyl)-2-[2-ethoxy-4-methoxy-5-(methoxy-methyl-sulfamoyl)-phenyl]-4,5-dihydro-imidazole-1-carbonyl}-piperazin-1-yl)-acetamide;

2-(4-{(4S,5R)-4,5-Bis-(4-chloro-phenyl)-2-[2-ethoxy-4-methoxy-5-(methoxy-methyl-sulfamoyl)-phenyl]-4,5-dihydro-imidazole-1-carbonyl}-piperazin-1-yl)-N,N-bis-(2-methoxy-ethyl)-acetamide;

2-(4-{(4S,5R)-4,5-Bis-(4-chloro-phenyl)-2-[2-ethoxy-4-methoxy-5-(methoxy-methyl-sulfamoyl)-phenyl]-4,5-dihydro-imidazole-1-carbonyl}-piperazin-1-yl)-N-methoxy-N-methyl-acetamide;

2-(4-{(4S,5R)-4,5-Bis-(4-chloro-phenyl)-2-[2-ethoxy-4-methoxy-5-(methoxy-methyl-sulfamoyl)-phenyl]-4,5-dihydro-imidazole-1-carbonyl}-piperazin-1-yl)-N-isopropyl-N-methyl-acetamide;

2-(4-{(4S,5R)-4,5-Bis-(4-chloro-phenyl)-2-[2-ethoxy-4-methoxy-5-(methoxy-methyl-sulfamoyl)-phenyl]-4,5-dihydro-imidazole-1-carbonyl}-piperazin-1-yl)-N-(2-cyano-ethyl)-N-methyl-acetamide;

2-(4-{(4S,5R)-4,5-Bis-(4-chloro-phenyl)-2-[2-ethoxy-4-methoxy-5-(methoxy-methyl-sulfamoyl)-phenyl]-4,5-dihydro-imidazole-1-carbonyl}-piperazin-1-yl)-N-(2-methoxy-1-methyl-ethyl)-acetamide;

5-{(4S,5R)-4,5-Bis-(4-chloro-phenyl)-1-[4-(3,5-dimethyl-isoxazole-4-carbonyl)-piperazine-1-carbonyl]-4,5-dihydro-1H-imidazol-2-yl}-4-ethoxy-2,N-dimethoxy-N-methyl-benzenesulfonamide;

5-[(4S,5R)-4,5-Bis-(4-chloro-phenyl)-1-(4-ethanesulfonyl-piperazine-1-carbonyl)-4,5-dihydro-1H-imidazol-2-yl]-4-ethoxy-2,N-dimethoxy-N-methyl-benzenesulfonamide;

5-{(4S,5R)-4,5-Bis-(4-chloro-phenyl)-1-[4-(2-methanesulfonylamino-ethyl)-piperazine-1-carbonyl]-4,5-dihydro-1H-imidazol-2-yl}-4-ethoxy-2,N-dimethoxy-N-methyl-benzenesulfonamide;

5-{(4S,5R)-4,5-Bis-(4-chloro-phenyl)-1-[4-(3-methane-sulfonyl-propyl)-piperazine-1-carbonyl]-4,5-dihydro-1H-imidazol-2-yl}-4-ethoxy-2,N-dimethoxy-N-methyl-benzenesulfonamide;

5-{(4S,5R)-4,5-Bis-(4-chloro-phenyl)-1-[4-(2-methane-sulfonyl-ethyl)-piperazine-1-carbonyl]-4,5-dihydro-1H-imidazol-2-yl}-4-ethoxy-2,N-dimethoxy-N-methyl-benzenesulfonamide;

5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-4-ethoxy-2,N-dimethoxy-N-methyl-benzenesulfonamide;

4-[(4S,5R)-2-(4-Acetyl-2-ethoxy-phenyl)-4,5-bis-(4-chloro-phenyl)-4,5-dihydro-imidazole-1-carbonyl]-piperazin-2-one;

1-(4-{(4S,5R)-4,5-Bis-(4-chloro-phenyl)-1-[4-(2-methane-sulfonyl-ethyl)-piperazine-1-carbonyl]-4,5-dihydro-1H-imidazol-2-yl}-3-ethoxy-phenyl)-ethanone hydrochloride;

2-{4-[(4S,5R)-2-(4-Acetyl-2-ethoxy-phenyl)-4,5-bis-(4-chloro-phenyl)-4,5-dihydro-imidazole-1-carbonyl]-piperazin-1-yl}-1-morpholin-4-yl-ethanone hydrochloride;

1-(4-{(4S,5R)-4,5-Bis-(4-chloro-phenyl)-1-[4-(3-methane-sulfonyl-propyl)-piperazine-1-carbonyl]-4,5-dihydro-1H-imidazol-2-yl}-3-ethoxy-phenyl)-ethanone hydrochloride;

[(4S,5R)-4,5-Bis-(4-chloro-phenyl)-2-(2-ethoxy-4-trifluoroprop-1-ynyl-phenyl)-4,5-dihydro-imidazol-1-yl]-[4-(3-methanesulfonyl-propyl)-piperazin-1-yl]-methanone hydrochloride;

N-tert-Butyl-2-{4-[(4S,5R)-2-(5-tert-butylsulfamoyl-2-ethoxy-phenyl)-4,5-bis-(4-chloro-phenyl)-4,5-dihydro-imidazole-1-carbonyl]-piperazin-1-yl}-acetamide;

2-{4-[(4S,5R)-2-(5-tert-Butylsulfamoyl-2-ethoxy-phenyl)-4,5-bis-(4-chloro-phenyl)-4,5-dihydro-imidazole-1-carbonyl]-piperazin-1-yl}-acetamide;

2-{4-[(4S,5R)-2-(5-tert-Butylsulfamoyl-2-ethoxy-phenyl)-4,5-bis-(4-chloro-phenyl)-4,5-dihydro-imidazole-1-carbonyl]-piperazin-1-yl}-N,N-bis-(2-methoxy-ethyl)-acetamide;

2-{4-[(4S,5R)-2-(5-tert-Butylsulfamoyl-2-ethoxy-phenyl)-4,5-bis-(4-chloro-phenyl)-4,5-dihydro-imidazole-1-carbonyl]-piperazin-1-yl}-N-methoxy-N-methyl-acetamide;

2-{4-[(4S,5R)-2-(5-tert-Butylsulfamoyl-2-ethoxy-phenyl)-4,5-bis-(4-chloro-phenyl)-4,5-dihydro-imidazole-1-carbonyl]-piperazin-1-yl}-N-isopropyl-N-methyl-acetamide;

2-{4-[(4S,5R)-2-(5-tert-Butylsulfamoyl-2-ethoxy-phenyl)-4,5-bis-(4-chloro-phenyl)-4,5-dihydro-imidazole-1-carbonyl]-piperazin-1-yl}-N-(2-cyano-ethyl)-N-methyl-acetamide;

2-{4-[(4S,5R)-2-(5-tert-Butylsulfamoyl-2-ethoxy-phenyl)-4,5-bis-(4-chloro-phenyl)-4,5-dihydro-imidazole-1-carbonyl]-piperazin-1-yl}-N-(2-methoxy-1-methyl-ethyl)-acetamide;

3-{(4S,5R)-4,5-Bis-(4-chloro-phenyl)-1-[4-(3,5-dimethyl-isoxazole-4-carbonyl)-piperazine-1-carbonyl]-4,5-dihydro-1H-imidazol-2-yl}-N-tert-butyl-4-ethoxy-benzenesulfonamide;

3-[(4S,5R)-4,5-Bis-(4-chloro-phenyl)-1-(4-ethanesulfonyl-piperazine-1-carbonyl)-4,5-dihydro-1H-imidazol-2-yl]-N-tert-butyl-4-ethoxy-benzenesulfonamide;

3-{(4S,5R)-4,5-Bis-(4-chloro-phenyl)-1-[4-(2-methane-sulfonylamino-ethyl)-piperazine-1-carbonyl]-4,5-dihydro-1H-imidazol-2-yl}-N-tert-butyl-4-ethoxy-benzenesulfonamide;

3-{(4S,5R)-4,5-Bis-(4-chloro-phenyl)-1-[4-(3-methane-sulfonyl-propyl)-piperazine-1-carbonyl]-4,5-dihydro-1H-imidazol-2-yl}-N-tert-butyl-4-ethoxy-benzenesulfonamide;

3-{(4S,5R)-4,5-Bis-(4-chloro-phenyl)-1-[4-(2-methane-sulfonyl-ethyl)-piperazine-1-carbonyl]-4,5-dihydro-1H-imidazol-2-yl}-N-tert-butyl-4-ethoxy-benzenesulfonamide;

3-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-N-tert-butyl-4-ethoxy-benzenesulfonamide;

2-(4-{(4S,5R)-4,5-Bis-(4-chloro-phenyl)-2-[2-ethoxy-5-(piperidine-1-sulfonyl)-phenyl]-4,5-dihydro-imidazole-1-carbonyl}-piperazin-1-yl)-N-tert-butyl-acetamide;

2-(4{(4S,5R)-4,5-Bis-(4-chloro-phenyl)-2-[2-ethoxy-5-(piperidine-1-sulfonyl)-phenyl]-4,5-dihydro-imidazole-1-carbonyl}-piperazin-1-yl)-acetamide;

2-(4{(4S,5R)-4,5-Bis-(4-chloro-phenyl)-2-[2-ethoxy-5-(piperidine-1-sulfonyl)-phenyl]-4,5-dihydro-imidazole-1-carbonyl}piperazin-1-yl)-N,N-bis-(2-methoxy-ethyl)-acetamide;

2-(4-{(4S,5R)-4,5-Bis-(4-chloro-phenyl)-2-[2-ethoxy-5-(piperidine-1-sulfonyl)-phenyl]-4,5-dihydro-imidazole-1-carbonyl}-piperazin-1-yl)-N-methoxy-N-methyl-acetamide;

2-(4-{(4S,5R)-4,5-Bis-(4-chloro-phenyl)-2-[2-ethoxy-5-(piperidine-1-sulfonyl)-phenyl]-4,5-dihydro-imidazole-1-carbonyl}-piperazin-1-yl)-N-isopropyl-N-methyl-acetamide;

2-(4-{(4S,5R)-4,5-Bis-(4-chloro-phenyl)-2-[2-ethoxy-5-(piperidine-1-sulfonyl)-phenyl]-4,5-dihydro-imidazole-1-carbonyl}-piperazin-1-yl)-N-(2-cyano-ethyl)-N-methyl-acetamide;

2-(4-{(4S,5R)-4,5-Bis-(4-chloro-phenyl)-2-[2-ethoxy-5-(piperidine-1-sulfonyl)-phenyl]-4,5-dihydro-imidazole-1-carbonyl}-piperazin-1-yl)-N-(2-methoxy-1-methyl-ethyl)-acetamide;

{(4S,5R)-4,5-Bis-(4-chloro-phenyl)-2-[2-ethoxy-5-(piperidine-1-sulfonyl)-phenyl]-4,5-dihydro-imidazol-1-yl}-[4-(3,5-dimethyl-isoxazole-4-carbonyl)-piperazin-1-yl]-methanone;

{(4S,5R)-4,5-Bis-(4-chloro-phenyl)-2-[2-ethoxy-5-(piperidine-1-sulfonyl)-phenyl]-4,5-dihydro-imidazol-1-yl}-(4-ethanesulfonyl-piperazin-1-yl)-methanone;

N-[2-(4-{(4S,5R)-4,5-Bis-(4-chloro-phenyl)-2-[2-ethoxy-5-(piperidine-1-sulfonyl)-phenyl]-4,5-dihydro-imidazole-1-carbonyl}-piperazin-1-yl)-ethyl]-methanesulfonamide;

{(4S,5R)-4,5-Bis-(4-chloro-phenyl)-2-[2-ethoxy-5-(piperidine-1-sulfonyl)-phenyl]-4,5-dihydro-imidazol-1-yl}-[4-(3-methanesulfonyl-propyl)-piperazin-1-yl]-methanone;

{(4S,5R)-4,5-Bis-(4-chloro-phenyl)-2-[2-ethoxy-5-(piperidine-1-sulfonyl)-phenyl]-4,5-dihydro-imidazol-1-yl}-[4-(2-methanesulfonyl-ethyl)-piperazin-1-yl]-methanone;

2-(4{(4S,5R)-4,5-Bis-(4-chloro-phenyl)-2-[2-ethoxy-5-(piperidine-1-sulfonyl)-phenyl]-4,5-dihydro-imidazole-1-carbonyl}-piperazin-1-yl)-1-morpholin-4-yl-ethanone;

2-(4-{(4S,5R)-4,5-Bis-(4-chloro-phenyl)-2-[2-ethoxy-5-(methoxy-methyl-sulfamoyl)-phenyl]-4,5-dihydro-imidazole-1-carbonyl}-piperazin-1-yl)-N-tert-butyl-acetamide;

2-(4-{(4S,5R)-4,5-Bis-(4-chloro-phenyl)-2-[2-ethoxy-5-(methoxy-methyl-sulfamoyl)-phenyl]-4,5-dihydro-imidazole-1-carbonyl}-piperazin-1-yl)-acetamide;

2-(4-{(4S,5R)-4,5-Bis-(4-chloro-phenyl)-2-[2-ethoxy-5-(methoxy-methyl-sulfamoyl)-phenyl]-4,5-dihydro-imidazole-1-carbonyl}-piperazin-1-yl)-N,N-bis-(2-methoxy-ethyl)-acetamide;

2-(4-{(4S,5R)-4,5-Bis-(4-chloro-phenyl)-2-[2-ethoxy-5-(methoxy-methyl-sulfamoyl)-phenyl]-4,5-dihydro-imidazole-1-carbonyl}-piperazin-1-yl)-N-methoxy-N-methyl-acetamide;

2-(4-{(4S,5R)-4,5-Bis-(4-chloro-phenyl)-2-[2-ethoxy-5-(methoxy-methyl-sulfamoyl)-phenyl]-4,5-dihydro-imidazole-1-carbonyl}-piperazin-1-yl)-N-isopropyl-N-methyl-acetamide;

2-(4-{(4S,5R)-4,5-Bis-(4-chloro-phenyl)-2-[2-ethoxy-5-(methoxy-methyl-sulfamoyl)-phenyl]-4,5-dihydro-imidazole-1-carbonyl}-piperazin-1-yl)-N-(2-cyano-ethyl)-N-methyl-acetamide;

2-(4-{(4S,5R)-4,5-Bis-(4-chloro-phenyl)-2-[2-ethoxy-5-(methoxy-methyl-sulfamoyl)-phenyl]-4,5-dihydro-imidazole-1-carbonyl}-piperazin-1-yl)-N-(2-methoxy-1-methyl-ethyl)-acetamide;

3-{(4S,5R)-4,5-Bis-(4-chloro-phenyl)-1-[4-(3,5-dimethyl-isoxazole-4-carbonyl)-piperazine-1-carbonyl]-4,5-dihydro-1H-imidazol-2-yl}-4-ethoxy-N-methoxy-N-methyl-benzenesulfonamide;

3-[(4S,5R)-4,5-Bis-(4-chloro-phenyl)-1-(4-ethanesulfonyl-piperazine-1-carbonyl)-4,5-dihydro-1H-imidazol-2-yl]-4-ethoxy-N-methoxy-N-methyl-benzenesulfonamide;

3-{(4S,5R)-4,5-Bis-(4-chloro-phenyl)-1-[4-(2-methanesulfonylamino-ethyl)-piperazine-1-carbonyl]-4,5-dihydro-1H-imidazol-2-yl}-4-ethoxy-N-methoxy-N-methyl-benzenesulfonamide;

3-{(4S,5R)-4,5-Bis-(4-chloro-phenyl)-1-[4-(3-methanesulfonyl-propyl)-piperazine-1-carbonyl]-4,5-dihydro-1H-imidazol-2-yl}-4-ethoxy-N-methoxy-N-methyl-benzenesulfonamide;

3-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-4-ethoxy-N-methoxy-N-methyl-benzenesulfonamide;

3-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-4-ethoxy-N-methoxy-N-methyl-benzenesulfonamide;

{(4S,5R)-4,5-Bis-(4-chloro-phenyl)-2-[4-(3,3-dimethyl-but-1-ynyl)-2-ethoxy-phenyl]-4,5-dihydro-imidazol-1-yl}-[4-(2-methanesulfonyl-ethyl)-piperazin-1-yl]-methanone hydrochloride;

2-(4-{(4S,5R)-4,5-Bis-(4-chloro-phenyl)-2-[4-(3,3-dimethyl-but-1-ynyl)-2-ethoxy-phenyl]-4,5-dihydro-imidazole-1-carbonyl}-piperazin-1-yl)-1-morpholin-4-yl-ethanone hydrochloride;

2-{4-[(4S,5R)-2-(5-tert-Butylsulfamoyl-2-ethoxy-4-methoxy-phenyl)-4,5-bis-(4-chloro-phenyl)-4,5-dihydro-imidazole-1-carbonyl]-piperazin-1-yl}-acetamide;

N-tert-Butyl-2-{4-[(4S,5R)-2-(5-tert-butylsulfamoyl-2-ethoxy-4-methoxy-phenyl)-4,5-bis-(4-chloro-phenyl)-4,5-dihydro-imidazole-1-carbonyl]-piperazin-1-yl}-acetamide;

2-{4-[(4S,5R)-2-(5-tert-Butylsulfamoyl-2-ethoxy-4-methoxy-phenyl)-4,5-bis-(4-chloro-phenyl)-4,5-dihydro-imidazole-1-carbonyl]-piperazin-1-yl}-N-methoxy-N-methyl-acetamide;

2-{4-[(4S,5R)-2-(5-tert-Butylsulfamoyl-2-ethoxy-4-methoxy-phenyl)-4,5-bis-(4-chloro-phenyl)-4,5-dihydro-imidazole-1-carbonyl]-piperazin-1-yl}-N-isopropyl-N-methyl-acetamide;

5-{(4S,5R)-4,5-Bis-(4-chloro-phenyl)-1-[4-(3-methanesulfonyl-propyl)-piperazine-1-carbonyl]-4,5-dihydro-1H-imidazol-2-yl}-N-tert-butyl-4-ethoxy-2-methoxy-benzenesulfonamide and 5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-N-tert-butyl-4-ethoxy-2-methoxy-benzenesulfonamide.

"Effective amount" means an amount that is effective to prevent, alleviate or ameliorate symptoms of disease or prolong the survival of the subject being treated.

"Halogen" means fluorine, chlorine, bromine or iodine.

"Hetero atom" means an atom selected from N, O and S.

"$IC_{50}$" refers to the concentration of a particular compound required to inhibit 50% of a specific measured activity. $IC_{50}$ can be measured, inter alia, as is described subsequently.

"Alkyl" denotes a straight-chained or branched saturated aliphatic hydrocarbon.

"Lower alkyl" groups denote C1-C6 alkyl groups and include methyl, ethyl, propyl, isopropyl, butyl, t-butyl, 2-butyl, pentyl, hexyl, and the like. Generally, lower alkyl is preferably C1-C4 alkyl, and more preferably C1-C3 alkyl.

As used herein, "cycloalkyl" is intended to refer to any stable monocyclic or polycyclic system which consists of carbon atoms only, any ring of which being saturated. Examples of cycloalkyls include, but are not limited to, cyclopropyl, cyclobutyl, cyclopentyl, cyclohexyl, cycloheptyl, adamantyl, cyclooctyl, bicycloalkyls, including bicyclooctanes such as [2.2.2]bicyclooctane or [3.3.0]bicyclooctane, bicyclononanes such as [4.3.0]bicyclononane, and bicyclodecanes such as [4.4.0]bicyclodecane (decalin), or spiro compounds.

"Alkoxy" denotes —O-alkyl. "Lower alkoxy" denotes —O-lower alkyl.

"Pharmaceutically acceptable ester" refers to a conventionally esterified compound of formula I having a carboxyl group, which esters retain the biological effectiveness and properties of the compounds of formula I and are cleaved in vivo (in the organism) to the corresponding active carboxylic acid.

Information concerning esters and the use of esters for the delivery of pharmaceutical compounds is available in Design of Prodrugs. Bundgaard H ed. (Elsevier, 1985). See also, H. Ansel et. al., Pharmaceutical Dosage Forms and Drug Delivery Systems (6th Ed. 1995) at pp. 108-109; Krogsgaard-Larsen, et. al., Textbook of Drug Design and Development (2d Ed. 1996) at pp. 152-191.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp. 196 and 1456-1457.

"Pharmaceutically acceptable," such as pharmaceutically acceptable carrier, excipient, etc., means pharmacologically acceptable and substantially non-toxic to the subject to which the particular compound is administered.

"Substituted" means that the substitution can occur at one or more positions and, unless otherwise indicated, that the substituents at each substitution site are independently selected from the specified options.

"Therapeutically effective amount" means an amount of at least one designated compound, that significantly inhibits proliferation and/or prevents differentiation of a human tumor cell, including human tumor cell lines.

Compounds of the present invention as exemplified advantageously show IC50s from about 0.005 uM to about 1 uM.

The compounds of the present invention are useful in the treatment or control of cell proliferative disorders, in particular oncological disorders. These compounds and formulations containing said compounds may be useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

The present invention also provides pharmaceutical compositions comprising at least one compound of formula I, or a pharmaceutically acceptable salt or ester thereof, and a pharmaceutically acceptable carrier or excipient.

The compounds of the present invention can be prepared according to the following scheme 1.

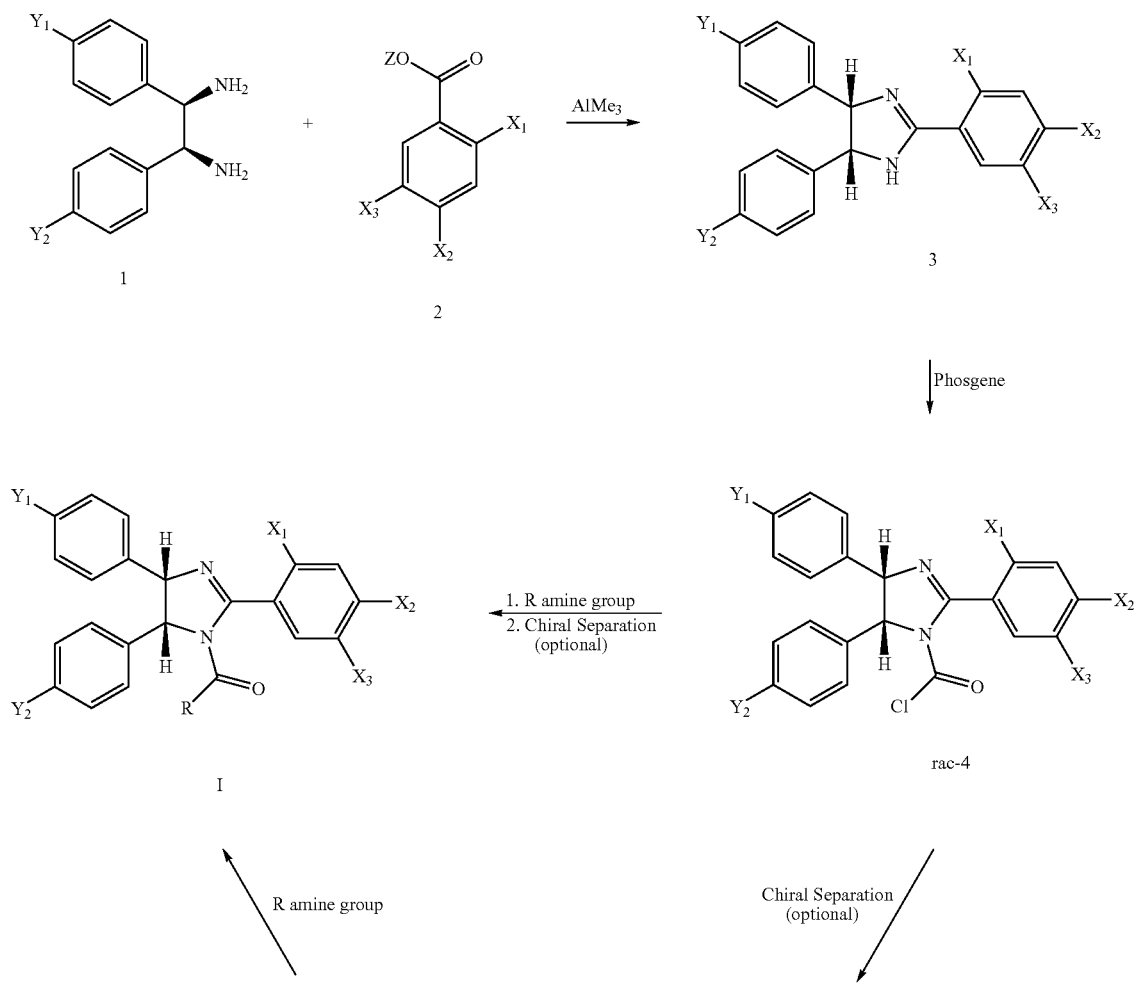

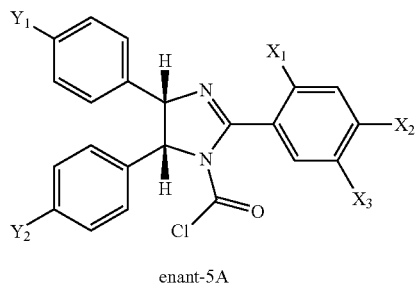

enant-5A

+

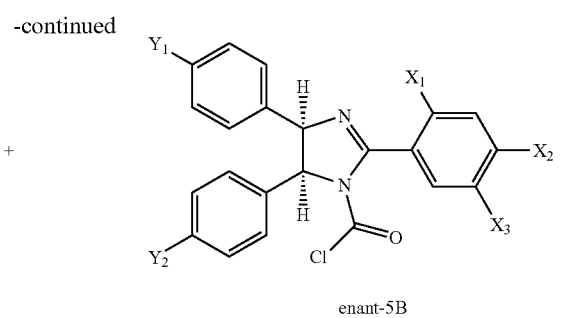

enant-5B

The synthesis commences with the coupling reaction of the benzoic acid ester 2 (Z=methyl, ethyl, etc.) with meso-1,2-bis-(4-chlorophenyl)-ethane-1,2-diamine 1 (prepared according to the procedure described by Jennerwein, M. et al. *Cancer Res. Clin. Oncol.* 1988, 114, 347-58; Vogtle, F.; Goldschmitt, E. *Chem. Ber.* 1976, 109, 1-40) using trimethylaluminum as a catalyst in a solvent such as toluene with heating at reflux (Moormann, A. E. et al *J. Med. Chem.* 1990, 33, 614-626). Benzoic acid esters 2 are prepared using the procedures known in the art. Treatment of the imidazoline 3 with phosgene in the presence of a base such as triethylamine gives the racemic carbamoyl chloride 4. Coupling of the racemic carbamoyl chloride 4 with appropriate R amine groups provides the compounds of the formula I as racemic mixtures. Many R amine groups are commercially available. If it is desired, R amine groups can be prepared using synthetic methods known in the art. Suitable processes for making these R amine groups are provided in the examples.

If it is desired to prepare the optically active compounds of formula I, the enantiomers of the carbamoyl chloride rac-4 can be separated using chiral chromatography. The chiral stationary phase R,R-Whelk-O1, available through Regis Technologies, can be used. Coupling of the desired enantiomer 5A with appropriate R amine groups provides the compounds of the formula I.

Also the optically active compounds of formula I can be obtained by chiral separation of the racemic mixtures of I. The chiral stationary phase Diacel ChiralPak OD or AD can be used.

The absolute stereochemistry of the preferred enantiomer of I is determined based on the crystal structure of its complex with the human MDM2 (Vassilev et al. Science, 2004, 303, 844-848.

The following examples and references are provided to aid the understanding of the present invention, the true scope of which is set forth in the appended claims.

EXAMPLE 1

Methyl 4-cyano-2-ethoxybenzoate

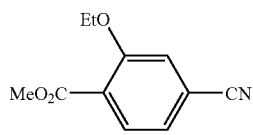

Iron (16.19 g, 290 mmol) was added to a slurry mixture of 2-ethoxy-4-nitrobenzoic acid (24.00 g, 114 mmol) in ethanol (200 mL) and saturated aqueous solution of ammonium chloride (120 mL). The mixture was stirred at 80° C. for 2 h. The reaction mixture was cooled to room temperature and filtered through Celite. It was rinsed with methylene chloride and the combined filtrate diluted with water and extracted with methylene chloride and dried over anhydrous sodium sulfate. Evaporation of the solvent and chromatography of the brown residue over silica gel using 1-5% methanol in methylene chloride produced 4-amino-2-ethoxybenzoic acid as a yellow solid (14.94 g, 73%).

To a cooled solution of 4-amino-2-ethoxybenzoic acid (500 mg, 2.76 mmol) in 2 M hydrochloric acid (1.0 mL) was added a solution of sodium nitrite (192 mg, 2.8 mmol) in water (0.55 mL). The mixture was stirred for 15 min and neutralized by adding small amounts of solid sodium bicarbonate. This solution was then added to a freshly prepared solution of copper(I) cyanide at 0° C. (prepared from sodium cyanide and copper(I) chloride according to *Org. Syn. Coll. Vol VI*, p. 514) in water (7.5 mL) and benzene (2.5 mL). The reaction was allowed to warm up to room temperature and stirred for 2 h. The mixture was filtered through Celite and the filtrate extracted with ethyl acetate. The aqueous phase was acidified with 2 M hydrochloric acid and extracted with ethyl acetate. The combined organic extracts were washed with brine, dried over anhydrous sodium sulfate and concentrated to give 4-cyano-2-ethoxybenzoic acid as a light brown solid (280 mg, 53%), which was used in the next step without further purification.

(Trimethylsilyl)diazomethane (2 M in hexanes, 1.47 mL, 2.93 mmol) was added to a solution of 4-cyano-2-ethoxybenzoic acid (280 mg, 1.47 mmol) in benzene (8.0 mL) and methanol (1.6 mL). The reaction was stirred for 1 h and then degassed with air for 30 min. Evaporation of the solvent and purification of the crude residue by flash column chromatography (silica gel, eluting with 0-20% ethyl acetate in hexanes) gave methyl 4-cyano-2-ethoxybenzoate as a yellow solid (218 mg, 71%).

EXAMPLE 2

Ethyl 2-ethoxy-5-(N,N-dimethylsulfonamide)benzoate

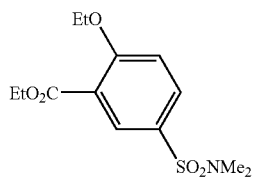

To a cooled solution of chlorosulfonic acid (12.0 mL) and thionyl chloride (3.4 mL) was added ethyl 2-ethoxybenzoate (10.7 g, 59.0 mmol) dropwise over 30 min. The reaction was stirred overnight at room temperature and carefully added to ice (300 g). The resulting white solid was filtered, washed with water and dried in vacuo overnight to give ethyl 2-ethoxy-5-(chlorosulfonyl) benzoate as a white solid (9.5 g, 59%).

To a cooled solution of ethyl 2-ethoxy-5-(chlorosulfonyl) benzoate (480 mg, 1.6 mmol) in methylene chloride (5.0 mL) was added triethylamine (0.35 mL, 2.5 mmol) and dimethylamine (2 M in tetrahydrofuran, 4.5 mL, 9.0 mmol). The reaction was stirred at room temperature for 2 h and concentrated. Purification of the crude residue by flash column chromatography (silica gel, eluting with 20-50% ethyl acetate in hexanes) gave ethyl 2-ethoxy-5-(N,N-dimethylsulfonamide) benzoate as a off-white solid (210 mg, 43%

In an analogous manner, there were obtained:
ethyl 2-ethoxy-4-methoxy-5-(piperidine-1-sulfonyl)-benzoate
ethyl 2-ethoxy-4-methyl-5-(piperidine-1-sulfonyl)-benzoate
ethyl 2-ethoxy-4-methyl-5-(pyrrolidine-1-sulfonyl)-benzoate
ethyl 2-ethoxy-5-(2-methoxy-1-methyl-ethylsulfamoyl)-benzoate
ethyl 2-ethoxy-5-(isobutyl-methyl-sulfamoyl)-benzoate
ethyl 2-ethoxy-5-(methoxy-methyl-sulfamoyl)-4-methyl-benzoate
ethyl 2-ethoxy-5-(methoxy-methyl-sulfamoyl)-benzoate
ethyl 2-ethoxy-5-(piperidine-1-sulfonyl)-benzoate
ethyl 2-ethoxy-5-(pyrrolidine-1-sulfonyl)-benzoate
ethyl 2-ethoxy-5-isopropylsulfamoyl-4-methyl-benzoate
ethyl 2-ethoxy-5-methylsulfamoyl-4-methyl-benzoate
ethyl 4-chloro-2-ethoxy-5-(morpholine-4-sulfonyl)-benzoate
ethyl 4-chloro-2-ethoxy-5-(piperidine-1-sulfonyl)-benzoate
ethyl 4-chloro-2-ethoxy-5-(pyrrolidine-1-sulfonyl)-benzoate
ethyl 4-chloro-2-ethoxy-5-isopropylsulfamoyl-benzoate
ethyl 4-chloro-2-ethoxy-5-methylsulfamoyl-benzoate
ethyl 4-chloro-5-dimethylsulfamoyl-2-ethoxy-benzoate
ethyl 5-[bis-(2-methoxy-ethyl)-sulfamoyl]-2-ethoxy-benzoate
ethyl 5-dimethylsulfamoyl-2-ethoxy-4-fluoro-benzoate
ethyl 5-dimethylsulfamoyl-2-ethoxy-4-methoxy-benzoate
ethyl 5-tert-butylsulfamoyl-2-ethoxy-4-methoxy-benzoate
ethyl 5-tert-butylsulfamoyl-2-ethoxy-4-methyl-benzoate
ethyl 5-tert-butylsulfamoyl-2-ethoxy-benzoate
ethyl 5-tert-butylsulfamoyl-4-chloro-2-ethoxy-benzoate
ethyl 2-ethoxy-4-methyl-5-(morpholine-4-sulfonyl)-benzoate.

EXAMPLE 3

8-carboethoxy-7-ethoxy-2-methyl-1,1-dioxo-1,2,3,4-tetrahydro-benzo[1,6-b][1,4,5]oxathiazepine

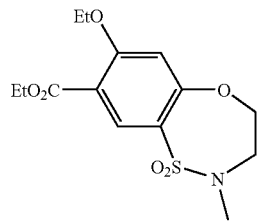

To a cooled solution of ethyl 4-fluoro-2-ethoxy-5-(chlorosulfonyl)benzoate (1.0 g, 3.2 mmol, example 2) in methylene chloride (25 mL) was added 2-(methylamine)ethanol (0.75 mL, 10.6 mmol). The reaction was stirred at room temperature for 1 h and concentrated. Purification of the crude residue by flash column chromatography (silica gel, eluting with 30-70% ethyl acetate in hexanes) gave ethyl 4-fluoro-2-ethoxy-5-(N-methyl-N-(2-hydroxyethyl)sulfonamide)benzoate (0.76 g, 64%).

Sodium hydride (89 mg, 2.2 mmol, 60% in mineral oil) was added to a solution of 4-fluoro-2-ethoxy-5-(N-methyl-N-(2-hydroxyethyl)sulfonamide)benzoate (520 mg, 1.5 mmol) in dimethylformamide (8.0 mL) at 0° C. The reaction was stirred at 0° C. for 1 h. The reaction mixture was quenched with a dilute aqueous solution of ammonium chloride and extracted with diethyl ether. The organic extracts were washed with brine, dried over anhydrous sodium sulfate and concentrated. Purification of the crude residue by flash column chromatography (silica gel, eluting with 25-50% ethyl acetate in hexanes) gave 8-carboethoxy-7-ethoxy-2-methyl-1,1-dioxo-1,2,3,4-tetrahydro-benzo[1,6-b][1,4,5]oxathiazepine as a white solid (430 mg, 88%).

EXAMPLE 4

2-Ethoxy-5-(piperidine-1-carbonyl)-benzoic acid ethyl ester

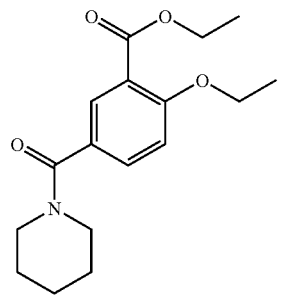

To a stirring solution of 2-ethoxy-5-formyl-benzoic acid ethyl ester (1.0 g, 4.5 mmol) in 10 mL of dimethylformamide was added dropwise sulfamic acid (610.4 mg, 6.3 mmol) in 5 mL of water. After addition of sulfamic acid, sodium chlorite (737.2 mg, 8.2 mmol) in 5 mL of water was added dropwise. Reaction was allowed to stir for 2 h at room temperature. Reaction was diluted with brine and extracted with ethyl acetate. Organic extract was dried with anhydrous magnesium sulfate, filtered and concentrated in vacuo to give 4-ethoxy isopthalic acid 3-ethyl ester as a white solid (900 mg, 84%). LC-MS: 239.2 [(M+H)$^+$].

To a solution of 4-ethoxy isopthalic acid 3-ethyl ester (600 mg, 2.5 mmol) in 10 mL of acetonitrile was added piperidine (429 mg, 5.0 mmol). The resulting mixture was cooled to 0° C. To this solution was added HBTU (1.4 g, 3.78 mmol, in 5 mL of acetonitrile) followed by N,N-diisopropylethylamine (2.2 mL, 12.6 mmol). The reaction was allowed to stir overnight at room temperature. The reaction mixture was concentrated in vacuo. The residue was diluted with 10% potassium carbonate and extracted with methylene chloride. The organic extract was concentrated and purification of the crude residue by flash column chromatography (silica gel, eluting with a gradient of ethyl acetate in hexanes) gave 632 mg (2.07 mmol, 82%) of pure 2-ethoxy-5-(piperidine-1-carbonyl)-benzoic acid ethyl ester. LC-MS: 306.3 [(M+H)$^+$].

In an analogous manner, there were obtained:
6-ethoxy-N,N-dimethyl-isophthalamic acid ethyl ester
2-ethoxy-5-(pyrrolidine-1-carbonyl)-benzoic acid ethyl ester
2-ethoxy-4-(piperidine-1-carbonyl)-benzoic acid ethyl ester.

EXAMPLE 5

4-Chloro-5-cyano-2-ethoxy-benzoic acid ethyl ester

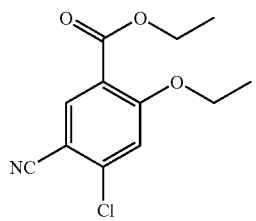

To a solution of 4-chloro-2-ethoxy-benzoic acid ethyl ester (1.46 g, 6.4 mmol) in 13 mL of water and methylene chloride (1:1 mixture) was added bromine (360 uL, 7 mmol). The reaction was stirred for three days. The organic layer was separated. It was washed with brine, dried over anhydrous magnesium sulfate, and concentrated in vacuo. Purification of the crude residue by flash column chromatography (silica gel, eluting with a gradient of ethyl acetate in hexanes) gave 5-bromo-4-chloro-2-ethoxy-benzoic acid ethyl ester (1.26 g, 64%). LC-MS: 307.1 [(M+H)$^+$].

To a solution of 5-bromo-4-chloro-2-ethoxy-benzoic acid ethyl ester (940 mg, 3.0 mmol) in 20 mL of dimethylformamide was added copper(I) cyanide (327 mg, 3.65 mmol). The reaction was stirred at reflux overnight. The reaction was diluted with methylene chloride. It was washed twice with brine, dried over anhydrous magnesium sulfate and concentrated in vacuo. Purification of the crude residue by flash column chromatography (silica gel, eluting with a gradient of ethyl acetate in hexanes) gave 4-chloro-5-cyano-2-ethoxy-benzoic acid ethyl ester (359 mg, 47%). LC-MS: 254.1 [(M+H)$^+$].

EXAMPLE 6

5-Cyano-4-dimethylamino-2-ethoxy-benzoic acid methyl ester

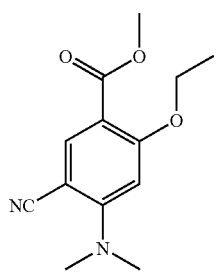

To a solution of 5-bromo-4-ethoxy-2-fluoro-benzonitrile (2 g, 8.2 mmol) in 16.5 mL of dioxane was added dimethylamine (16.5 mL, 33 mmol, 2.0 M in tetrahydrofuran). The reaction was stirred at 80° C. overnight. The reaction mixture was concentrated in vacuo. Purification of the crude residue by flash column chromatography (silica gel, eluting with a gradient of ethyl acetate in hexanes) gave 5-bromo-2-dimethylamino-4-ethoxy-benzonitrile (1.95 g, 88%). LC-MS: 269.2 [(M+H)$^+$].

To a solution of 5-bromo-2-dimethylamino-4-ethoxy-benzonitrile (1.95 g, 7.3 mmol) in 7.25 mL of dioxane was added sodium methoxide (581 mg, 10.77 mmol), methyl formate (1.85 mL, 30 mmol), and trans-dichlorobis(triphenylphosphine) palladium(II) (281 mg, 0.4 mmol). The mixture was agitated by bubbling nitrogen gas through the solution. To the opening of the vial is affixed a balloon. The reaction was cautiously warmed to 60° C. as gas evolution can cause a froth to enter the balloon. The reaction mixture was stirred for 20 h at 65° C. It was diluted with dioxane and stirred for an additional 5 min. The warm solution was filtered through Celite, and the filtrate was concentrated in vacuo. Purification of the crude residue by flash column chromatography (silica gel, eluting with a gradient of ethyl acetate in hexanes) gave cyano-4-dimethylamino-2-ethoxy-benzoic acid methyl ester (218 mg, 12%).

EXAMPLE 7

2-Ethoxy-4-(piperidine-1-carbonyl)-benzoic acid methyl ester

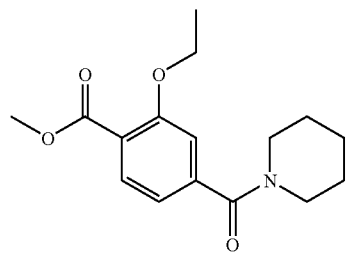

To a solution of 3-hydroxy-4-iodo-benzoic acid (4 g, 15.15 mmol) in 2-butanone (100 mL) were added potassium carbonate (20 g, finely ground) and ethyl iodide (4.85 mL). The mixture was stirred at reflux overnight. Upon cooling to room temperature, the solids were filtered off, and the filtrate was concentrated. The residue was partitioned between ethyl acetate and water, and the organic layer was washed with 10% sodium carbonate solution, brine, and concentrated. The residue reconstituted in methanol. 1.0 M sodium hydroxide was added giving a cloudy solution. Tetrahydrofuran was added to clarify and the mixture stirred at room temperature for one hour. The volatiles were evaporated and the residue was dissolved in water. It was washed once with diethyl ether and then acidified with 37% hydrochloric acid to precipitate a white solid. The solid was filtered, washed with water and dried in a vacuum oven to give 3-ethoxy-4-iodo-benzoic acid (2.73 g, 62%). LC-MS: 293 [(M+H)$^+$].

3-Ethoxy-4-iodo-benzoic acid (2.73 grams, 9.36 mmol) was suspended in methylene chloride (25 mL), and oxalyl chloride (5.15 mL, 2.0 M in methylene chloride, 10.3 mmol) was added by pipette. Three drops of dimethylformamide was added and this mixture was stirred overnight at room temperature. The volatiles from the now homogeneous reaction were removed under vacuum and the residue reconstituted in methylene chloride. One half of this was treated with piperidine (2.0 mL, 20 mmol). The mixture was stirred at room temperature for 2 h. The reaction was diluted with methylene chloride, washed with 1.0 M hydrochloric acid, water, saturated sodium bicarbonate solution and brine. The organic layers was dried (magnesium sulfate), filtered and concentrated to give (3-ethoxy-4-iodo-phenyl)-piperidin-1-yl-methanone (1.69 g, 100%).

(3-Ethoxy-4-iodo-phenyl)-piperidin-1-yl-methanone was methoxycarbonylated using the procedure described in example 6 to give 2-ethoxy-4-(piperidine-1-carbonyl)-benzoic acid methyl ester.

In an analogous manner, there was obtained:
N-tert-butyl-2-ethoxy-terephthalamic acid methyl ester.

EXAMPLE 8

5-Cyano-2-ethoxy-4-methoxy-benzoic acid ethyl ester

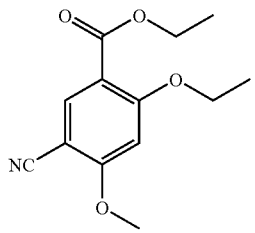

To a stirring solution of 2-ethoxy-4-methoxy-benzoic acid ethyl ester (1.5 g, 6.7 mmol) in 1,2-dichloroethane (2 mL) was added chlorosulfonyl isocyanate (0.923 mL, 10.6 mmol, in 1 mL of 1,2-dichloroethane) in several portions. The reaction was stirred at 50° C. overnight. Reaction was diluted with methylene chloride (2 mL) and water (1 mL), and extracted. The organic layer was washed with brine and concentrated in vacuo. Purification of the crude residue by flash column chromatography (silica gel, eluting with a gradient of ethyl acetate in hexanes) gave 900 mg (54% yield) of 5-cyano-2-ethoxy-4-methoxy-benzoic acid ethyl ester. LC-MS: 236.2 [(M+H—CH$_3$)$^+$].

EXAMPLE 9 a) Ethyl 4-methylsulfinyl-2-ethoxybenzoate

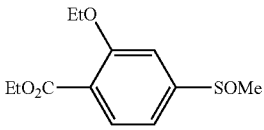

Potassium carbonate (14.0 g, 101 mmol) and iodoethane (3.3 mL, 40.4 mmol) were added to a stirred solution of 4-thiomethyl-2-ethoxy-benzoic acid (4.3 g, 20.2 mmol, prepared according to Robertson, D. et al. *J. Med. Chem.* 1985, 28, 717-727) in acetone (203 mL). The resulting mixture was heated in a 60° C. oil bath for 16 h and then allowed to cool. The reaction mixture was washed with sodium bicarbonate solution (2×), dried over anhydrous magnesium sulfate, and evaporated to give ethyl 4-methylthio-2-ethoxybenzoate as a yellow oil (4.3 g, 90%). It was used without further purification.

To a cooled solution of ethyl 4-methylthio-2-ethoxybenzoate (1.1 g, 4.6 mmol) in methylene chloride (40 mL) was added 3-chloroperoxybenzoic acid (1.1 g, 4.5 mmol, 77%) in several portions. The reaction mixture was stirred at 0° C. for 15 min, after which TLC (50% ethyl acetate in hexanes) showed consumption of starting material. The reaction mixture was quenched with a solution of sodium thiosulfate and neutralize with a solution of sodium bicarbonate. The product was extracted three times with methylene chloride. The organic layer was washed with sodium bicarbonate, dried over magnesium sulfate, and concentrated. Purification of the crude residue by flash column chromatography (silica gel, eluting with 50% ethyl acetate in hexanes) gave ethyl 2-ethoxy-4-methanesulfinylbenzoate as a yellow oil (0.70 g, 58%). LC-MS: 257.2 [(M+H)$^+$].

b) Ethyl 4-methylsulfonyl-2-ethoxybenzoate

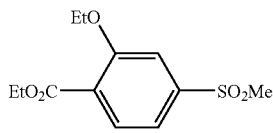

To a cooled solution of ethyl 4-methylthio-2-ethoxybenzoate (1.6 g, 6.7 mmol) in methylene chloride (60 mL) was added 3-chloroperoxybenzoic acid (3.0 g, 13.3 mmol, 77%). The reaction mixture was stirred at 0° C. for 15 min, quenched with a saturated solution of sodium thiosulfate, and neutralized with a saturated solution of sodium bicarbonate. The solution was extracted with methylene chloride. The combined organic phases were washed with sodium bicarbonate, brine and dried over magnesium sulfate and evaporated. Purification of the crude residue by flash column chromatography (silica gel, eluting with 50% ethyl acetate in hexanes) gave ethyl 4-(methylsulfonyl)-2-ethoxy-benzoate as a clear oil (1.45 g, 83%).

EXAMPLE 10

Ethyl 4-methylsulfonyl-2-ethoxybenzoate

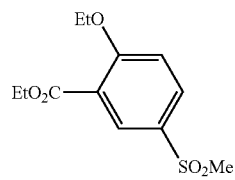

Potassium carbonate (22.0 g, 159 mmol) and iodoethane (9.0 mL, 112 mmol) were added to a stirred solution of 5-methylthio-2-hydroxy-benzoic acid (5.00 g, 27 mmol) in 2-butanone (125 mL). The resulting mixture was heated in an oil bath (80° C.) for 16 h and then allowed to cool. The solution was concentrated and redissolved in methylene chloride. The organic phase was washed with water and brine, dried over anhydrous magnesium sulfate and concentrated. Purification of the crude residue by flash column chromatography (silica gel, eluting with 5-15% ethyl acetate in hexanes) gave ethyl 5-methylthio-2-ethoxybenzoate as a yellow oil (5.5 g, 85%).

To a cooled solution of ethyl 5-methylthio-2-ethoxybenzoate (1.1 g, 4.6 mmol) in methylene chloride (40 mL) was added 3-chloroperoxybenzoic acid (2.0 g, 9.0 mmol, 77%). The reaction mixture was stirred at 0° C. for 2 h, quenched with a saturated solution of sodium thiosulfate, and neutralized with a saturated solution of sodium bicarbonate. The solution was extracted with methylene chloride. The combined organic phases were washed with sodium bicarbonate, brine and dried over sodium sulfate and evaporated. Purification of the crude residue by flash column chromatography (silica gel, eluting with 25-50% ethyl acetate in hexanes) gave ethyl 4-methylsulfonyl-2-ethoxybenzoate as a yellow oil (0.54 g, 43%).

EXAMPLE 11

Methyl 4-dimethylsulfamoyl-2-ethoxybenzoate

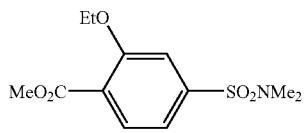

2-Ethoxy-4-thiol-benzoic acid (1.6 g, 8.08 mmol, prepared according to Robertson, D. et al. *J. Med. Chem.* 1985, 28, 717-727) was taken up in methanol (80 mL) and cooled to 0° C. Thionyl chloride (1.2 mL, 16.2 mmol) was added slowly. The reaction mixture was allowed to warm slowly to room temperature and stirred overnight. Evaporation of the solvents afforded a mixture of sulfide and disulfide methyl ester (1.9 g, 100%) as a yellow oil, which was used without further purification. This crude sulfide/disulfide ester was taken up in acetic acid and cooled to 0° C. A small amount of toluene was added to the reaction mixture to prevent the reaction mixture from freezing. Chlorine gas (Cl$_2$) was bubbled into the reaction mixture until TLC (50% ethyl acetate in hexanes) showed consumption of starting material. Argon gas (Ar) was bubbled into the reaction mixture to remove excess chlorine. The reaction mixture was concentrated to dryness in vacuo to give quantitative yield of the methyl 4-chlorosulfonyl-2-ethoxybenzoate.

Methyl 4-chlorosulfonyl-2-ethoxy-benzoate (1.3 g, 4.55 mmol) was taken up in anhydrous methylene chloride (30 mL) and cooled to 0° C. Dimethylamine (9.1 mL, 18.2 mmol) was added. The reaction mixture was allowed to slowly warm to room temperature and stirred at room temperature for 16 h. The reaction mixture was washed with water, dried over magnesium sulfate and concentrated. Purification of the crude residue by flash column chromatography (silica gel, eluting with 20-50% ethyl acetate in hexanes) gave methyl 4-dimethylsulfamoyl-2-ethoxybenzoate as a yellow solid (0.528 g, 41%). LC-MS: 288.1 [(M+H)$^+$].

In an analogous manner, there was obtained:
2-ethoxy-4-(morpholine-4-sulfonyl)-benzoic acid methyl ester
2-ethoxy-4-(pyrrolidine-1-sulfonyl)-benzoic acid methyl ester.

EXAMPLE 12 a) Ethyl 4-dimethylamino-5-dimethylsulfamoyl-2-ethoxybenzoate

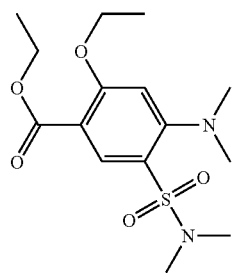

Ethyl 5-chlorosulfonyl-2-ethoxy-4-fluorobenzoate (1.5 g, 4.84 mmol; prepared as described in example 2) was taken up in 36 mL of anhydrous methylene chloride and cooled to 0° C. Dimethylamine (7.3 mL, 14.5 mmol) was added and the reaction mixture was stirred at 0° C. for 2 h and concentrated in vacuo. Purification of the crude residue by flash column chromatography (silica gel, eluting with 20-40% ethyl acetate in hexanes) gave ethyl 5-dimethylsulfamoyl-2-ethoxy-4-fluoro-benzoate as a white solid (1.02 g, 68%). LC-MS: 320.2 [(M+H)$^+$].

Ethyl 5-dimethylsulfamoyl-2-ethoxy-4-fluoro-benzoate (1.02 g, 3.20 mmol) was taken up in 5 mL of anhydrous dimethylformamide. Dimethylamine (8.0 mL, 15.9 mmol) was added and the reaction mixture was heated at 50° C. for 16 h. The reaction was allowed to cool to room temperature and diluted with water. The product was extracted three times with methylene chloride. The combined organics extracts were washed with brine, dried over magnesium sulfate and concentrated to give ethyl 4-dimethylamino-5-dimethylsulfamoyl-2-ethoxy-benzoate as a tan solid (1.05 g, 95%). LC-MS: 345.3 [(M+H)$^+$].

b) Ethyl 4-piperidino-5-piperidinosulfamoyl-2-ethoxybenzoate

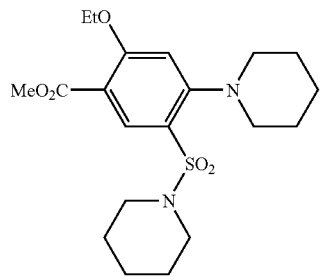

To a cooled solution of ethyl 4-fluoro-2-ethoxy-5-(chlorosulfonyl)benzoate (1.3 g, 4.2 mmol; prepared as described in example 2) in methylene chloride (25 mL) was added piperidine (1.5 mL, 18 mmol). The reaction was stirred at room temperature for 2 h and concentrated. Purification of the crude residue by chromatography over silica gel using 25-50% ethyl acetate in hexanes gave ethyl 4-piperidino-5-piperidinosulfamoyl-2-ethoxybenzoate (1.25 g, 70%).

EXAMPLE 13

Ethyl 4-methanesulfonylamino-2-ethoxybenzoate

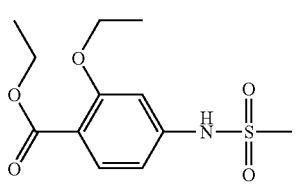

Potassium carbonate (60.4 g, 437 mmol) and iodoethane (17.6 mL, 218.4 mmol) were added to a mechanically stirred solution of 2-hydroxy-4-nitro-benzoic acid (10.0 g, 54.6 mmol) in 2-butanone (165 mL). The resulting mixture was heated in an 80° C. oil bath for 16 h and then allowed to cool. TLC (20% ethyl acetate in hexanes) showed consumption of starting material. The reaction mixture was concentrated to dryness, and the residue was taken up in ethyl acetate and washed three times with a saturated solution of sodium thiosulfate, dried over magnesium sulfate and concentrated to give ethyl 2-ethoxy-4-nitro-benzoate as a yellow solid (12.7 g, 97%). LC-MS: 240.1 [(M+H)+].

To a solution of ethyl 2-ethoxy-4-nitro-benzoate (12.7 g, 53.1 mmol) in ethanol (94 mL) was added a solution of ammonium chloride (56 mL). The formation of a precipitate was observed. Iron (15.2 g, 271 mmol) was added and the reaction mixture was heated at 80° C. for 16 h. The reaction mixture was cooled and filtered through Celite, and the Celite was rinsed with methylene chloride. Water was added and the product was extracted three times with methylene chloride. The organic layers were dried over magnesium sulfate and concentrated. Purification of the crude residue by flash column chromatography (silica gel, eluting with 0-3% methanol in chloroform) gave ethyl 4-amino-2-ethoxy-benzoate as a tan solid (10.3 g, 99%).

4-Amino-2-ethoxy-benzoic acid ethyl ester (1.0 g, 5.13 mmol) was taken up in pyridine (40 mL) and cooled to 0° C. Methanesulfonyl chloride (1.5 mL, 15.3 mmol) was added and the reaction temperature was allowed to warm slowly to room temperature and stirred for 16 h. The reaction mixture was diluted with methylene chloride and washed with 1N hydrochloric acid until aqueous phase remained acidic. The organic layers were dried over magnesium sulfate and concentrated to give ethyl 4-dimethylamino-5-dimethylsulfamoyl-2-ethoxybenzoate as an orange solid (1.3 g, 87%). It was used without further purification.

In an analogous manner, there were obtained:
2-ethoxy-4-[methanesulfonyl-(3-oxo-piperazine-1-carbonyl)-amino]-benzoic acid ethyl ester
4-(2,2-Dimethyl-propionylamino)-2-ethoxy-benzoic acid ethyl ester.

EXAMPLE 14

Ethyl 4-cyano-5-dimethylsulfamoyl-2-ethoxybenzoate

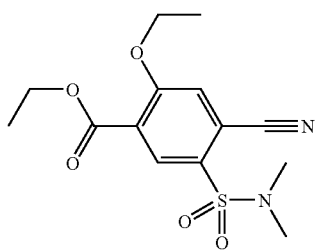

Potassium carbonate (100 g, 724 mmol) and iodoethane (29.1 mL, 364 mmol) were added to a mechanically stirred solution of 2-hydroxy-4-iodobenzoic acid (16.0 g, 60.6 mmol, prepared according to Singh, S.; et al. *J. Med. Chem.* 1997, 40, 2472-2481) in 2-butanone (250 mL). The resulting mixture was heated at 80° C. for 16 h and then allowed to cool. Diethyl ether (250 mL) was added to the reaction vessel and the supernatant was transferred to a separatory funnel. Diethyl ether (250 mL) was again added to the reaction vessel to wash the remaining solid and the supernatant was again transferred to the separatory funnel. Water (400 mL) was added and the phases were separated. The aqueous phase was washed twice with diethyl ether (500 mL, 200 mL) and then the combined organic phases were washed with water (400 mL), brine (400 mL), dried over magnesium sulfate and concentrated. Purification of the crude residue by flash column chromatography (silica gel, eluting with 10% ethyl acetate in hexanes) gave ethyl 2-ethoxy-4-iodobenzoate as an off-white solid (9.50 g, 49%).

Chlorosulfonic acid (2.3 mL) and thionyl chloride (0.6 mL) were combined and stirred in and ice-salt bath. Ethyl 2-ethoxy-4-iodobenzoate (0.800 g, 2.50 mmol) was added in portions over approximately 2 m. The cooling bath was removed and the reaction mixture was stirred for 16 h at room temperature. The reaction mixture was then warmed to 60° C. for 1.75 h then allowed to cool and poured carefully into a vigorously stirred mixture of ice and water (~50 mL). The resulting mixture was washed with ethyl acetate (2×30 mL) and the combined organic phases were dried over magnesium sulfate and evaporated to yield the sulfonyl chloride which was used without further purification. This crude sulfonyl chloride was dissolved in methylene chloride (12 mL) and cooled in an ice-salt bath. Triethylamine (1.74 mL, 12.5 mmol) and dimethylamine (12.5 mL, 25.0 mmol, 2.0 M in tetrahydrofuran) were added. The cooling bath was removed and the reaction mixture was stirred for 1.5 h and then concentrated. Purification of the crude residue by flash column chromatography (silica gel, eluting with 25% ethyl acetate in hexanes) gave ethyl 5-dimethylsulfamoyl-2-ethoxy-4-iodobenzoate as a white solid (0.599 g, 56%). LC-MS: 427.9 [(M+H)+].

Ethyl 5-dimethylsulfamoyl-2-ethoxy-4-iodobenzoate (1.01 g, 2.36 mmol), zinc cyanide (0.167 g, 1.42 mmol) and tetrakis(triphenylphosphine)palladium(0) (0.191 g, 0.165 mmol) were combined under nitrogen in a flame-dried Schlenk tube. Dimethylformamide (9 mL) was added and the reaction mixture was put through three freeze-pump-thaw cycles and then put under a nitrogen atmosphere and heated at 80° C. for 16 h. After cooling to room temperature, water (50 mL) was added and the resulting mixture was extracted with diethyl ether (100 mL, 2×50 mL). The combined organic phases were washed with brine (3×50 mL) and then dried over magnesium sulfate and concentrated. Purification of the crude residue by flash column chromatography (silica gel, eluting with 33% ethyl acetate in hexanes) gave ethyl 4-cyano-5-dimethylsulfamoyl-2-ethoxybenzoate as an off-white solid (0.708 g, 92%). LC-MS: 327.1 [(M+H)+].

EXAMPLE 15

Ethyl 4-cyano-2,5-diethoxy-benzoate

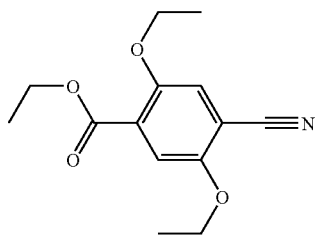

A solution of bromine (0.338 mL, 6.60 mmol) in acetic acid (6 mL) was added dropwise to a mixture of ethyl 2,5-diethoxybenzoate (1.36 mL, 6.02 mmol) and acetic acid (24 mL) cooled in a water bath. After stirring 1 h, more bromine (0.102 mL, 1.99 mmol) was added dropwise to the reaction mixture. After stirring an additional 4 h, the reaction mixture was concentrated under reduced pressure and the residue was purified by flash column chromatography (eluting with 10% diethyl ether in hexanes) to give ethyl 4-bromo-2,5-diethoxy-benzoate as an off-white solid (0.610 g, 32%).

Ethyl 4-bromo-2,5-diethoxybenzoate (0.615 g, 1.94 mmol), zinc cyanide (0.137 g, 1.17 mmol) and tetrakis(triphenylphosphine)palladium(0) (0.157 g, 0.136 mmol) were combined under nitrogen in a flame-dried Schlenk tube. Dimethylformamide (7 mL) was added and the reaction mixture was put through three freeze-pump-thaw cycles and then put under a nitrogen atmosphere and heated at 80° C. for 16 h. After cooling to room temperature, water (50 mL) was added and the resulting mixture was extracted with diethyl ether (100 mL, 2×50 mL). The combined organic phases were washed with brine (3×50 mL) and then dried over magnesium sulfate and concentrated. Purification of the crude residue by flash column chromatography (silica gel, eluting with 33% ethyl acetate in hexanes) gave ethyl 4-cyano-2,5-diethoxybenzoate as an off-white solid (0.416 g, 81%).

EXAMPLE 16

Ethyl 4-trifluoroprop-1-ynylbenzoate

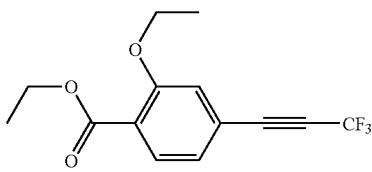

3,3,3-Trifluoro-1-propyne (approx. 0.6 mL, approx. 6 mmol) was condensed in a flame-dried Schlenk tube immersed in a dry ice/acetone bath. Tetrahydrofuran (3 mL) was added followed by a solution of butyllithium in hexanes (2.15 mL, 3.44 mmol, 1.6 M). After stirring 2.5 h at −78° C., zinc chloride (6.87 mL, 3.44 mmol, 0.5 M solution in tetrahydrofuran) was added to the reaction mixture and the reaction vessel was transferred to an ice-water bath and maintained at 0° C. for 30 min. Ethyl 2-ethoxy-4-iodobenzoate (1.00 g, 3.12 mmol, prepared as described in example 14) and tetrakis(triphenylphosphine)palladium(0) (0.18 g, 0.16 mmol) were then added. The reaction vessel was allowed to warm to room temperature and then after 1 h warmed to 50° C. for 18 h. After cooling, the reaction mixture was partitioned between brine (70 mL) and methylene chloride (2×100 mL), dried over magnesium sulfate and evaporated. Purification of the crude residue by flash column chromatography (silica gel, eluting with 1/1 mixture of methylene chloride and hexanes) gave ethyl 4-trifluoroprop-1-ynylbenzoate as an off-white solid (0.474 g, 53%).

EXAMPLE 17

Ethyl 2-ethoxy-4-trimethylsilanylethynylbenzoate

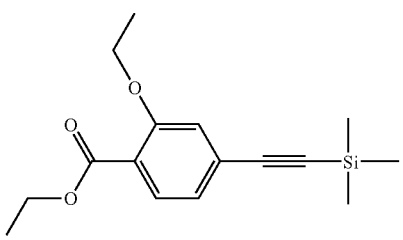

Ethyl 2-ethoxy-4-iodobenzoate (0.763 g, 2.38 mmol, example 14), copper(I) iodide (0.0227 g, 0.119 mmol), dichlorobis(triphenylphosphine)palladium(II) (0.167 g, 0.238 mmol) and (trimethylsilyl)acetylene (0.404 mL, 2.86 mmol) were dissolved under nitrogen in a flame-dried flask in a mixture of triethylamine (3.5 mL) and dimethylformamide (3.5 mL). The reaction mixture was heated at 50° C. for 2 h and then allowed to cool. Water (100 mL) was added and the mixture was extracted with diethyl ether (3×100 mL). The combined organic phases were washed with water (100 mL), brine (100 mL), dried over Sodium sulfate and evaporated. Purification of the crude residue by flash column chromatography (silica gel, eluting with 10% ethyl acetate in hexanes) gave ethyl 2-ethoxy-4-trimethylsilanylethynyl-benzoate as a yellow oil (0.624 g, 90%).

EXAMPLE 18

Ethyl 5-dimethylsulfamoyl-2-ethoxy-4-trimethylsilanylethynylbenzoate

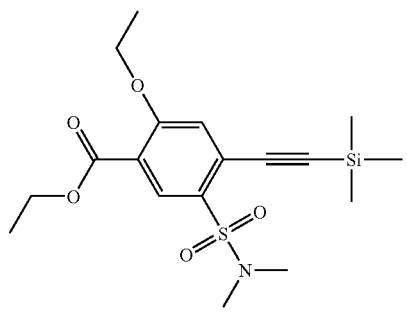

Ethyl 5-dimethylsulfamoyl-2-ethoxy-4-iodobenzoate (0.142 g, 0.332 mmol; prepared as described in example 14), dichlorobis(triphenylphosphine)palladium(II) (0.023 g, 0.032 mmol), copper(II) iodide (3.2 mg, 0.017 mmol) dimethylformamide (0.5 mL), triethylamine (0.5 mL) and (trimethylsilyl)acetylene (0.066 mL, 0.47 mmol) were added sequentially to a flame-dried Schienk tube. The reaction mixture was heated at 50° C. oil bath for 2 h, allowed to cool to room temperature overnight and then partitioned between water (20 mL) and diethyl ether (3×20 mL), dried over magnesium sulfate and evaporated. The residue was purified by flash column chromatography (eluting with 20% ethyl acetate in hexanes) to give ethyl 5-dimethylsulfamoyl-2-ethoxy-4-trimethylsilanylethynylbenzoate as an off-white glass (0.111 g, 84%). LC-MS: 398.3 [(M+H)$^+$].

EXAMPLE 19

(3,5-Dimethyl-isoxazol-4-yl)-piperazin-1-yl-methanone

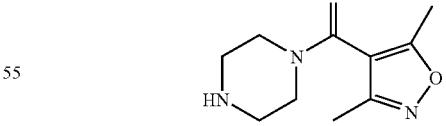

A solution of 1-tert-butyloxycarbonyl-piperazine (4.581 mmol) and diisopropylethylamine (5.09 mmol) in methylene chloride (5 mL) was added to a 40 mL vial. 3,5-Dimethyl-isoxazole-4-carbonyl chloride (5.09 mmol) was added to the vial and the reaction was shaken overnight at room temperature. When the reaction was complete, it was diluted with methylene chloride (5 mL) and washed with 4 mL of 1 N hydrochloric acid followed by 4 mL of 10% potassium carbonate. The organic layer was concentrated in vacuo. The crude residue was dissolved in 5 mL of dioxane and 5 mL of 4M hydrochloric acid in dioxane. The reaction mixture was shaken overnight at room temperature then centrifuged. The supernatant was removed and the remaining solid was shaken with hexanes then centrifuged. The supernatant was removed, and the solids were collected and dried in vacuo to give (3,5-dimethyl-isoxazol-4-yl)-piperazin-1-yl-methanone. LR-MS: 210.2 [(M+H)$^+$].

In an analogous manner, there were obtained:
cyclopropyl-piperazin-1-yl-methanone
3-methyl-1-piperazin-1-yl-but-2-en-1-one.

EXAMPLE 20

1-Ethanesulfonyl-piperazine

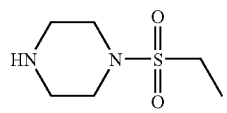

The title compound was prepared from 1-tert-butyloxycarbonyl-piperazine and ethylsulfonyl chloride using the procedure described in example 12.

In an analogous manner, there was obtained:
-1-(3,5-Dimethyl-isoxazole-4-sulfonyl)-piperazine from 3,5-dimethylisoxazole-4-sulfonyl chloride (Oakwood Products).

EXAMPLE 21

N-(2-Methoxy-1-methyl-ethyl)-2-piperazin-1-yl-acetamide

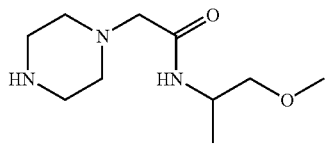

2-Methoxy-1-methyl-ethylamine (15 mmol) and diisopropylethylamine (17 mmol) were diluted with methylene chloride to give a total volume of 8 mL. The amine solution was added in a portion-wise fashion via a syringe to a solution of chloroacetylchloride (13 mmol) in methylene chloride (10 mL) cooled to approximately 40° C. in a sealed 40 mL vial. The reaction mixture was stirred for 1 h at reduced temperature. The solution was then made acidic with 1N hydrochloric acid and then diluted with 10 mL of methylene chloride. The vial was agitated and centrifuged. The organic layer was transferred to 40 mL vials and concentrated in vacuo. The residue (1.69 g, 10.21 mmol) was diluted with 10 mL of dimethylformamide. Piperazine-1-carboxylic acid tert-butyl ester (8.67 mmol) and diisopropylethylamine (13.27 mmol) were added. The reaction mixture was shaken at 65° C. overnight and concentrated in vacuo. The crude residue was dissolved in 10 mL of dioxane and 10 mL of 4 M hydrochloric acid in dioxane. The solution was shaken overnight at room temperature then centrifuged. The supernatant was removed, and the remaining solids were shaken with hexanes then centrifuged. The supernatant was removed, and the solids was collected and dried in vacuo to give N-(2-methoxy-1-methylethyl)-2-piperazin-1-yl-acetamide. LR-MS: 216.4 [(M+H)$^+$].

EXAMPLE 22 a) N,N-Bis-(2-methoxy-ethyl)-2-piperazin-1-yl-acetamide

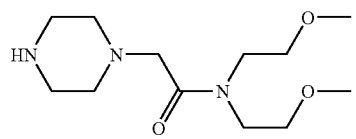

The title compound was prepared from 1-tert-butyloxycarbonyl-piperazine, chloroacetylchloride and N,N-bis-(2-methoxy-ethyl)amine in an analogous manner as described in example 21.

b) N-Methoxy-N-methyl-2-piperazin-1-yl-acetamide

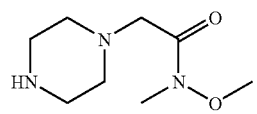

The title compound was prepared from 1-tert-butyloxycarbonyl-piperazine, chloroacetylchloride and N-methoxy-N-methylamine in an analogous manner as described in example 21.

c) N-Isopropyl-N-methyl-2-piperazin-1-yl-acetamide

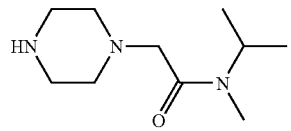

The title compound was prepared from 1-tert-butyloxycarbonyl-piperazine, chloroacetylchloride and N-isopropyl-N-methylamine in an analogous manner as described in example 21.

d) N-(2-Cyano-ethyl)-N-methyl-2-piperazin-1-yl-acetamide

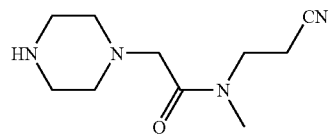

The title compound was prepared from 1-tert-butyloxycarbonyl-piperazine, chloroacetylchloride and N-(2-cyanoethyl)-N-methylamine in an analogous manner as described in example 21.

e) 1-(3-Methanesulfonyl-propyl)-piperazine

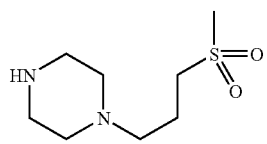

The title compound was prepared from 1-tert-butyloxycarbonyl-piperazine and methanesulfonic acid 3-methanesulfonyl-propyl ester (prepared according to Baerlocher, F. J. et al. *Aust. J. Chem.* 1999, 52, 167-172) in an analogous manner as described in example 21.

f) 3-Piperazin-1-yl-propionitrile

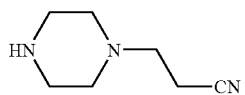

The title compound was prepared from 1-tert-butyloxycarbonyl-piperazine and 3-bromopropionitrile in an analogous manner as described in example 21.

g) N-tert-Butyl-2-piperazin-1-yl-acetamide

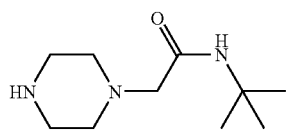

The title compound was prepared from 1-tert-butyloxycarbonyl-piperazine, chloroacetyl-chloride and N-tert-butylamine in an analogous manner as described in example 21.

h) N-Cyanomethyl-N-methyl-2-piperazin-1-yl-acetamide

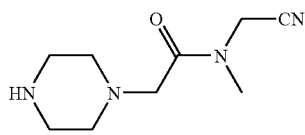

The title compound was prepared from 1-tert-butyloxycarbonyl-piperazine, chloroacetylchloride and N-cyanomethyl-N-methylamine in an analogous manner as described in example 21.

i) 2-piperazin-1-yl-1-piperidin-1-yl-ethanone

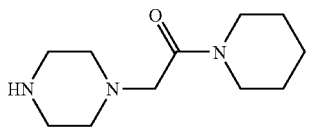

The title compound was prepared from 1-tert-butyloxycarbonyl-piperazine, chloroacetylchloride and piperidine in an analogous manner as described in example 21.

j) N-cyclopropyl-2-piperazin-1-yl-acetamide

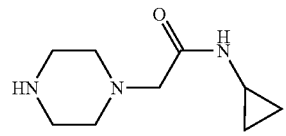

The title compound was prepared from 1-tert-butyloxycarbonyl-piperazine, chloroacetyl-chloride and cyclopropylamine in an analogous manner as described in example 21.

k) N-(2-Methoxy-ethyl)-2-piperazin-1-yl-acetamide

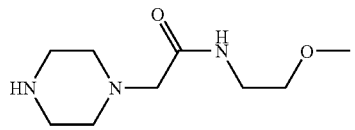

The title compound was prepared from 1-tert-butyloxycarbonyl-piperazine, chloroacetylchloride and 2-methoxyethylamine in an analogous manner as described in example 21.

EXAMPLE 23

1-(2-Methanesulfonylethyl)piperazine bishydrochloride

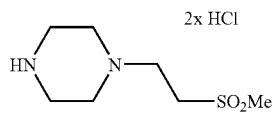

Methyl vinyl sulfone (1.8 mL, 20.1 mmol) was added to a solution of 1-(tert-butyloxycarbonyl)piperazine (1.50 g, 8 mmol) in methanol (84 mL). The reaction mixture was stirred at room temperature for 4 h and concentrated to a white solid. Purification of the solid by flash column chromatography (silica gel, eluting with 1-5% methanol in methylene chloride) gave 1-tert-butyloxycarbonyl-4-(2-methanesulfonylethyl)piperazine as a white solid (2.29 g, 95%).

Hydrochloric acid (42 mL, 168 mmol, 4 M in 1,4-dioxane) was added to a cooled solution of 1-tert-butyloxycarbonyl-4-(2-methanesulfonylethyl)piperazine (2.29 g, 7.8 mmol) in 1,4-dioxane (42 mL). The mixture was stirred at room temperature overnight then concentrated to give 1-(2-methanesulfonylethyl)piperazine bishydrochloride as a white solid (2.05 g).

EXAMPLE 24

N-(2-methanosulfonylethyl)-piperazine hydrochloride

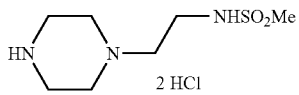

Methanesulfonyl chloride (0.7 mL, 9.0 mmol) was added to a cooled solution of 4-(2-amino-ethyl)-piperazine-1-carboxylic acid tert-butyl ester (1.33 g, 5.8 mmol) in pyridine (25.0 mL). The reaction was stirred for 12 h and partitioned between partitioned between aqueous sodium bicarbonate and methylene chloride. The organic phase was washed with 1 M hydrochloric acid, aqueous sodium bicarbonate, and brine, dried over anhydrous magnesium sulfate and concentrated. Purification of the crude residue by chromatography over silica gel using 0-5% methanol in methylene chloride gave 4-(2-methanesulfonylamino-ethyl)-piperazine-1-carboxylic acid tert-butyl ester (0.70 g, 70%).

To a cooled solution of 4-(2-methanesulfonylamino-ethyl)-piperazine-1-carboxylic acid tert-butyl ester (0.64 g, 0.2 mmol) in dioxane (20 mL) was added hydrochloric acid (4M in dioxane, 10 mL) and the reaction was stirred at room temperature for 12 h and concentrated to give N-(2-methanosulfonylethyl)-piperazine hydrochloride as a white solid (0.55 g, 95%).

EXAMPLE 25

4-[4,5-Bis-(4-chloro-phenyl)-4,5-dihydro-1H-imidazol-2-yl]-3-ethoxy-benzonitrile

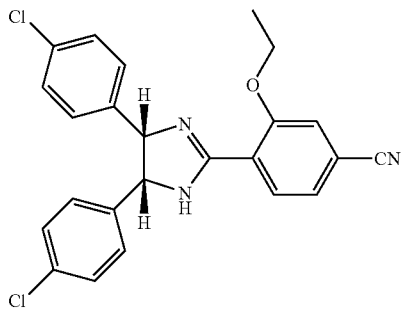

To a solution of meso-1,2-bis-(4-chlorophenyl)ethane-1,2-diamine (1.7 g, 6.04 mmol) in toluene (60 mL) was added dropwise trimethylaluminum (2.62 mL, 2.0 M solution in toluene, diluted with 2.2 mL of toluene). At the end of addition, the mixture was stirred at 80° C. until the gas evolution was completed. The reaction was cooled to room temperature and methyl 4-cyano-2-ethoxybenzoate (1.2 g, 5.75 mmol, example 1) in toluene (6 mL) was added. The reaction was at 100° C. for 7 h and cooled back to room temperature. Water (1.9 mL) was added dropwise, followed by methylene chloride (5 mL) and methanol (5 mL). This mixture was refluxed for 20 min, cooled to room temperature and filtered through a small pad of sodium sulfate. The solids were washed with toluene, methylene chloride, and methanol. The filtrate was concentrated, and the residue was reconstituted in ethyl acetate. It was refluxed for 30 min, and the hot solution was filtered through sodium sulfate and concentrated. Purification of the crude residue by flash column chromatography (silica gel, eluting with a gradient of ethyl acetate in hexanes) gave 4-[4,5-bis-(4-chloro-phenyl)-4,5-dihydro-1H-imidazol-2-yl]-3-ethoxy-benzonitrile (1.25 g, 48%).

EXAMPLE 26

4,5-bis-(4-chlorophenyl)-2-(2-ethoxy-4-ethynylphenyl)-4,5-dihydro-1H-imidazole

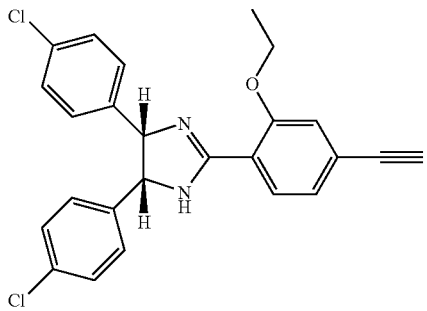

A solution of meso-1,2-bis-(4-chlorophenyl)ethane-1,2-diamine (3.60 g, 12.8 mmol) in toluene (41 mL) was added dropwise to a solution of trimethylaluminum (6.4 mL, 2 M in toluene) in toluene (36 mL) cooled in an ice-salt bath. After addition was complete, the cooling bath was removed and the reaction mixture was stirred for 45 min. A solution of ethyl 2-ethoxy-4-trimethylsilanylethynylbenzoate (2.48 g, 8.54 mmol, example 17) in toluene (37 mL) was added and the reaction mixture was heated to reflux for 6 h and then allowed to cool to room temperature and stirred for 10 h more. Water (4.31 mL), methanol (11.3 mL) and methylene chloride (11.3 mL) were added and the reaction mixture was heated at 100° C. for 15 min. After cooling to room temperature, the reaction mixture was dried over sodium sulfate and concentrated. The residue was dissolved in ethyl acetate (100 mL) and heated at 100° C. for 15 min and then concentrated. The residue was purified by flash column chromatography (silica gel, eluting with 2% methanol in chloroform) to give 4,5-bis-(4-chlorophenyl)-2-(2-ethoxy-4-trimethylsilanylethynylphenyl)-4,5-dihydro-1H-imidazole as a faintly yellow glass (3.96 g, 91%). LC-MS: 507.3 [(M+H)$^+$].

A solution of tetrabutylammonium fluoride in tetrahydrofuran (3.45 mL, 3.45 mmol) was added dropwise to a solution of methanol (1.33 mL) and 4,5-bis-(4-chlorophenyl)-2-(2-ethoxy-4-trimethylsilanylethynylphenyl)-4,5-dihydro-1H-imidazole (3.50 g, 6.90 mmol) in tetrahydrofuran (70 mL) cooled in an ice bath. After stirring for 30 min, the reaction mixture was poured into saturated aqueous ammonium chloride (100 mL) and extracted with methylene chloride (300 mL, 2×100 mL). The combined organic phases were dried over magnesium sulfate and evaporated. The residue was purified by flash column chromatography (silica gel, eluting with 2% methanol in chloroform) to give 4,5-bis-(4-chlorophenyl)-2-(2-ethoxy-4-ethynylphenyl)-4,5-dihydro-1H-imidazole as a yellow foam (2.66 g, 89%). LC-MS: 435.2 [(M+H)$^+$].

EXAMPLE 27

1-{4-[4,5-Bis-(4-chlorophenyl)-4,5-dihydro-1H-imidazol-2-yl]-3-ethoxyphenyl}ethanone

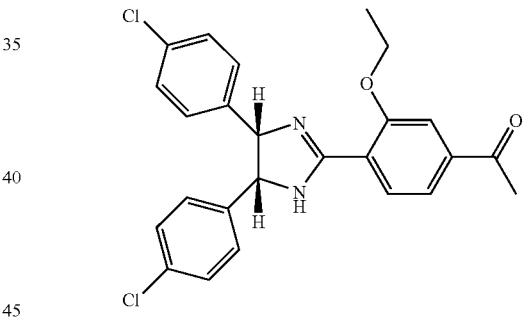

A solution of meso-1,2-bis-(4-chlorophenyl)ethane-1,2-diamine (1.58 g, 5.62 mmol) in toluene (18 mL) was added dropwise to a solution of trimethylaluminum (2.81 mL, 5.62 mmol, 2 M in toluene) in toluene (12 mL) cooled in an ice-salt bath. After addition was complete, the cooling bath was removed and the reaction mixture was stirred for 45 min. A solution of ethyl 2-ethoxy-4-iodobenzoate (1.20 g, 3.75 mmol; example 14) in toluene (18 mL) was added and the reaction mixture was heated to reflux for 6 h and then allowed to cool to room temperature and stirred 12 h more. Water (1.9 mL), methanol (5.0 mL) and methylene chloride (5.0 mL) were added and the reaction mixture was heated at 100° C. for 15 min. After cooling to room temperature, the reaction mixture was dried over sodium sulfate and evaporated. The residue was dissolved in ethyl acetate (50 mL) and heated at 100° C. for 15 min, then dried over sodium sulfate, evaporated. The residue was purified by column chromatography (silica gel, eluting with 1% methanol in chloroform) to give 4,5-bis-(4-chlorophenyl)-2-(2-ethoxy-4-iodophenyl)-4,5-dihydro-1H-imidazole as a faintly yellow glass (1.80 g, 90%). LC-MS: 537.2 [(M+H)$^+$].

4,5-Bis-(4-chlorophenyl)-2-(2-ethoxy-4-iodophenyl)-4,5-dihydro-1H-imidazole (0.900 g, 1.68 mmol), tributyl-(1-ethoxyvinyl)tin (0.679 mL, 2.01 mmol) and tetrakis(triphenyl-phosphine)-palladium(0) (0.194 g, 0.168 mmol) were combined in toluene (10 mL) in a flame-dried Schlenk tube then heat at 120° C. for 20 h. After evaporation of volatiles, the residue was purified by flash column chromatography (silica gel, eluting with a gradient of 2-5% methanol in chloroform) to give 4,5-bis-(4-chlorophenyl)-2-[2-ethoxy-4-(1-ethoxyvinyl)phenyl]-4,5-dihydro-1H-imidazole as a faintly green foam (0.639 g, 79%). LC-MS: 481.4 [(M+H)$^+$].

An aqueous solution of hydrochloric acid (2 M, 18 mL) was sparged for 10 min with nitrogen and then used to slurry 4,5-bis-(4-chlorophenyl)-2-[2-ethoxy-4-(1-ethoxyvinyl) phenyl]-4,5-dihydro-1H-imidazole (0.638 g, 1.33 mmol). Tetrahydrofuran (18 mL) was added to create a homogeneous solution. After stirring 1 h, the reaction mixture was poured into a mixture of 2 M sodium hydroxide (16 mL) and 10% sodium carbonate solution (50 mL) and extracted with methylene chloride (2×100 mL). The combined organic extracts were dried over sodium sulfate and concentrated. The residue was purified by flash column chromatography (silica gel, eluting with a gradient of 1-3% methanol in chloroform) to give 1-{4-[4,5-bis-(4-chlorophenyl)-4,5-dihydro-1H-imidazol-2-yl]-3-ethoxyphenyl}ethanone as a faintly yellow foam (0.392 g, 65%). LC-MS: 453.3 [(M+H)$^+$].

EXAMPLE 28

4,5-Bis-(4-chlorophenyl)-2-[4-(3,3-dimethylbut-1-ynyl)-2-ethoxyphenyl]-4,5-dihydro-1H-imidazole

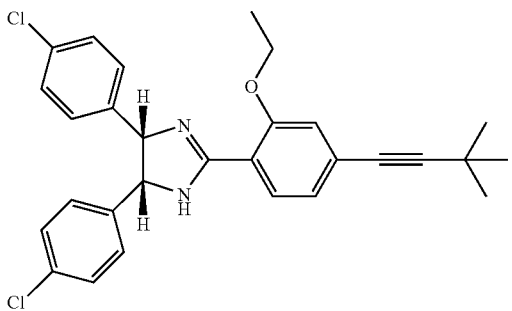

4,5-Bis-(4-chlorophenyl)-2-(2-ethoxy-4-iodophenyl)-4,5-dihydro-1H-imidazole (566 mg, 1.05 mmol, example 27), copper(I) iodide (9.5 mg, 0.11 mmol), dichlorobis(triphenylphosphine)-palladium(II) (148 mg, 0.211 mmol) and 3,3-dimethyl-1-butyne (0.182 mL, 1.48 mmol) were dissolved under nitrogen in a flame-dried Schlenk tube in a mixture of triethylamine (1.7 mL) and dimethylformamide (1.7 mL). The reaction mixture was warmed in a 50° C. oil bath for 20 h, allowed to cool to room temperature and then partitioned between 2% sodium carbonate solution (70 mL) and diethyl ether (2×100 mL). The combined organic phases were washed with water (2×50 mL) and brine (50 mL), then dried over sodium sulfate and evaporated. The residue was purified by flash column chromatography (silica gel, eluting with 1% methanol in methylene chloride) to give 4,5-bis-(4-chlorophenyl)-2-[4-(3,3-dimethylbut-1-ynyl)-2-ethoxyphenyl]-4,5-dihydro-1H-imidazole as an off-white foam (0.432 g, 83%). LC-MS: 491.3 [(M+H)$^+$].

EXAMPLE 29

(4S,5R)-4,5-Bis-(4-chloro-phenyl)-2-(4-cyano-2-ethoxy-phenyl)-4,5-dihydro-imidazole-1-carbonyl chloride

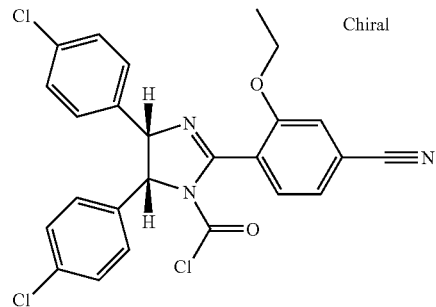

4,5-Bis-(4-chloro-phenyl)-2-(4-cyano-2-ethoxy-phenyl)-4,5-dihydro-imidazole (1.25 g, 2.88 mmol, example 25) was dissolved in methylene chloride and diisopropylethylamine (2.41 mL, 13.8 mmol) was added. The mixture was cooled in an ice bath and phosgene (6.09 mL, 11.52 mmol, 20% in toluene) was added. The reaction mixture was stirred for 30 mm at ice temperature and concentrated. Purification of the crude residue by flash column chromatography (silica gel, eluting with a gradient of ethyl acetate in hexanes) gave 4,5-bis-(4-chloro-phenyl)-2-(4-cyano-2-ethoxy-phenyl)-4,5-dihydro-imidazole-1-carbonyl chloride (1.35 g, 94%).

The enantiomers of 4,5-bis-(4-chloro-phenyl)-2-(4-cyano-2-ethoxy-phenyl)-4,5-dihydro-imidazole-1-carbonyl chloride were separated by chiral chromatography using a R,R-Whelk-01 column (25 cm×2 in). Eluent: 35% methylene chloride in hexanes. Flow rate: 85 mL/min. The first peak coming off the column is the desired (4S,5R)-4,5-bis-(4-chloro-phenyl)-2-(4-cyano-2-ethoxy-phenyl)-4,5-dihydro-imidazole-1-carbonyl chloride (retention time: ~19 min).

The unwanted isomer, (4R,5S)-4,5-bis-(4-chloro-phenyl)-2-(4-cyano-2-ethoxy-phenyl)-4,5-dihydro-imidazole-1-carbonyl chloride (retention time: ~28 min), was isolated and reconstituted in methylene chloride. This was stirred biphasically with 5% sodium carbonate and 5% dimethylaminopyridine to yield the parent imidazoline, 4,5-bis-(4-chloro-phenyl)-2-(4-cyano-2-ethoxy-phenyl)-4,5-dihydro-imidazole, which could be treated again with phosgene to give the racemic 4,5-bis-(4-chloro-phenyl)-2-(4-cyano-2-ethoxy-phenyl)-4,5-dihydro-imidazole-1-carbonyl chloride.

EXAMPLE 30

(4S,5R)-2-(4-Chloro-2-ethoxy-5-methylsulfamoyl-phenyl)-4,5-bis-(4-chloro-phenyl)-4,5-dihydro-imidazole-1-carboxylic acid benzotriazol-1-yl ester

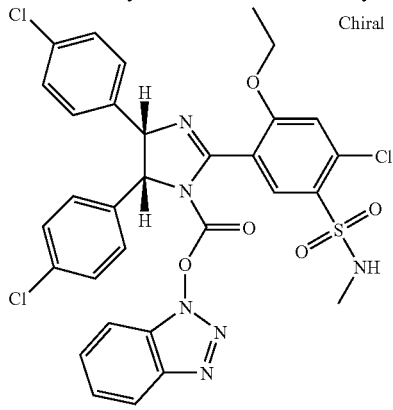

In an analogous manner as described in example 29, 5-[4,5-bis-(4-chloro-phenyl)-4,5-dihydro-1H-imidazol-2-yl]-2- chloro-4-ethoxy-N-methyl-benzenesulfonamide was treated with phosgene and diisopropylethylamine in methylene chloride to give 2-(4-chloro-2-ethoxy-5-methylsulfamoyl-phenyl)-4,5-bis-(4-chloro-phenyl)-4,5-dihydro-imidazole-1-carbonyl chloride. The crude carbamoyl chloride was then reacted with 1-hydroxybenzotriazole hydrate and diisopropylethylamine in methylene chloride to give the racemic 2-(4-chloro-2-ethoxy-5-methylsulfamoyl-phenyl)-4,5-bis-(4-chloro-phenyl)-4,5-dihydro-imidazole-1-carboxylic acid benzotriazol-1-yl ester after purification by flash column chromatography (silica gel, eluting with a gradient of ethyl acetate in hexanes).

The enantiomers of 2-(4-chloro-2-ethoxy-5-methylsulfamoyl-phenyl)-4,5-bis-(4-chloro-phenyl)-4,5-dihydro-imidazole-1-carboxylic acid benzotriazol-1-yl ester were separated by chiral chromatography using a R,R-Whelk-01 column (25 cm×10 mm). eluting with 15% iso-propanol in hexanes. The first peak coming off the column is the desired (4S,5R)-2-(4-chloro-2-ethoxy-5-methylsulfamoyl-phenyl)-4,5-bis-(4-chloro-phenyl)-4,5-dihydro-imidazole-1-carboxylic acid benzotriazol-1-yl ester.

EXAMPLE 31

4-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-3-ethoxy-benzonitrile hydrochloride

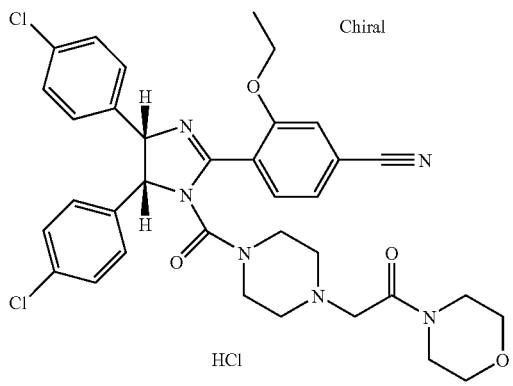

A solution of morpholin-4-yl-2-piperazin-1-yl-ethanone (17 mg, 0.081 mmol, Oakwood Products) and diisopropylethylamine (10 mg, 0.077 mmol) in 0.5 mL of methylene chloride was added to a solution of (4S,5R)-4,5-bis-(4-chloro-phenyl)-2-(4-cyano-2-ethoxy-phenyl)-4,5-dihydro-imidazole-1-carbonyl chloride (35 mg, 0.070 mmol, example 29) in 0.5 mL of methylene in a 4-mL vial. The vial was then capped and shaken for 1 h at room temperature. The reaction mixture was diluted with 1 mL of methylene chloride and 1 mL of water. The vial was agitated and centrifuged. The organic layer was transferred to a 4-mL vial and concentrated in vacuo. The crude was dissolved in 0.5 mL of acetonitrile, and then 0.6 mL of water and 0.492 mL of 0.5 M hydrochloric acid (2.46 mmol) were added to the sample. The sample was frozen with liquid nitrogen and lyophilized to give 4-{(4S, 5R)-4,5-bis-(4-chloro-phenyl)-1-[4-(2-morpholin-4-yl-2-oxo-ethyl)-piperazine-1-carbonyl]-4,5-dihydro-1H-imidazol-2-yl}-3-ethoxy-benzonitrile hydrochloride (47.6 mg, 91% yield). LC-MS: 675.3 [(M+H)$^+$].

EXAMPLE 32

5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-2-chloro-4-ethoxy-N-methyl-benzenesulfonamide

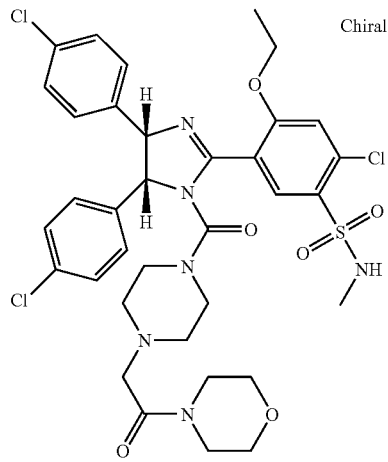

To a solution of (4S,5R)-2-(4-chloro-2-ethoxy-5-methylsulfamoyl-phenyl)-4,5-bis-(4-chloro-phenyl)-4,5-dihydro-imidazole-1-carboxylic acid benzotriazol-1-yl ester (9 mg, 0.0124 mmol) in 0.5 mL of dimethylformamide was added a solution of 1-morpholin-4-yl-2-piperazin-1-yl-ethanone (5.3 mg, 0.026 mmol) and diisopropylethylamine (4.53 uL). The resulting mixture was heated to 40° C. for 1 h. The solution was concentrated in vacuo then extracted from 1 mL of water with 1 mL of methylene chloride. The organic extract was applied to a 4 gram silica gel cartridge. The product was eluted using a gradient of methanol in methylene chloride to give 5-{(4S,5R)-4,5-bis-(4-chloro-phenyl)-1-[4-(2-morpholin-4-yl-2-oxo-ethyl)-piperazine-1-carbonyl]-4,5-dihydro-1H-imidazol-2-yl}-2-chloro-4-ethoxy-N-methyl-benzenesulfonamide (9.69 mg, 97%). LC-MS: 777.3 [(M+H)$^+$].

EXAMPLE 33

5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-2-chloro-4-ethoxy-N,N-dimethyl-benzenesulfonamide

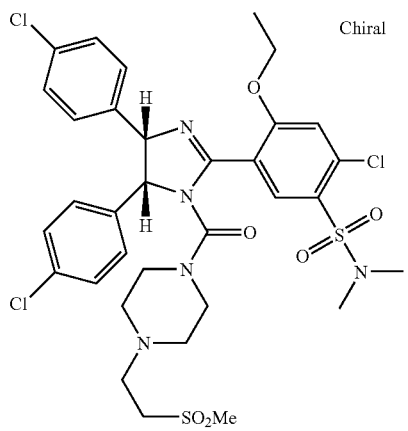

The racemic 5-{4,5-bis-(4-chloro-phenyl)-1-[4-(2-methanesulfonyl-ethyl)-piperazine-1-carbonyl]-4,5-dihydro-1H- imidazol-2-yl}-2-chloro-4-ethoxy-N,N-dimethyl-benzenesulfonamide was prepared from meso-1,2-bis-(4-chlorophenyl)ethane-1,2-diamine, ethyl 4-chloro-5-dimethylsulfamoyl-2-ethoxy-benzoate (example 2) and 1-(2-methanesulfonylethyl)piperazine bishydrochloride (example 23) following successively the procedures described for examples 25, 29 and 31.

The enantiomers of 5-{4,5-bis-(4-chloro-phenyl)-1-[4-(2-methanesulfonyl-ethyl)-piperazine-1-carbonyl]-4,5-dihydro-1H-imidazol-2-yl}-2-chloro-4-ethoxy-N,N-dimethyl-benzenesulfonamide (105 mg) were separated by chiral chromatography using a Diacel Chiralpak AD column (21 mm×250 mm) eluting with i-propanol/ethanol (7:3) containing 0.05% trifluoroacetic acid at a flow rate of 30 mL/min. Injection volume: 3.0 mL (10-15 mg of the racemic compound). Retention time: 3.35 min and 5.50 min. After the volatiles were evaporate, the resulting trifluoroacetate salts were lyophilized with hydrochloric acid to give the two enantiomers as white solids (40 mg).

EXAMPLE 34

5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-2-chloro-4-ethoxy-benzenesulfonamide

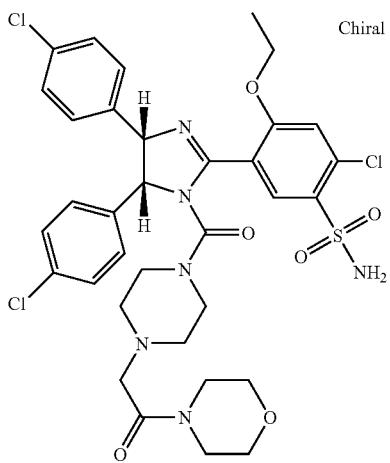

5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-N-tert-butyl-2-chloro-4-ethoxy-benzenesulfonamide was prepared from meso-1,2-bis-(4-chlorophenyl)ethane-1,2-diamine, ethyl 5-tert-butylsulfamoyl-4-chloro-2-ethoxy-benzoate (example 2) and 1-morpholin-4-yl-2-piperazin-1-yl-ethanone (Oakwood Products) following successively the procedures described for examples 25, 29 and 31.

5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-N-tert-butyl-2-chloro-4-ethoxy-benzenesulfonamide (~10 mg) was dissolved in 2 mL of trifluoroacetic acid and heated to 80° C. for 30 min. The reaction mixture was diluted with 2 mL of methylene chloride and 1.5 mL of 10% potassium carbonate solution then agitated. The organic layer was separated and concentrated in vacuo to give 5-{(4S,5R)-4,5-bis-(4-chloro-phenyl)-1-[4-(2-morpholin-4-yl-2-oxo-ethyl)-piperazine-1-carbonyl]-4,5-dihydro-1H-imidazol-2-yl}-2-chloro-4-ethoxy-benzenesulfonamide as trifluoroacetate salt. LC-MS: 763.3 [(M+H)⁺].

EXAMPLE 35

4-[4,5-Bis-(4-chloro-phenyl)-1-(3-oxo-piperazine-1-carbonyl)-4,5-dihydro-1H-imidazol-2-yl]-3-ethoxy-benzonitrile

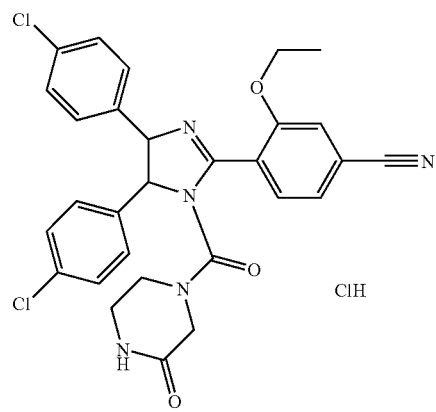

The title compound was prepared from 4-[4,5-bis-(4-chloro-phenyl)-4,5-dihydro-1H-imidazol-2-yl]-3-ethoxy-benzonitrile (example 25) and 2-piperazinone (Avocado Organics) following successively the procedures described for examples 29 and 31. LC-MS: 562.4 [(M+H)⁺].

EXAMPLE 36

4-{4,5-Bis-(4-chloro-phenyl)-1-[4-(2-hydroxy-ethyl)-piperazine-1-carbonyl]-4,5-dihydro-1H-imidazol-2-yl}-3-ethoxy-benzonitrile

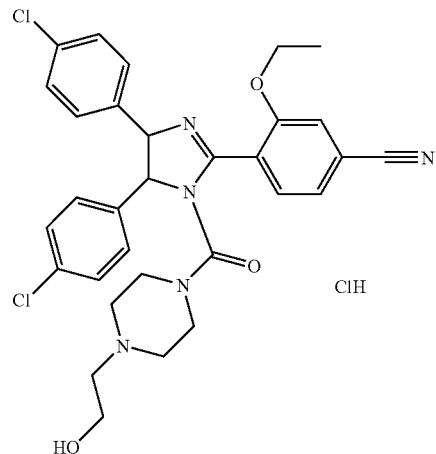

The title compound was prepared from 4-[4,5-bis-(4-chloro-phenyl)-4,5-dihydro-1H-imidazol-2-yl]-3-ethoxy-benzonitrile (example 25) and 1-(2-hydroxy-ethyl)-piperazine (Aldrich) following successively the procedures described for examples 29 and 31. LC-MS: 592.4 [(M+H)⁺].

EXAMPLE 37

4-[4,5-Bis-(4-chloro-phenyl)-1-(4-pyrrolidin-1-yl-piperidine-1-carbonyl)-4,5-dihydro-1H-imidazol-2-yl]-3-ethoxy-benzonitrile

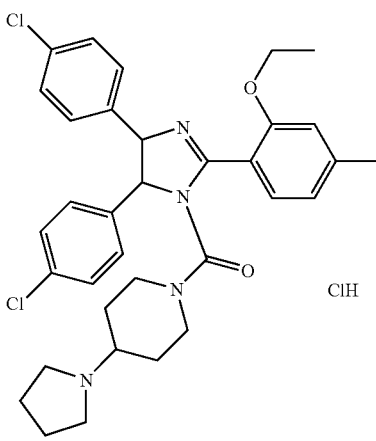

The title compound was prepared from 4-[4,5-bis-(4-chloro-phenyl)-4,5-dihydro-1H-imidazol-2-yl]-3-ethoxy-benzonitrile (example 25) and 4-pyrrolidin-1-yl-piperidine (Aldrich) following successively the procedures described for examples 29 and 31. LC-MS: 616.4 [(M+H)$^+$].

EXAMPLE 38

3-[4,5-Bis-(4-chloro-phenyl)-1-(3-oxo-piperazine-1-carbonyl)-4,5-dihydro-1H-imidazol-2-yl]-4-ethoxy-N,N-dimethyl-benzenesulfonamide

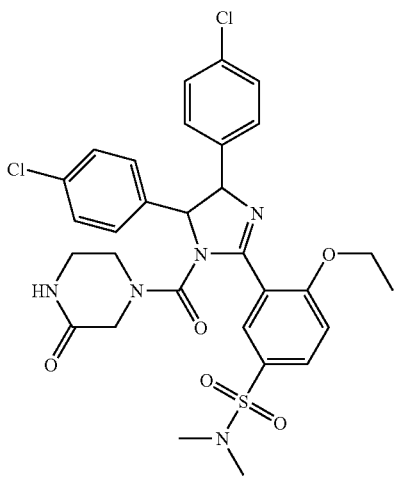

The title compound was prepared from meso-1,2-bis-(4-chlorophenyl)ethane-1,2-diamine, ethyl 2-ethoxy-5-(N,N-dimethylsulfonamide)benzoate (example 2) and 2-piperazinone (Avocado Organics) in an analogous manner using procedures described for examples 25, 29 and 31 (except chiral purification). LC-MS: 644.3 [(M+H)$^+$]

EXAMPLE 39

3-{4,5-Bis-(4-chloro-phenyl)-1-[4-(2-hydroxy-ethyl)-piperazine-1-carbonyl]-4,5-dihydro-1H-imidazol-2-yl}-4-ethoxy-N,N-dimethyl-benzenesulfonamide

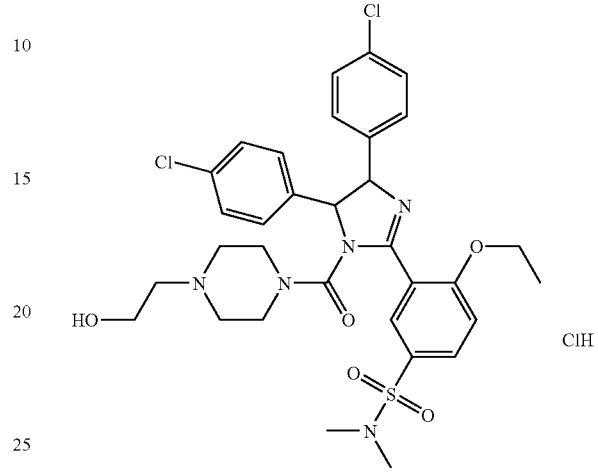

The title compound was prepared from meso-1,2-bis-(4-chlorophenyl)ethane-1,2-diamine, ethyl 2-ethoxy-5-(N,N-dimethylsulfonamide)benzoate (example 2) and 1-(2-hydroxy-ethyl)-piperazine (Aldrich) in an analogous manner using the procedures described for examples 25, 29 and 31 (except chiral purification). LC-MS: 674.3 [(M+H)$^+$].

EXAMPLE 40

3-{4,5-Bis-(4-chloro-phenyl)-1-(4-Pyrrolidin-1-yl-piperidine-1-carbonyl)-4,5-dihydro-1H-imidazol-2-yl}-4-ethoxy-N,N-dimethyl-benzenesulfonamide

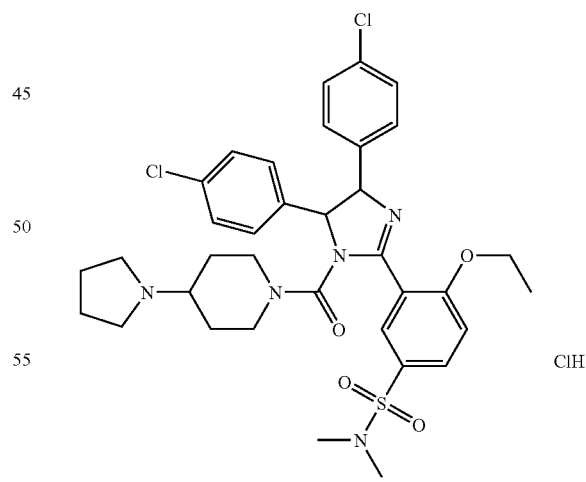

The title compound was prepared from meso-1,2-bis-(4-chlorophenyl)ethane-1,2-diamine, ethyl 2-ethoxy-5-(N,N-dimethylsulfonamide)benzoate (example 2) and 4-pyrrolidin-1-yl-piperidine (Aldrich) in an analogous manner using the procedures described for examples 25, 29 and 31 (except chiral purification). LC-MS: 698.5 [(M+H)$^+$].

EXAMPLE 41

5-[4,5-Bis-(4-chloro-phenyl)-1-(3-oxo-piperazine-1-carbonyl)-4,5-dihydro-1H-imidazol-2-yl]-2-chloro-4-ethoxy-N,N-dimethyl-benzenesulfonamide

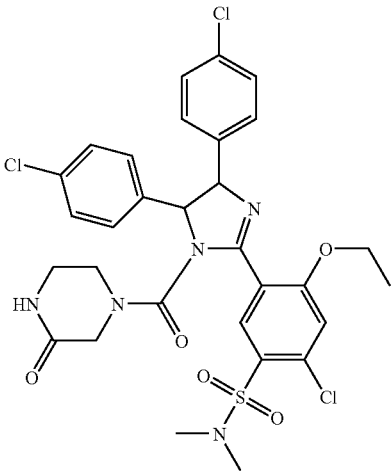

The title compound was prepared from meso-1,2-bis-(4-chlorophenyl)ethane-1,2-diamine, ethyl 4-chloro-5-dimethylsulfamoyl-2-ethoxy-benzoate (example 2) and 2-piperazinone (Avocado Organics) in an analogous manner using the procedures described for examples 25, 29 and 31 (except chiral purification). LC-MS: 678.4 [(M+H)$^+$].

EXAMPLE 42

5-{4,5-Bis-(4-chloro-phenyl)-1-[4-(2-morpholin-4-yl-2-oxo-ethyl)-piperazine-1-carbonyl]-4,5-dihydro-1H-imidazol-2-yl}-2-chloro-4-ethoxy-N,N-dimethyl-benzenesulfonamide

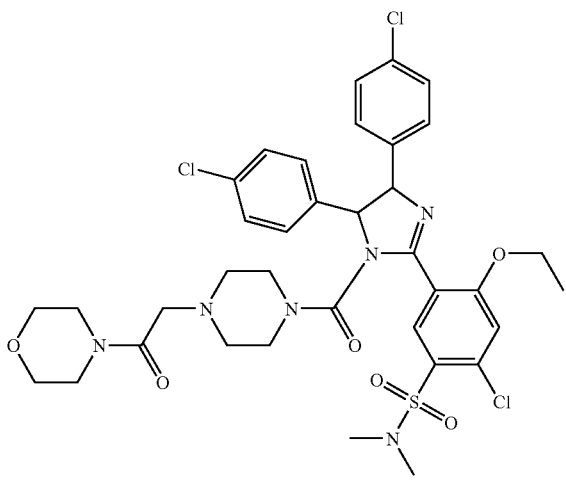

The title compound was prepared from meso-1,2-bis-(4-chlorophenyl)ethane-1,2-diamine, ethyl 4-chloro-5-dimethylsulfamoyl-2-ethoxy-benzoate (example 2) and 1-morpholin-4-yl-2-piperazin-1-yl-ethanone (Oakwood Products) in an analogous manner using the procedures described for examples 25, 29 and 31 (except chiral purification). LC-MS: 791.5 [(M+H)$^+$].

EXAMPLE 43

5-{4,5-Bis-(4-chloro-phenyl)-1-[4-(2-hydroxy-ethyl)-3-oxo-piperazine-1-carbonyl]-4,5-dihydro-1H-imidazol-2-yl}-2-chloro-4-ethoxy-N,N-dimethyl-benzenesulfonamide

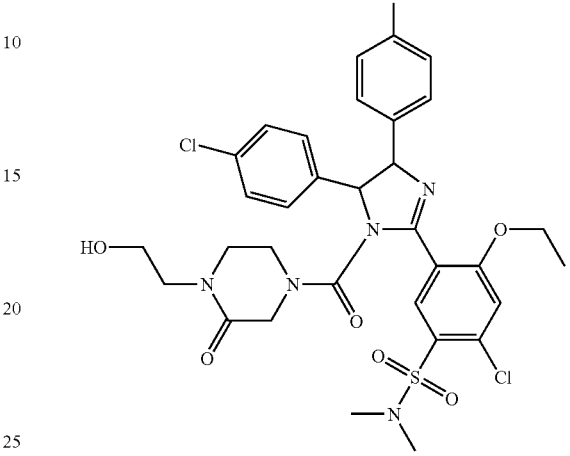

Sodium hydride (0.35 g, 8.6 mmol, 60% in mineral oil) was added to a solution of 4-tert-butyloxycarbonyl-piperazin-2-one (0.86 g, 4.3 mmol) in dimethylformamide (20.0 mL) at 0° C. The reaction was stirred at 0° C. for 0.5 h. To this mixture was added 2-bromoethoxy-tert-butyldimethylsilane (2.3 mL, 10.8 mmol) and the reaction was stirred for 2 h at room temperature. The reaction mixture was quenched with a dilute aqueous solution of sodium bicarbonate and extracted with methylene chloride. The organic extracts were washed with brine and dried over anhydrous sodium sulfate. Purification of the crude residue by flash column chromatography (silica gel, eluting with 20% ethyl acetate in hexanes) gave 4-tert-butyloxycarbonyl-1-[2-(tert-butyldimethylsilyloxy)ethyl]-piperazin-2-one (1.17 g, 76%).

To a solution of 4-tert-butyloxycarbonyl-1-[2-(tert-butyldimethylsilyloxy)ethyl]-piperazin-2-one (0.88 g, 2.5 mmol) in tetrahydrofuran (30 mL) was added tetrabutylammonium fluoride (3.6 mL, 3.6 mmol, 1.0 M in tetrahydrofuran) and the reaction mixture was stirred at room temperature for 2 h. The reaction mixture was quenched with a dilute aqueous solution of sodium bicarbonate and extracted with ethyl acetate. The organic extracts were washed with brine and dried over anhydrous sodium sulfate. Purification of the crude residue by flash column chromatography (silica gel, eluting with 30% ethyl acetate in hexanes) gave 4-tert-butyloxycarbonyl-1-(2-hydroxyethyl)-piperazin-2-one (0.45 g, 75%).

Hydrochloric acid (1.8 mL, 7.4 mmol, 4 M in 1,4-dioxane) was added to a solution of 4-tert-butyloxycarbonyl-1-(2-hydroxyethyl)-piperazin-2-one (0.45 g, 1.8 mmol) in 1,4-dioxane (5.0 mL). The mixture was stirred overnight and concentrated to give 1-(2-hydroxyethyl)-piperazin-2-one hydrochloride as an off-white solid (0.30 g, 91%).

5-{4,5-Bis-(4-chloro-phenyl)-1-[4-(2-hydroxy-ethyl)-3-oxo-piperazine-1-carbonyl]-4,5-dihydro-1H-imidazol-2-yl}-2-chloro-4-ethoxy-N,N-dimethyl-benzenesulfonamide was prepared from meso-1,2-bis-(4-chlorophenyl)ethane-1,2-diamine, ethyl 4-chloro-5-dimethylsulfamoyl-2-ethoxy-benzoate (example 2) and 1-(2-hydroxyethyl)-piperazin-2-one hydrochloride in an analogous manner using the procedures described for examples 25, 29 and 31 (except chiral purification). LC-MS: 722.1 [(M+H)+].

EXAMPLE 44

5-[4,5-Bis-(4-chloro-phenyl)-1-(3-oxo-piperazine-1-carbonyl)-4,5-dihydro-1H-imidazol-2-yl]-4-ethoxy-2-methoxy-N,N-dimethyl-benzenesulfonamide

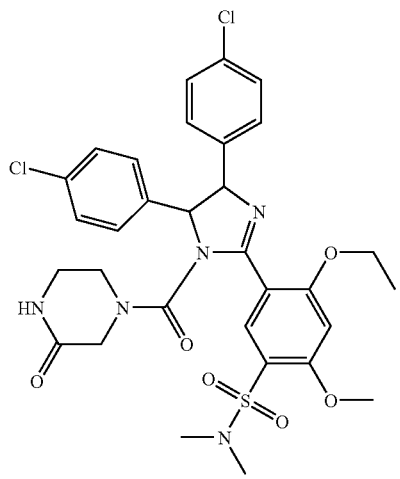

The title compound was prepared from meso-1,2-bis-(4-chlorophenyl)ethane-1,2-diamine, ethyl 5-dimethylsulfamoyl-2-ethoxy-4-methoxy-benzoate (example 2) and 2-piperazinone (Avocado Organics) in an analogous manner using the procedures described for examples 25, 29 and 31 (except chiral purification). LC-MS: 674.3 [(M+H)+].

EXAMPLE 45

5-{4,5-Bis-(4-chloro-phenyl)-1-[4-(2-hydroxy-ethyl)-piperazine-1-carbonyl]-4,5-dihydro-1H-imidazol-2-yl}-4-ethoxy-2-methoxy-N,N-dimethyl-benzenesulfonamide

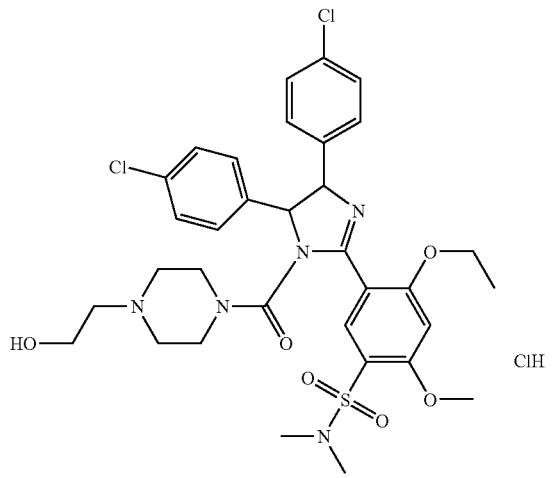

The title compound was prepared from meso-1,2-bis-(4-chlorophenyl)ethane-1,2-diamine, ethyl 5-dimethylsulfamoyl-2-ethoxy-4-methoxy-benzoate (example 2) and 1-(2-hydroxy-ethyl)-piperazine (Aldrich) in an analogous manner using the procedures described for examples 25, 29 and 31 (except chiral purification). LC-MS: 704.3 [(M+H)+].

EXAMPLE 46

2-{(4-[4,5-Bis-(4-chloro-phenyl)-2-(5-dimethylsulfamoyl-2-ethoxy-4-methoxy-phenyl)-4,5-dihydro-imidazole-1-carbonyl]-piperazin-1-yl}-N,N-dimethyl-acetamide

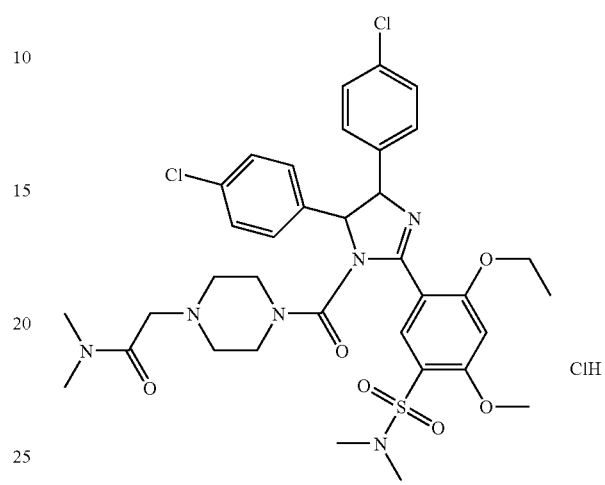

The title compound was prepared from meso-1,2-bis-(4-chlorophenyl)ethane-1,2-diamine, ethyl 5-dimethylsulfamoyl-2-ethoxy-4-methoxy-benzoate (example 2) and N,N-dimethyl-2-piperazin-1-yl-acetamide (Oakwood Products) in an analogous manner using the procedures described for examples 25, 29 and 31 (except chiral purification). LC-MS: 745.3 [(M+H)+].

EXAMPLE 47

5-[4,5-Bis-(4-chloro-phenyl)-1-{4-(2-methanesulfonyl-ethyl)-piperazine-1-carbonyl]-4,5-dihydro-1H-imidazol-2-yl}-4-ethoxy-2-methoxy-N,N-dimethyl-benzenesulfonamide

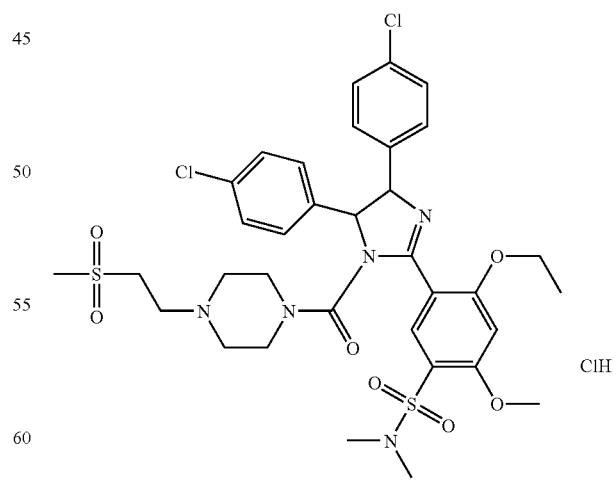

The title compound was prepared from meso-1,2-bis-(4-chlorophenyl)ethane-1,2-diamine, ethyl 5-dimethylsulfamoyl-2-ethoxy-4-methoxy-benzoate (example 2) and 1-(2-methanesulfonylethyl)piperazine bishydrochloride (example 23) in an analogous manner using the procedures described for examples 25, 29 and 31 (except chiral purification). LC-MS: 766.3 [(M+H)+].

EXAMPLE 48

4-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-3-ethoxy-benzonitrile

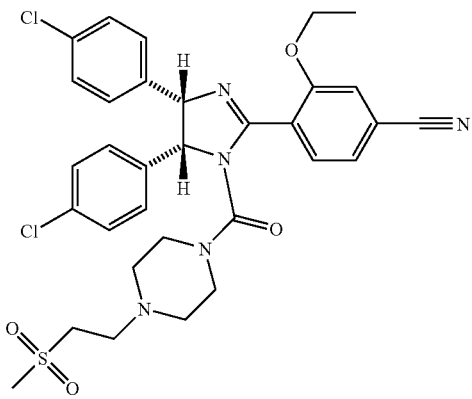

The title compound was prepared from 4-[4,5-bis-(4-chloro-phenyl)-4,5-dihydro-1H-imidazol-2-yl]-3-ethoxy-benzonitrile (example 25) and 1-(2-methanesulfonylethyl)piperazine bishydrochloride (example 23) following successively the procedures described for examples 29 and 31. LC-MS: 654.2 [(M+H)+].

EXAMPLE 49

5-{(4S,5R)-4,5-Bis-(4-chloro-phenyl)-1-[4-(2-hydroxy-ethyl)-piperazine-1-carbonyl]-4,5-dihydro-1H-imidazol-2-yl}-2-chloro-4-ethoxy-N,N-dimethyl-benzenesulfonamide

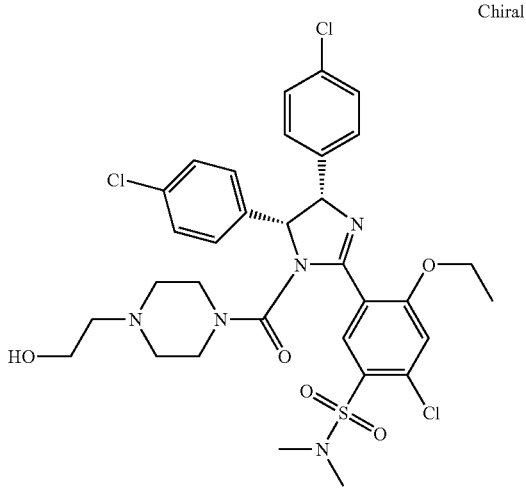

The title compound was prepared from meso-1,2-bis-(4-chlorophenyl)ethane-1,2-diamine, ethyl 4-chloro-5-dimethylsulfamoyl-2-ethoxy-benzoate (example 2) and 1-(2-hydroxy-ethyl)-piperazine (Aldrich) following successively the procedures described for examples 25, 29 and 31. The enantiomers were separated using the procedure described in example 33. LC-MS: 708.3 [(M+H)+].

EXAMPLE 50

4-[4,5-Bis-(4-chloro-phenyl)-2-(2-ethoxy-4-methanesulfinyl-phenyl)-4,5-dihydro-imidazole-1-carbonyl]-piperazin-2-one

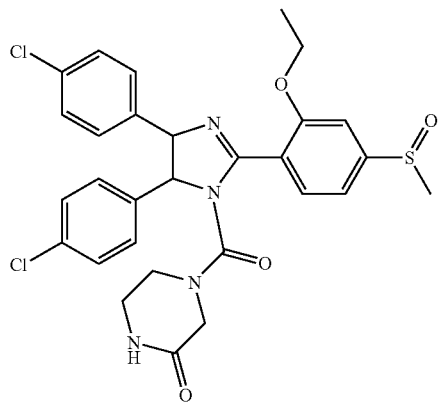

The title compound was prepared from meso-1,2-bis-(4-chlorophenyl)ethane-1,2-diamine, ethyl 4-methylsulfinyl-2-ethoxybenzoate (example 9a) and 2-piperazinone (Avocado Organics) in an analogous manner using the procedures described for examples 25, 29 and 31 (except chiral purification). LC-MS: [(M+H)+].

EXAMPLE 51

4-[4,5-Bis-(4-chloro-phenyl)-2-(2-ethoxy-4-methanesulfonyl-phenyl)-4,5-dihydro-imidazole-1-carbonyl]-piperazin-2-one

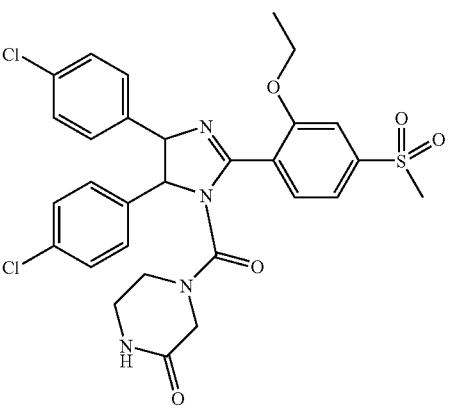

The title compound was prepared from meso-1,2-bis-(4-chlorophenyl)ethane-1,2-diamine, ethyl 4-methylsulfonyl-2-ethoxybenzoate (example 9b) and 2-piperazinone (Avocado Organics) in an analogous manner using the procedures described for examples 25, 29 and 31 (except chiral purification). LC-MS: [(M+H)+].

EXAMPLE 52

2-{4-[4,5-Bis-(4-chloro-phenyl)-2-(2-ethoxy-4-methanesulfinyl-phenyl)-4,5-dihydro-imidazole-1-carbonyl]-piperazin-1-yl}-N,N-dimethyl-acetamide

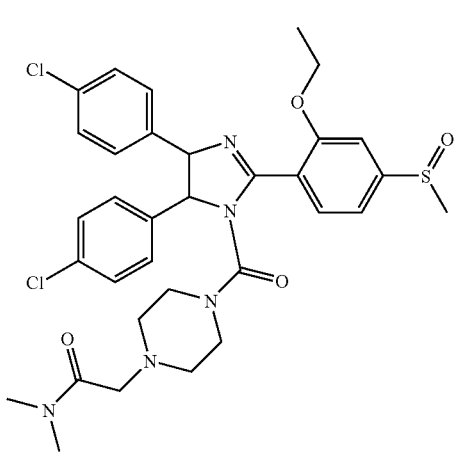

The title compound was prepared from meso-1,2-bis-(4-chlorophenyl)ethane-1,2-diamine, ethyl 4-methylsulfinyl-2-ethoxybenzoate (example 9a) and N,N-dimethyl-2-piperazin-1-yl-acetamide (Oakwood Products) in an analogous manner using the procedures described for examples 25, 29 and 31 (except chiral purification). LC-MS: [(M+H)+].

EXAMPLE 53

2-{4-[4,5-Bis-(4-chloro-phenyl)-2-(2-ethoxy-4-methanesulfonyl-phenyl)-4,5-dihydro-imidazole-1-carbonyl]-piperazin-1-yl}-N,N-dimethyl-acetamide

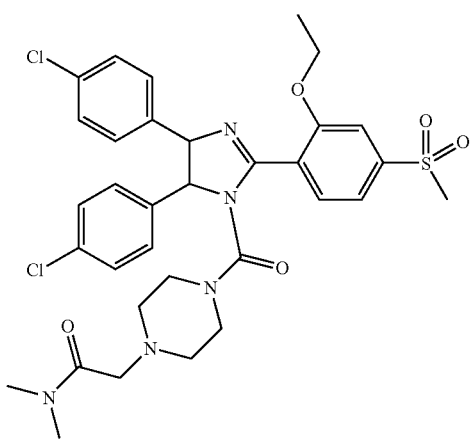

The title compound was prepared from meso-1,2-bis-(4-chlorophenyl)ethane-1,2-diamine, ethyl 4-methylsulfonyl-2-ethoxybenzoate (example 9b) and N,N-dimethyl-2-piperazin-1-yl-acetamide (Oakwood Products) in an analogous manner using the procedures described for examples 25, 29 and 31 (except chiral purification). LC-MS: [(M+H)+].

EXAMPLE 54

[4,5-Bis-(4-chloro-phenyl)-2-(2-ethoxy-4-methanesulfinyl-phenyl)-4,5-dihydro-imidazol-1-yl]-[4-(2-methanesulfonyl-ethyl)-piperazin-1-yl]-methanone

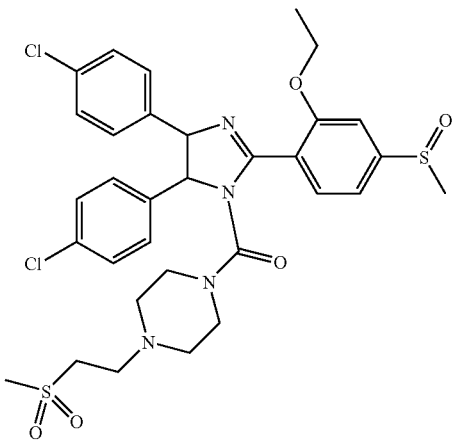

The title compound was prepared from meso-1,2-bis-(4-chlorophenyl)ethane-1,2-diamine, ethyl 4-methylsulfinyl-2-ethoxybenzoate (example 9a) and 1-(2-methanesulfonyl-ethyl)-piperazine bishydrochloride (example 23) in an analogous manner using the procedures described for examples 25, 29 and 31 (except chiral purification). LC-MS: [(M+H)+].

EXAMPLE 55

[4,5-Bis-(4-chloro-phenyl)-2-(2-ethoxy-4-methanesulfonyl-phenyl)-4,5-dihydro-imidazol-1-yl]-[4-(2-methanesulfonyl-ethyl)-piperazin-1-yl]-methanone

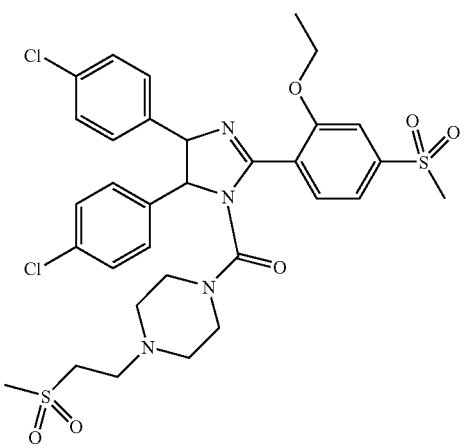

The title compound was prepared from meso-1,2-bis-(4-chlorophenyl)ethane-1,2-diamine, ethyl 4-methylsulfonyl-2-ethoxybenzoate (example 9b) and 1-(2-methanesulfonyl-ethyl)piperazine bishydrochloride (example 23) in an analogous manner using the procedures described for examples 25, 29 and 31 (except chiral purification). LC-MS: [(M+H)+].

EXAMPLE 56

[4,5-Bis-(4-chloro-phenyl)-2-(2-ethoxy-4-methane-sulfinyl-phenyl)-4,5-dihydro-imidazol-1-yl]-[4-(2-hydroxy-ethyl)-piperazin-1-yl]-methanone

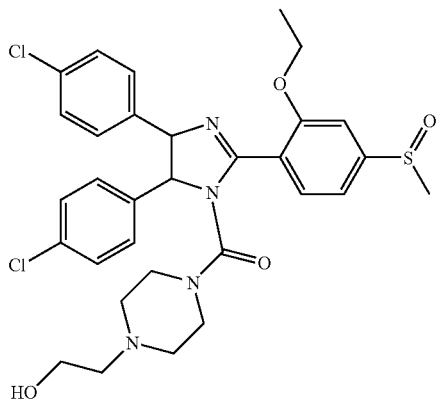

The title compound was prepared from meso-1,2-bis-(4-chlorophenyl)ethane-1,2-diamine, ethyl 4-methylsulfinyl-2-ethoxybenzoate (example 9a) and 1-(2-hydroxy-ethyl)-piperazine (Aldrich) in an analogous manner using the procedures described for examples 25, 29 and 31 (except chiral purification). LC-MS: [(M+H)$^+$].

EXAMPLE 57

[4,5-Bis-(4-chloro-phenyl)-2-(2-ethoxy-4-methane-sulfonyl-phenyl)-4,5-dihydro-imidazol-1-yl]-[4-(2-hydroxy-ethyl)-piperazin-1-yl]-methanone

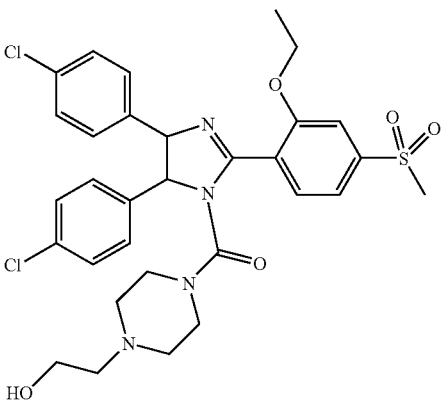

The title compound was prepared from meso-1,2-bis-(4-chlorophenyl)ethane-1,2-diamine, ethyl 4-methylsulfonyl-2-ethoxybenzoate (example 9b) and 1-(2-hydroxy-ethyl)-piperazine (Aldrich) in an analogous manner using the procedures described for examples 25, 29 and 31 (except chiral purification). LC-MS: [(M+H)$^+$].

EXAMPLE 58

1-[(4S,5R)-4,5-Bis-(4-chloro-phenyl)-2-(4-cyano-2-ethoxy-phenyl)-4,5-dihydro-imidazole-1-carbonyl]-piperidine-4-carboxylic acid amide

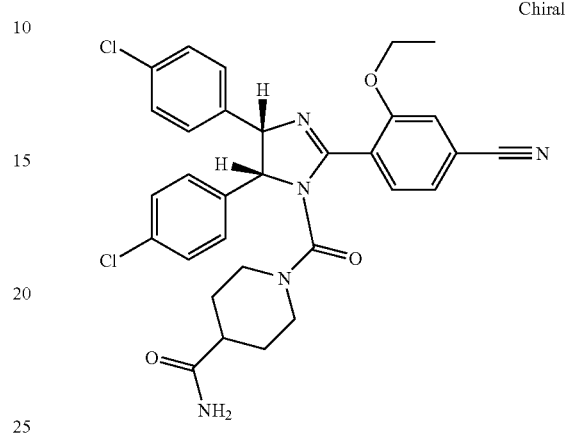

The title compound was prepared from 4-[4,5-bis-(4-chloro-phenyl)-4,5-dihydro-1H-imidazol-2-yl]-3-ethoxy-benzonitrile (example 25) and piperidine-4-carboxylic acid amide (Aldrich) following successively the procedures described for examples 29 and 31. LC-MS: 590.3 [(M+H)$^+$].

EXAMPLE 59

4-{(4S,5R)-4,5-Bis-(4-chloro-phenyl)-1-[4-(3,5-dimethyl-isoxazole-4-carbonyl)-piperazine-1-carbonyl]-4,5-dihydro-1H-imidazol-2-yl}-3-ethoxy-benzonitrile

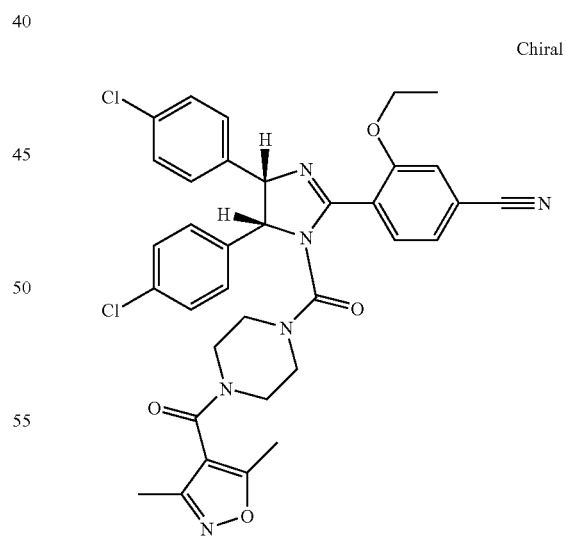

The title compound was prepared from 4-[4,5-bis-(4-chloro-phenyl)-4,5-dihydro-1H-imidazol-2-yl]-3-ethoxy-benzonitrile (example 25) and (3,5-dimethyl-isoxazol-4-yl)-piperazin-1-yl-methanone (example 19) following successively the procedures described for examples 29 and 31. LC-MS: 671.4 [(M+H)$^+$].

EXAMPLE 60

4-[(4S,5R)-4,5-Bis-(4-chloro-phenyl)-1-(4-cyclopropanecarbonyl-piperazine-1-carbonyl)-4,5-dihydro-1H-imidazol-2-yl]-3-ethoxy-benzonitrile Chiral

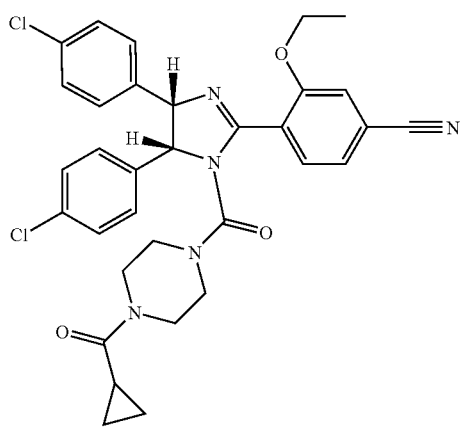

The title compound was prepared from 4-[4,5-bis-(4-chloro-phenyl)-4,5-dihydro-1H-imidazol-2-yl]-3-ethoxy-benzonitrile (example 25) and cyclopropyl-piperazin-1-yl-methanone (example 19) following successively the procedures described for examples 29 and 31. LC-MS: 616.3 [(M+H)$^+$].

EXAMPLE 61

4-{(4S,5R)-4,5-Bis-(4-chloro-phenyl)-1-[4-(3-methyl-but-2-enoyl)-piperazine-1-carbonyl]-4,5-dihydro-1H-imidazol-2-yl}-3-ethoxy-benzonitrile Chiral

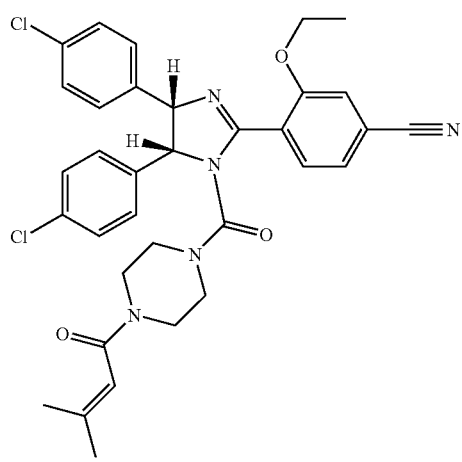

The title compound was prepared from 4-[4,5-bis-(4-chloro-phenyl)-4,5-dihydro-1H-imidazol-2-yl]-3-ethoxy-benzonitrile (example 25) and 3-methyl-1-piperazin-1-yl-but-2-en-1-one (example 19) following successively the procedures described for examples 29 and 31. LC-MS: 630.3 [(M+H)$^+$].

EXAMPLE 62

4-{(4S,5R)-4,5-Bis-(4-chloro-phenyl)-1-[4-(3,5-dimethyl-isoxazole-4-sulfonyl)-piperazine-1-carbonyl]-4,5-dihydro-1H-imidazol-2-yl}-3-ethoxy-benzonitrile Chiral

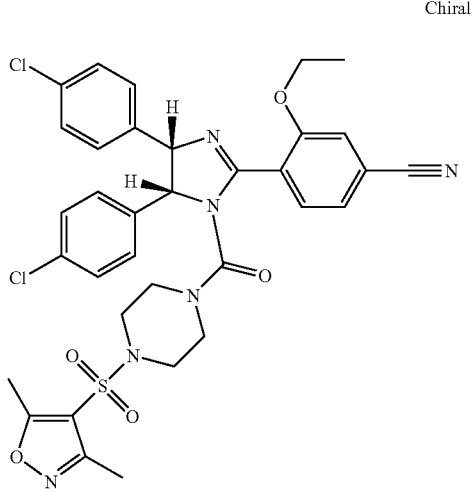

The title compound was prepared from 4-[4,5-bis-(4-chloro-phenyl)-4,5-dihydro-1H-imidazol-2-yl]-3-ethoxy-benzonitrile (example 25) and 1-(3,5-dimethyl-isoxazole-4-sulfonyl)-piperazine (example 20) following successively the procedures described for examples 29 and 31. LC-MS: 707.2 [(M+H)$^+$].

EXAMPLE 63

4-{(4S,5R)-4,5-Bis-(4-chloro-phenyl)-1-[4-(2-hydroxy-ethyl)-piperazine-1-carbonyl]-4,5-dihydro-1H-imidazol-2-yl}-3-ethoxy-benzonitrile Chiral

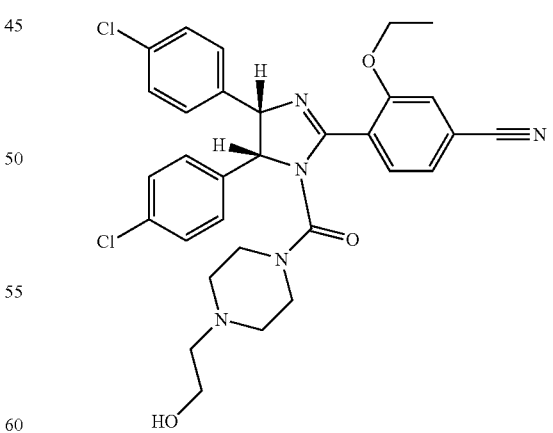

The title compound was prepared from 4-[4,5-bis-(4-chloro-phenyl)-4,5-dihydro-1H-imidazol-2-yl]-3-ethoxy-benzonitrile (example 25) and 1-(2-hydroxy-ethyl)-piperazine (Aldrich) following successively the procedures described for examples 29 and 31. LC-MS: 592.3 [(M+H)$^+$].

EXAMPLE 64

4-{(4S,5R)-4,5-Bis-(4-chloro-phenyl)-1-[4-(2-cyano-ethyl)-piperazine-1-carbonyl]-4,5-dihydro-1H-imidazol-2-yl}-3-ethoxy-benzonitrile

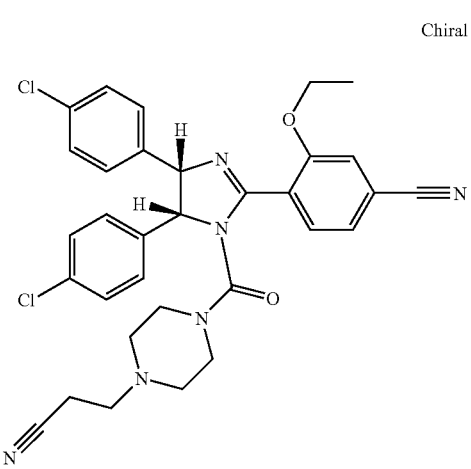

The title compound was prepared from 4-[4,5-bis-(4-chloro-phenyl)-4,5-dihydro-1H-imidazol-2-yl]-3-ethoxy-benzonitrile (example 25) and 3-piperazin-1-yl-propionitrile (example 22f) following successively the procedures described for examples 29 and 31. LC-MS: 601.2 [(M+H)$^+$].

EXAMPLE 65

4-{(4S,5R)-4,5-Bis-(4-chloro-phenyl)-1-[4-(2-methoxy-ethyl)-piperazine-1-carbonyl]-4,5-dihydro-1H-imidazol-2-yl}-3-ethoxy-benzonitrile

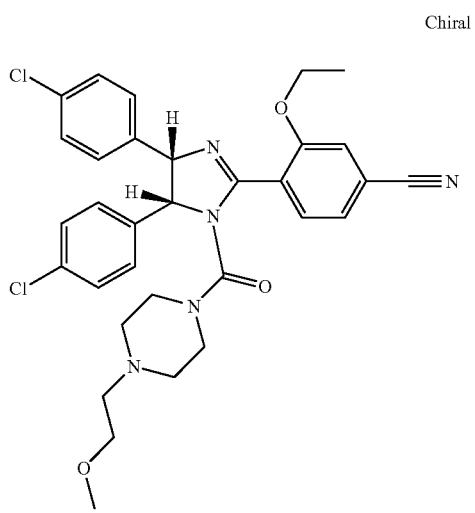

The title compound was prepared from 4-[4,5-bis-(4-chloro-phenyl)-4,5-dihydro-1H-imidazol-2-yl]-3-ethoxy-benzonitrile (example 25) and 1-(2-hydroxy-ethyl)-piperazine (Aldrich) following successively the procedures described for examples 29 and 31. LC-MS: 606.2 [(M+H)$^+$].

EXAMPLE 66

4-((4S,5R)-4,5-Bis-(4-chloro-phenyl)-1-{4-[2-(3-oxo-piperazin-1-yl)-acetyl]-piperazine-1-carbonyl}-4,5-dihydro-1H-imidazol-2-yl)-3-ethoxy-benzonitrile

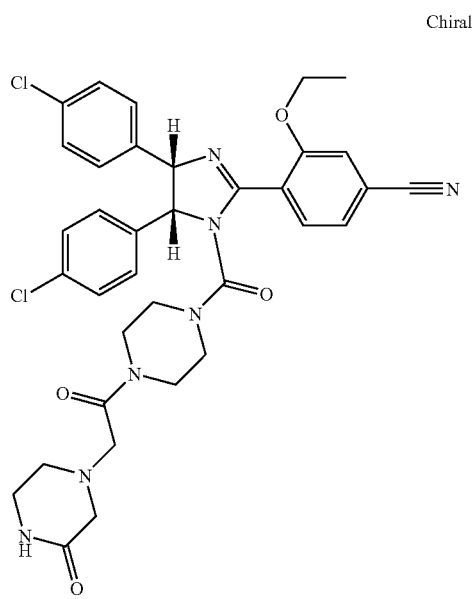

The title compound was prepared from 4-[4,5-bis-(4-chloro-phenyl)-4,5-dihydro-1H-imidazol-2-yl]-3-ethoxy-benzonitrile (example 25) and 2-piperazinone (Avocado Organics) following successively the procedures described for examples 29 and 31. LC-MS: 688.3 [(M+H)$^+$].

EXAMPLE 67

1-[(4S,5R)-4,5-Bis-(4-chloro-phenyl)-2-(4-cyano-2-ethoxy-phenyl)-4,5-dihydro-imidazole-1-carbonyl]-piperidine-3-carboxylic acid amide

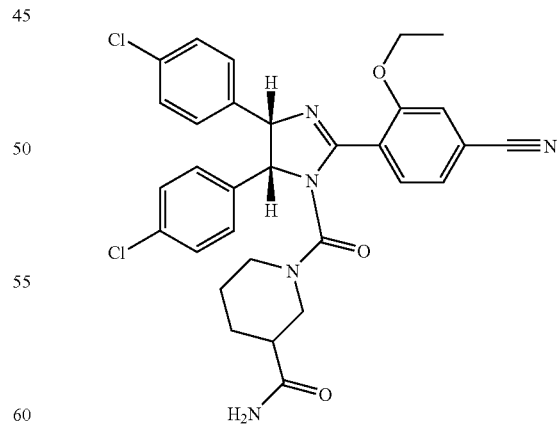

The title compound was prepared from 4-[4,5-bis-(4-chloro-phenyl)-4,5-dihydro-1H-imidazol-2-yl]-3-ethoxy-benzonitrile (example 25) and piperidine-3-carboxylic acid amide (Aldrich) following successively the procedures described for examples 29 and 31. LC-MS: 590.3 [(M+H)$^+$].

EXAMPLE 68

4-[(4S,5R)-1-{4-[2-(4-Acetyl-piperazin-1-yl)-2-oxo-ethyl]-piperazine-1-carbonyl}-4,5-bis-(4-chloro-phenyl)-4,5-dihydro-1H-imidazol-2-yl]-3-ethoxy-benzonitrile

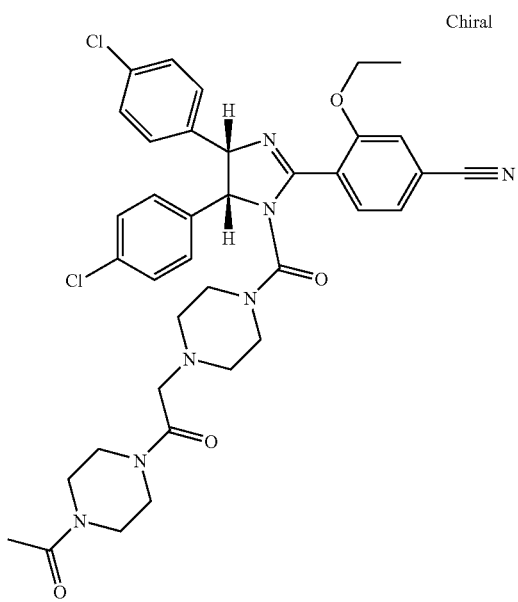

The title compound was prepared from 4-[4,5-bis-(4-chloro-phenyl)-4,5-dihydro-1H-imidazol-2-yl]-3-ethoxy-benzonitrile (example 25) and 1-acetylpiperazine (Aldrich) following successively the procedures described for examples 29 and 31. LC-MS: 716.2 [(M+H)$^+$].

EXAMPLE 69

2-{4-[(4S,5R)-4,5-Bis-(4-chloro-phenyl)-2-(4-cyano-2-ethoxy-phenyl)-4,5-dihydro-imidazole-1-carbonyl]-piperazin-1-yl}-N-(2-methoxy-1-methyl-ethyl)-acetamide

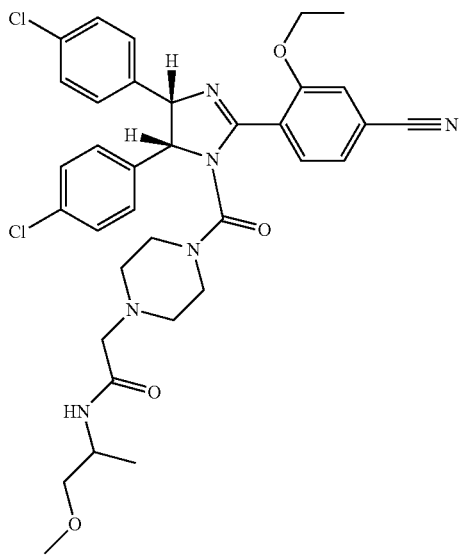

The title compound was prepared from 4-[4,5-bis-(4-chloro-phenyl)-4,5-dihydro-1H-imidazol-2-yl]-3-ethoxy-benzonitrile (example 25) and N-(2-methoxy-1-methyl-ethyl)-2-piperazin-1-yl-acetamide (example 21) following successively the procedures described for examples 29 and 31. LC-MS: 677.3 [(M+H)$^+$].

EXAMPLE 70

4-[(4S,5R)-4,5-Bis-(4-chloro-phenyl)-1-(4-hydroxymethyl-piperidine-1-carbonyl)-4,5-dihydro-1H-imidazol-2-yl]-3-ethoxy-benzonitrile

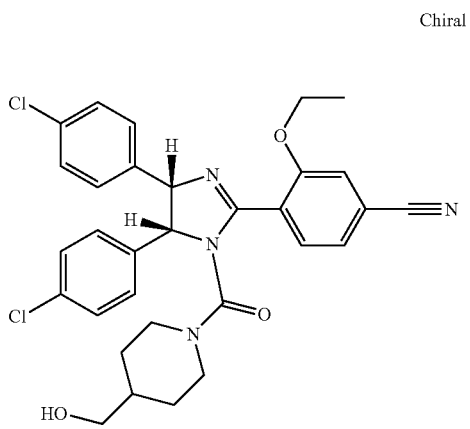

The title compound was prepared from 4-[4,5-bis-(4-chloro-phenyl)-4,5-dihydro-1H-imidazol-2-yl]-3-ethoxy-benzonitrile (example 25) and 4-piperidinemethanol (Aldrich) following successively the procedures described for examples 29 and 31. LC-MS: 577.2 [(M+H)$^+$].

EXAMPLE 71

4-[(4S,5R)-4,5-Bis-(4-chloro-phenyl)-1-(3-hydroxy-piperidine-1-carbonyl)-4,5-dihydro-1H-imidazol-2-yl]-3-ethoxy-benzonitrile

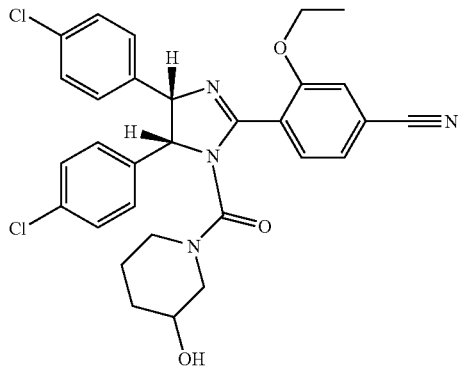

The title compound was prepared from 4-[4,5-bis-(4-chloro-phenyl)-4,5-dihydro-1H-imidazol-2-yl]-3-ethoxy-benzonitrile (example 25) and 3-hydroxypiperidine (Aldrich) following successively the procedures described for examples 29 and 31. LC-MS: 563.3 [(M+H)$^+$].

EXAMPLE 72

4-[(4S,5R)-4,5-Bis-(4-chloro-phenyl)-1-(3-oxo-piperazine-1-carbonyl)-4,5-dihydro-1H-imidazol-2-yl]-3-ethoxy-benzonitrile

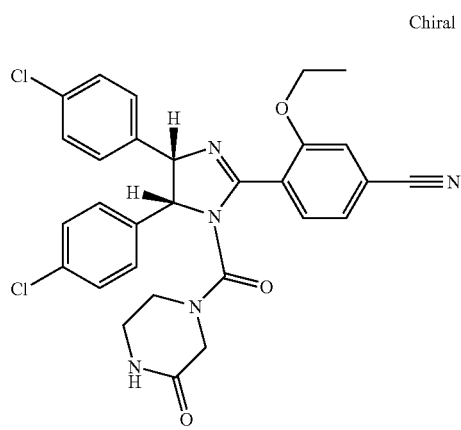

The title compound was prepared from 4-[4,5-bis-(4-chloro-phenyl)-4,5-dihydro-1H-imidazol-2-yl]-3-ethoxy-benzonitrile (example 25) and 2-piperazinone (Avocado Organics) following successively the procedures described for examples 29 and 31. LC-MS: 562.3 [(M+H)$^+$].

EXAMPLE 73

2-{4-[(4S,5R)-4,5-Bis-(4-chloro-phenyl)-2-(4-cyano-2-ethoxy-phenyl)-4,5-dihydro-imidazole-1-carbonyl]-piperazin-1-yl}-N,N-dimethyl-acetamide

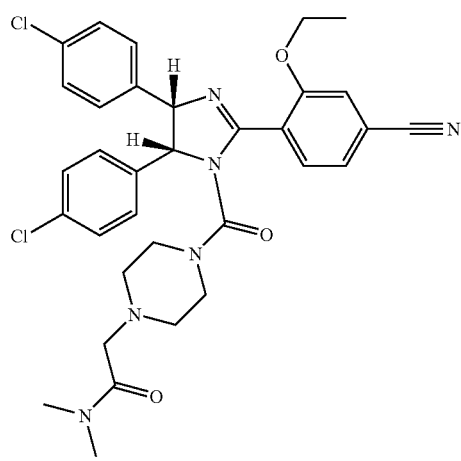

The title compound was prepared from 4-[4,5-bis-(4-chloro-phenyl)-4,5-dihydro-1H-imidazol-2-yl]-3-ethoxy-benzonitrile (example 25) and N,N-dimethyl-2-piperazin-1-yl-acetamide (Oakwood Products) following successively the procedures described for examples 29 and 31. LC-MS: 633.2 [(M+H)$^+$].

EXAMPLE 74

4-{(4S,5R)-4,5-Bis-(4-chloro-phenyl)-1-[4-(2-oxo-2-piperidin-1-yl-ethyl)-piperazine-1-carbonyl]-4,5-dihydro-1H-imidazol-2-yl}-3-ethoxy-benzonitrile

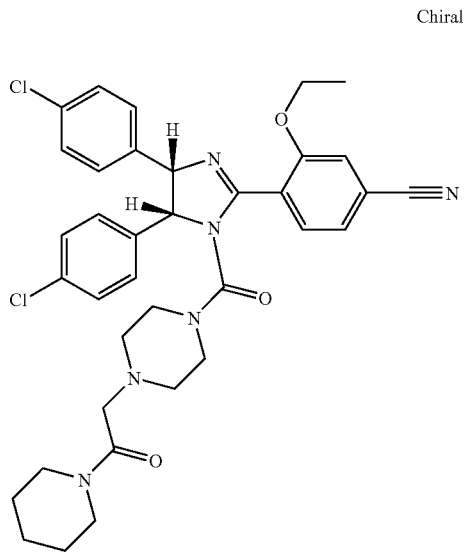

The title compound was prepared from 4-[4,5-bis-(4-chloro-phenyl)-4,5-dihydro-1H-imidazol-2-yl]-3-ethoxy-benzonitrile (example 25) and 2-piperazin-1-yl-1-piperidin-1-yl-ethanone (example 22i) following successively the procedures described for examples 29 and 31. LC-MS: 673.3 [(M+H)$^+$].

EXAMPLE 75

4-[(4S,5R)-4,5-Bis-(4-chloro-phenyl)-1-(4-ethanesulfonyl-piperazine-1-carbonyl)-4,5-dihydro-1H-imidazol-2-yl]-3-ethoxy-benzonitrile

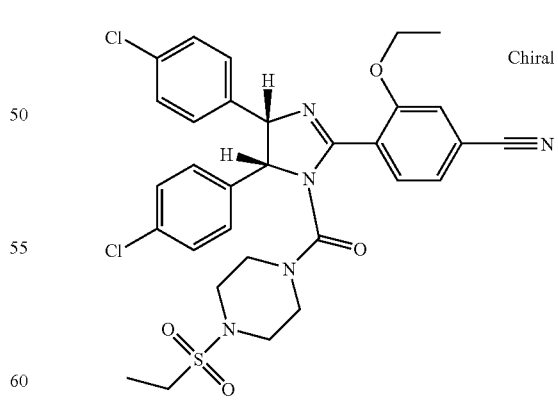

The title compound was prepared from 4-[4,5-bis-(4-chloro-phenyl)-4,5-dihydro-1H-imidazol-2-yl]-3-ethoxy-benzonitrile (example 25) and 1-ethanesulfonyl-piperazine (example 20) following successively the procedures described for examples 29 and 31. LC-MS: 640.1 [(M+H)$^+$].

EXAMPLE 76

1-[4,5-Bis-(4-chloro-phenyl)-2-(5-dimethylsulfamoyl-2-ethoxy-phenyl)-4,5-dihydro-imidazole-1-carbonyl]-piperidine-4-carboxylic acid amide

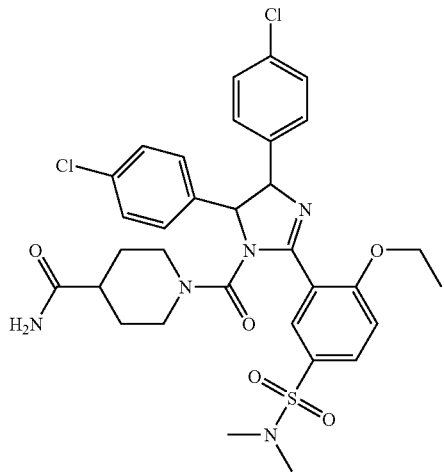

The title compound was prepared from meso-1,2-bis-(4-chlorophenyl)ethane-1,2-diamine, ethyl 2-ethoxy-5-(N,N-dimethylsulfonamide)benzoate (example 2) and piperidine-4-carboxylic acid amide (Aldrich) in an analogous manner using the procedures described for examples 25, 29 and 31 (except chiral purification). LC-MS: 672.4 [(M+H)+].

EXAMPLE 77

3-{4,5-Bis-(4-chloro-phenyl)-1-[4-(3,5-dimethyl-isoxazole-4-carbonyl)-piperazine-1-carbonyl]-4,5-dihydro-1H-imidazol-2-yl}-4-ethoxy-N,N-dimethyl-benzenesulfonamide

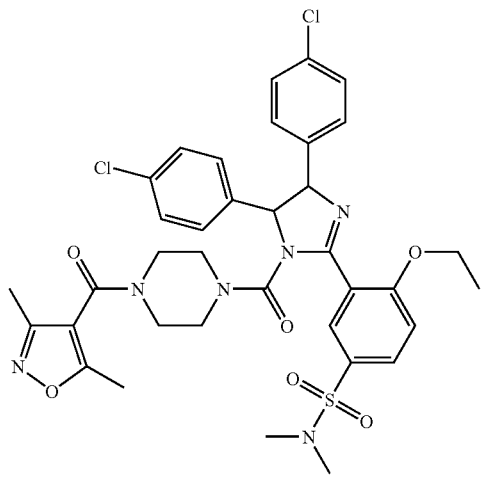

The title compound was prepared from meso-1,2-bis-(4-chlorophenyl)ethane-1,2-diamine, ethyl 2-ethoxy-5-(N,N-dimethylsulfonamide)benzoate (example 2) and (3,5-dimethyl-isoxazol-4-yl)-piperazin-1-yl-methanone (example 19) in an analogous manner using the procedures described for examples 25, 29 and 31 (except chiral purification). LC-MS: 753.3 [(M+H)+].

EXAMPLE 78

3-[4,5-Bis-(4-chloro-phenyl)-1-(4-cyclopropanecarbonyl-piperazine-1-carbonyl)-4,5-dihydro-1H-imidazol-2-yl]-4-ethoxy-N,N-dimethyl-benzenesulfonamide

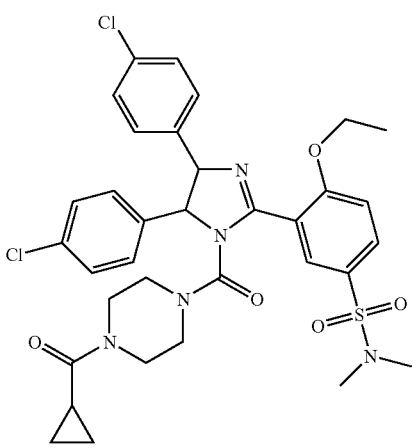

The title compound was prepared from meso-1,2-bis-(4-chlorophenyl)ethane-1,2-diamine, ethyl 2-ethoxy-5-(N,N-dimethylsulfonamide)benzoate (example 2) and cyclopropyl-piperazin-1-yl-methanone (example 19) in an analogous manner using the procedures described for examples 25, 29 and 31 (except chiral purification). LC-MS: 698.4 [(M+H)+].

EXAMPLE 79

3-{4,5-Bis-(4-chloro-phenyl)-1-[4-(3-methyl-but-2-enoyl)-piperazine-1-carbonyl]-4,5-dihydro-1H-imidazol-2-yl}-4-ethoxy-N,N-dimethyl-benzenesulfonamide

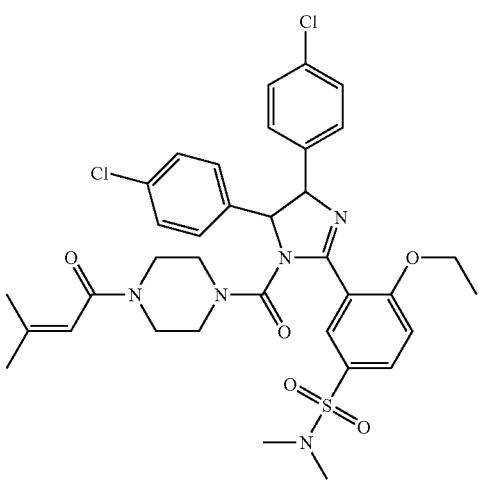

The title compound was prepared from meso-1,2-bis-(4-chlorophenyl)ethane-1,2-diamine, ethyl 2-ethoxy-5-(N,N-dimethylsulfonamide)benzoate (example 2) and 3-methyl-1-piperazin-1-yl-but-2-en-1-one (example 19) in an analogous manner using the procedures described for examples 25, 29 and 31 (except chiral purification). LC-MS: 712.3 [(M+H)+].

EXAMPLE 80

3-{4,5-Bis-(4-chloro-phenyl)-1-[4-(3,5-dimethyl-isoxazole-4-sulfonyl)-piperazine-1-carbonyl]-4,5-dihydro-1H-imidazol-2-yl}-4-ethoxy-N,N-dimethyl-benzenesulfonamide

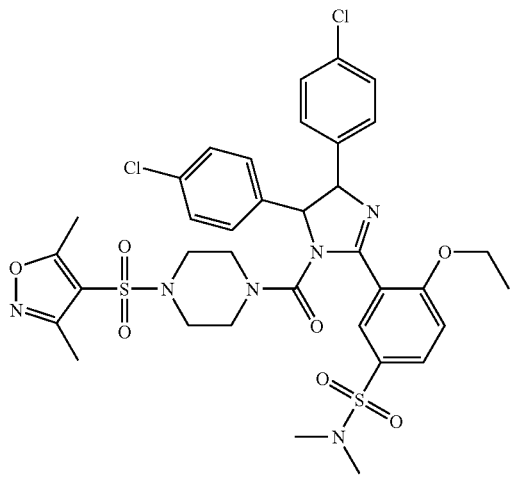

The title compound was prepared from meso-1,2-bis-(4-chlorophenyl)ethane-1,2-diamine, ethyl 2-ethoxy-5-(N,N-dimethylsulfonamide)benzoate (example 2) and 1-(3,5-dimethyl-isoxazole-4-sulfonyl)-piperazine (example 20) in an analogous manner using the procedures described for examples 25, 29 and 31 (except chiral purification). LC-MS: 789.3 [(M+H)$^+$].

EXAMPLE 81

3-{4,5-Bis-(4-chloro-phenyl)-1-[4-(2-cyano-ethyl)-piperazine-1-carbonyl]-4,5-dihydro-1H-imidazol-2-yl}-4-ethoxy-N,N-dimethyl-benzenesulfonamide

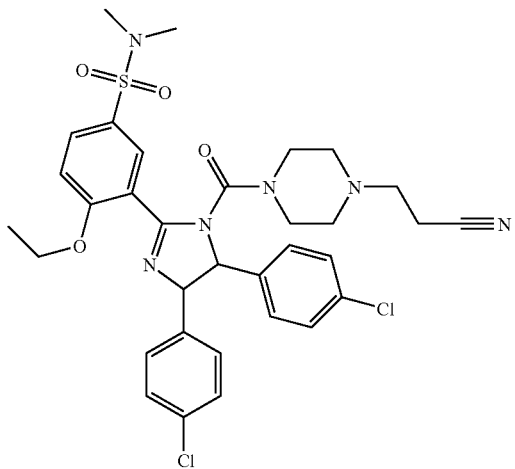

The title compound was prepared from meso-1,2-bis-(4-chlorophenyl)ethane-1,2-diamine, ethyl 2-ethoxy-5-(N,N-dimethylsulfonamide)benzoate (example 2) and 3-piperazin-1-yl-propionitrile (example 22f) in an analogous manner using the procedures described for examples 25, 29 and 31 (except chiral purification). LC-MS: 683.3 [(M+H)$^+$].

EXAMPLE 82

3-{4,5-Bis-(4-chloro-phenyl)-1-[4-(2-methoxy-ethyl)-piperazine-1-carbonyl]-4,5-dihydro-1H-imidazol-2-yl}-4-ethoxy-N,N-dimethyl-benzenesulfonamide

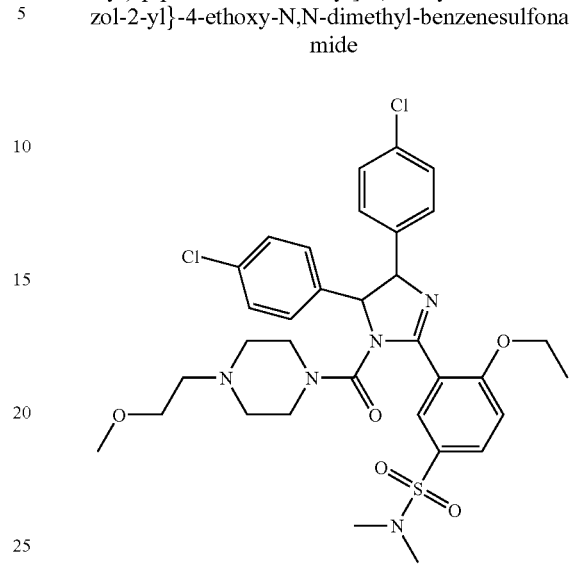

The title compound was prepared from meso-1,2-bis-(4-chlorophenyl)ethane-1,2-diamine, ethyl 2-ethoxy-5-(N,N-dimethylsulfonamide)benzoate (example 2) and 1-(2-hydroxy-ethyl)-piperazine (Aldrich) in an analogous manner using the procedures described for examples 25, 29 and 31 (except chiral purification). LC-MS: 688.2 [(M+H)$^+$].

EXAMPLE 83

3-(4,5-Bis-(4-chloro-phenyl)-1-{4-[2-(3-oxo-piperazin-1-yl)-acetyl]-piperazine-1-carbonyl}-4,5-dihydro-1H-imidazol-2-yl)-4-ethoxy-N,N-dimethyl-benzenesulfonamide

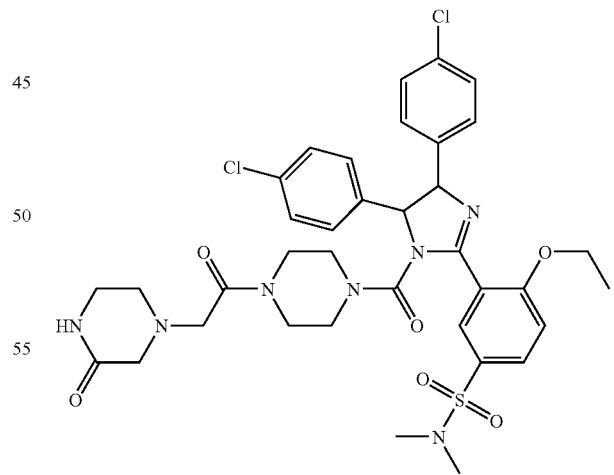

The title compound was prepared from meso-1,2-bis-(4-chlorophenyl)ethane-1,2-diamine, ethyl 2-ethoxy-5-(N,N-dimethylsulfonamide)benzoate (example 2) and 2-piperazinone (Avocado Organics) in an analogous manner using the procedures described for examples 25, 29 and 31 (except chiral purification). LC-MS: 770.3 [(M+H)$^+$].

EXAMPLE 84

2-{4-[4,5-Bis-(4-chloro-phenyl)-2-(5-dimethylsulfamoyl-2-ethoxy-phenyl)-4,5-dihydro-imidazole-1-carbonyl]-piperazin-1-yl}-N-methyl-acetamide

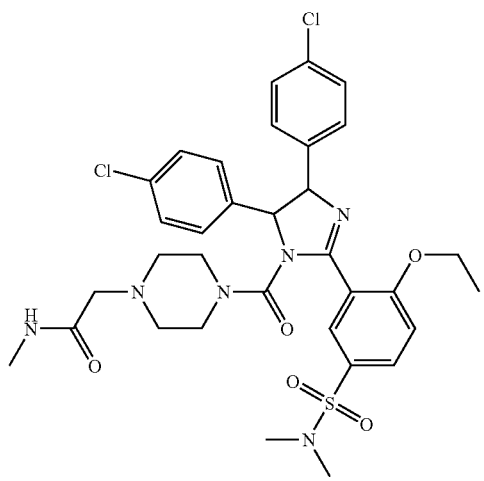

The title compound was prepared from meso-1,2-bis-(4-chlorophenyl)ethane-1,2-diamine, ethyl 2-ethoxy-5-(N,N-dimethylsulfonamide)benzoate (example 2) and N-methyl-2-piperazin-1-yl-acetamide (example 22h) in an analogous manner using the procedures described for examples 25, 29 and 31 (except chiral purification). LC-MS: 701.3 [(M+H)+].

EXAMPLE 85

1-[4,5-Bis-(4-chloro-phenyl)-2-(5-dimethylsulfamoyl-2-ethoxy-phenyl)-4,5-dihydro-imidazole-1-carbonyl]-piperidine-3-carboxylic acid amide

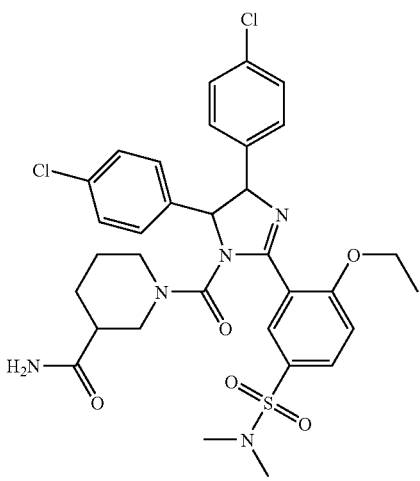

The title compound was prepared from meso-1,2-bis-(4-chlorophenyl)ethane-1,2-diamine, ethyl 2-ethoxy-5-(N,N-dimethylsulfonamide)benzoate (example 2) and piperidine-3-carboxylic acid amide (Aldrich) in an analogous manner using the procedures described for examples 25, 29 and 31 (except chiral purification). LC-MS: 672.3 [(M+H)+].

EXAMPLE 86

3-[1-{4-[2-(4-Acetyl-piperazin-1-yl)-2-oxo-ethyl]-piperazine-1-carbonyl}-4,5-bis-(4-chloro-phenyl)-4,5-dihydro-1H-imidazol-2-yl]-4-ethoxy-N,N-dimethyl-benzenesulfonamide

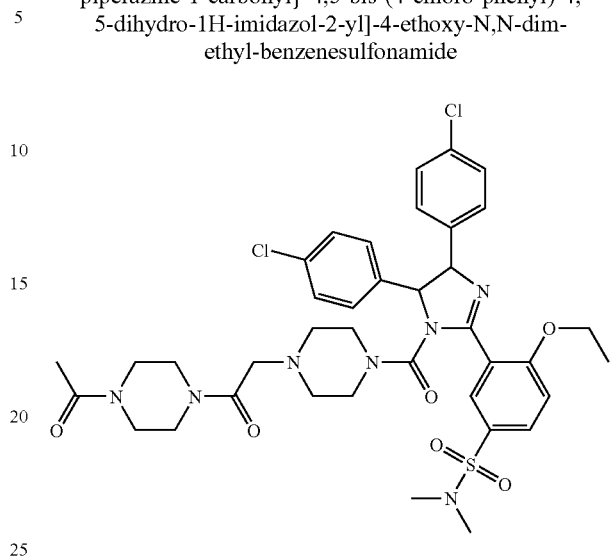

The title compound was prepared from meso-1,2-bis-(4-chlorophenyl)ethane-1,2-diamine, ethyl 2-ethoxy-5-(N,N-dimethylsulfonamide)benzoate (example 2) and 1-acetylpiperazine (Aldrich) in an analogous manner using the procedures described for examples 25, 29 and 31 (except chiral purification). LC-MS: 798.3 [(M+H)+].

EXAMPLE 87

2-{4-[4,5-Bis-(4-chloro-phenyl)-2-(5-dimethylsulfamoyl-2-ethoxy-phenyl)-4,5-dihydro-imidazole-1-carbonyl]-piperazin-1-yl}-N-(2-methoxy-1-methyl-ethyl)-acetamide

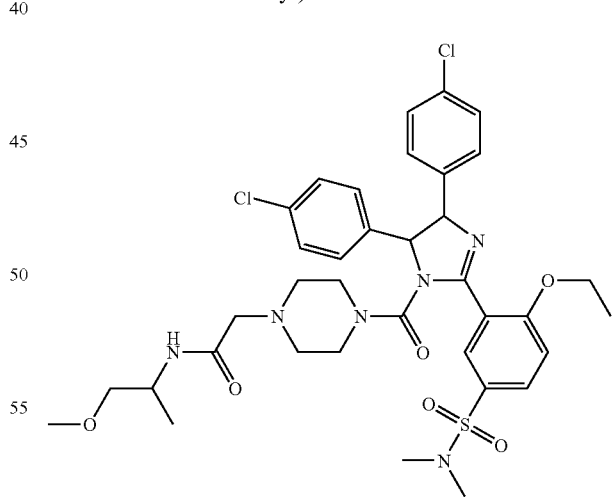

The title compound was prepared from meso-1,2-bis-(4-chlorophenyl)ethane-1,2-diamine, ethyl 2-ethoxy-5-(N,N-dimethylsulfonamide)benzoate (example 2) and N-(2-methoxy-1-methyl-ethyl)-2-piperazin-1-yl-acetamide (example 21) in an analogous manner using the procedures described for examples 25, 29 and 31 (except chiral purification). LC-MS: 759.4 [(M+H)+].

EXAMPLE 88

3-[4,5-Bis-(4-chloro-phenyl)-1-(4-hydroxymethyl-piperidine-1-carbonyl)-4,5-dihydro-1H-imidazol-2-yl]-4-ethoxy-N,N-dimethyl-benzenesulfonamide

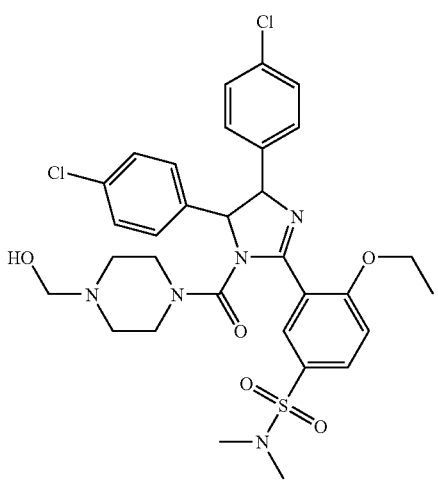

The title compound was prepared from meso-1,2-bis-(4-chlorophenyl)ethane-1,2-diamine, ethyl 2-ethoxy-5-(N,N-dimethylsulfonamide)benzoate (example 2) and 4-piperidinemethanol (Aldrich) in an analogous manner using the procedures described for examples 25, 29 and 31 (except chiral purification). LC-MS: 659.2 [(M+H)$^+$].

EXAMPLE 89

3-[4,5-Bis-(4-chloro-phenyl)-1-(3-hydroxy-piperidine-1-carbonyl)-4,5-dihydro-1H-imidazol-2-yl]-4-ethoxy-N,N-dimethyl-benzenesulfonamide

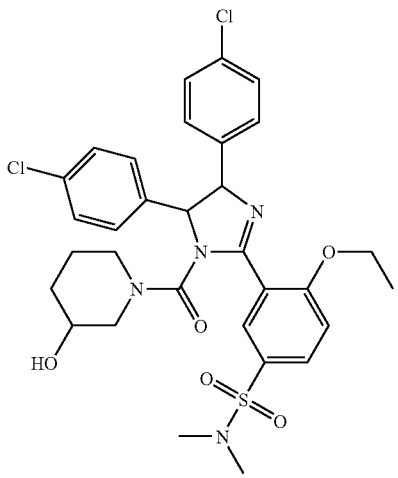

The title compound was prepared from meso-1,2-bis-(4-chlorophenyl)ethane-1,2-diamine, ethyl 2-ethoxy-5-(N,N-dimethylsulfonamide)benzoate (example 2) and 3-hydroxypiperidine (Aldrich) in an analogous manner using the procedures described for examples 25, 29 and 31 (except chiral purification). LC-MS: 645.3 [(M+H)$^+$].

EXAMPLE 90

2-{4-[4,5-Bis-(4-chloro-phenyl)-2-(5-dimethylsulfamoyl-2-ethoxy-phenyl)-4,5-dihydro-imidazole-1-carbonyl]-piperazin-1-yl}-N,N-dimethyl-acetamide

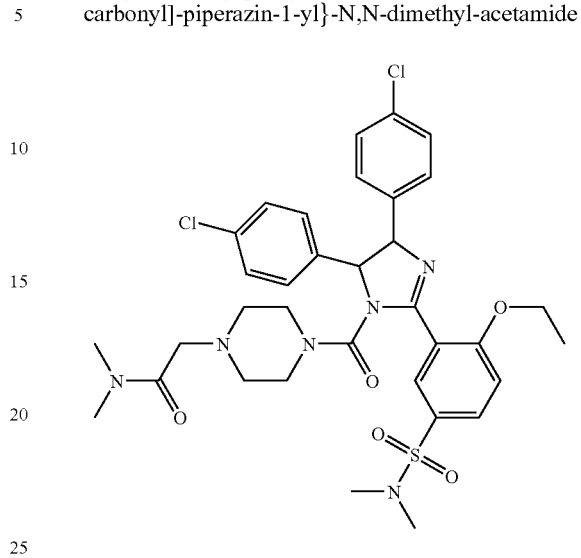

The title compound was prepared from meso-1,2-bis-(4-chlorophenyl)ethane-1,2-diamine, ethyl 2-ethoxy-5-(N,N-dimethylsulfonamide)benzoate (example 2) and N,N-dimethyl-2-piperazin-1-yl-acetamide (Oakwood Products) in an analogous manner using the procedures described for examples 25, 29 and 31 (except chiral purification). LC-MS: 715.1 [(M+H)$^+$].

EXAMPLE 91

3-{4,5-Bis-(4-chloro-phenyl)-1-[4-(2-morpholin-4-yl-2-oxo-ethyl)-piperazine-1-carbonyl]-4,5-dihydro-1H-imidazol-2-yl}-4-ethoxy-N,N-dimethyl-benzenesulfonamide

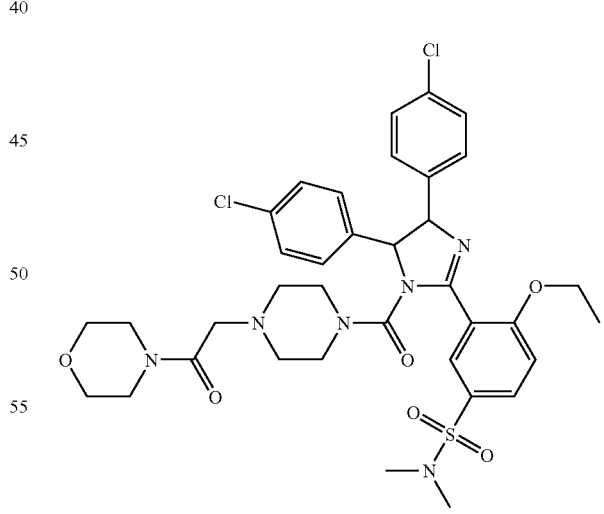

The title compound was prepared from meso-1,2-bis-(4-chlorophenyl)ethane-1,2-diamine, ethyl 2-ethoxy-5-(N,N-dimethylsulfonamide)benzoate (example 2) and 1-morpholin-4-yl-2-piperazin-1-yl-ethanone (Oakwood Products) in an analogous manner using the procedures described for examples 25, 29 and 31 (except chiral purification). LC-MS: 757.3 [(M+H)$^+$].

EXAMPLE 92

3-{4,5-Bis-(4-chloro-phenyl)-1-[4-(2-oxo-2-piperidin-1-yl-ethyl)-piperazine-1-carbonyl]-4,5-dihydro-1H-imidazol-2-yl}-4-ethoxy-N,N-dimethyl-benzenesulfonamide

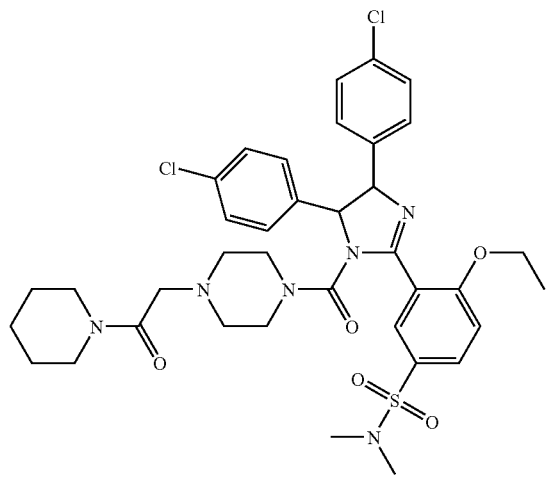

The title compound was prepared from meso-1,2-bis-(4-chlorophenyl)ethane-1,2-diamine, ethyl 2-ethoxy-5-(N,N-dimethylsulfonamide)benzoate (example 2) and 2-piperazin-1-yl-1-piperidin-1-yl-ethanone (example 22i) in an analogous manner using the procedures described for examples 25, 29 and 31 (except chiral purification). LC-MS: 755.3 [(M+H)$^+$].

EXAMPLE 93

3-[4,5-Bis-(4-chloro-phenyl)-1-(4-ethanesulfonyl-piperazine-1-carbonyl)-4,5-dihydro-1H-imidazol-2-yl]-4-ethoxy-N,N-dimethyl-benzenesulfonamide

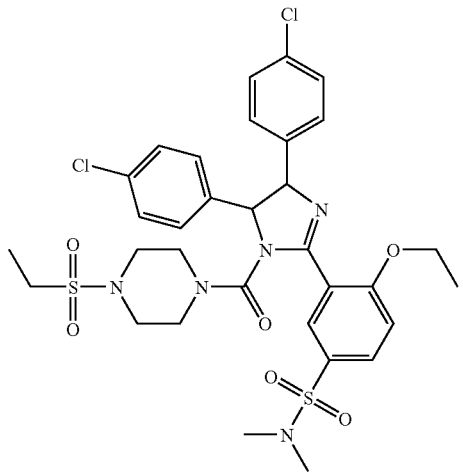

The title compound was prepared from meso-1,2-bis-(4-chlorophenyl)ethane-1,2-diamine, ethyl 2-ethoxy-5-(N,N-dimethylsulfonamide)benzoate (example 2) and 1-ethanesulfonyl-piperazine (example 20) in an analogous manner using the procedures described for examples 25, 29 and 31 (except chiral purification). LC-MS: 722.3 [(M+H)$^+$].

EXAMPLE 94

3-[4,5-Bis-(4-chloro-phenyl)-1-(3-oxo-piperazine-1-carbonyl)-4,5-dihydro-1H-imidazol-2-yl]-4-ethoxy-N-isobutyl-N-methyl-benzenesulfonamide

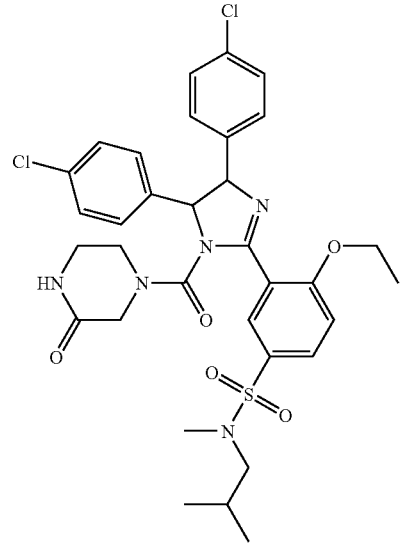

The title compound was prepared from meso-1,2-bis-(4-chlorophenyl)ethane-1,2-diamine, ethyl 2-ethoxy-5-(isobutyl-methyl-sulfamoyl)-benzoate (example 2) and 2-piperazinone (Avocado Organics) in an analogous manner using the procedures described for examples 25, 29 and 31 (except chiral purification). LC-MS: 686.2 [(M+H)$^+$].

EXAMPLE 95

3-{4,5-Bis-(4-chloro-phenyl)-1-[4-(2-methanesulfonyl-ethyl)-piperazine-1-carbonyl]-4,5-dihydro-1H-imidazol-2-yl}-4-ethoxy-N-isobutyl-N-methyl-benzenesulfonamide

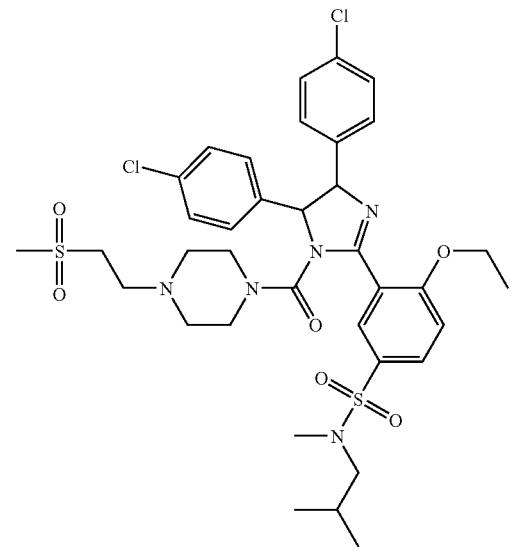

The title compound was prepared from meso-1,2-bis-(4-chlorophenyl)ethane-1,2-diamine, ethyl 2-ethoxy-5-(isobutyl-methyl-sulfamoyl)-benzoate (example 2) and 1-(2-methanesulfonylethyl)-piperazine bishydrochloride (example 23) in an analogous manner using the procedures described for examples 25, 29 and 31 (except chiral purification). LC-MS: 778.5 [(M+H)$^+$].

EXAMPLE 96

2-(4-{4,5-Bis-(4-chloro-phenyl)-2-[2-ethoxy-5-(isobutyl-methyl-sulfamoyl)-phenyl]-4,5-dihydro-imidazole-1-carbonyl}-piperazin-1-yl-N,N-dimethyl-acetamide

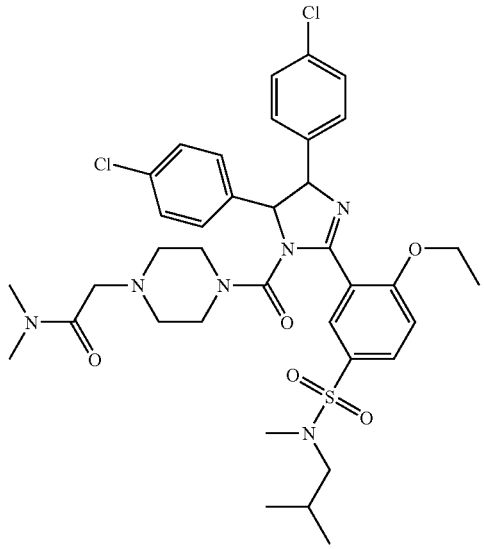

The title compound was prepared from meso-1,2-bis-(4-chlorophenyl)ethane-1,2-diamine, ethyl 2-ethoxy-5-(isobutyl-methyl-sulfamoyl)-benzoate (example 2) and N,N-dimethyl-2-piperazin-1-yl-acetamide (Oakwood Products) in an analogous manner using the procedures described for examples 25, 29 and 31 (except chiral purification). LC-MS: 757.3 [(M+H)+].

EXAMPLE 97

3-[4,5-Bis-(4-chloro-phenyl)-1-(4-ethanesulfonyl-piperazine-1-carbonyl)-4,5-dihydro-1H-imidazol-2-yl]-4-ethoxy-N-isobutyl-N-methyl-benzenesulfonamide

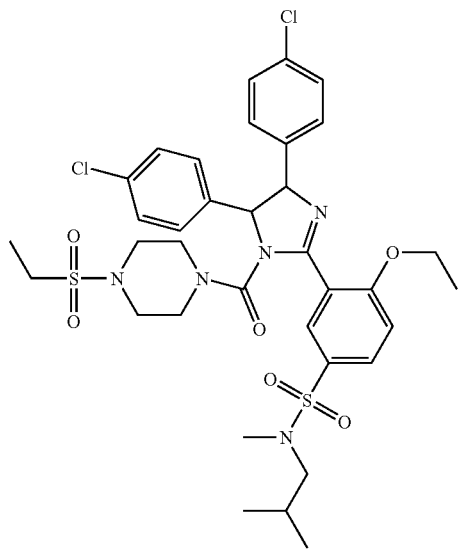

The title compound was prepared from meso-1,2-bis-(4-chlorophenyl)ethane-1,2-diamine, ethyl 2-ethoxy-5-(isobutyl-methyl-sulfamoyl)-benzoate (example 2) and 1-ethanesulfonyl-piperazine (example 20) in an analogous manner using the procedures described for examples 25, 29 and 31 (except chiral purification). LC-MS: 764.4 [(M+H)+].

EXAMPLE 98

3-(4,5-Bis-(4-chloro-phenyl)-1-{4-[2-(3-oxo-piperazin-1-yl)-acetyl]-piperazine-1-carbonyl}-4,5-dihydro-1H-imidazol-2-yl)-4-ethoxy-N-isobutyl-N-methyl-benzenesulfonamide

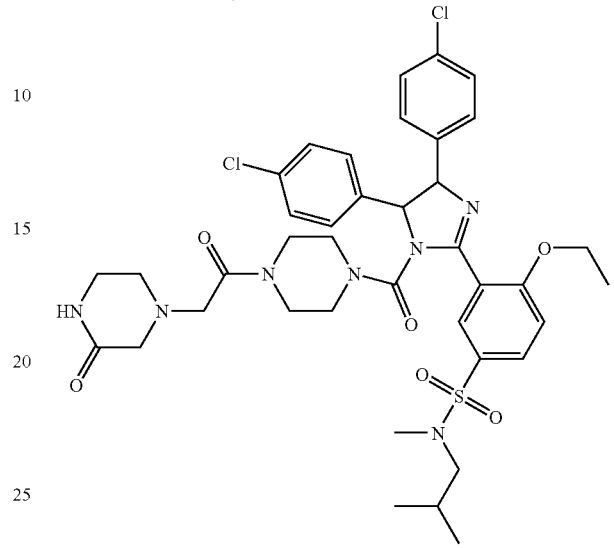

The title compound was prepared from meso-1,2-bis-(4-chlorophenyl)ethane-1,2-diamine, ethyl 2-ethoxy-5-(isobutyl-methyl-sulfamoyl)-benzoate (example 2) and 2-piperazinone (Avocado Organics) in an analogous manner using the procedures described for examples 25, 29 and 31 (except chiral purification). LC-MS: 812.3 [(M+H)+].

EXAMPLE 99

2-(4-{4,5-Bis-(4-chloro-phenyl)-2-[2-ethoxy-5-(isobutyl-methyl-sulfamoyl)-phenyl]-4,5-dihydro-imidazole-1-carbonyl}-piperazin-1-yl)-N-(2-methoxy-1-methyl-ethyl)-acetamide

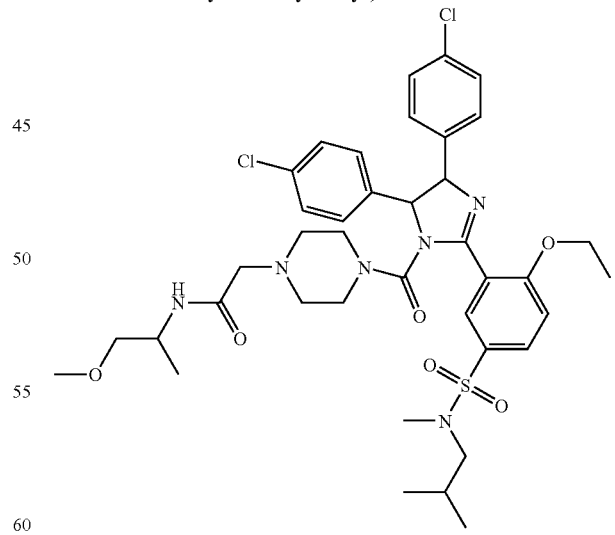

The title compound was prepared from meso-1,2-bis-(4-chlorophenyl)ethane-1,2-diamine, ethyl 2-ethoxy-5-(isobutyl-methyl-sulfamoyl)-benzoate (example 2) and N-(2-methoxy-1-methyl-ethyl)-2-piperazin-1-yl-acetamide (example 21) in an analogous manner using the procedures described for examples 25, 29 and 31 (except chiral purification). LC-MS: 801.4 [(M+H)+].

EXAMPLE 100

3-{4,5-Bis-(4-chloro-phenyl)-1-[4-(2-hydroxy-ethyl)-piperazine-1-carbonyl]-4,5-dihydro-1H-imidazol-2-yl}-4-ethoxy-N-isobutyl-N-methyl-benzenesulfonamide

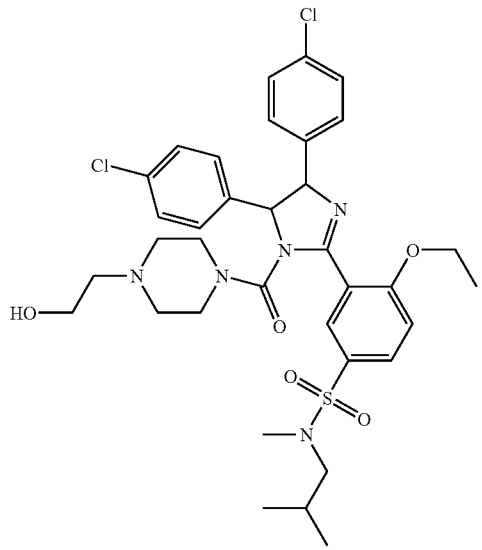

The title compound was prepared from meso-1,2-bis-(4-chlorophenyl)ethane-1,2-diamine, ethyl 2-ethoxy-5-(isobutyl-methyl-sulfamoyl)-benzoate (example 2) and 1-(2-hydroxy-ethyl)-piperazine (Aldrich) in an analogous manner using the procedures described for examples 25, 29 and 31 (except chiral purification). LC-MS: 716.2 [(M+H)$^+$].

EXAMPLE 101

2-(4-{4,5-Bis-(4-chloro-phenyl)-2-[2-ethoxy-5-(isobutyl-methyl-sulfamoyl)-phenyl]-4,5-dihydro-imidazole-1-carbonyl}-piperazin-1-yl)-N-methyl-acetamide

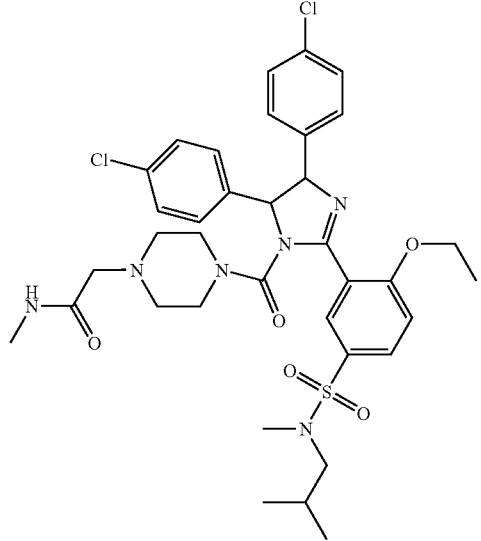

The title compound was prepared from meso-1,2-bis-(4-chlorophenyl)ethane-1,2-diamine, ethyl 2-ethoxy-5-(isobutyl-methyl-sulfamoyl)-benzoate (example 2) and N-methyl-2-piperazin-1-yl-acetamide (example 22h) in an analogous manner using the procedures described for examples 25, 29 and 31 (except chiral purification). LC-MS: 743.3 [(M+H)$^+$].

EXAMPLE 102

3-{4,5-Bis-(4-chloro-phenyl)-1-[4-(2-morpholin-4-yl-2-oxo-ethyl)-piperazine-1-carbonyl]-4,5-dihydro-1H-imidazol-2-yl}-4-ethoxy-N-isobutyl-N-methyl-benzenesulfonamide

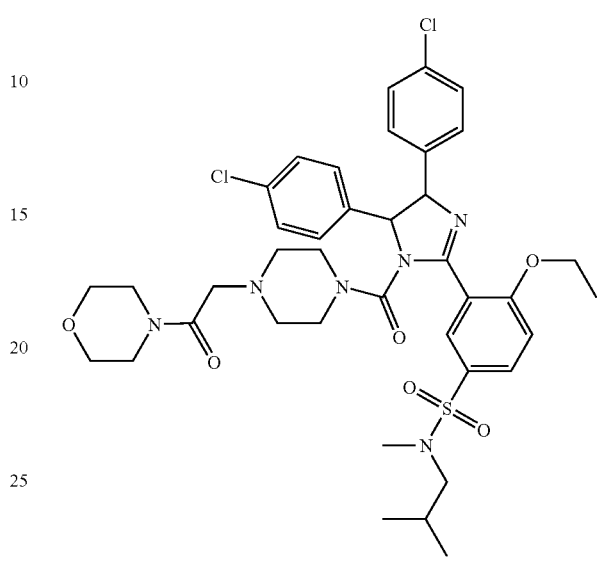

The title compound was prepared from meso-1,2-bis-(4-chlorophenyl)ethane-1,2-diamine, ethyl 2-ethoxy-5-(isobutyl-methyl-sulfamoyl)-benzoate (example 2) and 1-morpholin-4-yl-2-piperazin-1-yl-ethanone (Oakwood Products) in an analogous manner using the procedures described for examples 25, 29 and 31 (except chiral purification). LC-MS: 799.4 [(M+H)$^+$].

EXAMPLE 103

3-[4,5-Bis-(4-chloro-phenyl)-1-(4-cyclopropanecarbonyl-piperazine-1-carbonyl)-4,5-dihydro-1H-imidazol-2-yl]-4-ethoxy-N-isobutyl-N-methyl-benzenesulfonamide

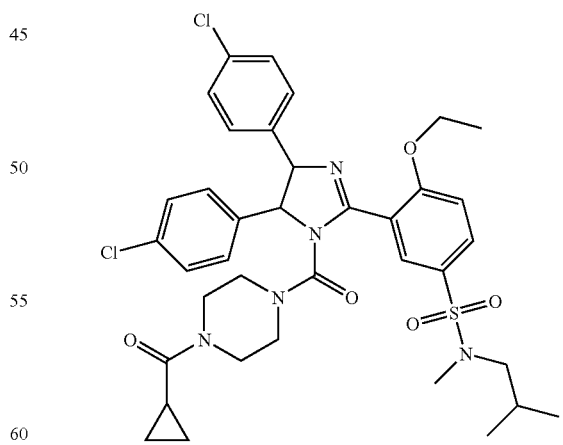

The title compound was prepared from meso-1,2-bis-(4-chlorophenyl)ethane-1,2-diamine, ethyl 2-ethoxy-5-(isobutyl-methyl-sulfamoyl)-benzoate (example 2) and cyclopropyl-piperazin-1-yl-methanone (example 19) in an analogous manner using the procedures described for examples 25, 29 and 31 (except chiral purification). LC-MS: 740.3 [(M+H)$^+$].

EXAMPLE 104

3-{4,5-Bis-(4-chloro-phenyl)-1-[4-(2-methoxy-ethyl)-piperazine-1-carbonyl]-4,5-dihydro-1H-imidazol-2-yl}-4-ethoxy-N-isobutyl-N-methyl-benzenesulfonamide

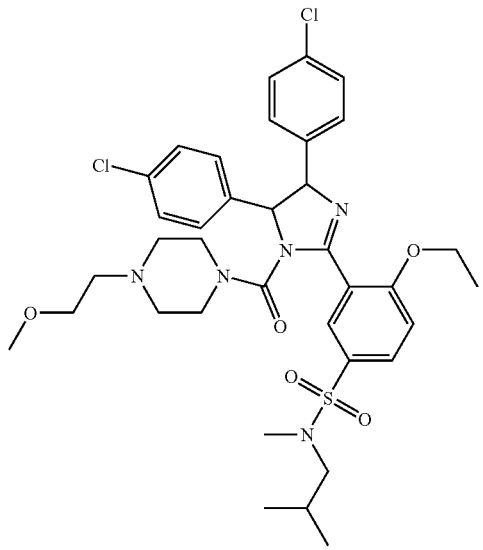

The title compound was prepared from meso-1,2-bis-(4-chlorophenyl)ethane-1,2-diamine, ethyl 2-ethoxy-5-(isobutyl-methyl-sulfamoyl)-benzoate (example 2) and 1-(2-hydroxy-ethyl)-piperazine (Aldrich) in an analogous manner using the procedures described for examples 25, 29 and 31 (except chiral purification). LC-MS: 730.3 [(M+H)+].

EXAMPLE 105

3-[4,5-Bis-(4-chloro-phenyl)-1-(3-oxo-piperazine-1-carbonyl)-4,5-dihydro-1H-imidazol-2-yl]-4-ethoxy-N,N-bis-(2-methoxy-ethyl)-benzenesulfonamide

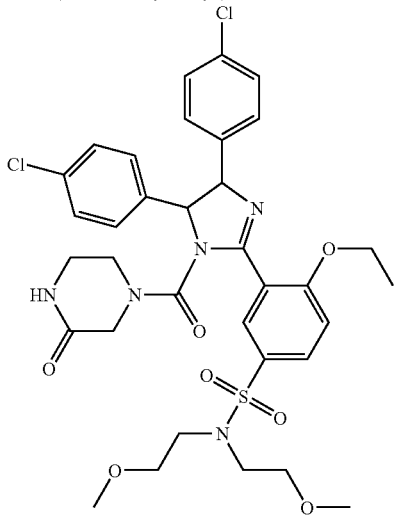

The title compound was prepared from meso-1,2-bis-(4-chlorophenyl)ethane-1,2-diamine, ethyl 5-[bis-(2-methoxy-ethyl)-sulfamoyl]-2-ethoxy-benzoate (example 2) and 2-piperazinone (Avocado Organics) in an analogous manner using the procedures described for examples 25, 29 and 31 (except chiral purification). LC-MS: 732.3 [(M+H)+].

EXAMPLE 106

3-{4,5-Bis-(4-chloro-phenyl)-1-[4-(2-methanesulfonyl-ethyl)-piperazine-1-carbonyl]-4,5-dihydro-1H-imidazol-2-yl}-4-ethoxy-N,N-bis-(2-methoxy-ethyl)-benzenesulfonamide

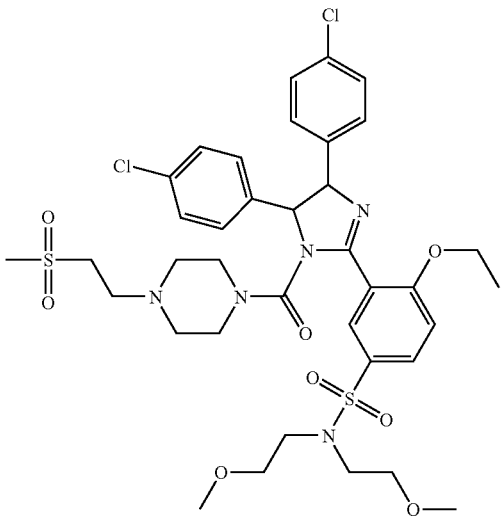

The title compound was prepared from meso-1,2-bis-(4-chlorophenyl)ethane-1,2-diamine, ethyl 5-[bis-(2-methoxy-ethyl)-sulfamoyl]-2-ethoxy-benzoate (example 2) and 1-(2-methanesulfonylethyl)piperazine bishydrochloride (example 23) in an analogous manner using the procedures described for examples 25, 29 and 31 (except chiral purification). LC-MS: 824.3 [(M+H)+].

EXAMPLE 107

2-{4-[2-{5-[Bis-(2-methoxy-ethyl)-sulfamoyl]-2-ethoxy-phenyl}-4,5-bis-(4-chloro-phenyl)-4,5-dihydro-imidazole-1-carbonyl]-piperazin-1-yl}-N,N-dimethyl-acetamide

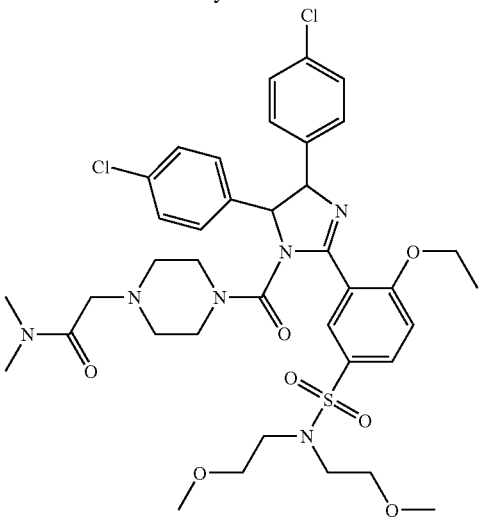

The title compound was prepared from meso-1,2-bis-(4-chlorophenyl)ethane-1,2-diamine, ethyl 5-[bis-(2-methoxy-ethyl)-sulfamoyl]-2-ethoxy-benzoate (example 2) and N,N-dimethyl-2-piperazin-1-yl-acetamide (Oakwood Products) in an analogous manner using the procedures described for examples 25, 29 and 31 (except chiral purification). LC-MS: 803.5 [(M+H)+].

EXAMPLE 108

3-(4,5-Bis-(4-chloro-phenyl)-1-{4-[2-(3-oxo-piperazin-1-yl)-acetyl]-piperazine-1-carbonyl}-4,5-dihydro-1H-imidazol-2-yl)-4-ethoxy-N,N-bis-(2-methoxy-ethyl)-benzenesulfonamide

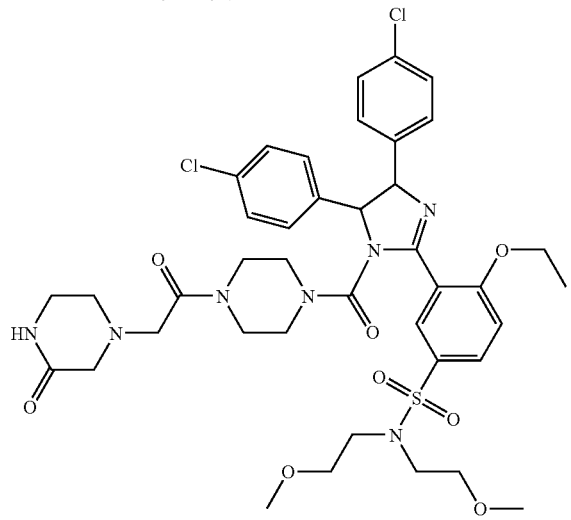

The title compound was prepared from meso-1,2-bis-(4-chlorophenyl)ethane-1,2-diamine, ethyl 5-[bis-(2-methoxy-ethyl)-sulfamoyl]-2-ethoxy-benzoate (example 2) and 2-piperazinone (Avocado Organics) in an analogous manner using the procedures described for examples 25, 29 and 31 (except chiral purification). LC-MS: 858.5 [(M+H)$^+$].

EXAMPLE 109

2-{4-[2-{5-[Bis-(2-methoxy-ethyl)-sulfamoyl]-2-ethoxy-phenyl}-4,5-bis-(4-chloro-phenyl)-4,5-dihydro-imidazole-1-carbonyl]-piperazin-1-yl}-N-(2-methoxy-1-methyl-ethyl)-acetamide

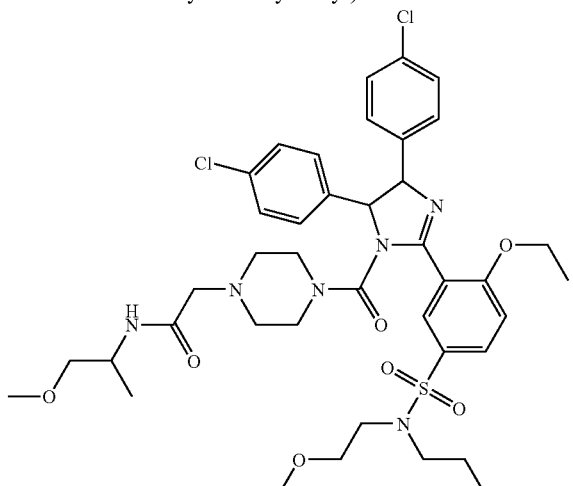

The title compound was prepared from meso-1,2-bis-(4-chlorophenyl)ethane-1,2-diamine, ethyl 5-[bis-(2-methoxy-ethyl)-sulfamoyl]-2-ethoxy-benzoate (example 2) and N-(2-methoxy-1-methyl-ethyl)-2-piperazin-1-yl-acetamide (example 21) in an analogous manner using the procedures described for examples 25, 29 and 31 (except chiral purification). LC-MS: 847.4 [(M+H)$^+$]

EXAMPLE 110

2-{4-[2-{5-[Bis-(2-methoxy-ethyl)-sulfamoyl]-2-ethoxy-phenyl}-4,5-bis-(4-chloro-phenyl)-4,5-dihydro-imidazole-1-carbonyl]-piperazin-1-yl}-N-methyl-acetamide

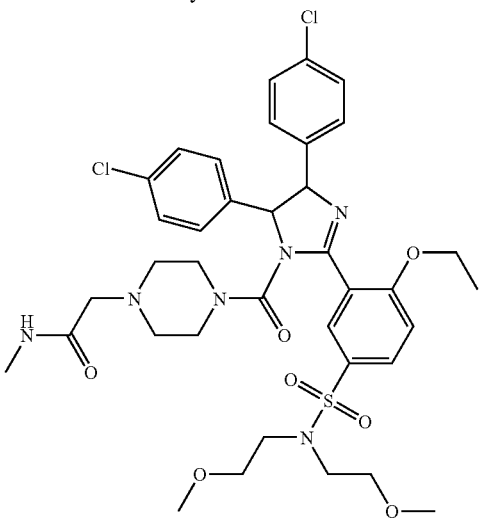

The title compound was prepared from meso-1,2-bis-(4-chlorophenyl)ethane-1,2-diamine, ethyl 5-[bis-(2-methoxy-ethyl)-sulfamoyl]-2-ethoxy-benzoate (example 2) and N-methyl-2-piperazin-1-yl-acetamide (example 22h) in an analogous manner using the procedures described for examples 25, 29 and 31 (except chiral purification). LC-MS: 789.4 [(M+H)$^+$].

EXAMPLE 111

3-{4,5-Bis-(4-chloro-phenyl)-1-[4-(2-morpholin-4-yl-2-oxo-ethyl)-piperazine-1-carbonyl]-4,5-dihydro-1H-imidazol-2-yl}-4-ethoxy-N,N-bis-(2-methoxy-ethyl)-benzenesulfonamide

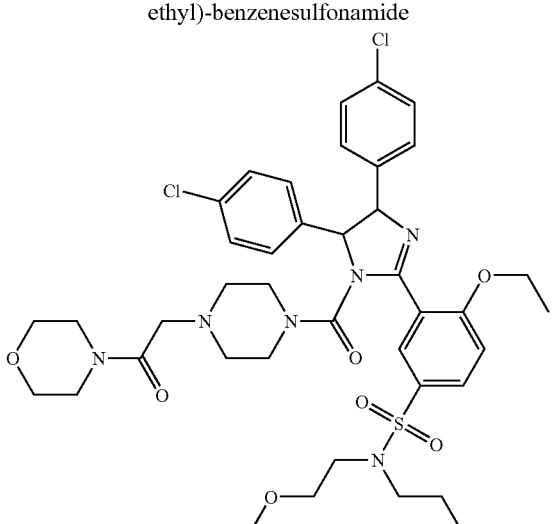

The title compound was prepared from meso-1,2-bis-(4-chlorophenyl)ethane-1,2-diamine, ethyl 5-[bis-(2-methoxy-ethyl)-sulfamoyl]-2-ethoxy-benzoate (example 2) and 1-morpholin-4-yl-2-piperazin-1-yl-ethanone (Oakwood Products) in an analogous manner using the procedures described for examples 25, 29 and 31 (except chiral purification). LC-MS: 845.4 [(M+H)$^+$].

EXAMPLE 112

3-[4,5-Bis-(4-chloro-phenyl)-1-(4-cyclopropanecarbonyl-piperazine-1-carbonyl)-4,5-dihydro-1H-imidazol-2-yl]-4-ethoxy-N,N-bis-(2-methoxy-ethyl)-benzenesulfonamide

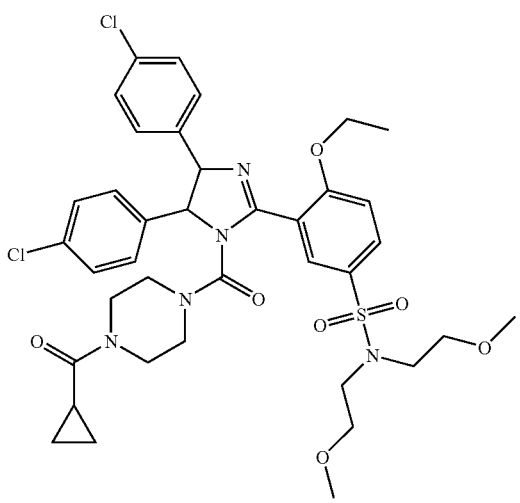

The title compound was prepared from meso-1,2-bis-(4-chlorophenyl)ethane-1,2-diamine, ethyl 5-[bis-(2-methoxy-ethyl)-sulfamoyl]-2-ethoxy-benzoate (example 2) and cyclopropyl-piperazin-1-yl-methanone (example 19) in an analogous manner using the procedures described for examples 25, 29 and 31 (except chiral purification). LC-MS: 786.3 [(M+H)+].

EXAMPLE 113

4-{4,5-Bis-(4-chloro-phenyl)-2-[2-ethoxy-5-(piperidine-1-sulfonyl)-phenyl]-4,5-dihydro-imidazole-1-carbonyl}-piperazin-2-one

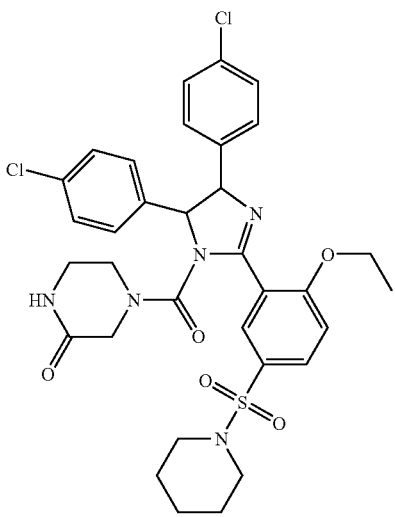

The title compound was prepared from meso-1,2-bis-(4-chlorophenyl)ethane-1,2-diamine, ethyl 2-ethoxy-5-(piperidine-1-sulfonyl)-benzoate (example 2) and 2-piperazinone (Avocado Organics) in an analogous manner using the procedures described for examples 25, 29 and 31 (except chiral purification). LC-MS: 684.3 [(M+H)+].

EXAMPLE 114

{4,5-Bis-(4-chloro-phenyl)-2-[2-ethoxy-5-(piperidine-1-sulfonyl)-phenyl]-4,5-dihydro-imidazol-1-yl}-[4-(2-methanesulfonyl-ethyl)-piperazin-1-yl]-methanone

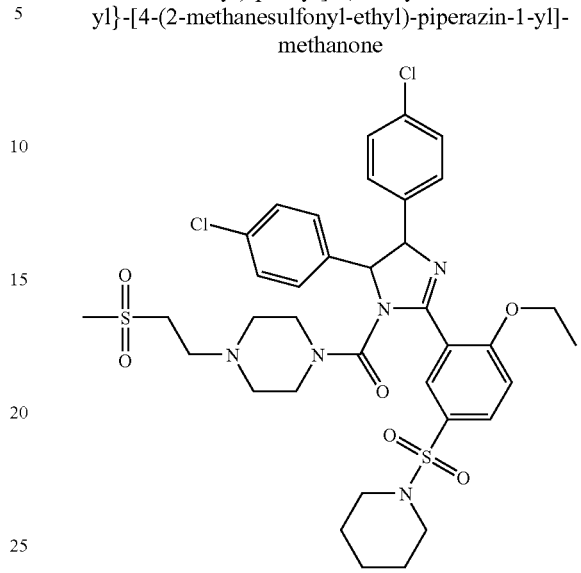

The title compound was prepared from meso-1,2-bis-(4-chlorophenyl)ethane-1,2-diamine, ethyl 2-ethoxy-5-(piperidine-1-sulfonyl)-benzoate (example 2) and 1-(2-methanesulfonyl-ethyl)piperazine bishydrochloride (example 23) in an analogous manner using the procedures described for examples 25, 29 and 31 (except chiral purification). LC-MS: 776.4 [(M+H)+].

EXAMPLE 115

2-(4-{4,5-Bis-(4-chloro-phenyl)-2-[2-ethoxy-5-(piperidine-1-sulfonyl)-phenyl]-4,5-dihydro-imidazole-1-carbonyl}-piperazin-1-yl)-N,N-dimethyl-acetamide

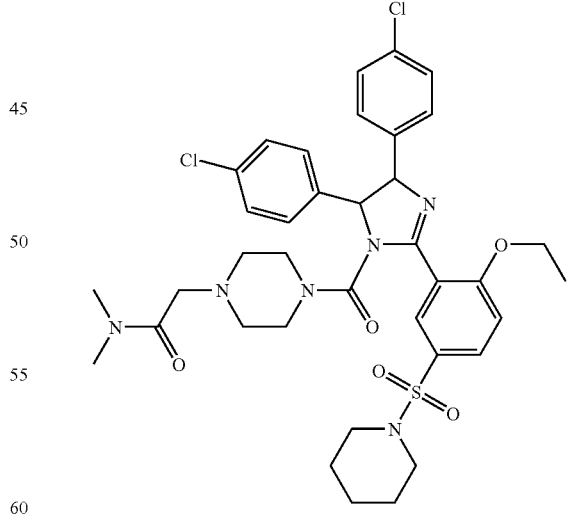

The title compound was prepared from meso-1,2-bis-(4-chlorophenyl)ethane-1,2-diamine, ethyl 2-ethoxy-5-(piperidine-1-sulfonyl)-benzoate (example 2) and N,N-dimethyl-2-piperazin-1-yl-acetamide (Oakwood Products) in an analogous manner using the procedures described for examples 25, 29 and 31 (except chiral purification). LC-MS: 755.4 [(M+H)+].

EXAMPLE 116

{4,5-Bis-(4-chloro-phenyl)-2-[2-ethoxy-5-(piperidine-1-sulfonyl)-phenyl]-4,5-dihydro-imidazol-1-yl}-(4-ethanesulfonyl-piperazin-1-yl)-methanone

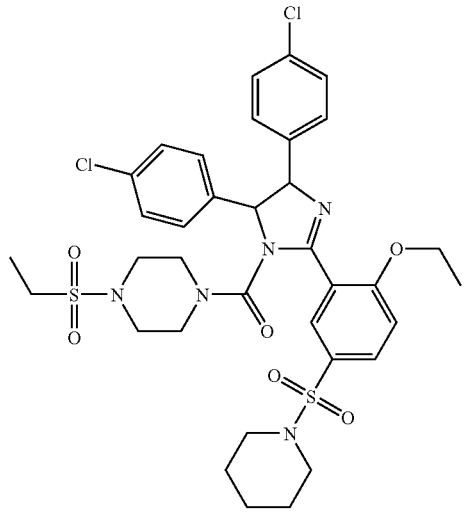

The title compound was prepared from meso-1,2-bis-(4-chlorophenyl)ethane-1,2-diamine, ethyl 2-ethoxy-5-(piperidine-1-sulfonyl)-benzoate (example 2) and 1-ethanesulfonyl-piperazine (example 20) in an analogous manner using the procedures described for examples 25, 29 and 31 (except chiral purification). LC-MS: 762.3 [(M+H)+].

EXAMPLE 117

4-[2-(4-{4,5-Bis-(4-chloro-phenyl)-2-[2-ethoxy-5-(piperidine-1-sulfonyl)-phenyl]-4,5-dihydro-imidazole-1-carbonyl}-piperazin-1-yl)-2-oxo-ethyl]-piperazin-2-one

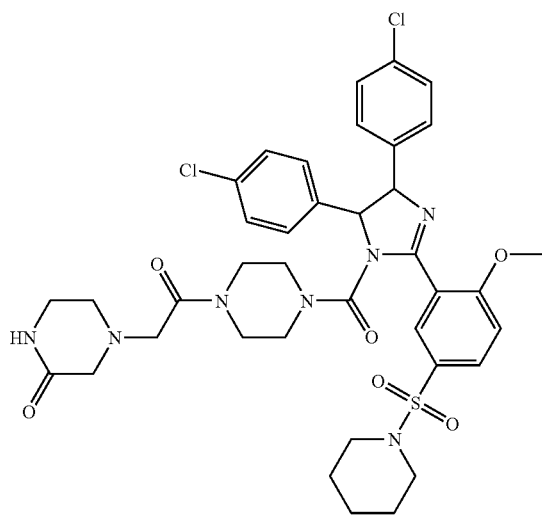

The title compound was prepared from meso-1,2-bis-(4-chlorophenyl)ethane-1,2-diamine, ethyl 2-ethoxy-5-(piperidine-1-sulfonyl)-benzoate (example 2) and 2-piperazinone (Avocado Organics) in an analogous manner using the procedures described for examples 25, 29 and 31 (except chiral purification). LC-MS: 810.4 [(M+H)+].

EXAMPLE 118

2-(4-{4,5-Bis-(4-chloro-phenyl)-2-[2-ethoxy-5-(piperidine-1-sulfonyl)-phenyl]-4,5-dihydro-imidazole-1-carbonyl}-piperazin-1-yl)-N-(2-methoxy-1-methyl-ethyl)-acetamide

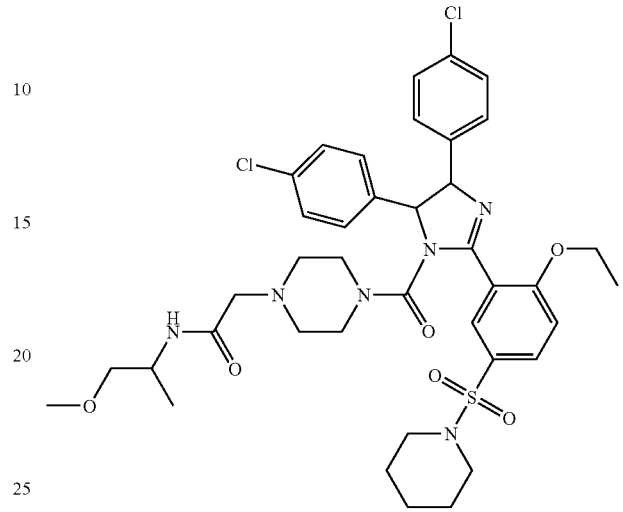

The title compound was prepared from meso-1,2-bis-(4-chlorophenyl)ethane-1,2-diamine, ethyl 2-ethoxy-5-(piperidine-1-sulfonyl)-benzoate (example 2) and N-(2-methoxy-1-methyl-ethyl)-2-piperazin-1-yl-acetamide (example 21) in an analogous manner using the procedures described for examples 25, 29 and 31 (except chiral purification). LC-MS: 799.4 [(M+H)+].

EXAMPLE 119

{4,5-Bis-(4-chloro-phenyl)-2-[2-ethoxy-5-(piperidine-1-sulfonyl)-phenyl]-4,5-dihydro-imidazol-1-yl}-[4-(2-hydroxy-ethyl)-piperazin-1-yl]-methanone

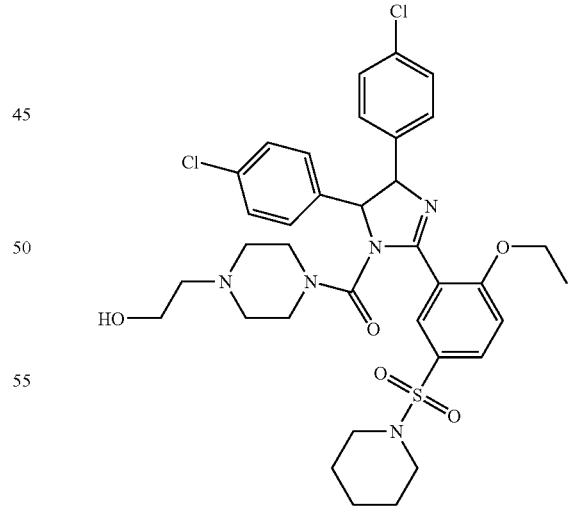

The title compound was prepared from meso-1,2-bis-(4-chlorophenyl)ethane-1,2-diamine, ethyl 2-ethoxy-5-(piperidine-1-sulfonyl)-benzoate (example 2) and 1-(2-hydroxy-ethyl)-piperazine (Aldrich) in an analogous manner using the procedures described for examples 25, 29 and 31 (except chiral purification). LC-MS: 714.2 [(M+H)+].

EXAMPLE 120

2-(4-{4,5-Bis-(4-chloro-phenyl)-2-[2-ethoxy-5-(piperidine-1-sulfonyl)-phenyl]-4,5-dihydro-imidazole-1-carbonyl}-piperazin-1-yl)-N-methyl-acetamide

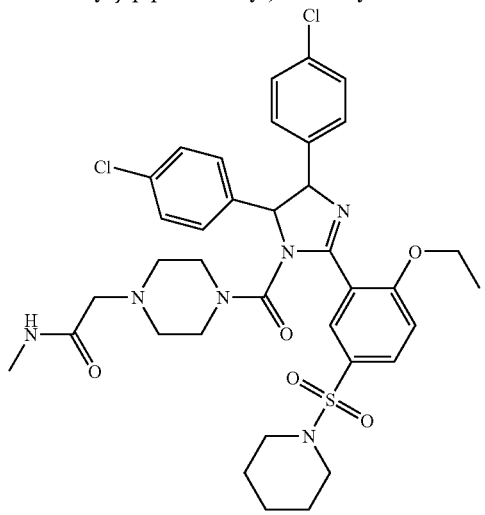

The title compound was prepared from meso-1,2-bis-(4-chlorophenyl)ethane-1,2-diamine, ethyl 2-ethoxy-5-(piperidine-1-sulfonyl)-benzoate (example 2) and N-methyl-2-piperazin-1-yl-acetamide (example 22h) in an analogous manner using the procedures described for examples 25, 29 and 31 (except chiral purification). LC-MS: 741.3 [(M+H)$^+$].

EXAMPLE 121

2-(4-{4,5-Bis-(4-chloro-phenyl)-2-[2-ethoxy-5-(piperidine-1-sulfonyl)-phenyl]-4,5-dihydro-imidazole-1-carbonyl}-piperazin-1-yl)-1-morpholin-4-yl-ethanone

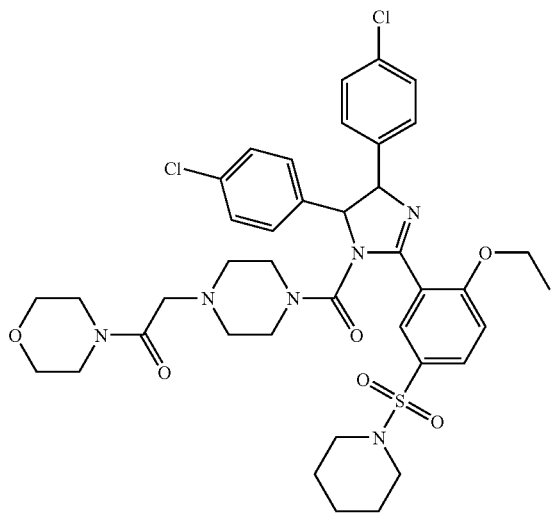

The title compound was prepared from meso-1,2-bis-(4-chlorophenyl)ethane-1,2-diamine, ethyl 2-ethoxy-5-(piperidine-1-sulfonyl)-benzoate (example 2) and 1-morpholin-4-yl-2-piperazin-1-yl-ethanone (Oakwood Products) in an analogous manner using the procedures described for examples 25, 29 and 31 (except chiral purification). LC-MS: 797.3 [(M+H)$^+$].

EXAMPLE 122

{4,5-Bis-(4-chloro-phenyl)-2-[2-ethoxy-5-(piperidine-1-sulfonyl)-phenyl]-4,5-dihydro-imidazol-1-yl}-(4-cyclopropanecarbonyl-piperazin-1-yl)-methanone

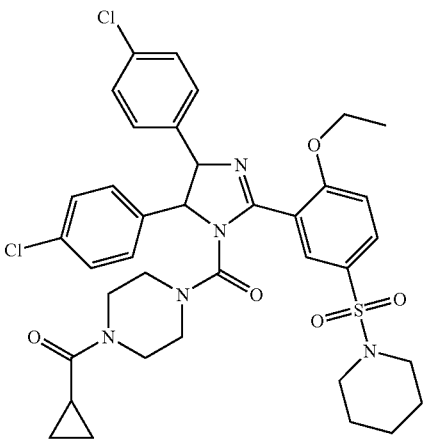

The title compound was prepared from meso-1,2-bis-(4-chlorophenyl)ethane-1,2-diamine, ethyl 2-ethoxy-5-(piperidine-1-sulfonyl)-benzoate (example 2) and cyclopropyl-piperazin-1-yl-methanonein an analogous manner using the procedures described for examples 25, 29 and 31 (except chiral purification). LC-MS: 738.4 [(M+H)$^+$].

EXAMPLE 123

3-[4,5-Bis-(4-chloro-phenyl)-1-(3-oxo-piperazine-1-carbonyl)-4,5-dihydro-1H-imidazol-2-yl]-4-ethoxy-N-(2-methoxy-1-methyl-ethyl)-benzenesulfonamide

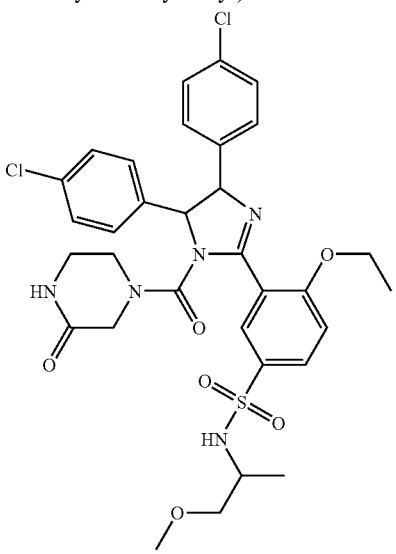

The title compound was prepared from meso-1,2-bis-(4-chlorophenyl)ethane-1,2-diamine, ethyl 2-ethoxy-5-(2-methoxy-1-methyl-ethylsulfamoyl)-benzoate (example 2) and 2-piperazinone (Avocado Organics) in an analogous manner using the procedures described for examples 25, 29 and 31 (except chiral purification). LC-MS: 688.2 [(M+H)$^+$].

EXAMPLE 124

3-{4,5-Bis-(4-chloro-phenyl)-1-[4-(2-methanesulfo-nyl-ethyl)-piperazine-1-carbonyl]-4,5-dihydro-1H-imidazol-2-yl}-4-ethoxy-N-(2-methoxy-1-methyl-ethyl)-benzenesulfonamide

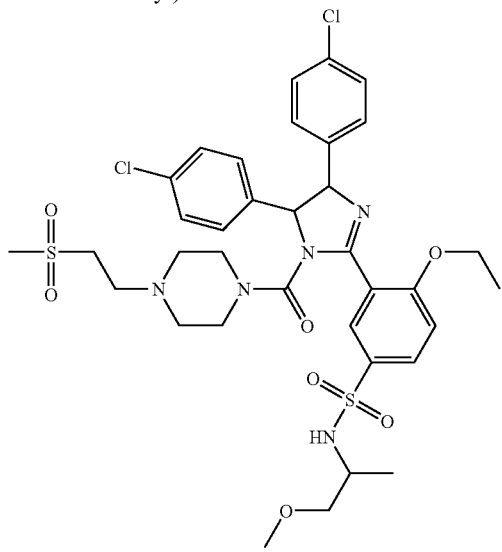

The title compound was prepared from meso-1,2-bis-(4-chlorophenyl)ethane-1,2-diamine, ethyl 2-ethoxy-5-(2-methoxy-1-methyl-ethylsulfamoyl)-benzoate (example 2) and 1-(2-methanesulfonylethyl)piperazine bishydrochloride (example 23) in an analogous manner using the procedures described for examples 25, 29 and 31 (except chiral purification). LC-MS: 780.3 [(M+H)+].

EXAMPLE 125

2-(4-{4,5-Bis-(4-chloro-phenyl)-2-[2-ethoxy-5-(2-methoxy-1-methyl-ethylsulfamoyl)-phenyl]-4,5-dihydro-imidazole-1-carbonyl}-piperazin-1-yl)-N,N-dimethyl-acetamide

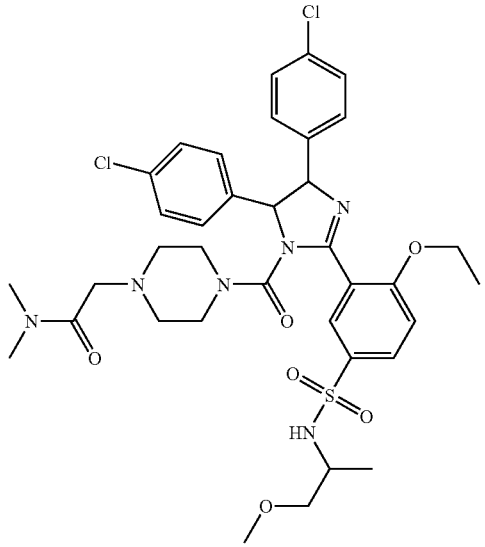

The title compound was prepared from meso-1,2-bis-(4-chlorophenyl)ethane-1,2-diamine, ethyl 2-ethoxy-5-(2-methoxy-1-methyl-ethylsulfamoyl)-benzoate (example 2) and N,N-dimethyl-2-piperazin-1-yl-acetamide (Oakwood Products) in an analogous manner using the procedures described for examples 25, 29 and 31 (except chiral purification). LC-MS: 759.4 [(M+H)+].

EXAMPLE 126

3-[4,5-Bis-(4-chloro-phenyl)-1-(4-ethanesulfonyl-piperazine-1-carbonyl)-4,5-dihydro-1H-imidazol-2-yl]-4-ethoxy-N-(2-methoxy-1-methyl-ethyl)-benzenesulfonamide

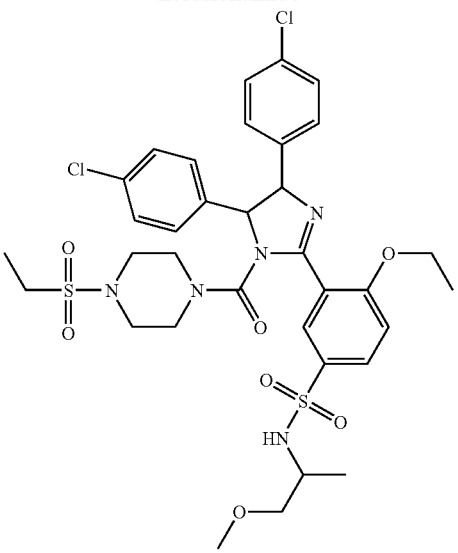

The title compound was prepared from meso-1,2-bis-(4-chlorophenyl)ethane-1,2-diamine, ethyl 2-ethoxy-5-(2-methoxy-1-methyl-ethylsulfamoyl)-benzoate (example 2) and 1-ethanesulfonyl-piperazine (example 20) in an analogous manner using the procedures described for examples 25, 29 and 31 (except chiral purification). LC-MS: 766.3 [(M+H)+].

EXAMPLE 127

3-(4,5-Bis-(4-chloro-phenyl)-1-{4-[2-(3-oxo-piperazin-1-yl)-acetyl]-piperazine-1-carbonyl}-4,5-dihydro-1H-imidazol-2-yl)-4-ethoxy-N-(2-methoxy-1-methyl-ethyl)-benzenesulfonamide

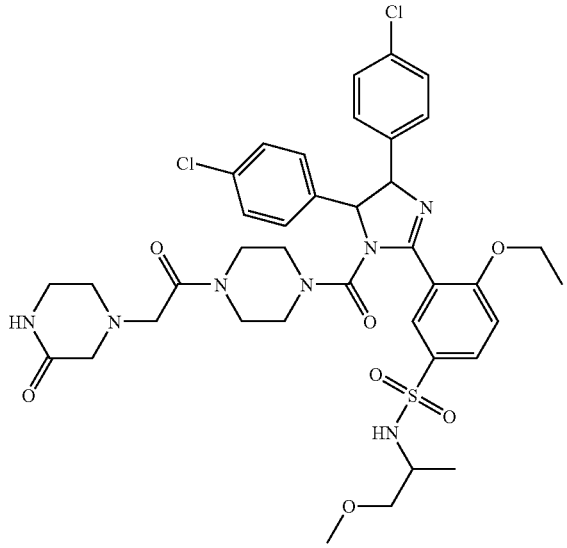

The title compound was prepared from meso-1,2-bis-(4-chlorophenyl)ethane-1,2-diamine, ethyl 2-ethoxy-5-(2-methoxy-1-methyl-ethylsulfamoyl)-benzoate (example 2) and 2-piperazinone (Avocado Organics) in an analogous manner using the procedures described for examples 25, 29 and 31 (except chiral purification). LC-MS: 814.3 [(M+H)+].

EXAMPLE 128

2-(4-{4,5-Bis-(4-chloro-phenyl)-2-[2-ethoxy-5-(2-methoxy-1-methyl-ethylsulfamoyl)-phenyl]-4,5-dihydro-imidazole-1-carbonyl}-piperazin-1-yl)-N-(2-methoxy-1-methyl-ethyl)-acetamide

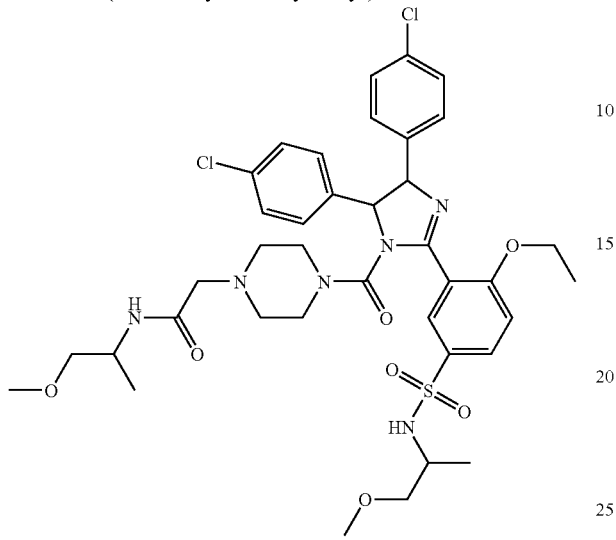

The title compound was prepared from meso-1,2-bis-(4-chlorophenyl)ethane-1,2-diamine, ethyl 2-ethoxy-5-(2-methoxy-1-methyl-ethylsulfamoyl)-benzoate (example 2) and N-(2-methoxy-1-methyl-ethyl)-2-piperazin-1-yl-acetamide (example 21) in an analogous manner using the procedures described for examples 25, 29 and 31 (except chiral purification). LC-MS: 803.5 [(M+H)$^+$].

EXAMPLE 129

3-{4,5-Bis-(4-chloro-phenyl)-1-[4-(2-hydroxy-ethyl)-piperazine-1-carbonyl]-4,5-dihydro-1H-imidazol-2-yl}-4-ethoxy-N-(2-methoxy-1-methyl-ethyl)-benzenesulfonamide

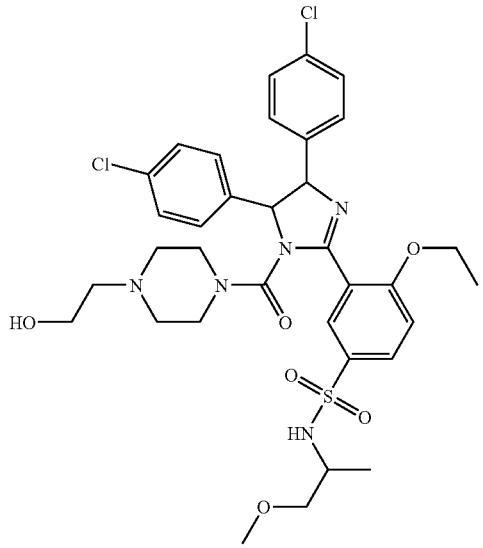

The title compound was prepared from meso-1,2-bis-(4-chlorophenyl)ethane-1,2-diamine, ethyl 2-ethoxy-5-(2-methoxy-1-methyl-ethylsulfamoyl)-benzoate (example 2) and 1-(2-hydroxy-ethyl)-piperazine (Aldrich) in an analogous manner using the procedures described for examples 25, 29 and 31 (except chiral purification). LC-MS: 718.3 [(M+H)$^+$].

EXAMPLE 130

2-(4-{4,5-Bis-(4-chloro-phenyl)-2-[2-ethoxy-5-(2-methoxy-1-methyl-ethylsulfamoyl)-phenyl]-4,5-dihydro-imidazole-1-carbonyl}-piperazin-1-yl)-N-methyl-acetamide

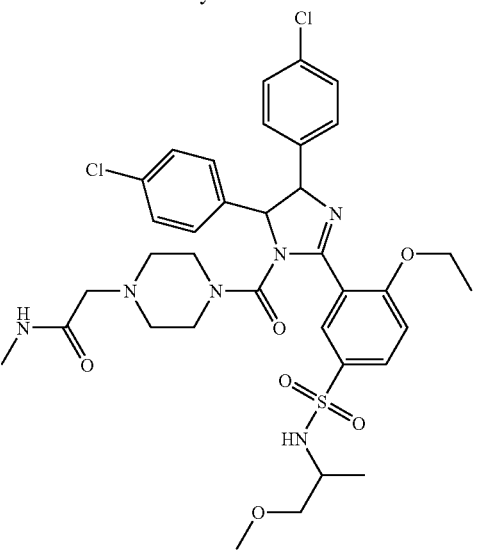

The title compound was prepared from meso-1,2-bis-(4-chlorophenyl)ethane-1,2-diamine, ethyl 2-ethoxy-5-(2-methoxy-1-methyl-ethylsulfamoyl)-benzoate (example 2) and N-methyl-2-piperazin-1-yl-acetamide (example 22h) in an analogous manner using the procedures described for examples 25, 29 and 31 (except chiral purification). LC-MS: 745.3 [(M+H)$^+$].

EXAMPLE 131

4-{4,5-Bis-(4-chloro-phenyl)-2-[2-ethoxy-5-(pyrrolidine-1-sulfonyl)-phenyl]-4,5-dihydro-imidazole-1-carbonyl}-piperazin-2-one

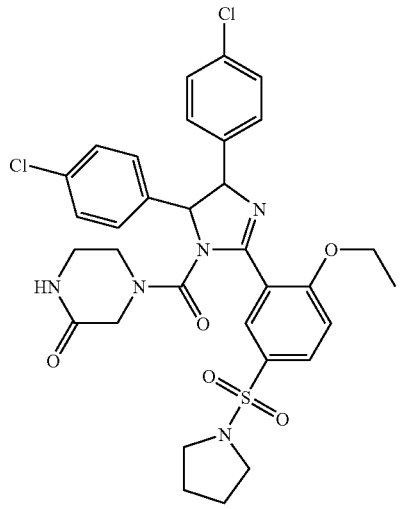

The title compound was prepared from meso-1,2-bis-(4-chlorophenyl)ethane-1,2-diamine, ethyl 2-ethoxy-5-(pyrrolidine-1-sulfonyl)-benzoate (example 2) and 2-piperazinone (Avocado Organics) in an analogous manner using the procedures described for examples 25, 29 and 31 (except chiral purification). LC-MS: 670.3 [(M+H)$^+$].

EXAMPLE 132

{4,5-Bis-(4-chloro-phenyl)-2-[2-ethoxy-5-(pyrrolidine-1-sulfonyl)-phenyl]-4,5-dihydro-imidazol-1-yl}-[4-(2-methanesulfonyl-ethyl)-piperazin-1-yl]-methanone

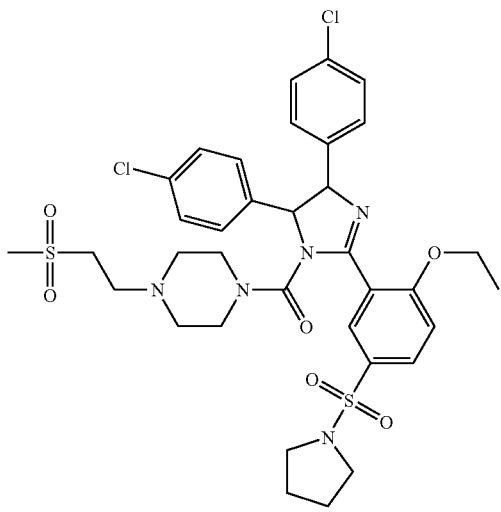

The title compound was prepared from meso-1,2-bis-(4-chlorophenyl)ethane-1,2-diamine, ethyl 2-ethoxy-5-(pyrrolidine-1-sulfonyl)-benzoate (example 2) and 1-(2-methanesulfonylethyl)piperazine bishydrochloride (example 23) in an analogous manner using the procedures described for examples 25, 29 and 31 (except chiral purification). LC-MS: 762.3 [(M+H)$^+$].

EXAMPLE 133

2-(4-{4,5-Bis-(4-chloro-phenyl)-2-[2-ethoxy-5-(pyrrolidine-1-sulfonyl)-phenyl]-4,5-dihydro-imidazole-1-carbonyl}-piperazin-1-yl)-N,N-dimethyl-acetamide

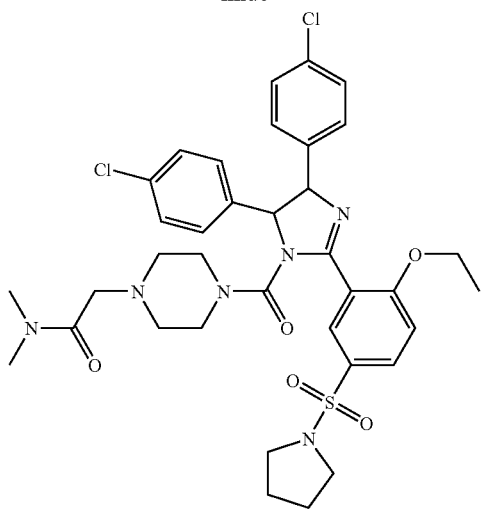

The title compound was prepared from meso-1,2-bis-(4-chlorophenyl)ethane-1,2-diamine, ethyl 2-ethoxy-5-(pyrrolidine-1-sulfonyl)-benzoate (example 2) and N,N-dimethyl-2-piperazin-1-yl-acetamide (Oakwood Products) in an analogous manner using the procedures described for examples 25, 29 and 31 (except chiral purification). LC-MS: 741.3 [(M+H)$^+$].

EXAMPLE 134

4-[2-(4-{4,5-Bis-(4-chloro-phenyl)-2-[2-ethoxy-5-(pyrrolidine-1-sulfonyl)-phenyl]-4,5-dihydro-imidazole-1-carbonyl}-piperazin-1-yl)-2-oxo-ethyl]-piperazin-2-one

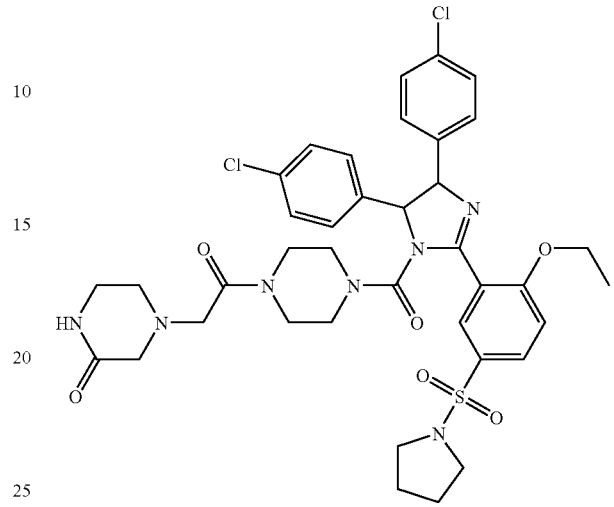

The title compound was prepared from meso-1,2-bis-(4-chlorophenyl)ethane-1,2-diamine, ethyl 2-ethoxy-5-(pyrrolidine-1-sulfonyl)-benzoate (example 2) and 2-piperazinone (Avocado Organics) in an analogous manner using the procedures described for examples 25, 29 and 31 (except chiral purification). LC-MS: 796.3 [(M+H)$^+$].

EXAMPLE 135

2-(4-{4,5-Bis-(4-chloro-phenyl)-2-[2-ethoxy-5-(pyrrolidine-1-sulfonyl)-phenyl]-4,5-dihydro-imidazole-1-carbonyl}-piperazin-1-yl)-N-(2-methoxy-1-methyl-ethyl)-acetamide

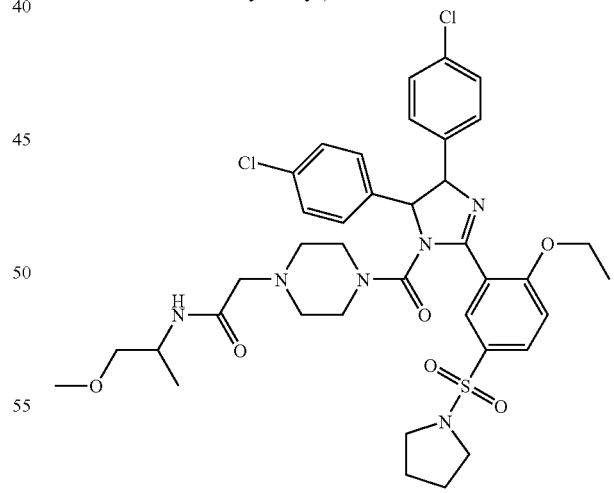

The title compound was prepared from meso-1,2-bis-(4-chlorophenyl)ethane-1,2-diamine, ethyl 2-ethoxy-5-(pyrrolidine-1-sulfonyl)-benzoate (example 2) and N-(2-methoxy-1-methyl-ethyl)-2-piperazin-1-yl-acetamide (example 21) in an analogous manner using the procedures described for examples 25, 29 and 31 (except chiral purification). LC-MS: 785.3 [(M+H)$^+$].

EXAMPLE 136

{4,5-Bis-(4-chloro-phenyl)-2-[2-ethoxy-5-(pyrrolidine-1-sulfonyl)-phenyl]-4,5-dihydro-imidazol-1-yl}-[4-(2-hydroxy-ethyl)-piperazin-1-yl]-methanone

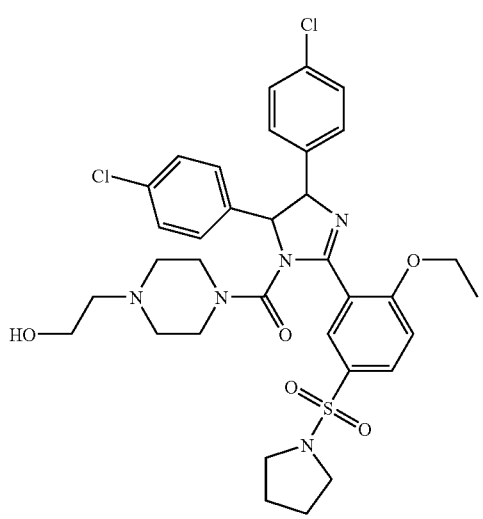

The title compound was prepared from meso-1,2-bis-(4-chlorophenyl)ethane-1,2-diamine, ethyl 2-ethoxy-5-(pyrrolidine-1-sulfonyl)-benzoate (example 2) and 1-(2-hydroxy-ethyl)-piperazine (Aldrich) in an analogous manner using the procedures described for examples 25, 29 and 31 (except chiral purification). LC-MS: 700.3 [(M+H)$^+$].

EXAMPLE 137

5-[4,5-Bis-(4-chloro-phenyl)-1-(3-oxo-piperazine-1-carbonyl)-4,5-dihydro-1H-imidazol-2-yl]-4-ethoxy-2-fluoro-N,N-dimethyl-benzenesulfonamide

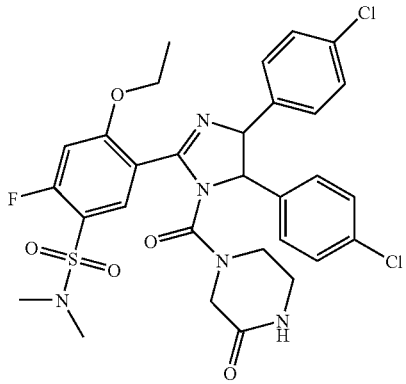

The title compound was prepared from meso-1,2-bis-(4-chlorophenyl)ethane-1,2-diamine, ethyl 5-dimethylsulfamoyl-2-ethoxy-4-fluoro-benzoate (example 2) and 2-piperazinone (Avocado Organics) in an analogous manner using the procedures described for examples 25, 29 and 31 (except chiral purification). LC-MS: 662.2 [(M+H)$^+$].

EXAMPLE 138

5-{4,5-Bis-(4-chloro-phenyl)-1-[4-(2-hydroxy-ethyl)-piperazine-1-carbonyl]-4,5-dihydro-1H-imidazol-2-yl}-4-ethoxy-2-fluoro-N,N-dimethyl-benzenesulfonamide

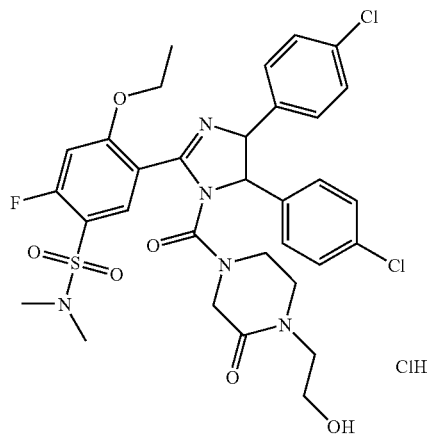

The title compound was prepared from meso-1,2-bis-(4-chlorophenyl)ethane-1,2-diamine, ethyl 5-dimethylsulfamoyl-2-ethoxy-4-fluoro-benzoate (example 2) and 1-(2-hydroxy-ethyl)-piperazine (Aldrich) in an analogous manner using the procedures described for examples 25, 29 and 31 (except chiral purification). LC-MS: 692.3 [(M+H)$^+$].

EXAMPLE 139

2-{4-[4,5-Bis-(4-chloro-phenyl)-2-(5-dimethylsulfamoyl-2-ethoxy-4-fluoro-phenyl)-4,5-dihydro-imidazole-1-carbonyl]-piperazin-1-yl}-N,N-dimethyl-acetamide

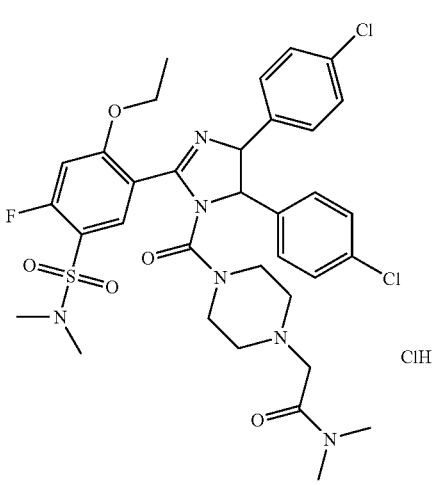

The title compound was prepared from meso-1,2-bis-(4-chlorophenyl)ethane-1,2-diamine, ethyl 5-dimethylsulfamoyl-2-ethoxy-4-fluoro-benzoate (example 2) and N,N-dimethyl-2-piperazin-1-yl-acetamide (Oakwood Products) in an analogous manner using the procedures described for examples 25, 29 and 31 (except chiral purification). LC-MS: 733.3 [(M+H)$^+$].

EXAMPLE 140

5{-4,5-Bis-(4-chloro-phenyl)-1-[4-(2-methanesulfonyl-ethyl)-piperazine-1-carbonyl]-4,5-dihydro-1H-imidazol-2-yl}-4-ethoxy-2-fluoro-N,N-dimethyl-benzenesulfonamide

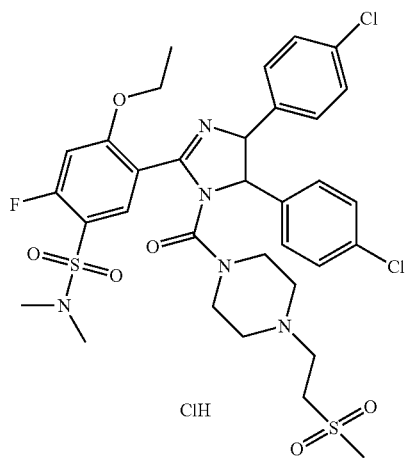

The title compound was prepared from meso-1,2-bis-(4-chlorophenyl)ethane-1,2-diamine, ethyl 5-dimethylsulfamoyl-2-ethoxy-4-fluoro-benzoate (example 2) and 1-(2-methanesulfonylethyl)-piperazine bishydrochloride (example 23) in an analogous manner using the procedures described for examples 25, 29 and 31 (except chiral purification). LC-MS: 754.2 [(M+H)+].

EXAMPLE 141

4-[4,5-Bis-(4-chloro-phenyl)-2-(7-ethoxy-2-methyl-1,1-dioxo-1,2,3,4-tetrahydro-1λ6-benzo[b][1,4,5]oxathiazepin-8-yl)-4,5-dihydro-imidazole-1-carbonyl]-piperazin-2-one

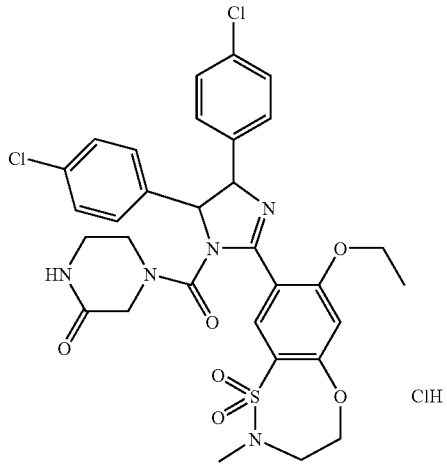

The title compound was prepared from meso-1,2-bis-(4-chlorophenyl)ethane-1,2-diamine, 8-carboethoxy-7-ethoxy-2-methyl-1,1-dioxo-1,2,3,4-tetrahydro-benzo[1,6-b][1,4,5]oxathiazepine (example 3) and 2-piperazinone (Avocado Organics) in an analogous manner using the procedures described for examples 25, 29 and 31 (except chiral purification). LC-MS: 672.2 [(M+H)+].

EXAMPLE 142

[4,5-Bis-(4-chloro-phenyl)-2-(7-ethoxy-2-methyl-1,1-dioxo-1,2,3,4-tetrahydro-1λ6-benzo[b][1,4,5]oxathiazepin-8-yl)-4,5-dihydro-imidazol-1-yl]-[4-(2-methanesulfonyl-ethyl)-piperazin-1-yl]-methanone

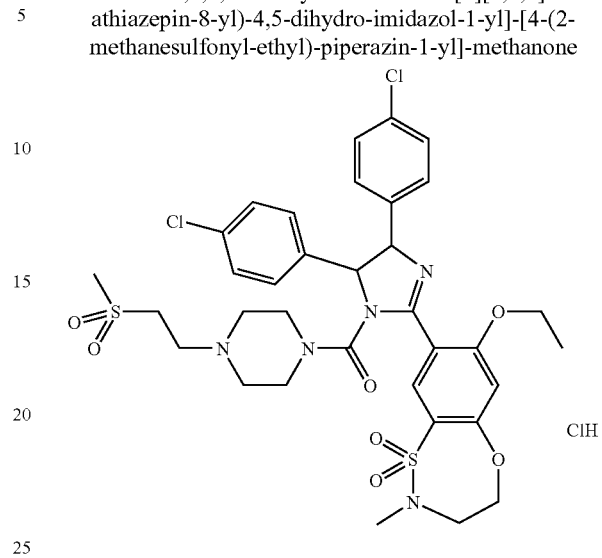

The title compound was prepared from meso-1,2-bis-(4-chlorophenyl)ethane-1,2-diamine, 8-carboethoxy-7-ethoxy-2-methyl-1,1-dioxo-1,2,3,4-tetrahydro-benzo[1,6-b][1,4,5]oxathiazepine (example 3) and 1-(2-methanesulfonylethyl)piperazine bishydrochloride (example 23) in an analogous manner using the procedures described for examples 25, 29 and 31 (except chiral purification). LC-MS: 764.1 [(M+H)+].

EXAMPLE 143

2-{4-[4,5-Bis-(4-chloro-phenyl)-2-(7-ethoxy-2-methyl-1,1-dioxo-1,2,3,4-tetrahydro-1λ6-benzo[b][1,4,5]oxathiazepin-8-yl)-4,5-dihydro-imidazole-1-carbonyl]-piperazin-1-yl}-1-morpholin-4-yl-ethanone

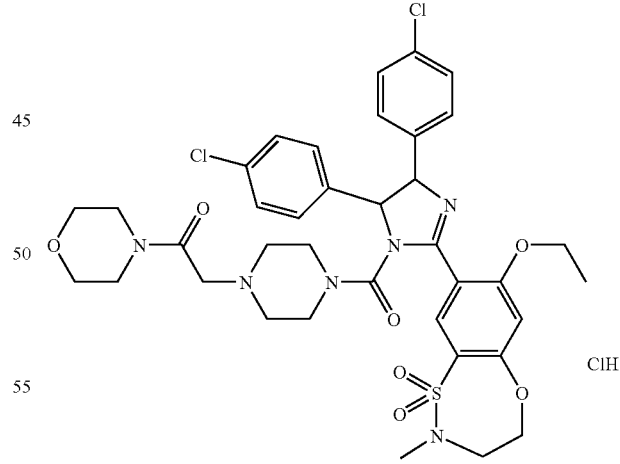

The title compound was prepared from meso-1,2-bis-(4-chlorophenyl)ethane-1,2-diamine, 8-carboethoxy-7-ethoxy-2-methyl-1,1-dioxo-1,2,3,4-tetrahydro-benzo[1,6-b][1,4,5]oxathiazepine (example 3) and 1-morpholin-4-yl-2-piperazin-1-yl-ethanone (Oakwood Products) in an analogous manner using the procedures described for examples 25, 29 and 31 (except chiral purification). LC-MS: 785.2 [(M+H)+].

EXAMPLE 144

2-{4-[(4S,5R)-4,5-Bis-(4-chloro-phenyl)-2-(5-dimethylsulfamoyl-2-ethoxy-4-fluoro-phenyl)-4,5-dihydro-imidazole-1-carbonyl]-piperazin-1-yl}-N,N-dimethyl-acetamide hydrochloride

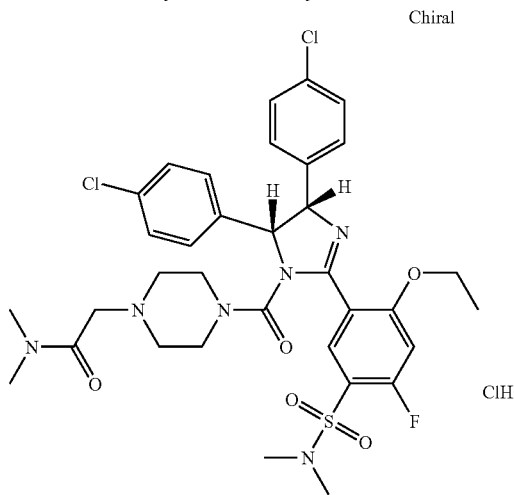

The title compound was prepared from meso-1,2-bis-(4-chlorophenyl)ethane-1,2-diamine, ethyl 5-dimethylsulfamoyl-2-ethoxy-4-fluoro-benzoate (example 2) and N,N-dimethyl-2-piperazin-1-yl-acetamide (Oakwood Products) following successively the procedures described for examples 25, 29 and 31. LC-MS: 733.3 [(M+H)+].

EXAMPLE 145

5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-4-ethoxy-2-fluoro-N,N-dimethyl-benzenesulfonamide hydrochloride

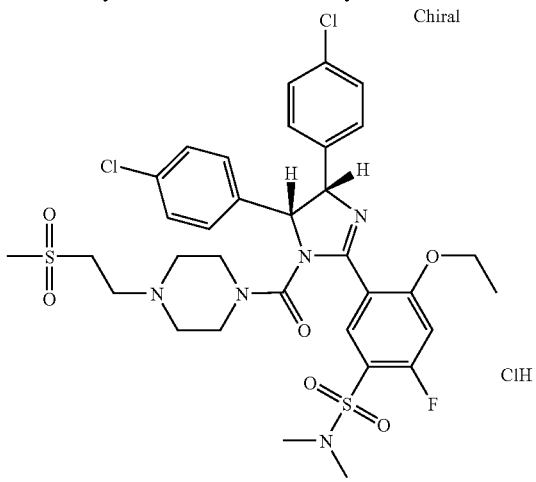

The title compound was prepared from meso-1,2-bis-(4-chlorophenyl)ethane-1,2-diamine, ethyl 5-dimethylsulfamoyl-2-ethoxy-4-fluoro-benzoate (example 2) and 1-(2-methanesulfonylethyl)piperazine bishydrochloride (example 23) following successively the procedures described for examples 25, 29 and 31. LC-MS: 754.2 [(M+H)+].

EXAMPLE 146

5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-4-ethoxy-2-fluoro-N,N-dimethyl-benzenesulfonamide hydrochloride

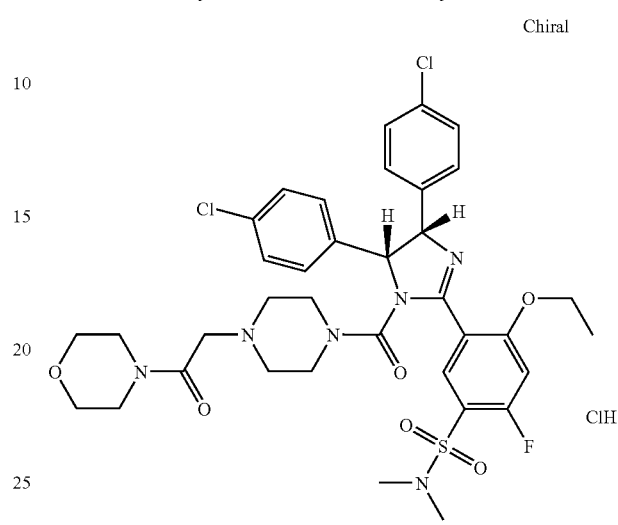

The title compound was prepared from meso-1,2-bis-(4-chlorophenyl)ethane-1,2-diamine, ethyl 5-dimethylsulfamoyl-2-ethoxy-4-fluoro-benzoate (example 2) and 1-morpholin-4-yl-2-piperazin-1-yl-ethanone (Oakwood Products) following successively the procedures described for examples 25, 29 and 31. LC-MS: 775.3 [(M+H)+].

EXAMPLE 147

4-[4,5-Bis-(4-chloro-phenyl)-1-(3-oxo-piperazine-1-carbonyl)-4,5-dihydro-1H-imidazol-2-yl]-3-ethoxy-N,N-dimethyl-benzenesulfonamide hydrochloride

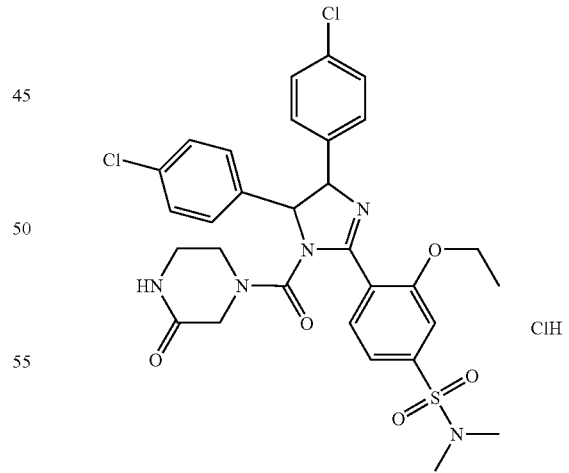

The title compound was prepared from meso-1,2-bis-(4-chlorophenyl)ethane-1,2-diamine, methyl 4-dimethylsulfamoyl-2-ethoxybenzoate (example 11) and 2-piperazinone (Avocado Organics) in an analogous manner using the procedures described for examples 25, 29 and 31 (except chiral purification). LC-MS: 644.4 [(M+H)+].

EXAMPLE 148

4-{4,5-Bis-(4-chloro-phenyl)-1-[4-(2-methanesulfonyl-ethyl)-piperazine-1-carbonyl]-4,5-dihydro-1H-imidazol-2-yl}-3-ethoxy-N,N-dimethyl-benzenesulfonamide hydrochloride

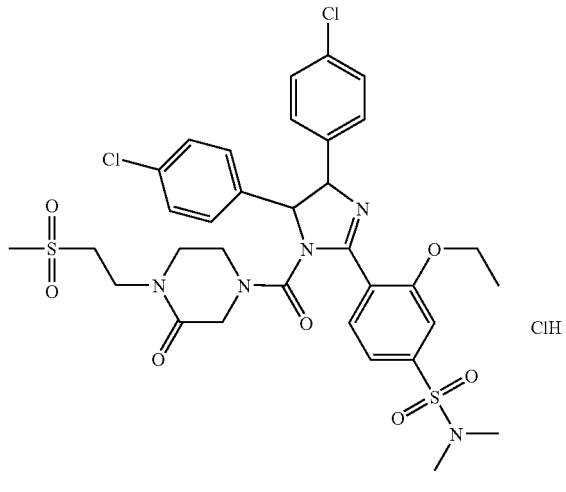

The title compound was prepared from meso-1,2-bis-(4-chlorophenyl)ethane-1,2-diamine, methyl 4-dimethylsulfamoyl-2-ethoxybenzoate (example 11) and 1-(2-methanesulfonylethyl)piperazine bishydrochloride (example 23) in an analogous manner using the procedures described for examples 25, 29 and 31 (except chiral purification). LC-MS: 736.3 [(M+H)+].

EXAMPLE 149

4-{4,5-Bis-(4-chloro-phenyl)-1-[4-(2-morpholin-4-yl-2-oxo-ethyl)-piperazine-1-carbonyl]-4,5-dihydro-1H-imidazol-2-yl}-3-ethoxy-N,N-dimethyl-benzenesulfonamide hydrochloride

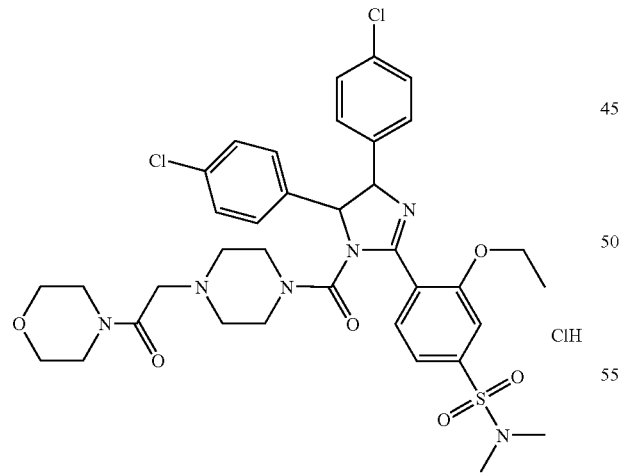

The title compound was prepared from meso-1,2-bis-(4-chlorophenyl)ethane-1,2-diamine, methyl 4-dimethylsulfamoyl-2-ethoxybenzoate (example 11) and 1-morpholin-4-yl-2-piperazin-1-yl-ethanone (Oakwood Products) in an analogous manner using the procedures described for examples 25, 29 and 31 (except chiral purification). LC-MS: 757.3 [(M+H)+].

EXAMPLE 150

2-{4-[4,5-Bis-(4-chloro-phenyl)-2-(4-dimethylsulfamoyl-2-ethoxy-phenyl)-4,5-dihydro-imidazole-1-carbonyl]-piperazin-1-yl}-N,N-dimethyl-acetamide hydrochloride

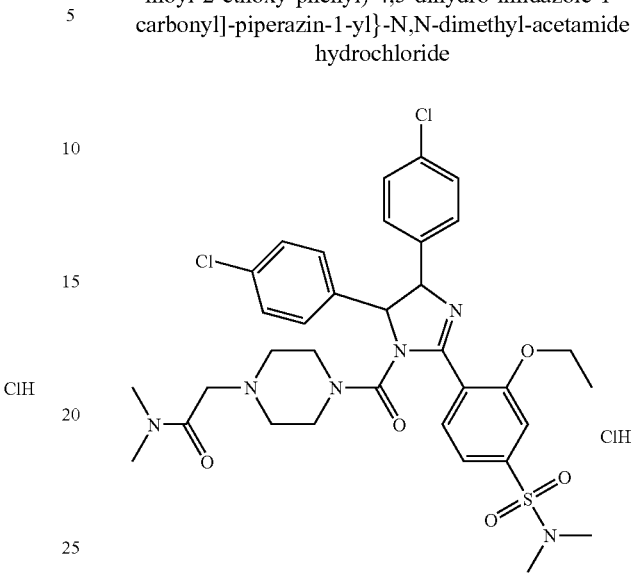

The title compound was prepared from meso-1,2-bis-(4-chlorophenyl)ethane-1,2-diamine, methyl 4-dimethylsulfamoyl-2-ethoxybenzoate (example 11) and N,N-dimethyl-2-piperazin-1-yl-acetamide (Oakwood Products) in an analogous manner using the procedures described for examples 25, 29 and 31 (except chiral purification). LC-MS: 715.4 [(M+H)+].

EXAMPLE 151

4-[4,5-Bis-(4-chloro-phenyl)-2-(2-ethoxy-5-methanesulfonyl-phenyl)-4,5-dihydro-imidazole-1-carbonyl]-piperazin-2-one

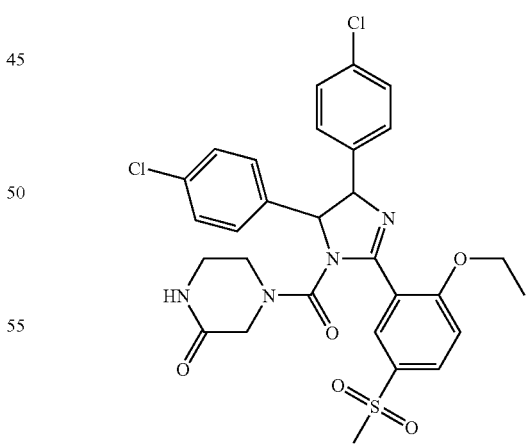

The title compound was prepared from meso-1,2-bis-(4-chlorophenyl)ethane-1,2-diamine, ethyl 5-methylsulfonyl-2-ethoxybenzoate (example 10) and 2-piperazinone (Avocado Organics) in an analogous manner using the procedures described for examples 25, 29 and 31 (except chiral purification). LC-MS: 615.2 [(M+H)+].

EXAMPLE 152

[4,5-Bis-(4-chloro-phenyl)-2-(2-ethoxy-5-methane-sulfonyl-phenyl)-4,5-dihydro-imidazol-1-yl]-[4-(2-methanesulfonyl-ethyl)-piperazin-1-yl]-methanone hydrochloride

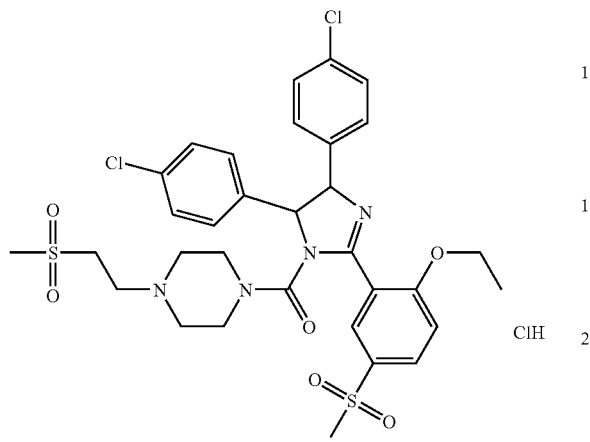

The title compound was prepared from meso-1,2-bis-(4-chlorophenyl)ethane-1,2-diamine, ethyl 5-methylsulfonyl-2-ethoxybenzoate (example 10) and 1-(2-methanesulfonyl-ethyl)piperazine bishydrochloride (example 23) in an analogous manner using the procedures described for examples 25, 29 and 31 (except chiral purification). LC-MS: 707.2 [(M+H)$^+$].

EXAMPLE 153

2-{(4-[4,5-Bis-(4-chloro-phenyl)-2-(2-ethoxy-5-methanesulfonyl-phenyl)-4,5-dihydro-imidazole-1-carbonyl]-piperazin-1-yl}-1-morpholin-4-yl-ethanone hydrochloride

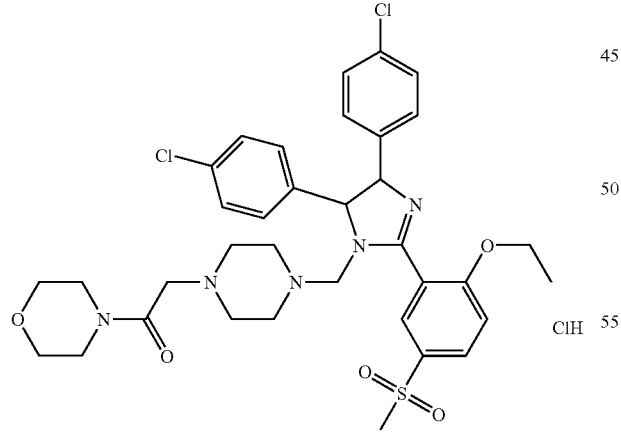

The title compound was prepared from meso-1,2-bis-(4-chlorophenyl)ethane-1,2-diamine, ethyl 5-methylsulfonyl-2-ethoxybenzoate (example 10) and 1-morpholin-4-yl-2-piperazin-1-yl-ethanone (Oakwood Products) in an analogous manner using the procedures described for examples 25, 29 and 31 (except chiral purification). LC-MS: 728.3 [(M+H)$^+$].

EXAMPLE 154

5-[(4S,5R)-4,5-Bis-(4-chloro-phenyl)-1-(3-oxo-piperazine-1-carbonyl)-4,5-dihydro-1H-imidazol-2-yl]-2-cyano-4-ethoxy-N,N-dimethyl-benzenesulfonamide

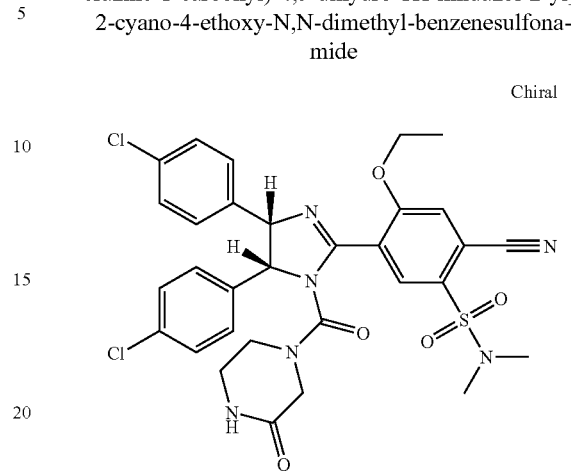

The title compound was prepared from meso-1,2-bis-(4-chlorophenyl)ethane-1,2-diamine, ethyl 4-cyano-5-dimethylsulfamoyl-2-ethoxybenzoate (example 14) and 2-piperazinone (Avocado Organics) following successively the procedures described for examples 25, 29 and 31. LC-MS: 669.4 [(M+H)$^+$].

EXAMPLE 155

2-{4-[(4S,5R)-4,5-Bis-(4-chloro-phenyl)-2-(4-cyano-5-dimethylsulfamoyl-2-ethoxy-phenyl)-4,5-dihydro-imidazole-1-carbonyl]-piperazin-1-yl}-N,N-dimethyl-acetamide hydrochloride

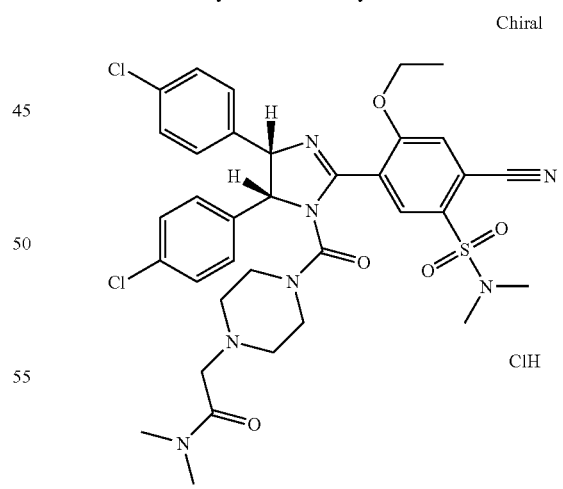

The title compound was prepared from meso-1,2-bis-(4-chlorophenyl)ethane-1,2-diamine, ethyl 4-cyano-5-dimethylsulfamoyl-2-ethoxybenzoate (example 14) and N,N-dimethyl-2-piperazin-1-yl-acetamide (Oakwood Products) following successively the procedures described for examples 25, 29 and 31. LC-MS: 740.2 [(M+H)$^+$].

EXAMPLE 156

5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-2-cyano-4-ethoxy-N,N-dimethyl-benzenesulfonamide hydrochloride

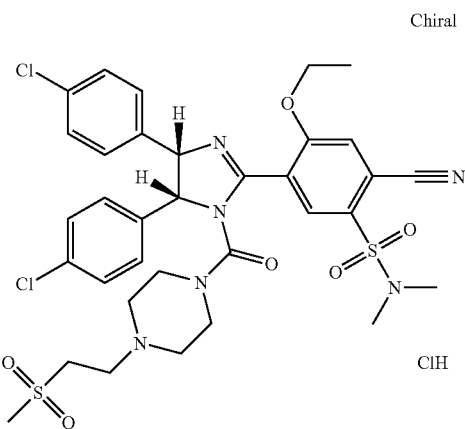

The title compound was prepared from meso-1,2-bis-(4-chlorophenyl)ethane-1,2-diamine, ethyl 4-cyano-5-dimethylsulfamoyl-2-ethoxybenzoate (example 14) and 1-(2-methanesulfonylethyl)piperazine bishydrochloride (example 23) following successively the procedures described for examples 25, 29 and 31. LC-MS: 761.1 [(M+H)+].

EXAMPLE 157

5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-2-cyano-4-ethoxy-N,N-dimethyl-benzenesulfonamide hydrochloride

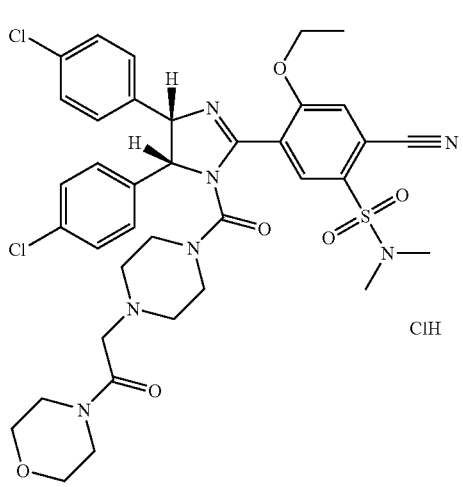

The title compound was prepared from meso-1,2-bis-(4-chlorophenyl)ethane-1,2-diamine, ethyl 4-cyano-5-dimethylsulfamoyl-2-ethoxybenzoate (example 14) and 1-morpholin-4-yl-2-piperazin-1-yl-ethanone (Oakwood Products) following successively the procedures described for examples 25, 29 and 31. LC-MS: 782.8 [(M+H)+].

EXAMPLE 158

5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-4-ethoxy-2-methoxy-benzonitrile hydrochloride

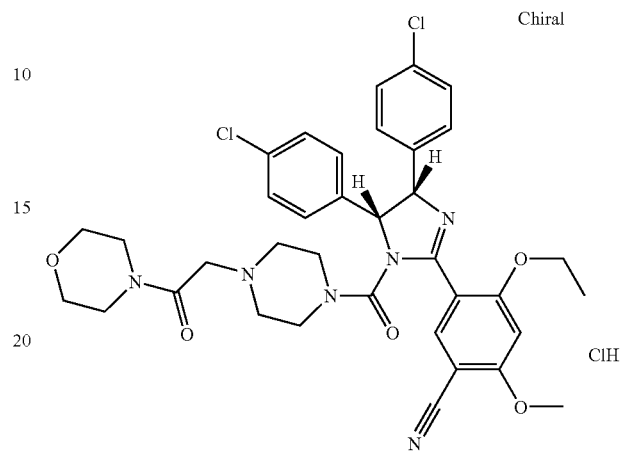

The title compound was prepared from meso-1,2-bis-(4-chlorophenyl)ethane-1,2-diamine, 5-cyano-2-ethoxy-4-methoxy-benzoic acid ethyl ester (example 8) and 1-morpholin-4-yl-2-piperazin-1-yl-ethanone (Oakwood Products) following successively the procedures described for examples 25, 29 and 31. LC-MS: 705.3 [(M+H)+].

EXAMPLE 159

5-[(4S,5R)-4,5-Bis-(4-chloro-phenyl)-1-(3-oxo-piperazine-1-carbonyl)-4,5-dihydro-1H-imidazol-2-yl]-4-ethoxy-2-methoxy-benzonitrile hydrochloride

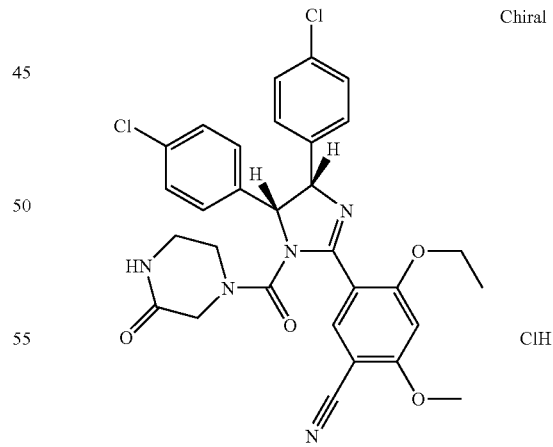

The title compound was prepared from meso-1,2-bis-(4-chlorophenyl)ethane-1,2-diamine, 5-cyano-2-ethoxy-4-methoxy-benzoic acid ethyl ester (example 8) and 2-piperazinone (Avocado Organics) following successively the procedures described for examples 25, 29 and 31. LC-MS: 592.3 [(M+H)+].

EXAMPLE 160

5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-4-ethoxy-2-methoxy-benzonitrile hydrochloride

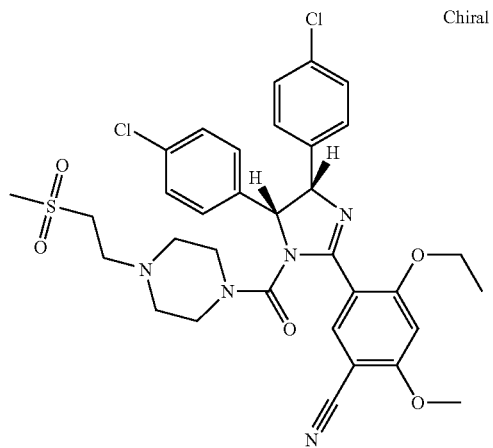

The title compound was prepared from meso-1,2-bis-(4-chlorophenyl)ethane-1,2-diamine, 5-cyano-2-ethoxy-4-methoxy-benzoic acid ethyl ester (example 8) and 1-(2-methanesulfonylethyl)piperazine bishydrochloride (example 23) following successively the procedures described for examples 25, 29 and 31. LC-MS: 684.3 [(M+H)+].

EXAMPLE 161

2-{4-[(4S,5R)-4,5-Bis-(4-chloro-phenyl)-2-(5-dimethylsulfamoyl-2-ethoxy-4-methoxy-phenyl)-4,5-dihydro-imidazole-1-carbonyl]-piperazin-1-yl}-N,N-dimethyl-acetamide hydrochloride

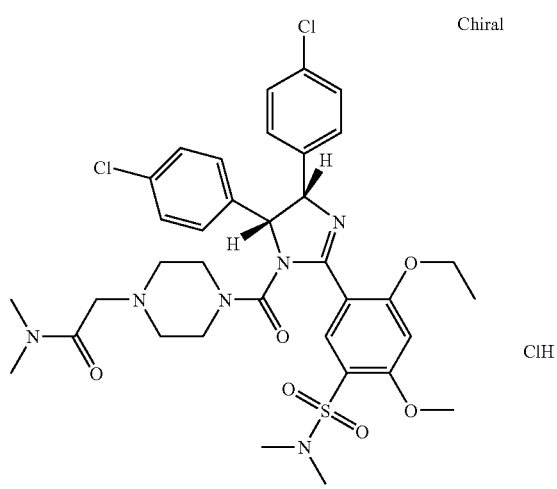

The title compound was prepared from meso-1,2-bis-(4-chlorophenyl)ethane-1,2-diamine, ethyl 5-dimethylsulfamoyl-2-ethoxy-4-methoxy-benzoate (example 2) and N,N-dimethyl-2-piperazin-1-yl-acetamide (Oakwood Products) following successively the procedures described for examples 25, 29 and 31. LC-MS: 745.3 [(M+H)+].

EXAMPLE 162

5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-4-ethoxy-2-methoxy-N,N-dimethyl-benzenesulfonamide hydrochloride

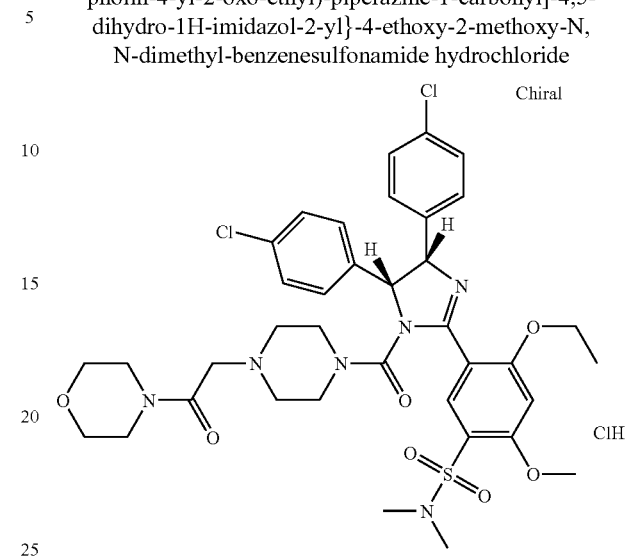

The title compound was prepared from meso-1,2-bis-(4-chlorophenyl)ethane-1,2-diamine, ethyl 5-dimethylsulfamoyl-2-ethoxy-4-methoxy-benzoate (example 2) and 1-morpholin-4-yl-2-piperazin-1-yl-ethanone (Oakwood Products) following successively the procedures described for examples 25, 29 and 31. LC-MS: 787.3 [(M+H)+].

EXAMPLE 163

3-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-4-ethoxy-N,N-dimethyl-benzamide hydrochloride

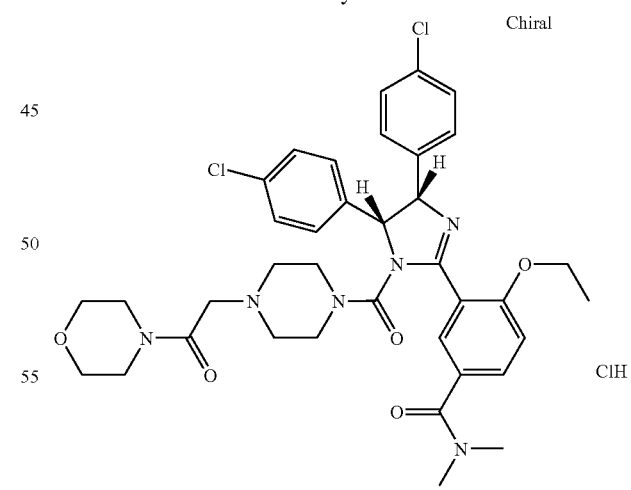

The title compound was prepared from meso-1,2-bis-(4-chlorophenyl)ethane-1,2-diamine, 6-ethoxy-N,N-dimethyl-isophthalamic acid ethyl ester (example 4) and 1-morpholin-4-yl-2-piperazin-1-yl-ethanone (Oakwood Products) following successively the procedures described for examples 25, 29 and 31. LC-MS: 721.3 [(M+H)+].

EXAMPLE 164

3-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-4-ethoxy-N,N-dimethyl-benzamide hydrochloride

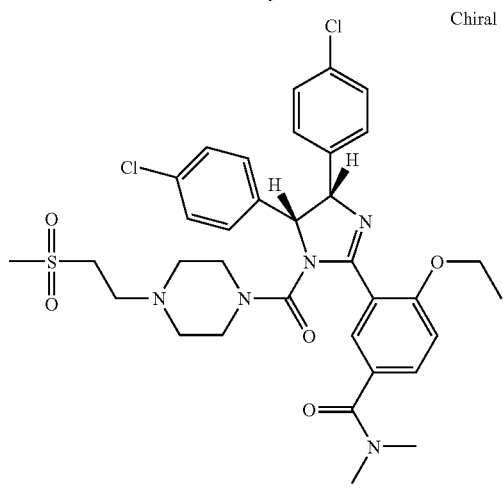

The title compound was prepared from meso-1,2-bis-(4-chlorophenyl)ethane-1,2-diamine, 6-ethoxy-N,N-dimethyl-isophthalamic acid ethyl ester (example 4) and 1-(2-methanesulfonylethyl)piperazine bishydrochloride (example 23) following successively the procedures described for examples 25, 29 and 31. LC-MS: 700.3 [(M+H)$^+$].

EXAMPLE 165

3-[(4S,5R)-4,5-Bis-(4-chloro-phenyl)-1-(3-oxo-piperazine-1-carbonyl)-4,5-dihydro-1H-imidazol-2-yl]-4-ethoxy-N N-dimethyl-benzamide hydrochloride

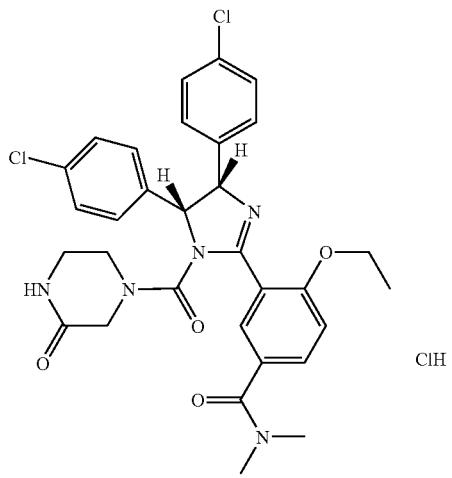

The title compound was prepared from meso-1,2-bis-(4-chlorophenyl)ethane-1,2-diamine, 6-ethoxy-N,N-dimethyl-isophthalamic acid ethyl ester (example 4) and 2-piperazinone (Avocado Organics) following successively the procedures described for examples 25, 29 and 31. LC-MS: 608.1 [(M+H)$^+$].

EXAMPLE 166

2-(4-{(4S,5R)-4,5-Bis-(4-chloro-phenyl)-2-[2-ethoxy-5-(pyrrolidine-1-carbonyl)-phenyl]-4,5-dihydro-imidazole-1-carbonyl}-piperazin-1-yl)-1-morpholin-4-yl-ethanone hydrochloride

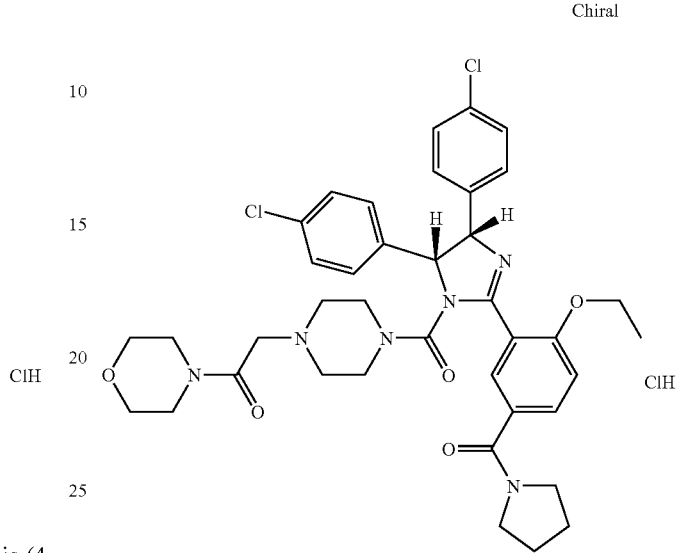

The title compound was prepared from meso-1,2-bis-(4-chlorophenyl)ethane-1,2-diamine, 2-ethoxy-5-(pyrrolidine-1-carbonyl)-benzoic acid ethyl ester (example 4) and 1-morpholin-4-yl-2-piperazin-1-yl-ethanone (Oakwood Products) following successively the procedures described for examples 25, 29 and 31. LC-MS: 747.3 [(M+H)$^+$].

EXAMPLE 167

{(4S,5R)-4,5-Bis-(4-chloro-phenyl)-2-[2-ethoxy-5-(pyrrolidine-1-carbonyl)-phenyl]-4,5-dihydro-imidazol-1-yl}-[4-(2-methanesulfonyl-ethyl)-piperazin-1-yl]-methanone hydrochloride

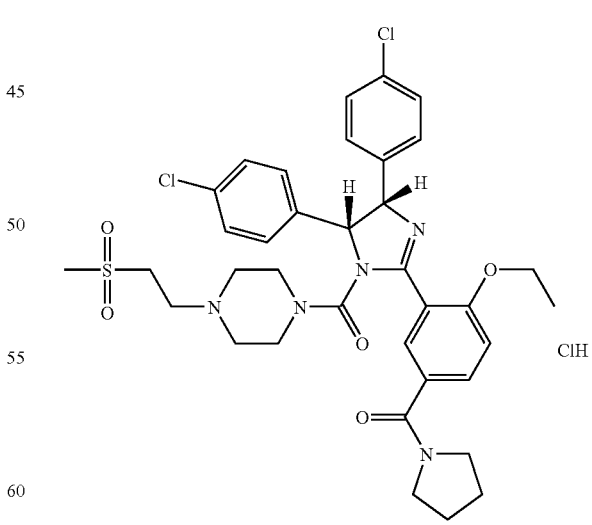

The title compound was prepared from meso-1,2-bis-(4-chlorophenyl)ethane-1,2-diamine, 2-ethoxy-5-(pyrrolidine-1-carbonyl)-benzoic acid ethyl ester (example 4) and 1-(2-methanesulfonylethyl)piperazine bishydrochloride (example 23) following successively the procedures described for examples 25, 29 and 31. LC-MS: 726.3 [(M+H)$^+$].

EXAMPLE 168

2-(4-{(4S,5R)-4,5-Bis-(4-chloro-phenyl)-2-[2-ethoxy-5-(piperidine-1-carbonyl)-phenyl]-4,5-dihydro-imidazole-1-carbonyl}-piperazin-1-yl)-1-morpholin-4-yl-ethanone hydrochloride Chiral

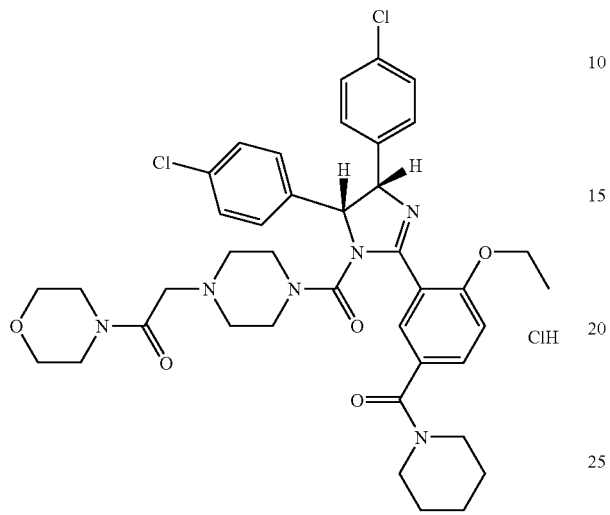

The title compound was prepared from meso-1,2-bis-(4-chlorophenyl)ethane-1,2-diamine, 2-ethoxy-5-(piperidine-1-carbonyl)-benzoic acid ethyl ester (example 4) and 1-morpholin-4-yl-2-piperazin-1-yl-ethanone (Oakwood Products) following successively the procedures described for examples 25, 29 and 31. LC-MS: 761.3 [(M+H)$^+$].

EXAMPLE 169

{(4S,5R)-4,5-Bis-(4-chloro-phenyl)-2-[2-ethoxy-5-(piperidine-1-carbonyl)-phenyl]-4,5-dihydro-imidazol-1-yl}-[4-(2-methanesulfonyl-ethyl)-piperazin-1-yl]-methanone hydrochloride Chiral

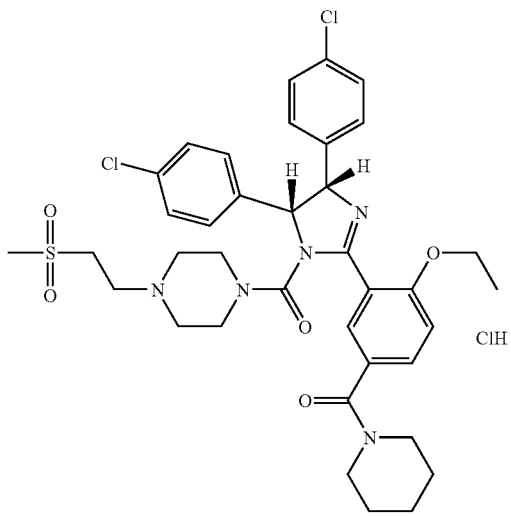

The title compound was prepared from meso-1,2-bis-(4-chlorophenyl)ethane-1,2-diamine, 2-ethoxy-5-(piperidine-1-carbonyl)-benzoic acid ethyl ester (example 4) and 1-(2-methanesulfonylethyl)piperazine bishydrochloride (example 23) following successively the procedures described for examples 25, 29 and 31. LC-MS: 740.3 [(M+H)$^+$].

EXAMPLE 170

4-{(4S,5R)-4,5-Bis-(4-chloro-phenyl)-2-[2-ethoxy-5-(piperidine-1-carbonyl)-phenyl]-4,5-dihydro-imidazole-1-carbonyl}-piperazin-2-one hydrochloride Chiral

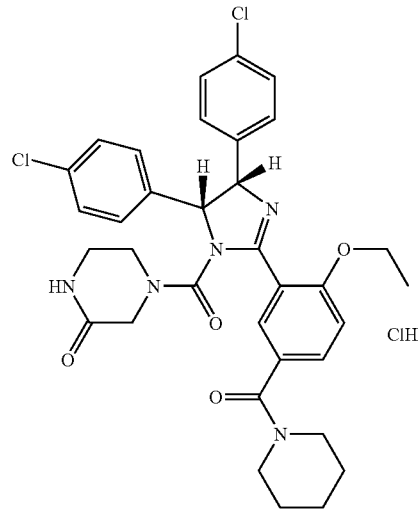

The title compound was prepared from meso-1,2-bis-(4-chlorophenyl)ethane-1,2-diamine, 2-ethoxy-5-(piperidine-1-carbonyl)-benzoic acid ethyl ester (example 4) and 2-piperazinone (Avocado Organics) following successively the procedures described for examples 25, 29 and 31. LC-MS: 648.2 [(M+H)$^+$].

EXAMPLE 171

2-(4-{(4S,5R)-4,5-Bis-(4-chloro-phenyl)-2-[2-ethoxy-5-(morpholine-4-carbonyl)-phenyl]-4,5-dihydro-imidazole-1-carbonyl}-piperazin-1-yl)-1-morpholin-4-yl-ethanone hydrochloride Chiral

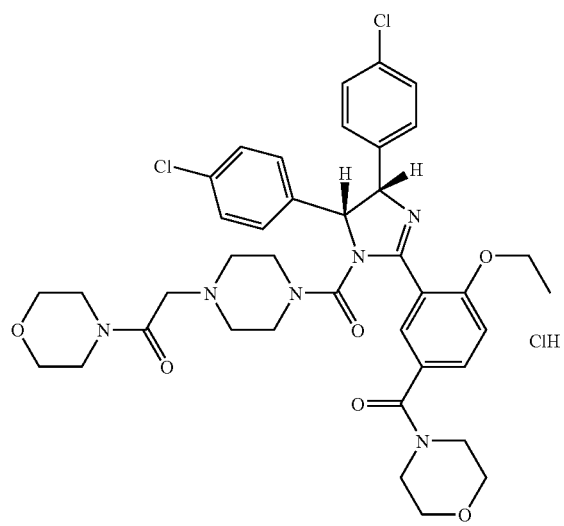

The title compound was prepared from meso-1,2-bis-(4-chlorophenyl)ethane-1,2-diamine, 2-ethoxy-5-(morpholine-1-carbonyl)-benzoic acid ethyl ester (example 4) and 1-morpholin-4-yl-2-piperazin-1-yl-ethanone (Oakwood Products) following successively the procedures described for examples 25, 29 and 31. LC-MS: 763.3 [(M+H)$^+$].

EXAMPLE 172

5-[(4S,5R)-4,5-Bis-(4-chloro-phenyl)-1-(3-oxo-piperazine-1-carbonyl)-4,5-dihydro-1H-imidazol-2-yl]-4-ethoxy-2-fluoro-N,N-dimethyl-benzenesulfonamide Chiral

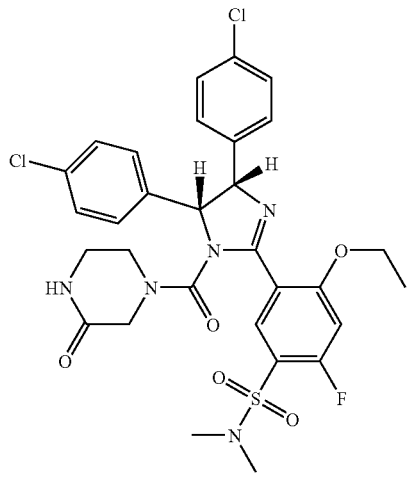

The title compound was prepared from meso-1,2-bis-(4-chlorophenyl)ethane-1,2-diamine, ethyl 5-dimethylsulfamoyl-2-ethoxy-4-fluoro-benzoate (example 2) and 2-piperazinone (Avocado Organics) following successively the procedures described for examples 25, 29 and 31. LC-MS: 662.2 [(M+H)$^+$].

EXAMPLE 173

2-(4-{(4S,5R)-4,5-Bis-(4-chloro-phenyl)-2-[2-ethoxy-4-methyl-5-(pyrrolidine-1-sulfonyl)-phenyl]-4,5-dihydro-imidazole-1-carbonyl}-piperazin-1-yl)-1-morpholin-4-yl-ethanone hydrochloride Chiral

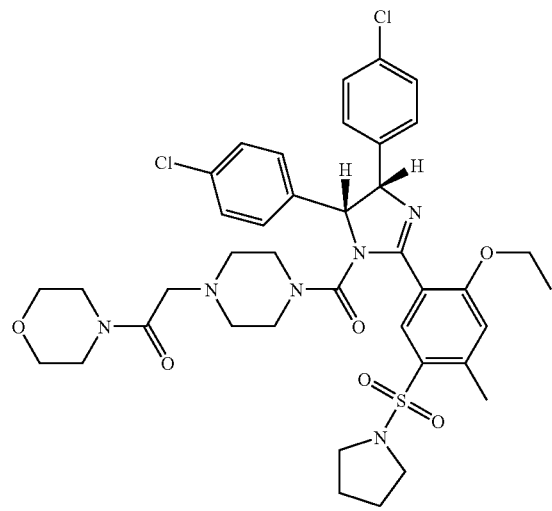

The title compound was prepared from meso-1,2-bis-(4-chlorophenyl)ethane-1,2-diamine, 2-ethoxy-4-methyl-5-(pyrrolidine-1-sulfonyl)-benzoic acid ethyl ester (example 2) and 1-morpholin-4-yl-2-piperazin-1-yl-ethanone (Oakwood Products) following successively the procedures described for examples 25, 29 and 31. LC-MS: 797.3 [(M+H)$^+$].

EXAMPLE 174

[(4S,5R)-2-[4-Chloro-2-ethoxy-5-(pyrrolidine-1-sulfonyl)-phenyl]-4,5-bis-(4-chloro-phenyl)-4,5-dihydro-imidazol-1-yl]-[4-(2-methanesulfonyl-ethyl)-piperazin-1-yl]-methanone hydrochloride Chiral

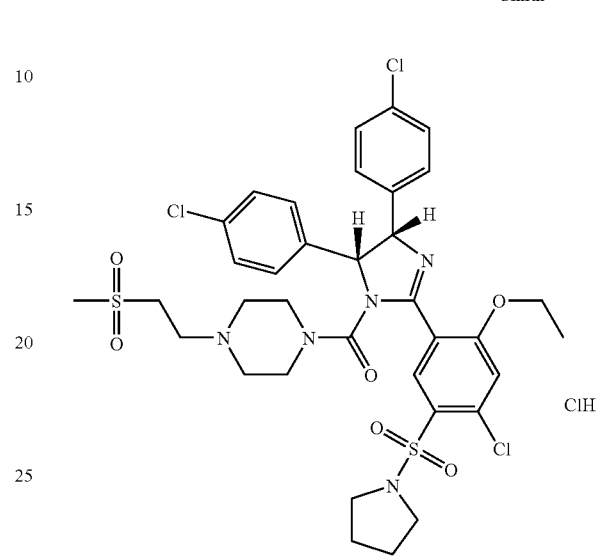

The title compound was prepared from meso-1,2-bis-(4-chlorophenyl)ethane-1,2-diamine, ethyl 4-chloro-2-ethoxy-5-(pyrrolidine-1-sulfonyl)-benzoate (example 2) and 1-(2-methanesulfonylethyl)piperazine bishydrochloride (example 23) following successively the procedures described for examples 25, 29 and 31. LC-MS: 796.2 [(M+H)$^+$].

EXAMPLE 175

2-{4-[(4S,5R)-2-[4-Chloro-2-ethoxy-5-(piperidine-1-sulfonyl)-phenyl]-4,5-bis-(4-chloro-phenyl)-4,5-dihydro-imidazole-1-carbonyl]-piperazin-1-yl}-1-morpholin-4-yl-ethanone hydrochloride Chiral

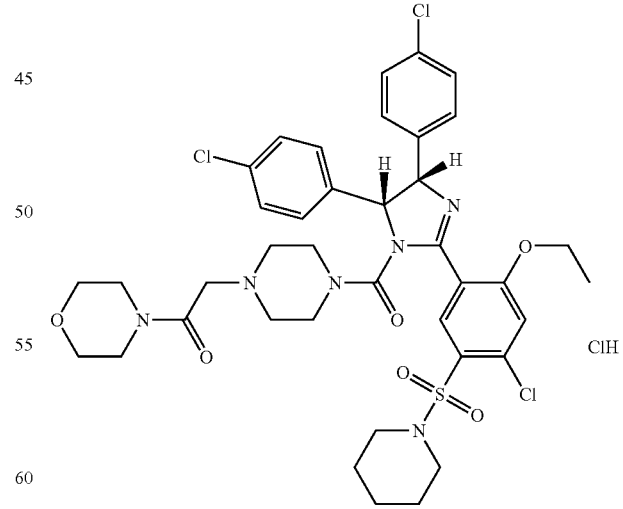

The title compound was prepared from meso-1,2-bis-(4-chlorophenyl)ethane-1,2-diamine, ethyl 4-chloro-2-ethoxy-5-(piperidine-1-sulfonyl)-benzoate (example 2) and 1-morpholin-4-yl-2-piperazin-1-yl-ethanone (Oakwood Products) following successively the procedures described for examples 25, 29 and 31. LC-MS: 831.2 [(M+H)$^+$].

EXAMPLE 176

[(4S,5R)-2-[4-Chloro-2-ethoxy-5-(piperidine-1-sulfonyl)-phenyl]-4,5-bis-(4-chloro-phenyl)-4,5-dihydro-imidazol-1-yl]-[4-(2-methanesulfonyl-ethyl)-piperazin-1-yl]-methanone hydrochloride Chiral

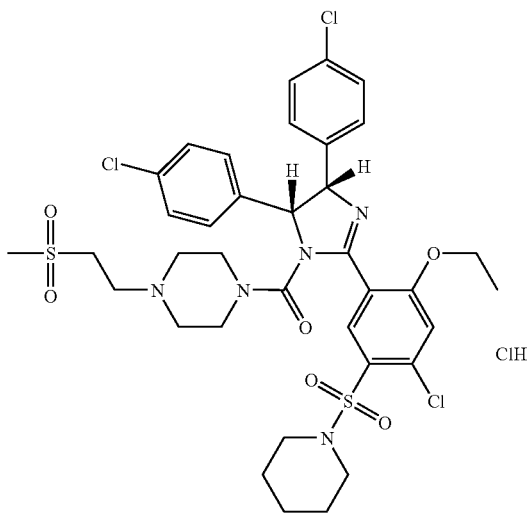

The title compound was prepared from meso-1,2-bis-(4-chlorophenyl)ethane-1,2-diamine, ethyl 4-chloro-2-ethoxy-5-(piperidine-1-sulfonyl)-benzoate (example 2) and 1-(2-methanesulfonylethyl)piperazine bishydrochloride (example 23) following successively the procedures described for examples 25, 29 and 31. LC-MS: 810.2 [(M+H)$^+$].

EXAMPLE 177

4-[(4S,5R)-2-[4-Chloro-2-ethoxy-5-(piperidine-1-sulfonyl)-phenyl]-4,5-bis-(4-chloro-phenyl)-4,5-dihydro-imidazole-1-carbonyl]-piperazin-2-one hydrochloride Chiral

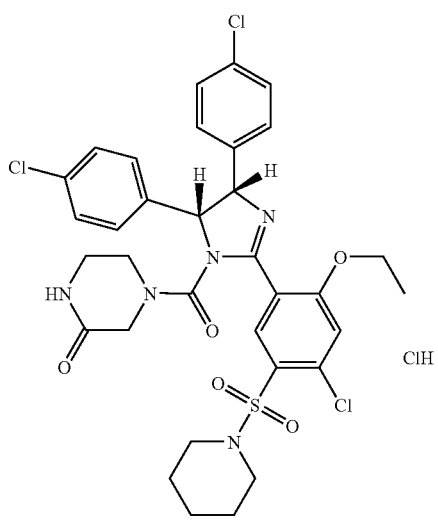

The title compound was prepared from meso-1,2-bis-(4-chlorophenyl)ethane-1,2-diamine, ethyl 4-chloro-2-ethoxy-5-(piperidine-1-sulfonyl)-benzoate (example 2) and 2-piperazinone (Avocado Organics) following successively the procedures described for examples 25, 29 and 31. LC-MS: 718.1 [(M+H)$^+$].

EXAMPLE 178

2-{4-[(4S,5R)-2-[4-Chloro-2-ethoxy-5-(morpholine-4-sulfonyl)-phenyl]-4,5-bis-(4-chloro-phenyl)-4,5-dihydro-imidazole-1-carbonyl]-piperazin-1-yl}-1-morpholin-4-yl-ethanone hydrochloride Chiral

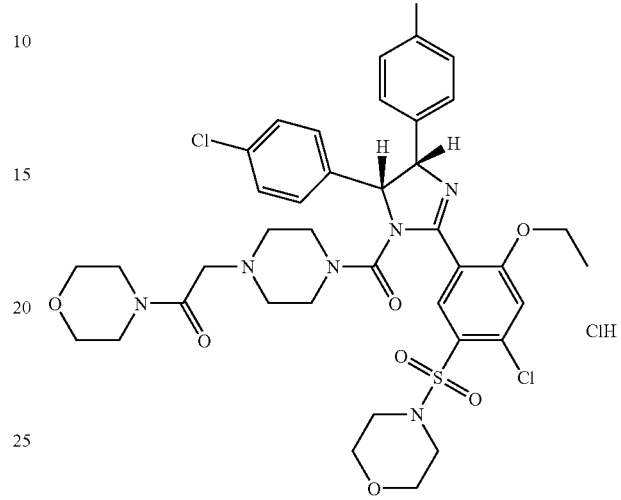

The title compound was prepared from meso-1,2-bis-(4-chlorophenyl)ethane-1,2-diamine, ethyl 4-chloro-2-ethoxy-5-(morpholine-4-sulfonyl)-benzoate (example 2) and 1-morpholin-4-yl-2-piperazin-1-yl-ethanone (Oakwood Products) following successively the procedures described for examples 25, 29 and 31. LC-MS: 833.2 [(M+H)$^+$].

EXAMPLE 179

[(4S,5R)-2-[4-Chloro-2-ethoxy-5-(morpholine-4-sulfonyl)-phenyl]-4,5-bis-(4-chloro-phenyl)-4,5-dihydro-imidazol-1-yl]-[4-(2-methanesulfonyl-ethyl)-piperazin-1-yl]-methanone hydrochloride Chiral

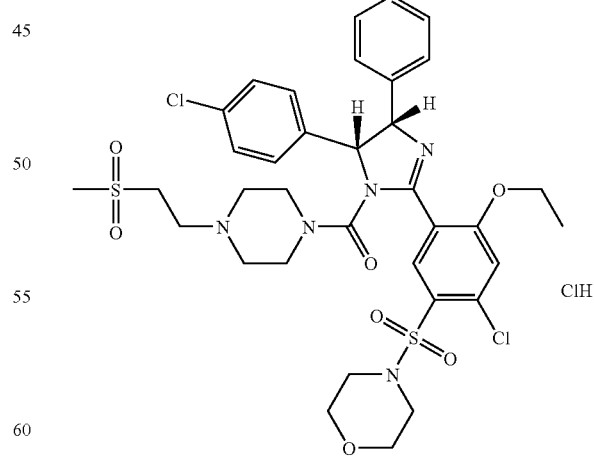

The title compound was prepared from meso-1,2-bis-(4-chlorophenyl)ethane-1,2-diamine, ethyl 4-chloro-2-ethoxy-5-(morpholine-4-sulfonyl)-benzoate (example 2) and 1-(2-methanesulfonylethyl)piperazine bishydrochloride (example 23) following successively the procedures described for examples 25, 29 and 31. LC-MS: 812.2 [(M+H)$^+$].

EXAMPLE 180

4-[(4S,5R)-2-[4-Chloro-2-ethoxy-5-(morpholine-4-sulfonyl)-phenyl]-4,5-bis-(4-chloro-phenyl)-4,5-dihydro-imidazole-1-carbonyl]-piperazin-2-one hydrochloride Chiral

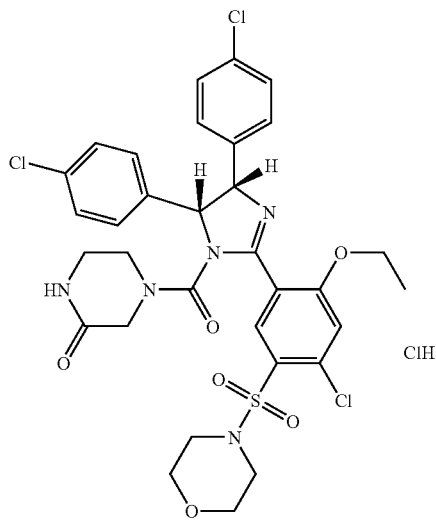

The title compound was prepared from meso-1,2-bis-(4-chlorophenyl)ethane-1,2-diamine, ethyl 4-chloro-2-ethoxy-5-(morpholine-4-sulfonyl)-benzoate (example 2) and 2-piperazinone (Avocado Organics) following successively the procedures described for examples 25, 29 and 31. LC-MS: 720 [(M+H)+].

EXAMPLE 181

{(4S,5R)-4,5-Bis-(4-chloro-phenyl)-2-[2-ethoxy-4-methyl-5-(pyrrolidine-1-sulfonyl)-phenyl]-4,5-dihydro-imidazol-1-yl}-[4-(2-methanesulfonyl-ethyl)-piperazin-1-yl]-methanone hydrochloride Chiral

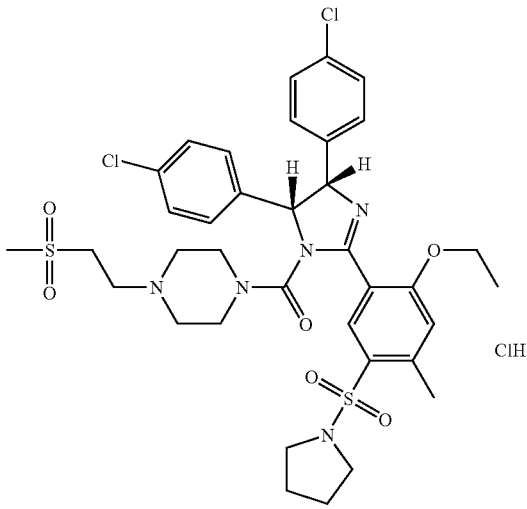

The title compound was prepared from meso-1,2-bis-(4-chlorophenyl)ethane-1,2-diamine, 2-ethoxy-4-methyl-5-(pyrrolidine-1-sulfonyl)-benzoic acid ethyl ester (example 2) and 1-(2-methanesulfonylethyl)piperazine bishydrochloride (example 23) following successively the procedures described for examples 25, 29 and 31. LC-MS: 776.3 [(M+H)+].

EXAMPLE 182

2-(4-{(4S,5R)-4,5-Bis-(4-chloro-phenyl)-2-[2-ethoxy-4-methyl-5-(piperidine-1-sulfonyl)-phenyl]-4,5-dihydro-imidazole-1-carbonyl}-piperazin-1-yl)-1-morpholin-4-yl-ethanone hydrochloride Chiral

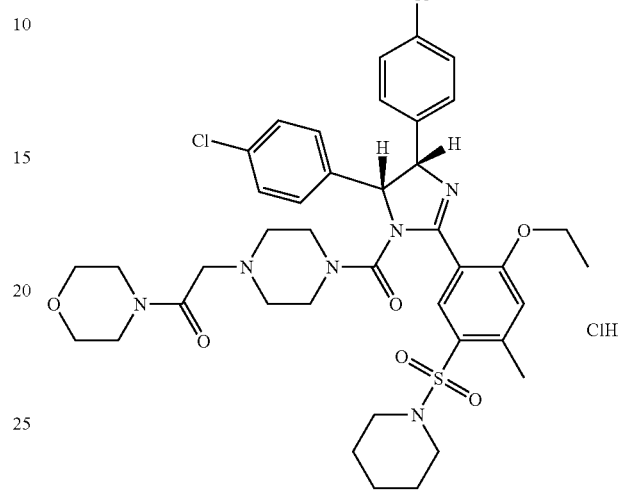

The title compound was prepared from meso-1,2-bis-(4-chlorophenyl)ethane-1,2-diamine, ethyl 2-ethoxy-4-methyl-5-(piperidine-1-sulfonyl)-benzoate (example 2) and 1-morpholin-4-yl-2-piperazin-1-yl-ethanone (Oakwood Products) following successively the procedures described for examples 25, 29 and 31. LC-MS: 811.3 [(M+H)+].

EXAMPLE 183

{(4S,5R)-4,5-Bis-(4-chloro-phenyl)-2-[2-ethoxy-4-methyl-5-(piperidine-1-sulfonyl)-phenyl]-4,5-dihydro-imidazol-1-yl}-[4-(2-methanesulfonyl-ethyl)-piperazin-1-yl]-methanone hydrochloride Chiral

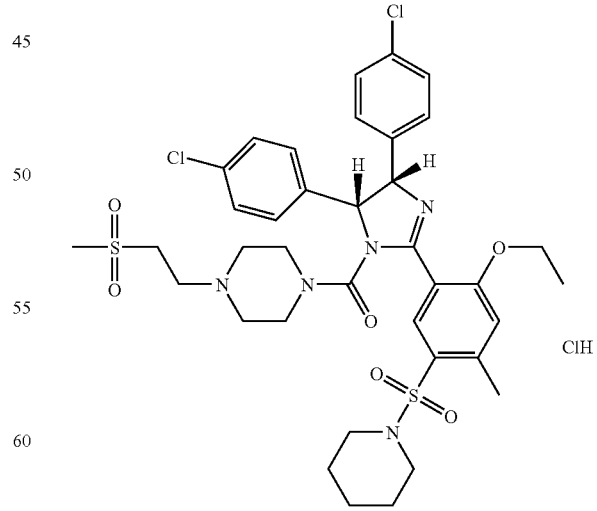

The title compound was prepared from meso-1,2-bis-(4-chlorophenyl)ethane-1,2-diamine, ethyl 2-ethoxy-4-methyl-5-(piperidine-1-sulfonyl)-benzoate (example 2) and 1-(2-methanesulfonylethyl)piperazine bishydrochloride (example 23) following successively the procedures described for examples 25, 29 and 31. LC-MS: 790.3 [(M+H)⁺].

EXAMPLE 184

4-{(4S,5R)-4,5-Bis-(4-chloro-phenyl)-2-[2-ethoxy-4-methyl-5-(piperidine-1-sulfonyl)-phenyl]-4,5-dihydro-imidazole-1-carbonyl}-piperazin-2-one hydrochloride

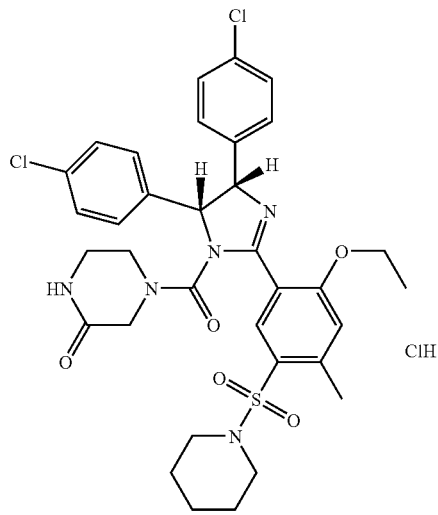

The title compound was prepared from meso-1,2-bis-(4-chlorophenyl)ethane-1,2-diamine, ethyl 2-ethoxy-4-methyl-5-(piperidine-1-sulfonyl)-benzoate (example 2) and 2-piperazinone (Avocado Organics) following successively the procedures described for examples 25, 29 and 31. LC-MS: 698.1 [(M+H)⁺].

EXAMPLE 185

2-(4-{(4S,5R)-4,5-Bis-(4-chloro-phenyl)-2-[2-ethoxy-4-methyl-5-(morpholine-4-sulfonyl)-phenyl]-4,5-dihydro-imidazole-1-carbonyl}-piperazin-1-yl)-1-morpholin-4-yl-ethanone hydrochloride

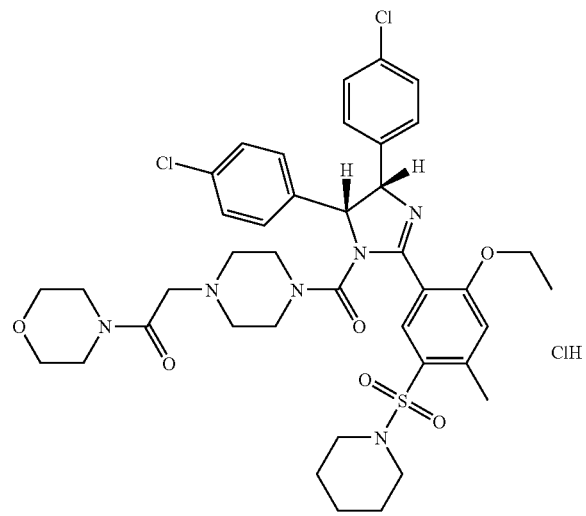

The title compound was prepared from meso-1,2-bis-(4-chlorophenyl)ethane-1,2-diamine, ethyl 2-ethoxy-4-methyl-5-(morpholine-4-sulfonyl)-benzoate (example 2) and 1-morpholin-4-yl-2-piperazin-1-yl-ethanone (Oakwood Products) following successively the procedures described for examples 25, 29 and 31. LC-MS: 813.3 [(M+H)⁺].

EXAMPLE 186

{(4S,5R)-4,5-Bis-(4-chloro-phenyl)-2-[2-ethoxy-4-methyl-5-(morpholine-4-sulfonyl)-phenyl]-4,5-dihydro-imidazol-1-yl}-[4-(2-methanesulfonyl-ethyl)-piperazin-1-yl]-methanone hydrochloride

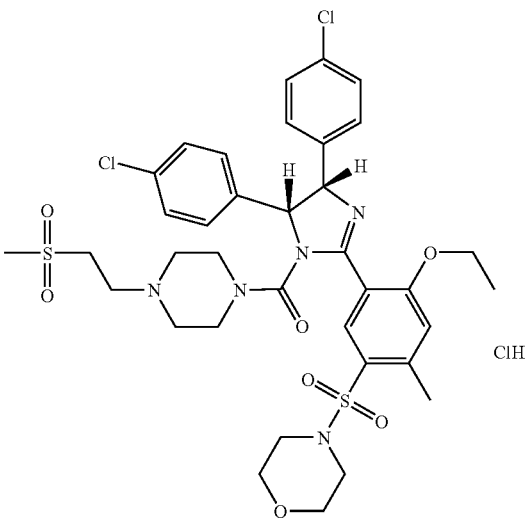

The title compound was prepared from meso-1,2-bis-(4-chlorophenyl)ethane-1,2-diamine, ethyl 2-ethoxy-4-methyl-5-(morpholine-4-sulfonyl)-benzoate (example 2) and 1-(2-methanesulfonylethyl)piperazine bishydrochloride (example 23) following successively the procedures described for examples 25, 29 and 31. LC-MS: 792.3 [(M+H)⁺].

EXAMPLE 187

4-{(4S,5R)-4,5-Bis-(4-chloro-phenyl)-2-[2-ethoxy-4-methyl-5-(morpholine-4-sulfonyl)-phenyl]-4,5-dihydro-imidazole-1-carbonyl}-piperazin-2-one hydrochloride

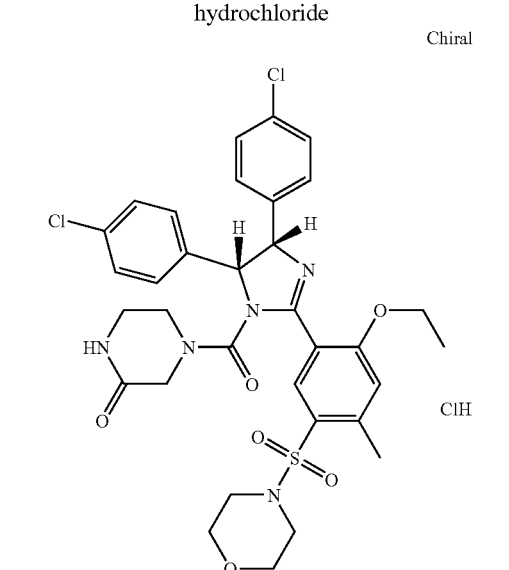

The title compound was prepared from meso-1,2-bis-(4-chlorophenyl)ethane-1,2-diamine, ethyl 2-ethoxy-4-methyl-5-(morpholine-4-sulfonyl)-benzoate (example 2) and 2-piperazinone (Avocado Organics) following successively the procedures described for examples 25, 29 and 31. LC-MS: 700.1 [(M+H)+].

EXAMPLE 188

2-{4-[(4S,5R)-2-[4-Chloro-2-ethoxy-5-(pyrrolidine-1-sulfonyl)-phenyl]-4,5-bis-(4-chloro-phenyl)-4,5-dihydro-imidazole-1-carbonyl]-piperazin-1-yl}-1-morpholin-4-yl-ethanone hydrochloride

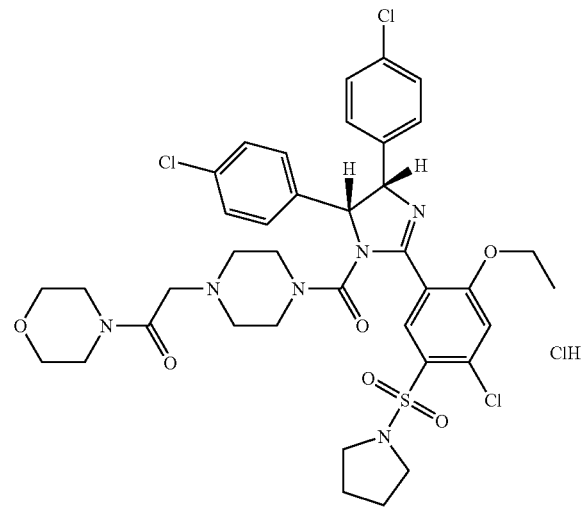

The title compound was prepared from meso-1,2-bis-(4-chlorophenyl)ethane-1,2-diamine, ethyl 4-chloro-2-ethoxy-5-(pyrrolidine-1-sulfonyl)-benzoate (example 2) and 1-morpholin-4-yl-2-piperazin-1-yl-ethanone (Oakwood Products) following successively the procedures described for examples 25, 29 and 31. LC-MS: 817.2 [(M+H)+].

EXAMPLE 189

4-[(4S,5R)-4,5-Bis-(4-chloro-phenyl)-1-(3-oxo-piperazine-1-carbonyl)-4,5-dihydro-1H-imidazol-2-yl]-3-ethoxy-N,N-dimethyl-benzenesulfonamide hydrochloride

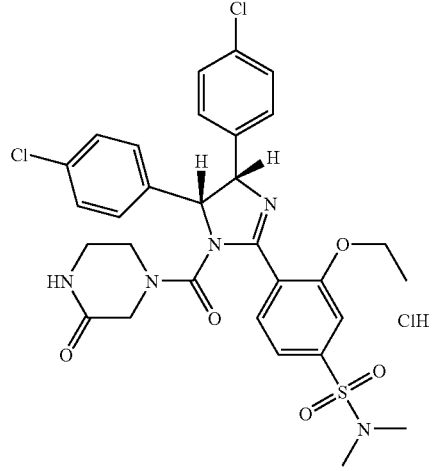

The title compound was prepared from meso-1,2-bis-(4-chlorophenyl)ethane-1,2-diamine, methyl 4-dimethylsulfamoyl-2-ethoxybenzoate (example 11) and 2-piperazinone (Avocado Organics) following successively the procedures described for examples 25, 29 and 31. LC-MS: 644.3 [(M+H)+].

EXAMPLE 190

4-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-3-ethoxy-N,N-dimethyl-benzenesulfonamide hydrochloride

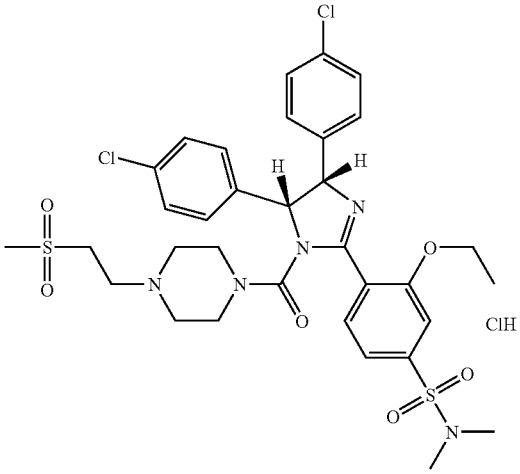

The title compound was prepared from meso-1,2-bis-(4-chlorophenyl)ethane-1,2-diamine, methyl 4-dimethylsulfamoyl-2-ethoxybenzoate (example 11) and 1-(2-methanesulfonylethyl)piperazine bishydrochloride (example 23) following successively the procedures described for examples 25, 29 and 31. LC-MS: 736.3 [(M+H)+].

EXAMPLE 191

4-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-3-ethoxy-N,N-dimethyl-benzenesulfonamide hydrochloride

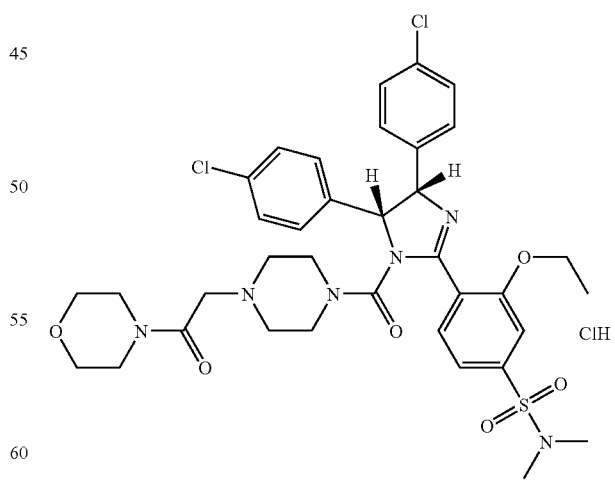

The title compound was prepared from meso-1,2-bis-(4-chlorophenyl)ethane-1,2-diamine, methyl 4-dimethylsulfamoyl-2-ethoxybenzoate (example 11) and 1-morpholin-4-yl-2-piperazin-1-yl-ethanone (Oakwood Products) following successively the procedures described for examples 25, 29 and 31. LC-MS: 754.3 [(M+H)+].

EXAMPLE 192

2-{4-[(4S,5R)-4,5-Bis-(4-chloro-phenyl)-2-(4-dimethylsulfamoyl-2-ethoxy-phenyl)-4,5-dihydro-imidazole-1-carbonyl]-piperazin-1-yl}-N,N-dimethyl-acetamide hydrochloride

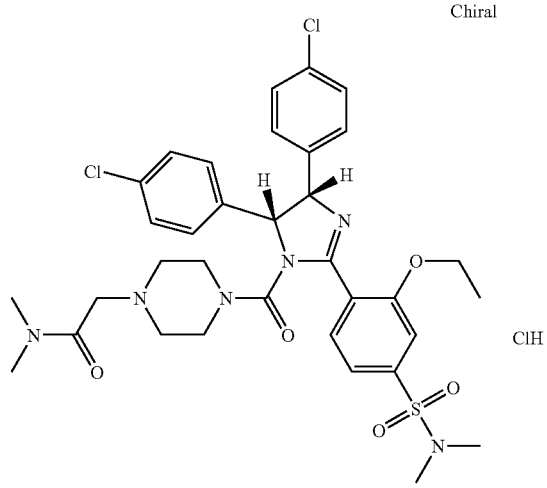

The title compound was prepared from meso-1,2-bis-(4-chlorophenyl)ethane-1,2-diamine, methyl 4-dimethylsulfamoyl-2-ethoxybenzoate (example 11) and N,N-dimethyl-2-piperazin-1-yl-acetamide (Oakwood Products) following successively the procedures described for examples 25, 29 and 31. LC-MS: 715.3 [(M+H)$^+$].

EXAMPLE 193

2-{4-[(4S,5R)-4,5-Bis-(4-chloro-phenyl)-2-(4-cyano-2-ethoxy-phenyl)-4,5-dihydro-imidazole-1-carbonyl]-piperazin-1-yl}-N-tert-butyl-acetamide

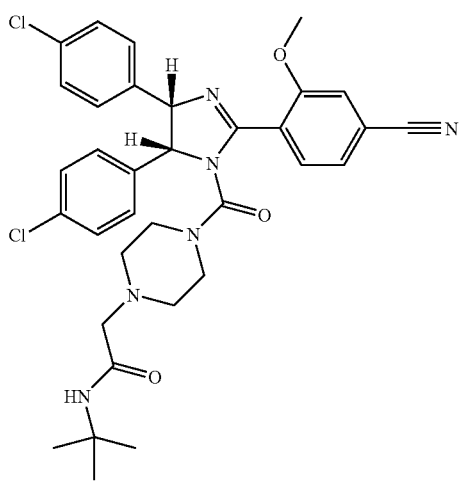

The title compound was prepared from 4-[4,5-bis-(4-chloro-phenyl)-4,5-dihydro-1H-imidazol-2-yl]-3-ethoxy-benzonitrile (example 25) and N-tert-butyl-2-piperazin-1-yl-acetamide (example 22g) following successively the procedures described for examples 29 and 31. LC-MS: 661.3 [(M+H)$^+$].

EXAMPLE 194

2-{4-[(4S,5R)-4,5-Bis-(4-chloro-phenyl)-2-(4-cyano-2-ethoxy-phenyl)-4,5-dihydro-imidazole-1-carbonyl]-piperazin-1-yl}-acetamide

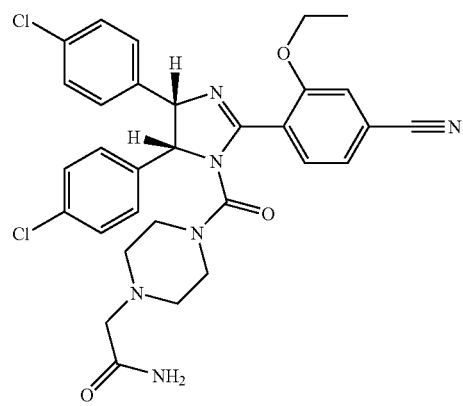

The title compound was prepared from 4-[4,5-bis-(4-chloro-phenyl)-4,5-dihydro-1H-imidazol-2-yl]-3-ethoxy-benzonitrile (example 25) and 2-piperazin-1-yl-acetamide (Matrix) following successively the procedures described for examples 29 and 31. LC-MS: 605.2 [(M+H)$^+$].

EXAMPLE 195

2-{4-[(4S,5R)-4,5-Bis-(4-chloro-phenyl)-2-(4-cyano-2-ethoxy-phenyl)-4,5-dihydro-imidazole-1-carbonyl]-piperazin-1-yl}-N-cyanomethyl-N-methyl-acetamide

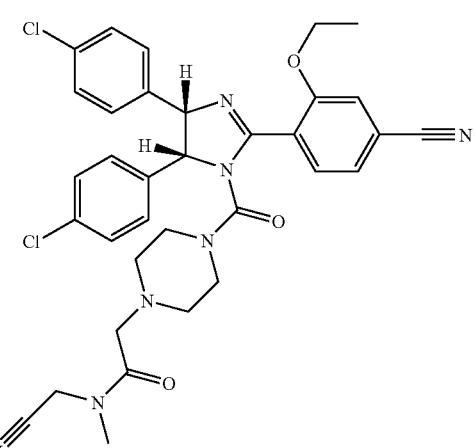

The title compound was prepared from 4-[4,5-bis-(4-chloro-phenyl)-4,5-dihydro-1H-imidazol-2-yl]-3-ethoxy-benzonitrile (example 25) and N-cyanomethyl-N-methyl-2-piperazin-1-yl-acetamide (example 22h) following successively the procedures described for examples 29 and 31. LC-MS: 658.3 [(M+H)$^+$].

EXAMPLE 196

2-{4-[(4S,5R)-4,5-Bis-(4-chloro-phenyl)-2-(4-cyano-2-ethoxy-phenyl)-4,5-dihydro-imidazole-1-carbonyl]-piperazin-1-yl}-N-cyclopropyl-acetamide Chiral

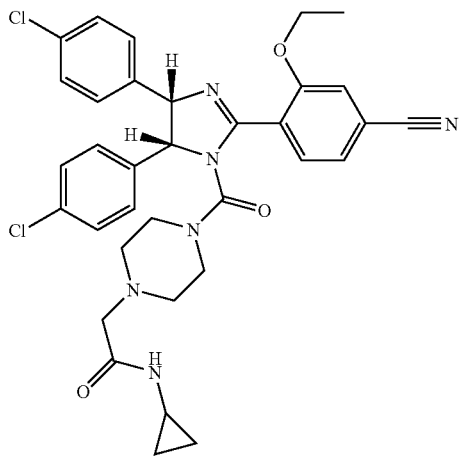

The title compound was prepared from 4-[4,5-bis-(4-chloro-phenyl)-4,5-dihydro-1H-imidazol-2-yl]-3-ethoxy-benzonitrile (example 25) and N-cyclopropyl-2-piperazin-1-yl-acetamide (example 22j) following successively the procedures described for examples 29 and 31. LC-MS: 645.3 [(M+H)+].

EXAMPLE 197

2-{4-[(4S,5R)-4,5-Bis-(4-chloro-phenyl)-2-(4-cyano-2-ethoxy-phenyl)-4,5-dihydro-imidazole-1-carbonyl]-piperazin-1-yl}-N-(2-methoxy-ethyl)-acetamide Chiral

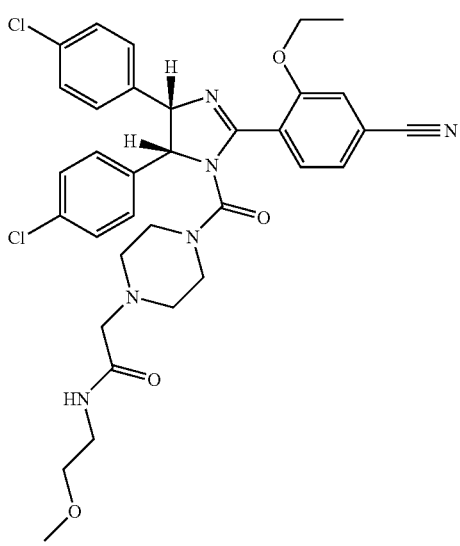

The title compound was prepared from 4-[4,5-bis-(4-chloro-phenyl)-4,5-dihydro-1H-imidazol-2-yl]-3-ethoxy-benzonitrile (example 25) and N-(2-methoxy-ethyl)-2-piperazin-1-yl-acetamide (example 22k) following successively the procedures described for examples 29 and 31. LC-MS: 663.3 [(M+H)+].

EXAMPLE 198

2-{4-[(4S,5R)-4,5-Bis-(4-chloro-phenyl)-2-(4-cyano-2-ethoxy-phenyl)-4,5-dihydro-imidazole-1-carbonyl]-piperazin-1-yl}-N,N-bis-(2-methoxy-ethyl)-acetamide Chiral

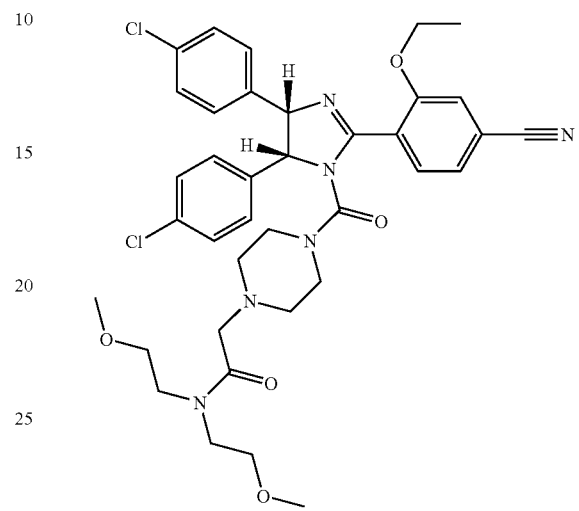

The title compound was prepared from 4-[4,5-bis-(4-chloro-phenyl)-4,5-dihydro-1H-imidazol-2-yl]-3-ethoxy-benzonitrile (example 25) and N,N-bis-(2-methoxy-ethyl)-2-piperazin-1-yl-acetamide (example 22a) following successively the procedures described for examples 29 and 31. LC-MS: 721.4 [(M+H)+].

EXAMPLE 199

2-{4-[(4S,5R)-4,5-Bis-(4-chloro-phenyl)-2-(4-cyano-2-ethoxy-phenyl)-4,5-dihydro-imidazole-1-carbonyl]-piperazin-1-yl}-N-methoxy-N-methyl-acetamide Chiral

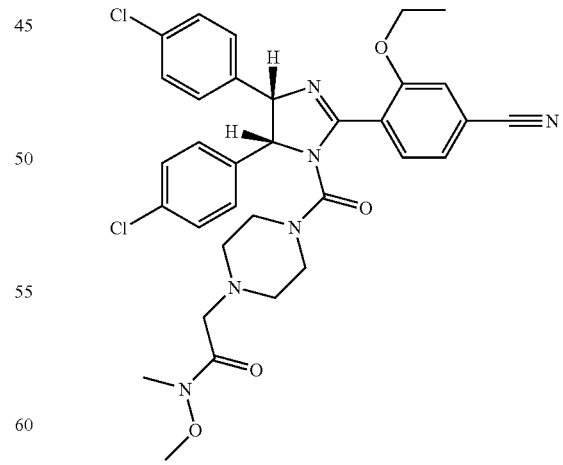

The title compound was prepared from 4-[4,5-bis-(4-chloro-phenyl)-4,5-dihydro-1H-imidazol-2-yl]-3-ethoxy-benzonitrile (example 25) and N-methoxy-N-methyl-2-piperazin-1-yl-acetamide (example 22b) following successively the procedures described for examples 29 and 31. LC-MS: 649.3 [(M+H)+].

EXAMPLE 200

2-{4-[(4S,5R)-4,5-Bis-(4-chloro-phenyl)-2-(4-cyano-2-ethoxy-phenyl)-4,5-dihydro-imidazole-1-carbonyl]-piperazin-1-yl}-N-isopropyl-N-methyl-acetamide Chiral

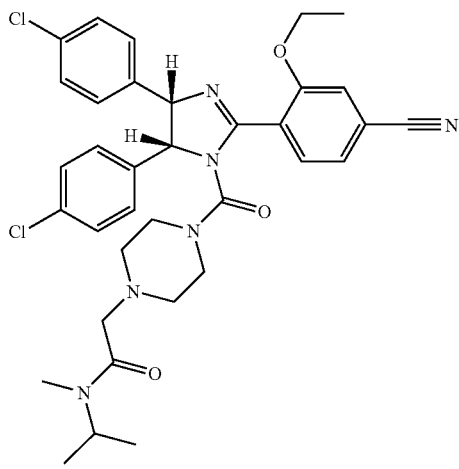

The title compound was prepared from 4-[4,5-bis-(4-chloro-phenyl)-4,5-dihydro-1H-imidazol-2-yl]-3-ethoxy-benzonitrile (example 25) and N-isopropyl-N-methyl-2-piperazin-1-yl-acetamide (example 22c) following successively the procedures described for examples 29 and 31. LC-MS: 661.3 [(M+H)+].

EXAMPLE 201

2-{4-[(4S,5R)-4,5-Bis-(4-chloro-phenyl)-2-(4-cyano-2-ethoxy-phenyl)-4,5-dihydro-imidazole-1-carbonyl]-piperazin-1-yl}-N-(2-cyano-ethyl)-N-methyl-acetamide Chiral

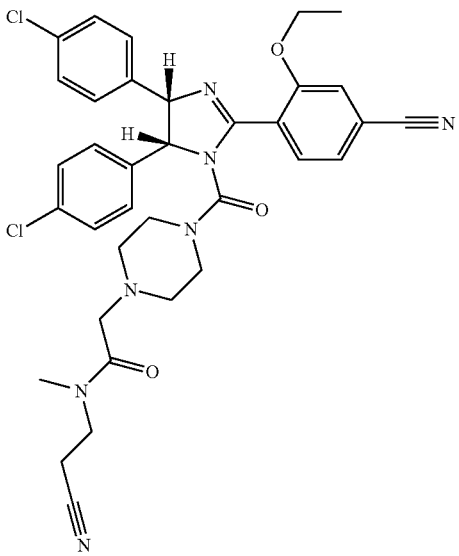

The title compound was prepared from 4-[4,5-bis-(4-chloro-phenyl)-4,5-dihydro-1H-imidazol-2-yl]-3-ethoxy-benzonitrile (example 25) and N-(2-cyano-ethyl)-N-methyl-2-piperazin-1-yl-acetamide (example 22d) following successively the procedures described for examples 29 and 31. LC-MS: 672.3 [(M+H)+].

EXAMPLE 202

4-[(4S,5R)-4,5-Bis-(4-chloro-phenyl)-1-(3-oxo-[1,4]diazepane-1-carbonyl)-4,5-dihydro-1H-imidazol-2-yl]-3-ethoxy-benzonitrile Chiral

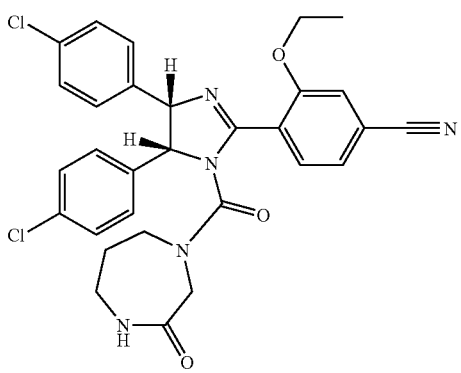

The title compound was prepared from 4-[4,5-bis-(4-chloro-phenyl)-4,5-dihydro-1H-imidazol-2-yl]-3-ethoxy-benzonitrile (example 25) and [1,4]diazepan-5-one (Oakwood Products) following successively the procedures described for examples 29 and 31. LC-MS: 576.2 [(M+H)+].

EXAMPLE 203

4-{(4S,5R)-4,5-Bis-(4-chloro-phenyl)-2-[2-ethoxy-4-fluoro-5-(morpholine-4-sulfonyl)-phenyl]-4,5-dihydro-imidazole-1-carbonyl}-piperazin-2-one Chiral

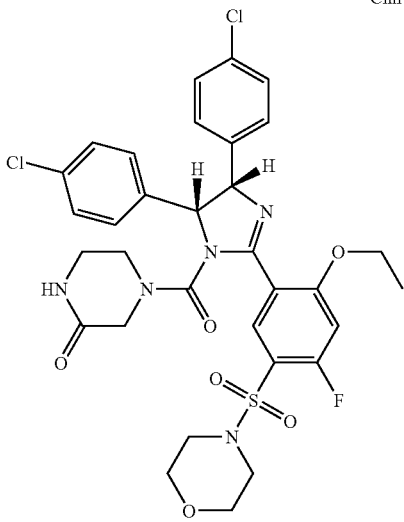

The title compound was prepared from meso-1,2-bis-(4-chlorophenyl)ethane-1,2-diamine, ethyl 2-ethoxy-4-fluoro-5-(morpholine-4-sulfonyl)-benzoate (example 2) and 2-piperazinone (Avocado Organics) following successively the procedures described for examples 25, 29 and 31. LC-MS: 704.3 [(M+H)+]

EXAMPLE 204

1-{(4S,5R)-4,5-Bis-(4-chloro-phenyl)-2-[2-ethoxy-4-fluoro-5-(morpholine-4-sulfonyl)-phenyl]-4,5-dihydro-imidazole-1-carbonyl}-[1,4]diazepan-5-one Chiral

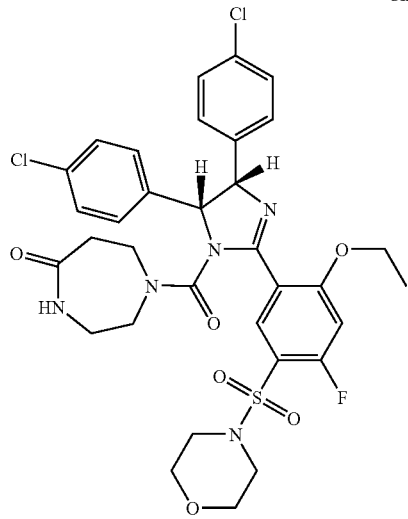

The title compound was prepared from meso-1,2-bis-(4-chlorophenyl)ethane-1,2-diamine, ethyl 2-ethoxy-4-fluoro-5-(morpholine-4-sulfonyl)-benzoate (example 2) and [1,4]diazepan-5-one (Oakwood Products) following successively the procedures described for examples 25, 29 and 31. LC-MS: 718.2 [(M+H)$^+$].

EXAMPLE 205

{(4S,5R)-4,5-Bis-(4-chloro-phenyl)-2-[2-ethoxy-4-fluoro-5-(morpholine-4-sulfonyl)-phenyl]-4,5-dihydro-imidazol-1-yl}-[4-(2-methanesulfonyl-ethyl)-piperazin-1-yl]-methanone hydrochloride Chiral

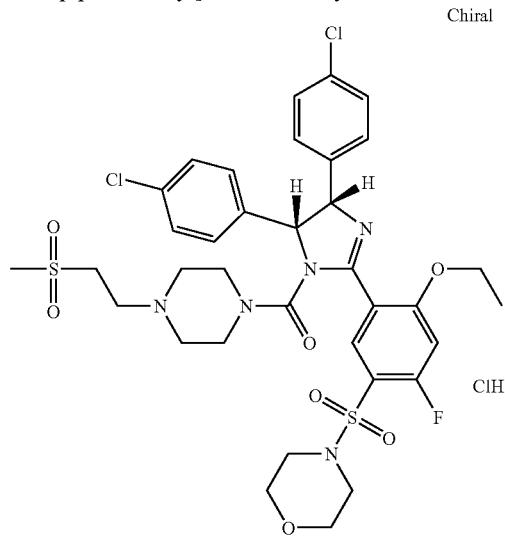

The title compound was prepared from meso-1,2-bis-(4-chlorophenyl)ethane-1,2-diamine, ethyl 2-ethoxy-4-fluoro-5-(morpholine-4-sulfonyl)-benzoate (example 2) and 1-(2-methanesulfonylethyl)piperazine bishydrochloride (example 23) following successively the procedures described for examples 25, 29 and 31. LC-MS: 796.2 [(M+H)$^+$].

EXAMPLE 206

2-(4-{(4S,5R)-4,5-Bis-(4-chloro-phenyl)-2-[2-ethoxy-4-fluoro-5-(morpholine-4-sulfonyl)-phenyl]-4,5-dihydro-imidazole-1-carbonyl}-piperazin-1-yl)-1-morpholin-4-yl-ethanone hydrochloride Chiral

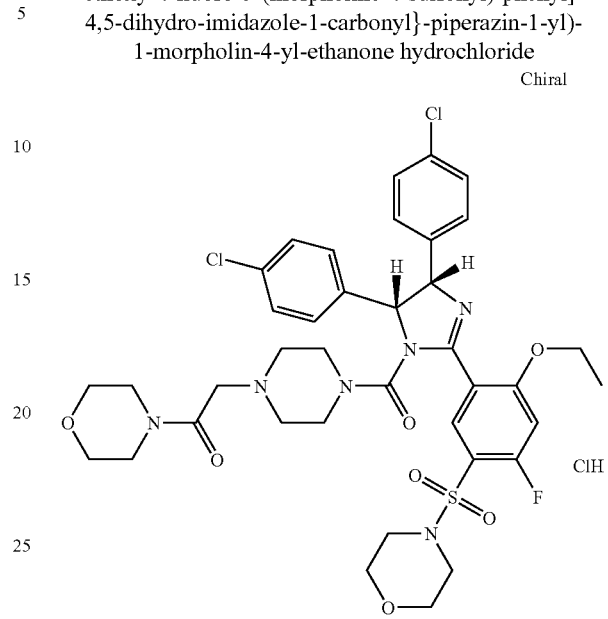

The title compound was prepared from meso-1,2-bis-(4-chlorophenyl)ethane-1,2-diamine, ethyl 2-ethoxy-4-fluoro-5-(morpholine-4-sulfonyl)-benzoate (example 2) and 1-morpholin-4-yl-2-piperazin-1-yl-ethanone (Oakwood Products) following successively the procedures described for examples 25, 29 and 31. LC-MS: 817.2 [(M+H)$^+$].

EXAMPLE 207

4-{(4S,5R)-4,5-Bis-(4-chloro-phenyl)-2-[2-ethoxy-4-(morpholine-4-sulfonyl)-phenyl]-4,5-dihydro-imidazole-1-carbonyl}-piperazin-2-one hydrochloride Chiral

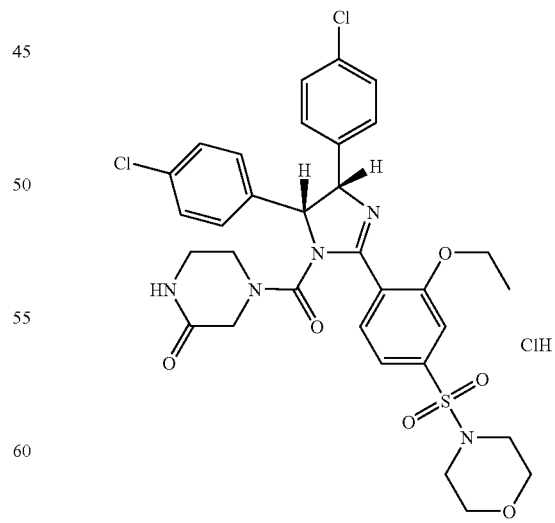

The title compound was prepared from meso-1,2-bis-(4-chlorophenyl)ethane-1,2-diamine, 2-ethoxy-4-(morpholine-4-sulfonyl)-benzoic acid methyl ester (example 11) and

EXAMPLE 208

{(4S,5R)-4,5-Bis-(4-chloro-phenyl)-2-[2-ethoxy-4-(morpholine-4-sulfonyl)-phenyl]-4,5-dihydro-imidazol-1-yl}-[4-(2-methanesulfonyl-ethyl)-piperazin-1-yl]-methanone hydrochloride

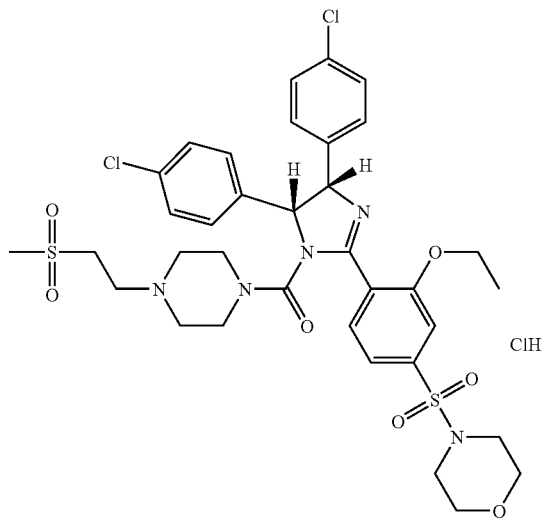

The title compound was prepared from meso-1,2-bis-(4-chlorophenyl)ethane-1,2-diamine, 2-ethoxy-4-(morpholine-4-sulfonyl)-benzoic acid methyl ester (example 11) and 1-(2-methanesulfonylethyl)piperazine bishydrochloride (example 23) following successively the procedures described for examples 25, 29 and 31. LC-MS: 778.3 [(M+H)$^+$].

EXAMPLE 209

2-(4-{(4S,5R)-4,5-Bis-(4-chloro-phenyl)-2-[2-ethoxy-4-(morpholine-4-sulfonyl)-phenyl]-4,5-dihydro-imidazole-1-carbonyl}-piperazin-1-yl)-1-morpholin-4-yl-ethanone hydrochloride

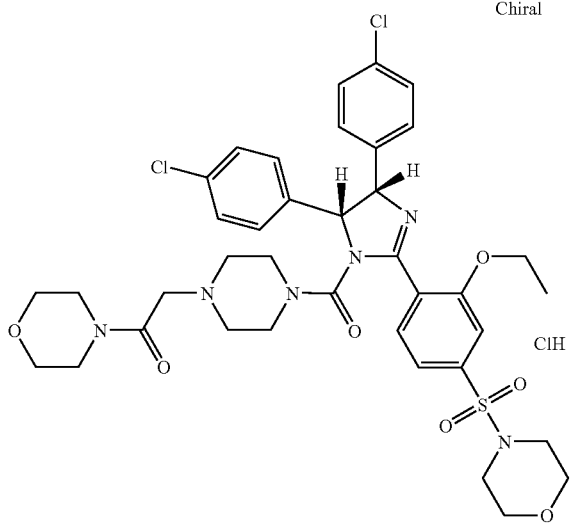

The title compound was prepared from meso-1,2-bis-(4-chlorophenyl)ethane-1,2-diamine, 2-ethoxy-4-(morpholine-4-sulfonyl)-benzoic acid methyl ester (example 11) and 1-morpholin-4-yl-2-piperazin-1-yl-ethanone (Oakwood Products) following successively the procedures described for examples 25, 29 and 31. LC-MS: 799.4 [(M+H)$^+$].

EXAMPLE 210

4-{(4S,5R)-4,5-Bis-(4-chloro-phenyl)-2-[2-ethoxy-4-(pyrrolidine-1-sulfonyl)-phenyl]-4,5-dihydro-imidazole-1-carbonyl}-piperazin-2-one hydrochloride

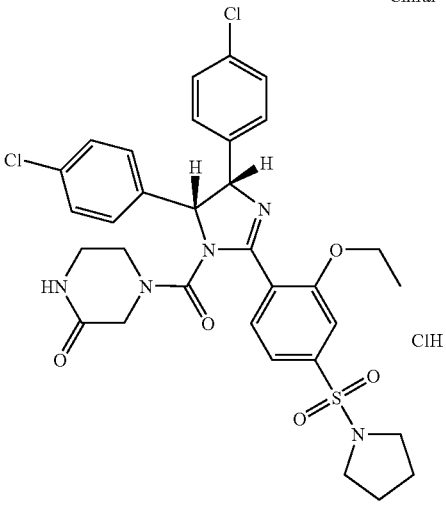

The title compound was prepared from meso-1,2-bis-(4-chlorophenyl)ethane-1,2-diamine, 2-ethoxy-4-(pyrrolidine-1-sulfonyl)-benzoic acid methyl ester (example 11) and 2-piperazinone (Avocado Organics) following successively the procedures described for examples 25, 29 and 31. LC-MS: 670.3 [(M+H)$^+$].

EXAMPLE 211

{(4S,5R)-4,5-Bis-(4-chloro-phenyl)-2-[2-ethoxy-4-(pyrrolidine-1-sulfonyl)-phenyl]-4,5-dihydro-imidazol-1-yl}-[4-(2-methanesulfonyl-ethyl)-piperazin-1-yl]-methanone hydrochloride

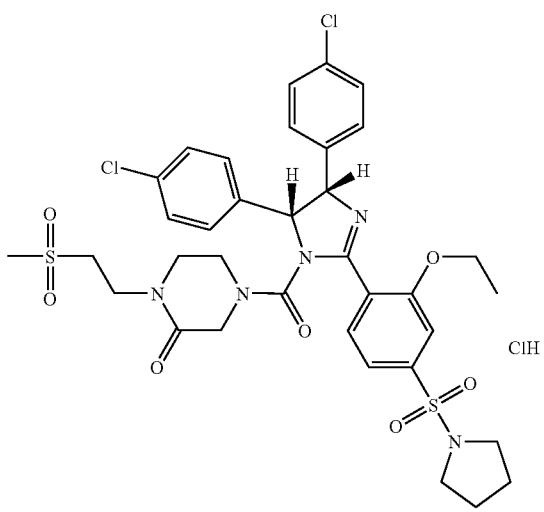

The title compound was prepared from meso-1,2-bis-(4-chlorophenyl)ethane-1,2-diamine, 2-ethoxy-4-(pyrrolidine- 1-sulfonyl)-benzoic acid methyl ester (example 11) and 1-(2-methanesulfonylethyl)piperazine bishydrochloride (example 23) following successively the procedures described for examples 25, 29 and 31. LC-MS: 762.4 [(M+H)+].

EXAMPLE 212

2-(4-{(4S,5R)-4,5-Bis-(4-chloro-phenyl)-2-[2-ethoxy-4-(pyrrolidine-1-sulfonyl)-phenyl]-4,5-dihydro-imidazole-1-carbonyl}-piperazin-1-yl)-1-morpholin-4-yl-ethanone hydrochloride Chiral

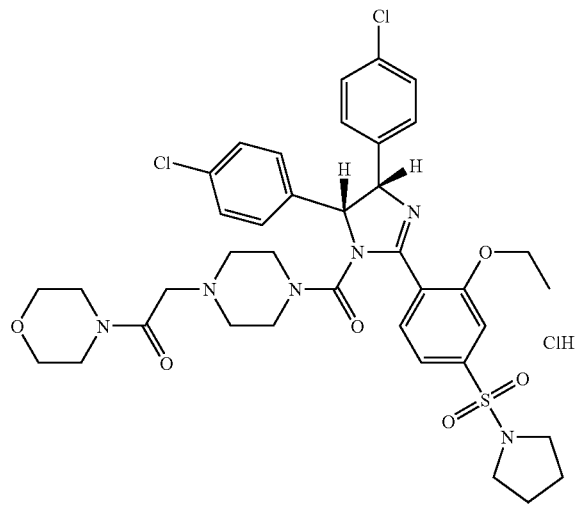

The title compound was prepared from meso-1,2-bis-(4-chlorophenyl)ethane-1,2-diamine, 2-ethoxy-4-(pyrrolidine-1-sulfonyl)-benzoic acid methyl ester (example 11) and 1-morpholin-4-yl-2-piperazin-1-yl-ethanone (Oakwood Products) following successively the procedures described for examples 25, 29 and 31. LC-MS: 783.4 [(M+H)+].

EXAMPLE 213

5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-4-ethoxy-N-methoxy-2,N-dimethyl-benzenesulfonamide Chiral

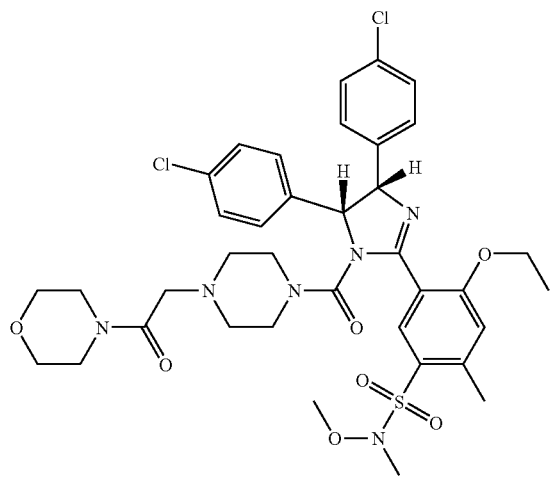

The title compound was prepared from meso-1,2-bis-(4-chlorophenyl)ethane-1,2-diamine, ethyl 2-ethoxy-5-(methoxy-methyl-sulfamoyl)-4-methyl-benzoate (example 2) and 1-morpholin-4-yl-2-piperazin-1-yl-ethanone (Oakwood Products) following successively the procedures described for examples 25, 30 and 32. LC-MS: 787.3 [(M+H)+].

EXAMPLE 214

4-[(4S,5R)-4,5-Bis-(4-chloro-phenyl)-1-(3-oxo-piperazine-1-carbonyl)-4,5-dihydro-1H-imidazol-2-yl]-2,5-diethoxy-benzonitrile Chiral

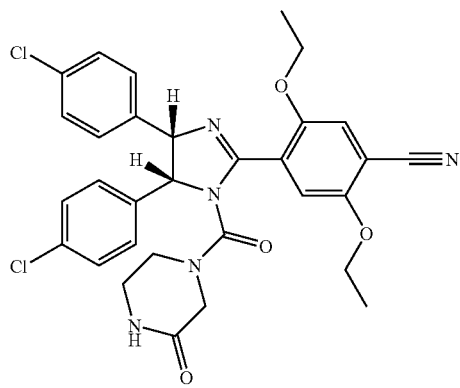

The title compound was prepared from meso-1,2-bis-(4-chlorophenyl)ethane-1,2-diamine, ethyl 4-cyano-2,5-diethoxy-benzoate (example 15) and 2-piperazinone (Avocado Organics) following successively the procedures described for examples 25, 29 and 31. LC-MS: 606.3 [(M+H)+].

EXAMPLE 215

4-[(4S,5R)-4,5-Bis-(4-chloro-phenyl)-1-(5-oxo-[1,4]diazepane-1-carbonyl)-4,5-dihydro-1H-imidazol-2-yl]-2,5-diethoxy-benzonitrile Chiral

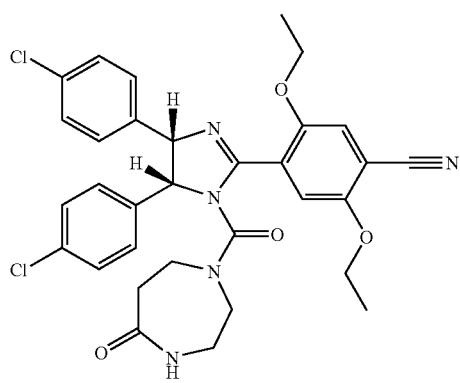

The title compound was prepared from meso-1,2-bis-(4-chlorophenyl)ethane-1,2-diamine, ethyl 4-cyano-2,5-diethoxy-benzoate (example 15) and [1,4]diazepan-5-one (Oakwood Products) following successively the procedures described for examples 25, 29 and 31. LC-MS: 620.3 [(M+H)+].

EXAMPLE 216

4-[(4S,5R)-4,5-Bis-(4-chloro-phenyl)-1-[4-(2-methanesulfonyl-ethyl)-piperazine-1-carbonyl]-4,5-dihydro-1H-imidazol-2-yl]-2,5-diethoxy-benzonitrile hydrochloride Chiral

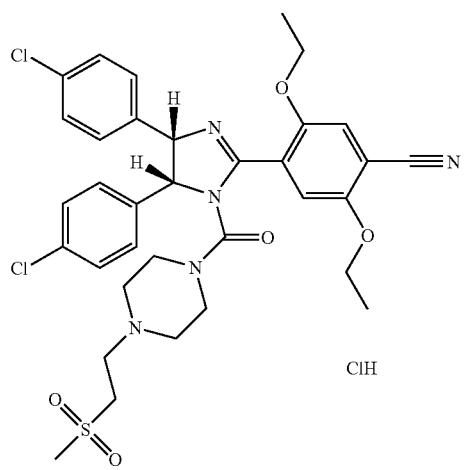

The title compound was prepared from meso-1,2-bis-(4-chlorophenyl)ethane-1,2-diamine, ethyl 4-cyano-2,5-diethoxy-benzoate (example 15) and 1-(2-methanesulfonyl-ethyl)piperazine bishydrochloride (example 23) following successively the procedures described for examples 25, 29 and 31. LC-MS: 698.3 [(M+H)$^+$].

EXAMPLE 217

4-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-2,5-diethoxy-benzonitrile hydrochloride Chiral

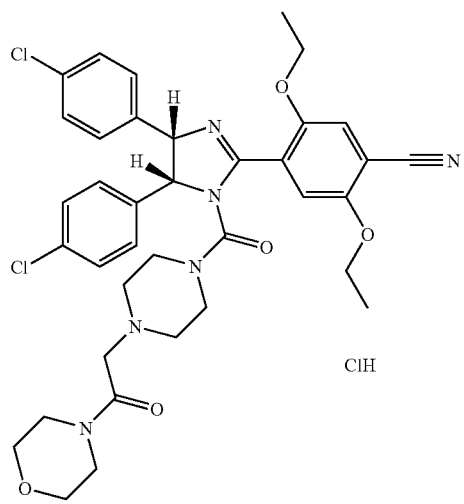

The title compound was prepared from meso-1,2-bis-(4-chlorophenyl)ethane-1,2-diamine, ethyl 4-cyano-2,5-diethoxy-benzoate (example 15) and 1-morpholin-4-yl-2-piperazin-1-yl-ethanone (Oakwood Products) following successively the procedures described for examples 25, 29 and 31. LC-MS: 719.4 [(M+H)$^+$].

EXAMPLE 218

4-{(4S,5R)-4,5-Bis-(4-chloro-phenyl)-2-[2-ethoxy-5-(piperidine-1-sulfonyl)-4-piperidin-1-yl-phenyl]-4,5-dihydro-imidazole-1-carbonyl}-piperazin-2-one hydrochloride Chiral

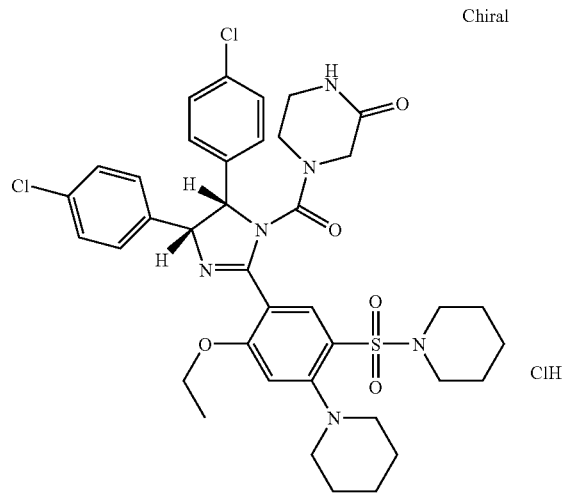

The title compound was prepared from meso-1,2-bis-(4-chlorophenyl)ethane-1,2-diamine, ethyl 4-piperidino-5-piperidinosulfamoyl-2-ethoxybenzoate (example 12b) and 2-piperazinone (Avocado Organics) following successively the procedures described for examples 25, 29 and 31. LC-MS: 767.3 [(M+H)$^+$].

EXAMPLE 219

1-{(4S,5R)-4,5-Bis-(4-chloro-phenyl)-2-[2-ethoxy-5-(piperidine-1-sulfonyl)-4-piperidin-1-yl-phenyl]-4,5-dihydro-imidazole-1-carbonyl}-[1,4]diazepan-5-one hydrochloride Chiral

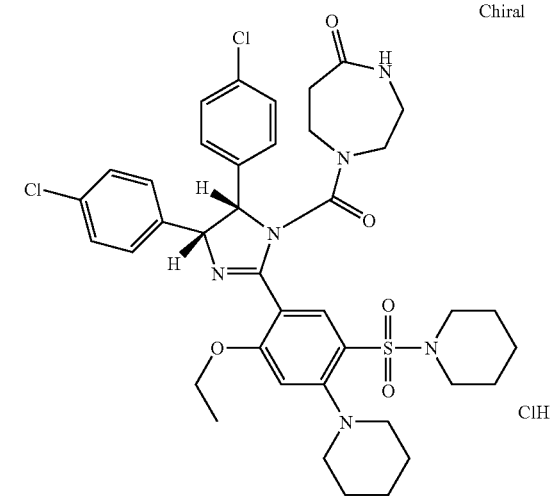

The title compound was prepared from meso-1,2-bis-(4-chlorophenyl)ethane-1,2-diamine, ethyl 4-piperidino-5-piperidinosulfamoyl-2-ethoxybenzoate (example 12b) and [1,4]

diazepan-5-one (Oakwood Products) following successively the procedures described for examples 25, 29 and 31. LC-MS: 781.4 [(M+H)+].

EXAMPLE 220

{(4S,5R)-4,5-Bis-(4-chloro-phenyl)-2-[2-ethoxy-5-(piperidine-1-sulfonyl)-4-piperidin-1-yl-phenyl]-4,5-dihydro-imidazol-1-yl}-[4-(2-methanesulfonyl-ethyl)-piperazin-1-yl]-methanone hydrochloride Chiral

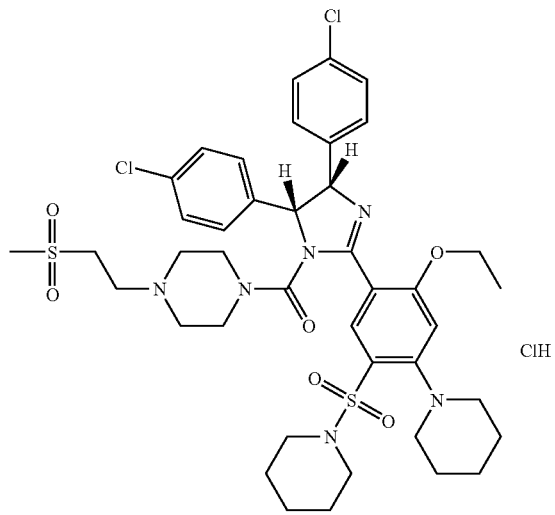

The title compound was prepared from meso-1,2-bis-(4-chlorophenyl)ethane-1,2-diamine, ethyl 4-piperidino-5-piperidinosulfamoyl-2-ethoxybenzoate (example 12b) and 1-(2-methanesulfonylethyl)piperazine bishydrochloride (example 23) following successively the procedures described for examples 25, 29 and 31. LC-MS: 859.4 [(M+H)+].

EXAMPLE 221

2-(4-{(4S,5R)-4,5-Bis-(4-chloro-phenyl)-2-[2-ethoxy-5-(piperidine-1-sulfonyl)-4-piperidin-1-yl-phenyl]-4,5-dihydro-imidazole-1-carbonyl}-piperazin-1-yl)-1-morpholin-4-yl-ethanone hydrochloride Chiral

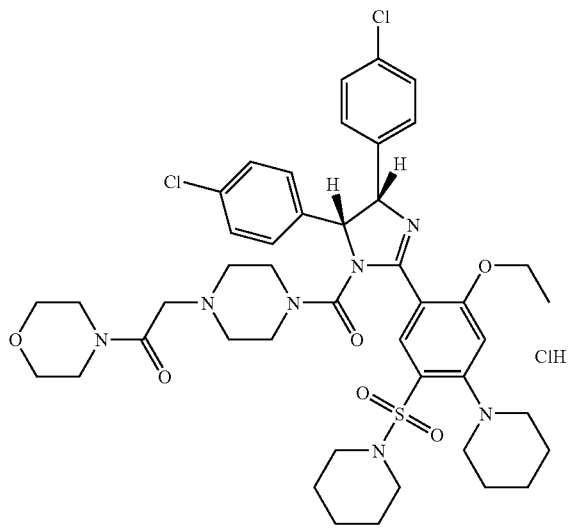

The title compound was prepared from meso-1,2-bis-(4-chlorophenyl)ethane-1,2-diamine, ethyl 4-piperidino-5-piperidinosulfamoyl-2-ethoxybenzoate (example 12b) and 1-morpholin-4-yl-2-piperazin-1-yl-ethanone (Oakwood Products) following successively the procedures described for examples 25, 29 and 31. LC-MS: 879.3 [(M+H)+].

EXAMPLE 222

4,5-Bis-(4-chloro-phenyl)-2-(4-dimethylamino-5-dimethylsulfamoyl-2-ethoxy-phenyl)-4,5-dihydro-imidazole-1-carboxylic acid ethyl ester hydrochloride

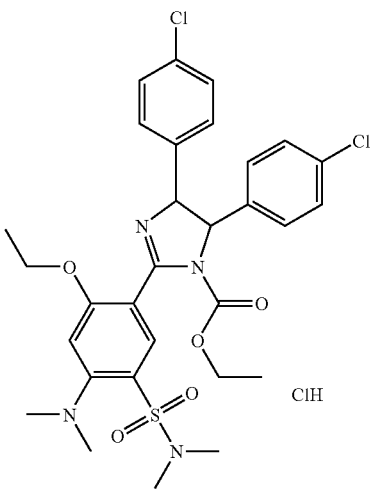

The title compound was prepared from meso-1,2-bis-(4-chlorophenyl)ethane-1,2-diamine, ethyl 4-dimethylamino-5-dimethylsulfamoyl-2-ethoxybenzoate (example 12a) and ethyl chloroformate (Aldrich) in an analogous manner using the procedures described for examples 25, 29 and 31 (except chiral purification). LC-MS: 633.2 [(M+H)+].

EXAMPLE 223

5-[(4S,5R)-4,5-Bis-(4-chloro-phenyl)-1-(3-oxo-piperazine-1-carbonyl)-4,5-dihydro-1H-imidazol-2-yl]-2-dimethylamino-4-ethoxy-N,N-dimethyl-benzenesulfonamide hydrochloride Chiral

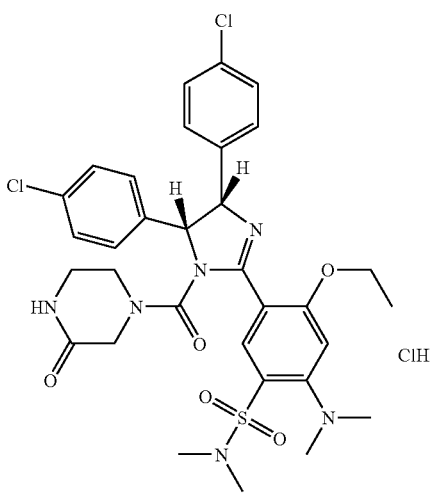

The title compound was prepared from meso-1,2-bis-(4-chlorophenyl)ethane-1,2-diamine, ethyl 4-dimethylamino-5- dimethylsulfamoyl-2-ethoxybenzoate (example 12a) and 2-piperazinone (Avocado Organics) following successively the procedures described for examples 25, 29 and 31. LC-MS: 687.3 [(M+H)$^+$].

EXAMPLE 224

5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-2-dimethylamino-4-ethoxy-N,N-dimethyl-benzenesulfonamide hydrochloride

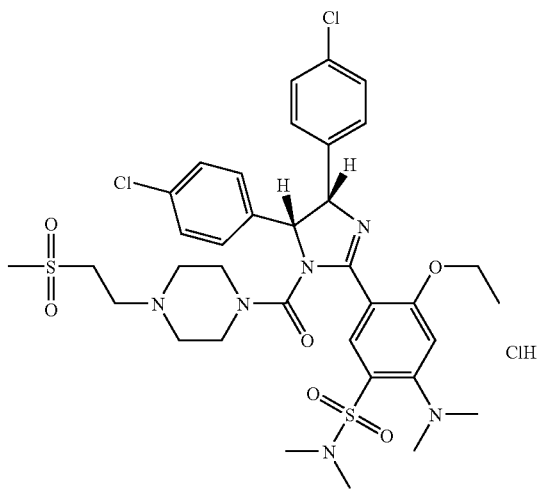

The title compound was prepared from meso-1,2-bis-(4-chlorophenyl)ethane-1,2-diamine, ethyl 4-dimethylamino-5-dimethylsulfamoyl-2-ethoxybenzoate (example 12a) and 1-(2-methanesulfonylethyl)piperazine bishydrochloride (example 23) following successively the procedures described for examples 25, 29 and 31. LC-MS: 779.3 [(M+H)$^+$].

EXAMPLE 225

5-[(4S,5R)-4,5-Bis-(4-chloro-phenyl)-1-(5-oxo-[1,4]diazepane-1-carbonyl)-4,5-dihydro-1H-imidazol-2-yl]-2-dimethylamino-4-ethoxy-N,N-dimethyl-benzenesulfonamide hydrochloride

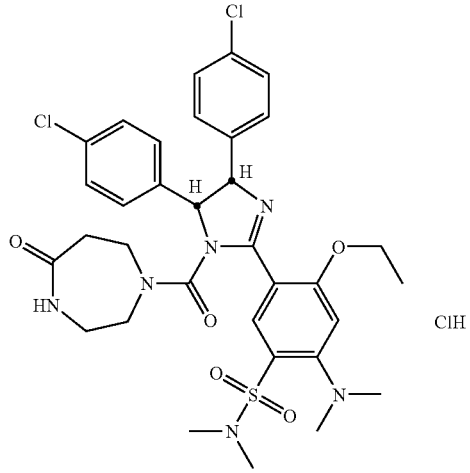

The title compound was prepared from meso-1,2-bis-(4-chlorophenyl)ethane-1,2-diamine, ethyl 4-dimethylamino-5-dimethylsulfamoyl-2-ethoxybenzoate (example 12a) and [1,4]diazepan-5-one (Oakwood Products) following successively the procedures described for examples 25, 29 and 31. LC-MS: 701.3 [(M+H)$^+$].

EXAMPLE 226

5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-2-dimethylamino-4-ethoxy-N,N-dimethyl-benzenesulfonamide hydrochloride

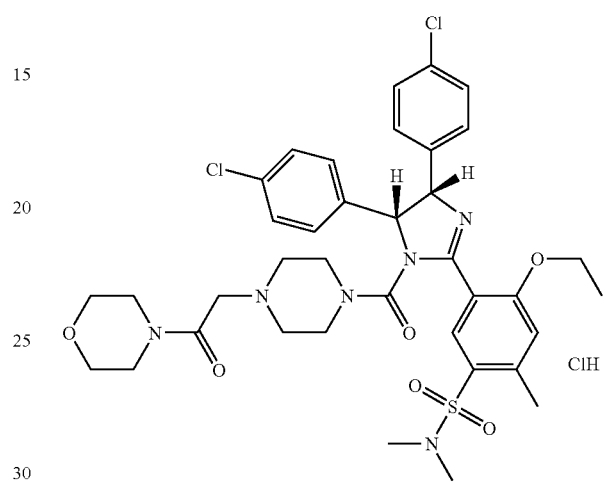

The title compound was prepared from meso-1,2-bis-(4-chlorophenyl)ethane-1,2-diamine, ethyl 4-dimethylamino-5-dimethylsulfamoyl-2-ethoxybenzoate (example 12a) and 1-morpholin-4-yl-2-piperazin-1-yl-ethanone (Oakwood Products) following successively the procedures described for examples 25, 29 and 31. LC-MS: 800.4 [(M+H)$^+$].

EXAMPLE 227

5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-2-chloro-4-ethoxy-benzonitrile

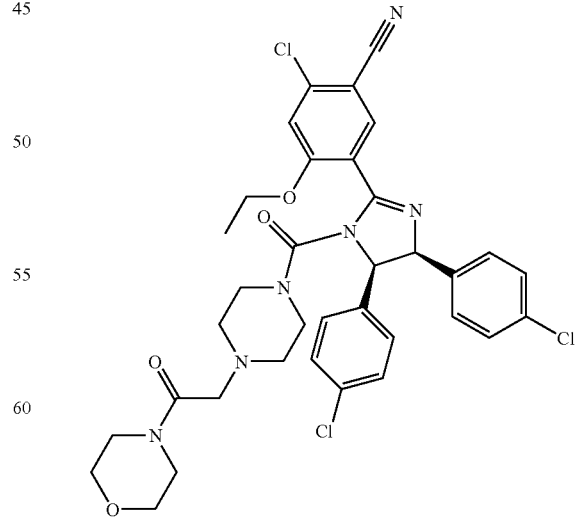

The title compound was prepared from meso-1,2-bis-(4-chlorophenyl)ethane-1,2-diamine, 4-chloro-5-cyano-2-ethoxy-benzoic acid ethyl ester (example 5) and 1-morpholin-4-yl-2-piperazin-1-yl-ethanone (Oakwood Products) following successively the procedures described for examples 25, 29 and 31. LC-MS: 709.3 [(M+H)⁺].

EXAMPLE 228

5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-4-ethoxy-N-isopropyl-2-methyl-benzenesulfonamide

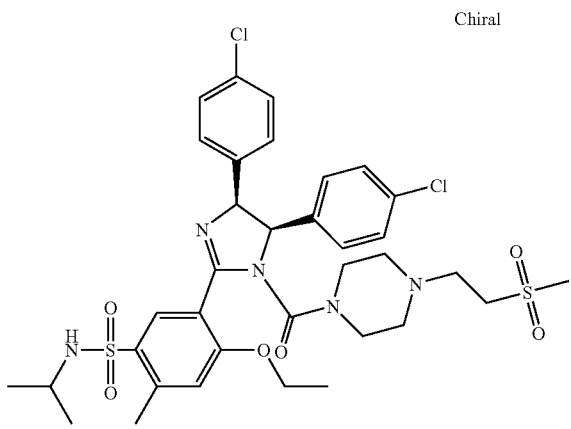

The title compound was prepared from meso-1,2-bis-(4-chlorophenyl)ethane-1,2-diamine, ethyl 2-ethoxy-5-isopropylsulfamoyl-4-methyl-benzoate (example 2) and 1-(2-methanesulfonylethyl)piperazine bishydrochloride (example 23) following successively the procedures described for examples 25, 29 and 31. LC-MS: 764.3 [(M+H)⁺].

EXAMPLE 229

5-[(4S,5R)-4,5-Bis-(4-chloro-phenyl)-1-(3-oxo-piperazine-1-carbonyl)-4,5-dihydro-1H-imidazol-2-yl]-4-ethoxy-N-isopropyl-2-methyl-benzenesulfonamide

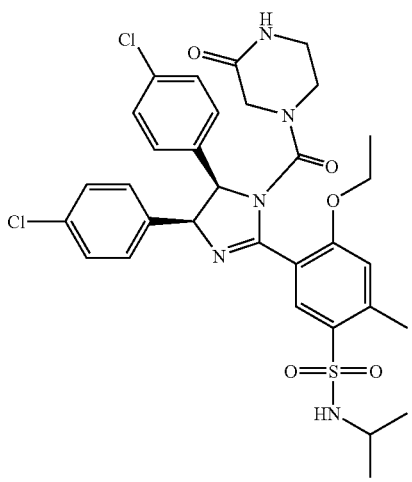

The title compound was prepared from meso-1,2-bis-(4-chlorophenyl)ethane-1,2-diamine, ethyl 2-ethoxy-5-isopropylsulfamoyl-4-methyl-benzoate (example 2) and 2-piperazinone (Avocado Organics) following successively the procedures described for examples 25, 29 and 31. LC-MS: 672.3 [(M+H)⁺].

EXAMPLE 230

5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-4-ethoxy-2,N-dimethyl-benzenesulfonamide

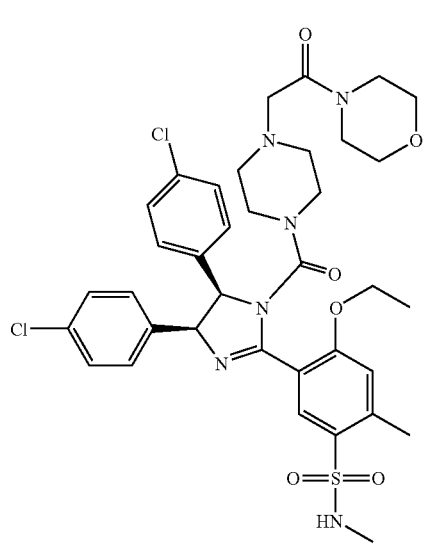

The title compound was prepared from meso-1,2-bis-(4-chlorophenyl)ethane-1,2-diamine, ethyl 2-ethoxy-5-methylsulfamoyl-4-methyl-benzoate (example 2) and 1-morpholin-4-yl-2-piperazin-1-yl-ethanone (Oakwood Products) following successively the procedures described for examples 25, 29 and 31. LC-MS: 757.5 [(M+H)⁺].

EXAMPLE 231

5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-4-ethoxy-2,N-dimethyl-benzenesulfonamide

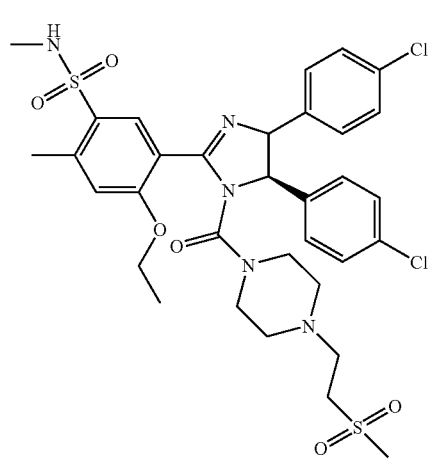

The title compound was prepared from meso-1,2-bis-(4-chlorophenyl)ethane-1,2-diamine, ethyl 2-ethoxy-5-methylsulfamoyl-4-methyl-benzoate (example 2) and 1-(2-methanesulfonylethyl)piperazine bishydrochloride (example 23) following successively the procedures described for examples 25, 29 and 31. LC-MS: 736.3 [(M+H)⁺].

EXAMPLE 232

5-[(4S,5R)-4,5-Bis-(4-chloro-phenyl)-1-(3-oxo-piperazine-1-carbonyl)-4,5-dihydro-1H-imidazol-2-yl]-4-ethoxy-2,N-dimethyl-benzenesulfonamide

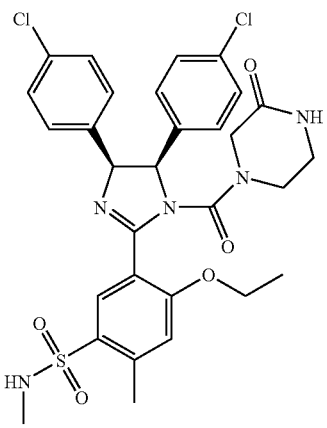

The title compound was prepared from meso-1,2-bis-(4-chlorophenyl)ethane-1,2-diamine, ethyl 2-ethoxy-5-methyl-sulfamoyl-4-methyl-benzoate (example 2) and 2-piperazinone (Avocado Organics) following successively the procedures described for examples 25, 29 and 31. LC-MS: 644.3 [(M+H)+].

EXAMPLE 233

5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-2-chloro-4-ethoxy-benzonitrile

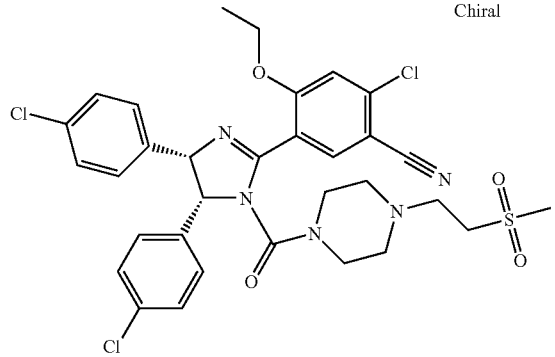

The title compound was prepared from meso-1,2-bis-(4-chlorophenyl)ethane-1,2-diamine, 4-chloro-5-cyano-2-ethoxy-benzoic acid ethyl ester (example 5) and 1-(2-methanesulfonylethyl)piperazine bishydrochloride (example 23) following successively the procedures described for examples 25, 29 and 31. LC-MS: 688.3 [(M+H)+].

EXAMPLE 234

5-[(4S,5R)-4,5-Bis-(4-chloro-phenyl)-1-(3-oxo-piperazine-1-carbonyl)-4,5-dihydro-1H-imidazol-2-yl]-2-chloro-4-ethoxy-benzonitrile

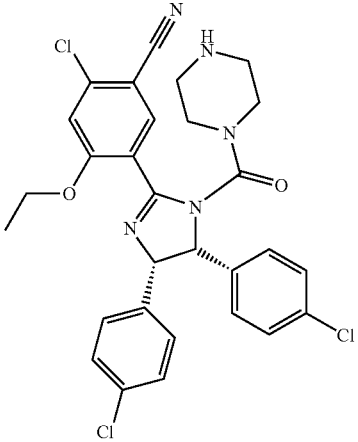

The title compound was prepared from meso-1,2-bis-(4-chlorophenyl)ethane-1,2-diamine, 4-chloro-5-cyano-2-ethoxy-benzoic acid ethyl ester (example 5) and 2-piperazinone (Avocado Organics) following successively the procedures described for examples 25, 29 and 31. LC-MS: 596.1 [(M+H)+].

EXAMPLE 235

5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-2-dimethylamino-4-ethoxy-benzonitrile

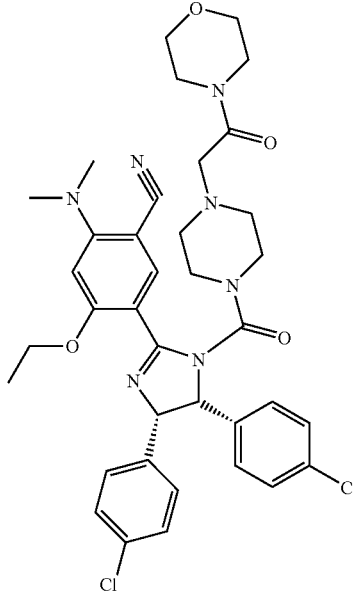

The title compound was prepared from meso-1,2-bis-(4-chlorophenyl)ethane-1,2-diamine, 5-cyano-4-dimethylamino-2-ethoxy-benzoic acid methyl ester (example 6) and 1-morpholin-4-yl-2-piperazin-1-yl-ethanone (Oakwood Products) following successively the procedures described for examples 25, 29 and 31. LC-MS: 718.4 [(M+H)+].

EXAMPLE 236

5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-2-dimethylamino-4-ethoxy-benzonitrile

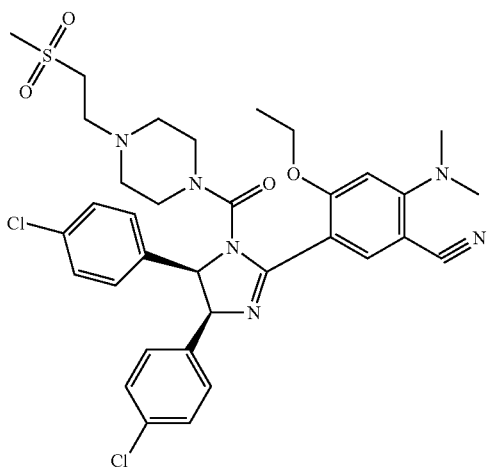

The title compound was prepared from meso-1,2-bis-(4-chlorophenyl)ethane-1,2-diamine, 5-cyano-4-dimethylamino-2-ethoxy-benzoic acid methyl ester (example 6) and 1-(2-methanesulfonylethyl)piperazine bishydrochloride (example 23) following successively the procedures described for examples 25, 29 and 31. LC-MS: 697.3 [(M+H)$^+$].

EXAMPLE 237

5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-4-ethoxy-N-isopropyl-2-methyl-benzenesulfonamide

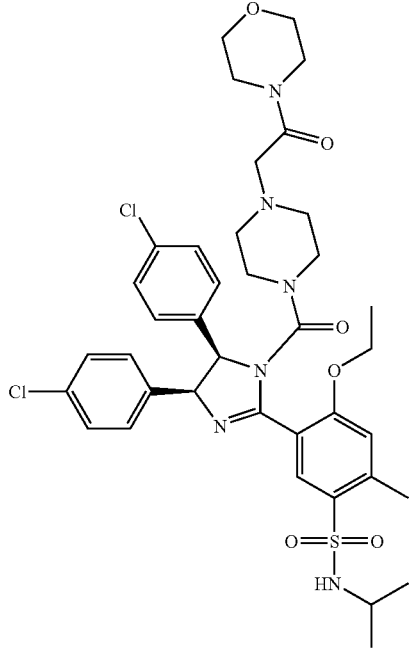

The title compound was prepared from meso-1,2-bis-(4-chlorophenyl)ethane-1,2-diamine, ethyl 2-ethoxy-5-isopropylsulfamoyl-4-methyl-benzoate (example 2) and 1-morpholin-4-yl-2-piperazin-1-yl-ethanone (Oakwood Products) following successively the procedures described for examples 25, 29 and 31. LC-MS: 785.4 [(M+H)$^+$].

EXAMPLE 238

4-[(4S,5R)-4,5-Bis-(4-chloro-phenyl)-2-(2-ethoxy-4-ethynyl-phenyl)-4,5-dihydro-imidazole-1-carbonyl]-piperazin-2-one

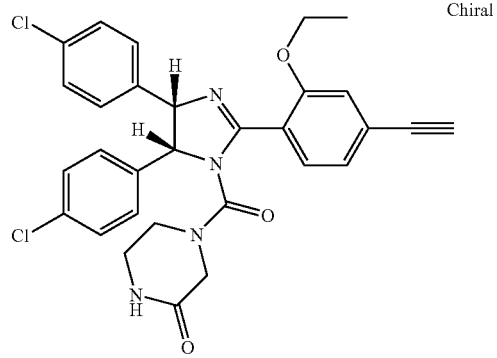

The title compound was prepared from 4,5-bis-(4-chlorophenyl)-2-(2-ethoxy-4-ethynylphenyl)-4,5-dihydro-1H-imidazole (example 26) and 2-piperazinone (Avocado Organics) following successively the procedures described for examples 29 and 31. LC-MS: 561.3 [(M+H)$^+$].

EXAMPLE 239

1-[(4S,5R)-4,5-Bis-(4-chloro-phenyl)-2-(2-ethoxy-4-ethynyl-phenyl)-4,5-dihydro-imidazole-1-carbonyl]-[1,4]diazepan-5-one

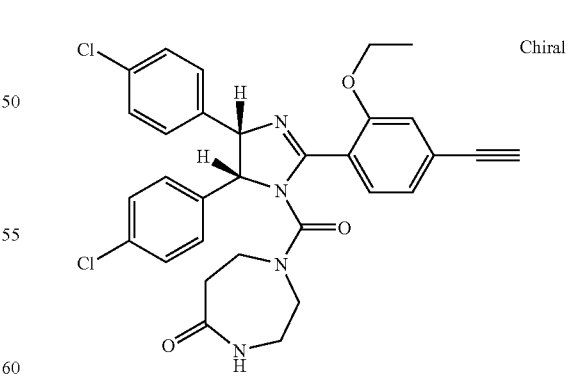

The title compound was prepared from 4,5-bis-(4-chlorophenyl)-2-(2-ethoxy-4-ethynylphenyl)-4,5-dihydro-1H-imidazole (example 26) and [1,4]diazepan-5-one (Oakwood Products) following successively the procedures described for examples 29 and 31. LC-MS: 575.3 [(M+H)$^+$].

EXAMPLE 240

[(4S,5R)-4,5-Bis-(4-chloro-phenyl)-2-(2-ethoxy-4-ethynyl-phenyl)-4,5-dihydro-imidazol-1-yl]-[4-(2-methanesulfonyl-ethyl)-piperazin-1-yl]-methanone hydrochloride

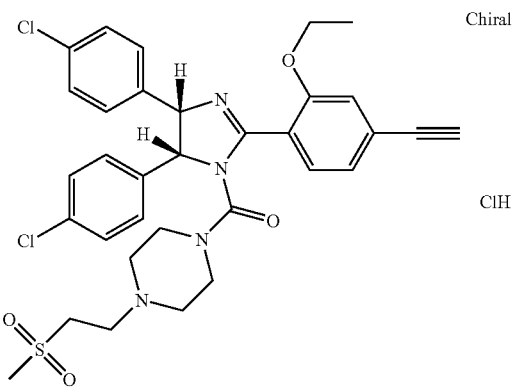

The title compound was prepared from 4,5-bis-(4-chlorophenyl)-2-(2-ethoxy-4-ethynylphenyl)-4,5-dihydro-1H-imidazole (example 26) and 1-(2-methanesulfonylethyl)piperazine bishydrochloride (example 23) following successively the procedures described for examples 29 and 31. LC-MS: 653.3 [(M+H)$^+$].

EXAMPLE 241

2-{4-[(4S,5R)-4,5-Bis-(4-chloro-phenyl)-2-(2-ethoxy-4-ethynyl-phenyl)-4,5-dihydro-imidazole-1-carbonyl]-piperazin-1-yl}-1-morpholin-4-yl-ethanone hydrochloride

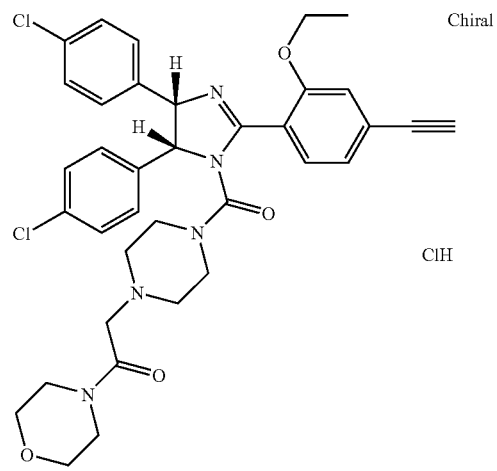

The title compound was prepared from 4,5-bis-(4-chlorophenyl)-2-(2-ethoxy-4-ethynylphenyl)-4,5-dihydro-1H-imidazole (example 26) and 1-morpholin-4-yl-2-piperazin-1-yl-ethanone (Oakwood Products) following successively the procedures described for examples 29 and 31. LC-MS: 674.4 [(M+H)$^+$].

EXAMPLE 242

5-[(4S,5R)-4,5-Bis-(4-chloro-phenyl)-1-(4-ethanesulfonyl-piperazine-1-carbonyl)-4,5-dihydro-1H-imidazol-2-yl]-N-tert-butyl-2-chloro-4-ethoxy-benzenesulfonamide hydrochloride

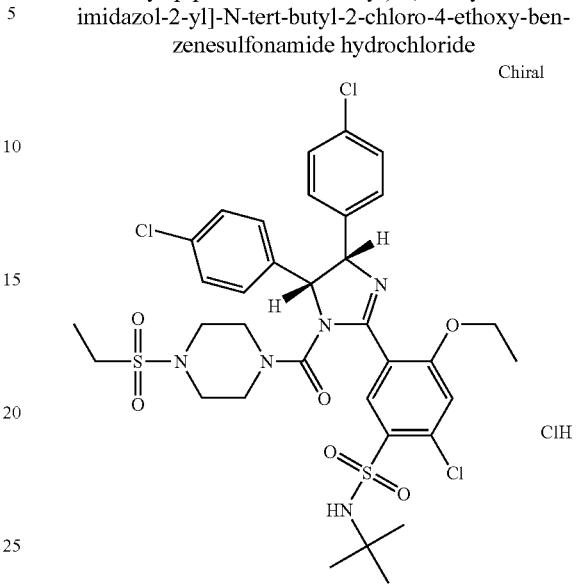

The title compound was prepared from meso-1,2-bis-(4-chlorophenyl)ethane-1,2-diamine, ethyl 5-tert-butylsulfamoyl-4-chloro-2-ethoxy-benzoate (example 2) and 1-ethanesulfonyl-piperazine (example 20) following successively the procedures described for examples 25, 29 and 31. LC-MS: 784.1 [(M+H)$^+$].

EXAMPLE 243

5-{(4S,5R)-4,5-Bis-(4-chloro-phenyl)-1-[4-(3,5-dimethyl-isoxazole-4-carbonyl)-piperazine-1-carbonyl]-4,5-dihydro-1H-imidazol-2-yl}-2-chloro-4-ethoxy-benzenesulfonamide

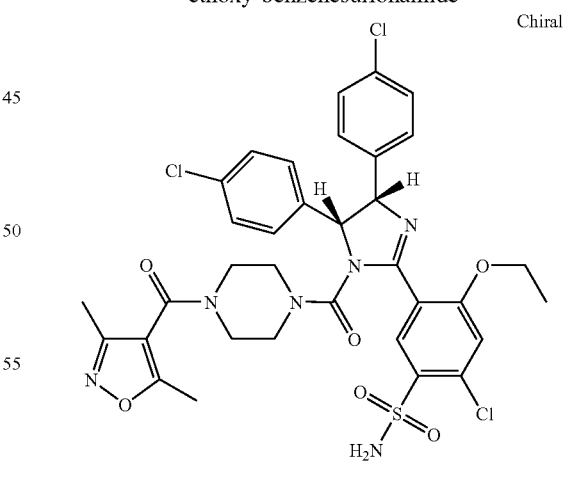

The title compound was prepared from meso-1,2-bis-(4-chlorophenyl)ethane-1,2-diamine, ethyl 5-tert-butylsulfamoyl-4-chloro-2-ethoxy-benzoate (example 2), and (3,5-dimethyl-isoxazol-4-yl)-piperazin-1-yl-methanone (example 19) following successively the procedures described for examples 25, 29, 31 and 34. LC-MS: 759.2 [(M+H)$^+$].

EXAMPLE 244

N-tert-Butyl-2-{4-[(4S,5R)-2-(4-chloro-2-ethoxy-5-sulfamoyl-phenyl)-4,5-bis-(4-chloro-phenyl)-4,5-dihydro-imidazole-1-carbonyl]-piperazin-1-yl}-acetamide

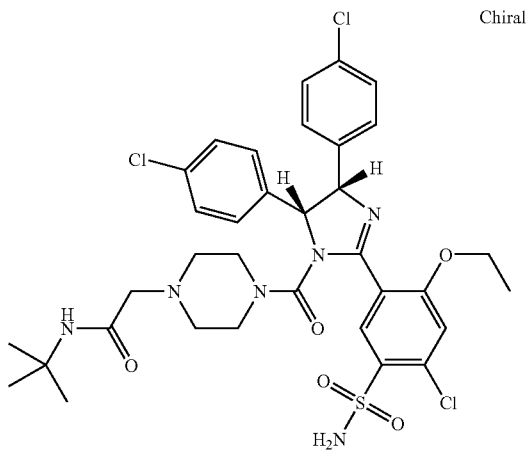

The title compound was prepared from meso-1,2-bis-(4-chlorophenyl)ethane-1,2-diamine, ethyl 5-tert-butylsulfamoyl-4-chloro-2-ethoxy-benzoate (example 2) and N-tert-butyl-2-piperazin-1-yl-acetamide (example 22g) following successively the procedures described for examples 25, 29, 31 and 34. LC-MS: 749.3 [(M+H)$^+$].

EXAMPLE 245

5-[(4S,5R)-4,5-Bis-(4-chloro-phenyl)-1-(3-oxo-piperazine-1-carbonyl)-4,5-dihydro-1H-imidazol-2-yl]-2-chloro-4-ethoxy-benzenesulfonamide

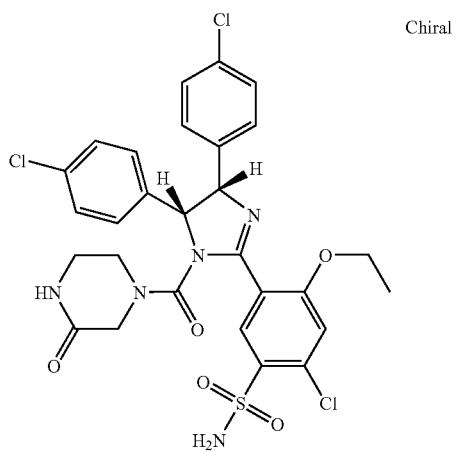

The title compound was prepared from meso-1,2-bis-(4-chlorophenyl)ethane-1,2-diamine, ethyl 5-tert-butylsulfamoyl-4-chloro-2-ethoxy-benzoate (example 2) and 2-piperazinone (Avocado Organics) following successively the procedures described for examples 25, 29, 31 and 34. LC-MS: 650.1 [(M+H)$^+$].

EXAMPLE 246

5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-2-chloro-4-ethoxy-benzenesulfonamide

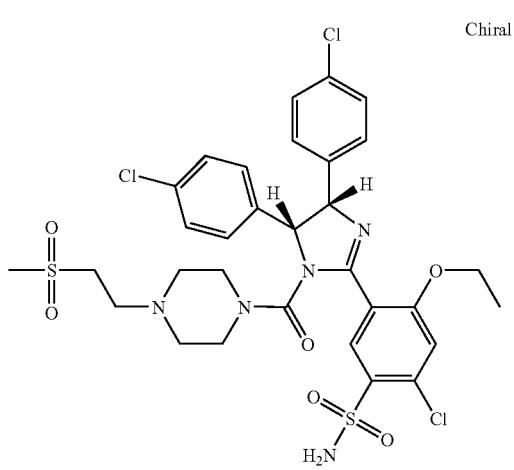

The title compound was prepared from meso-1,2-bis-(4-chlorophenyl)ethane-1,2-diamine, ethyl 5-tert-butylsulfamoyl-4-chloro-2-ethoxy-benzoate (example 2) and 1-(2-methanesulfonylethyl)piperazine bishydrochloride (example 23) following successively the procedures described for examples 25, 29, 31 and 34. LC-MS: 742.3 [(M+H)$^+$].

EXAMPLE 247

2-{4-[(4S,5R)-2-(4-Chloro-2-ethoxy-5-sulfamoyl-phenyl)-4,5-bis-(4-chloro-phenyl)-4,5-dihydro-imidazole-1-carbonyl]-piperazin-1-yl}-acetamide

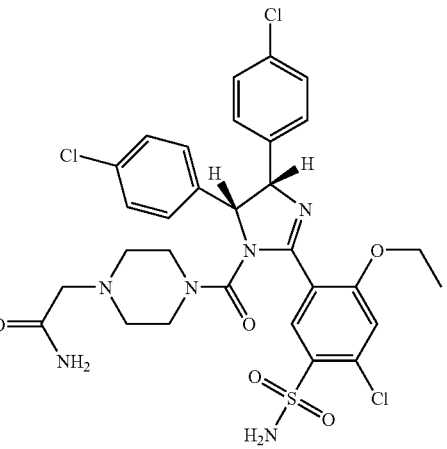

The title compound was prepared from meso-1,2-bis-(4-chlorophenyl)ethane-1,2-diamine, ethyl 5-tert-butylsulfamoyl-4-chloro-2-ethoxy-benzoate (example 2) and 2-piperazin-1-yl-acetamide (Matrix) following successively the procedures described for examples 25, 29, 31 and 34. LC-MS: 693.2 [(M+H)$^+$].

EXAMPLE 248

2-{4-[(4S,5R)-2-(4-Chloro-2-ethoxy-5-sulfamoyl-phenyl)-4,5-bis-(4-chloro-phenyl)-4,5-dihydro-imidazole-1-carbonyl]-piperazin-1-yl}-N-isopropyl-N-methyl-acetamide

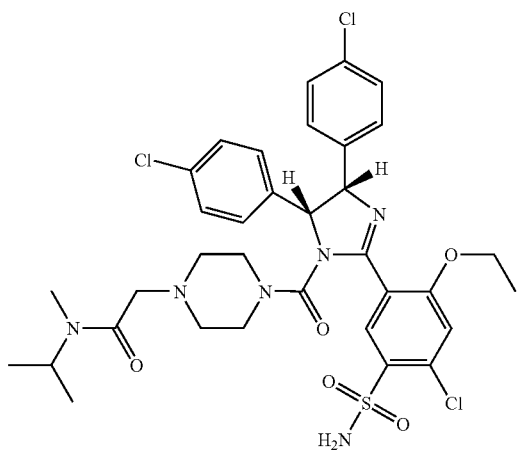

The title compound was prepared from meso-1,2-bis-(4-chlorophenyl)ethane-1,2-diamine, ethyl 5-tert-butylsulfamoyl-4-chloro-2-ethoxy-benzoate (example 2) and N-isopropyl-N-methyl-2-piperazin-1-yl-acetamide (example 22c) following successively the procedures described for examples 25, 29, 31 and 34. LC-MS: 749.3 [(M+H)$^+$].

EXAMPLE 249

5-[(4S,5R)-4,5-Bis-(4-chloro-phenyl)-1-(4-ethanesulfonyl-piperazine-1-carbonyl)-4,5-dihydro-1H-imidazol-2-yl]-2-chloro-4-ethoxy-benzenesulfonamide

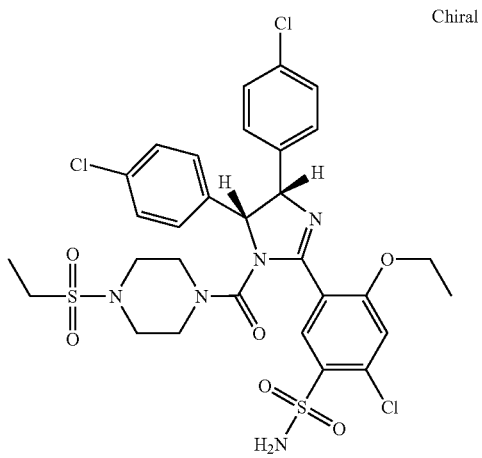

The title compound was prepared from meso-1,2-bis-(4-chlorophenyl)ethane-1,2-diamine, ethyl 5-tert-butylsulfamoyl-4-chloro-2-ethoxy-benzoate (example 2) and 1-ethanesulfonyl-piperazine (example 20) following successively the procedures described for examples 25, 29, 31 and 34. LC-MS: 728.2 [(M+H)$^+$].

EXAMPLE 250

4-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-N-tert-butyl-3-ethoxy-benzamide

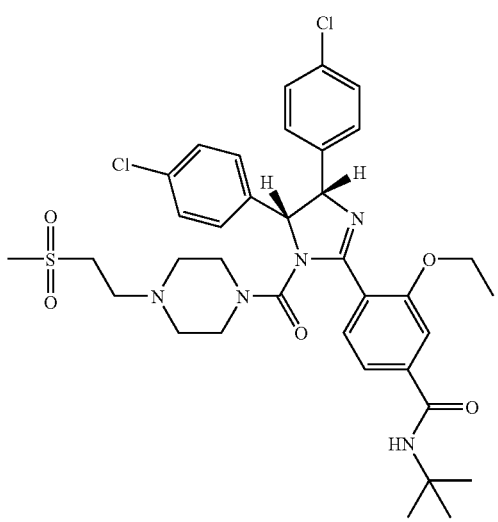

The title compound was prepared from meso-1,2-bis-(4-chlorophenyl)ethane-1,2-diamine, N-tert-butyl-2-ethoxy-terephthalamic acid methyl ester (example 7) and 1-(2-methanesulfonylethyl)piperazine bishydrochloride (example 23) following successively the procedures described for examples 25, 29 and 31. LC-MS: 728.2 [(M+H)$^+$].

EXAMPLE 251

N-tert-Butyl-4-[(4S,5R)-1-(4-carbamoylmethyl-piperazine-1-carbonyl)-4,5-bis-(4-chloro-phenyl)-4,5-dihydro-1H-imidazol-2-yl]-3-ethoxy-benzamide

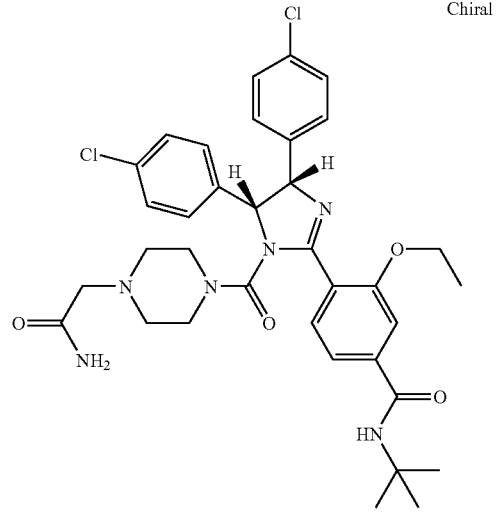

The title compound was prepared from meso-1,2-bis-(4-chlorophenyl)ethane-1,2-diamine, N-tert-butyl-2-ethoxy-terephthalamic acid methyl ester (example 7) and 2-piperazin-1-yl-acetamide (Matrix) following successively the procedures described for examples 25, 29 and 31. LC-MS: 679.2 [(M+H)$^+$].

EXAMPLE 252

{(4S,5R)-4,5-Bis-(4-chloro-phenyl)-2-[2-ethoxy-4-(piperidine-1-carbonyl)-phenyl]-4,5-dihydro-imidazol-1-yl}-[4-(3,5-dimethyl-isoxazole-4-carbonyl)-piperazin-1-yl]-methanone

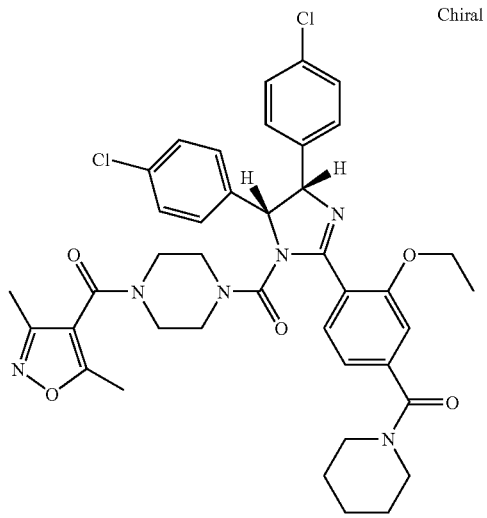

The title compound was prepared from meso-1,2-bis-(4-chlorophenyl)ethane-1,2-diamine, 2-ethoxy-4-(piperidine-1-carbonyl)-benzoic acid methyl ester (example 7) and (3,5-dimethyl-isoxazol-4-yl)-piperazin-1-yl-methanone (example 19) following successively the procedures described for examples 25, 29 and 31. LC-MS: 757.2 [(M+H)⁺].

EXAMPLE 253

2-(4-{(4S,5R)-4,5-Bis-(4-chloro-phenyl)-2-[2-ethoxy-4-(piperidine-1-carbonyl)-phenyl]-4,5-dihydro-imidazole-1-carbonyl}-piperazin-1-yl)-1-morpholin-4-yl-ethanone

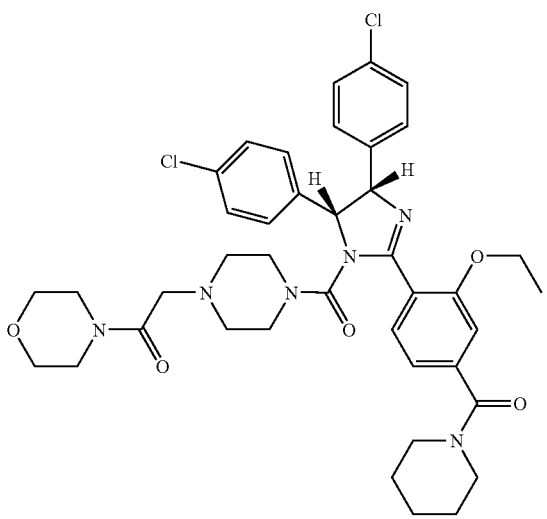

The title compound was prepared from meso-1,2-bis-(4-chlorophenyl)ethane-1,2-diamine, 2-ethoxy-4-(piperidine-1-carbonyl)-benzoic acid methyl ester (example 7) and 1-morpholin-4-yl-2-piperazin-1-yl-ethanone (Oakwood Products) following successively the procedures described for examples 25, 29 and 31. LC-MS: 761.3 [(M+H)⁺].

EXAMPLE 254

2-(4-{(4S,5R)-4,5-Bis-(4-chloro-phenyl)-2-[2-ethoxy-4-(piperidine-1-carbonyl)-phenyl]-4,5-dihydro-imidazole-1-carbonyl}-piperazin-1-yl)-N-tert-butyl-acetamide

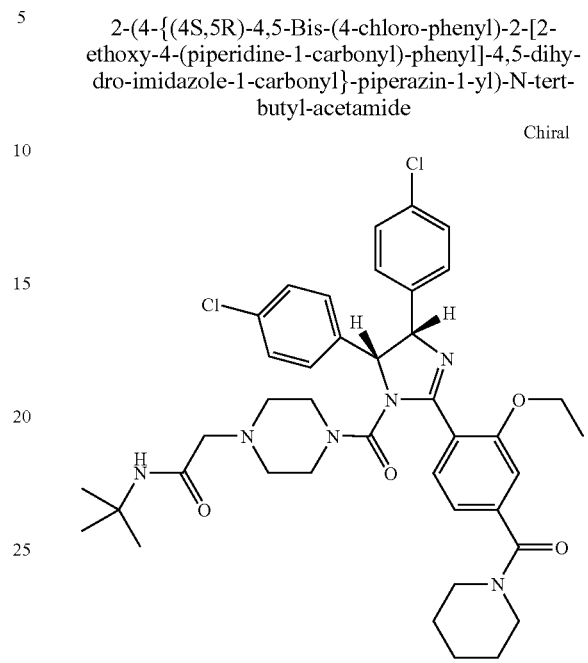

The title compound was prepared from meso-1,2-bis-(4-chlorophenyl)ethane-1,2-diamine, 2-ethoxy-4-(piperidine-1-carbonyl)-benzoic acid methyl ester (example 7) and N-tert-butyl-2-piperazin-1-yl-acetamide (example 22g) following successively the procedures described for examples 25, 29 and 31. LC-MS: 747.3 [(M+H)⁺].

EXAMPLE 255

4-{(4S,5R)-4,5-Bis-(4-chloro-phenyl)-2-[2-ethoxy-4-(piperidine-1-carbonyl)-phenyl]-4,5-dihydro-imidazole-1-carbonyl}-piperazin-2-one

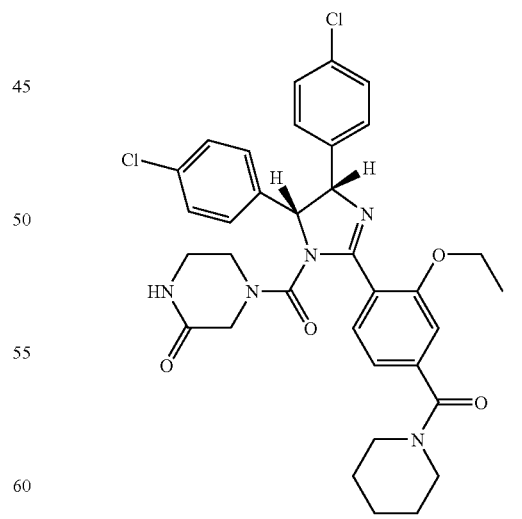

The title compound was prepared from meso-1,2-bis-(4-chlorophenyl)ethane-1,2-diamine, 2-ethoxy-4-(piperidine1-carbonyl)-benzoic acid methyl ester (example 7) and 2-piperazinone (Avocado Organics) following successively the procedures described for examples 25, 29 and 31. LC-MS: 648.1 [(M+H)⁺]. -

EXAMPLE 256

{(4S,5R)-4,5-Bis-(4-chloro-phenyl)-2-[2-ethoxy-4-(piperidine-1-carbonyl)-phenyl]-4,5-dihydro-imidazol-1-yl}-[4-(2-methanesulfonyl-ethyl)-piperazin-1-yl]-methanone

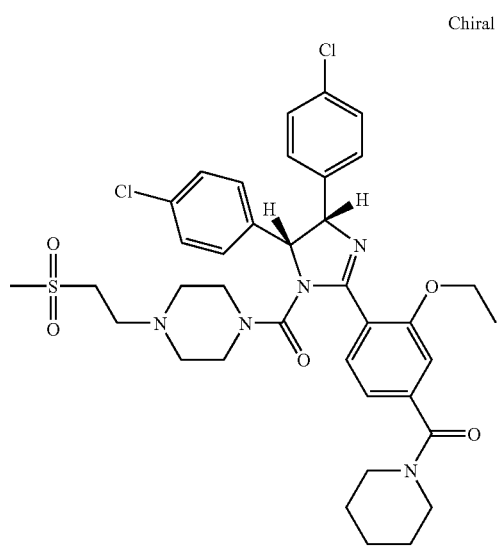

The title compound was prepared from meso-1,2-bis-(4-chlorophenyl)ethane-1,2-diamine, 2-ethoxy-4-(piperidine-1-carbonyl)-benzoic acid methyl ester (example 7) and 1-(2-methanesulfonylethyl)piperazine bishydrochloride (example 23) following successively the procedures described for examples 25, 29 and 31. LC-MS: 740.3 [(M+H)$^+$].

EXAMPLE 257

2-(4-{(4S,5R)-4,5-Bis-(4-chloro-phenyl)-2-[2-ethoxy-4-(piperidine-1-carbonyl)-phenyl]-4,5-dihydro-imidazole-1-carbonyl}-piperazin-1-yl)-acetamide

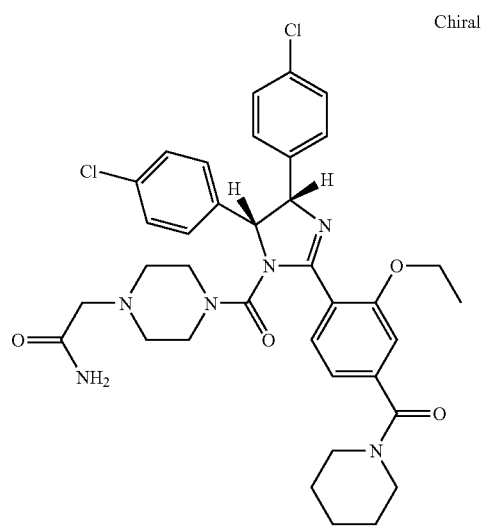

The title compound was prepared from meso-1,2-bis-(4-chlorophenyl)ethane-1,2-diamine, 2-ethoxy-4-(piperidine-1-carbonyl)-benzoic acid ethyl ester (example 4) and 2-piperazin-1-yl-acetamide (Matrix) following successively the procedures described for examples 25, 29 and 31. LC-MS: 691.2 [(M+H)$^+$].

EXAMPLE 258

2-(4-{(4S,5R)-4,5-Bis-(4-chloro-phenyl)-2-[2-ethoxy-4-(piperidine-1-carbonyl)-phenyl]-4,5-dihydro-imidazole-1-carbonyl}-piperazin-1-yl)-N-isopropyl-N-methyl-acetamide

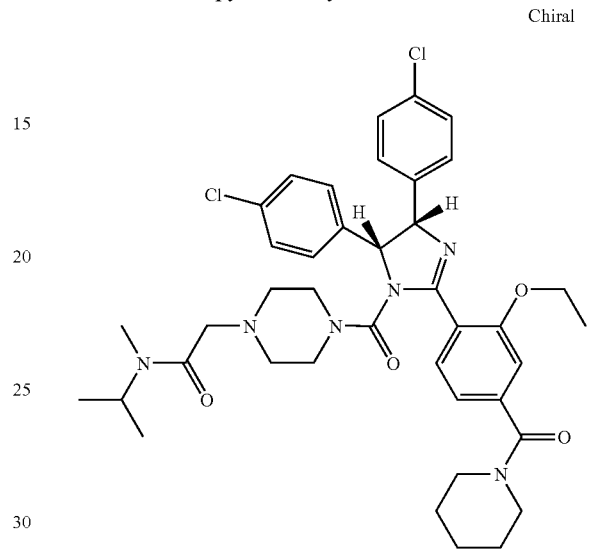

The title compound was prepared from meso-1,2-bis-(4-chlorophenyl)ethane-1,2-diamine, 2-ethoxy-4-(piperidine-1-carbonyl)-benzoic acid methyl ester (example 7) and N-isopropyl-N-methyl-2-piperazin-1-yl-acetamide (example 22c) following successively the procedures described for examples 25, 29 and 31. LC-MS: 747.3 [(M+H)$^+$].

EXAMPLE 259

{(4S,5R)-4,5-Bis-(4-chloro-phenyl)-2-[2-ethoxy-4-(piperidine-1-carbonyl)-phenyl]-4,5-dihydro-imidazol-1-yl}-(4-ethanesulfonyl-piperazin-1-yl)-methanone

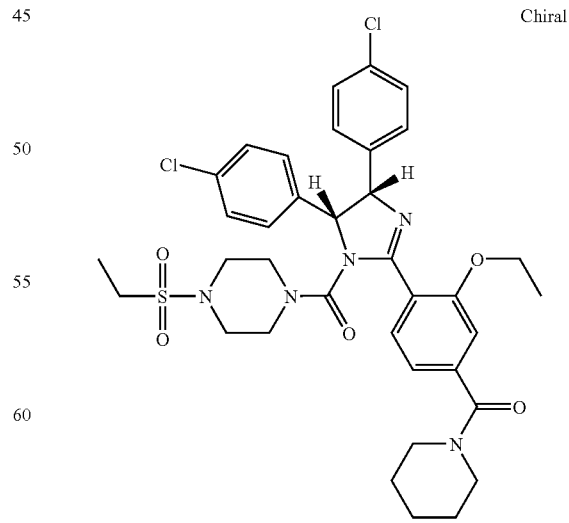

The title compound was prepared from meso-1,2-bis-(4-chlorophenyl)ethane-1,2-diamine, 2-ethoxy-4-(piperidine-1-carbonyl)-benzoic acid methyl ester (example 7) and 1-ethanesulfonyl-piperazine (example 20) following successively the procedures described for examples 25, 29 and 31. LC-MS: 726.2 [(M+H)+].

EXAMPLE 260

5-{(4S,5R)-4,5-Bis-(4-chloro-phenyl)-1-[4-(3,5-dimethyl-isoxazole-4-carbonyl)-piperazine-1-carbonyl]-4,5-dihydro-1H-imidazol-2-yl}-2-chloro-4-ethoxy-N-methyl-benzenesulfonamide

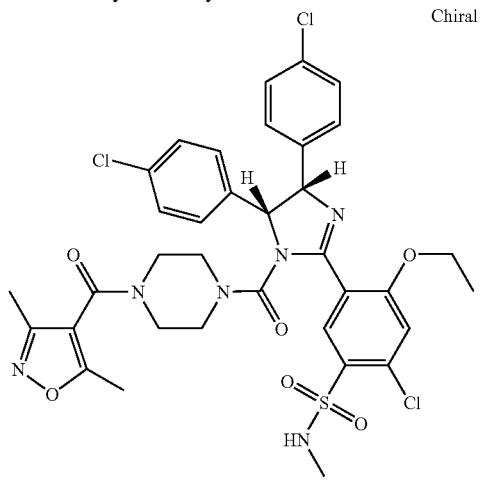

The title compound was prepared from meso-1,2-bis-(4-chlorophenyl)ethane-1,2-diamine, ethyl 2-ethoxy-5-methylsulfamoyl-4-methyl-benzoate (example 2) and (3,5-dimethyl-isoxazol-4-yl)-piperazin-1-yl-methanone (example 19) following successively the procedures described for examples 25, 30 and 32. LC-MS: 773.2 [(M+H)+].

EXAMPLE 261

5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-2-chloro-4-ethoxy-N-isopropyl-benzenesulfonamide

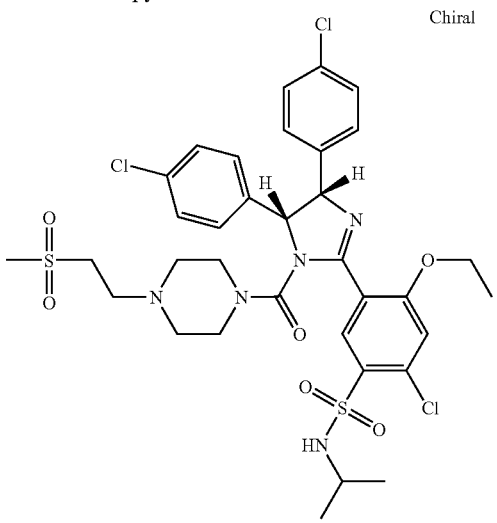

The title compound was prepared from meso-1,2-bis-(4-chlorophenyl)ethane-1,2-diamine, ethyl 4-chloro-2-ethoxy-5-isopropylsulfamoyl-benzoate (example 2) and 1-(2-methanesulfonylethyl)piperazine bishydrochloride (example 23) following successively the procedures described for examples 25, 30 and 32. LC-MS: 784.2 [(M+H)+].

EXAMPLE 262

2-{4-[(4S,5R)-2-(4-Chloro-2-ethoxy-5-isopropylsulfamoyl-phenyl)-4,5-bis-(4-chloro-phenyl)-4,5-dihydro-imidazole-1-carbonyl]-piperazin-1-yl}-acetamide

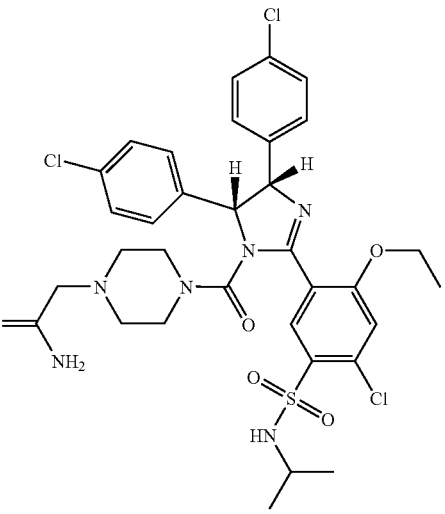

The title compound was prepared from meso-1,2-bis-(4-chlorophenyl)ethane-1,2-diamine, ethyl 4-chloro-2-ethoxy-5-isopropylsulfamoyl-benzoate (example 2) and 2-piperazin-1-yl-acetamide (Matrix) following successively the procedures described for examples 25, 30 and 32. LC-MS: 735.1 [(M+H)+].

EXAMPLE 263

2-{4-[(4S,5R)-2-(4-Chloro-2-ethoxy-5-isopropylsulfamoyl-phenyl)-4,5-bis-(4-chloro-phenyl)-4,5-dihydro-imidazole-1-carbonyl]-piperazin-1-yl}-N-isopropyl-N-methyl-acetamide

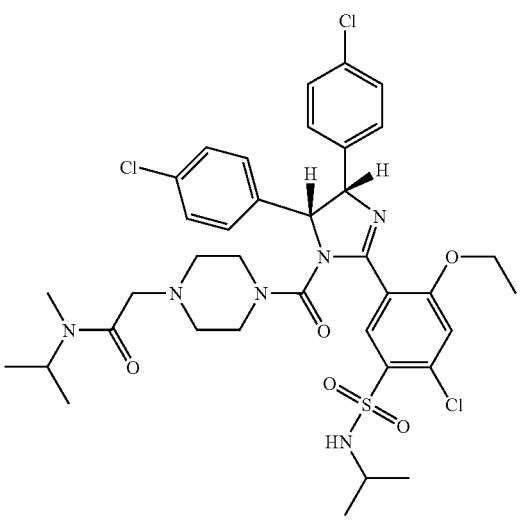

The title compound was prepared from meso-1,2-bis-(4-chlorophenyl)ethane-1,2-diamine, ethyl 4-chloro-2-ethoxy-5-isopropylsulfamoyl-benzoate (example 2) and N-isopropyl-N-methyl-2-piperazin-1-yl-acetamide (example 22c) following successively the procedures described for examples 25, 30 and 32. LC-MS: 791.3 [(M+H)+].

EXAMPLE 264

5-[(4S,5R)-4,5-Bis-(4-chloro-phenyl)-1-(4-ethane-sulfonyl-piperazine-1-carbonyl)-4,5-dihydro-1H-imidazol-2-yl]-2-chloro-4-ethoxy-N-isopropyl-benzenesulfonamide

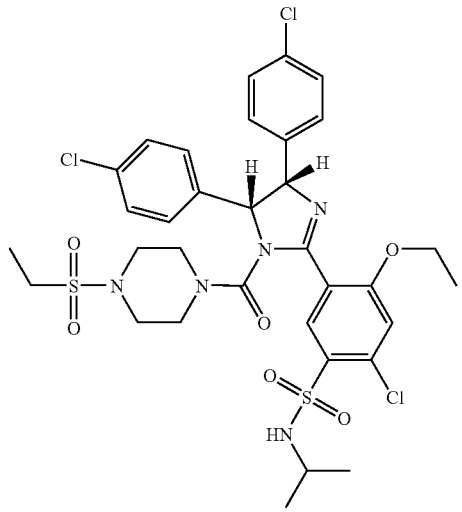

The title compound was prepared from meso-1,2-bis-(4-chlorophenyl)ethane-1,2-diamine, ethyl 4-chloro-2-ethoxy-5-isopropylsulfamoyl-benzoate (example 2) and 1-ethane-sulfonyl-piperazine (example 20) following successively the procedures described for examples 25, 30 and 32. LC-MS: 770.2 [(M+H)$^+$].

EXAMPLE 265

N-tert-Butyl-2-{4-[(4S,5R)-2-(4-chloro-2-ethoxy-5-methylsulfamoyl-phenyl)-4,5-bis-(4-chloro-phenyl)-4,5-dihydro-imidazole-1-carbonyl]-piperazin-1-yl}-acetamide

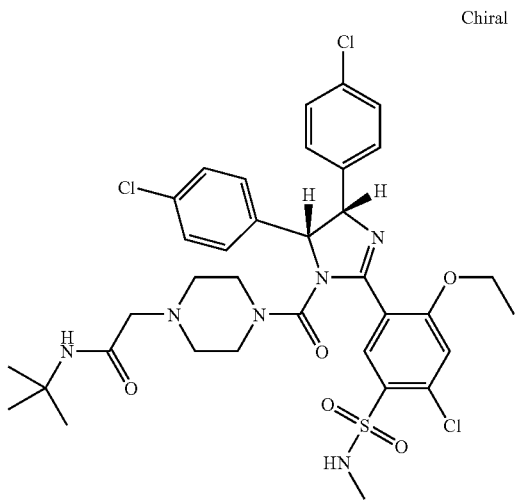

The title compound was prepared from meso-1,2-bis-(4-chlorophenyl)ethane-1,2-diamine, ethyl 4-chloro-2-ethoxy-5-methylsulfamoyl-benzoate (example 2) and N-tert-butyl-2-piperazin-1-yl-acetamide (example 22g) following successively the procedures described for examples 25, 30 and 32. LC-MS: 763.2 [(M+H)$^+$].

EXAMPLE 266

5-[(4S,5R)-4,5-Bis-(4-chloro-phenyl)-1-(3-oxo-piperazine-1-carbonyl)-4,5-dihydro-1H-imidazol-2-yl]-2-chloro-4-ethoxy-N-methyl-benzenesulfonamide

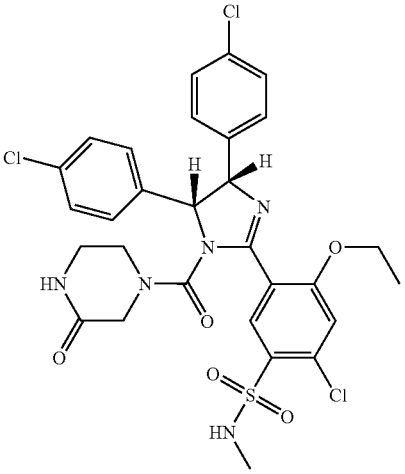

The title compound was prepared from meso-1,2-bis-(4-chlorophenyl)ethane-1,2-diamine, ethyl 4-chloro-2-ethoxy-5-methylsulfamoyl-benzoate (example 2) and 2-piperazinone (Avocado Organics) following successively the procedures described for examples 25, 30 and 32. LC-MS: 664 [(M+H)$^+$].

EXAMPLE 267

5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-2-chloro-4-ethoxy-N-methyl-benzenesulfonamide

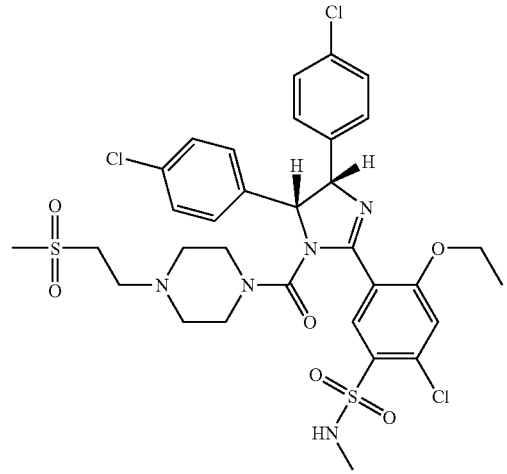

The title compound was prepared from meso-1,2-bis-(4-chlorophenyl)ethane-1,2-diamine, ethyl 4-chloro-2-ethoxy-5-methylsulfamoyl-benzoate (example 2) and 1-(2-methanesulfonylethyl)piperazine bishydrochloride (example 23) following successively the procedures described for examples 25, 30 and 32. LC-MS: 756.2 [(M+H)$^+$].

EXAMPLE 268

2-{4-[(4S,5R)-2-(4-Chloro-2-ethoxy-5-methylsulfamoyl-phenyl)-4,5-bis-(4-chloro-phenyl)-4,5-dihydro-imidazole-1-carbonyl]-piperazin-1-yl}-acetamide Chiral

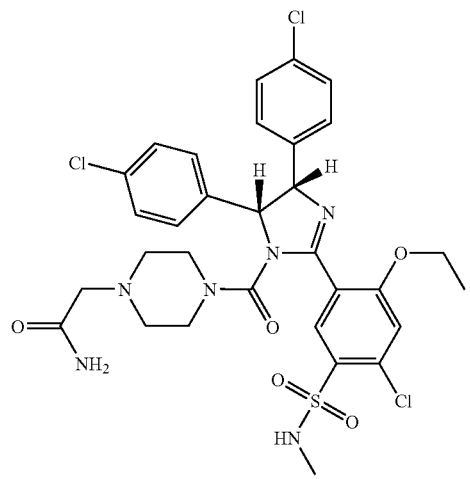

The title compound was prepared from meso-1,2-bis-(4-chlorophenyl)ethane-1,2-diamine, ethyl 4-chloro-2-ethoxy-5-methylsulfamoyl-benzoate (example 2) and 2-piperazin-1-yl-acetamide (Matrix) following successively the procedures described for examples 25, 30 and 32. LC-MS: 707.1 [(M+H)+].

EXAMPLE 269

2-{4-[(4S,5R)-2-(4-Chloro-2-ethoxy-5-methylsulfamoyl-phenyl)-4,5-bis-(4-chloro-phenyl)-4,5-dihydro-imidazole-1-carbonyl]-piperazin-1-yl}-N-isopropyl-N-methyl-acetamide Chiral

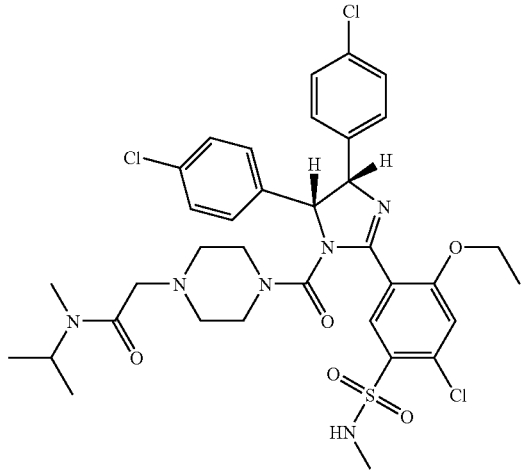

The title compound was prepared from meso-1,2-bis-(4-chlorophenyl)ethane-1,2-diamine, ethyl 4-chloro-2-ethoxy-5-methylsulfamoyl-benzoate (example 2) and N-isopropyl-N-methyl-2-piperazin-1-yl-acetamide (example 22c) following successively the procedures described for examples 25, 30 and 32. LC-MS: 763.2 [(M+H)+].

EXAMPLE 270

5-[(4S,5R)-4,5-Bis-(4-chloro-phenyl)-1-(4-ethanesulfonyl-piperazine-1-carbonyl)-4,5-dihydro-1H-imidazol-2-yl]-2-chloro-4-ethoxy-N-methyl-benzenesulfonamide Chiral

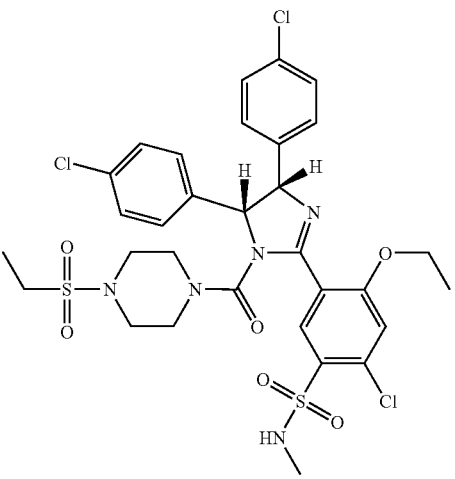

The title compound was prepared from meso-1,2-bis-(4-chlorophenyl)ethane-1,2-diamine, ethyl 4-chloro-2-ethoxy-5-methylsulfamoyl-benzoate (example 2) and 1-ethanesulfonyl-piperazine (example 20) following successively the procedures described for examples 25, 30 and 32. LC-MS: 742.2 [(M+H)+].

EXAMPLE 271

5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-2-chloro-4-ethoxy-N-isopropyl-benzenesulfonamide Chiral

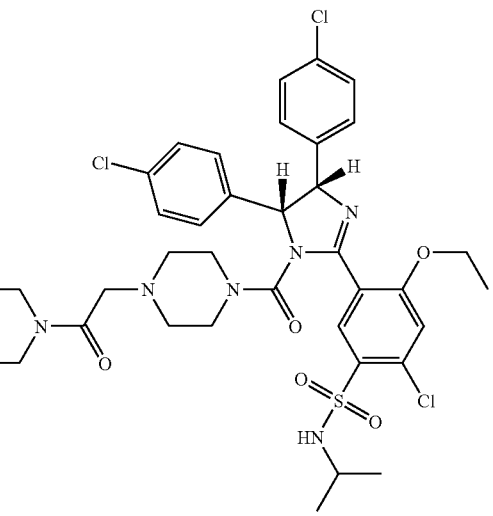

The title compound was prepared from meso-1,2-bis-(4-chlorophenyl)ethane-1,2-diamine, ethyl 4-chloro-2-ethoxy-5-isopropylsulfamoyl-benzoate (example 2) and 1-morpholin-4-yl-2-piperazin-1-yl-ethanone (Oakwood Products) following successively the procedures described for examples 25, 30 and 32. LC-MS: 805.3 [(M+H)+].

EXAMPLE 272

5-{(4S,5R)-4,5-Bis-(4-chloro-phenyl)-1-[4-(3,5-dimethyl-isoxazole-4-carbonyl)-piperazine-1-carbonyl]-4,5-dihydro-1H-imidazol-2-yl}-2-chloro-4-ethoxy-N-isopropyl-benzenesulfonamide Chiral

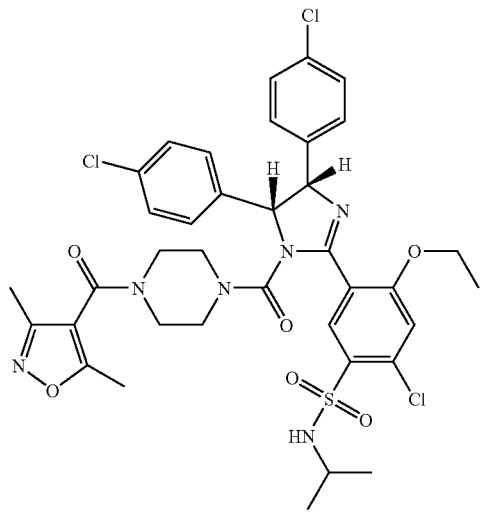

The title compound was prepared from meso-1,2-bis-(4-chlorophenyl)ethane-1,2-diamine, ethyl 4-chloro-2-ethoxy-5-isopropylsulfamoyl-benzoate (example 2) and (3,5-dimethyl-isoxazol-4-yl)-piperazin-1-yl-methanone (example 19) following successively the procedures described for examples 25, 30 and 32. LC-MS: 801.2 [(M+H)$^+$].

EXAMPLE 273

N-tert-Butyl-2-{4-[(4S,5R)-2-(4-chloro-2-ethoxy-5-isopropylsulfamoyl-phenyl)-4,5-bis-(4-chloro-phenyl)-4,5-dihydro-imidazole-1-carbonyl]-piperazin-1-yl}acetamide Chiral

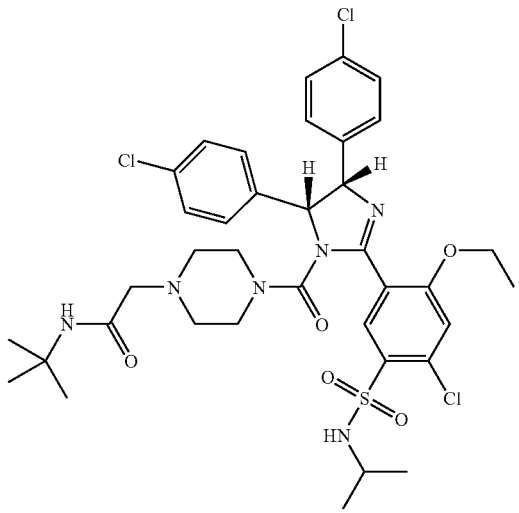

The title compound was prepared from meso-1,2-bis-(4-chlorophenyl)ethane-1,2-diamine, ethyl 4-chloro-2-ethoxy-5-isopropylsulfamoyl-benzoate (example 2) and N-tert-butyl-2-piperazin-1-yl-acetamide (example 22g) following successively the procedures described for examples 25, 30 and 32. LC-MS: 791.3 [(M+H)$^+$].

EXAMPLE 274

5-[(4S,5R)-4,5-Bis-(4-chloro-phenyl)-1-(3-oxo-piperazine-1-carbonyl)-4,5-dihydro-1H-imidazol-2-yl]-2-chloro-4-ethoxy-N-isopropyl-benzenesulfonamide Chiral

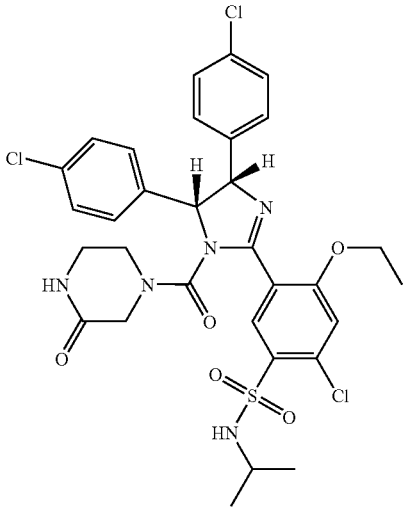

The title compound was prepared from meso-1,2-bis-(4-chlorophenyl)ethane-1,2-diamine, ethyl 4-chloro-2-ethoxy-5-isopropylsulfamoyl-benzoate (example 2) and 2-piperazinone (Avocado Organics) following successively the procedures described for examples 25, 30 and 32. LC-MS: 692.1 [(M+H)$^+$].

EXAMPLE 275

N-{4-[(4S,5R)-4,5-Bis-(4-chloro-phenyl)-1-(3-oxo-piperazine-1-carbonyl)-4,5-dihydro-1H-imidazol-2-yl]-3-ethoxy-phenyl}-N-(3-oxo-piperazine-1-carbonyl)-methanesulfonamide Chiral

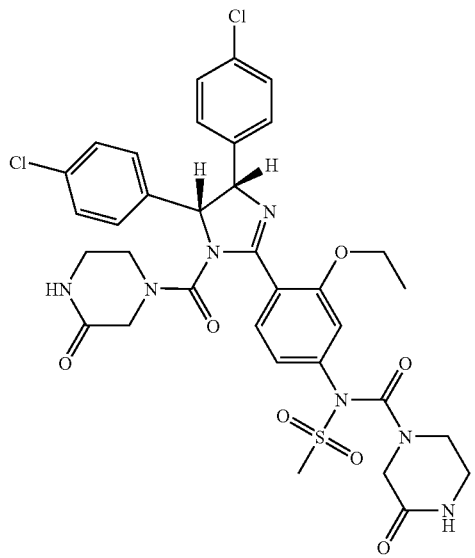

The title compound was prepared from meso-1,2-bis-(4-chlorophenyl)ethane-1,2-diamine, 2-ethoxy-4-[methanesulfonyl-(3-oxo-piperazine-1-carbonyl)-amino]-benzoic acid ethyl ester (example 13) and 2-piperazinone (Avocado Organics) following successively the procedures described for examples 25, 29 and 31. LC-MS: 756.4 [(M+H)$^+$].

EXAMPLE 276

N-(4-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-3-ethoxy-phenyl)-methanesulfonamide hydrochloride Chiral

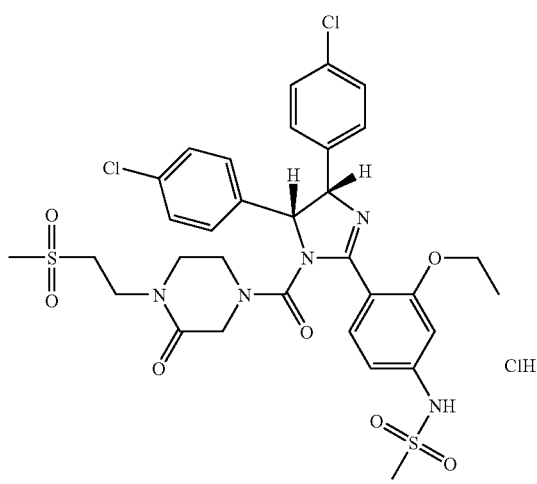

The title compound was prepared from meso-1,2-bis-(4-chlorophenyl)ethane-1,2-diamine, ethyl 4-methanesulfonylamino-2-ethoxybenzoate (example 13) and 1-(2-methanesulfonylethyl)piperazine bishydrochloride (example 23) following successively the procedures described for examples 25, 29 and 31. LC-MS: 940.4 [(M+H)$^+$].

EXAMPLE 277

N-{4-[(4S,5R)-4,5-Bis-(4-chloro-phenyl)-1-(3-oxo-piperazine-1-carbonyl)-4,5-dihydro-1H-imidazol-2-yl]-3-ethoxy-phenyl}-2,2-dimethyl-propionamide Chiral

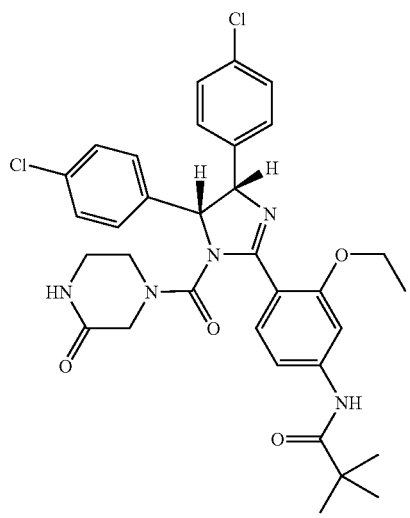

The title compound was prepared from meso-1,2-bis-(4-chlorophenyl)ethane-1,2-diamine, 4-(2,2-dimethyl-propionylamino)-2-ethoxy-benzoic acid ethyl ester (example 13) and 2-piperazinone (Avocado Organics) following successively the procedures described for examples 25, 29 and 31. LC-MS: 636.4 [(M+H)$^+$].

EXAMPLE 278

5-[(4S,5R)-4,5-Bis-(4-chloro-phenyl)-1-(3-oxo-piperazine-1-carbonyl)-4,5-dihydro-1H-imidazol-2-yl]-4-ethoxy-2-ethynyl-N,N-dimethyl-benzenesulfonamide Chiral

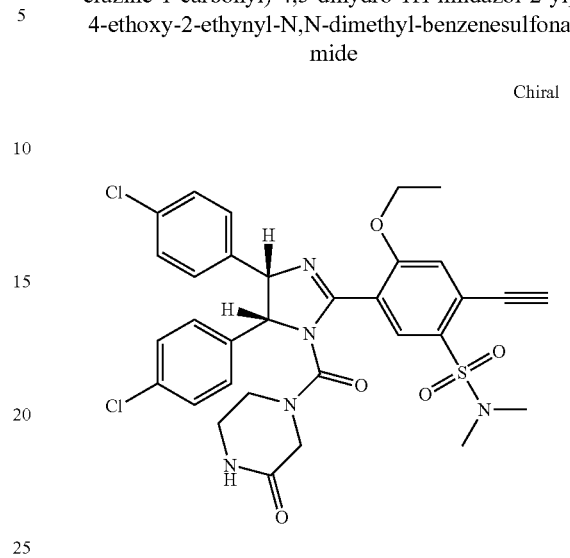

The title compound was prepared from meso-1,2-bis-(4-chlorophenyl)ethane-1,2-diamine, ethyl 5-dimethylsulfamoyl-2-ethoxy-4-trimethylsilanylethynylbenzoate (example 18) and 2-piperazinone (Avocado Organics) following successively the procedures described for examples 25, 29 and 31. LC-MS: 668.3 [(M+H)$^+$].

EXAMPLE 279

5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-4-ethoxy-2-ethynyl-N,N-dimethyl-benzenesulfonamide hydrochloride Chiral

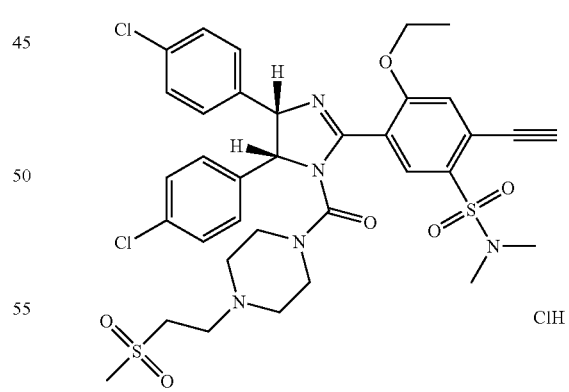

The title compound was prepared from meso-1,2-bis-(4-chlorophenyl)ethane-1,2-diamine, ethyl 5-dimethylsulfamoyl-2-ethoxy-4-trimethylsilanylethynylbenzoate (example 18) and 1-(2-methanesulfonylethyl)piperazine bishydrochloride (example 23) following successively the procedures described for examples 25, 29 and 31. LC-MS: 760.4 [(M+H)$^+$].

EXAMPLE 280

5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-4-ethoxy-2-ethynyl-N,N-dimethyl-benzenesulfonamide hydrochloride Chiral

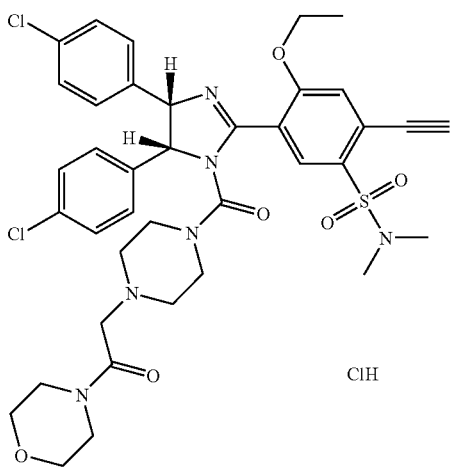

The title compound was prepared from meso-1,2-bis-(4-chlorophenyl)ethane-1,2-diamine, ethyl 5-dimethylsulfamoyl-2-ethoxy-4-trimethylsilanylethynylbenzoate (example 18) and 1-morpholin-4-yl-2-piperazin-1-yl-ethanone (Oakwood Products) following successively the procedures described for examples 25, 29 and 31. LC-MS: 781.4 [(M+H)$^+$].

EXAMPLE 281

2-{4-[(4S,5R)-4,5-Bis-(4-chloro-phenyl)-2-(5-dimethylsulfamoyl-2-ethoxy-4-ethynyl-phenyl)-4,5-dihydro-imidazole-1-carbonyl]-piperazin-1-yl}-N-isopropyl-N-methyl-acetamide hydrochloride Chiral

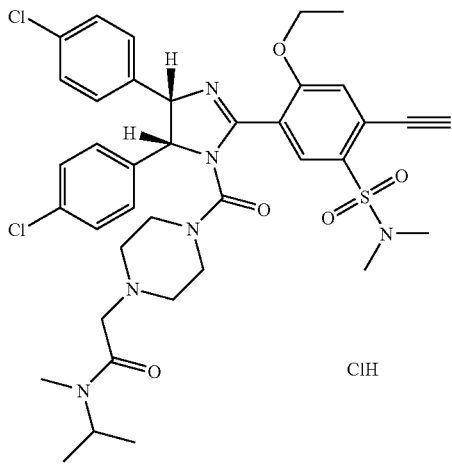

The title compound was prepared from meso-1,2-bis-(4-chlorophenyl)ethane-1,2-diamine, ethyl 5-dimethylsulfamoyl-2-ethoxy-4-trimethylsilanylethynyl-benzoate (example 18) and N-isopropyl-N-methyl-2-piperazin-1-yl-acetamide (example 22c) following successively the procedures described for examples 25, 29 and 31. LC-MS: 767.5 [(M+H)$^+$].

EXAMPLE 282

N-(4-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-3-ethoxy-phenyl)-2,2-dimethyl-propionamide hydrochloride Chiral

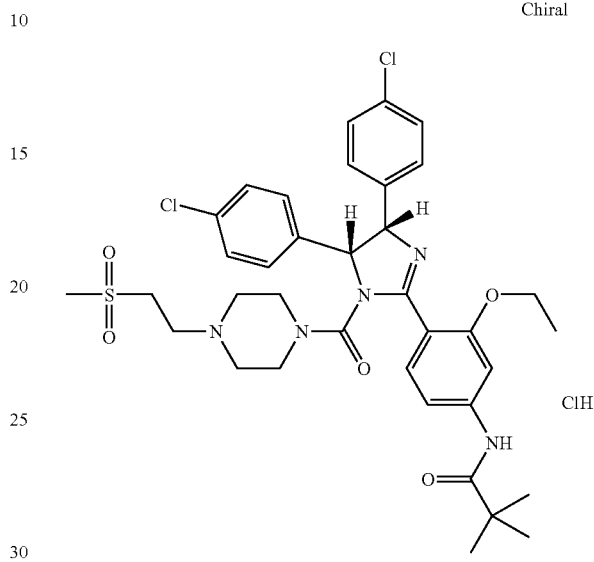

The title compound was prepared from meso-1,2-bis-(4-chlorophenyl)ethane-1,2-diamine, 4-(2,2-dimethyl-propionylamino)-2-ethoxy-benzoic acid ethyl ester (example 13) and 1-(2-methanesulfonylethyl)piperazine bishydrochloride (example 23) following successively the procedures described for examples 25, 29 and 31. LC-MS: 728.4 [(M+H)$^+$].

EXAMPLE 283

N-{4-[(4S,5R)-4,5-Bis-(4-chloro-phenyl)-1-(4-dimethylcarbamoylmethyl-piperazine-1-carbonyl)-4,5-dihydro-1H-imidazol-2-yl]-3-ethoxy-phenyl}-2,2-dimethyl-propionamide hydrochloride Chiral

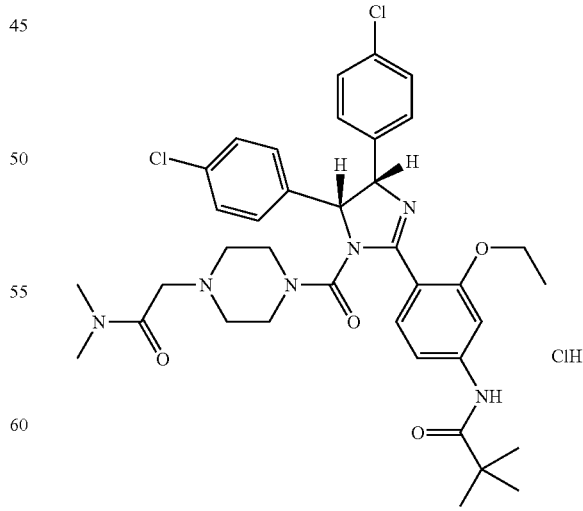

The title compound was prepared from meso-1,2-bis-(4-chlorophenyl)ethane-1,2-diamine, 4-(2,2-dimethyl-propionylamino)-2-ethoxy-benzoic acid ethyl ester (example 13) and N,N-dimethyl-2-piperazin-1-yl-acetamide (Oakwood Products) following successively the procedures described for examples 25, 29 and 31. LC-MS: 707.5 [(M+H)+].

EXAMPLE 284

N-(4-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-3-ethoxy-phenyl)-2,2-dimethyl-propionamide hydrochloride Chiral

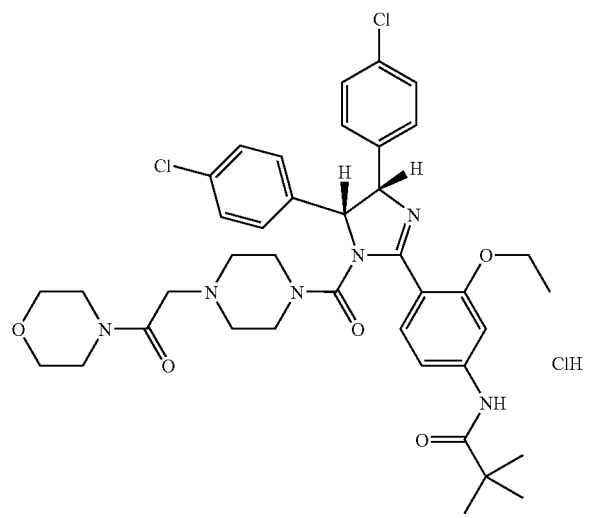

The title compound was prepared from meso-1,2-bis-(4-chlorophenyl)ethane-1,2-diamine, 4-(2,2-dimethyl-propionylamino)-2-ethoxy-benzoic acid ethyl ester (example 13) and 1-morpholin-4-yl-2-piperazin-1-yl-ethanone (Oakwood Products) following successively the procedures described for examples 25, 29 and 31. LC-MS: 749.5 [(M+H)+].

EXAMPLE 285

2-{4-[(4S,5R)-4,5-Bis-(4-chloro-phenyl)-2-(2-ethoxy-4-ethynyl-phenyl)-4,5-dihydro-imidazole-1-carbonyl]-piperazin-1-yl}-N-tert-butyl-acetamide hydrochloride Chiral

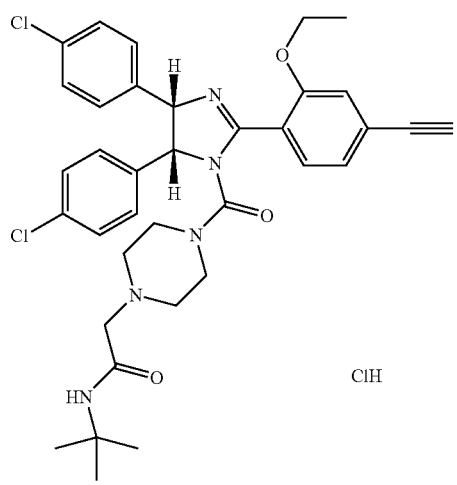

The title compound was prepared from 4,5-bis-(4-chlorophenyl)-2-(2-ethoxy-4-ethynylphenyl)-4,5-dihydro-1H-imidazole (example 26) and N-tert-butyl-2-piperazin-1-yl-acetamide (example 22g) following successively the procedures described for examples 29 and 31. LC-MS: 660.4 [(M+H)+].

EXAMPLE 286

2-{4-[(4S,5R)-4,5-Bis-(4-chloro-phenyl)-2-(2-ethoxy-4-ethynyl-phenyl)-4,5-dihydro-imidazole-1-carbonyl]-piperazin-1-yl}-N-methoxy-N-methyl-acetamide hydrochloride Chiral

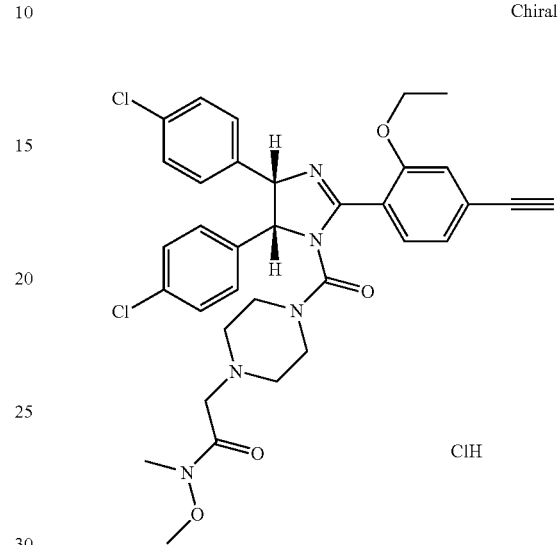

The title compound was prepared from 4,5-bis-(4-chlorophenyl)-2-(2-ethoxy-4-ethynylphenyl)-4,5-dihydro-1H-imidazole (example 26) and N-methoxy-N-methyl-2-piperazin-1-yl-acetamide (example 22b) following successively the procedures described for examples 29 and 31. LC-MS: 648.4 [(M+H)+].

EXAMPLE 287

N-(2-{(4-[(4S,5R)-4,5-Bis-(4-chloro-phenyl)-2-(2-ethoxy-4-ethynyl-phenyl)-4,5-dihydro-imidazole-1-carbonyl]-piperazin-1-yl}-ethyl)-methanesulfonamide hydrochloride Chiral

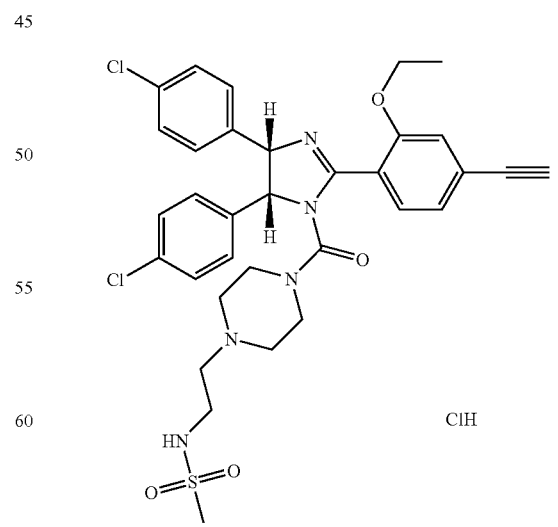

The title compound was prepared from 4,5-bis-(4-chlorophenyl)-2-(2-ethoxy-4-ethynylphenyl)-4,5-dihydro-1H- imidazole (example 26) and N-(2-methanosulfonylethyl)-piperazine hydrochloride (example 24) following successively the procedures described for examples 29 and 31. LC-MS: 668.4 [(M+H)+].

EXAMPLE 288

[(4S,5R)-4,5-Bis-(4-chloro-phenyl)-2-(2-ethoxy-4-ethynyl-phenyl)-4,5-dihydro-imidazol-1-yl]-(4-ethanesulfonyl-piperazin-1-yl)-methanone Chiral

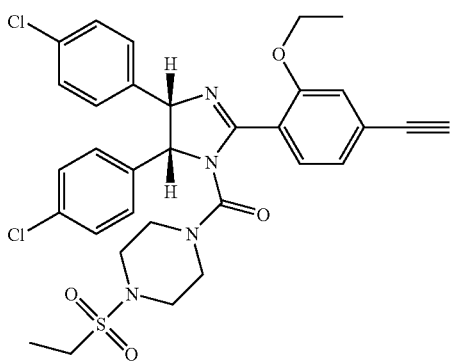

The title compound was prepared from 4,5-bis-(4-chlorophenyl)-2-(2-ethoxy-4-ethynylphenyl)-4,5-dihydro-1H-imidazole (example 26) and 1-ethanesulfonyl-piperazine (example 20) following successively the procedures described for examples 29 and 31. LC-MS: 639.4 [(M+H)+].

EXAMPLE 289

[(4S,5R)-4,5-Bis-(4-chloro-phenyl)-2-(2-ethoxy-4-ethynyl-phenyl)-4,5-dihydro-imidazol-1-yl]-[4-(2-methoxy-ethyl)-piperazin-1-yl]-methanone hydrochloride Chiral

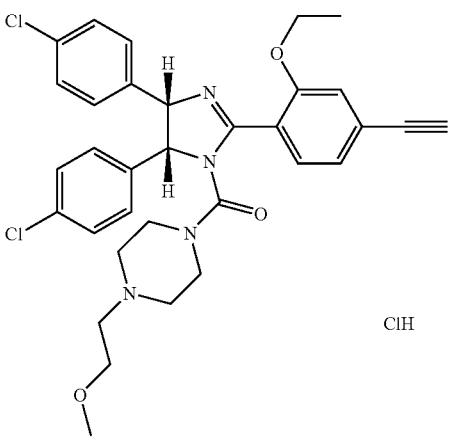

The title compound was prepared from 4,5-bis-(4-chlorophenyl)-2-(2-ethoxy-4-ethynylphenyl)-4,5-dihydro-1H-imidazole (example 26) and 1-(2-hydroxy-ethyl)-piperazine (Aldrich) following successively the procedures described for examples 29 and 31. LC-MS: 605.4 [(M+H)+].

EXAMPLE 290

1-{4-[(4S,5R)-4,5-Bis-(4-chloro-phenyl)-2-(2-ethoxy-4-ethynyl-phenyl)-4,5-dihydro-imidazole-1-carbonyl]-piperazin-1-yl}-ethanone Chiral

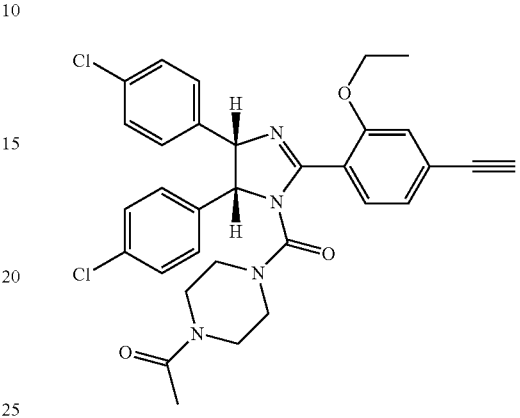

The title compound was prepared from 4,5-bis-(4-chlorophenyl)-2-(2-ethoxy-4-ethynylphenyl)-4,5-dihydro-1H-imidazole (example 26) and 1-acetylpiperazine (Aldrich) following successively the procedures described for examples 29 and 31. LC-MS: 589.4 [(M+H)+].

EXAMPLE 291

3-{4-[(4S,5R)-4,5-Bis-(4-chloro-phenyl)-2-(2-ethoxy-4-ethynyl-phenyl)-4,5-dihydro-imidazole-1-carbonyl]-piperazin-1-yl}-propionitrile hydrochloride Chiral

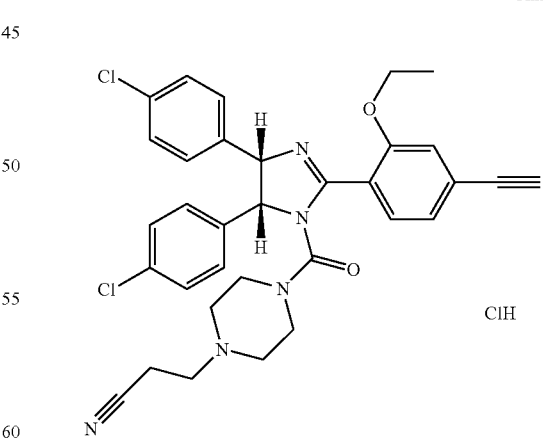

The title compound was prepared from 4,5-bis-(4-chlorophenyl)-2-(2-ethoxy-4-ethynylphenyl)-4,5-dihydro-1H-imidazole (example 26) and 3-piperazin-1-yl-propionitrile (example 22f) following successively the procedures described for examples 29 and 31. LC-MS: 600.4 [(M+H)+].

EXAMPLE 292

[(4S,5R)-4,5-Bis-(4-chloro-phenyl)-2-(2-ethoxy-4-ethynyl-phenyl)-4,5-dihydro-imidazol-1-yl]-[4-(3-methanesulfonyl-propyl)-piperazin-1-yl]-methanone hydrochloride Chiral

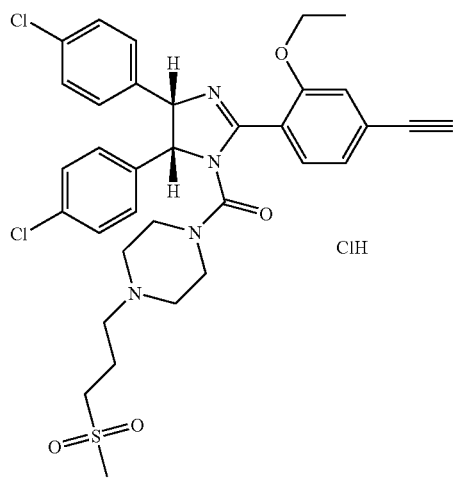

The title compound was prepared from 4,5-bis-(4-chlorophenyl)-2-(2-ethoxy-4-ethynylphenyl)-4,5-dihydro-1H-imidazole (example 26) and 1-(3-methanesulfonyl-propyl)-piperazine (example 22e) following successively the procedures described for examples 29 and 31. LC-MS: 667.4 [(M+H)$^+$].

EXAMPLE 293

2-{4-[(4S,5R)-4,5-Bis-(4-chloro-phenyl)-2-(2-ethoxy-4-ethynyl-phenyl)-4,5-dihydro-imidazole-1-carbonyl]-piperazin-1-yl}-acetamide hydrochloride Chiral

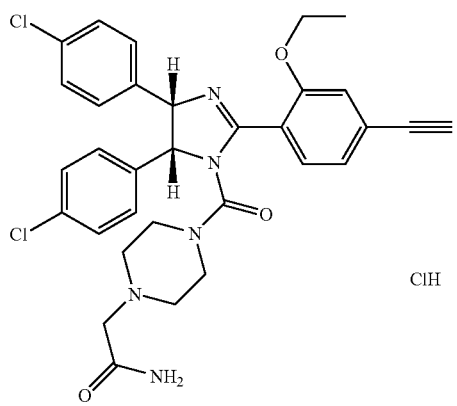

The title compound was prepared from 4,5-bis-(4-chlorophenyl)-2-(2-ethoxy-4-ethynylphenyl)-4,5-dihydro-1H-imidazole (example 26) and 2-piperazin-1-yl-acetamide (Matrix) following successively the procedures described for examples 29 and 31. LC-MS: 604.4 [(M+H)$^+$].

EXAMPLE 294

2-{4-[(4S,5R)-4,5-Bis-(4-chloro-phenyl)-2-(2-ethoxy-4-ethynyl-phenyl)-4,5-dihydro-imidazole-1-carbonyl]-piperazin-1-yl}-N-isopropyl-N-methyl-acetamide hydrochloride Chiral

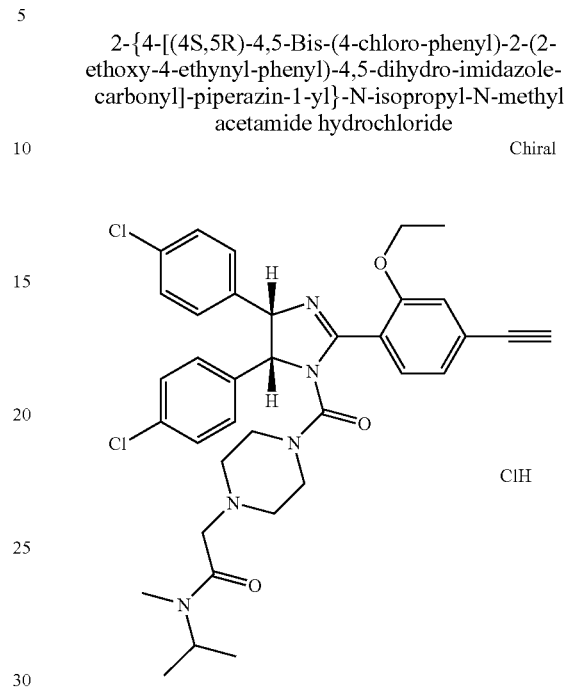

The title compound was prepared from 4,5-bis-(4-chlorophenyl)-2-(2-ethoxy-4-ethynylphenyl)-4,5-dihydro-1H-imidazole (example 26) and N-isopropyl-N-methyl-2-piperazin-1-yl-acetamide (example 22c) following successively the procedures described for examples 29 and 31. LC-MS: 660.4 [(M+H)$^+$].

EXAMPLE 295

3-{4-[(4S,5R)-4,5-Bis-(4-chloro-phenyl)-2-(2-ethoxy-4-ethynyl-phenyl)-4,5-dihydro-imidazole-1-carbonyl]-piperazin-1-yl}-propionic acid hydrochloride Chiral

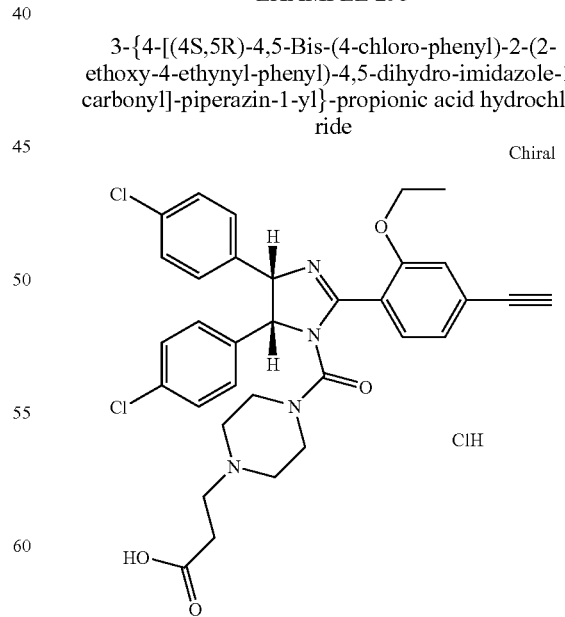

The title compound was prepared from 4,5-bis-(4-chlorophenyl)-2-(2-ethoxy-4-ethynylphenyl)-4,5-dihydro-1H-imidazole (example 26) and 3-piperazinyl-propionic acid (Oakwood Products) following successively the procedures described for examples 29 and 31. LC-MS: 619.4 [(M+H)+].

EXAMPLE 296

4-[(4S,5R)-4,5-Bis-(4-chloro-phenyl)-2-(2-ethoxy-4-trifluoroprop-1-ynyl-phenyl)-4,5-dihydro-imidazole-1-carbonyl]-piperazin-2-one

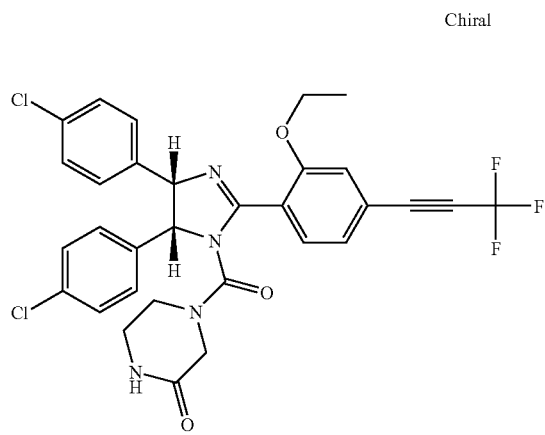

The title compound was prepared from meso-1,2-bis-(4-chlorophenyl)ethane-1,2-diamine, ethyl 4-trifluoroprop-1-ynylbenzoate (example 16) and 2-piperazinone (Avocado Organics) following successively the procedures described for examples 25, 29 and 31. LC-MS: 629.4 [(M+H)+].

EXAMPLE 297

[(4S,5R)-4,5-Bis-(4-chloro-phenyl)-2-(2-ethoxy-4-trifluoroprop-1-ynyl-phenyl)-4,5-dihydro-imidazol-1-yl]-[4-(2-methanesulfonyl-ethyl)-piperazin-1-yl]-methanone hydrochloride

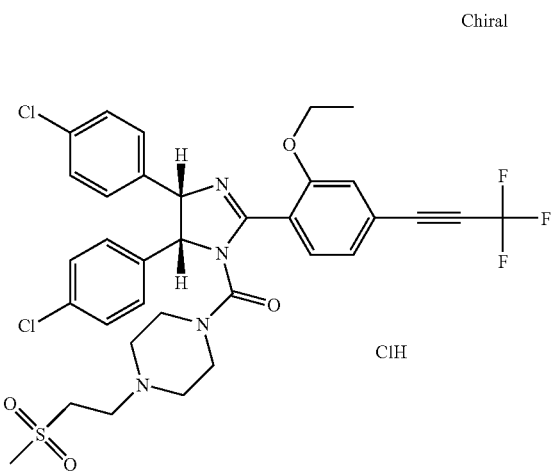

The title compound was prepared from meso-1,2-bis-(4-chlorophenyl)ethane-1,2-diamine, ethyl 4-trifluoroprop-1-ynylbenzoate (example 16) and 1-(2-methanesulfonylethyl)piperazine bishydrochloride (example 23) following successively the procedures described for examples 25, 29 and 31. LC-MS: 721.3 [(M+H)+].

EXAMPLE 298

2-{4-[(4S,5R)-4,5-Bis-(4-chloro-phenyl)-2-(2-ethoxy-4-trifluoroprop-1-ynyl-phenyl)-4,5-dihydro-imidazole-1-carbonyl]-piperazin-1-yl}-1-morpholin-4-yl-ethanone hydrochloride

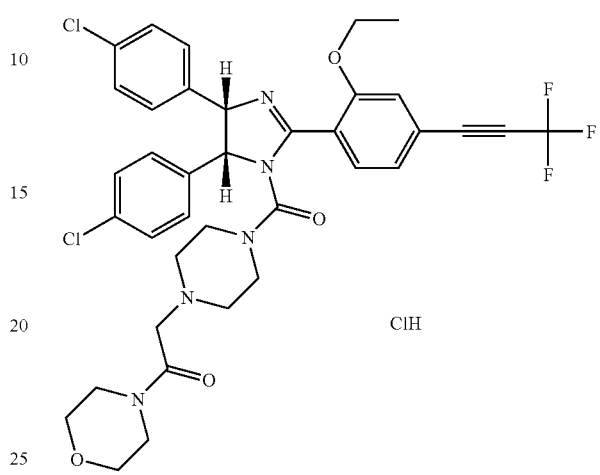

The title compound was prepared from meso-1,2-bis-(4-chlorophenyl)ethane-1,2-diamine, ethyl 4-trifluoroprop-1-ynylbenzoate (example 16) and 1-morpholin-4-yl-2-piperazin-1-yl-ethanone (Oakwood Products) following successively the procedures described for examples 25, 29 and 31. LC-MS: 742.4 [(M+H)+].

EXAMPLE 299

2-{4-[(4S,5R)-4,5-Bis-(4-chloro-phenyl)-2-(2-ethoxy-4-trifluoroprop-1-ynyl-phenyl)-4,5-dihydro-imidazole-1-carbonyl]-piperazin-1-yl}-N-isopropyl-N-methyl-acetamide hydrochloride

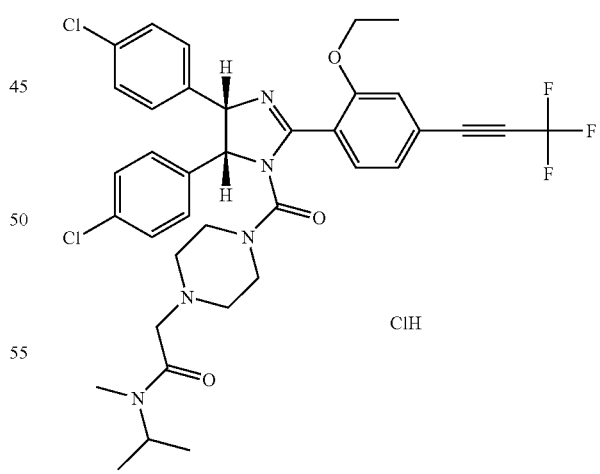

The title compound was prepared from meso-1,2-bis-(4-chlorophenyl)ethane-1,2-diamine, ethyl 4-trifluoroprop-1-ynylbenzoate (example 16) and N-isopropyl-N-methyl-2-piperazin-1-yl-acetamide (example 22c) following successively the procedures described for examples 25, 29 and 31. LC-MS: 728.4 [(M+H)+].

EXAMPLE 300

2-(4-{(4S,5R)-4,5-Bis-(4-chloro-phenyl)-2-[2-ethoxy-4-methyl-5-(piperidine-1-sulfonyl)-phenyl]-4,5-dihydro-imidazole-1-carbonyl}-piperazin-1-yl)-N-tert-butyl-acetamide

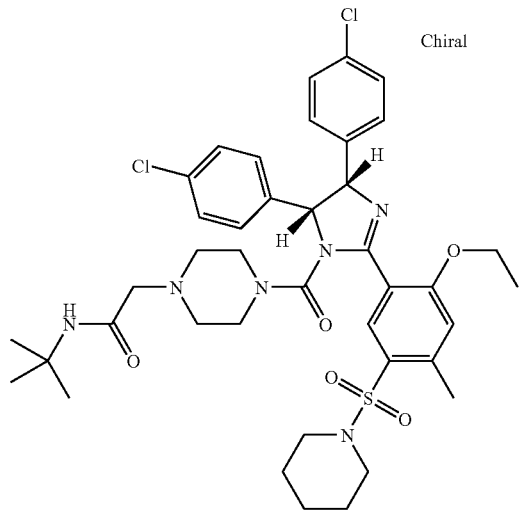

The title compound was prepared from meso-1,2-bis-(4-chlorophenyl)ethane-1,2-diamine, ethyl 2-ethoxy-4-methyl-5-(piperidine-1-sulfonyl)-benzoate (example 2) and N-tert-butyl-2-piperazin-1-yl-acetamide (example 22g) following successively the procedures described for examples 25, 29 and 31. LC-MS: 797.3 [(M+H)$^+$].

EXAMPLE 301

2-(4-{(4S,5R)-4,5-Bis-(4-chloro-phenyl)-2-[2-ethoxy-4-methyl-5-(piperidine-1-sulfonyl)-phenyl]-4,5-dihydro-imidazole-1-carbonyl}-piperazin-1-yl)-acetamide

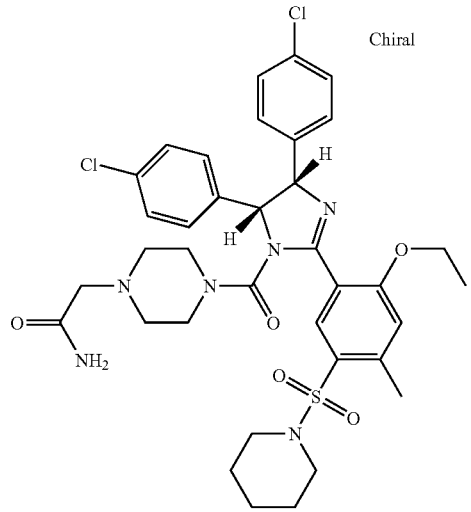

The title compound was prepared from meso-1,2-bis-(4-chlorophenyl)ethane-1,2-diamine, ethyl 2-ethoxy-4-methyl-5-(piperidine-1-sulfonyl)-benzoate (example 2) and 2-piperazin-1-yl-acetamide (Matrix) following successively the procedures described for examples 25, 29 and 31. LC-MS: 741.2 [(M+H)$^+$]. r-

EXAMPLE 302

2-(4-{(4S,5R)-4,5-Bis-(4-chloro-phenyl)-2-[2-ethoxy-4-methyl-5-(piperidine-1-sulfonyl)-phenyl]-4,5-dihydro-imidazole-1-carbonyl}-piperazin-1-yl)-N,N-bis-(2-methoxy-ethyl)-acetamide

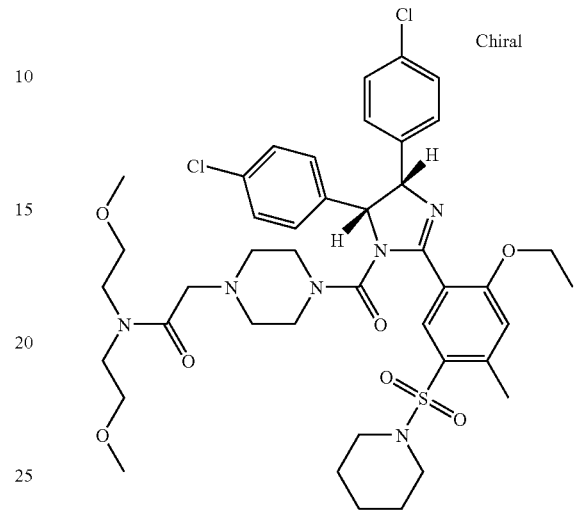

The title compound was prepared from meso-1,2-bis-(4-chlorophenyl)ethane-1,2-diamine, ethyl 2-ethoxy-4-methyl-5-(piperidine-1-sulfonyl)-benzoate (example 2) and N,N-bis-(2-methoxy-ethyl)-2-piperazin-1-yl-acetamide (example 22a) following successively the procedures described for examples 25, 29 and 31. LC-MS: 857.4 [(M+H)$^+$].

EXAMPLE 303

2-(4-{(4S,5R)-4,5-Bis-(4-chloro-phenyl)-2-[2-ethoxy-4-methyl-5-(piperidine-1-sulfonyl)-phenyl]-4,5-dihydro-imidazole-1-carbonyl}-piperazin-1-yl)-N-methoxy-N-methyl-acetamide

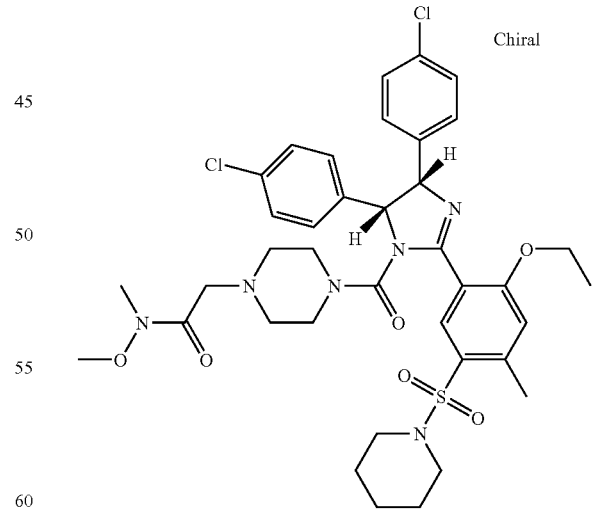

The title compound was prepared from meso-1,2-bis-(4-chlorophenyl)ethane-1,2-diamine, ethyl 2-ethoxy-4-methyl-5-(piperidine-1-sulfonyl)-benzoate (example 2) and N-methoxy-N-methyl-2-piperazin-1-yl-acetamide (example 22b) following successively the procedures described for examples 25, 29 and 31. LC-MS: 785.2 [(M+H)$^+$].

EXAMPLE 304

2-(4-{(4S,5R)-4,5-Bis-(4-chloro-phenyl)-2-[2-ethoxy-4-methyl-5-(piperidine-1-sulfonyl)-phenyl]-4,5-dihydro-imidazole-1-carbonyl}-piperazin-1-yl)-N-isopropyl-N-methyl-acetamide

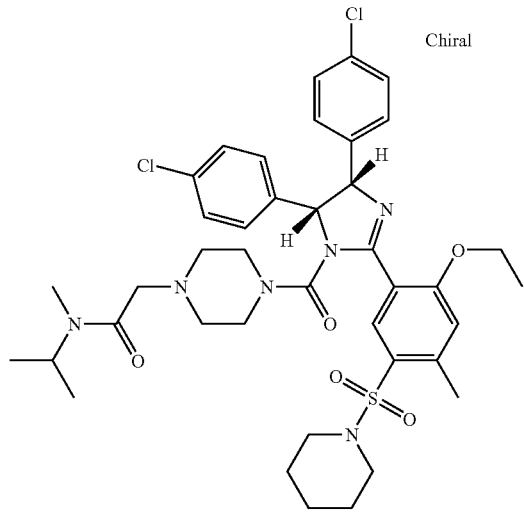

The title compound was prepared from meso-1,2-bis-(4-chlorophenyl)ethane-1,2-diamine, ethyl 2-ethoxy-4-methyl-5-(piperidine-1-sulfonyl)-benzoate (example 2) and N-isopropyl-N-methyl-2-piperazin-1-yl-acetamide (example 22c) following successively the procedures described for examples 25, 29 and 31. LC-MS: 797.3 [(M+H)$^+$].

EXAMPLE 305

2-(4-{(4S,5R)-4,5-Bis-(4-chloro-phenyl)-2-[2-ethoxy-4-methyl-5-(piperidine-1-sulfonyl)-phenyl]-4,5-dihydro-imidazole-1-carbonyl}-piperazin-1-yl)-N-(2-cyano-ethyl)-N-methyl-acetamide

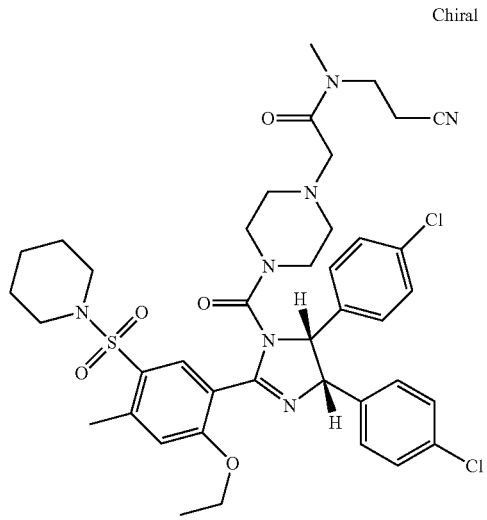

The title compound was prepared from meso-1,2-bis-(4-chlorophenyl)ethane-1,2-diamine, ethyl 2-ethoxy-4-methyl-5-(piperidine-1-sulfonyl)-benzoate (example 2) and N-(2-cyano-ethyl)-N-methyl-2-piperazin-1-yl-acetamide (example 22d) following successively the procedures described for examples 25, 29 and 31. LC-MS: 808.3 [(M+H)$^+$].

EXAMPLE 306

2-(4-{(4S,5R)-4,5-Bis-(4-chloro-phenyl)-2-[2-ethoxy-4-methyl-5-(piperidine-1-sulfonyl)-phenyl]-4,5-dihydro-imidazole-1-carbonyl}-piperazin-1-yl)-N-(2-methoxy-1-methyl-ethyl)-acetamide

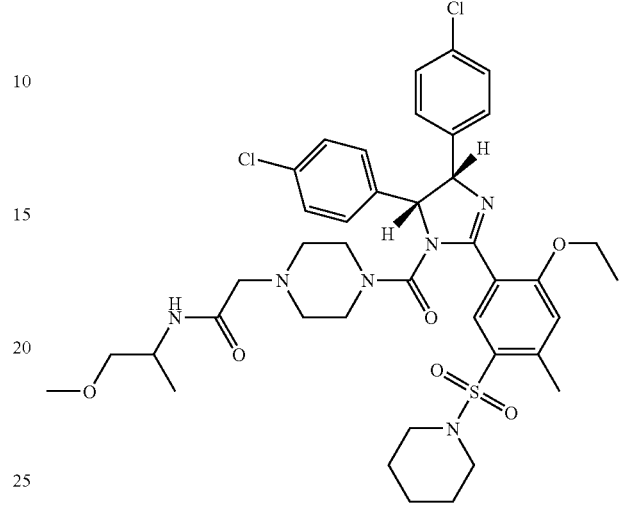

The title compound was prepared from meso-1,2-bis-(4-chlorophenyl)ethane-1,2-diamine, ethyl 2-ethoxy-4-methyl-5-(piperidine-1-sulfonyl)-benzoate (example 2) and N-(2-methoxy-1-methyl-ethyl)-2-piperazin-1-yl-acetamide (example 21) following successively the procedures described for examples 25, 29 and 31. LC-MS: 813.3 [(M+H)$^+$].

EXAMPLE 307

{(4S,5R)-4,5-Bis-(4-chloro-phenyl)-2-[2-ethoxy-4-methyl-5-(piperidine-1-sulfonyl)-phenyl]-4,5-dihydro-imidazol-1-yl}-[4-(3,5-dimethyl-isoxazole-4-carbonyl)-piperazin-1-yl]-methanone

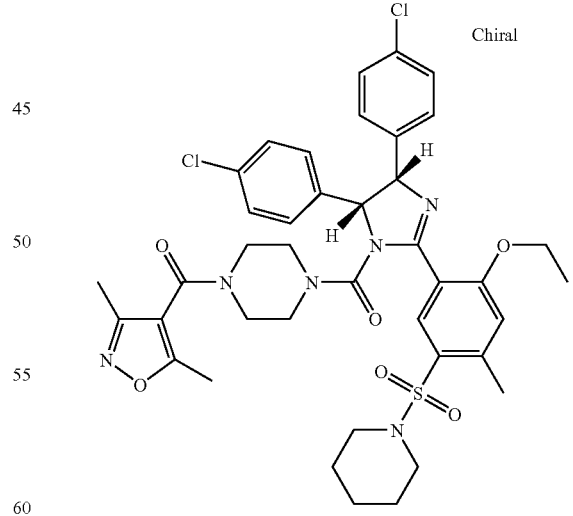

The title compound was prepared from meso-1,2-bis-(4-chlorophenyl)ethane-1,2-diamine, ethyl 2-ethoxy-4-methyl-5-(piperidine-1-sulfonyl)-benzoate (example 2) and (3,5-dimethyl-isoxazol-4-yl)-piperazin-1-yl-methanone (example 19) following successively the procedures described for examples 25, 29 and 31. LC-MS: 807.3 [(M+H)$^+$].

EXAMPLE 308

{(4S,5R)-4,5-Bis-(4-chloro-phenyl)-2-[2-ethoxy-4-methyl-5-(piperidine-1-sulfonyl)-phenyl]-4,5-dihydro-imidazol-1-yl}-(4-ethanesulfonyl-piperazin-1-yl)-methanone

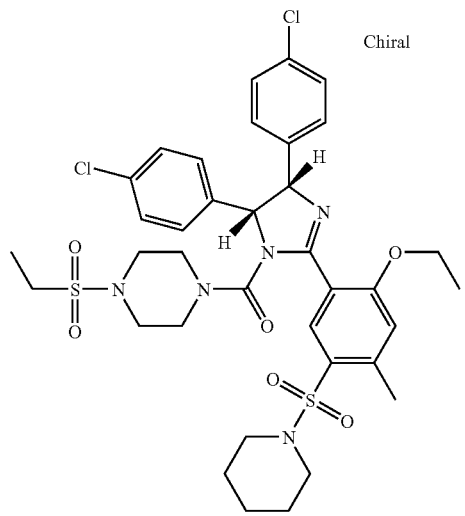

The title compound was prepared from meso-1,2-bis-(4-chlorophenyl)ethane-1,2-diamine, ethyl 2-ethoxy-4-methyl-5-(piperidine-1-sulfonyl)-benzoate (example 2) and 1-ethanesulfonyl-piperazine (example 20) following successively the procedures described for examples 25, 29 and 31. LC-MS: 776.3 [(M+H)$^+$].

EXAMPLE 309

N-[2-(4-{(4S,5R)-4,5-Bis-(4-chloro-phenyl)-2-[2-ethoxy-4-methyl-5-(piperidine-1-sulfonyl)-phenyl]-4,5-dihydro-imidazole-1-carbonyl}-piperazin-1-yl)-ethyl]-methanesulfonamide

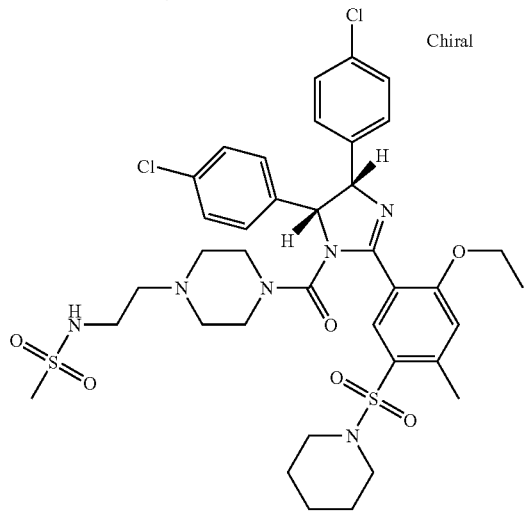

The title compound was prepared from meso-1,2-bis-(4-chlorophenyl)ethane-1,2-diamine, ethyl 2-ethoxy-4-methyl-5-(piperidine-1-sulfonyl)-benzoate (example 2) and N-(2-methanosulfonylethyl)-piperazine hydrochloride (example 24) following successively the procedures described for examples 25, 29 and 31. LC-MS: 805.3 [(M+H)$^+$].

EXAMPLE 310

{(4S,5R)-4,5-Bis-(4-chloro-phenyl)-2-[2-ethoxy-4-methyl-5-(piperidine-1-sulfonyl)-phenyl]-4,5-dihydro-imidazol-1-yl}-[4-(3-methanesulfonyl-propyl)-piperazin-1-yl]-methanone

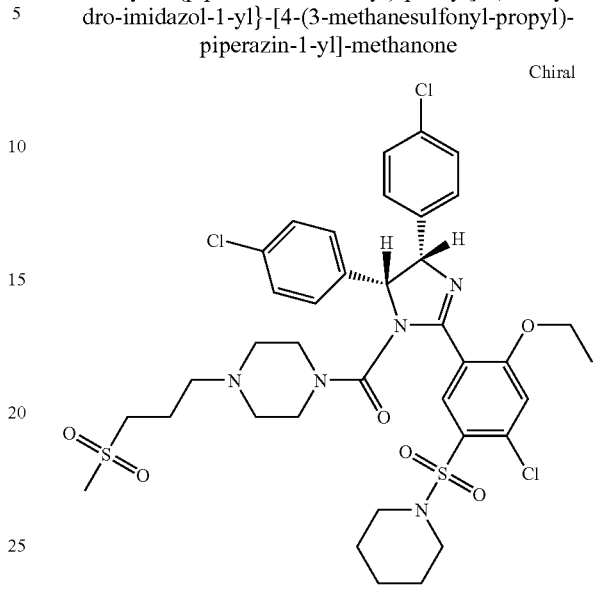

The title compound was prepared from meso-1,2-bis-(4-chlorophenyl)ethane-1,2-diamine, ethyl 2-ethoxy-4-methyl-5-(piperidine-1-sulfonyl)-benzoate (example 2) and 1-(3-methanesulfonyl-propyl)-piperazine (example 22e) following successively the procedures described for examples 25, 29 and 31. LC-MS: 804.3 [(M+H)$^+$].

EXAMPLE 311

N-tert-Butyl-2-{4-[(4S,5R)-2-(5-tert-butylsulfamoyl-2-ethoxy-4-methyl-phenyl)-4,5-bis-(4-chloro-phenyl)-4,5-dihydro-imidazole-1-carbonyl]-piperazin-1-yl}-acetamide

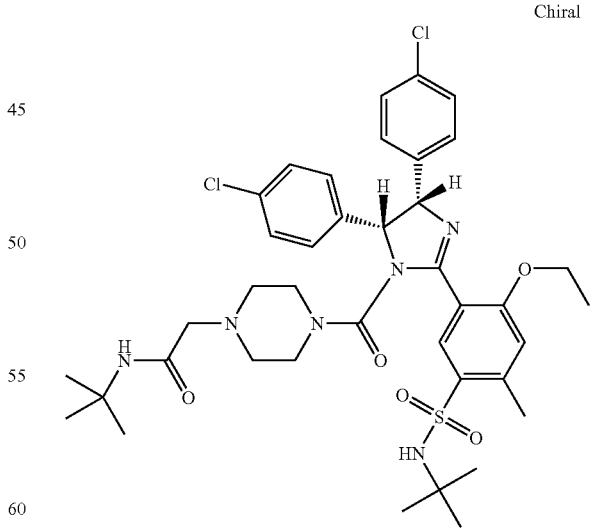

The title compound was prepared from meso-1,2-bis-(4-chlorophenyl)ethane-1,2-diamine, ethyl 5-tert-butylsulfamoyl-2-ethoxy-4-methyl-benzoate (example 2) and N-tert-butyl-2-piperazin-1-yl-acetamide (example 22g) following successively the procedures described for examples 25, 29 and 31. LC-MS: 785.4 [(M+H)$^+$]

EXAMPLE 312

2-{4-[(4S,5R)-2-(5-tert-Butylsulfamoyl-2-ethoxy-4-methyl-phenyl)-4,5-bis-(4-chloro-phenyl)-4,5-dihydro-imidazole-1-carbonyl]-piperazin-1-yl}-acetamide

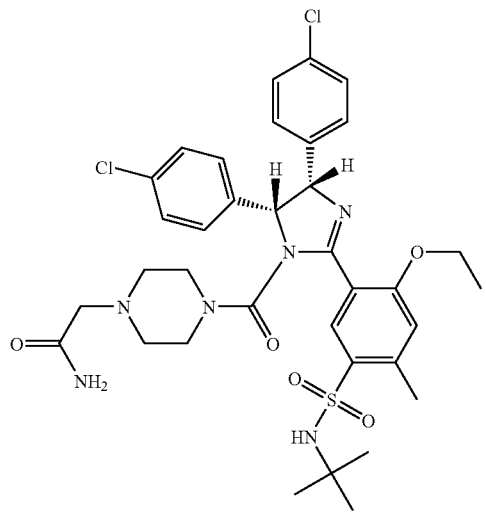

The title compound was prepared from meso-1,2-bis-(4-chlorophenyl)ethane-1,2-diamine, ethyl 5-tert-butylsulfamoyl-2-ethoxy-4-methyl-benzoate (example 2) and 2-piperazin-1-yl-acetamide (Matrix) following successively the procedures described for examples 25, 29 and 31. LC-MS: 729.3 [(M+H)$^+$].

EXAMPLE 313

2-{4-[(4S,5R)-2-(5-tert-Butylsulfamoyl-2-ethoxy-4-methyl-phenyl)-4,5-bis-(4-chloro-phenyl)-4,5-dihydro-imidazole-1-carbonyl]-piperazin-1-yl}-N,N-bis-(2-methoxy-ethyl)-acetamide

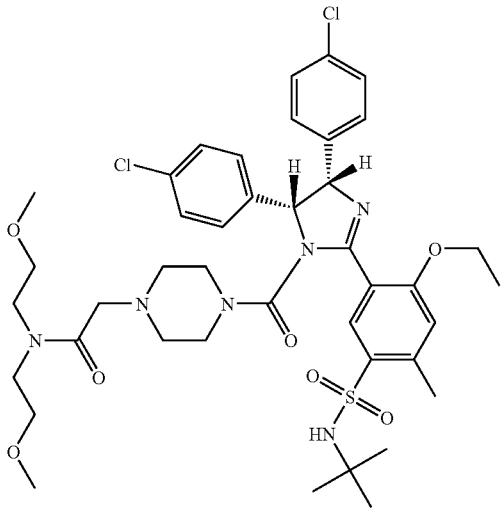

The title compound was prepared from meso-1,2-bis-(4-chlorophenyl)ethane-1,2-diamine, ethyl 5-tert-butylsulfamoyl-2-ethoxy-4-methyl-benzoate (example 2) and N,N-bis-(2-methoxy-ethyl)-2-piperazin-1-yl-acetamide (example 22a) following successively the procedures described for examples 25, 29 and 31. LC-MS: 845.4 [(M+H)$^+$].

EXAMPLE 314

2-{4-[(4S,5R)-2-(5-tert-Butylsulfamoyl-2-ethoxy-4-methyl-phenyl)-4,5-bis-(4-chloro-phenyl)-4,5-dihydro-imidazole-1-carbonyl]-piperazin-1-yl}-N-methoxy-N-methyl-acetamide

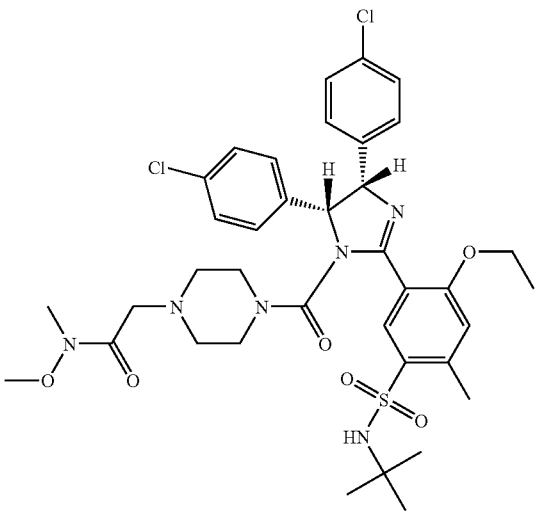

The title compound was prepared from meso-1,2-bis-(4-chlorophenyl)ethane-1,2-diamine, ethyl 5-tert-butylsulfamoyl-2-ethoxy-4-methyl-benzoate (example 2) and N-methoxy-N-methyl-2-piperazin-1-yl-acetamide (example 22b) following successively the procedures described for examples 25, 29 and 31. LC-MS: 773.3 [(M+H)$^+$].

EXAMPLE 315

2-{4-[(4S,5R)-2-(5-tert-Butylsulfamoyl-2-ethoxy-4-methyl-phenyl)-4,5-bis-(4-chloro-phenyl)-4,5-dihydro-imidazole-1-carbonyl]-piperazin-1-yl}-N-isopropyl-N-methyl-acetamide

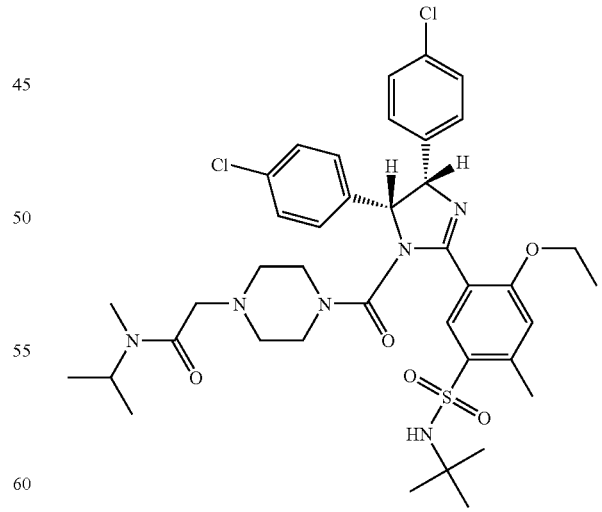

he title compound was prepared from meso-1,2-bis-(4-chlorophenyl)ethane-1,2-diamine, ethyl 5-tert-butylsulfamoyl-2-ethoxy-4-methyl-benzoate (example 2) and N-isopropyl-N-methyl-2-piperazin-1-yl-acetamide (example 22c) following successively the procedures described for examples 25, 29 and 31. LC-MS: 785.4 [(M+H)$^+$].

EXAMPLE 316

2-{4-[(4S,5R)-2-(5-tert-Butylsulfamoyl-2-ethoxy-4-methyl-phenyl)-4,5-bis-(4-chloro-phenyl)-4,5-dihydro-imidazole-1-carbonyl]-piperazin-1-yl}-N-(2-cyano-ethyl)-N-methyl-acetamide

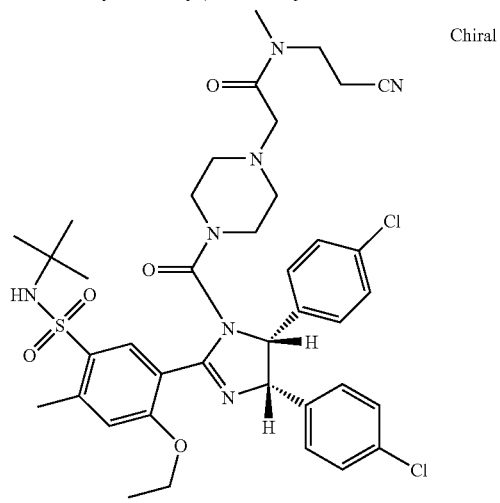

The title compound was prepared from meso-1,2-bis-(4-chlorophenyl)ethane-1,2-diamine, ethyl 5-tert-butylsulfamoyl-2-ethoxy-4-methyl-benzoate (example 2) and N-(2-cyano-ethyl)-N-methyl-2-piperazin-1-yl-acetamide (example 22d) following successively the procedures described for examples 25, 29 and 31. LC-MS: 796.3 [(M+H)$^+$].

EXAMPLE 317

2-{4-[(4S,5R)-2-(5-tert-Butylsulfamoyl-2-ethoxy-4-methyl-phenyl)-4,5-bis-(4-chloro-phenyl)-4,5-dihydro-imidazole-1-carbonyl]-piperazin-1-yl}-N-(2-methoxy-1-methyl-ethyl)-acetamide

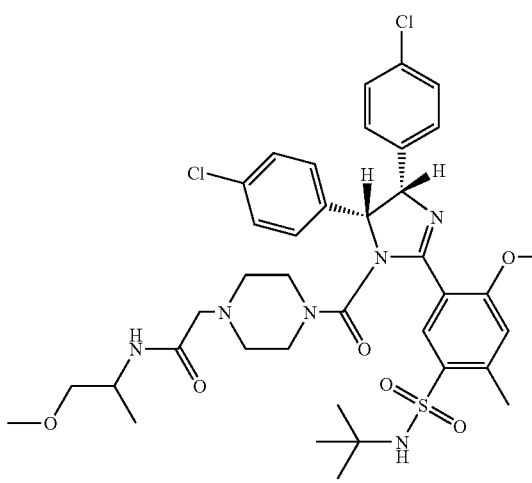

The title compound was prepared from meso-1,2-bis-(4-chlorophenyl)ethane-1,2-diamine, ethyl 5-tert-butylsulfamoyl-2-ethoxy-4-methyl-benzoate (example 2) and N-(2-methoxy-1-methyl-ethyl)-2-piperazin-1-yl-acetamide (example 21) following successively the procedures described for examples 25, 29 and 31. LC-MS: 801.4 [(M+H)$^+$].

EXAMPLE 318

5-{(4S,5R)-4,5-Bis-(4-chloro-phenyl)-1-[4-(3,5-dimethyl-isoxazole-4-carbonyl)-piperazine-1-carbonyl]-4,5-dihydro-1H-imidazol-2-yl}-N-tert-butyl-4-ethoxy-2-methyl-benzenesulfonamide

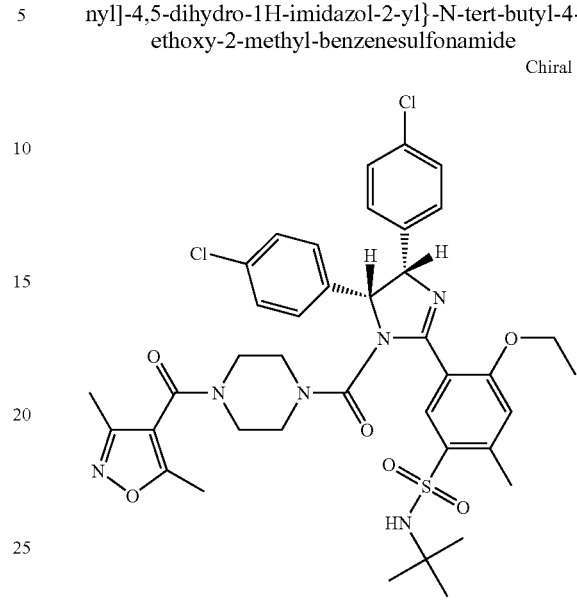

The title compound was prepared from meso-1,2-bis-(4-chlorophenyl)ethane-1,2-diamine, ethyl 5-tert-butylsulfamoyl-2-ethoxy-4-methyl-benzoate (example 2) and (3,5-dimethyl-isoxazol-4-yl)-piperazin-1-yl-methanone (example 19) following successively the procedures described for examples 25, 29 and 31. LC-MS: 795.3 [(M+H)$^+$].

EXAMPLE 319

5-[(4S,5R)-4,5-Bis-(4-chloro-phenyl)-1-(4-ethanesulfonyl-piperazine-1-carbonyl)-4,5-dihydro-1H-imidazol-2-yl]-N-tert-butyl-4-ethoxy-2-methyl-benzenesulfonamide

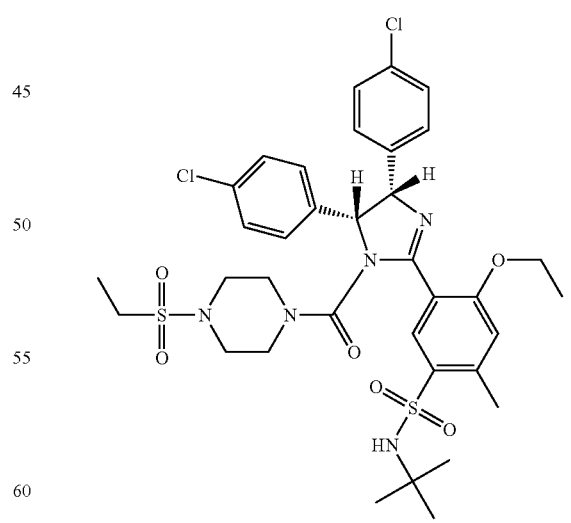

The title compound was prepared from meso-1,2-bis-(4-chlorophenyl)ethane-1,2-diamine, ethyl 5-tert-butylsulfamoyl-2-ethoxy-4-methyl-benzoate (example 2) and 1-ethanesulfonyl-piperazine (example 20) following successively the procedures described for examples 25, 29 and 31. LC-MS: 764.3 [(M+H)$^+$].

EXAMPLE 320

5-{(4S,5R)-4,5-Bis-(4-chloro-phenyl)-1-[4-(2-methanesulfonylamino-ethyl)-piperazine-1-carbonyl]-4,5-dihydro-1H-imidazol-2-yl}-N-tert-butyl-4-ethoxy-2-methyl-benzenesulfonamide

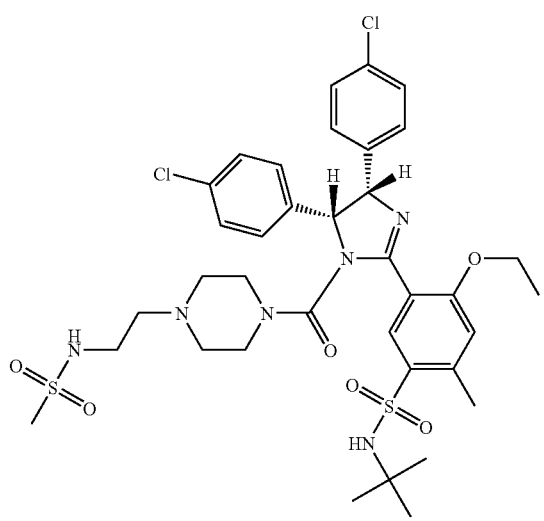

The title compound was prepared from meso-1,2-bis-(4-chlorophenyl)ethane-1,2-diamine, ethyl 5-tert-butylsulfamoyl-2-ethoxy-4-methyl-benzoate (example 2) and N-(2-methanosulfonylethyl)-piperazine hydrochloride (example 24) following successively the procedures described for examples 25, 29 and 31. LC-MS: 793.4 [(M+H)$^+$].

EXAMPLE 321

5-{(4S,5R)-4,5-Bis-(4-chloro-phenyl)-1-[4-(3-methanesulfonyl-propyl)-piperazine-1-carbonyl]-4,5-dihydro-1H-imidazol-2-yl}-N-tert-butyl-4-ethoxy-2-methyl-benzenesulfonamide

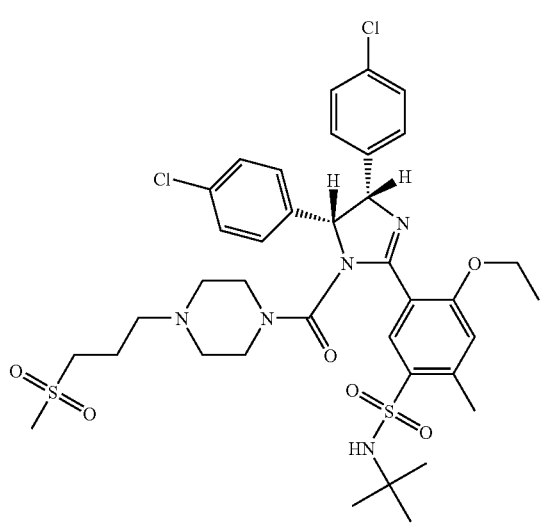

The title compound was prepared from meso-1,2-bis-(4-chlorophenyl)ethane-1,2-diamine, ethyl 5-tert-butylsulfamoyl-2-ethoxy-4-methyl-benzoate (example 2) and 1-(3-methanesulfonyl-propyl)-piperazine (example 22e) following successively the procedures described for examples 25, 29 and 31. LC-MS: 792.4 [(M+H)$^+$].

EXAMPLE 322

5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-N-tert-butyl-4-ethoxy-2-methyl-benzenesulfonamide

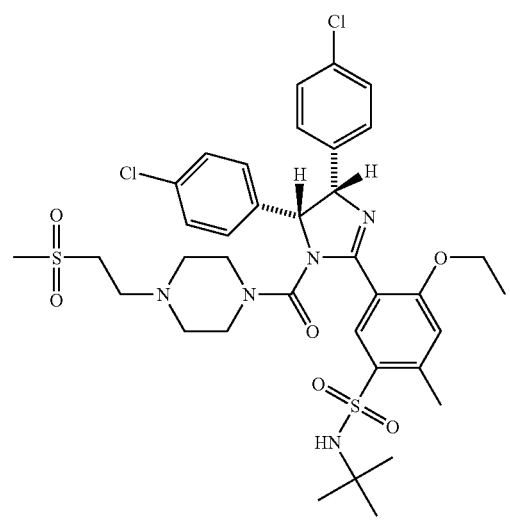

The title compound was prepared from meso-1,2-bis-(4-chlorophenyl)ethane-1,2-diamine, ethyl 5-tert-butylsulfamoyl-2-ethoxy-4-methyl-benzoate (example 2) and 1-(2-methanesulfonylethyl)piperazine bishydrochloride (example 23) following successively the procedures described for examples 25, 29 and 31. LC-MS: 778.3 [(M+H)$^+$].

EXAMPLE 323

5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-N-tert-butyl-4-ethoxy-2-methyl-benzenesulfonamide

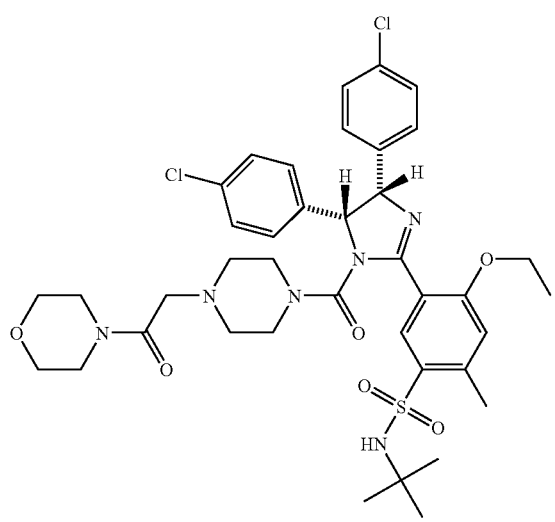

The title compound was prepared from meso-1,2-bis-(4-chlorophenyl)ethane-1,2-diamine, ethyl 5-tert-butylsulfamoyl-2-ethoxy-4-methyl-benzoate (example 2) and 1-morpholin-4-yl-2-piperazin-1-yl-ethanone (Oakwood Products) following successively the procedures described for examples 25, 29 and 31. LC-MS: 799.3 [(M+H)+].

EXAMPLE 324

2-(4-{(4S,5R)-4,5-Bis-(4-chloro-phenyl)-2-[2-ethoxy-5-(methoxy-methyl-sulfamoyl)-4-methyl-phenyl]-4,5-dihydro-imidazole-1-carbonyl}-piperazin-1-yl)-N-tert-butyl-acetamide

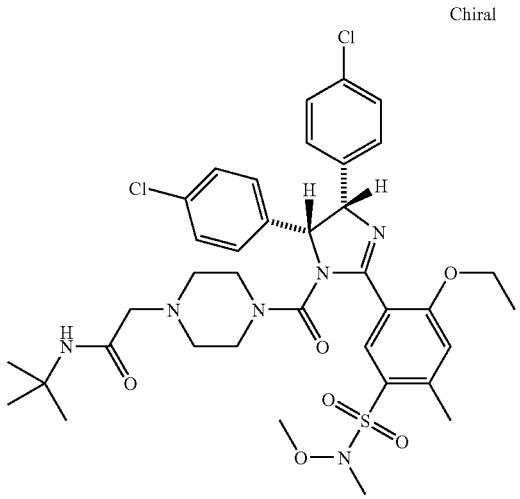

The title compound was prepared from meso-1,2-bis-(4-chlorophenyl)ethane-1,2-diamine, ethyl 2-ethoxy-5-(methoxy-methyl-sulfamoyl)-4-methyl-benzoate (example 2) and N-tert-butyl-2-piperazin-1-yl-acetamide (example 22g) following successively the procedures described for examples 25, 29 and 31. LC-MS: 773.3 [(M+H)+].

EXAMPLE 325

2-(4-{(4S,5R)-4,5-Bis-(4-chloro-phenyl)-2-[2-ethoxy-5-(methoxy-methyl-sulfamoyl)-4-methyl-phenyl]-4,5-dihydro-imidazole-1-carbonyl}-piperazin-1-yl)-acetamide

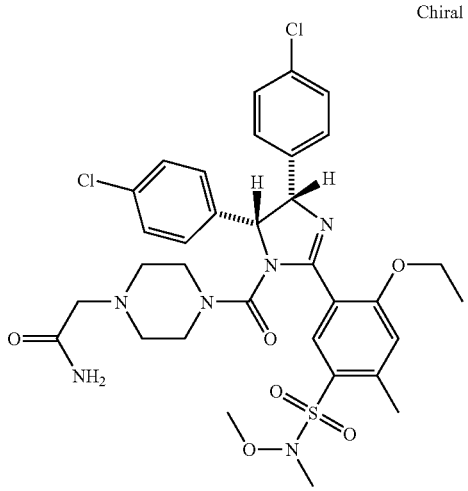

The title compound was prepared from meso-1,2-bis-(4-chlorophenyl)ethane-1,2-diamine, ethyl 2-ethoxy-5-(methoxy-methyl-sulfamoyl)-4-methyl-benzoate (example 2) and 2-piperazin-1-yl-acetamide (Matrix) following successively the procedures described for examples 25, 29 and 31. LC-MS: 717.2 [(M+H)+].

EXAMPLE 326

2-(4-{(4S,5R)-4,5-Bis-(4-chloro-phenyl)-2-[2-ethoxy-5-(methoxy-methyl-sulfamoyl)-4-methyl-phenyl]-4,5-dihydro-imidazole-1-carbonyl}-piperazin-1-yl)-N,N-bis-(2-methoxy-ethyl)-acetamide

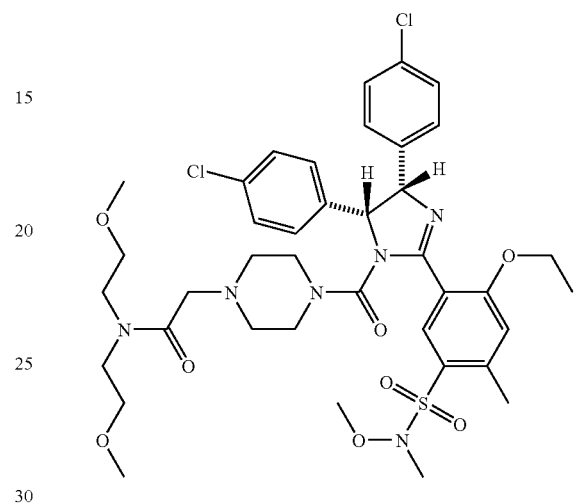

The title compound was prepared from meso-1,2-bis-(4-chlorophenyl)ethane-1,2-diamine, ethyl 2-ethoxy-5-(methoxy-methyl-sulfamoyl)-4-methyl-benzoate (example 2) and N,N-bis-(2-methoxy-ethyl)-2-piperazin-1-yl-acetamide (example 22a) following successively the procedures described for examples 25, 29 and 31. LC-MS: 833.4 [(M+H)+].

EXAMPLE 327

2-(4-{(4S,5R)-4,5-Bis-(4-chloro-phenyl)-2-[2-ethoxy-5-(methoxy-methyl-sulfamoyl)-4-methyl-phenyl]-4,5-dihydro-imidazole-1-carbonyl}-piperazin-1-yl)-N-methoxy-N-methyl-acetamide

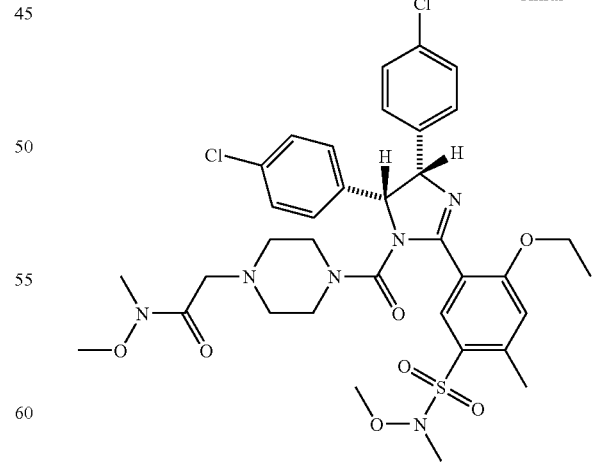

The title compound was prepared from meso-1,2-bis-(4-chlorophenyl)ethane-1,2-diamine, ethyl 2-ethoxy-5-(methoxy-methyl-sulfamoyl)-4-methyl-benzoate (example 2) and N-methoxy-N-methyl-2-piperazin-1-yl-acetamide (example 22b) following successively the procedures described for examples 25, 29 and 31. LC-MS: 761.3 [(M+H)+].

EXAMPLE 328

2-(4-{(4S,5R)-4,5-Bis-(4-chloro-phenyl)-2-[2-ethoxy-5-(methoxy-methyl-sulfamoyl)-4-methyl-phenyl]-4,5-dihydro-imidazole-1-carbonyl}-piperazin-1-yl)-N-isopropyl-N-methyl-acetamide

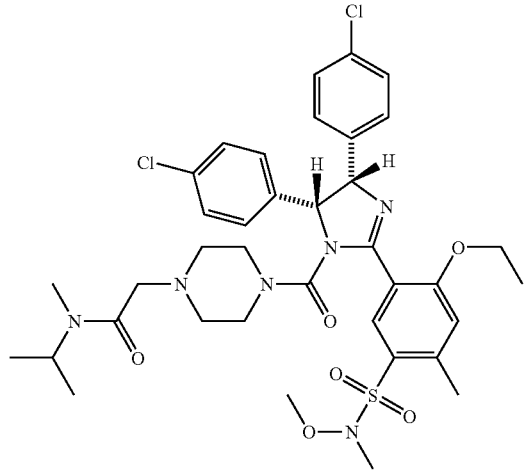

The title compound was prepared from meso-1,2-bis-(4-chlorophenyl)ethane-1,2-diamine, ethyl 2-ethoxy-5-(methoxy-methyl-sulfamoyl)-4-methyl-benzoate (example 2) and N-isopropyl-N-methyl-2-piperazin-1-yl-acetamide (example 22c) following successively the procedures described for examples 25, 29 and 31. LC-MS: 773.3 [(M+H)+].

EXAMPLE 329

2-(4-{(4S,5R)-4,5-Bis-(4-chloro-phenyl)-2-[2-ethoxy-5-(methoxy-methyl-sulfamoyl)-4-methyl-phenyl]-4,5-dihydro-imidazole-1-carbonyl}-piperazin-1-yl)-N-(2-methoxy-1-methyl-ethyl)-acetamide

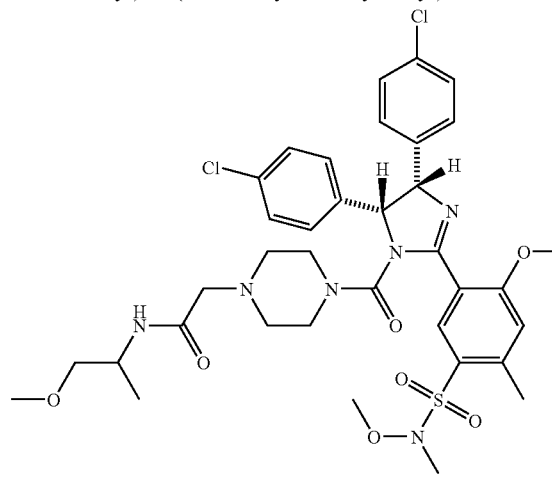

The title compound was prepared from meso-1,2-bis-(4-chlorophenyl)ethane-1,2-diamine, ethyl 2-ethoxy-5-(methoxy-methyl-sulfamoyl)-4-methyl-benzoate (example 2) and N-(2-methoxy-1-methyl-ethyl)-2-piperazin-1-yl-acetamide (example 21) following successively the procedures described for examples 25, 29 and 31. LC-MS: 789.3 [(M+H)+].

EXAMPLE 330

5-{(4S,5R)-4,5-Bis-(4-chloro-phenyl)-1-[4-(3,5-dimethyl-isoxazole-4-carbonyl)-piperazine-1-carbonyl]-4,5-dihydro-1H-imidazol-2-yl}-4-ethoxy-N-methoxy-2,N-dimethyl-benzenesulfonamide

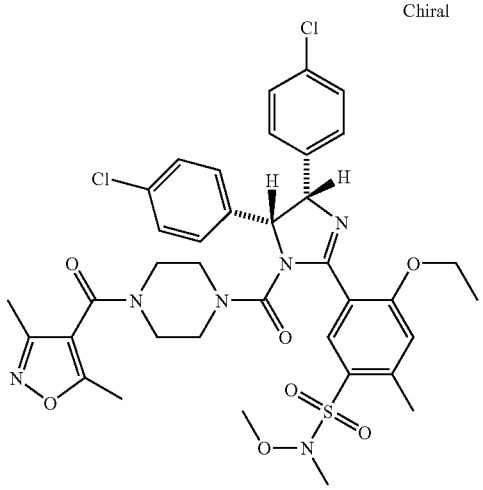

The title compound was prepared from meso-1,2-bis-(4-chlorophenyl)ethane-1,2-diamine, ethyl 2-ethoxy-5-(methoxy-methyl-sulfamoyl)-4-methyl-benzoate (example 2) and (3,5-dimethyl-isoxazol-4-yl)-piperazin-1-yl-methanone (example 19) following successively the procedures described for examples 25, 29 and 31. LC-MS: 783.3 [(M+H)+].

EXAMPLE 331

5-[(4S,5R)-4,5-Bis-(4-chloro-phenyl)-1-(4-ethane-sulfonyl-piperazine-1-carbonyl)-4,5-dihydro-1H-imidazol-2-yl]-4-ethoxy-N-methoxy-2,N-dimethyl-benzenesulfonamide

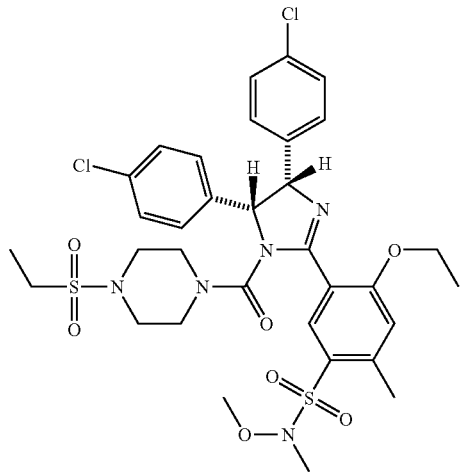

The title compound was prepared from meso-1,2-bis-(4-chlorophenyl)ethane-1,2-diamine, ethyl 2-ethoxy-5-(methoxy-methyl-sulfamoyl)-4-methyl-benzoate (example 2) and 1-ethanesulfonyl-piperazine (example 20) following successively the procedures described for examples 25, 29 and 31. LC-MS: 752.3 [(M+H)+].

EXAMPLE 332

5-{(4S,5R)-4,5-Bis-(4-chloro-phenyl)-1-[4-(3-methanesulfonyl-propyl)-piperazine-1-carbonyl]-4,5-dihydro-1H-imidazol-2-yl}-4-ethoxy-N-methoxy-2,N-dimethyl-benzenesulfonamide Chiral

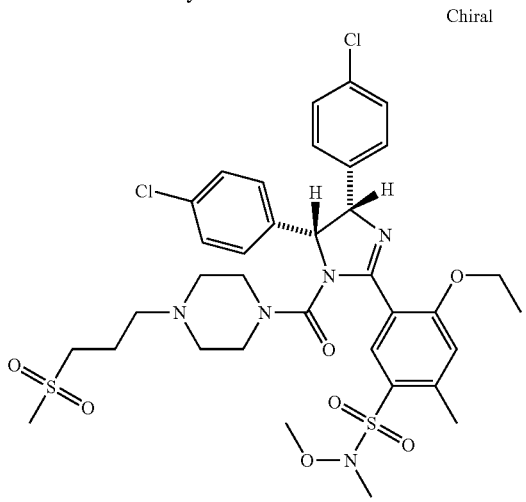

The title compound was prepared from meso-1,2-bis-(4-chlorophenyl)ethane-1,2-diamine, ethyl 2-ethoxy-5-(methoxy-methyl-sulfamoyl)-4-methyl-benzoate (example 2) and 1-(3-methanesulfonyl-propyl)-piperazine (example 22e) following successively the procedures described for examples 25, 29 and 31. LC-MS: 780.3 [(M+H)+].

EXAMPLE 333

5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-4-ethoxy-N-methoxy-2,N-dimethyl-benzenesulfonamide Chiral

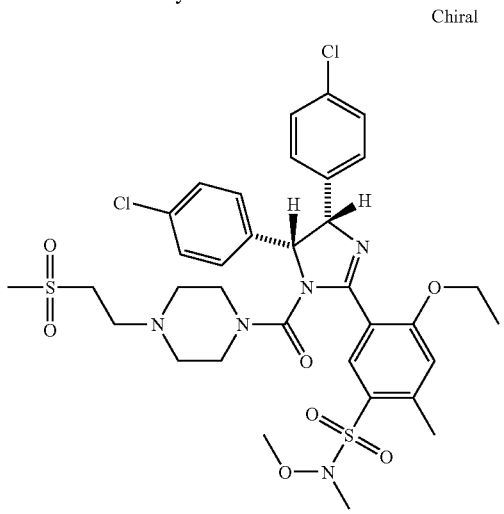

The title compound was prepared from meso-1,2-bis-(4-chlorophenyl)ethane-1,2-diamine, ethyl 2-ethoxy-5-(methoxy-methyl-sulfamoyl)-4-methyl-benzoate (example 2) and 1-(2-methanesulfonylethyl)piperazine bishydrochloride (example 23) following successively the procedures described for examples 25, 29 and 31. LC-MS: 766.3 [(M+H)+].

EXAMPLE 334

2-(4-{(4S,5R)-4,5-Bis-(4-chloro-phenyl)-2-[2-ethoxy-4-methoxy-5-(piperidine-1-sulfonyl)-phenyl]-4,5-dihydro-imidazole-1-carbonyl}-piperazin-1-yl)-N-tert-butyl-acetamide Chiral

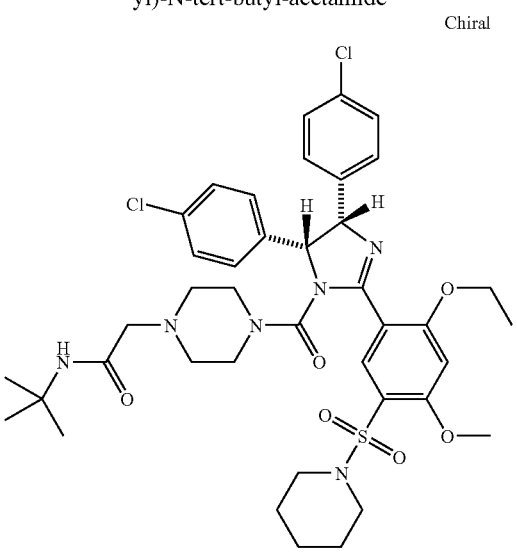

The title compound was prepared from meso-1,2-bis-(4-chlorophenyl)ethane-1,2-diamine, ethyl 2-ethoxy-4-methoxy-5-(piperidine-1-sulfonyl)-benzoate (example 2) and N-tert-butyl-2-piperazin-1-yl-acetamide (example 22g) following successively the procedures described for examples 25, 29 and 31. LC-MS: 813.3 [(M+H)+].

EXAMPLE 335

2-(4-{(4S,5R)-4,5-Bis-(4-chloro-phenyl)-2-[2-ethoxy-4-methoxy-5-(piperidine-1-sulfonyl)-phenyl]-4,5-dihydro-imidazole-1-carbonyl}-piperazin-1-yl)-acetamide Chiral

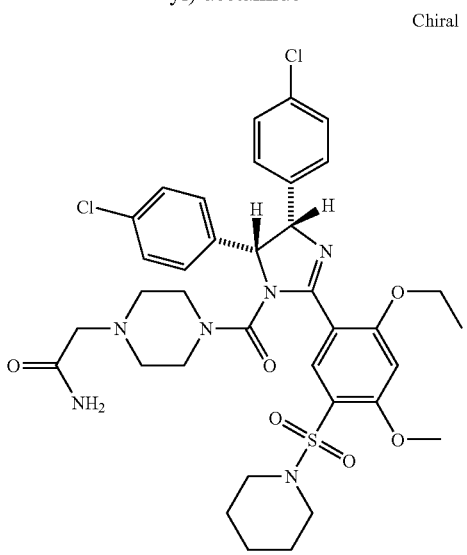

The title compound was prepared from meso-1,2-bis-(4-chlorophenyl)ethane-1,2-diamine, ethyl 2-ethoxy-4-methoxy-5-(piperidine-1-sulfonyl)-benzoate (example 2) and 2-piperazin-1-yl-acetamide (Matrix) following successively the procedures described for examples 25, 29 and 31. LC-MS: 757.1 [(M+H)+].

EXAMPLE 336

2-(4-{(4S,5R)-4,5-Bis-(4-chloro-phenyl)-2-[2-ethoxy-4-methoxy-5-(piperidine-1-sulfonyl)-phenyl]-4,5-dihydro-imidazole-1-carbonyl}-piperazin-1-yl)-N,N-bis-(2-methoxy-ethyl)-acetamide

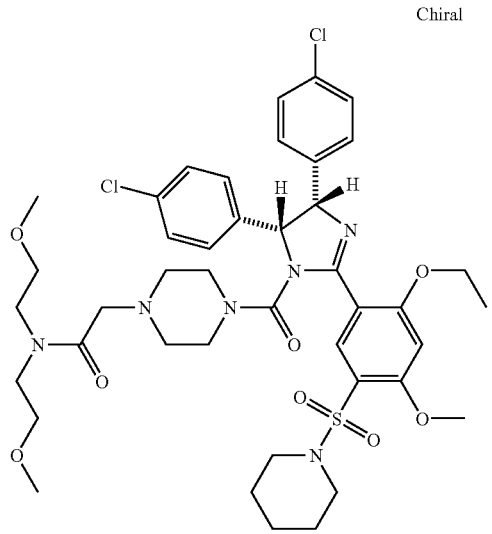

The title compound was prepared from meso-1,2-bis-(4-chlorophenyl)ethane-1,2-diamine, ethyl 2-ethoxy-4-methoxy-5-(piperidine-1-sulfonyl)-benzoate (example 2) and N,N-bis-(2-methoxy-ethyl)-2-piperazin-1-yl-acetamide (example 22a) following successively the procedures described for examples 25, 29 and 31. LC-MS: 873.3 [(M+H)+].

EXAMPLE 337

2-(4-{(4S,5R)-4,5-Bis-(4-chloro-phenyl)-2-[2-ethoxy-4-methoxy-5-(piperidine-1-sulfonyl)-phenyl]-4,5-dihydro-imidazole-1-carbonyl}-piperazin-1-yl)-N-methoxy-N-methyl-acetamide

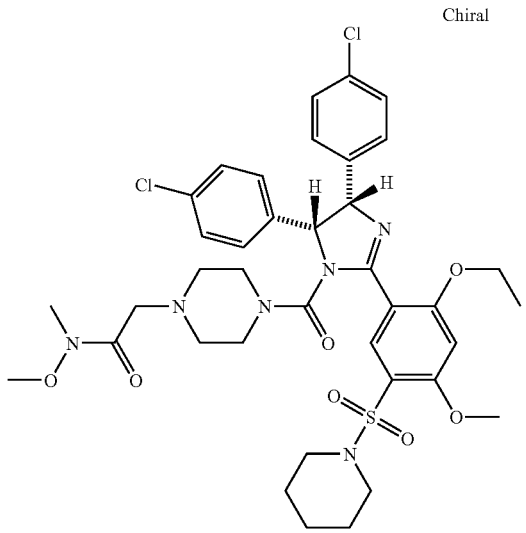

The title compound was prepared from meso-1,2-bis-(4-chlorophenyl)ethane-1,2-diamine, ethyl 2-ethoxy-4-methoxy-5-(piperidine-1-sulfonyl)-benzoate (example 2) and N-methoxy-N-methyl-2-piperazin-1-yl-acetamide (example 22b) following successively the procedures described for examples 25, 29 and 31. LC-MS: 801.2 [(M+H)+].

EXAMPLE 338

2-(4-{(4S,5R)-4,5-Bis-(4-chloro-phenyl)-2-[2-ethoxy-4-methoxy-5-(piperidine-1-sulfonyl)-phenyl]-4,5-dihydro-imidazole-1-carbonyl}-piperazin-1-yl)-N-isopropyl-N-methyl-acetamide

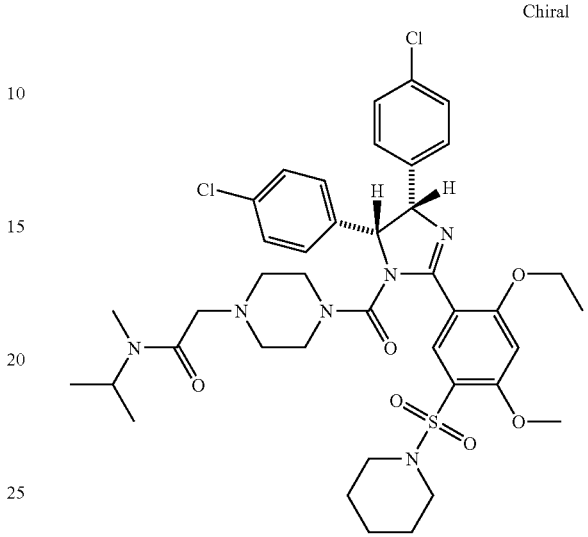

The title compound was prepared from meso-1,2-bis-(4-chlorophenyl)ethane-1,2-diamine, ethyl 2-ethoxy-4-methoxy-5-(piperidine-1-sulfonyl)-benzoate (example 2) and N-isopropyl-N-methyl-2-piperazin-1-yl-acetamide (example 22c) following successively the procedures described for examples 25, 29 and 31. LC-MS: 813.3 [(M+H)+].

EXAMPLE 339

2-(4-{(4S,5R)-4,5-Bis-(4-chloro-phenyl)-2-[2-ethoxy-4-methoxy-5-(piperidine-1-sulfonyl)-phenyl]-4,5-dihydro-imidazole-1-carbonyl}-piperazin-1-yl)-N-(2-cyano-ethyl)-N-methyl-acetamide

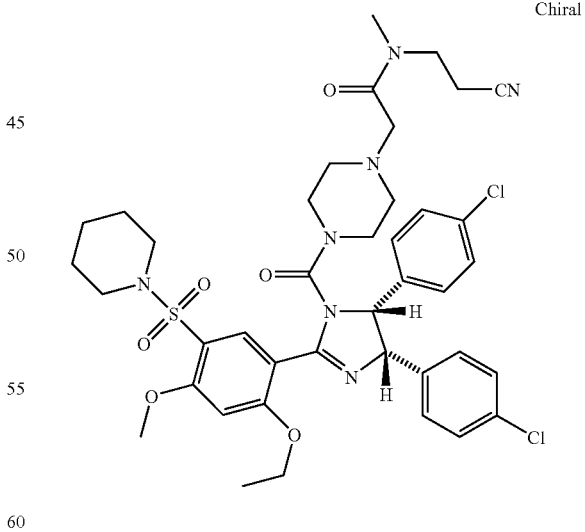

The title compound was prepared from meso-1,2-bis-(4-chlorophenyl)ethane-1,2-diamine, ethyl 2-ethoxy-4-methoxy-5-(piperidine-1-sulfonyl)-benzoate (example 2) and N-(2-cyano-ethyl)-N-methyl-2-piperazin-1-yl-acetamide (example 22d) following successively the procedures described for examples 25, 29 and 31. LC-MS: 824.2 [(M+H)+].

EXAMPLE 340

2-(4-{(4S,5R)-4,5-Bis-(4-chloro-phenyl)-2-[2-ethoxy-4-methoxy-5-(piperidine-1-sulfonyl)-phenyl]-4,5-dihydro-imidazole-1-carbonyl}-piperazin-1-yl)-N-(2-methoxy-1-methyl-ethyl)-acetamide

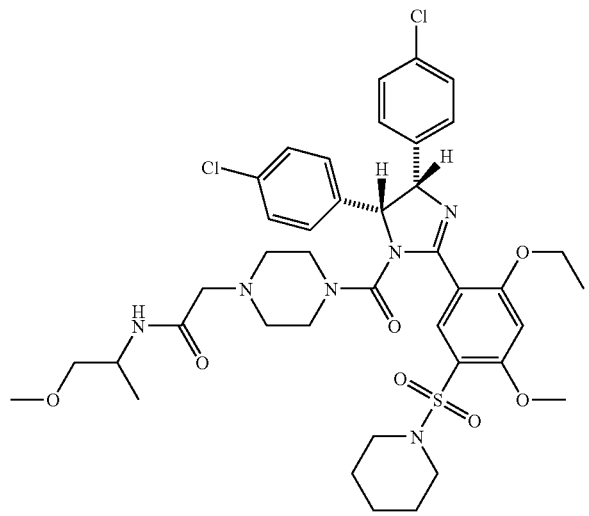

The title compound was prepared from meso-1,2-bis-(4-chlorophenyl)ethane-1,2-diamine, ethyl 2-ethoxy-4-methoxy-5-(piperidine-1-sulfonyl)-benzoate (example 2) and N-(2-methoxy-1-methyl-ethyl)-2-piperazin-1-yl-acetamide (example 21) following successively the procedures described for examples 25, 29 and 31. LC-MS: 829.3 [(M+H)$^+$].

EXAMPLE 341

{(4S,5R)-4,5-Bis-(4-chloro-phenyl)-2-[2-ethoxy-4-methoxy-5-(piperidine-1-sulfonyl)-phenyl]-4,5-dihydro-imidazol-1-yl}-[4-(3,5-dimethyl-isoxazole-4-carbonyl)-piperazin-1-yl]-methanone

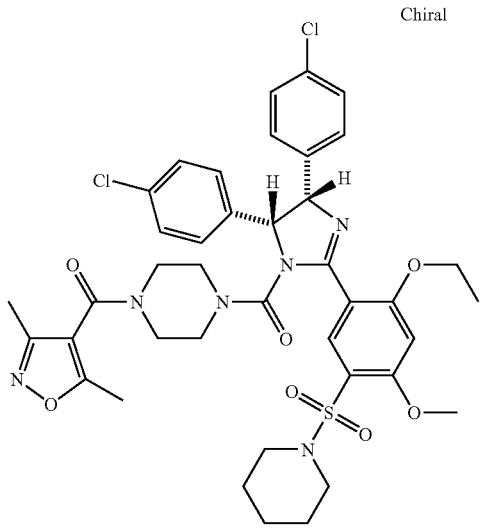

The title compound was prepared from meso-1,2-bis-(4-chlorophenyl)ethane-1,2-diamine, ethyl 2-ethoxy-4-methoxy-5-(piperidine-1-sulfonyl)-benzoate (example 2) and (3,5-dimethyl-isoxazol-4-yl)-piperazin-1-yl-methanone (example 19) following successively the procedures described for examples 25, 29 and 31. LC-MS: 823.2 [(M+H)$^+$].

EXAMPLE 342

{(4S,5R)-4,5-Bis-(4-chloro-phenyl)-2-[2-ethoxy-4-methoxy-5-(piperidine-1-sulfonyl)-phenyl]-4,5-dihydro-imidazol-1-yl}-(4-ethanesulfonyl-piperazin-1-yl)-methanone

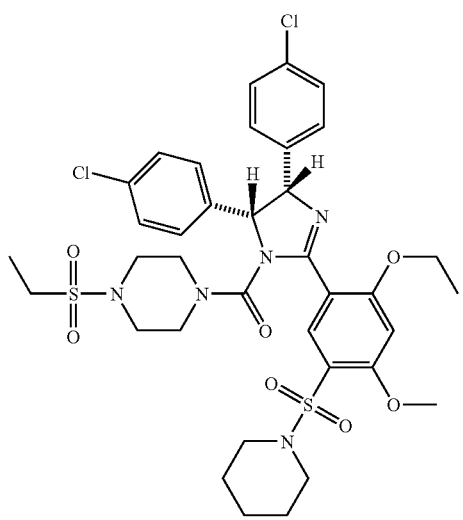

The title compound was prepared from meso-1,2-bis-(4-chlorophenyl)ethane-1,2-diamine, ethyl 2-ethoxy-4-methoxy-5-(piperidine-1-sulfonyl)-benzoate (example 2) and 1-ethanesulfonyl-piperazine (example 20) following successively the procedures described for examples 25, 29 and 31. LC-MS: 792.2 [(M+H)$^+$].

EXAMPLE 343

N-[2-(4-{(4S,5R)-4,5-Bis-(4-chloro-phenyl)-2-[2-ethoxy-4-methoxy-5-(piperidine-1-sulfonyl)-phenyl]-4,5-dihydro-imidazole-1-carbonyl}-piperazin-1-yl)-ethyl]-methanesulfonamide

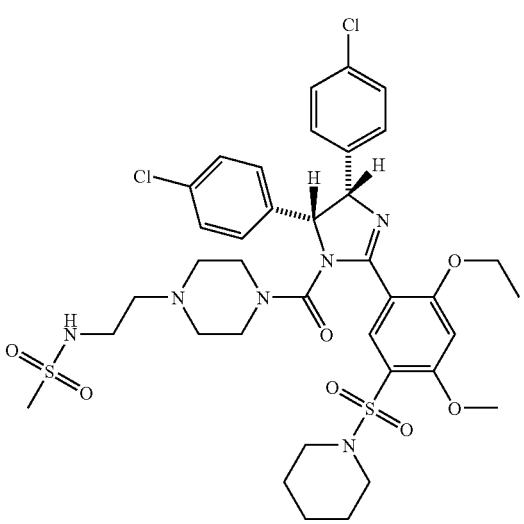

The title compound was prepared from meso-1,2-bis-(4-chlorophenyl)ethane-1,2-diamine, ethyl 2-ethoxy-4-methoxy-5-(piperidine-1-sulfonyl)-benzoate (example 2) and N-(2-methanosulfonylethyl)-piperazine hydrochloride (ex-

EXAMPLE 344

{(4S,5R)-4,5-Bis-(4-chloro-phenyl)-2-[2-ethoxy-4-methoxy-5-(piperidine-1-sulfonyl)-phenyl]-4,5-dihydro-imidazol-1-yl}-[4-(3-methanesulfonyl-propyl)-piperazin-1-yl]-methanone

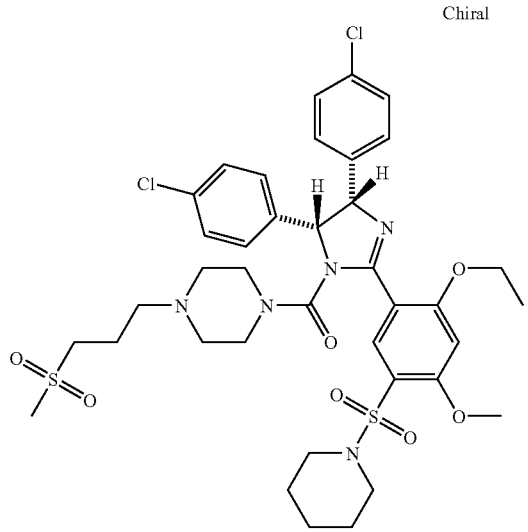

The title compound was prepared from meso-1,2-bis-(4-chlorophenyl)ethane-1,2-diamine, ethyl 2-ethoxy-4-methoxy-5-(piperidine-1-sulfonyl)-benzoate (example 2) and 1-(3-methanesulfonyl-propyl)-piperazine (example 22e) following successively the procedures described for examples 25, 29 and 31. LC-MS: 820.3 [(M+H)$^+$].

EXAMPLE 345

{(4S,5R)-4,5-Bis-(4-chloro-phenyl)-2-[2-ethoxy-4-methoxy-5-(piperidine-1-sulfonyl)-phenyl]-4,5-dihydro-imidazol-1-yl}-[4-(2-methanesulfonyl-ethyl)-piperazin-1-yl]-methanone

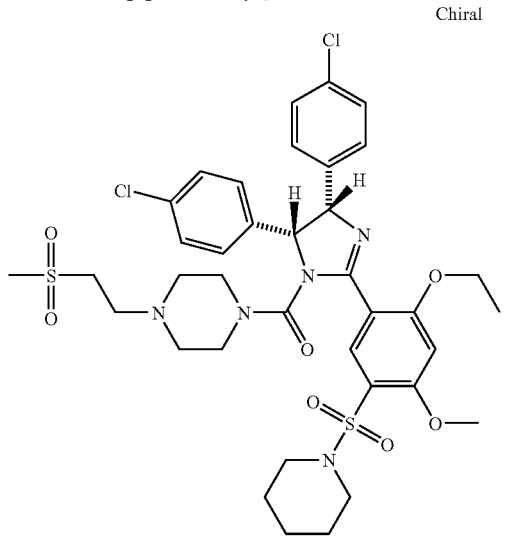

The title compound was prepared from meso-1,2-bis-(4-chlorophenyl)ethane-1,2-diamine, ethyl 2-ethoxy-4-methoxy-5-(piperidine-1-sulfonyl)-benzoate (example 2) and 1-(2-methanesulfonylethyl)piperazine bishydrochloride (example 24) following successively the procedures described for examples 25, 29 and 31. LC-MS: 821.2 [(M+H)$^+$].

EXAMPLE 346

2-(4-{(4S,5R)-4,5-Bis-(4-chloro-phenyl)-2-[2-ethoxy-4-methoxy-5-(piperidine-1-sulfonyl)-phenyl]-4,5-dihydro-imidazole-1-carbonyl}-piperazin-1-yl)-1-morpholin-4-yl-ethanone

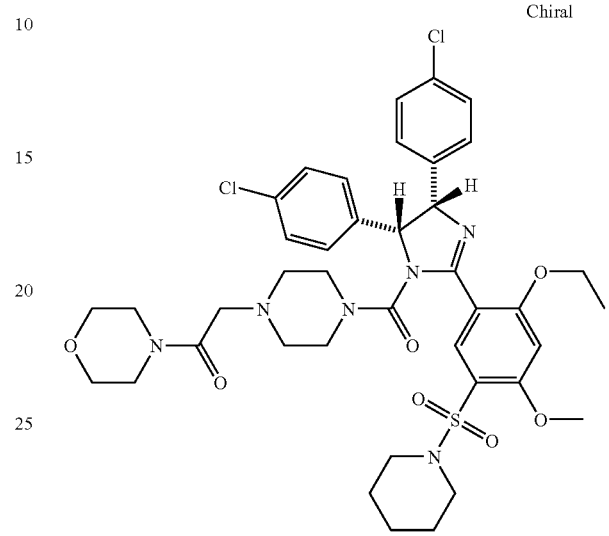

The title compound was prepared from meso-1,2-bis-(4-chlorophenyl)ethane-1,2-diamine, ethyl 2-ethoxy-4-methoxy-5-(piperidine-1-sulfonyl)-benzoate (example 2) and 1-morpholin-4-yl-2-piperazin-1-yl-ethanone (Oakwood Products) following successively the procedures described for examples 25, 29 and 31. LC-MS: 827.2 [(M+H)$^+$].

EXAMPLE 347

2-(4-{(4S,5R)-4,5-Bis-(4-chloro-phenyl)-2-[2-ethoxy-4-methoxy-5-(methoxy-methyl-sulfamoyl)-phenyl]-4,5-dihydro-imidazole-1-carbonyl}-piperazin-1-yl)-N-tert-butyl-acetamide

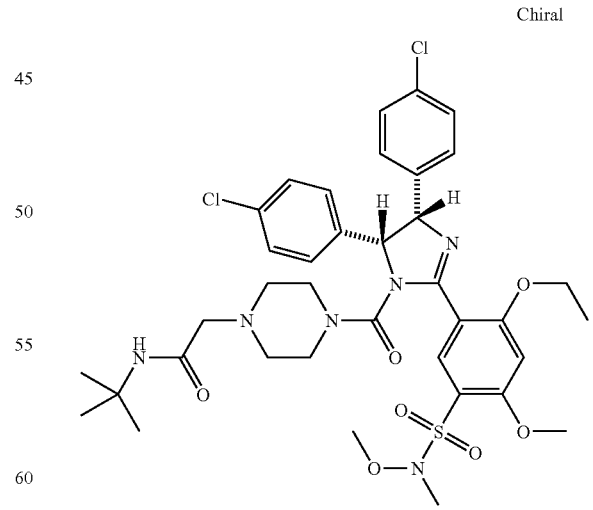

The title compound was prepared from meso-1,2-bis-(4-chlorophenyl)ethane-1,2-diamine, ethyl 2-ethoxy-4-methoxy-5-(methoxy-methyl-sulfamoyl)-benzoate (example 2) and N-tert-butyl-2-piperazin-1-yl-acetamide (example 22g) following successively the procedures described for examples 25, 29 and 31. LC-MS: 789.2 [(M+H)$^+$].

EXAMPLE 348

2-(4-{(4S,5R)-4,5-Bis-(4-chloro-phenyl)-2-[2-ethoxy-4-methoxy-5-(methoxy-methyl-sulfamoyl)-phenyl]-4,5-dihydro-imidazole-1-carbonyl}-piperazin-1-yl)-acetamide

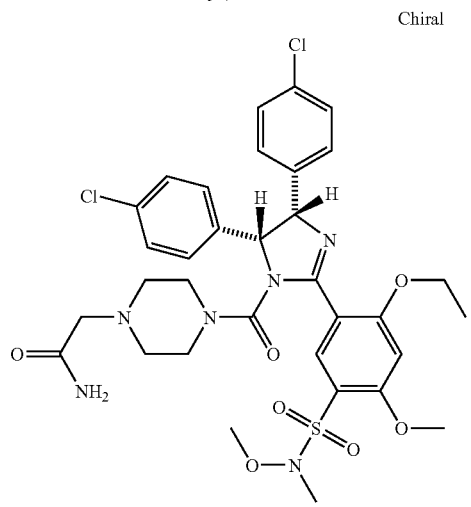

The title compound was prepared from meso-1,2-bis-(4-chlorophenyl)ethane-1,2-diamine, ethyl 2-ethoxy-4-methoxy-5-(methoxy-methyl-sulfamoyl)-benzoate (example 2) and 2-piperazin-1-yl-acetamide (Matrix) following successively the procedures described for examples 25, 29 and 31. LC-MS: 733.1 [(M+H)$^+$].

EXAMPLE 349

2-(4-{(4S,5R)-4,5-Bis-(4-chloro-phenyl)-2-[2-ethoxy-4-methoxy-5-(methoxy-methyl-sulfamoyl)-phenyl]-4,5-dihydro-imidazole-1-carbonyl}-piperazin-1-yl)-N,N-bis-(2-methoxy-ethyl)-acetamide

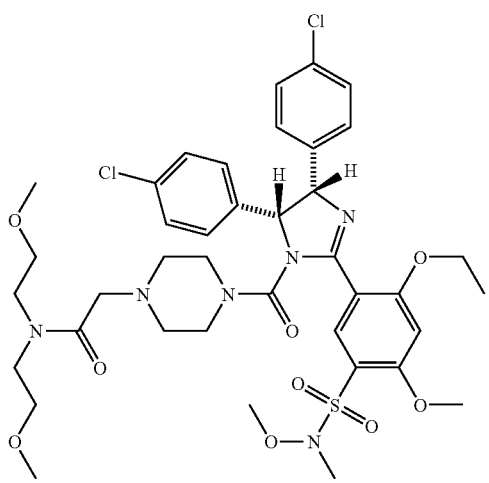

The title compound was prepared from meso-1,2-bis-(4-chlorophenyl)ethane-1,2-diamine, ethyl 2-ethoxy-4-methoxy-5-(methoxy-methyl-sulfamoyl)-benzoate (example 2) and N,N-bis-(2-methoxy-ethyl)-2-piperazin-1-yl-acetamide (example 22a) following successively the procedures described for examples 25, 29 and 31. LC-MS: 849.2 [(M+H)$^+$].

EXAMPLE 350

2-(4-{(4S,5R)-4,5-Bis-(4-chloro-phenyl)-2-[2-ethoxy-4-methoxy-5-(methoxy-methyl-sulfamoyl)-phenyl]-4,5-dihydro-imidazole-1-carbonyl}-piperazin-1-yl)-N-methoxy-N-methyl-acetamide

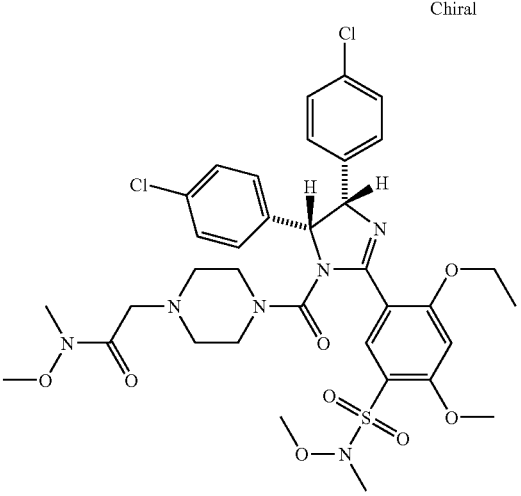

The title compound was prepared from meso-1,2-bis-(4-chlorophenyl)ethane-1,2-diamine, ethyl 2-ethoxy-4-methoxy-5-(methoxy-methyl-sulfamoyl)-benzoate (example 2) and N-methoxy-N-methyl-2-piperazin-1-yl-acetamide (example 22b) following successively the procedures described for examples 25, 29 and 31. LC-MS: 777.1 [(M+H)$^+$].

EXAMPLE 351

2-(4-{(4S,5R)-4,5-Bis-(4-chloro-phenyl)-2-[2-ethoxy-4-methoxy-5-(methoxy-methyl-sulfamoyl)-phenyl]-4,5-dihydro-imidazole-1-carbonyl}-piperazin-1-yl)-N-isopropyl-N-methyl-acetamide

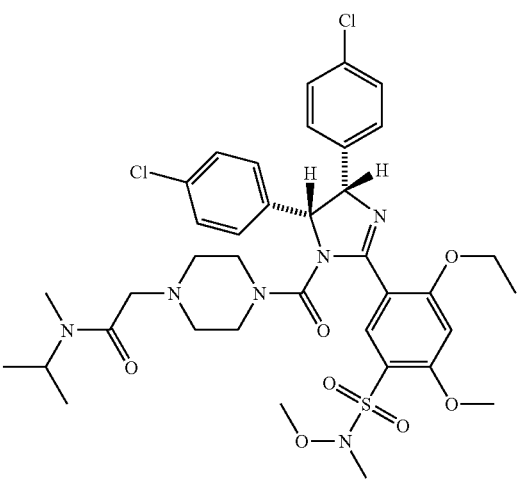

The title compound was prepared from meso-1,2-bis-(4-chlorophenyl)ethane-1,2-diamine, ethyl 2-ethoxy-4-methoxy-5-(methoxy-methyl-sulfamoyl)-benzoate (example 2) and N-isopropyl-N-methyl-2-piperazin-1-yl-acetamide (example 22c) following successively the procedures described for examples 25, 29 and 31. LC-MS: 789.2 [(M+H)$^+$].

EXAMPLE 352

2-(4-{(4S,5R)-4,5-Bis-(4-chloro-phenyl)-2-[2-ethoxy-4-methoxy-5-(methoxy-methyl-sulfamoyl)-phenyl]-4,5-dihydro-imidazole-1-carbonyl}-piperazin-1-yl)-N-(2-cyano-ethyl)-N-methyl-acetamide Chiral

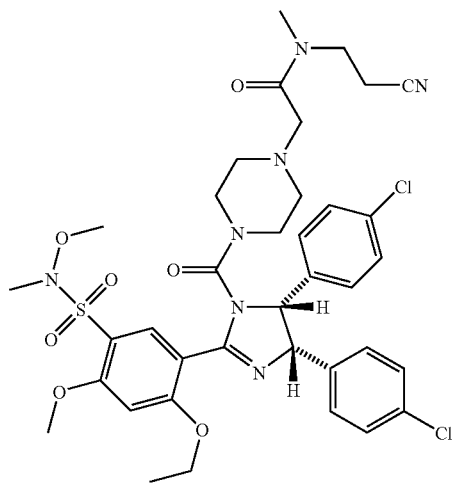

The title compound was prepared from meso-1,2-bis-(4-chlorophenyl)ethane-1,2-diamine, ethyl 2-ethoxy-4-methoxy-5-(methoxy-methyl-sulfamoyl)-benzoate (example 2) and N-(2-cyano-ethyl)-N-methyl-2-piperazin-1-yl-acetamide (example 22d) following successively the procedures described for examples 25, 29 and 31. LC-MS: 800.2 [(M+H)$^+$].

EXAMPLE 353

2-(4-{(4S,5R)-4,5-Bis-(4-chloro-phenyl)-2-[2-ethoxy-4-methoxy-5-(methoxy-methyl-sulfamoyl)-phenyl]-4,5-dihydro-imidazole-1-carbonyl}-piperazin-1-yl)-N-(2-methoxy-1-methyl-ethyl)-acetamide Chiral

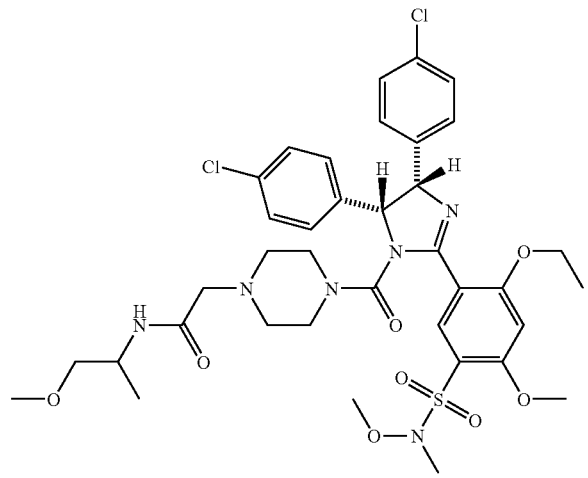

The title compound was prepared from meso-1,2-bis-(4-chlorophenyl)ethane-1,2-diamine, ethyl 2-ethoxy-4-methoxy-5-(methoxy-methyl-sulfamoyl)-benzoate (example 2) and N-(2-methoxy-1-methyl-ethyl)-2-piperazin-1-yl-acetamide (example 21) following successively the procedures described for examples 25, 29 and 31. LC-MS: 805.2 [(M+H)$^+$].

EXAMPLE 354

5-{(4S,5R)-4,5-Bis-(4-chloro-phenyl)-1-[4-(3,5-dimethyl-isoxazole-4-carbonyl)-piperazine-1-carbonyl]-4,5-dihydro-1H-imidazol-2-yl}-4-ethoxy-2,N-dimethoxy-N-methyl-benzenesulfonamide Chiral

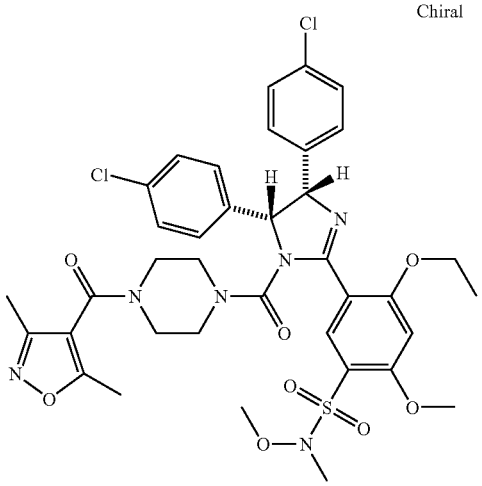

The title compound was prepared from meso-1,2-bis-(4-chlorophenyl)ethane-1,2-diamine, ethyl 2-ethoxy-4-methoxy-5-(methoxy-methyl-sulfamoyl)-benzoate (example 2) and (3,5-dimethyl-isoxazol-4-yl)-piperazin-1-yl-methanone (example 19) following successively the procedures described for examples 25, 29 and 31. LC-MS: 799.1 [(M+H)$^+$].

EXAMPLE 355

5-[(4S,5R)-4,5-Bis-(4-chloro-phenyl)-1-(4-ethane-sulfonyl-piperazine-1-carbonyl)-4,5-dihydro-1H-imidazol-2-yl]-4-ethoxy-2,N-dimethoxy-N-methyl-benzenesulfonamide Chiral

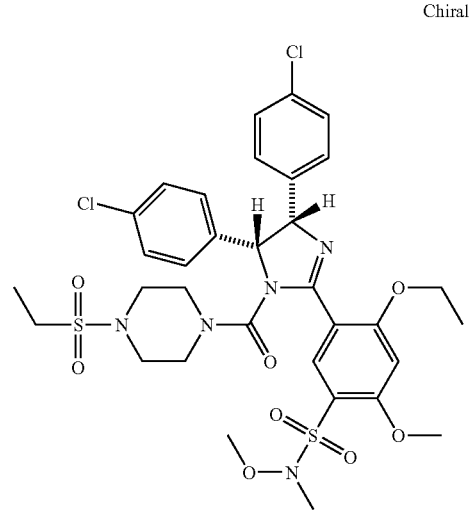

The title compound was prepared from meso-1,2-bis-(4-chlorophenyl)ethane-1,2-diamine, ethyl 2-ethoxy-4-methoxy-5-(methoxy-methyl-sulfamoyl)-benzoate (example 2) and 1-ethanesulfonyl-piperazine (example 20) following successively the procedures described for examples 25, 29 and 31. LC-MS: 768.1 [(M+H)$^+$]

EXAMPLE 356

5-{(4S,5R)-4,5-Bis-(4-chloro-phenyl)-1-[4-(2-methanesulfonylamino-ethyl)-piperazine-1-carbonyl]-4,5-dihydro-1H-imidazol-2-yl}-4-ethoxy-2,N-dimethoxy-N-methyl-benzenesulfonamide Chiral

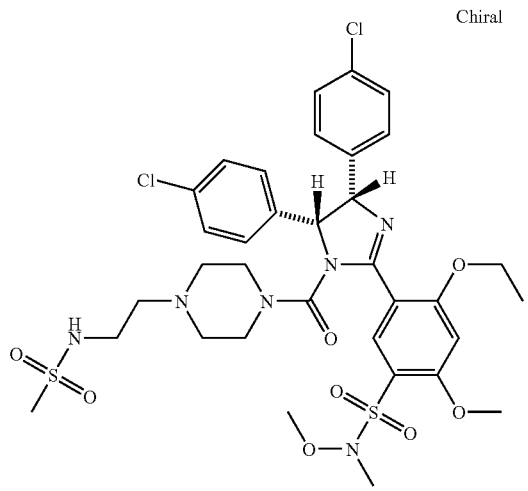

The title compound was prepared from meso-1,2-bis-(4-chlorophenyl)ethane-1,2-diamine, ethyl 2-ethoxy-4-methoxy-5-(methoxy-methyl-sulfamoyl)-benzoate (example 2) and N-(2-methanosulfonylethyl)-piperazine hydrochloride (example 24) following successively the procedures described for examples 25, 29 and 31. LC-MS: 797.2 [(M+H)$^+$].

EXAMPLE 357

5-{(4S,5R)-4,5-Bis-(4-chloro-phenyl)-1-[4-(3-methanesulfonyl-propyl)-piperazine-1-carbonyl]-4,5-dihydro-1H-imidazol-2-yl}-4-ethoxy-2,N-dimethoxy-N-methyl-benzenesulfonamide Chiral

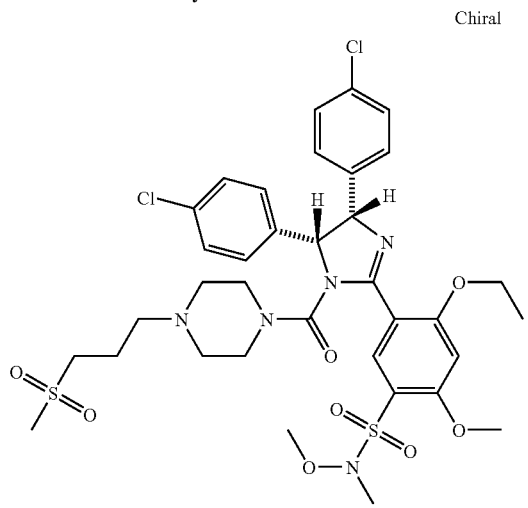

The title compound was prepared from meso-1,2-bis-(4-chlorophenyl)ethane-1,2-diamine, ethyl 2-ethoxy-4-methoxy-5-(methoxy-methyl-sulfamoyl)-benzoate (example 2) and 1-(3-methanesulfonyl-propyl)-piperazine (example 22e) following successively the procedures described for examples 25, 29 and 31. LC-MS: 796.2 [(M+H)$^+$].

EXAMPLE 358

5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-4-ethoxy-2,N-dimethoxy-N-methyl-benzenesulfonamide Chiral

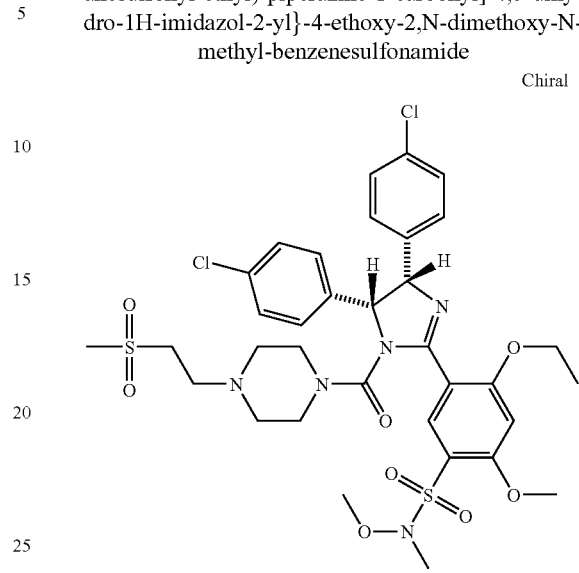

The title compound was prepared from meso-1,2-bis-(4-chlorophenyl)ethane-1,2-diamine, ethyl 2-ethoxy-4-methoxy-5-(methoxy-methyl-sulfamoyl)-benzoate (example 2) and 1-(2-methanesulfonylethyl)piperazine bishydrochloride (example 23) following successively the procedures described for examples 25, 29 and 31. LC-MS: 782.2 [(M+H)$^+$].

EXAMPLE 359

5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-4-ethoxy-2,N-dimethoxy-N-methyl-benzenesulfonamide Chiral

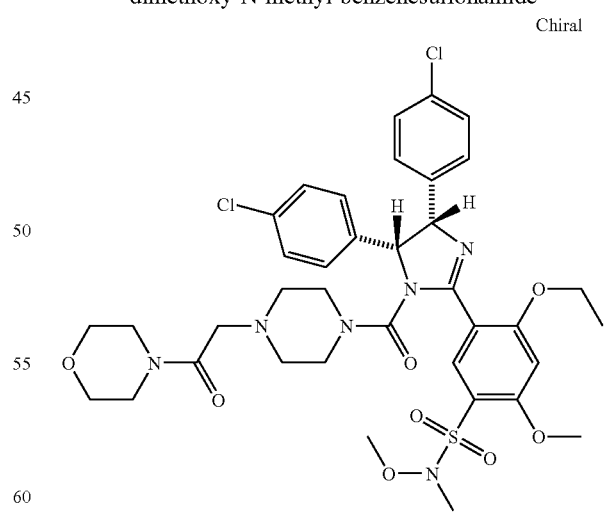

The title compound was prepared from meso-1,2-bis-(4-chlorophenyl)ethane-1,2-diamine, ethyl 2-ethoxy-4-methoxy-5-(methoxy-methyl-sulfamoyl)-benzoate (example 2) and 1-morpholin-4-yl-2-piperazin-1-yl-ethanone (Oakwood Products) following successively the procedures described for examples 25, 29 and 31. LC-MS: 803.2 [(M+H)$^+$].

EXAMPLE 360

4-[(4S,5R)-2-(4-Acetyl-2-ethoxy-phenyl)-4,5-bis-(4-chloro-phenyl)-4,5-dihydro-imidazole-1-carbonyl]-piperazin-2-one

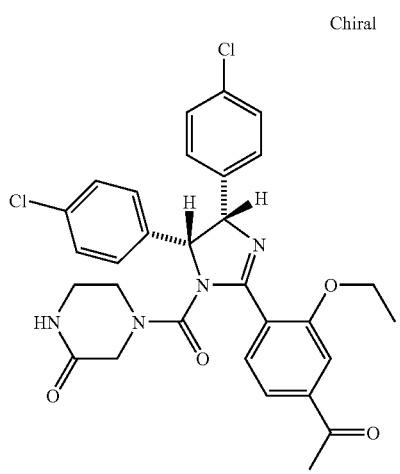

The title compound was prepared from 1-{4-[4,5-bis-(4-chlorophenyl)-4,5-dihydro-1H-imidazol-2-yl]-3-ethoxyphenyl}ethanone (example 27) and 2-piperazinone (Avocado Organics) following successively the procedures described for examples 29 and 31. LC-MS: 579.4 [(M+H)$^+$].

EXAMPLE 361

1-(4-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-3-ethoxy-phenyl)-ethanone hydrochloride

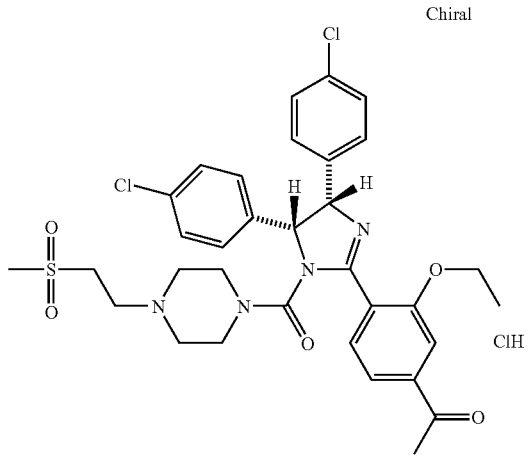

The title compound was prepared from 1-{4-[4,5-bis-(4-chlorophenyl)-4,5-dihydro-1H-imidazol-2-yl]-3-ethoxyphenyl}ethanone (example 27) and 1-(2-methanesulfonylethyl)piperazine bishydrochloride (example 23) following successively the procedures described for examples 29 and 31. LC-MS: 671.4 [(M+H)$^+$].

EXAMPLE 362

2-{4-[(4S,5R)-2-(4-Acetyl-2-ethoxy-phenyl)-4,5-bis-(4-chloro-phenyl)-4,5-dihydro-imidazole-1-carbonyl]-piperazin-1-yl}-1-morpholin-4-yl-ethanone hydrochloride

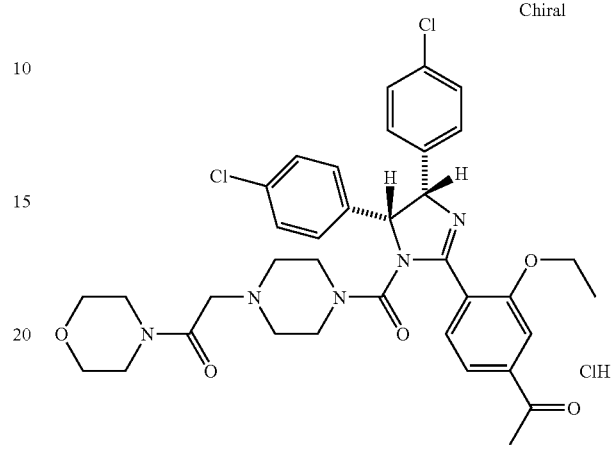

The title compound was prepared from 1-{4-[4,5-bis-(4-chlorophenyl)-4,5-dihydro-1H-imidazol-2-yl]-3-ethoxyphenyl}ethanone (example 27) and 1-morpholin-4-yl-2-piperazin-1-yl-ethanone (Oakwood Products) following successively the procedures described for examples 29 and 31. LC-MS: 692.4 [(M+H)$^+$].

EXAMPLE 363

1-(4-{(4S,5R)-4,5-Bis-(4-chloro-phenyl)-1-[4-(3-methanesulfonyl-propyl)-piperazine-1-carbonyl]-4,5-dihydro-1H-imidazol-2-yl}-3-ethoxy-phenyl)-ethanone hydrochloride

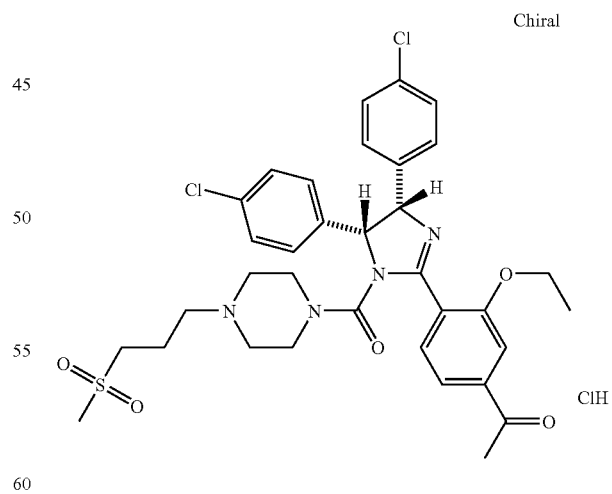

The title compound was prepared from 1-{4-[4,5-bis-(4-chlorophenyl)-4,5-dihydro-1H-imidazol-2-yl]-3-ethoxyphenyl}ethanone (example 27) and 1-(3-methanesulfonyl-propyl)-piperazine (example 22e) following successively the procedures described for examples 29 and 31. LC-MS: 685.4 [(M+H)$^+$].

EXAMPLE 364

[(4S,5R)-4,5-Bis-(4-chloro-phenyl)-2-(2-ethoxy-4-trifluoroprop-1-ynyl-phenyl)-4,5-dihydro-imidazol-1-yl]-[4-(3-methanesulfonyl-propyl)-piperazin-1-yl]-methanone hydrochloride

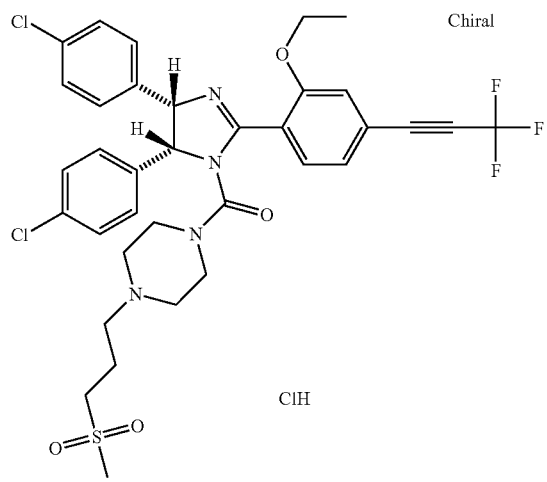

The title compound was prepared from meso-1,2-bis-(4-chlorophenyl)ethane-1,2-diamine, ethyl 4-trifluoroprop-1-ynylbenzoate (example 16) and 1-(3-methanesulfonyl-propyl)-piperazine (example 22e) following successively the procedures described for examples 25, 29 and 31. LC-MS: 735.4 [(M+H)$^+$].

EXAMPLE 365

N-tert-Butyl-2-{4-[(4S,5R)-2-(5-tert-butylsulfamoyl-2-ethoxy-phenyl)-4,5-bis-(4-chloro-phenyl)-4,5-dihydro-imidazole-1-carbonyl]-piperazin-1-yl}-acetamide

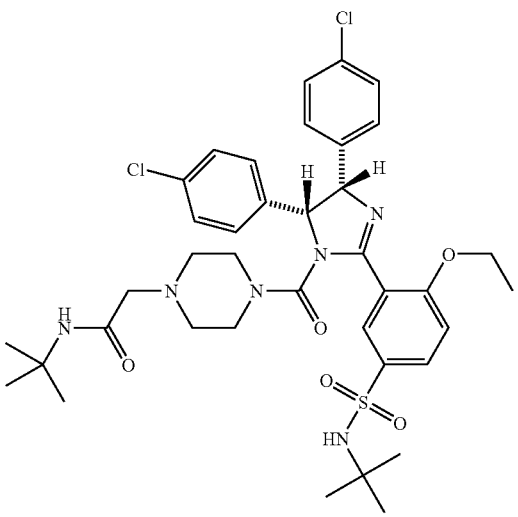

The title compound was prepared from meso-1,2-bis-(4-chlorophenyl)ethane-1,2-diamine, ethyl 5-tert-butylsulfamoyl-2-ethoxy-benzoate (example 2) and N-tert-butyl-2-piperazin-1-yl-acetamide (example 22g) following successively the procedures described for examples 25, 29 and 31. LC-MS: 771.3 [(M+H)$^+$].

EXAMPLE 366

2-{4-[(4S,5R)-2-(5-tert-Butylsulfamoyl-2-ethoxy-phenyl)-4,5-bis-(4-chloro-phenyl)-4,5-dihydro-imidazole-1-carbonyl]-piperazin-1-yl}-acetamide

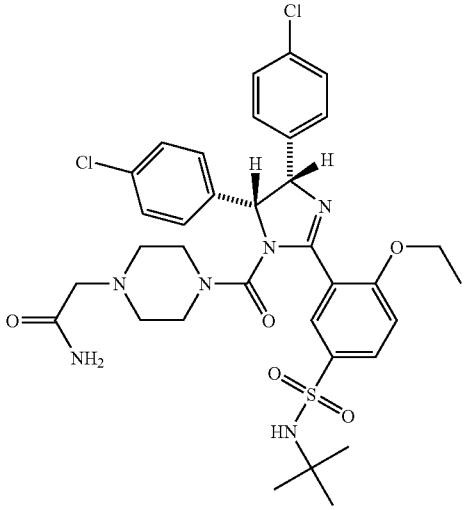

The title compound was prepared from meso-1,2-bis-(4-chlorophenyl)ethane-1,2-diamine, ethyl 5-tert-butylsulfamoyl-2-ethoxy-benzoate (example 2) and 2-piperazin-1-yl-acetamide (Matrix) following successively the procedures described for examples 25, 29 and 31. LC-MS: 715.2 [(M+H)$^+$].

EXAMPLE 367

2-{4-[(4S,5R)-2-(5-tert-Butylsulfamoyl-2-ethoxy-phenyl)-4,5-bis-(4-chloro-phenyl)-4,5-dihydro-imidazole-1-carbonyl]-piperazin-1-yl}-N,N-bis-(2-methoxy-ethyl)-acetamide

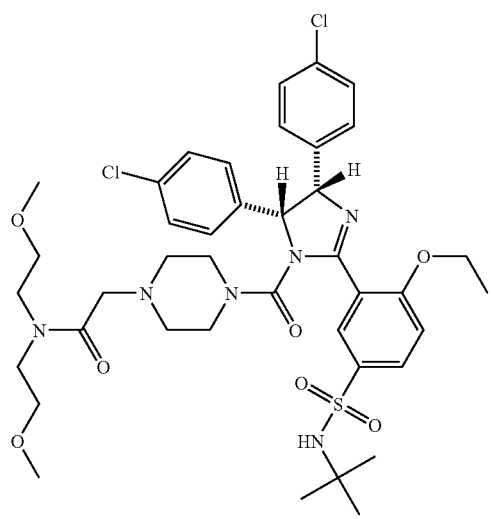

The title compound was prepared from meso-1,2-bis-(4-chlorophenyl)ethane-1,2-diamine, ethyl 5-tert-butylsulfamoyl-2-ethoxy-benzoate (example 2) and N,N-bis-(2-methoxy-ethyl)-2-piperazin-1-yl-acetamide (example 22a) following successively the procedures described for examples 25, 29 and 31. LC-MS: 831.3 [(M+H)$^+$].

EXAMPLE 368

2-{4-[(4S,5R)-2-(5-tert-Butylsulfamoyl-2-ethoxy-phenyl)-4,5-bis-(4-chloro-phenyl)-4,5-dihydro-imidazole-1-carbonyl]-piperazin-1-yl}-N-methoxy-N-methyl-acetamide

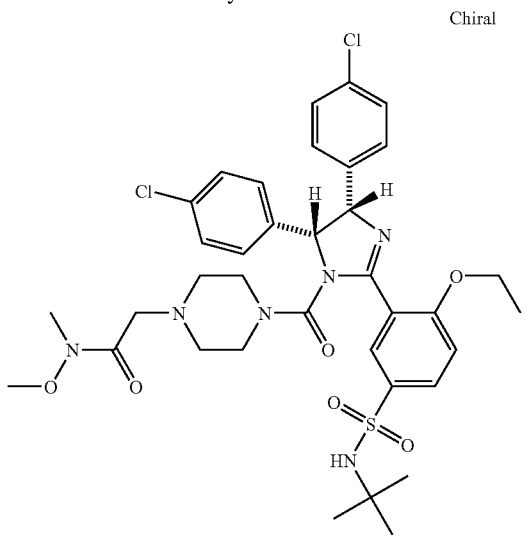

The title compound was prepared from meso-1,2-bis-(4-chlorophenyl)ethane-1,2-diamine, ethyl 5-tert-butylsulfamoyl-2-ethoxy-benzoate (example 2) and N-methoxy-N-methyl-2-piperazin-1-yl-acetamide (example 22b) following successively the procedures described for examples 25, 29 and 31. LC-MS: 759.2 [(M+H)$^+$].

EXAMPLE 369

2-{4-[(4S,5R)-2-(5-tert-Butylsulfamoyl-2-ethoxy-phenyl)-4,5-bis-(4-chloro-phenyl)-4,5-dihydro-imidazole-1-carbonyl]-piperazin-1-yl}-N-isopropyl-N-methyl-acetamide

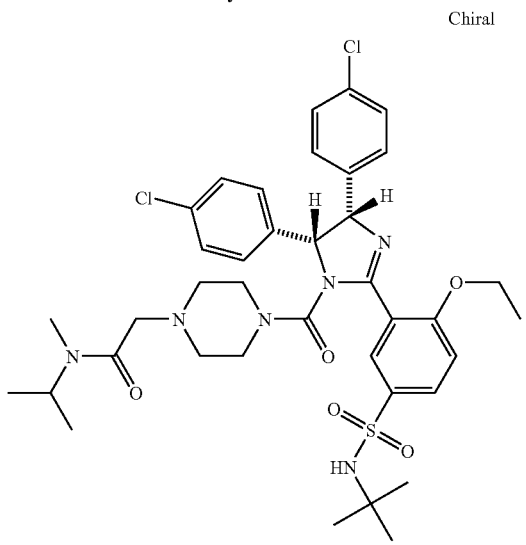

The title compound was prepared from meso-1,2-bis-(4-chlorophenyl)ethane-1,2-diamine, ethyl 5-tert-butylsulfamoyl-2-ethoxy-benzoate (example 2) and N-isopropyl-N-methyl-2-piperazin-1-yl-acetamide (example 22c) following successively the procedures described for examples 25, 29 and 31. LC-MS: 771.3 [(M+H)$^+$].

EXAMPLE 370

2-{4-[(4S,5R)-2-(5-tert-Butylsulfamoyl-2-ethoxy-phenyl)-4,5-bis-(4-chloro-phenyl)-4,5-dihydro-imidazole-1-carbonyl]-piperazin-1-yl}-N-(2-cyano-ethyl)-N-methyl-acetamide

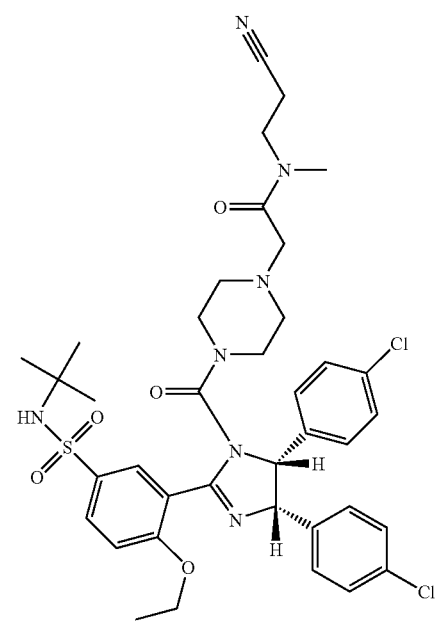

The title compound was prepared from meso-1,2-bis-(4-chlorophenyl)ethane-1,2-diamine, ethyl 5-tert-butylsulfamoyl-2-ethoxy-benzoate (example 2) and N-(2-cyano-ethyl)-N-methyl-2-piperazin-1-yl-acetamide (example 22d) following successively the procedures described for examples 25, 29 and 31. LC-MS: 782.2 [(M+H)$^+$].

EXAMPLE 371

2-{4-[(4S,5R)-2-(5-tert-Butylsulfamoyl-2-ethoxy-phenyl)-4,5-bis-(4-chloro-phenyl)-4,5-dihydro-imidazole-1-carbonyl]-piperazin-1-yl}-N-(2-methoxy-1-methyl-ethyl)-acetamide

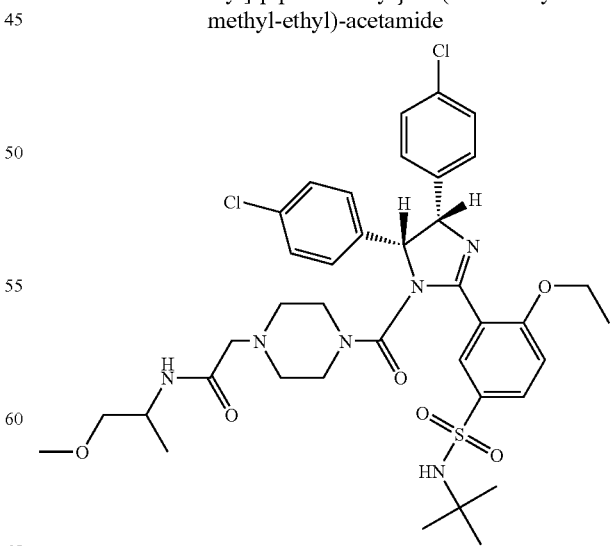

The title compound was prepared from meso-1,2-bis-(4-chlorophenyl)ethane-1,2-diamine, ethyl 5-tert-butylsulfamoyl-2-ethoxy-benzoate (example 2) and N-(2-methoxy-1-methyl-ethyl)-2-piperazin-1-yl-acetamide (example 21) following successively the procedures described for examples 25, 29 and 31. LC-MS: 787.3 [(M+H)+].

EXAMPLE 372

3-{(4S,5R)-4,5-Bis-(4-chloro-phenyl)-1-[4-(3,5-dimethyl-isoxazole-4-carbonyl)-piperazine-1-carbonyl]-4,5-dihydro-1H-imidazol-2-yl}-N-tert-butyl-4-ethoxy-benzenesulfonamide Chiral

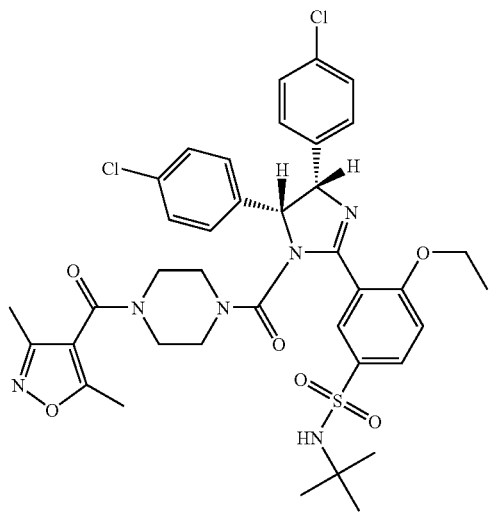

The title compound was prepared from meso-1,2-bis-(4-chlorophenyl)ethane-1,2-diamine, ethyl 5-tert-butylsulfamoyl-2-ethoxy-benzoate (example 2) and (3,5-dimethyl-isoxazol-4-yl)-piperazin-1-yl-methanone (example 19) following successively the procedures described for examples 25, 29 and 31. LC-MS: 781.2 [(M+H)+].

EXAMPLE 373

3-[(4S,5R)-4,5-Bis-(4-chloro-phenyl)-1-(4-ethanesulfonyl-piperazine-1-carbonyl)-4,5-dihydro-1H-imidazol-2-yl]-N-tert-butyl-4-ethoxy-benzenesulfonamide Chiral

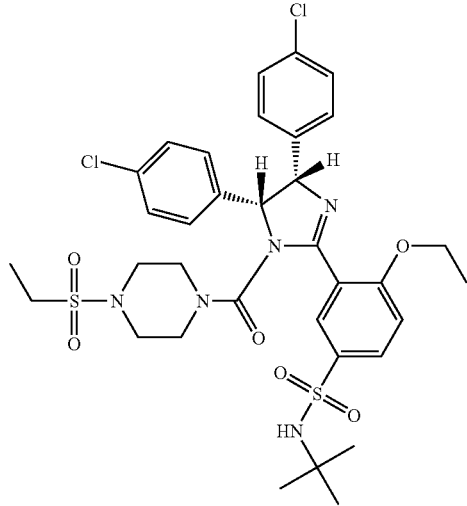

The title compound was prepared from meso-1,2-bis-(4-chlorophenyl)ethane-1,2-diamine, ethyl 5-tert-butylsulfamoyl-2-ethoxy-benzoate (example 2) and 1-ethanesulfonyl-piperazine (example 20) following successively the procedures described for examples 25, 29 and 31. LC-MS: 750.2 [(M+H)+].

EXAMPLE 374

3-{(4S,5R)-4,5-Bis-(4-chloro-phenyl)-1-[4-(2-methanesulfonylamino-ethyl)-piperazine-1-carbonyl]-4,5-dihydro-1H-imidazol-2-yl}-N-tert-butyl-4-ethoxy-benzenesulfonamide Chiral

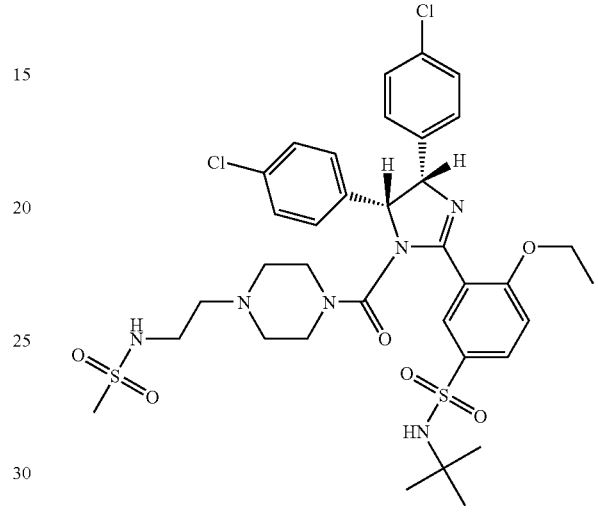

The title compound was prepared from meso-1,2-bis-(4-chlorophenyl)ethane-1,2-diamine, ethyl 5-tert-butylsulfamoyl-2-ethoxy-benzoate (example 2) and N-(2-methanosulfonylethyl)-piperazine hydrochloride (example 24) following successively the procedures described for examples 25, 29 and 31. LC-MS: 779.3 [(M+H)+].

EXAMPLE 375

3-{(4S,5R)-4,5-Bis-(4-chloro-phenyl)-1-[4-(3-methanesulfonyl-propyl)-piperazine-1-carbonyl]-4,5-dihydro-1H-imidazol-2-yl}-N-tert-butyl-4-ethoxy-benzenesulfonamide Chiral

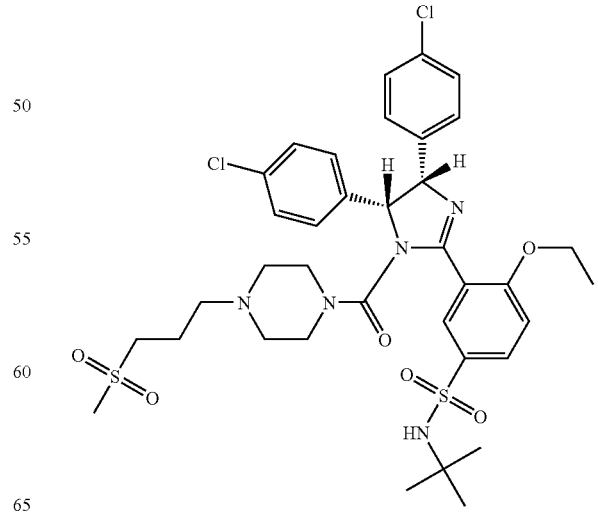

The title compound was prepared from meso-1,2-bis-(4-chlorophenyl)ethane-1,2-diamine, ethyl 5-tert-butylsulfamoyl-2-ethoxy-benzoate (example 2) and 1-(3-methanesulfonyl-propyl)-piperazine (example 22e) following successively the procedures described for examples 25, 29 and 31. LC-MS: 778.3 [(M+H)+].

EXAMPLE 376

3-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-N-tert-butyl-4-ethoxy-benzenesulfonamide

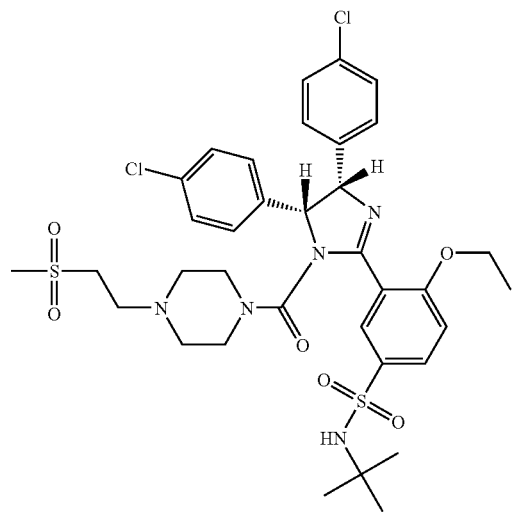

The title compound was prepared from meso-1,2-bis-(4-chlorophenyl)ethane-1,2-diamine, ethyl 5-tert-butylsulfamoyl-2-ethoxy-benzoate (example 2) and 1-(2-methanesulfonylethyl)piperazine bishydrochloride (example 23) following successively the procedures described for examples 25, 29 and 31. LC-MS: 764.2 [(M+H)+].

EXAMPLE 377

3-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-N-tert-butyl-4-ethoxy-benzenesulfonamide

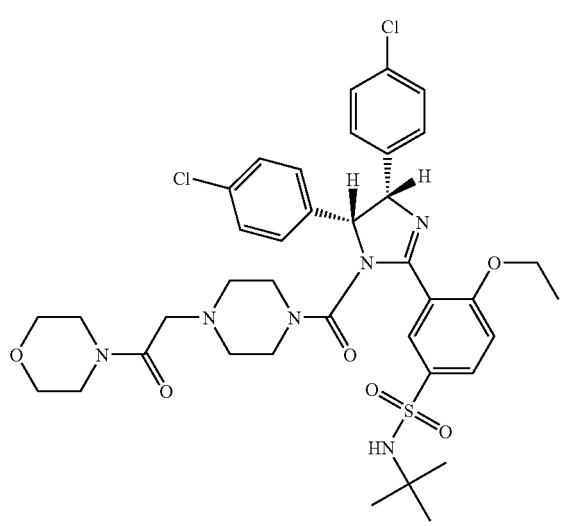

The title compound was prepared from meso-1,2-bis-(4-chlorophenyl)ethane-1,2-diamine, ethyl 5-tert-butylsulfamoyl-2-ethoxy-benzoate (example 2) and 1-morpholin-4-yl-2-piperazin-1-yl-ethanone (Oakwood Products) following successively the procedures described for examples 25, 29 and 31. LC-MS: 785.2 [(M+H)+].

EXAMPLE 378

2-(4-{(4S,5R)-4,5-Bis-(4-chloro-phenyl)-2-[2-ethoxy-5-(piperidine-1-sulfonyl)-phenyl]-4,5-dihydro-imidazole-1-carbonyl}-piperazin-1-yl)-N-tert-butyl-acetamide

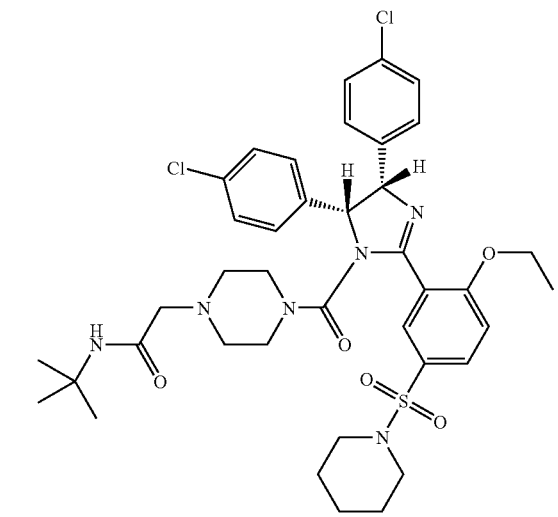

The title compound was prepared from meso-1,2-bis-(4-chlorophenyl)ethane-1,2-diamine, ethyl 2-ethoxy-5-(piperidine-1-sulfonyl)-benzoate (example 2) and N-tert-butyl-2-piperazin-1-yl-acetamide (example 22g) following successively the procedures described for examples 25, 29 and 31. LC-MS: 783.3 [(M+H)+].

EXAMPLE 379

2-(4-{(4S,5R)-4,5-Bis-(4-chloro-phenyl)-2-[2-ethoxy-5-(piperidine-1-sulfonyl)-phenyl]-4,5-dihydro-imidazole-1-carbonyl}-piperazin-1-yl)-acetamide

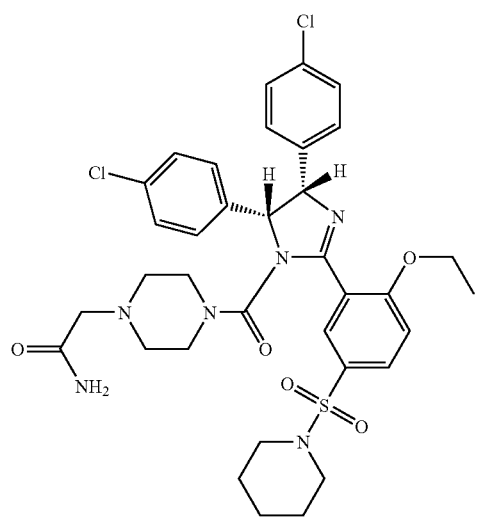

The title compound was prepared from meso-1,2-bis-(4-chlorophenyl)ethane-1,2-diamine, ethyl 2-ethoxy-5-(piperidine-1-sulfonyl)-benzoate (example 2) and 2-piperazin-1-yl-acetamide (Matrix) following successively the procedures described for examples 25, 29 and 31. LC-MS: 727.2 [(M+H)$^+$].

EXAMPLE 380

2-(4-{(4S,5R)-4,5-Bis-(4-chloro-phenyl)-2-[2-ethoxy-5-(piperidine-1-sulfonyl)-phenyl]-4,5-dihydro-imidazole-1-carbonyl}-piperazin-1-yl)-N,N-bis-(2-methoxy-ethyl)-acetamide Chiral

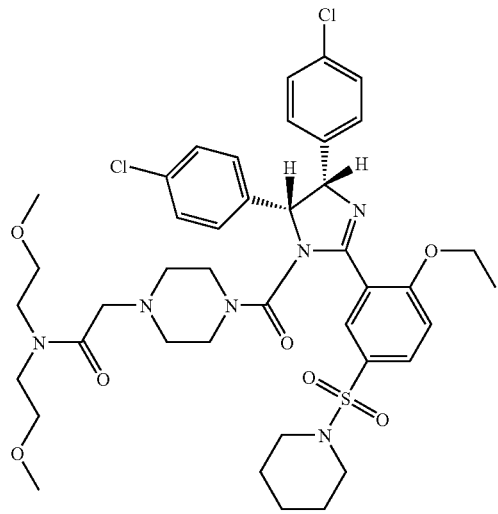

The title compound was prepared from meso-1,2-bis-(4-chlorophenyl)ethane-1,2-diamine, ethyl 2-ethoxy-5-(piperidine-1-sulfonyl)-benzoate (example 2) and N,N-bis-(2-methoxy-ethyl)-2-piperazin-1-yl-acetamide (example 22a) following successively the procedures described for examples 25, 29 and 31. LC-MS: 843.3 [(M+H)$^+$].

EXAMPLE 381

2-(4-{(4S,5R)-4,5-Bis-(4-chloro-phenyl)-2-[2-ethoxy-5-(piperidine-1-sulfonyl)-phenyl]-4,5-dihydro-imidazole-1-carbonyl}-piperazin-1-yl)-N-methoxy-N-methyl-acetamide Chiral

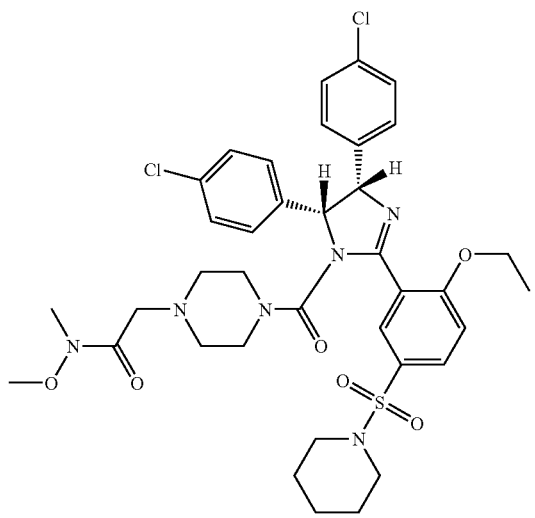

The title compound was prepared from meso-1,2-bis-(4-chlorophenyl)ethane-1,2-diamine, ethyl 2-ethoxy-5-(piperidine-1-sulfonyl)-benzoate (example 2) and N-methoxy-N-methyl-2-piperazin-1-yl-acetamide (example 22b) following successively the procedures described for examples 25, 29 and 31. LC-MS: 771.2 [(M+H)$^+$].

EXAMPLE 382

2-(4-{(4S,5R)-4,5-Bis-(4-chloro-phenyl)-2-[2-ethoxy-5-(piperidine-1-sulfonyl)-phenyl]-4,5-dihydro-imidazole-1-carbonyl}-piperazin-1-yl)-N-isopropyl-N-methyl-acetamide Chiral

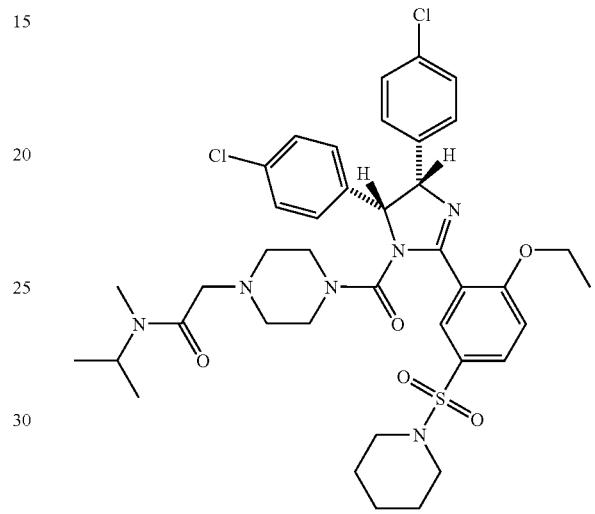

The title compound was prepared from meso-1,2-bis-(4-chlorophenyl)ethane-1,2-diamine, ethyl 2-ethoxy-5-(piperidine-1-sulfonyl)-benzoate (example 2) and N-isopropyl-N-methyl-2-piperazin-1-yl-acetamide (example 22c) following successively the procedures described for examples 25, 29 and 31. LC-MS: 783.3 [(M+H)$^+$].

EXAMPLE 383

2-(4-{(4S,5R)-4,5-Bis-(4-chloro-phenyl)-2-[2-ethoxy-5-(piperidine-1-sulfonyl)-phenyl]-4,5-dihydro-imidazole-1-carbonyl}-piperazin-1-yl)-N-(2-cyano-ethyl)-N-methyl-acetamide Chiral

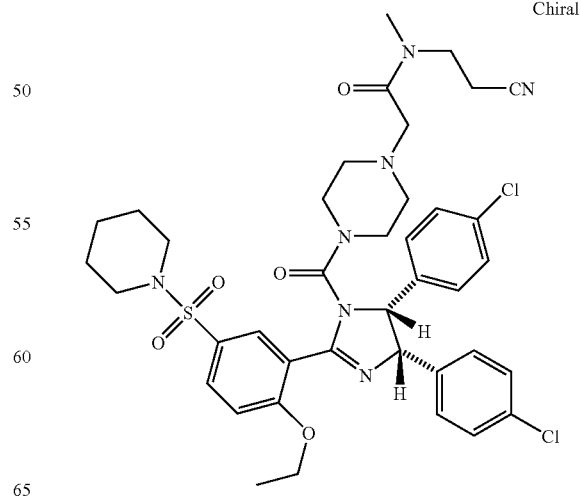

The title compound was prepared from meso-1,2-bis-(4-chlorophenyl)ethane-1,2-diamine, ethyl 2-ethoxy-5-(piperidine-1-sulfonyl)-benzoate (example 2) and N-(2-cyano-ethyl)-N-methyl-2-piperazin-1-yl-acetamide (example 22d) following successively the procedures described for examples 25, 29 and 31. LC-MS: 794.3 [(M+H)+].

EXAMPLE 384

2-(4-{(4S,5R)-4,5-Bis-(4-chloro-phenyl)-2-[2-ethoxy-5-(piperidine-1-sulfonyl)-phenyl]-4,5-dihydro-imidazole-1-carbonyl}-piperazin-1-yl)-N-(2-methoxy-1-methyl-ethyl)-acetamide

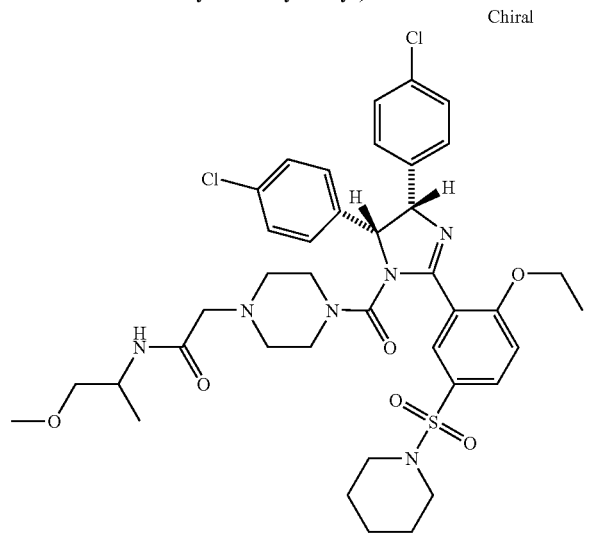

The title compound was prepared from meso-1,2-bis-(4-chlorophenyl)ethane-1,2-diamine, ethyl 2-ethoxy-5-(piperidine-1-sulfonyl)-benzoate (example 2) and N-(2-methoxy-1-methyl-ethyl)-2-piperazin-1-yl-acetamide (example 21) following successively the procedures described for examples 25, 29 and 31. LC-MS: 799.3 [(M+H)+].

EXAMPLE 385

{(4S,5R)-4,5-Bis-(4-chloro-phenyl)-2-[2-ethoxy-5-(piperidine-1-sulfonyl)-phenyl]-4,5-dihydro-imidazol-1-yl}-[4-(3,5-dimethyl-isoxazole-4-carbonyl)-piperazin-1-yl]-methanone

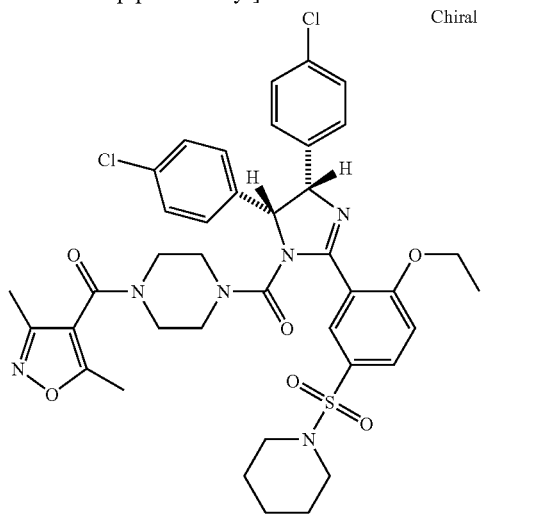

The title compound was prepared from meso-1,2-bis-(4-chlorophenyl)ethane-1,2-diamine, ethyl 2-ethoxy-5-(piperidine-1-sulfonyl)-benzoate (example 2) and (3,5-dimethyl-isoxazol-4-yl)-piperazin-1-yl-methanone (example 19) following successively the procedures described for examples 25, 29 and 31. LC-MS: 793.2 [(M+H)+].

EXAMPLE 386

{(4S,5R)-4,5-Bis-(4-chloro-phenyl)-2-[2-ethoxy-5-(piperidine-1-sulfonyl)-phenyl]-4,5-dihydro-imidazol-1-yl}-(4-ethanesulfonyl-piperazin-1-yl)-methanone

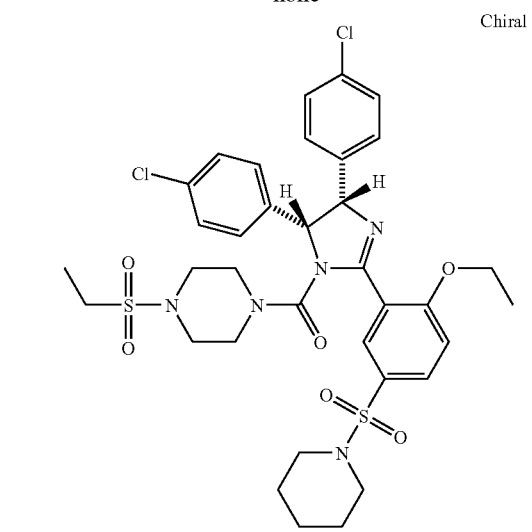

The title compound was prepared from meso-1,2-bis-(4-chlorophenyl)ethane-1,2-diamine, ethyl 2-ethoxy-5-(piperidine-1-sulfonyl)-benzoate (example 2) and 1-ethanesulfonyl-piperazine (example 20) following successively the procedures described for examples 25, 29 and 31. LC-MS: 762.2 [(M+H)+].

EXAMPLE 387

N-[2-(4-{(4S,5R)-4,5-Bis-(4-chloro-phenyl)-2-[2-ethoxy-5-(piperidine-1-sulfonyl)-phenyl]-4,5-dihydro-imidazole-1-carbonyl}-piperazin-1-yl)-ethyl]-methanesulfonamide

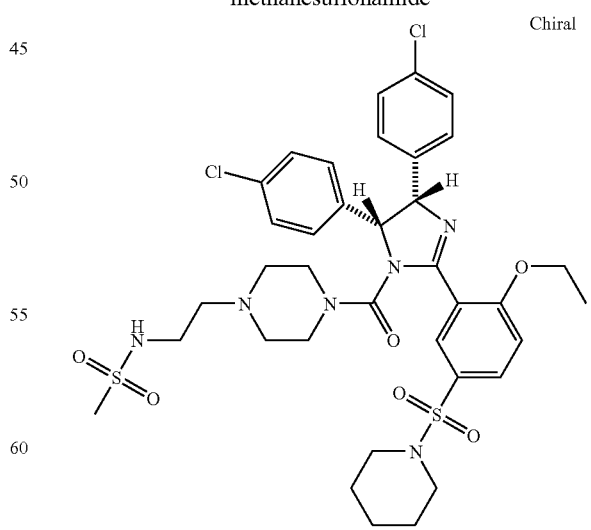

The title compound was prepared from meso-1,2-bis-(4-chlorophenyl)ethane-1,2-diamine, ethyl 2-ethoxy-5-(piperidine-1-sulfonyl)-benzoate (example 2) and N-(2-methanosulfonylethyl)-piperazine hydrochloride (example 24)

EXAMPLE 388

{(4S,5R)-4,5-Bis-(4-chloro-phenyl)-2-[2-ethoxy-5-(piperidine-1-sulfonyl)-phenyl]-4,5-dihydro-imidazol-1-yl}-[4-(3-methanesulfonyl-propyl)-piperazin-1-yl]-methanone

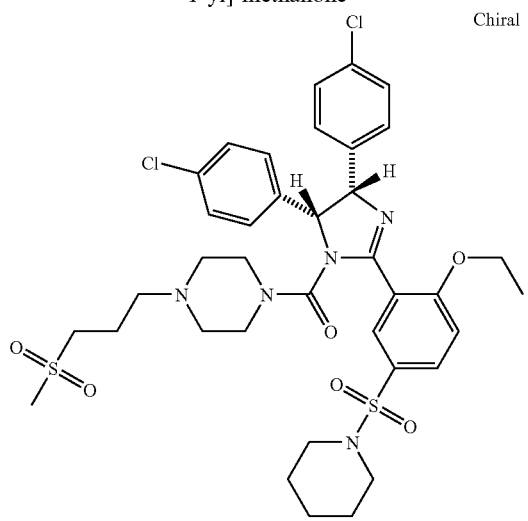

The title compound was prepared from meso-1,2-bis-(4-chlorophenyl)ethane-1,2-diamine, ethyl 2-ethoxy-5-(piperidine-1-sulfonyl)-benzoate (example 2) and 1-(3-methanesulfonyl-propyl)-piperazine (example 22e) following successively the procedures described for examples 25, 29 and 31. LC-MS: 790.3 [(M+H)$^+$].

EXAMPLE 389

{(4S,5R)-4,5-Bis-(4-chloro-phenyl)-2-[2-ethoxy-5-(piperidine-1-sulfonyl)-phenyl]-4,5-dihydro-imidazol-1-yl}-[4-(2-methanesulfonyl-ethyl)-piperazin-1-yl]-methanone

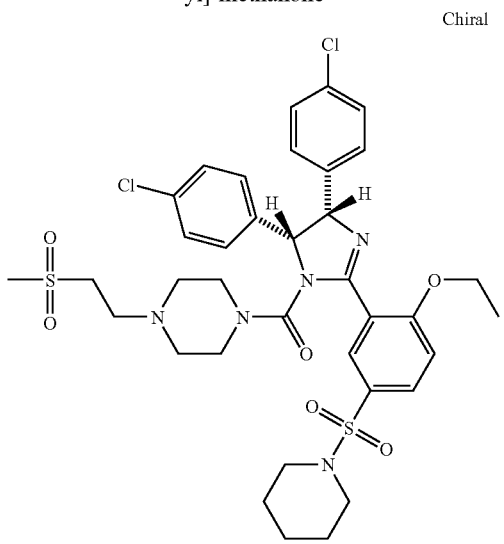

The title compound was prepared from meso-1,2-bis-(4-chlorophenyl)ethane-1,2-diamine, ethyl 2-ethoxy-5-(piperidine-1-sulfonyl)-benzoate (example 2) and 1-(2-methanesulfonylethyl)piperazine bishydrochloride (example 23) following successively the procedures described for examples 25, 29 and 31. LC-MS: 776.2 [(M+H)$^+$].

EXAMPLE 390

2-(4-{(4S,5R)-4,5-Bis-(4-chloro-phenyl)-2-[2-ethoxy-5-(piperidine-1-sulfonyl)-phenyl]-4,5-dihydro-imidazole-1-carbonyl}-piperazin-1-yl)-1-morpholin-4-yl-ethanone

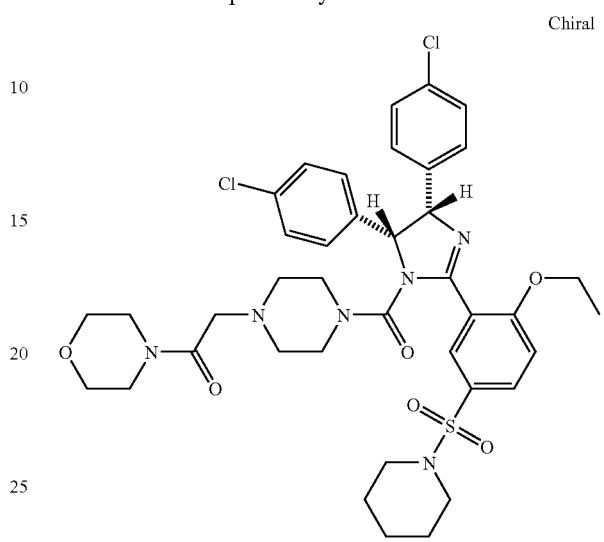

The title compound was prepared from meso-1,2-bis-(4-chlorophenyl)ethane-1,2-diamine, ethyl 2-ethoxy-5-(piperidine-1-sulfonyl)-benzoate (example 2) and 1-morpholin-4-yl-2-piperazin-1-yl-ethanone (Oakwood Products) following successively the procedures described for examples 25, 29 and 31. LC-MS: 797.2 [(M+H)$^+$].

EXAMPLE 391

2-(4-{(4S,5R)-4,5-Bis-(4-chloro-phenyl)-2-[2-ethoxy-5-(methoxy-methyl-sulfamoyl)-phenyl]-4,5-dihydro-imidazole-1-carbonyl}-piperazin-1-yl)-N-tert-butyl-acetamide

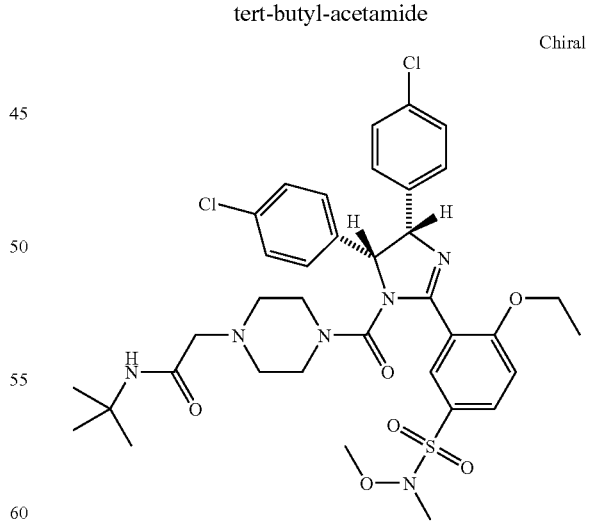

The title compound was prepared from meso-1,2-bis-(4-chlorophenyl)ethane-1,2-diamine, ethyl 2-ethoxy-5-(methoxy-methyl-sulfamoyl)-benzoate (example 2) and N-tert-butyl-2-piperazin-1-yl-acetamide (example 22g) following successively the procedures described for examples 25, 29 and 31. LC-MS: 759.3 [(M+H)$^+$].

EXAMPLE 392

2-(4-{(4S,5R)-4,5-Bis-(4-chloro-phenyl)-2-[2-ethoxy-5-(methoxy-methyl-sulfamoyl)-phenyl]-4,5-dihydro-imidazole-1-carbonyl}-piperazin-1-yl)-acetamide

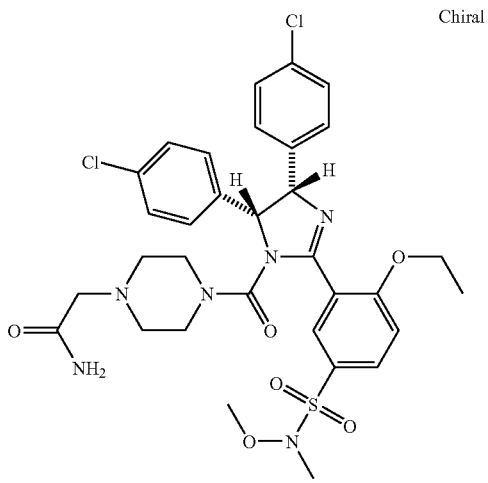

The title compound was prepared from meso-1,2-bis-(4-chlorophenyl)ethane-1,2-diamine, ethyl 2-ethoxy-5-(methoxy-methyl-sulfamoyl)-benzoate (example 2) and 2-piperazin-1-yl-acetamide (Matrix) following successively the procedures described for examples 25, 29 and 31. LC-MS: 703.2 [(M+H)$^+$].

EXAMPLE 393

2-(4-{(4S,5R)-4,5-Bis-(4-chloro-phenyl)-2-[2-ethoxy-5-(methoxy-methyl-sulfamoyl)-phenyl]-4,5-dihydro-imidazole-1-carbonyl}-piperazin-1-yl)-N,N-bis-(2-methoxy-ethyl)-acetamide

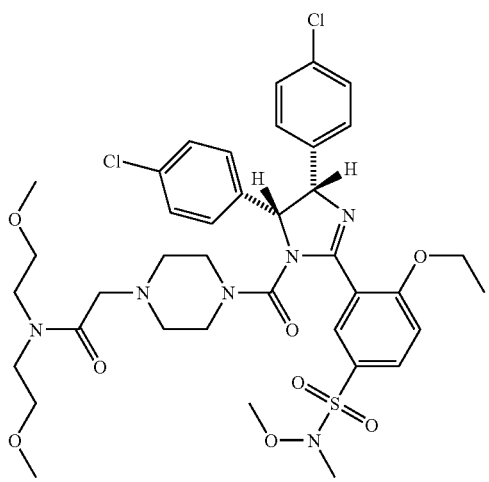

The title compound was prepared from meso-1,2-bis-(4-chlorophenyl)ethane-1,2-diamine, ethyl 2-ethoxy-5-(methoxy-methyl-sulfamoyl)-benzoate (example 2) and N,N-bis-(2-methoxy-ethyl)-2-piperazin-1-yl-acetamide (example 22a) following successively the procedures described for examples 25, 29 and 31. LC-MS: 819.4 [(M+H)$^+$]

EXAMPLE 394

2-(4-{(4S,5R)-4,5-Bis-(4-chloro-phenyl)-2-[2-ethoxy-5-(methoxy-methyl-sulfamoyl)-phenyl]-4,5-dihydro-imidazole-1-carbonyl}-piperazin-1-yl)-N-methoxy-N-methyl-acetamide

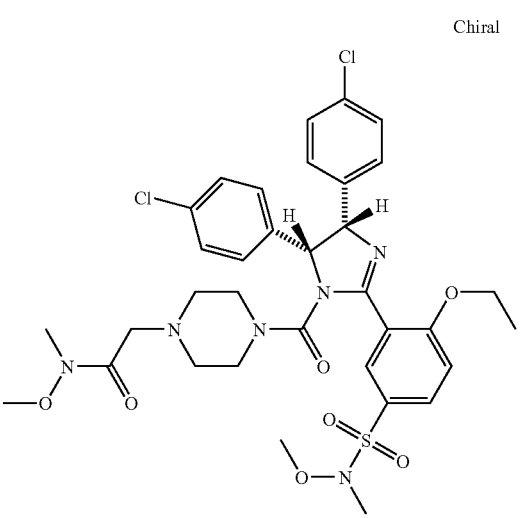

The title compound was prepared from meso-1,2-bis-(4-chlorophenyl)ethane-1,2-diamine, ethyl 2-ethoxy-5-(methoxy-methyl-sulfamoyl)-benzoate (example 2) and N-methoxy-N-methyl-2-piperazin-1-yl-acetamide (example 22b) following successively the procedures described for examples 25, 29 and 31. LC-MS: 747.3 [(M+H)$^+$].

EXAMPLE 395

2-(4-{(4S,5R)-4,5-Bis-(4-chloro-phenyl)-2-[2-ethoxy-5-(methoxy-methyl-sulfamoyl)-phenyl]-4,5-dihydro-imidazole-1-carbonyl}-piperazin-1-yl)-N-isopropyl-N-methyl-acetamide

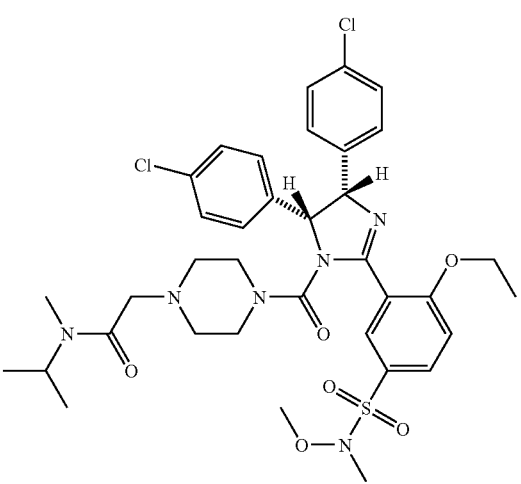

The title compound was prepared from meso-1,2-bis-(4-chlorophenyl)ethane-1,2-diamine, ethyl 2-ethoxy-5-(methoxy-methyl-sulfamoyl)-benzoate (example 2) and N-isopropyl-N-methyl-2-piperazin-1-yl-acetamide (example 22c) following successively the procedures described for examples 25, 29 and 31. LC-MS: 759.3 [(M+H)$^+$].

EXAMPLE 396

2-(4-{(4S,5R)-4,5-Bis-(4-chloro-phenyl)-2-[2-ethoxy-5-(methoxy-methyl-sulfamoyl)-phenyl]-4,5-dihydro-imidazole-1-carbonyl}-piperazin-1-yl)-N-(2-cyano-ethyl)-N-methyl-acetamide

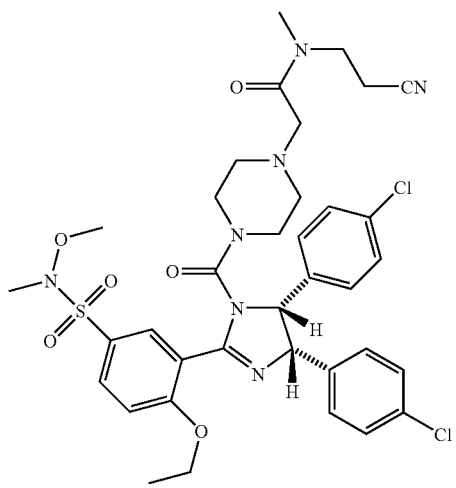

Chiral

The title compound was prepared from meso-1,2-bis-(4-chlorophenyl)ethane-1,2-diamine, ethyl 2-ethoxy-5-(methoxy-methyl-sulfamoyl)-benzoate (example 2) and N-(2-cyano-ethyl)-N-methyl-2-piperazin-1-yl-acetamide (example 22d) following successively the procedures described for examples 25, 29 and 31. LC-MS: 770.3 [(M+H)$^+$].

EXAMPLE 397

2-(4-{(4S,5R)-4,5-Bis-(4-chloro-phenyl)-2-[2-ethoxy-5-(methoxy-methyl-sulfamoyl)-phenyl]-4,5-dihydro-imidazole-1-carbonyl}-piperazin-1-yl)-N-(2-methoxy-1-methyl-ethyl)-acetamide

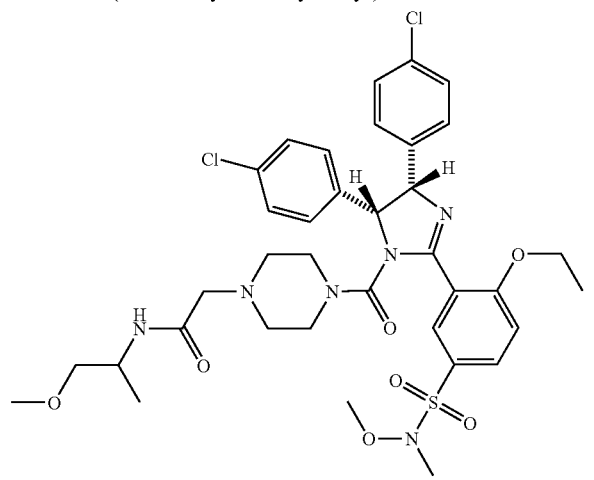

The title compound was prepared from meso-1,2-bis-(4-chlorophenyl)ethane-1,2-diamine, ethyl 2-ethoxy-5-(methoxy-methyl-sulfamoyl)-benzoate (example 2) and N-(2-methoxy-1-methyl-ethyl)-2-piperazin-1-yl-acetamide (example 21) following successively the procedures described for examples 25, 29 and 31. LC-MS: 775.3 [(M+H)$^+$].

EXAMPLE 398

3-{(4S,5R)-4,5-Bis-(4-chloro-phenyl)-1-[4-(3,5-dimethyl-isoxazole-4-carbonyl)-piperazine-1-carbonyl]-4,5-dihydro-1H-imidazol-2-yl}-4-ethoxy-N-methoxy-N-methyl-benzenesulfonamide

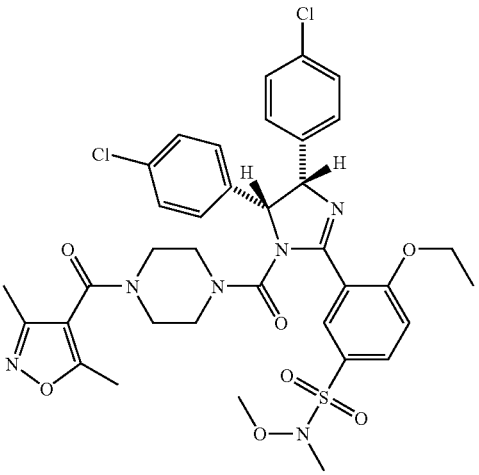

Chiral

The title compound was prepared from meso-1,2-bis-(4-chlorophenyl)ethane-1,2-diamine, ethyl 2-ethoxy-5-(methoxy-methyl-sulfamoyl)-benzoate (example 2) and (3,5-dimethyl-isoxazol-4-yl)-piperazin-1-yl-methanone (example 19) following successively the procedures described for examples 25, 29 and 31. LC-MS: 769.3 [(M+H)$^+$].

EXAMPLE 399

3-[(4S,5R)-4,5-Bis-(4-chloro-phenyl)-1-(4-ethane-sulfonyl-piperazine-1-carbonyl)-4,5-dihydro-1H-imidazol-2-yl]-4-ethoxy-N-methoxy-N-methyl-benzenesulfonamide

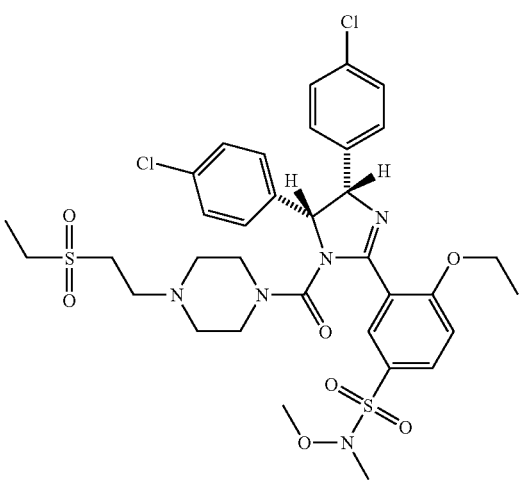

Chiral

The title compound was prepared from meso-1,2-bis-(4-chlorophenyl)ethane-1,2-diamine, ethyl 2-ethoxy-5-(methoxy-methyl-sulfamoyl)-benzoate (example 2) and 1-ethane-sulfonyl-piperazine (example 20) following successively the procedures described for examples 25, 29 and 31. LC-MS: 738.3 [(M+H)$^+$].

EXAMPLE 400

3-{(4S,5R)-4,5-Bis-(4-chloro-phenyl)-1-[4-(2-methanesulfonylamino-ethyl)-piperazine-1-carbonyl]-4,5-dihydro-1H-imidazol-2-yl}-4-ethoxy-N-methoxy-N-methyl-benzenesulfonamide

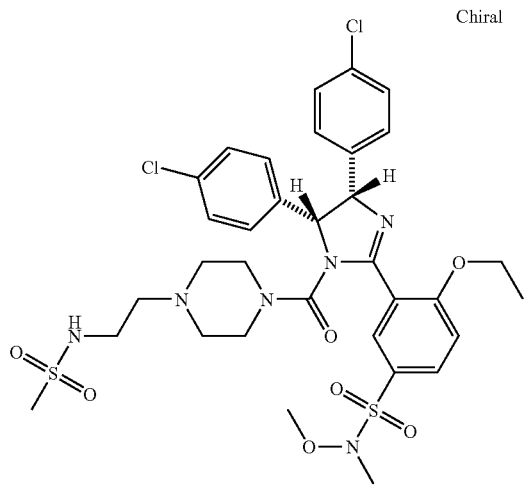

The title compound was prepared from meso-1,2-bis-(4-chlorophenyl)ethane-1,2-diamine, ethyl 2-ethoxy-5-(methoxy-methyl-sulfamoyl)-benzoate (example 2) and N-(2-methanosulfonylethyl)-piperazine hydrochloride (example 24) following successively the procedures described for examples 25, 29 and 31. LC-MS: 767.3 [(M+H)⁺].

EXAMPLE 401

3-{(4S,5R)-4,5-Bis-(4-chloro-phenyl)-1-[4-(3-methanesulfonyl-propyl)-piperazine-1-carbonyl]-4,5-dihydro-1H-imidazol-2-yl}-4-ethoxy-N-methoxy-N-methyl-benzenesulfonamide

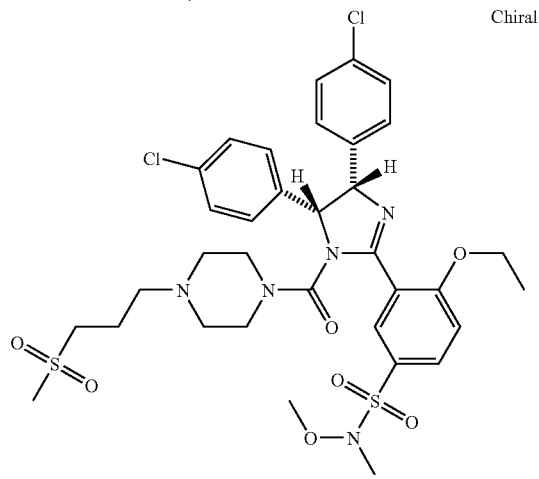

The title compound was prepared from meso-1,2-bis-(4-chlorophenyl)ethane-1,2-diamine, ethyl 2-ethoxy-5-(methoxy-methyl-sulfamoyl)-benzoate (example 2) and 1-(3-methanesulfonyl-propyl)-piperazine (example 22e) following successively the procedures described for examples 25, 29 and 31. LC-MS: 766.3 [(M+H)⁺].

EXAMPLE 402

3-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-4-ethoxy-N-methoxy-N-methyl-benzenesulfonamide

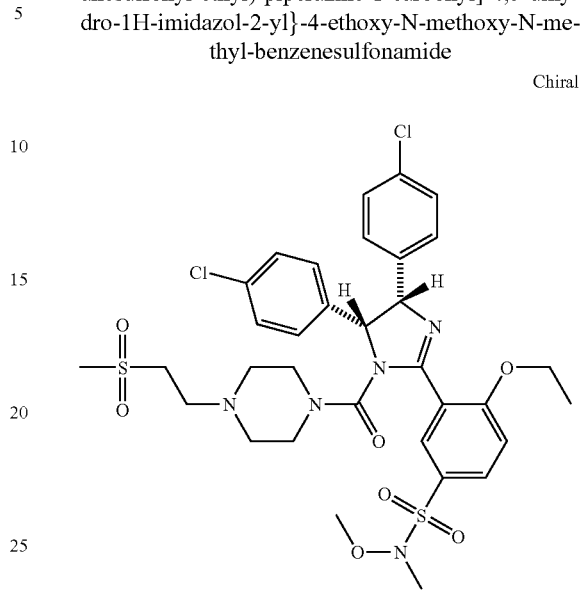

The title compound was prepared from meso-1,2-bis-(4-chlorophenyl)ethane-1,2-diamine, ethyl 2-ethoxy-5-(methoxy-methyl-sulfamoyl)-benzoate (example 2) and 1-(2-methanesulfonylethyl)piperazine bishydrochloride (example 23) following successively the procedures described for examples 25, 29 and 31. LC-MS: 752.3 [(M+H)⁺].

EXAMPLE 403

3-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-4-ethoxy-N-methoxy-N-methyl-benzenesulfonamide

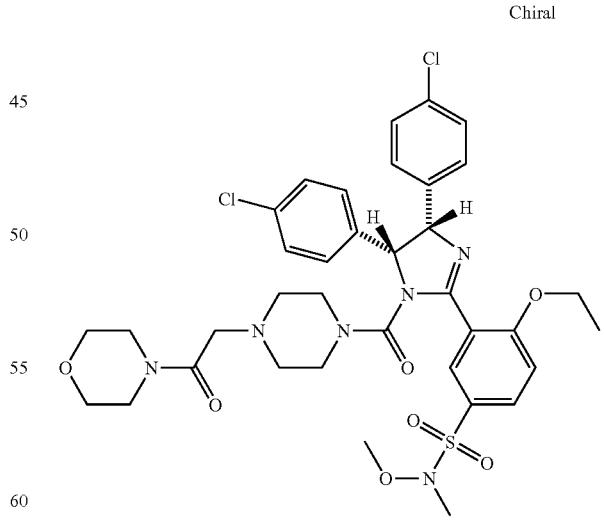

The title compound was prepared from meso-1,2-bis-(4-chlorophenyl)ethane-1,2-diamine, ethyl 2-ethoxy-5-(methoxy-methyl-sulfamoyl)-benzoate (example 2) and 1-morpholin-4-yl-2-piperazin-1-yl-ethanone (Oakwood Products) following successively the procedures described for examples 25, 29 and 31. LC-MS: 773.3 [(M+H)⁺].

EXAMPLE 404

{(4S,5R)-4,5-Bis-(4-chloro-phenyl)-2-[4-(3,3-dimethyl-but-1-ynyl)-2-ethoxy-phenyl]-4,5-dihydro-imidazol-1-yl}-[4-(2-methanesulfonyl-ethyl)-piperazin-1-yl]-methanone hydrochloride

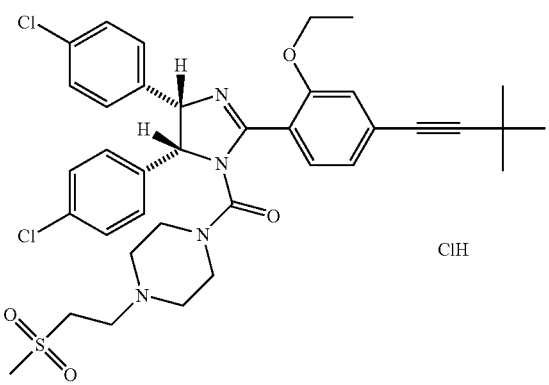

The title compound was prepared from 4,5-bis-(4-chlorophenyl)-2-[4-(3,3-dimethylbut-1-ynyl)-2-ethoxyphenyl]-4,5-dihydro-1H-imidazole (example 28) and 1-(2-methanesulfonylethyl)piperazine bishydrochloride (example 23) following successively the procedures described for examples 29 and 31. LC-MS: 709.4 [(M+H)$^+$].

EXAMPLE 405

2-(4-{(4S,5R)-4,5-Bis-(4-chloro-phenyl)-2-[4-(3,3-dimethyl-but-1-ynyl)-2-ethoxy-phenyl]-4,5-dihydro-imidazole-1-carbonyl}-piperazin-1-yl)-1-morpholin-4-yl-ethanone hydrochloride

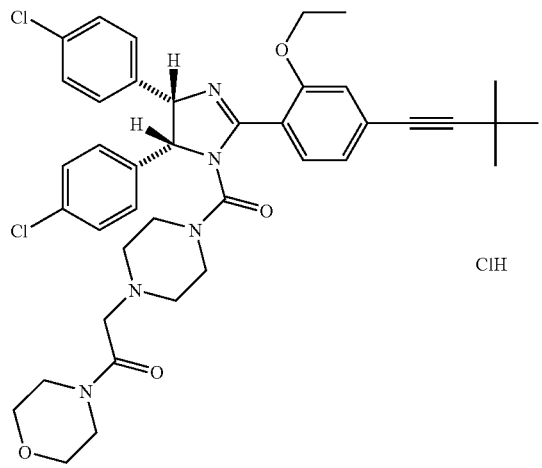

The title compound was prepared from 4,5-bis-(4-chlorophenyl)-2-[4-(3,3-dimethylbut-1-ynyl)-2-ethoxyphenyl]-4,5-dihydro-1H-imidazole (example 28) and 1-morpholin-4-yl-2-piperazin-1-yl-ethanone (Oakwood Products) following successively the procedures described for examples 29 and 31. LC-MS: 730.5 [(M+H)$^+$].

EXAMPLE 406

2-{4-[(4S,5R)-2-(5-tert-Butylsulfamoyl-2-ethoxy-4-methoxy-phenyl)-4,5-bis-(4-chloro-phenyl)-4,5-dihydro-imidazole-1-carbonyl]-piperazin-1-yl}-acetamide

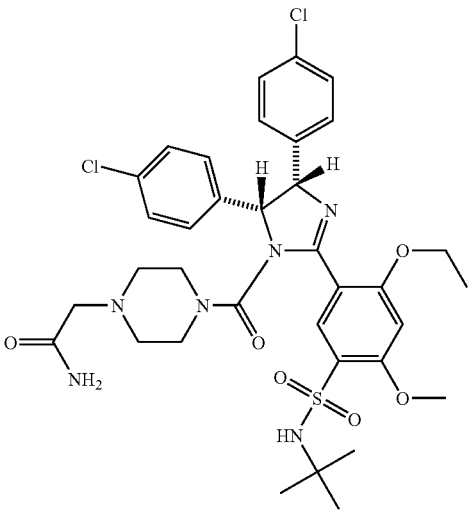

The title compound was prepared from meso-1,2-bis-(4-chlorophenyl)ethane-1,2-diamine, ethyl 5-tert-butylsulfamoyl-2-ethoxy-4-methoxy-benzoate (example 2) and 2-piperazin-1-yl-acetamide (Matrix) following successively the procedures described for examples 25, 29 and 31. LC-MS: 745.1 [(M+H)$^+$].

EXAMPLE 407

N-tert-Butyl-2-{4-[(4S,5R)-2-(5-tert-butylsulfamoyl-2-ethoxy-4-methoxy-phenyl)-4,5-bis-(4-chloro-phenyl)-4,5-dihydro-imidazole-1-carbonyl]-piperazin-1-yl}-acetamide

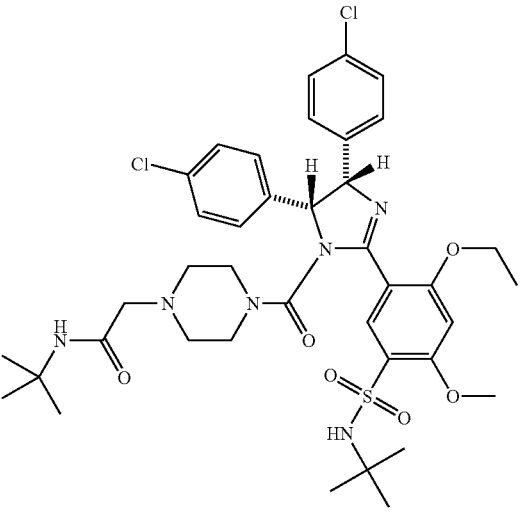

The title compound was prepared from meso-1,2-bis-(4-chlorophenyl)ethane-1,2-diamine, ethyl 5-tert-butylsulfamoyl-2-ethoxy-4-methoxy-benzoate (example 2) and N-tert-butyl-2-piperazin-1-yl-acetamide (example 22g) following successively the procedures described for examples 25, 29 and 31. LC-MS: 801.5 [(M+H)$^+$].

EXAMPLE 408

2-{4-[(4S,5R)-2-(5-tert-Butylsulfamoyl-2-ethoxy-4-methoxy-phenyl)-4,5-bis-(4-chloro-phenyl)-4,5-dihydro-imidazole-1-carbonyl]-piperazin-1-yl}-N-methoxy-N-methyl-acetamide Chiral

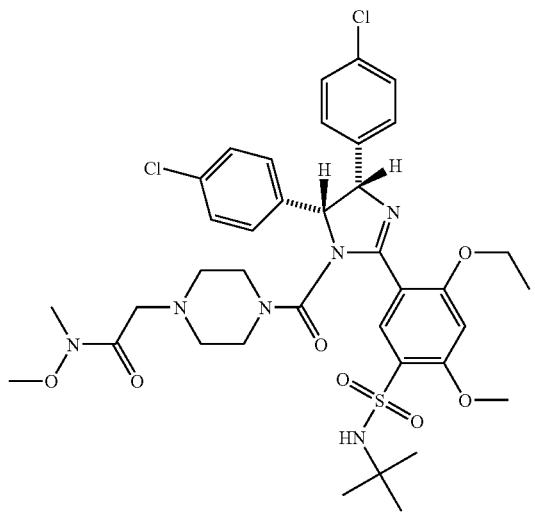

The title compound was prepared from meso-1,2-bis-(4-chlorophenyl)ethane-1,2-diamine, ethyl 5-tert-butylsulfamoyl-2-ethoxy-4-methoxy-benzoate (example 2) and N-methoxy-N-methyl-2-piperazin-1-yl-acetamide (example 22b) following successively the procedures described for examples 25, 29 and 31. LC-MS: 789.4 [(M+H)+].

EXAMPLE 409

2-{4-[(4S,5R)-2-(5-tert-Butylsulfamoyl-2-ethoxy-4-methoxy-phenyl)-4,5-bis-(4-chloro-phenyl)-4,5-dihydro-imidazole-1-carbonyl]-piperazin-1-yl}-N-isopropyl-N-methyl-acetamide Chiral

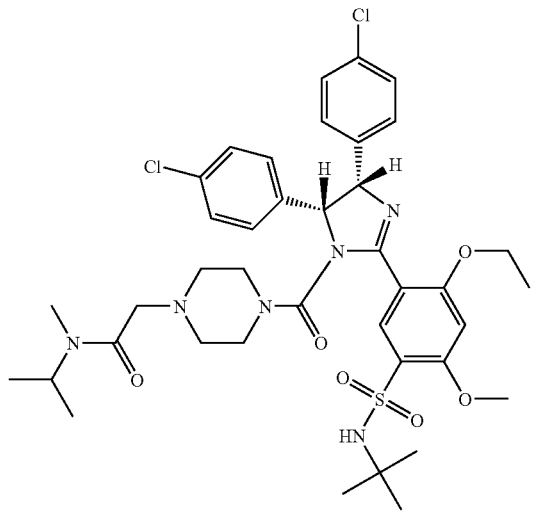

The title compound was prepared from meso-1,2-bis-(4-chlorophenyl)ethane-1,2-diamine, ethyl 5-tert-butylsulfamoyl-2-ethoxy-4-methoxy-benzoate (example 2) and N-isopropyl-N-methyl-2-piperazin-1-yl-acetamide (example 22c) following successively the procedures described for examples 25, 29 and 31. LC-MS: 801.5 [(M+H)+].

EXAMPLE 410

5-{(4S,5R)-4,5-Bis-(4-chloro-phenyl)-1-[4-(3-methanesulfonyl-propyl)-piperazine-1-carbonyl]-4,5-dihydro-1H-imidazol-2-yl}-N-tert-butyl-4-ethoxy-2-methoxy-benzenesulfonamide Chiral

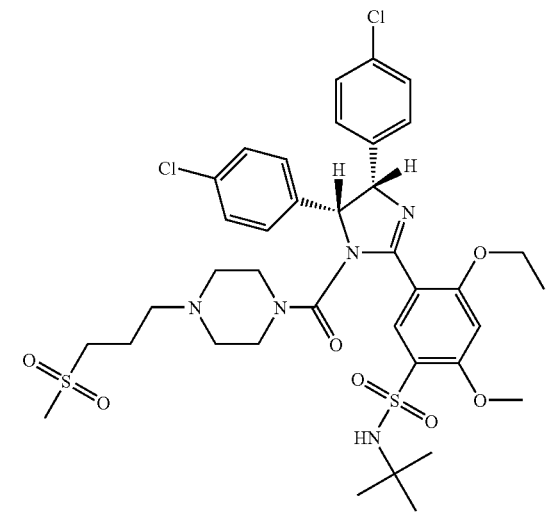

The title compound was prepared from meso-1,2-bis-(4-chlorophenyl)ethane-1,2-diamine, ethyl 5-tert-butylsulfamoyl-2-ethoxy-4-methoxy-benzoate (example 2) and 1-(3-methanesulfonyl-propyl)-piperazine (example 22e) following successively the procedures described for examples 25, 29 and 31. LC-MS: 808.5 [(M+H)+].

EXAMPLE 411

5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-N-tert-butyl-4-ethoxy-2-methoxy-benzenesulfonamide Chiral

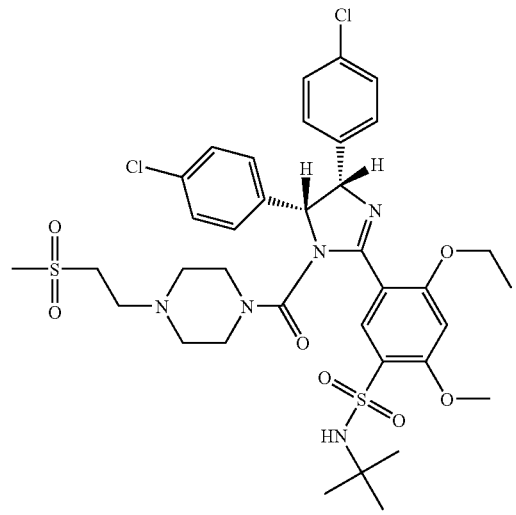

The title compound was prepared from meso-1,2-bis-(4-chlorophenyl)ethane-1,2-diamine, ethyl 5-tert-butylsulfamoyl-2-ethoxy-4-methoxy-benzoate (example 2) and 1-(2-methanesulfonylethyl)piperazine bishydrochloride (example 23) following successively the procedures described for examples 25, 29 and 31. LC-MS: 794.5 [(M+H)+].

EXAMPLE 412

In Vitro Activity Assay

The ability of the compounds to inhibit the interaction between p53 and MDM2 proteins was measured by an HTRF (homogeneous time-resolved fluorescence) assay in which recombinant GST-tagged MDM2 binds to a peptide that resembles the MDM2-interacting region of p53 (Lane et al.). Binding of GST-MDM2 protein and p53-peptide (biotinylated on its N-terminal end) is registered by the FRET (fluorescence resonance energy transfer) between Europium (Eu)-labeled anti-GST antibody and streptavidin-conjugated Allophycocyanin (APC).

Test is performed in black flat-bottom 384-well plates (Costar) in a total volume of 40 uL containing: 90 nM biotinylated peptide, 160 ng/ml GST-MDM2, 20 nM streptavidin-APC (PerkinElmerWallac), 2 nM Eu-labeled anti-GST-antibody (PerkinElmerWallac), 0.2% bovine serum albumin (BSA), 1 mM dithiothreitol (DTT) and 20 mM Tris-borate saline (TBS) buffer as follows: Add 10 uL of GST-MDM2 (640 ng/ml working solution) in reaction buffer to each well. Add 10 uL diluted compounds (1:5 dilution in reaction buffer) to each well, mix by shaking. Add 20 uL biotinylated p53 peptide (180 nM working solution) in reaction buffer to each well and mix on shaker. Incubate at 37° C. for 1 h. Add 20 uL streptavidin-APC and Eu-anti-GST antibody mixture (6 nM Eu-anti-GST and 60 nM streptavidin-APC working solution) in TBS buffer with 0.2% BSA, shake at room temperature for 30 minutes and read using a TRF-capable plate reader at 665 and 615 nm (Victor 5, Perkin ElmerWallac). If not specified, the reagents were purchased from Sigma Chemical Co.

$IC_{50}$s showing biological activity that applies to compounds of the subject matter of this invention ranges from about 0.005 uM to about 1 uM. Specific data for some examples are as follows:

| Example | $IC_{50}$ (μM) |
|---|---|
| 34 | 0.009 |
| 63 | 0.009 |
| 105 | 0.057 |
| 130 | 0.057 |
| 174 | 0.005 |
| 175 | 0.005 |
| 234 | 0.150 |
| 275 | 0.310 |
| 277 | 0.160 |
| 405 | 0.544 |

What is claimed:

1. A compound of formula I:

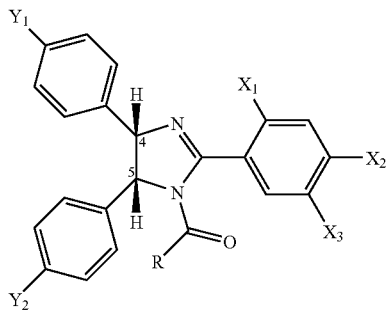

and the pharmaceutically acceptable salts and esters thereof, wherein $X_1$ is selected from the group consisting of:
  lower alkoxy,
  lower alkoxy substituted by trifluoromethyl or fluorine;
$X_2$ and $X_3$ are independently selected from the group consisting of:
  hydrogen,
  halogen,
  cyano,
  lower alkyl,
  lower alkoxy,
  —$NX_4X_5$,
  —$SO_2NX_4X_5$,
  —$C(O)NX_4X_5$,
  —$C(O)X_6$,
  —$SOX_6$, —$SO_2X_6$,
  —NC(O)-lower alkoxy
  —C≡C—$X_7$,
  with the proviso that $X_2$ and $X_3$ are both not hydrogen, lower alkyl, or lower alkoxy,
  with the proviso that when $X_2$ or $X_3$ is hydrogen, the other is not lower alkyl, lower alkoxy, or halogen,
$X_2$ and $X_3$ can be taken together to form a ring selected from 5 to 7 membered unsaturated rings, and 5 to 7 membered unsaturated rings that contain at least one hetero atom selected from S, N, and O;
$X_4$ and $X_5$ are independently selected from the group consisting of:
  hydrogen,
  lower alkyl,
  cycloalkyl,
  lower alkoxy,
  lower alkyl substituted with lower alkoxy,
  —$C(O)X_6$,
  —$SO_2X_6$,
$X_4$ and $X_5$ can be taken together to form a ring selected from 5 to 7 membered unsaturated rings, and 5 to 7 membered unsaturated rings that contain at least one hetero atom selected from S, N, and O;
$X_6$ is selected from the group consisting of:
  lower alkyl,
  morpholine,
  piperidine,
  piperazine,
  2-piperazinone,
  pyrrolidine;
$X_7$ is selected from the group consisting of:
  hydrogen,
  lower alkyl,
  trifluoromethyl;
$Y_1$ and $Y_2$ are independently selectect from the group consisting of:
  halogen,
  acetylene;
R is selected from the group consisting of:
  lower alkoxy,
  piperidinyl substituted by five or six membered heterocycle,
  piperidinyl substituted by hydroxy, —$CH_2OH$, or —$C(O)NH_2$,
  piperazinyl substituted by $R_1$,
  [1,4]diazepanyl substituted by $R_1$,
  $R_1$ is one or two substituents selected from the group consisting of:
    hydrogen,
    oxo, lower alkyl substituted by R$_2$,
—C(O)R$_3$,
—SO$_2$—R$_3$;
R$_2$ is selected from the group consisting of:
—SO$_2$-lower alkyl,
hydroxy,
lower alkoxy,
trifluoromethyl,
—NH—SO$_2$-lower alkyl,
—NH—C(O)-lower alkyl,
—C(O)-lower alkyl,
-cyano,
—C(O)R$_4$;
R$_3$ is selected from the group consisting of:
five membered heterocycle,
lower alkyl,
cycloalkyl,
lower alkyl substituted by lower alkoxy,
lower alkyl substituted by piperazinyl substituted by R$_1$,
—N-cycloalkyl,
lower alkoxy;
R$_4$ is selected from the group consisting of:
hydroxy,
lower alkoxy,
morpholine,
piperidine,
pyrrolidine,
piperazinyl substituted by R$_1$,
aziridine,
—NR$_5$R$_6$;
R$_5$ and R$_6$ are independently selected from the group consisting of:
hydrogen,
lower alkyl,
lower alkyl substituted by lower alkoxy or cyano,
lower alkoxy.

2. The compound of claim 1 wherein the two hydrogen of the imidazoline ring are in the cis configuration to each other.

3. The compound of claim 1 wherein Y$_1$ and Y$_2$ are selected from —Cl or —Br.

4. The compound of claim 3 wherein X$_1$ is ethoxy, isopropoxy, —OCH$_2$CF$_3$ or —OCH$_2$CH$_2$F.

5. The compound of claim 4 wherein X$_2$ is halogen, cyano, —SO$_2$NX$_4$X$_5$, —C(O)NX$_4$X$_5$, —C(O)X$_6$, —SO$_2$X$_6$, or —C≡C—X$_7$.

6. The compound of claim 4 wherein X$_3$ is —SO$_2$NX$_4$X$_5$, —C(O)NX$_4$X$_5$, or —SO$_2$X$_6$.

7. The compound of claim 6 wherein R is piperazinyl substituted by oxo or lower alkyl substituted by R$_2$ wherein R$_2$ is —SO$_2$-lower alkyl or —C(O)R$_4$.

8. The compound of claim 1 selected from the group consisting of:
4-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-3-ethoxy-benzonitrile;
5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-2-chloro-4-ethoxy-N-methyl-benzenesulfonamide;
5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-2-chloro-4-ethoxy-N,N-dimethyl-benzenesulfonamide;
5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-2-chloro-4-ethoxy-benzenesulfonamide;
4-[4,5-Bis-(4-chloro-phenyl)-1-(3-oxo-piperazine-1-carbonyl)-4,5-dihydro-1H-imidazol-2-yl]-3-ethoxy-benzonitrile;
4-{4,5-Bis-(4-chloro-phenyl)-1-[4-(2-hydroxy-ethyl)-piperazine-1-carbonyl]-4,5-dihydro-1H-imidazol-2-yl}-3-ethoxy-benzonitrile;
4-[4,5-Bis-(4-chloro-phenyl)-1-(4-pyrrolidin-1-yl-piperidine-1-carbonyl)-4,5-dihydro-1H-imidazol-2-yl]-3-ethoxy-benzonitrile;
3-[4,5-Bis-(4-chloro-phenyl)-1-(3-oxo-piperazine-1-carbonyl)-4,5-dihydro-1H-imidazol-2-yl]-4-ethoxy-N,N-dimethyl-benzenesulfonamide;
3-{4,5-Bis-(4-chloro-phenyl)-1-[4-(2-hydroxy-ethyl)-piperazine-1-carbonyl]-4,5-dihydro-1H-imidazol-2-yl}-4-ethoxy-N,N-dimethyl-benzenesulfonamide;
3-[4,5-Bis-(4-chloro-phenyl)-1-(4-pyrrolidin-1-yl-piperidine-1-carbonyl)-4,5-dihydro-1H-imidazol-2-yl]-4-ethoxy-N,N-dimethyl-benzenesulfonamide;
5-[4,5-Bis-(4-chloro-phenyl)-1-(3-oxo-piperazine-1-carbonyl)-4,5-dihydro-1H-imidazol-2-yl]-2-chloro-4-ethoxy-N,N-dimethyl-benzenesulfonamide and
5-{4,5-Bis-(4-chloro-phenyl)-1-[4-(2-morpholin-4-yl-2-oxo-ethyl)-piperazine-1-carbonyl]-4,5-dihydro-1H-imidazol-2-yl}-2-chloro-4-ethoxy-N,N-dimethyl-benzenesulfonamide.

9. The compound of claim 1 selected from the group consisting of:
5-[(4S,5R)-4,5-Bis-(4-chloro-phenyl)-1-(3-oxo-piperazine-1-carbonyl)-4,5-dihydro-1H-imidazol-2-yl]-4-ethoxy-2-fluoro-N,N-dimethyl-benzenesulfonamide;
2-(4-{(4S,5R)-4,5-Bis-(4-chloro-phenyl)-2-[2-ethoxy-4-methyl-5-(pyrrolidine-1-sulfonyl) phenyl]-4,5-dihydro-imidazole-1-carbonyl}-piperazin-1-yl)-1-morpholin-4-yl-ethanone hydrochloride;
[(4S,5R)-2-[4-Chloro-2-ethoxy-5-(pyrrolidine-1-sulfonyl)-phenyl]-4,5-bis-(4-chloro-phenyl)-4,5-dihydro-imidazol-1-yl]-[4-(2-methanesulfonyl-ethyl)-piperazin-1-yl]-methanone hydrochloride;
2-{4-[(4S,5R)-2-[4-Chloro-2-ethoxy-5-(piperidine-1-sulfonyl)-phenyl]-4,5-bis-(4chloro-phenyl)-4,5-dihydro-imidazole-1-carbonyl]-piperazin-1-yl}-1-morpholin-4-yl-ethanone hydrochloride;
[(4S,5R)-2-[4-Chloro-2-ethoxy-5-(piperidine-1-sulfonyl)-phenyl]-4,5-bis-(4-chloro-phenyl)-4,5-dihydro-imidazol-1-yl]-[4-(2-methanesulfonyl-ethyl)-piperazin-1-yl]-methanone hydrochloride;
4-[(4S,5R)-2-[4-Chloro-2-ethoxy-5-(piperidine-1-sulfonyl)-phenyl]-4,5-bis-(4-chloro-phenyl)-4,5-dihydro-imidazole-1-carbonyl]-piperazin-2-one hydrochloride;
2-{4-[(4S,5R)-2-[4-Chloro-2-ethoxy-5-(morpholine-4-sulfonyl)-phenyl]-4,5-bis-(4-chloro-phenyl)-4,5-dihydro-imidazole-1-carbonyl]-piperazin-1-yl}-1-morpholin-4-yl-ethanone hydrochloride;
[(4S,5R)-2-[4-Chloro-2-ethoxy-5-(morpholine-4-sulfonyl)-phenyl]-4,5-bis-(4-chloro-phenyl)-4,5-dihydro-imidazol-1-yl]-[4-(2-methanesulfonyl-ethyl)-piperazin-1-yl]-methanone hydrochloride;
4-[(4S,5R)-2-[4-Chloro-2-ethoxy-5-(morpholine-4-sulfonyl)-phenyl]-4,5-bis-(4-chloro-phenyl)-4,5-dihydro-imidazole-1-carbonyl]-piperazin-2-one hydrochloride;
{(4S,5R)-4,5-Bis-(4-chloro-phenyl)-2-[2-ethoxy-4-methyl-5-(pyrrolidine-1-sulfonyl)-phenyl]-4,5-dihydroimidazol-1-yl}-[4-(2-methanesulfonyl-ethyl)-piper-azin-1-yl]-methanone hydrochloride and 2-(4-{(4S,5R)-4,5-Bis-(4-chloro-phenyl)-2-[2-ethoxy-4-methyl-5-(piperidine-1-sulfonyl) phenyl]-4,5-dihydro-imidazole-1-carbonyl}-piperazin-1-yl)-1-morpholin-4-yl-ethanone hydrochloride.

10. The compound of claim 1 selected from the group consisting of:

5-[(4S,5R)-4,5-Bis-(4-chloro-phenyl)-1-(4-ethanesulfo-nyl-piperazine-1-carbonyl)-4,5-dihydro-1H-imidazol-2-yl]-N-tert-butyl-2-chloro-4-ethoxy-benzenesulfonamide hydrochloride;

5-{(4S,5R)-4,5-Bis-(4-chloro-phenyl)-1-[4-(3,5-dim-ethyl-isoxazole-4-carbonyl)-piperazine-1-carbonyl]-4,5-dihydro-1H-imidazol-2-yl}-2-chloro-4-ethoxy-ben-zenesulfonamide;

N-tert-Butyl-2-{4-[(4S,5R)-2-(4-chloro-2-ethoxy-5-sul-famoyl-phenyl)-4,5-bis-(4-chloro-phenyl) 4,5-dihydro-imidazole-1-carbonyl]-piperazin-1-yl}-acetamide;

5-[(4S,5R)-4,5-Bis-(4-chloro-phenyl)-1-(3-oxo-pipera-zine-1-carbonyl)-4,5-dihydro-1H-imidazol-2-yl]-2-chloro-4-ethoxy-benzenesulfonamide;

5-{(4S,5R)-4,5-Bis-(4-chloro-phenyl)-1-[4-(2-methane-sulfonyl-ethyl)-piperazine-1-carbonyl]-4,5-dihydro-1H-imidazol-2-yl}-2-chloro-4-ethoxy-benzenesulfona-mide;

2-{4-[(4S,5R)-2-(4-Chloro-2-ethoxy-5-sulfamoyl-phe-nyl)-4,5-bis-(4-chloro-phenyl)-4,5-dihydro-imidazole-1-carbonyl]-piperazin-1-yl}-acetamide;

2-{4-[(4S,5R)-2-(4-Chloro-2-ethoxy-5-sulfamoyl-phe-nyl)-4,5-bis-(4-chloro-phenyl)-4,5-dihydro-imidazole-1-carbonyl]-piperazin-1-yl}-N-isopropyl-N-methyl-ac-etamide;

5-[(4S,5R)-4,5-Bis-(4-chloro-phenyl)-1-(4-ethanesulfo-nyl-piperazine-1-carbonyl)-4,5-dihydro-1H-imidazol-2-yl]-2-chloro-4-ethoxy-benzenesulfonamide;

4-{(4S,5R)-4,5-Bis-(4-chloro-phenyl)-1-[4-(2-methane-sulfonyl-ethyl)-piperazine-1-carbonyl]-4,5-dihydro-1H-imidazol-2-yl}-N-tert-butyl-3-ethoxy-benzamide;

N-tert-Butyl-4-[(4S,5R)-1-(4-carbamoylmethyl-pipera-zine-1-carbonyl)-4,5-bis-(4-chloro-phenyl)-4,5-dihy-dro-1H-imidazol-2-yl]-3-ethoxy-benzamide and {(4S,5R)-4,5-Bis-(4-chloro-phenyl)-2-[2-ethoxy-4-(pip-eridine-1-carbonyl)-phenyl]-4,5-dihydro-imidazol-1-yl}-[4-(3,5-dimethyl-isoxazole-4-carbonyl)-piperazin-1-yl]-methanone.

11. A pharmaceutical composition which comprises at least one compound of the formula I:

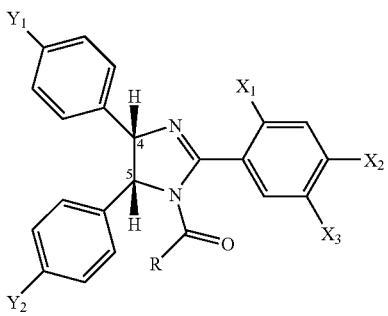

I and the pharmaceutically acceptable salts and esters thereof, wherein $X_1$ is selected from the group consisting of:
lower alkoxy,
lower alkoxy substituted by trifluoromethyl or fluorine;

$X_2$ and $X_3$ are independently selected from the group consisting of:
hydrogen,
halogen,
cyano,
lower alkyl,
lower alkoxy,
—$NX_4X_5$,
—$SO_2NX_4X_5$,
—$C(O)NX_4X_5$,
—$C(O)X_6$,
—$SOX_6$, —$SO_2X_6$,
—NC(O)-lower alkoxy
—C≡C—$X_7$,
with the proviso that $X_2$ and $X_3$ are both not hydrogen, lower alkyl, or lower alkoxy,
with the proviso that when $X_2$ or $X_3$ is hydrogen, the other is not lower alkyl, lower alkoxy, or halogen, $X_2$ and $X_3$ can be taken together to form a ring selected from 5 to 7 membered unsaturated rings, and 5 to 7 membered unsaturated rings that contain at least one hetero atom selected from S, N, and O;

$X_4$ and $X_5$ are independently selected from the group consisting of:
hydrogen,
lower alkyl,
cycloalkyl,
lower alkoxy,
lower alkyl substituted with lower alkoxy,
—$C(O)X_6$,
—$SO_2X_6$, $X_4$ and $X_5$ can be taken together to form a ring selected from 5 to 7 membered unsaturated rings, and 5 to 7 membered unsaturated rings that contain at least one hetero atom selected from S, N, and O;

$X_6$ is selected from the group consisting of:
lower alkyl,
morpholine,
piperidine,
piperazine,
2-piperazinone,
pyrrolidine;

$X_7$ is selected from the group consisting of:
hydrogen,
lower alkyl,
trifluoromethyl;

$Y_1$ and $Y_2$ are independently selectect from the group consisting of:
halogen,
acetylene;

R is selected from the group consisting of:
lower alkoxy,
piperidinyl substituted by five or six membered heterocycle,
piperidinyl substituted by hydroxy, —$CH_2OH$, or —$C(O)NH_2$,
piperazinyl substituted by $R_1$,
[1,4]diazepanyl substituted by $R_1$, $R_1$ is one or two substituents selected from the group consisting of:
hydrogen,
oxo, lower alkyl substituted by $R_2$,
—C(O)$R_3$,
—SO$_2$—$R_3$;
$R_2$ is selected from the group consisting of:
—SO$_2$-lower alkyl,
hydroxy,
lower alkoxy,
trifluoromethyl,
—NH—SO$_2$-lower alkyl,
—NH—C(O)-lower alkyl,
—C(O)-lower alkyl,
-cyano,
—C(O)$R_4$;
$R_3$ is selected from the group consisting of:
five membered heterocycle,
lower alkyl,
cycloalkyl,
lower alkyl substituted by lower alkoxy,
lower alkyl substituted by piperazinyl substituted by $R_1$,
—N-cycloalkyl,
lower alkoxy;
$R_4$ is selected from the group consisting of:
hydroxy,
lower alkoxy,
morpholine,
piperidine,
pyrrolidine,
piperazinyl substituted by $R_1$,
aziridine,
—N$R_5R_6$;
$R_5$ and $R_6$ are independently selected from the group consisting of:
hydrogen,
lower alkyl,
lower alkyl substituted by lower alkoxy or cyano,
lower alkoxy
together with a pharmaceutically acceptable carrier or excipient.

12. A compound of claim 1 selected from the group consisting of
5-{4,5-Bis-(4-chloro-phenyl)-1-[4-(2-hydroxy-ethyl)-3-oxo-piperazine-1-carbonyl]-4,5-dihydro-1H-imidazol-2-yl}-2-chloro-4-ethoxy-N,N-dimethyl-benzenesulfonamide;
5-[4,5-Bis-(4-chloro-phenyl)-1-(3-oxo-piperazine-1-carbonyl)-4,5-dihydro-1H-imidazol-2-yl]-4-ethoxy-2-methoxy-N,N-dimethyl-benzenesulfonamide;
5-{4,5-Bis-(4-chloro-phenyl)-1-[4-(2-hydroxy-ethyl)-piperazine-1-carbonyl]-4,5-dihydro-1H-imidazol-2-yl}-4-ethoxy-2-methoxy-N,N-dimethyl-benzenesulfonamide;
2-{4-[4,5-Bis-(4-chloro-phenyl)-2-(5-dimethylsulfamoyl-2-ethoxy-4-methoxy-phenyl)-4,5-dihydro-imidazole-1-carbonyl]-piperazin-1-yl}-N,N-dimethyl-acetamide;
5-{4,5-Bis-(4-chloro-phenyl)-1-[4-(2-methanesulfonyl-ethyl)-piperazine-1-carbonyl]-4,5-dihydro-1H-imidazol-2-yl}-4-ethoxy-2-methoxy-N,N-dimethyl-benzenesulfonamide;
4-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-3-ethoxy-benzonitrile;
5-{(4S,5R)-4,5-Bis-(4-chloro-phenyl)-1-[4-(2-hydroxy-ethyl)-piperazine-1-carbonyl]-4,5-dihydro-1H-imidazol-2-yl}-2-chloro-4-ethoxy-N,N-dimethyl-benzenesulfonamide;
4-[4,5-Bis-(4-chloro-phenyl)-2-(2-ethoxy-4-methanesulfinyl-phenyl)-4,5-dihydro-imidazole-1-carbonyl]-piperazin-2-one;
4-[4,5-Bis-(4-chloro-phenyl)-2-(2-ethoxy-4-methanesulfonyl-phenyl)-4,5-dihydro-imidazole-1-carbonyl]-piperazin-2-one;
2-{4-[4,5-Bis-(4-chloro-phenyl)-2-(2-ethoxy-4-methanesulfinyl-phenyl)-4,5-dihydro-imidazole-1-carbonyl]-piperazin-1-yl}-N,N-dimethyl-acetamide and
2-{4-[4,5-Bis-(4-chloro-phenyl)-2-(2-ethoxy-4-methanesulfonyl-phenyl)-4,5-dihydro-imidazole-1-carbonyl]-piperazin-1-yl}-N N-dimethyl-acetamide.

13. A compound of claim 1 selected from the group consisting of
[4,5-Bis-(4-chloro-phenyl)-2-(2-ethoxy-4-methanesulfinyl-phenyl)-4,5-dihydro-imidazol-1-yl]-[4-(2-methanesulfonyl-ethyl)-piperazin-1-yl]-methanone;
[4,5-Bis-(4-chloro-phenyl)-2-(2-ethoxy-4-methanesulfonyl-phenyl)-4,5-dihydro-imidazol-1-yl]-[4-(2-methanesulfonyl-ethyl)-piperazin-1-yl]-methanone;
[4,5-Bis-(4-chloro-phenyl)-2-(2-ethoxy-4-methanesulfinyl-phenyl)-4,5-dihydro-imidazol-1-yl]-[4-(2-hydroxy-ethyl)-piperazin-1-yl]-methanone;
[4,5-Bis-(4-chloro-phenyl)-2-(2-ethoxy-4-methanesulfonyl-phenyl)-4,5-dihydro-imidazol-1-yl]-[4-(2-hydroxy-ethyl)-piperazin-1-yl]-methanone;
1-[(4S,5R)-4,5-Bis-(4-chloro-phenyl)-2-(4-cyano-2-(4cyano-2-ethoxy-phenyl)-4,5-dihydro-imidazole-1-carbonyl]-piperidine-4-carboxylic acid amide;
4-{(4S,5R)-4,5-Bis-(4-chloro-phenyl)-1-[4-(3,5-dimethyl-isoxazole-4-carbonyl)-piperazine-1-carbonyl]-4,5-dihydro-1H-imidazol-2-yl}-3-ethoxy-benzonitrile;
4-[(4S,5R)-4,5-Bis-(4-chloro-phenyl)-1-(4-cyclopropanecarbonyl-piperazine-1-carbonyl)-4,5-dihydro-1H-imidazol-2-yl]-3-ethoxy-benzonitrile;
4-{(4S,5R)-4,5-Bis-(4-chloro-phenyl)-1-[4-(3-methyl-but-2-enoyl)-piperazine-1-carbonyl]-4,5-dihydro-1H-imidazol-2-yl}-3-ethoxy-benzonitrile;
4-{(4S,5R)-4,5-Bis-(4-chloro-phenyl)-1-[4-(3,5-dimethyl-isoxazole-4-sulfonyl)-piperazine-1-carbonyl]-4,5-dihydro-1H-imidazol-2-yl}-3-ethoxy-benzonitrile;
4-{(4S,5R)-4,5-Bis-(4-chloro-phenyl)-1-[4-(2-hydroxy-ethyl)-piperazine-1-carbonyl]-4,5-dihydro-1H-imidazol-2-yl}-3-ethoxy-benzonitrile and
4-{(4S,5R)-4,5-Bis-(4-chloro-phenyl)-1-[4-(2-cyano-ethyl)-piperazine-1-carbonyl]-4,5-dihydro-1H-imidazol-2-yl}-3-ethoxy-benzonitrile.

14. A compound of claim 1 selected from the group consisting of
4-{(4S,5R)-4,5-Bis-(4-chloro-phenyl)-1-[4-(2-methoxy-ethyl)-piperazine-1-carbonyl]-4,5-dihydro-1H-imidazol-2-yl}-3-ethoxy-benzonitrile;
4-((4S,5R)-4,5-Bis-(4-chloro-phenyl)-1-{4-[2-(3-oxo-piperazin-1-yl)-acetyl]-piperazine-1-carbonyl}-4,5-dihydro-1H-imidazol-2-yl)-3-ethoxy-benzonitrile;
1-[(4S,5R)-4,5-Bis-(4-chloro-phenyl)-2-(4-cyano-2-ethoxy-phenyl)-4,5-dihydro-imidazole-1-carbonyl]-piperidine-3-carboxylic acid amide;
4-[(4S,5R)-1-{4-[2-(4-Acetyl-piperazin-1-yl)-2-oxo-ethyl]-piperazine-1-carbonyl}-4,5-bis-(4-chloro-phenyl)-4,5-dihydro-1H-imidazol-2-yl]-3-ethoxy-benzonitrile;
2-{4-[(4S,5R)-4,5-Bis-(4-chloro-phenyl)-2-(4-cyano-2-ethoxy-phenyl)-4,5-dihydro-imidazole-1-carbonyl]-piperazin-1-yl}-N-(2-methoxy-1-methyl-ethyl)-acetamide;

4-[(4S,5R)-4,5-Bis-(4-chloro-phenyl)-1-(4-hydroxym-ethyl-piperidine-1-carbonyl)-4,5-dihydro-1H-imidazol-2-yl]-3-ethoxy-benzonitrile;

4-[(4S,5R)-4,5-Bis-(4-chloro-phenyl)-1-(3-hydroxy-piperidine-1-carbonyl)-4,5-dihydro-1H-imidazol-2-yl]-3-ethoxy-benzonitrile;

4-[(4S,5R)-4,5-Bis-(4-chloro-phenyl)-1-(3-oxo-piperazine-1-carbonyl)-4,5-dihydro-1H-imidazol-2-yl]-3-ethoxy-benzonitrile;

2-{4-[(4S,5R)-4,5-Bis-(4-chloro-phenyl)-2-(4-cyano-2-ethoxy-phenyl)-4,5-dihydro-imidazole-1-carbonyl]-piperazin-1-yl}-N,N-dimethyl-acetamide;

4-{(4S,5R)-4,5-Bis-(4-chloro-phenyl)-1-[4-(2-oxo-2-piperidin-1-yl-ethyl)-piperazine-1-carbonyl]-4,5-dihydro-1H-imidazol-2-yl}-3-ethoxy-benzonitrile;

4-[(4S,5R)-4,5-Bis-(4-chloro-phenyt)-1-(4-ethanesulfonyl-piperazine-1-carbonyl)-4,5-dihydro-1H-imidazol-2-yl]-3-ethoxy-benzonitrile and 1-[4,5-Bis-(4-chloro-phenyl)-2-(5-dimethylsulfamoyl-2-ethoxy-phenyl)-4,5-dihydro-imidazole-1-carbonyl]-piperidine-4-carboxylic acid amide.

15. A compound of claim 1 selected from the group consisting of

3-{4,5-Bis-(4-chloro-phenyl)-1-[4-(3,5S-dimethyl-isoxazole-4-carbonyl)-piperazine-1-carbonyl]-4,5-dihydro-1H-imidazol-2-yl}-4-ethoxy-N,N-dimethyl-benzenesulfonamide;

3-[4,5-Bis-(4-chloro-phenyl)-1-(4-cyclopropanecarbonyl-piperazine-1-carbonyl)-4,5-dihydro-1H-imidazol-2-yl]-4-ethoxy-N,N-dimethyl-benzenesulfonamide;

3-{4,5-Bis-(4-chloro-phenyl)-1-[4-(3-methyl-but-2-enoyl)-piperazine-1-carbonyl]-4,5-dihydro-1H-imidazol-2-yl}-4-ethoxy-N,N-dimethyl-benzenesulfonamide;

3-{4,5-Bis-(4-chloro-phenyl)-1-[4-(3,5-dimethyl-isoxazole-4-sulfonyl)-piperazine-1-carbonyl]-4,5-dihydro-1H-imidazol-2-yl}-4-ethoxy-N,N-dimethyl-benzenesuifonamide;

3-{4,5-Bis-(4-chloro-phenyl)-1-[4-(2-cyano-ethyl)-piperazine-1-carbonyl]-4,5-dihydro-1H-imidazol-2-yl}-4-ethoxy-N,N-dimethyl-benzenesulfonamide;

3-{4,5-Bis-(4-chloro-phenyl)-1-[4-(2-methoxy-ethyl)-piperazine-1-carbonyl]-4,5-dihydro-1H-imidazol-2-yl}-4-ethoxy-N,N-dimethyl-benzenesulfonamide;

3-(4,5-Bis-(4-chloro-phenyl)-1-{4-[2-(3-oxo-piperazin-1-yl)-acetyl]-piperazine-1-carbonyl}-4,5-dihydro-1H-imidazol-2-yl)-4-ethoxy-N,N-dimethyl-benzenesulfonamide;

2-{4-[4,5-Bis-(4-chloro-phenyl)-2-(5-dimethylsulfamoyl-2-ethoxy-phenyl)-4,5-dihydro-imidazole-1-carbonyl]-piperazin-1-yl}-N-methyl-acetamide;

1-[4,5-Bis-(4-chloro-phenyl)-2-(5-dimethylsulfamoyl-2-ethoxy-phenyl)-4,5-dihydro-imidazole-1-carbonyl]-piperidine-3-carboxylic acid amide;

3-[1-{4-[2-(4-Acetyl-piperazin-1-yl)-2-oxo-ethyl]-piperazine-1-carbonyl}-4,5-bis-(4-chloro-phenyl)-4,5-dihydro-1H-imidazol-2-yl]-4-ethoxy-N,N-dimethyl-benzenesuifonamide;

2-{4-[4,5-Bis-(4-chloro-phenyl)-2-(5-dimethylsulfamoyl-2-ethoxy-phenyl)-4,5-dihydro-imidazole-1-carbonyl]-piperazin-1-yl}-N-(2-methoxy-1-methyl-ethyl)-acetamide and 3-[4,5-Bis-(4-chloro-phenyl)-1-(4-hydroxymethyl-piperidine-1-carbonyl)-4,5-dihydro-1H-imidazol-2-yl]-4-ethoxy-N,N-dimethyl-benzenesulfonamide.

16. A compound of claim 1 selected from the group consisting of

3-[4,5-Bis-(4-chloro-phenyl)-1-(3-hydroxy-piperidine-1-carbonyl)-4,5-dihydro-1H-imidazol-2-yl]-4-ethoxy-N,N-dimethyl-benzenesulfonamide;

2-{4-[4,5-Bis-(4-chloro-phenyl)-2-(5-dimethylsulfamoyl-2-ethoxy-phenyl)-4,5-dihydro-imidazole-1-carbonyl]-piperazin-1-yl}-N,N-dimethyl-acetamide;

3-{4,5-Bis-(4-chloro-phenyl)-1-[4-(2-morpholin-4-yl-2-oxo-ethyl)-piperazine-1-carbonyl]-4,5-dihydro-1H-imidazol-2-yl}-4-ethoxy-N,N-dimethyl-benzenesulfonamide; 3-{4,5-Bis-(4-chloro-phenyl)-1-[4-(2-oxo-2-piperidin-1-yl-ethyl)-piperazine-1-carbonyl]-4,5-dihydro-1H-imidazol-2-yl}-4-ethoxy-N,N-dimethyl-benzenesulfonamide;

3-[4,5-Bis-(4-chloro-phenyl)-1-(4-ethanesulfonyl-piperazine-1-carbonyl)-4,5-dihydro-1H-imidazol-2-yl]-4-ethoxy-N,N-dimethyl-benzenesulfonamide;

3-[4,5-Bis-(4-chloro-phenyl)-1-(3-oxo-piperazine-1-carbonyl)-4,5-dihydro-1H-imidazol-2-yl]-4-ethoxy-N-isobutyl-N-methyl-benzenesulfonamide;

3-{4,5-Bis-(4-chloro-phenyl)-1-[4-(2-methanesulfonyl-ethyl)-piperazine-1-carbonyl]-4,5-dihydro-1H-imidazol-2-yl}-4-ethoxy-N-isobutyl-N-methyl-benzenesulfonamide;

2-(4-{4,5-Bis-(4-chloro-phenyl)-2-[2-ethoxy-5-(isobutyl-methyl-sulfamoyl)-phenyl]-4,5-dihydro-imidazole-1-carbonyl}-piperazin-1-yl)-N,N-dimethyl-acetamide;

3-[4,5-Bis-(4-chloro-phenyl)-1-(4-ethanesulfonyl-piperazine-1-carbonyl)-4,5-dihydro-1H-imidazol-2-yl]-4-ethoxy-N-isobutyl-N-methyl-benzenesulfonamide;

3-(4,5-Bis-(4-chloro-phenyl)-1-{4-[2-(3-oxo-piperazin-1-yl)-acetyl]-piperazine-1-carbonyl}-4,5-dihydro-1H-imidazol-2-yl)-4-ethoxy-N-isobutyl-N-methyl-benzenesulfonamide and 2-(4-{4,5-Bis-(4-chloro-phenyl)-2-[2-ethoxy-5-(isobutyl-methyl-sulfamoyl)-phenyl]-4,5-dihydro-imidazole-1-carbonyl}-piperazin-1-yl)-N-(2-methoxy-1-methyl-ethyl)-acetamide.

17. A compound of claim 1 selected from the group consisting of

3-{4,5-Bis-(4-chloro-phenyl)-1-[4-(2-hydroxy-ethyl)-piperazine-1-carbonyl]-4,5-dihydro-1H-imidazol-2-yl}-4-ethoxy-N-isobutyl-N-methyl-benzenesulfonamide;

2-(4-{4,5-Bis-(4-chloro-phenyl)-2-[2-ethoxy-5-(isobutyl-methyl-sulfa moyl)-phenyl]-4,5-dihydro-imidazole-1-carbonyl}-piperazin-1-yl)-N-methyl-acetamide;

3-{4,5-Bis-(4-chloro-phenyl)-1-[4-(2-morpholin-4-yl-2-oxo-ethyl)-piperazine-1-carbonyl]-4,5-dihydro-1H-imidazol-2-yl}-4-ethoxy-N-isobutyl-N-methyl-benzenesulfonamide;

3-[4,5-Bis-(4-chloro-phenyl)-1-(4-cyclopropanecarbonyl-piperazine-1-carbonyl)-4,5-dihydro-1H-imidazol-2-yl]-4-ethoxy-N-isobutyl-N-methyl-benzenesulfonamide;

3-{4,5-Bis-(4-chloro-phenyl)-1-[4-(2-methoxy-ethyl)-piperazine-1-carbonyl]-4,5-dihydro-1H-imidazol-2-yl}-4-ethoxy-N-isobutyl-N-methyl-benzenesulfonamide;

3-[4,5-Bis-(4-chloro-phenyl)-1-(3-oxo-piperazine-1-carbonyl)-4,5-dihydro-1H-imidazol-2-yl]-4-ethoxy-N,N-bis-(2-methoxy-ethyl)-benzenesulfonamide;

3-{4,5-Bis-(4-chloro-phenyl)-1-[4-(2-methanesulfonyl-ethyl)-piperazine-1-carbonyl]-4,5-dihydro-1H-imidazol-2-yl}-4-ethoxy-N,N-bis-(2-methoxy-ethyl)-benzenesulfonamide;

2-{4-[2-{5-[Bis-(2-methoxy-ethyl)-sulfamoyl]-2-ethoxy-phenyl}-4,5-bis-(4-chloro-phenyl)-4,5-dihydro-imidazole-1-carbonyl]-piperazin-1-yl}-N,N-dimethyl-acetamide;

3-(4,5-Bis-(4-chloro-phenyl)-1-{4-[2-(3-oxo-piperazin-1-yl)-acetyl]-piperazine-1-carbonyl}-4,5-dihydro-1H-imidazol-2-yl)-4-ethoxy-N,N-bis-(2-methoxy-ethyl)-benzenesulfonamide;

2-{4-[2-{5-[Bis-(2-methoxy-ethyl)-sulfamoyl]-2-ethoxy-phenyl}-4,5-bis-(4-chloro-phenyl)-4,5-dihydro-imidazole-1-carbonyl]-piperazin-1-yl}-N-(2-methoxy-1-methyl-ethyl)-acetamide and 2-{4-[2-{5-[Bis-(2-methoxy-ethyl)-sulfamoyl]-2-ethoxy-phenyl}-4,5-bis-(4-chloro-phenyl)-4,5-dihydro-imidazole-1-carbonyl]-piperazin-1-yl}-N-methyl-acetamide.

18. A compound of claim 1 selected from the group consisting of

3-{4,5-Bis-(4-chloro-phenyl)-1-[4-(2-morpholin-4-yl-2-oxo-ethyl)-piperazine-1-carbonyl]-4,5-dihydro-1H-imidazol-2-yl}-4-ethoxy-N,N-bis-(2-methoxy-ethyl)-benzenesulfonamide;

3-[4,5-Bis-(4-chloro-phenyl)-1-(4-cyclopropanecarbonyl-piperazine-1-carbonyl)-4,5-dihydro-1H-imidazol-2-yl]-4-ethoxy-N,N-bis-(2-methoxy-ethyl)-benzenesulfonamide;

4-{4,5-Bis-(4-chloro-phenyl)-2-[2-ethoxy-5-(piperidine-1-sulfonyl)-phenyl]-4,5-dihydro-imidazole-1-carbonyl}-piperazin-2-one;

{4,5-Bis-(4-chloro-phenyl)-2-[2-ethoxy-5-(piperidine-1-sulfonyl)-phenyl]-4,5-dihydro-imidazol-1-yl}-[4-(2-methanesulfonyl-ethyl)-piperazin-1-yl]-methanone;

2-(4-{4,5-Bis-(4-chloro-phenyl)-2-[2-ethoxy-5-(piperidine-1-sulfonyl)-phenyl]-4,5-dihydro-imidazole-1-carbonyl}-piperazin-1-yl)-N,N-dimethyl-acetamide;

{4,5-Bis-(4-chloro-phenyl)-2-[2-ethoxy-5-(piperidine-1-sulfonyl)-phenyl]-4,5-dihydro-imidazol-1-yl}-(4-ethanesulfonyl-piperazin-1-yl)-methanone;

4-[2-(4-{4,5-Bis-(4-chloro-phenyl)-2-[2-ethoxy-5-(piperidine-1-sulfonyl)-phenyl]-4,5-dihydro-imidazole-1-carbonyl}-piperazin-1-yl)-2-oxo-ethyl]-piperazin-2-one;

2-(4-{4,5-Bis-(4-chloro-phenyl)-2-[2-ethoxy-5-(piperidine-1-sulfonyl)-phenyl]-4,5-dihydro-imidazole-1-carbonyl}-piperazin-1-yl)-N-(2-methoxy-1-methyl-ethyl)-acetamide;

{4,5-Bis-(4-chloro-phenyl)-2-[2-ethoxy-5-(piperidine-1-sulfonyl)-phenyl]-4,5-dihydro-imidazol-1-yl}-[4-(2-hydroxy-ethyl)-piperazin-1-yl]-methanone;

2-(4-{4,5-Bis-(4-chloro-phenyl)-2-[2-ethoxy-5-(piperidine-1-sulfonyl)-phenyl]-4,5-dihydro-imidazole-1-carbonyl}-piperazin-1-yl)-N-methyl-acetamide and 2-(4-{4,5-Bis-(4-chloro-phenyl)-2-[2-ethoxy-5-(piperidine-1-sulfonyl)-phenyl]-4,5-dihydro-imidazole-1-carbonyl}-piperazin-1-yl)-1-morpholin-4-yl-ethanone.

19. A compound of claim 1 selected from the group consisting of

{4,5-Bis-(4-chloro-phenyl)-2-[2-ethoxy-5-(piperidine-1-sulfonyl)-phenyl]-4,5-dihydro-imidazol-1-yl}-(4-cyclopropanecarbonyl-piperazin-1-yl)-methanone;

3-[4,5-Bis-(4-chloro-phenyl)-1-(3-oxo-piperazine-1-carbonyl)-4,5-dihydro-1H-imidazol-2-yl]-4-ethoxy-N-(2-methoxy-1-methyl-ethyl)-benzenesulfonamide;

3-{4,5-Bis-(4-chloro-phenyl)-1-[4-(2-methanesulfonyl-ethyl)-piperazine-1-carbonyl]-4,5-dihydro-1H-imidazol-2-yl}-4-ethoxy-N-(2-methoxy-1-methyl-ethyl)-benzenesulfonamide;

2-(4-{4,5-Bis-(4-chloro-phenyl)-2-[2-ethoxy-5-(2-methoxy-1-methyl-ethylsulfamoyl)-phenyl]-4,5-dihydro-imidazole-1-carbonyl}-piperazin-1-yl)-N,N-dimethyl-acetamide;

3-[4,5-Bis-(4-chloro-phenyl)-1-(4-ethanesulfonyl-piperazine-1-carbonyl)-4,5-dihydro-1H-imidazol-2-yl]-4-ethoxy-N-(2-methoxy-1-methyl-ethyl)-benzenesulfonamide;

3-(4,5-Bis-(4-chloro-phenyl)-1-{4-[2-(3-oxo-piperazin-1-yl)-acetyl]-piperazine-1-carbonyl}-4,5-dihydro-1H-imidazol-2-yl)-4-ethoxy-N-(2-methoxy-1-methyl-ethyl)-benzenesulfonamide;

2-(4-{4,5-Bis-(4-chloro-phenyl)-2-[2-ethoxy-5-(2-methoxy-1-methyl-ethylsulfamoyl)-phenyl]-4,5-dihydro-imidazole-1-carbonyl}-piperazin-1-yl)-N-(2-methoxy-1-methyl-ethyl)-acetamide;

3-{4,5-Bis-(4-chloro-phenyl)-1-[4-(2-hydroxy-ethyl)-piperazine-1-carbonyl]-4,5-dihydro-1H-imidazol-2-yl}-4-ethoxy-N-(2-methoxy-1-methyl-ethyl)-benzenesulfonamide;

2-(4-{4,5-Bis-(4-chloro-phenyl)-2-[2-ethoxy-5-(2-methoxy-1-methyl-ethylsulfamoyl)-phenyl]-4,5-dihydro-imidazole-1-carbonyl}-piperazin-1-yl)-N-methyl-acetamide;

4-{4,5-Bis-(4-chloro-phenyl)-2-[2-ethoxy-5-(pyrrolidine-1-sulfonyl)-phenyl]-4,5-dihydro-imidazole-1-carbonyl}-piperazin-2-one and {4,5-Bis-(4-chloro-phenyl)-2-[2-ethoxy-5-(pyrrolidine-1-sulfonyl)-phenyl]-4,5-dihydro-imidazol-1-yl}-[4-(2-methanesulfonyl-ethyl)-piperazin-1-yl]-methanone.

20. A compound of claim 1 selected from the group consisting of 2-(4-{4,5-Bis-(4-chloro-phenyl)-2-[2-ethoxy-5-(pyrrolidine-1-sulfonyl)-phenyl]-4,5-dihydro-imidazole-1-carbonyl}-piperazin-1-yl)-N,N-dimethyl-acetamide;

4-[2-(4-{4,5-Bis-(4-chloro-phenyl)-2-[2-ethoxy-5-(pyrrolidine-1-sulfonyl)-phenyl]-4,5-dihydro-imidazole-1-carbonyl}-piperazin-1-yl)-2-oxo-ethyl]-piperazin-2-one;

2-(4-{4,5-Bis-(4-chloro-phenyl)-2-[2-ethoxy-5-(pyrrolidine-1-sulfonyl)-phenyl]-4,5-dihydro-imidazole-1-carbonyl}-piperazin-1-yl)-N-(2-methoxy-1-methyl-ethyl)-acetamide;

{4,5-Bis-(4-chloro-phenyl)-2-[2-ethoxy-5-(pyrrolidine-1-sulfonyl)-phenyl]-4,5-dihydro-imidazol-1-yl}-[4-(2-hydroxy-ethyl)-piperazin-1-yl]-methanone;

5-[4,5-Bis-(4-chloro-phenyl)-1-(3-oxo-piperazine-1-carbonyl)-4,5-dihydro-1H-imidazol-2-yl]-4-ethoxy-2-fluoro-N,N-dimethyl-benzenesulfonamide;

5-{4,5-Bis-(4-chloro-phenyl)-1-[4-(2-hydroxy-ethyl)-piperazine-1-carbonyl]-4,5-dihydro-1H-imidazol-2-yl}-4-ethoxy-2-fluoro-N,N-dimethyl-benzenesulfonamide;

2-{4-[4,5-Bis-(4-chloro-phenyl)-2-(5-dimethylsulfamoyl-2-ethoxy-4-fluoro-phenyl)-4,5-dihydro-imidazole-1-carbonyl]-piperazin-1-yl}-N,N-dimethyl-acetamide;

5-{4,5-Bis-(4-chloro-phenyl)-1-[4-(2-methanesulfonyl-ethyl)-piperazine-1-carbonyl]-4,5-dihydro-1H-imidazol-2-yl}-4-ethoxy-2-fluoro-N,N-dimethyl-benzenesulfonamide;

4-[4,5-Bis-(4-chloro-phenyl)-2-(7-ethoxy-2-methyl-1,1-dioxo-1,2 3,4-tetrahydro-1λ6-benzo[b][1,4,5]oxathiazepin-8-yl)-4,5-dihydro-imidazole-1-carbonyl]-piperazin-2-one;

[4,5-Bis-(4-chloro-phenyl)-2-(7-ethoxy-2-methyl-1,1-dioxo-1,2,3,4-tetrahydro-1λ6-benzo[b][1,4,5]oxathiazepin-8-yl)-4,5-dihydro-imidazol-1-yl]-[4-(2-methane-sulfonyl-ethyl)-piperazin-1-yl]-methanone and 2-{4-[4,5-Bis-(4-chloro-phenyl)-2-(7-ethoxy-2-methyl-1,1-dioxo-1,2,3,4-tetrahydro-1λ6-benzo[b][1,4,5]oxathi-azepin-8-yl)-4,5-dihydro-imidazole-1-carbonyl]-piper-azin-1-yl}-1-morpholin-4-yl-ethanone.

21. A compound of claim 1 selected from the group consisting of

2-{4-[(4S,5R)-4,5-Bis-(4-chloro-phenyl)-2-(5-dimethyl-sulfamoyl-2-ethoxy-4-fluoro-phenyl)-4,5-dihydro-imi-dazole-1-carbonyl]-piperazin-1-yl}-N,N-dimethyl-ac-etamide hydrochloride;

5-{(4S,5R)-4,5-Bis-(4-chloro-phenyl)-1-[4-(2-methane-sulfonyl-ethyl)-piperazine-1-carbonyl]-4,5-dihydro-1H-imidazol-2-yl}-4-ethoxy-2-fluoro-N,N-dimethyl-benzenesulfonamide hydrochloride;

5-{(4S,5R)-4,5-Bis-(4-chloro-phenyl)-1-[4-(2-morpho-lin-4-yl-2-oxo-ethyl)-piperazine-1-carbonyl]-4,5-dihy-dro-1H-imidazol-2-yl}-4-ethoxy-2-fluoro-N,N-dim-ethyl-benzenesulfonamide hydrochloride;

4-[4,5-Bis-(4-chloro-phenyl)-1-(3-oxo-piperazine-1-car-bonyl)-4,5-dihydro-1H-imidazol-2-yl]-3-ethoxy-N,N-dimethyl-benzenesulfonamide hydrochloride;

4-{4,5-Bis-(4-chloro-phenyl)-1-[4-(2-methanesulfonyl-ethyl)-piperazine-1-carbonyl]-4,5-dihydro-1H-imida-zol-2-yl}-3-ethoxy-N,N-dimethyl-benzenesulfonamide hydrochloride;

4-{4,5-Bis-(4-chloro-phenyl)-1-[4-(2-morpholin-4-yl-2-oxo-ethyl)-piperazine-1-carbonyl]-4,5-dihydro-1H-imidazol-2-yl}-3-ethoxy-N,N-dimethyl-benzene-sulfonamide hydrochloride;

2-{4-[4,5-Bis-(4-chloro-phenyl)-2-(4-dimethylsulfa-moyl-2-ethoxy-phenyl)-4,5-dihydro-imidazole-1-car-bonyl]-piperazin-1-yl}-N,N-dimethyl-acetamide hydrochloride;

4-[4,5-Bis-(4-chloro-phenyl)-2-(2-ethoxy-5-methane-sulfonyl-phenyl)-4,5-dihydro-imidazole-1-carbonyl]-piperazin-2-one;

[4,5-Bis-(4-chloro-phenyl)-2-(2-ethoxy-5-methanesulfo-nyl-phenyl)-4,5-dihydro-imidazol-1-yl]-[4-(2-meth-anesulfonyl-ethyl)-piperazin-1-yl]-methanone hydro-chloride;

2-{4-[4,5-Bis-(4-chloro-phenyl)-2-(2-ethoxy-5-methane-sulfonyl-phenyl)-4,5-dihydro-imidazole-1-carbonyl]-piperazin-1-yl}-1-morpholin-4-yl-ethanone hydrochlo-ride and 5-[(4S,5R)-4,5-Bis-(4-chloro-phenyl)-1-(3-oxo-pipera-zine-1-carbonyl)-4,5-dihydro-1H-imidazol-2-yl]-2-cy-ano-4-ethoxy-N,N-dimethyl-benzenesulfonamide.

22. A compound of claim 1 selected from the group consisting of

2-{4-[(4S,5R)-4,5-Bis-(4-chloro-phenyl)-2-(4-cyano-5-dimethylsulfamoyl-2-ethoxy-phenyl)-4,5-dihydro-imi-dazole-1-carbonyl]-piperazin-1-yl}-N,N-dimethyl-ac-etamide hydrochloride;

5-{(4S,5R)-4,5-Bis-(4-chloro-phenyl)-1-[4-(2-methane-sulfonyl-ethyl)-piperazine-1-carbonyl]-4,5-dihydro-1H-imidazol-2-yl}-2-cyano-4-ethoxy-N,N-dimethyl-benzenesulfonamide hydrochloride;

5-{(4S,5R)-4,5-Bis-(4-chloro-phenyl)-1-[4-(2-morpho-lin-4-yl-2-oxo-ethyl)-piperazine-1-carbonyl]-4,5-dihy-dro-1H-imidazol-2-yl}-2-cyano-4-ethoxy-N,N-dim-ethyl-benzenesulfonamide hydrochloride;

5-{(4S 5R)-4,5-Bis-(4-chloro-phenyl)-1-[4-(2-morpho-lin-4-yl-2-oxo-ethyl)-piperazine-1-carbonyl]-4,5-dihy-dro-1H-imidazol-2-yl}-4-ethoxy-2-methoxy-benzoni-trile hydrochloride;

5-[(4S 5R)-4,5-Bis-(4-chloro-phenyl)-1-(3-oxo-pipera-zine-1-carbonyl)-4,5-dihydro-1H-imidazol-2-yl]-4-ethoxy-2-methoxy-benzonitrile hydrochloride;

5-{(4S,5R)-4,5-Bis-(4-chloro-phenyl)-1-[4-(2-methane-sulfonyl-ethyl)-piperazine-1-carbonyl]-4,5-dihydro-1H-imidazol-2-yl}-4-ethoxy-2-methoxy-benzonitrile hydrochloride;

2-{4-[(4S,5R)-4,5-Bis-(4-chloro-phenyl)-2-(5-dimethyl-sulfamoyl-2-ethoxy-4-methoxy-phenyl)-4,5-dihydro-imidazole-1-carbonyl]-piperazin-1-yl}-N N-dimethyl-acetamide hydrochloride;

5-{(4S,5R)-4,5-Bis-(4-chloro-phenyl)-1-[4-(2-morpho-lin-4-yl-2-oxo-ethyl)-piperazine-1-carbonyl]-4,5-dihy-dro-1H-imidazol-2-yl}-4-ethoxy-2-methoxy-N,N-dim-ethyl-benzenesulfonamide hydrochloride;

3-{(4S,5R)-4,5-Bis-(4-chloro-phenyl)-1-[4-(2-morpho-lin-4-yl-2-oxo-ethyl)-piperazine-1-carbonyl]-4,5-dihy-dro-1H-imidazol-2-yl}-4-ethoxy-N,N-dimethyl-benza-mide hydrochloride;

3-{(4S,5R)-4,5-Bis-(4-chloro-phenyl)-1-[4-(2-methane-sulfonyl-ethyl)-piperazine-1-carbonyl]-4,5-dihydro-1H-imidazol-2-yl}-4-ethoxy-N N-dimethyl-benzamide hydrochloride;

3-[(4S,5R)-4,5-Bis-(4-chloro-phenyl)-1-(3-oxo-pipera-zine-1-carbonyl)-4,5-dihydro-1H-imidazol-2-yl]-4-ethoxy-N,N-dimethyl-benzamide hydrochloride;

2-(4-{(4S,5R)-4,5-Bis-(4-chloro-phenyl)-2-[2-ethoxy-5-(pyrrolidine-1-carbonyl)-phenyl]-4,5-dihydro-imida-zole-1-carbonyl}-piperazin-1-yl)-1-morpholin-4-yl-ethanone hydrochloride;

{(4S,5R)-4,5-Bis-(4-chloro-phenyl)-2-[2-ethoxy-5-(pyr-rolidine-1-carbonyl)-phenyl]-4,5-dihydro-imidazol-1-yl}-[4-(2-methanesulfonyl-ethyl)-piperazin-1-yl]-methanone hydrochloride;

2-(4-{(4S,5R)-4,5-Bis-(4-chloro-phenyl)-2-[2-ethoxy-5-(piperidine-1-carbonyl)-phenyl]-4,5-dihydro-imida-zole-1-carbonyl}-piperazin-1-yl)-1-morpholin-4-yl-ethanone hydrochloride;

{(4S,5R)-4,5-Bis-(4-chloro-phenyl)-2-[2-ethoxy-5-(pip-eridine-1-carbonyl)-phenyl]-4,5-dihydro-imidazol-1-yl}-[4-(2-methanesulfonyl-ethyl)-piperazin-1-yl]-methanone hydrochloride;

4-{(4S , 5R)-4,5-Bis-(4-chloro-phenyl)-2-[2-ethoxy-5-(piperidine-1-carbonyl)-phenyl]-4,5-dihydro-imida-zole-1-carbonyl}-piperazin-2-one hydrochloride and 2-(4-{(4S,5R)-4,5-Bis-(4-chloro-phenyl)-2-[2-ethoxy-5-(morpholine-4-carbonyl)-phenyl]-4,5-dihydro-imida-zole-1-carbonyl}-pi perazin-1-yl)-1-morpholin-4-yl-ethanone hydrochloride.

23. A compound of claim 1 selected from the group consisting of

{(4S,5R)-4,5-Bis-(4-chloro-phenyl)-2-[2-ethoxy-4-me-thyl-5-(piperidine-1-sulfonyl)-phenyl]-4,5-dihydro-imidazol-1-yl}-[4-(2-methanesulfonyl-ethyl)-piper-azin-1-yl]-methanone hydrochloride;

4-{(4S,5R)-4,5-Bis-(4-chloro-phenyl)-2-[2-ethoxy-4-me-thyl-5-(piperidine-1-sulfonyl)-phenyl]-4,5-dihydro-imidazole-1-carbonyl}-piperazin-2-one hydrochloride;

2-(4-{(4S 5R)-4,5-Bis-(4-chloro-phenyl)-2-[2-ethoxy-4-methyl-5-(morpholine-4-sulfonyl)-phenyl]-4,5-dihy-dro-imidazole-1-carbonyl}-piperazin-1-yl)-1-morpho-lin-4-yl-ethanone hydrochloride;

{(4S,5R)-4,5-Bis-(4-chloro-phenyl)-2-[2-ethoxy-4-me-thyl-5-(morpholine-4-sulfonyl)-phenyl]4,5-dihydro-imidazol-1-yl}-[4-(2-methanesulfonyl-ethyl)-piperazi-1-yl]-methanone hydrochloride;

4-{(4S,5R)-4,5-Bis-(4-chloro-phenyl)-2-[2-ethoxy-4-methyl-5-(morpholine-4-sulfonyl)-phenyl]-4,5-dihydro-imidazole-1-carbonyl}-piperazin-2-one hydrochloride;

2-{4-[(4S,5R)-2-[4-Chloro-2-ethoxy-5-(pyrrolidine-1-sulfonyl)-phenyl]-4,5-bis-(4-chloro-phenyl)-4,5-dihydro-imidazole-1-carbonyl]-piperazin-1-yl}-1-morpholin-4-yl-ethanone hydrochloride;

4-[(4S,5R)-4,5-Bis-(4-chloro-phenyl)-1-(3-oxo-piperazine-1-carbonyl)-4,5-dihydro-1H-imidazol-2-yl]-3-ethoxy-N,N-dimethyl-benzenesulfonamide hydrochloride;

4-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-3-ethoxy-N,N-dimethyl-benzenesulfonamide hydrochloride;

4-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-3-ethoxy-N,N-dimethyl-benzenesulfonamide hydrochloride;

2-{4-[(4S,5R)-4,5-Bis-(4-chloro-phenyl)-2-(4-dimethylsulfamoyl-2-ethoxy-phenyl)-4,5-dihydro-imidazole-1-carbonyl]-piperazin-1-yl}-N,N-dimethyl-acetamide hydrochloride and p1 2-{4-[(4S,5R)-4,5-Bis-(4-chloro-phenyl)-2-(4-cyano-2-ethoxy-phenyl)-4,5-dihydro-imidazole-1-carbonyl]-piperazin-1-yl}-N-tert-butyl-acetamide.

24. A compound of claim 1 selected from the group consisting of

2-{4-[(4S,5R)-4,5-Bis-(4-chloro-phenyl)-2-(4-cyano-2-ethoxy-phenyl)-4,5-dihydro-imidazole-1-carbonyl]-piperazin-1-yl}-acetamide;

2-{4-[(4S,5R)-4,5-Bis-(4-chloro-phenyl)-2-(4-cyano-2-ethoxy-phenyl)-4,5-dihydro-imidazole-1-carbonyl]-piperazin-1-yl}-N-cyanomethyl-N-methyl-acetamide;

2-{4-[(4S,5R)-4,5-Bis-(4-chloro-phenyl)-2-(4-cyano-2-ethoxy-phenyl)-4,5-dihydro-imidazole-1-carbonyl]-piperazin-1-yl}-N-cyclopropyl-acetamide;

2-{4-[(4S,5R)-4,5-Bis-(4-chloro-phenyl)-2-(4-cyano-2-ethoxy-phenyl)-4,5-dihydro-imidazole-1-carbonyl]-piperazin-1-yl}-N-(2-methoxy-ethyl)-acetamide;

2-{4-[(4S,5R)-4,5-Bis-(4-chloro-phenyl)-2-(4-cyano-2-ethoxy-phenyl)-4,5-dihydro-imidazole-1-carbonyl]-piperazin-1-yl}-N,N-bis-(2-methoxy-ethyl)-acetamide;

2-{4-[(4S,5R)-4,5-Bis-(4-chloro-phenyl)-2-(4-cyano-2-ethoxy-phenyl)-4,5-dihydro-imidazole-1-carbonyl]-piperazin-1-yl}-N-methoxy-N-methyl-acetamide;

2-{4-[(4S,5R)-4,5-Bis-(4-chloro-phenyl)-2-(4-cyano-2-ethoxy-phenyl)-4,5-dihydro-imidazole-1-carbonyl]-piperazin-1-yl}-N-isopropyl-N-methyl-acetamide;

2-{4-[(4S,5R)-4,5-Bis-(4-chloro-phenyl)-2-(4-cyano-2-ethoxy-phenyl)-4,5-dihydro-imidazole-1-carbonyl]-piperazi n-i -yl}-N-(2-cyano-ethyl)-N-methyl-acetamide;

4-[(4S,5R)-4,5-Bis-(4-chloro-phenyl)-1-(3-oxo-[1,4]diazepane-1-carbonyl)-4,5-dihydro-1H-imidazol-2-yl]-3-ethoxy-benzonitrile;

4-{(4S,5R)-4,5-Bis-(4-chloro-phenyl)-2-[2-ethoxy-4-fluoro-5-(morpholine-4-sulfonyl)-phenyl]-4,5-dihydro-imidazole-1-carbonyl}-piperazin-2-one and 1-{(4S,5R)-4,5-Bis-(4-chloro-phenyl)-2-[2-ethoxy-4-fluoro-5-(morpholine-4-sulfonyl)-phenyl]-4,5-dihydro-imidazole-1-carbonyl}-[1,4]diazepan-5-one.

25. A compound of claim 1 selected from the group consisting of

{(4S,5R)-4,5-Bis-(4-chloro-phenyl)-2-[2-ethoxy-4-fluoro-5-(morpholine-4-sulfonyl)-phenyl]-4,5-dihydro-imidazol-1-yl}-[4-(2-methanesulfonyl-ethyl)-piperazin-1-yl]-methanone hydrochloride;

2-(4-{(4S 5R)-4,5-Bis-(4-chloro-phenyl)-2-[2-ethoxy-4-fluoro-5-(morpholine-4-sulfonyl)-phenyl]-4,5-dihydro-imidazole-1-carbonyl}-piperazin-1-yl)-1-morpholin-4-yl-ethanone hydrochloride;

4-{(4S,5R)-4,5-Bis-(4-chloro-phenyl)-2-[2-ethoxy-4-(morpholine-4-sulfonyl)-phenyl]-4,5-dihydro-imidazole-1-carbonyl}-piperazin-2-one hydrochloride;

{(4S,5R)-4,5-Bis-(4-chloro-phenyl)-2-[2-ethoxy-4-(morpholine-4-sulfonyl)-phenyl]-4,5-dihydro-imidazol-1-yl}-[4-(2-methanesulfonyl-ethyl)-piperazin-1-yl]-methanone hydrochloride;

2-(4-{(4S,5R)-4,5-Bis-(4-chloro-phenyl)-2-[2-ethoxy-4-(morpholine-4-sulfonyl)-phenyl]-4,5-dihydro-imidazole-1-carbonyl}-piperazin-1-yl)-1-morpholin-4-yl-ethanone hydrochloride;

4-{(4S,5R)-4,5-Bis-(4-chloro-phenyl)-2-[2-ethoxy-4-(pyrrolidine-1-sulfonyl)-phenyl]-4,5dihydro-imidazole-1-carbonyl}-piperazin-2-one hydrochloride;

{(4S,5R)-4,5-Bis-(4-chloro-phenyl)-2-[2-ethoxy-4-(pyrrolidine-1-sulfonyl)-phenyl]-4,5-dihydro-imidazol-1-yl}-[4-(2-methanesulfonyl-ethyl)-piperazin-1-yl]-methanone hydrochloride;

2-(4-{(4S,5R)-4,5-Bis-(4-chloro-phenyl)-2-[2-ethoxy-4-(pyrrolidine-1-sulfonyl)-phenyl]-4,5-dihydro-imidazole-1-carbonyl}-piperazin-1-yl)-1-morpholin-4-yl-ethanone hydrochloride;

5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-4-ethoxy-N-methoxy-2,N-dimethyl-benzenesulfonamide;

4-[(4S5R)-4,5-Bis-(4-chloro-phenyl)-1-(3-oxo-piperazine-1-carbonyl)-4,5-dihydro-1H-imidazol-2-yl]-2,5-diethoxy-benzonitrile and 4-[(4S,5R)-4,5-Bis-(4-chloro-phenyl)-1-(5-oxo-[1,4]diazepane-1-carbonyl)-4,5-dihydro-1H-imidazol-2-yl]-2,5-diethoxy-benzonitrile.

26. A compound of claim 1 selected from the group consisting of

4-{(4S,5R)-4,5-Bis-(4-chloro-phenyl)-1-[4-(2-metha nesulfonyl-ethyl)-piperazine-1-carbonyl]-4,5-dihydro-1H-imidazol-2-yl}-2,5-diethoxy-benzonitrile hydrochloride;

4-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-2, 5-diethoxy-benzonitrile hydrochloride;

4-{(4S,5R)-4,5-Bis-(4-chloro-phenyl)-2-[2-ethoxy-5-(piperidine-1-sulfonyl)-4-piperidin-1-yl-phenyl]-4,5-dihydro-imidazole-1-carbonyl}-piperazin-2-one hydrochloride;

1-{(4S,5R)-4,5-Bis-(4-chloro-phenyl)-2-[2-ethoxy-5-(piperidine-1-sulfonyl)-4-piperidin-1-yl-phenyl]-4,5-dihydro-imidazole-1-carbonyl}-[1,4]diazepan-5-one hydrochloride;

{(4S,5R)-4,5-Bis-(4-chloro-phenyl)-2-[2-ethoxy-5-(piperidine-1-sulfonyl)-4-piperidin-1-yl-phenyl]-4,5-dihydro-imidazol-1-yl}-[4-(2-metha nesulfonyl-ethyl)-piperazin-1-yl]-methanone hydrochloride;

2-(4-{(4S,5R)-4,5-Bis-(4-chloro-phenyl)-2-[2-ethoxy-5-(piperidine-1-sulfonyl)-4-piperidin-1-yl-phenyl]-4,5-dihydro-imidazole-1-carbonyl}-piperazin-1-yl)-1-morpholin-4-yl-ethanone hydrochloride;

4,5-Bis-(4-chloro-phenyl)-2-(4-dimethylamino-5-dimethylsulfamoyl-2-ethoxy-phenyl)-4,5-dihydro-imidazole-1-carboxylic acid ethyl ester hydrochloride;

5-[(4S,5R)-4,5-Bis-(4-chloro-phenyl)-1-(3-oxo-piperazine-1-carbonyl)-4,5-dihydro-1H-imidazol-2-yl]-2-dimethylamino-4-ethoxy-N,N-dimethyl-benzenesulfonamide hydrochloride;

5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-2-dimethylamino-4-ethoxy-N,N-dimethyl-benzenesulfonamide hydrochloride;

5-[(4S,5R)-4,5-Bis-(4-chloro-phenyl)-1-(5-oxo-[1,4]diazepane-1-carbonyl)-4,5-dihydro-1H-imidazol-2-yl]-2-dimethylamino-4-ethoxy-N,N-dimethyl-benzenesulfonamide hydrochloride and 5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-2-dimethylamino-4-ethoxy-N,N-d imethyl-benzenesulfonamide hydrochloride.

27. A compound of claim 1 selected from the group consisting of

5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-2-chloro-4-ethoxy-benzonitrile;

5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-4-ethoxy-N-isopropyl-2-methyl-benzenesulfonamide;

5-[(4S,5R)-4,5-Bis-(4-chloro-phenyl)-1-(3-oxo-piperazine-1-carbonyl)-4,5-dihydro-1H-imidazol-2-yl]-4-ethoxy-N-isopropyl-2-methyl-benzenesulfonamide;

5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-4-ethoxy-2,N-dimethyl-benzenesulfonamide;

5-{(4S,5R)-4,5-Bis-(4-chloro-phenyl)-1-[4-(2-metha nesulfonyl-ethyl)-piperazine-1-carbonyl]-4,5-dihydro-1H-imidazol-2-yl}-4-ethoxy-2,N-dimethyl-benzenesulfonamide;

5-[(4S,5R)-4,5-Bis-(4-chloro-phenyl)-1-(3-oxo-piperazine-1-carbonyl)-4,5-dihydro-1H-imidazol-2-yl]-4-ethoxy-2,N-dimethyl-benzenesulfonamide;

5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-2-chloro-4-ethoxy-benzonitrile;

5-[(4S,5R)-4,5-Bis-(4-chloro-phenyl)-1-(3-oxo-piperazine-1-carbonyl)-4,5-dihydro-1H-imidazol-2-yl]-2-chloro-4-ethoxy-benzonitrile;

5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-2-dimethylamino-4-ethoxy-benzonitrile;

5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-2-dimethylamino-4-ethoxy-benzonitrile and 5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-4-ethoxy-N-isopropyl-2-methyl-benzenesulfonamide.

28. A compound of claim 1 selected from the group consisting of

4-[(4S,5R)-4,5-Bis-(4-chloro-phenyl)-2-(2-ethoxy-4-ethynyl-phenyl)-4,5-dihydro-imidazole-1-carbonyl]-piperazin-2-one;

1-[(4S,5R)-4,5-Bis-(4-chloro-phenyl)-2-(2-ethoxy-4-ethynyl-phenyl)-4,5-dihydro-imidazole-1-carbonyl]-[1,4]diazepan-5-one;

[(4S,5R)-4,5-Bis-(4-chloro-phenyl)-2-(2-ethoxy-4-ethynyl-phenyl)-4,5-dihydro-imidazol-1-yl]-[4-(2-methanesulfonyl-ethyl)-piperazin-1-yl]-methanone hydrochloride;

2-{4-[(4S,5R)-4,5-Bis-(4-chloro-phenyl)-2-(2-ethoxy-4-ethynyl-phenyl)-4,5-dihydro-imidazole-1-carbonyl]-piperazin-1-yl}-1-morpholin-4-yl-ethanone hydrochloride;

2-(4-{(4S,5R)-4,5-Bis-(4-chloro-phenyl)-2-[2-ethoxy-4-(piperidine-1-carbonyl)-phenyl]-4,5-dihydro-imidazole-1-carbonyl}-piperazin-1-yl)-1-morpholin-4-yl-ethanone;

2-(4-{(4S,5R)-4,5-Bis-(4-chloro-phenyl)-2-[2-ethoxy-4-(piperidine-1-carbonyl)-phenyl]-4,5-dihydro-imidazole-1-carbonyl}-piperazin-1-yl)-N-tert-butyl-acetamide;

4-{(4S,5R)-4,5-Bis-(4-chloro-phenyl)-2-[2-ethoxy-4-(piperidine-1-carbonyl)-phenyl]-4,5-dihydro-imidazole-1-carbonyl}-piperazin-2-one;

{(4S,5R)-4,5-Bis-(4-chloro-phenyl)-2-[2-ethoxy-4-(piperidine-1-carbonyl)-phenyl]-4,5-dihydro-imidazol-1-yl}-[4-(2-methanesulfonyl-ethyl)-piperazin-1-yl]-methanone;

2-(4-{(4S,5R)-4,5-Bis-(4-chloro-phenyl)-2-[2-ethoxy-4-(piperidine-1-carbonyl)-phenyl]-4,5-dihydro-imidazole-1-carbonyl}-piperazin-1-yl)-acetamide 2-(4-{(4S,5R)-4,5-Bis-(4-chloro-phenyl)-2-[2-ethoxy-4-(piperidine-1-carbonyl)-phenyl]4,5-dihydro-imidazole-1-carbonyl}-piperazin-1-yl)-N-isopropyl-N-methyl-acetamide and {(4S,5R)-4,5-Bis-(4-chloro-phenyl)-2-[2-ethoxy-4-(piperidine-1-carbonyl)-phenyl]-4,5-dihydro-imidazol-1-yl}-(4-ethanesulfonyl-piperazin-1-yl)-methanone.

29. A compound of claim 1 selected from the group consisting of 5-{(4S,5R)-4,5-Bis-(4-chloro-phenyl)-1-[4-(3,5-dimethyl-isoxazole-4-carbonyl)-piperazine-1-carbonyl]-4,5-dihyd ro-1H-imidazol-2-yl}-2-chloro-4-ethoxy-N-methyl-benzenesulfonamide;

5-{(4S,5R)-4,5-Bis-(4-chloro-phenyl)-1-[4-(2-metha nesulfonyl-ethyl)-piperazine-1-carbonyl]-4,5-dihydro-1H-imidazol-2-yl}-2-chloro-4-ethoxy-N-isopropyl-benzenesulfonamide;

2-{4-[(4S,5R)-2-(4-Chloro-2-ethoxy-5-isopropylsulfamoyl-phenyl)-4,5-bis-(4-chloro-phenyl)-4,5-dihydro-imidazole-1-carbonyl]-piperazin-1-yl}-acetamide;

2-{4-[(4S,5R)-2-(4-Chloro-2-ethoxy-5-isopropylsulfamoyl-phenyl)-4,5-bis-(4-chloro-phenyl)-4,5-dihydro-imidazole-1-carbonyl]-piperazin-1-yl}-N-isopropyl-N-methyl-acetamide;

5-[(4S,5R)-4,5-Bis-(4-chloro-phenyl)-1-(4-ethanesulfonyl-piperazine-1-carbonyl)-4,5-dihydro-1H-imidazol-2-yl]-2-chloro-4-ethoxy-N-isopropyl-benzenesulfonamide;

N-tert-Butyl-2-{4-[(4S,5R)-2-(4-chloro-2-ethoxy-5-methylsulfamoyl-phenyl)-4,5-bis-(4-chloro-phenyl)-4,5-dihydro-imidazole-1-carbonyl]-piperazin-1-yl}-acetamide;

5-[(4S,5R)-4,5-Bis-(4-chloro-phenyl)-1-(3-oxo-piperazine-1-carbonyl)-4,5-dihydro-1H-imidazol-2-yl]-2-chloro-4-ethoxy-N-methyl-benzenesulfonamide;

5-{(4S 5R)-4,5-Bis-(4-chloro-phenyl)-1-[4-(2-methanesuifonyl-ethyl)-piperazine-1-carbonyl]-4,5-dihydro-1H-imidazol-2-yl}-2-chloro-4-ethoxy-N-methyl-benzenesulfonamide;

2-{4-[(4S,5R)-2-(4-Chloro-2-ethoxy-5-methylsulfamoyl-phenyl)-4,5-bis-(4-chloro-phenyl)-4,5-dihydro-imidazole-1-carbonyl]-piperazin-1-yl}-acetamide;

2-{4-[(4S,5R)-2-(4-Chloro-2-ethoxy-5-methylsulfamoyl-phenyl)-4,5-bis-(4-chloro-phenyl)-4,5-dihydro-imidazole-1-carbonyl]-piperazin-1-yl}-N-isopropyl-N-methyl-acetamide and 5-[(4S,5R)-4,5-Bis-(4-chloro-phenyl)-1-(4-ethanesulfonyl-piperazine-1-carbonyl)-4,5-dihydro-1H-imidazol-2-yl]-2-chloro-4-ethoxy-N-methyl-benzenesulfonamide.

30. A compound of claim 1 selected from the group consisting of

5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-2-chloro-4-ethoxy-N-isopropyl-benzenesulfonamide;

5-{(4S,5R)-4,5-Bis-(4-chloro-phenyl)-1-[4-(3,5-dimethyl-isoxazole-4-carbonyl)-piperazine-1-carbonyl]-4,5-dihyd ro-1H-imidazol-2-yl}-2-chloro-4-ethoxy-N-isopropyl-benzenesulfonamide;

N-tert-Butyl-2-{4-[(4S 5R)-2-(4-chloro-2-ethoxy-5-isopropylsulfamoyl-phenyl)-4,5-bis-(4chloro-phenyl)-4,5-dihydro-imidazole-1-carbonyl]-piperazin-1-yl}-acetamide;

5-[(4S 5R)-4,5-Bis-(4-chloro-phenyl)-1-(3-oxo-piperazine-1-carbonyl)-4,5-dihydro-1H-imidazol-2-yl]-2-chloro-4-ethoxy-N-isopropyl-benzenesulfonamide;

N-{4-[(4S,5R)-4,5-Bis-(4-chloro-phenyl)-1-(3-oxo-piperazine-1-carbonyl)-4,5-dihydro-1H-imidazol-2-yl]-3-ethoxy-phenyl}-N-(3-oxo-piperazine-1-carbonyl)-methanesulfonamide;

N-(4-{(4S,5R)-4,5-Bis-(4-chloro-phenyl)-1-[4-(2-methanesuifonyl-ethyl)-piperazine-1-carbonyl]-4,5-dihydro-1H-imidazol-2-yl}-3-ethoxy-phenyl)-methanesulfonamide hydrochloride;

N-{4-[(4S,5R)-4,5-Bis-(4-chloro-phenyl)-1-(3-oxo-piperazine-1-carbonyl)-4,5-dihydro-1H-imidazol-2-yl]-3-ethoxy-phenyl}-2,2-dimethyl-propionamide;

5-[(4S,5R)-4,5-Bis-(4-chloro-phenyl)-1-(3-oxo-piperazine-1-carbonyl)-4,5-dihydro-1H-imidazol-2-yl]-4-ethoxy-2-ethynyl-N,N-dimethyl-benzenesulfonamide;

5-{(4S,5R)-4,5-Bis-(4-chloro-phenyl)-1-[4-(2-methanesulfonyl-ethyl)-piperazine-1-carbonyl]-4,5-dihyd ro-1H-imidazol-2-yl}-4-ethoxy-2-ethynyl-N,N-dimethyl-benzenesulfonamide hydrochloride;

5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-4-ethoxy-2-ethynyl-N,N-dimethyl-benzenesulfonamide hydrochloride and 2-{4-[(4S,5R)-4,5-Bis-(4-chloro-phenyl)-2-(5-d imethylsulfamoyl-2-ethoxy-4-ethynyl-phenyl)-4,5-dihydro-imidazole-1-carbonyl]-piperazin-1-yl}-N-isopropyl-N-methyl-acetamide hydrochloride.

31. A compound of claim 1 selected from the group consisting of

N-(4-{(4S,5R)-4,5-Bis-(4-chloro-phenyl)-1-[4-(2-methanesulfonyl-ethyl)-piperazine-1-carbonyl]-4,5-dihyd ro-1H-imidazol-2-yl}-3-ethoxy-phenyl)-2 2-dimethyl-propionamide hydrochloride;

N-{4-[(4S,5R)-4,5-Bis-(4-chloro-phenyl)-1-(4-dimethyl-carbamoylmethyl-piperazine-1-carbonyl)-4,5-dihydro-1H-imidazol-2-yl]-3-ethoxy-phenyl}-2,2-dimethyl-propionamide hydrochloride;

N-(4-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-3-ethoxy-phenyl)-2,2-dimethyl-propionamide hydrochloride;

2-{4-[(4S,5R)-4,5-Bis-(4-chloro-phenyl)-2-(2-ethoxy-4-ethynyl-phenyl)-4,5-dihydro-imidazole-1-carbonyl]-piperazin-1-yl}-N-tert-butyl-acetamide hydrochloride;

2-{4-[(4S,5R)-4,5-Bis-(4-chloro-phenyl)-2-(2-ethoxy-4-ethynyl-phenyl)-4,5-dihydro-imidazole-1-carbonyl]-piperazin-1-yl}-N-methoxy-N-methyl-acetamide hydrochloride;

N-(2-{4-[(4S 5R)-4,5-Bis-(4-chloro-phenyl)-2-(2-ethoxy-4-ethynyl-phenyl)-4,5-dihydro-imidazole-1-carbonyl]-piperazin-1-yl}-ethyl)-methanesulfonamide hydrochloride;

[(4S,5R)-4,5-Bis-(4-chloro-phenyl)-2-(2-ethoxy-4-ethynyl-phenyl)-4,5-dihydro-imidazol-1-yl]-(4-ethanesulfonyl-piperazin-1-yl)-methanone;

[(4S,5R)-4,5-Bis-(4-chloro-phenyl)-2-(2-ethoxy-4-ethynyl-phenyl)-4,5-dihyd ro-imidazol-1-yl]-[4-(2-methoxy-ethyl)-piperazin-1-yl]-methanone hydrochloride;

1-{4-[(4S,5R)-4,5-Bis-(4-chloro-phenyl)-2-(2-ethoxy-4-ethynyl-phenyl)-4,5-dihydro-imidazole-1-carbonyl]-piperazin-1-yl}-ethanone;

3-{4-[(4S,5R)-4,5-Bis-(4-chloro-phenyl)-2-(2-ethoxy-4-ethynyl-phenyl)-4,5-dihydro-imidazole-1-carbonyl]-piperazin-1-yl}-propionitrile hydrochloride and

[(4S,5R)-4,5-Bis-(4-chloro-phenyl)-2-(2-ethoxy-4-ethynyl-phenyl)-4,5-dihydro-imidazol-1-yl]-[4-(3-methanesulfonyl-propyl)-piperazin-1-yl]-methanone hydrochloride.

32. A compound of claim 1 selected from the group consisting of

2-{4-[(4S,5R)-4,5-Bis-(4-chloro-phenyl)-2-(2-ethoxy-4-ethynyl-phenyl)-4,5-dihydro-imidazole-1-carbonyl]-piperazin-1-yl}-acetamide hydrochloride;

2-{4-[(4S,5R)-4,5-Bis-(4-chloro-phenyl)-2-(2-ethoxy-4-ethynyl-phenyl)-4,5-dihydro-imidazole-1-carbonyl]-piperazin-1-yl}-N-isopropyl-N-methyl-acetamidehydrochloride;

3-{4-[(4S,5R)-4,5-Bis-(4-chloro-phenyl)-2-(2-ethoxy-4-ethynyl-phenyl)-4,5-dihydro-imidazole-1-carbonyl]-piperazin-1-yl}-propionic acid hydrochloride;

4-[(4S,5R)-4,5-Bis-(4-chloro-phenyl)-2-(2-ethoxy-4-trifluoroprop-1-ynyl-phenyl)-4,5-dihydro-imidazole-1-carbonyl]-piperazin-2-one;

[(4S,5R)-4,5-Bis-(4-chloro-phenyl)-2-(2-ethoxy-4-trifluoroprop-1-ynyl-phenyl)-4,5-dihydro-imidazol-1-yl]-[4-(2-methanesulfonyl-ethyl)-piperazin-1-yl]-methanone hydrochloride;

2-{4-[(4S,5R)-4,5-Bis-(4-chloro-phenyl)-2-(2-ethoxy-4-trifluoroprop-1-ynyl-phenyl)-4,5-dihydro-imidazole-1-carbonyl]-piperazin-1-yl}-1-morpholin-4-yl-ethanone hydrochloride;

2-{4-[(4S,5R)-4,5-Bis-(4-chloro-phenyl)-2-(2-ethoxy-4-trifluoroprop-1-ynyl-phenyl)-4,5-dihydro-imidazole-1-carbonyl]-piperazin-1-yl}-N-isopropyl-N-methyl-acetamide hydrochloride;

2-(4-{(4S,5 R)-4,5-Bis-(4-chloro-phenyl)-2-[2-ethoxy-4-methyl-5-(piperidine-1-sulfonyl)-phenyl]-4,5-dihydro-imidazole-1-carbonyl}-piperazin-1-yl)-N-tert-butyl-acetamide;

2-(4-{(4S 5R)-4,5-Bis-(4-chloro-phenyl)-2-[2-ethoxy-4-methyl-5-(piperidine-1-sulfonyl)-phenyl]-4,5-dihydro-imidazole-1-carbonyl}-piperazin-1-yl)-acetamide 2-(4-{(4S,5R)-4,5-Bis-(4-chloro-phenyl)-2-[2-ethoxy-4-methyl-5-(piperidine-1-sulfonyl)-phenyl]-4,5-dihydro-imidazole-1-carbonyl}-piperazin-1-yl)-N,N-bis-(2-methoxy-ethyl)-acetamide and 2-(4-{(4S,5R)-4,5-Bis-(4-chloro-phenyl)-2-[2-ethoxy-4-methyl-5-(piperidine-1-sulfonyl)-phenyl]-4,5-dihydro-imidazole-1-carbonyl}-piperazin-1-yl)-N-methoxy-N-methyl-acetamide.

33. A compound of claim 1 selected from the group consisting of 2-(4-{(4S,5R)-4,5-Bis-(4-chloro-phenyl)-2-[2-ethoxy-4-methyl-5-(piperidine-1-sulfonyl)-phenyl]-4,5-dihydro-imidazole-1-carbonyl}-piperazin-1-yl)-N-isopropyl-N-methyl-acetamide;

2-(4-{(4S,5R)-4,5-Bis-(4-chloro-phenyl)-2-[2-ethoxy-4-methyl-5-(piperidine-1-sulfonyl)-phenyl]-4,5-dihydro-imidazole-1-carbonyl}-piperazin-1-yl)-N-(2-cyano-ethyl)-N-methyl-acetamide;

2-(4-{(4S,5R)-4,5-Bis-(4-chloro-phenyl)-2-[2-ethoxy-4-methyl-5-(piperidine-1-sulfonyl)-phenyl]-4,5-dihydro-imidazole-1-carbonyl}-piperazin-1-yl)-N-(2-methoxy-1-methyl-ethyl)-acetamide;

{(4S,5R)-4,5-Bis-(4-chloro-phenyl)-2-[2-ethoxy-4-methyl-5-(piperidine-1-sulfonyl)-phenyl]-4,5-dihydro-imidazol-1-yl}-[4-(3,5-dimethyl-isoxazole-4-carbonyl)-piperazin-1-yl]-methanone;

{(4S,5R)-4,5-Bis-(4-chloro-phenyl)-2-[2-ethoxy-4-methyl-5-(piperidine-1-sulfonyl)-phenyl]-4,5-dihydro-imidazol-1-yl}-(4-ethanesulfonyl-piperazin-1-yl)-methanone;

N-[2-(4-{(4S,5R)-4,5-Bis-(4-chloro-phenyl)-2-[2-ethoxy-4-methyl-5-(piperidine-1-sulfonyl)-phenyl]-4,5-dihydro-imidazole-1-carbonyl}-piperazin-1-yl)-ethyl]-methanesulfonamide;

{(4S 5R)-4,5-Bis-(4-chloro-phenyl)-2-[2-ethoxy-4-methyl-5-(piperidine-1-sulfonyl)-phenyl]-4,5-dihydro-imidazol-1-yl}-[4-(3-methanesulfonyl-propyl)-piperazin-1-yl]-methanone;

N-tert-Butyl-2-{4-[(4S,5R)-2-(5-tert-butylsulfamoyl-2-ethoxy-4-methyl-phenyl)-4,5-bis-(4-chloro-phenyl)-4,5-dihydro-imidazole-1-carbonyl]-piperazin-1-yl}-acetamide;

2-{4-[(4S,5R)-2-(5-tert-Butylsulfamoyl-2-ethoxy-4-methyl-phenyl)-4,5-bis-(4-chloro-phenyl)-4,5-dihydro-imidazole-1-carbonyl]-piperazin-1-yl}-acetamide;

2-{4-[(4S,5R)-2-(5-tert-Butylsulfamoyl-2-ethoxy-4-methyl-phenyl)-4,5-bis-(4-chloro-phenyl)-4,5-dihydro-imidazole-1-carbonyl]-piperazin-1-yl}-N,N-bis-(2-methoxy-ethyl)-acetamide and 2-{4-[(4S,5R)-2-(5-tert-Butylsulfamoyl-2-ethoxy-4-methyl-phenyl)-4,5-bis-(4-chloro-phenyl)-4,5-dihydro-imidazole-1-carbonyl]-piperazin-1-yl}-N-methoxy-N-methyl-acetamide.

34. A compound of claim 1 selected from the group consisting of

2-{4-[(4S 5R)-2-(5-tert-Butylsulfamoyl-2-ethoxy-4-methyl-phenyl)-4,5-bis-(4-chloro-phenyl)-4,5-dihydro-imidazole-1-carbonyl]-piperazin-1-yl}-N-isopropyl-N-methyl-acetamide;

2-{4-[(4S,5R)-2-(5-tert-Butylsulfamoyl-2-ethoxy-4-methyl-phenyl)-4,5-bis-(4-chloro-phenyl)-4,5-dihydro-imidazole-1-carbonyl]-piperazin-1-yl}-N-(2-cyano-ethyl)-N-methyl-acetamide;

2-{4-[(4S 5R)-2-(5-tert-Butylsulfamoyl-2-ethoxy-4-methyl-phenyl)-4,5-bis-(4-chloro-phenyl)-4,5-dihydro-imidazole-1-carbonyl]-piperazin-1-yl}-N-(2-methoxy-1-methyl-ethyl)-acetamide;

5-{(4S,5R)-4,5-Bis-(4-chloro-phenyl)-1-[4-(3,5-dimethyl-isoxazole-4-carbonyl)-piperazine-1-carbonyl]-4,5-dihydro-1H-imidazol-2-yl}-N-tert-butyl-4-ethoxy-2-methyl-benzenesulfonamide;

5-[(4S,5R)-4,5-Bis-(4-chloro-phenyl)-1-(4-ethanesulfonyl-piperazine-1-carbonyl)-4,5-dihydro-1H-imidazol-2-yl]-N-tert-butyl-4-ethoxy-2-methyl-benzenesulfonamide;

5-{(4S,5R)-4,5-Bis-(4-chloro-phenyl)-1-[4-(2-methanesulfonylamino-ethyl)-piperazine-1-carbonyl]-4,5-dihydro-1H-imidazol-2-yl}-N-tert-butyl-4-ethoxy-2-methyl-benzenesulfonamide;

5-{(4S,5R)-4,5-Bis-(4-chloro-phenyl)-1-[4-(3-methanesulfonyl-propyl)-piperazine-1-carbonyl]-4,5-dihydro-1H-imidazol-2-yl}-N-tert-butyl-4-ethoxy-2-methyl-benzenesulfonamide;

5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-N-tert-butyl-4-ethoxy-2-methyl-benzenesulfonamide;

5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-N-tert-butyl-4-ethoxy-2-methyl-benzenesufonamide;

2-(4-{(4S,5R)-4,5-Bis-(4-chloro-phenyl)-2-[2-ethoxy-5-(methoxy-methyl-sulfamoyl)-4-methyl-phenyl]-4,5-dihydro-imidazole-1-carbonyl}-piperazin-1-yl)-N-tert-butyl-acetamide and 2-(4-{(4S,5R)-4,5-Bis-(4-chloro-phenyl)-2-[2-ethoxy-5-(methoxy-methyl-sulfamoyl)-4-methyl-phenyl]-4,5-dihydro-imidazole-1-carbonyl}-piperazin-1-yl)-acetamide.

35. A compound of claim 1 selected from the group consisting of 2-(4-{(4S,5R)-4,5-Bis-(4-chloro-phenyl)-2-[2-ethoxy-5-(methoxy-methyl-sulfa moyl)-4-methyl-phenyl]-4,5-dihydro-imidazole-1-carbonyl}-piperazin-1-yl)-N,N-bis-(2-methoxy-ethyl)-acetamide;

2-(4-{(4S,5R)-4,5-Bis-(4-chloro-phenyl)-2-[2-ethoxy-5-(methoxy-methyl-sulfamoyl)-4-methyl-phenyl]-4,5-dihydro-imidazole-1-carbonyl}-piperazin-1-yl)-N-methoxy-N-methyl-acetamide;

2-(4-{(4S,5R)-4,5-Bis-(4-chloro-phenyl)-2-[2-ethoxy-5-(methoxy-methyl-sulfamoyl)-4-methyl-phenyl]-4,5-dihydro-imidazole-1-carbonyl}-piperazin-1-yl)-N-isopropyl-N-methyl-acetamide;

2-(4-{(4S,5R)-4,5-Bis-(4-chloro-phenyl)-2-[2-ethoxy-5-(methoxy-methyl-sulfamoyl)-4-methyl-phenyl]-4,5-dihydro-imidazole-1-carbonyl}-piperazin-1-yl)-N-(2-methoxy-1-methyl-ethyl)-acetamide;

5-{(4S 5R)-4,5-Bis-(4-chloro-phenyl)-1-[4-(3,5-dimethyl-isoxazole-4-carbonyl)-piperazine-1-carbonyl]-4,5-dihydro-1H-imidazol-2-yl}-4-ethoxy-N-methoxy-2,N-dimethyl-benzenesulfonamide;

5-[(4S,5R)-4,5-Bis-(4-chloro-phenyl)-1-(4-ethanesulfonyl-piperazine-1-carbonyl)-4,5-dihydro-1H-imidazol-2-yl]-4-ethoxy-N-methoxy-2,N-d imethyl-benzenesulfonamide;

5-{(4S,5R)-4,5-Bis-(4-chloro-phenyl)-1-[4-(3-methanesulfonyl-propyl)-piperazine-1-carbonyl]-4,5-dihydro-1H-imidazol-2-yl}-4-ethoxy-N-methoxy-2,N-dimethyl-benzenesulfonamide;

5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-4-ethoxy-N-methoxy-2,N-dimethyl-benzenesulfonamide;

2-(4-{(4S,5R)-4,5-Bis-(4-chloro-phenyl)-2-[2-ethoxy-4-methoxy-5-(piperidine-1-sulfonyl)-phenyl]-4,5-dihydro-imidazole-1-carbonyl}-piperazin-1-yl)-N-tert-butyl-acetamide 2-(4-{(4S,5R)-4,5-Bis-(4-chloro-phenyl)-2-[2-ethoxy-4-methoxy-5-(piperidine-1-sulfonyl)-phenyl]-4,5-dihydro-imidazole-1-carbonyl}-piperazin-1-yl)-acetamide and 2-(4-{(4S,5R)-4,5-Bis-(4-chloro-phenyl)-2-[2-ethoxy-4-methoxy-5-(piperidine-1-sulfonyl)-phenyl]-4,5-dihydro-imidazole-1-carbonyl}-piperazin-1-yl)-N,N-bis-(2-methoxy-ethyl)-acetamide.

36. A compound of claim 1 selected from the group consisting of 2-(4-{(4S,5R)-4,5-Bis-(4-chloro-phenyl)-2-[2-ethoxy-4-methoxy-5-(piperidine-1-sulfonyl)-phenyl]-4,5-dihydro-imidazole-1-carbonyl}-piperazin-1-yl)-N-methoxy-N-methyl-acetamide;

2-(4-{(4S,5R)-4,5-Bis-(4-chloro-phenyl)-2-[2-ethoxy-4-methoxy-5-(piperidine-1-sulfonyl)-phenyl]-4,5-dihydro-imidazole-1-carbonyl}-piperazin-1-yl)-N-isopropyl-N-methyl-acetamide;

2-(4-{(4S,5R)-4,5-Bis-(4-chloro-phenyl)-2-[2-ethoxy-4-methoxy-5-(piperidine-1-sulfonyl)-phenyl]-4,5-dihydro-imidazole-1-carbonyl}-piperazin-1-yl)-N-(2-cyano-ethyl)-N-methyl-acetamide 2-(4-{(4S 5R)-4,5-Bis-(4-chloro-phenyl)-2-[2-ethoxy-4-methoxy-5-(piperidine-1-sulfonyl)-phenyl]-4,5-dihydro-imidazole-1-carbonyl}-piperazin-1-yl)-N-(2-methoxy-1-methyl-ethyl)-acetamide;

{(4S,5R)-4,5-Bis-(4-chloro-phenyl)-2-[2-ethoxy-4-methoxy-5-(piperidine-1-sulfonyl)-phenyl]-4,5-dihydro-imidazol-1-yl}-[4-(3,5-dimethyl-isoxazole-4-carbonyl)-piperazin-1-yl]-methanone;

{(4S,5R)-4,5-Bis-(4-chloro-phenyl)-2-[2-ethoxy-4-methoxy-5-(piperidine-1-sulfonyl)-phenyl]-4,5-dihydro-imidazol-1-yl}-(4-ethanesulfonyl-piperazin-1-yl)-methanone;

N-[2-(4-{(4S,5R)-4,5-Bis-(4-chloro-phenyl)-2-[2-ethoxy-4-methoxy-5-(piperidine-1-sulfonyl)-phenyl]-4,5-dihydro-imidazole-1-carbonyl}-piperazin-1-yl)-ethyl]-methanesulfonamide;

{(4S,5R)-4,5-Bis-(4-chloro-phenyl)-2-[2-ethoxy-4-methoxy-5-(piperidine-1-sulfonyl)-phenyl]-4,5-dihydro-imidazol-1-yl}-[4-(3-methanesulfonyl-propyl)-piperazin-1-yl]-methanone {(4S,5R)-4,5-Bis-(4-chloro-phenyl)-2-[2-ethoxy-4-methoxy-5-(piperidine-1-sulfonyl)-phenyl]-4,5-dihydro-imidazol-1-yl}-[4-(2-methanesulfonyl-ethyl)-piperazin-1-yl]-methanone;

2-(4-{(4S,5R)-4,5-Bis-(4-chloro-phenyl)-2-[2-ethoxy-4-methoxy-5-(piperidine-1-sulfonyl)-phenyl]-4,5-dihydro-imidazole-1-carbonyl}-piperazin-1-yl)-1-morpholin-4-yl-ethanone and 2-(4-{(4S,5R)-4,5-Bis-(4-chloro-phenyl)-2-[2-ethoxy-4-methoxy-5-(methoxy-methyl-sulfamoyl)-phenyl]-4,5-dihydro-imidazole-1-carbonyl}-piperazin-1-yl)-N-tert-butyl-acetamide.

37. A compound of claim 1 selected from the group consisting of 2-(4-{(4S 5R)-4,5-Bis-(4-chloro-phenyl)-2-[2-ethoxy-4-methoxy-5-(methoxy-methyl-sulfamoyl)-phenyl]-4,5-dihyd ro-imidazole-1-carbonyl}-piperazin-1-yl)-acetamide;

2-(4-{(4S,5R)-4,5-Bis-(4-chloro-phenyl)-2-[2-ethoxy-4-methoxy-5-(methoxy-methyl-sulfamoyl)-phenyl]-4,5-dihydro-imidazole-1-carbonyl}-piperazin-1-yl)-N N-bis-(2-methoxy-ethyl)-acetamide;

2-(4-{(4S,5R)-4,5-Bis-(4-chloro-phenyl)-2-[2-ethoxy-4-methoxy-5-(methoxy-methyl-sulfamoyl)-phenyl]-4,5-dihydro-imidazole-1-carbonyl}-piperazin-1-yl)-N-methoxy-N-methyl-acetamide;

2-(4-{(4S,5R)-4,5-Bis-(4-chloro-phenyl)-2-[2-ethoxy-4-methoxy-5-(methoxy-methyl-sulfamoyl)-phenyl]-4,5-dihydro-imidazole-1-carbonyl}-piperazin-1-yl)-N-isopropyl-N-methyl-acetamide;

2-(4-{(4S,5R)-4,5-Bis-(4-chloro-phenyl)-2-[2-ethoxy-4-methoxy-5-(methoxy-methyl-sulfamoyl)-phenyl]-4,5-dihydro-imidazole-1-carbonyl}-piperazin-1-yl)-N-(2-cyano-ethyl)-N-methyl-acetamide;

2-(4-{(4S,5R)-4,5-Bis-(4-chloro-phenyl)-2-[2-ethoxy-4-methoxy-5-(methoxy-methyl-sulfamoyl)-phenyl]-4,5-dihydro-imidazole-1-carbonyl}-piperazin-1-yl)-N-(2-methoxy-1-methyl-ethyl)-acetamide;

5-{(4S,5R)-4,5-Bis-(4-chloro-phenyl)-1-[4-(3,5-dimethyl-isoxazole-4-carbonyl)-piperazine-1-carbonyl]-4,5-dihydro-1H-imidazol-2-yl}-4-ethoxy-2,N-dimethoxy-N-methyl-benzenesulfonamide;

5-[(4S,5R)-4,5-Bis-(4-chloro-phenyl)-1-(4-ethanesulfonyl-piperazine-1-carbonyl)-4,5-dihydro-1H-imidazol-2-yl]-4-ethoxy-2,N-dimethoxy-N-methyl-benzenesulfonamide;

5-{(4S,5R)-4,5-Bis-(4-chloro-phenyl)-1-[4-(2-methanesulfonylamino-ethyl)-piperazine-1-carbonyl]-4,5-dihydro-1H-imidazol-2-yl}-4-ethoxy-2,N-dimethoxy-N-methyl-benzenesulfonamide;

5-{(4S,5R)-4,5-Bis-(4-chloro-phenyl)-1-[4-(3-methanesulfonyl-propyl)-piperazine-1-carbonyl]-4,5-dihydro-1H-imidazol-2-yl}-4-ethoxy-2,N-dimethoxy-N-methyl-benzenesulfonamide and 5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-4-ethoxy-2,N-dimethoxy-N-methyl-benzenesulfonamide.

38. A compound of claim 1 selected from the group consisting of

5-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-4-ethoxy-2,N-dimethoxy-N-methyl-benzenesulfonamide;

4-[(4S,5R)-2-(4-Acetyl-2-ethoxy-phenyl)-4,5-bis-(4-chloro-phenyl)-4,5-dihydro-imidazole-1-carbonyl]-piperazin-2-one;

1-(4-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-3-ethoxy-phenyl)-ethanone hydrochloride; 2-{4-[(4S,5R)-2-(4-Acetyl-2-ethoxy-phenyl)-4,5-bis-(4-chloro-phenyl)-4,5-dihydro-imidazole-1-carbonyl]-piperazin-1-yl}-1-morpholin-4-yl-ethanone hydrochloride;

1-(4-{(4S,5R)-4,5-Bis-(4-chloro-phenyl)-1-[4-(3-methanesulfonyl-propyl)-piperazine-1-carbonyl]-4,5-dihydro-1H-imidazol-2-yl}-3-ethoxy-phenyl)-ethanonehydrochloride;

[(4S,5R)-4,5-Bis-(4-chloro-phenyl)-2-(2-ethoxy-4-trifluoroprop-1-ynyl-phenyl)-4,5-dihydro-imidazol-1-yl]-[4-(3-methanesulfonyl-propyl)-piperazin-1-yl]-methanone hydrochloride;

N-tert-Butyl-2-{4-[(4S,5R)-2-(5-tert-butylsuifamoyl-2-ethoxy-phenyl)-4,5-bis-(4-chloro-phenyl)-4,5-dihydro-imidazole-1-carbonyl]-piperazin-1-yl}-acetamide;

2-{4-[(4S,5R)-2-(5-tert-Butylsulfamoyl-2-ethoxy-phenyl)-4,5-bis-(4-chloro-phenyl)-4,5-dihydro-imidazole-1-carbonyl]-piperazin-1-yl}-acetamide;

2-{4-[(4S,5R)-2-(5-tert-Butylsulfamoyl-2-ethoxy-phenyl)-4,5-bis-(4-chloro-phenyl)-4,5-dihydro-imidazole-1-carbonyl]-piperazin-1-yl}-N,N-bis-(2-methoxy-ethyl)-acetamide;

2-{4-[(4S,5R)-2-(5-tert-Butylsulfamoyl-2-ethoxy-phenyl)-4,5-bis-(4-chloro-phenyl)-4,5-dihydro-imidazole-1-carbonyl]-piperazin-1-yl}-N-methoxy-N-methyl-acetamide and 2-{4-[(4S 5R)-2-(5-tert-Butylsulfamoyl-2-ethoxy-phenyl)-4,5-bis-(4-chloro-phenyl)-4,5-dihydro-imidazole-1-carbonyl]-piperazin-1-yl}-N-isopropyl-N-methyl-acetamide.

39. A compound of claim 1 selected from the group consisting of

2-{4-[(4S,5R)-2-(5-tert-Butylsulfamoyl-2-ethoxy-phenyl)-4,5-bis-(4-chloro-phenyl)-4,5-dihydro-imidazole-1-carbonyl]-piperazin-1-yl}-N-(2-cyano-ethyl)-N-methyl-acetamide;

2-{4-[(4S,5R)-2-(5-tert-Butylsulfamoyl-2-ethoxy-phenyl)-4,5-bis-(4-chloro-phenyl)-4,5-dihydro-imidazole-1-carbonyl]-piperazin-1-yl}-N-(2-methoxy-1-methyl-ethyl)-acetamide;

3-{(4S,5R)-4,5-Bis-(4-chloro-phenyl)-1-[4-(3,5-dimethyl-isoxazole-4-carbonyl)-piperazine-1-carbonyl]-4,5-dihydro-1H-imidazol-2-yl}-N-tert-butyl-4-ethoxy-benzenesulfonamide;

3-[(4S,5R)-4,5-Bis-(4-chloro-phenyl)-1-(4-ethanesulfonyl-piperazine-1-carbonyl)-4,5-dihydro-1H-imidazol-2-yl]-N-tert-butyl-4-ethoxy-benzenesulfonamide;

3-{(4S,5R)-4,5-Bis-(4-chloro-phenyl)-1-[4-(2-methanesulfonylamino-ethyl)-piperazine-1-carbonyl]-4,5-dihydro-1H-imidazol-2-yl}-N-tert-butyl-4-ethoxy-benzenesulfonamide;

3-{(4S,5R)-4,5-Bis-(4-chloro-phenyl)-1-[4-(3-methanesulfonyl-propyl)-piperazine-1-carbonyl]-4,5-dihydro-1H-imidazol-2-yl}-N-tert-butyl-4-ethoxy-benzenesulfonamide;

3-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-N-tert-butyl-4-ethoxy-benzenesulfonamide;

3-{(4S,5R)-4,5-Bis-(4-chtoro-phenyl)-1-[4-(2-morpholin-4-yl-2-oxo-ethyl)-piperazine-1-carbonyl]-4,5-dihydro-1H-imidazol-2-yl}-N-tert-butyl-4-ethoxy-benzenesulfonamide;

2-(4-{(4S,5R)-4,5-Bis-(4-chloro-phenyl)-2-[2-ethoxy-5-(piperidine-1-sulfonyl)-phenyl]-4,5-dihydro-imidazole-1-carbonyl}-piperazin-1-yl)-N-tert-butyl-acetamide;

2-(4-{(4S,5R)-4,5-Bis-(4-chloro-phenyl)-2-[2-ethoxy-5-(piperidine-1-sulfonyl)-phenyl]-4,5-dihydro-imidazole-1-carbonyl}-piperazin-1-yl)-acetamide;

2-(4-{(4S,5R)-4,5-Bis-(4-chloro-phenyl)-2-[2-ethoxy-5-(piperidine-1-sulfonyl)-phenyl]-4,5-dihydro-imidazole-1-carbonyl}-piperazin-1-yl)-N,N-bis-(2-methoxy-ethyl)-acetamide and 2-(4-{(4S,5R)-4,5-Bis-(4-chloro-phenyl)-2-[2-ethoxy-5-(piperidine-1-sulfonyl)-phenyl]-4,5-dihydro-imidazole-1-carbonyl}-piperazin-1-yl)-N-methoxy-N-methyl-acetamide.

40. A compound of claim 1 selected from the group consisting of 2-(4-{(4S,5R)-4,5-Bis-(4-chloro-phenyl)-2-[2-ethoxy-5-(piperidme-1-sulfonyl)-phenyl]-4,5-dihydro-imidazole-1-carbonyl}-piperazin-1-yl)-N-isopropyl-N-methyl-acetamide;

2-(4-{(4S,5R)-4,5-Bis-(4-chloro-phenyl)-2-[2-ethoxy-5-(piperidine-1-sulfonyl)-phenyl]-4,5-dihydro-imidazole-1-carbonyl}-piperazin-1-yl)-N-(2-cyano-ethyl)-N-methyl-acetamide;

2-(4-{(4S,5R)-4,5-Bis-(4-chloro-phenyl)-2-[2-ethoxy-5-(piperidine-1-sulfonyl)-phenyl]-4,5-dihydro-imidazole-1-carbonyl}-piperazin-1-yl)-N-(2-methoxy-1-methyl-ethyl)-acetamide {(4S,5R)-4,5-Bis-(4-chloro-phenyl)-2-[2-ethoxy-5-(piperidine-1-sulfonyl)-phenyl]-4,5-dihydro-imidazol-1-yl}-[4-(3,5-dimethyl-isoxazole-4-carbonyl)-piperazin-1-yl]-methanone {(4S,5R)-4,5-Bis-(4-chloro-phenyl)-2-[2-ethoxy-5-(piperidine-1-sulfonyl)-phenyl]-4,5-dihydro-imidazol-1-yl}-(4-ethanesulfonyl-piperazin-1-yl)-methanone;

N-[2-(4-{(4S,5R)-4,5-Bis-(4-chloro-phenyl)-2-[2-ethoxy-5-(piperidine-1-sulfonyl)-phenyl]-4,5-dihydro-imidazole-1-carbonyl}-piperazin-1-yl)-ethyl]-methanesulfonamide;

{(4S 5R)-4,5-Bis-(4-chloro-phenyl)-2-[2-ethoxy-5-(piperidine-1-sulfonyl)-phenyl]-4,5-dihydro-imidazol-1-yl}-[4-(3-methanesulfonyl-propyl)-piperazin-1-yl]-methanone {(4S,5R)-4,5-Bis-(4-chloro-phenyl)-2-[2-ethoxy-5-(piperidine-1-sulfonyl)-phenyl]-4,5-dihydro-imidazol-1-yl}-[4-(2-methanesulfonyl-ethyl)-piperazin-1-yl]-methanone 2-(4-{(4S,5R)-4,5-Bis-(4-chloro-phenyl)-2-[2-ethoxy-5-(piperidine-1-sulfonyl)-phenyl]-4,5-dihydro-imidazole-1-carbonyl}-piperazin-1-yl)-1-morpholin-4-yl-ethanone 2-(4-{(4S,5R)-4,5-Bis-(4-chloro-phenyl)-2-[2-ethoxy-5-(methoxy-methyl-sulfa moyl)-phenyt]-4,5-dihydro-imidazole-1-carbonyl}-piperazin-1-yl)-N-tert-butyl-acetamide and 2-(4-{(4S,5R)-4,5-Bis-(4-chloro-phenyl)-2-[2-ethoxy-5-(methoxy-methyl-sulfamoyl)-phenyl]-4,5-dihydro-imidazole-1-carbonyl}-piperazin-1-yl)-acetamide.

41. A compound of claim 1 selected from the group consisting of 2-(4-{(4S,5R)-4,5-Bis-(4-chloro-phenyl)-2-[2-ethoxy-5-(methoxy-methyl-sulfamoyl)-phenyl]-4,5-dihydro-imidazole-1-carbonyl}-piperazin-1-yl)-N N-bis-(2-methoxy-ethyl)-acetamide;

2-(4-{(4S 5R)-4,5-Bis-(4-chloro-phenyl)-2-[2-ethoxy-5-(methoxy-methyl-sulfamoyl)-phenyl]-4,5-dihydro-imidazole-1-carbonyl}-piperazin-1-yl)-N-methoxy-N-methyl-acetamide;

2-(4-{(4S 5R)-4,5-Bis-(4-chloro-phenyl)-2-[2-ethoxy-5-(methoxy-methyl-sulfamoyl)-phenyl]-4,5-dihydro-imidazole-1-carbonyl}-piperazin-1-yl)-N-isopropyl-N-methyl-acetamide;

2-(4-{(4S,5R)-4,5-Bis-(4-chloro-phenyl)-2-[2-ethoxy-5-(methoxy-methyl-sulfamoyl)-phenyl]-4,5-dihydro-imidazole-1-carbonyl}-piperazin-1-yl)-N-(2-cyano-ethyl)-N-methyl-acetamide;

2-(4-{(4S,5R)-4,5-Bis-(4-chloro-phenyl)-2-[2-ethoxy-5-(methoxy-methyl-sulfamoyl)-phenyl]-4,5-dihydro-imidazole-1-carbonyl}-piperazin-1-yl)-N-(2-methoxy-1-methyl-ethyl)-acetamide;

3-{(4S,5R)-4,5-Bis-(4-chloro-phenyl)-1-[4-(3,5-dimethyl-isoxazole-4-carbonyl)-piperazine-1-carbonyl]-4,5-dihydro-1H-imidazol-2-yl}-4-ethoxy-N-methoxy-N-methyl-benzenesulfonamide;

3-[(4S,5R)-4,5-Bis-(4-chloro-phenyl)-1-(4-ethanesulfonyl-piperazine-1-carbonyl)-4,5-dihydro-1H-imidazol-2-yl]-4-ethoxy-N-methoxy-N-methyl-benzenesulfonamide;

3-{(4S5R)-4,5-Bis-(4-chloro-phenyl)-1-[4-(2-methanesulfonylamino-ethyl)-piperazine-1-carbonyl]-4,5-dihydro-1H-imidazol-2-yl}-4-ethoxy-N-methoxy-N-methyl-benzenesulfonamide;

3-{(4S,5R)-4,5-Bis-(4-chloro-phenyl)-1-[4-(3-methanesulfonyl-propyl)-piperazine-1-carbonyl]-4,5-dihydro-1H-imidazol-2-yl}-4-ethoxy-N-methoxy-N-methyl-benzenesulfonamide;

3-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-4-ethoxy-N-methoxy-N-methyl-benzenesulfonamide and 3-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-4-ethoxy-N-methoxy-N-methyl-benzenesulfonamide.

42. A compound of claim 1 selected from the group consisting of

{(4S,5R)-4,5-Bis-(4-chloro-phenyl)-2-[4-(3,3-dimethyl-but-1-ynyl)-2-ethoxy-phenyl]-4,5-dihydro-imidazol-1-yl}-[4-(2-methanesulfonyl-ethyl)-piperazin-1-yl]-methanone hydrochloride;

2-(4-{(4S 5R)-4,5-Bis-(4-chloro-phenyl)-2-[4-(3,3-dimethyl-but-1-ynyl)-2-ethoxy-phenyl]-4,5-dihydro-imidazole-1-carbonyl}-pi perazin-1-yl)-1-morpholin-4-yl-ethanone hydrochloride;

2-{4-[(4S,5R)-2-(5-tert-Butylsulfamoyl-2-ethoxy-4-methoxy-phenyl)-4,5-bis-(4-chloro-phenyl)-4,5-dihydro-imidazole-1-carbonyl]-piperazin-1-yl}-acetamide;

N-tert-Butyl-2-{4-[(4S,5R)-2-(5-tert-butylsulfamoyl-2-ethoxy-4-methoxy-phenyl)-4,5-bis-(4-chloro-phenyl)-4,5-dihydro-imidazole-1-carbonyl]-piperazin-1-yl}-acetamide;

2-{4-[(4S 5R)-2-(5-tert-Butylsulfamoyl-2-ethoxy-4-methoxy-phenyl)-4,5-bis-(4-chloro-phenyl)-4,5-dihydro-imidazole-1-carbonyl]-piperazin-1-yl}-N-methoxy-N-methyl-acetamide 2-{4-[(4S,5R)-2-(5-tert-Butylsulfamoyl-2-ethoxy-4-methoxy-phenyl)-4,5-bis-(4-chloro-phenyl)-4,5-dihydro-imidazole-1-carbonyl]-piperazin-1-yl}-N-isopropyl-N-methyl-acetamide 5-{(4S,5R)-4,5-Bis-(4-chloro-phenyl)-1-[4-(3-methanesutfonyl-propyl)-piperazine-1-carbonyl]-4,5-dihydro-1H-imidazol-2-yl}-N-tert-butyl-4-ethoxy-2-methoxy-benzenesulfonamide and 5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-N-tert-butyl-4-ethoxy-2-methoxy-benzenesulfonamide.

* * * * *

UNITED STATES PATENT AND TRADEMARK OFFICE
CERTIFICATE OF CORRECTION

PATENT NO. : 7,579,368 B2
APPLICATION NO. : 11/374407
DATED : August 25, 2009
INVENTOR(S) : Nader Fotouhi et al.

It is certified that error appears in the above-identified patent and that said Letters Patent is hereby corrected as shown below:

In Column 249, Claim 15, Line 25, please delete
"3-{4,5S-Bis-(4-chloro-phenyl)-1-[4-(3,5-dimethyl-isoxazole-4-carbonyl)-piperazine-1-carbonyl]"

and insert
--3-{4,5-Bis-(4-chloro-phenyl)-1-[4-(3,5-dimethyl-isoxazole-4-carbonyl)-piperazine-1-carbonyl]- --

In Column 255, Claim 23, Line 23, please delete
"2-{4-[(4S,5R)-4,5-Bis-(4-chloro-phenyl)-2-(4-dimethylsulfamoyl-2-ethoxy-phenyl)-4,5-dihydro-imidazole-1-carbonyl]-piperazin-1-yl}-N,N-dimethyl-acetamide hydrochloride and p1
2-{4-[(4S,5R)-4,5-Bis-(4-chloro-phenyl)-2-(4-cyano-2-ethoxy-phenyl)-4,5-dihydro-imidazole-1-carbonyl]-piperazin-1-yl}-N-tert-butyl-acetamide."

and insert
--2-{4-[(4S,5R)-4,5-Bis-(4-chloro-phenyl)-2-(4-dimethylsulfamoyl-2-ethoxy-phenyl)-4,5-dihydro-imidazole-1-carbonyl]-piperazin-1-yl}-N,N-dimethyl-acetamide hydrochloride and
2-{4-[(4S,5R)-4,5-Bis-(4-chloro-phenyl)-2-(4-cyano-2-ethoxy-phenyl)-4,5-dihydro-imidazole-1-carbonyl]-piperazin-1-yl}-N-tert-butyl-acetamide.--

In Column 255, Claim 24, Line 53, please delete
"2-{4-[(4S,5R)-4,5-Bis-(4-chloro-phenyl)-2-(4-cyano-2-ethoxy-phenyl)-4,5-dihydro-imidazole-1-carbonyl]-piperazi n-i-yl}-N-(2-cyano-ethyl)-N-methyl-acetamide;"

and insert
--2-{4-[(4S,5R)-4,5-Bis-(4-chloro-phenyl)-2-(4-cyano-2-ethoxy-phenyl)-4,5-dihydro-imidazole-1-carbonyl]-piperazin-1-yl}-N-(2-cyano-ethyl)-N-methyl-acetamide;--

In Column 256, Claim 25, Line 33, please delete
"4-[(4S5R)-4,5-Bis-(4-chloro-phenyl)-1-(3-oxo-piperazine-1-carbonyl)-4,5-dihydro-1H-imidazol-2-yl]-2,5-diethoxy-benzonitrile and"

and insert
--4-[(4S,5R)-4,5-Bis-(4-chloro-phenyl)-1-(3-oxo-piperazine-1-carbonyl)-4,5-dihydro-1H-imidazol-2-yl]-2,5-diethoxy-benzonitrile and--

In Column 256, Claim 26, Line 47, please delete
"4-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-2, 5-diethoxy-benzonitrile hydrochloride;"

and insert
--4-{(4S,5R)-4,5-Bis-(4-chloro-phenyl)-1-[4-(2-morpholin-4-yl-2-oxo-ethyl)-piperazine-1-carbonyl]-4,5-dihydro-1H-imidazol-2-yl}-2,5-diethoxy-benzonitrile hydrochloride;--

In Column 258, Claim 29, Line 61, please delete
"5-{(4S5R)-4,5-Bis-(4-chloro-phenyl)-1-[4-(2-methanesulfonyl-ethyl)-piperazine-1-carbonyl]-4,5-dihydro-1H-imidazol-2-yl}-2-chloro-4-ethoxy-N-methyl-benzenesulfonamide;"

and insert
--5-{(4S,5R)-4,5-Bis-(4-chloro-phenyl)-1-[4-(2-methanesulfonyl-ethyl)-piperazine-1-carbonyl]-4,5-dihydro-1H-imidazol-2-yl}-2-chloro-4-ethoxy-N-methyl-benzenesulfonamide;--

In Column 259, Claim 30, Line 20, please delete
"N-tert-Butyl-2-{4-[(4S 5R)-2-(4-chloro-2-ethoxy-5-isopropylsulfamoyl-phenyl)-4,5-bis-(4-chloro-phenyl)-4,5-dihydro-imidazole-1-carbonyl]-piperazin-1-yl}-acetamide;"

and insert
--N-tert-Butyl-2-{4[(4S,5R)-2-(4-chloro-2-ethoxy-5-isopropylsulfamoyl-phenyl)-4,5-bis-(4-chloro-phenyl)-4,5-dihydro-imidazole-1-carbonyl]-piperazin-1-yl}-acetamide;--

In Column 259, Claim 30, Line 23, please delete
"5-[(4S 5R)-4,5-Bis-(4-chloro-phenyl)-1-(3-oxo-piperazine-1-carbonyl)-4,5-dihydro-1H-imidazol-2-yl]-2-chloro-4-ethoxy-N-isopropyl-benzenesulfonamide;"

and insert
--5-[(4S,5R)-4,5-Bis-(4-chloro-phenyl)-1-(3-oxo-piperazine-1-carbonyl)-4,5-dihydro-1H-imidazol-2-yl]-2-chloro-4-ethoxy-N-isopropyl-benzenesulfonamide;--

In Column 259, Claim 31, Line 57, please delete
"dihydro-1H-imidazol-2-yl}-3-ethoxy-phenyl)-2 2-dimethyl-propionamide hydrochloride;"

and insert
--dihydro-1H-imidazol-2-yl}-3-ethoxy-phenyl)-2,2-dimethyl-propionamide hydrochloride;--

In Column 260, Claim 31, Line 16, please delete
"ethynyl-phenyl)-4,5-dihyd ro-imidazol-1-yl]-[4-(2-methoxy-ethyl)-piperazin-1-yl]-methanone hydrochloride;"

and insert
--ethynyl-phenyl)-4,5-dihydro-imidazol-1-yl]-[4-(2-methoxy-ethyl)-piperazin-1-yl]-methanone hydrochloride;--

In Column 260, Claim 32, Line 61, please delete
"2-(4-{(4S 5R)-4,5-Bis-(4-chloro-phenyl)-2-[2-ethoxy-4-methyl-5-(piperidine-1-sulfonyl)-phenyl]-4,5-dihydro-imidazole-1-carbonyl}-piperazin-1-yl)-acetamide;"

and insert
--2-(4-{(4S,5R)-4,5-Bis-(4-chloro-phenyl)-2-[2-ethoxy-4-methyl-5-(piperidine-1-sulfonyl)-phenyl]-4,5-dihydro-imidazole-1-carbonyl}-piperazin-1-yl)-acetamide;--

CERTIFICATE OF CORRECTION (continued)
U.S. Pat. No. 7,579,368 B2

In Column 261, Claim 33, Line 31, please delete
"{(4S 5R)-4,5-Bis-(4-chloro-phenyl)-2-[2-ethoxy-4-methyl-5-(piperidine-1-sulfonyl)-"

and insert
--{(4S,5R)-4,5-Bis-(4-chloro-phenyl)-2-[2-ethoxy-4-methyl-5-(piperidine-1-sulfonyl)- --

In Column 261, Claim 34, Line 52, delete
"2-{4-[(4S 5R)-2-(5-tert-Butylsulfamoyl-2-ethoxy-4-methyl-phenyl)-4,5-bis-(4-chloro-phenyl)"

and insert
--2-{4-[(4S,5R)-2-(5-tert-Butylsulfamoyl-2-ethoxy-4-methyl-phenyl)-4,5-bis-(4-chloro-phenyl)--

In Column 261, Claim 34, Line 60, delete
"2-{4-[(4S 5R)-2-(5-tert-Butylsulfamoyl-2-ethoxy-4-methyl-phenyl)-4,5-bis-(4-chloro-phenyl)-"

and insert
--2-{4-{(4S,5R)-2-(5-tert-Butylsulfamoyl-2-ethoxy-4-methyl-phenyl)-4,5-bis-(4-chloro-phenyl)- --

In Column 262, Claim 35, Line 32, delete
"2-(4-{(4S,5R)-4,5-Bis-(4-chloro-phenyl)-2-[2-ethoxy-5-(methoxy-methyl-sulfa moyl)-4-methyl-phenyl]-4,5-dihydro-imidazole-1-carbonyl}-piperazin-1-yl)-N,N-bis-(2-methoxy-ethyl)-acetamide;"

and insert
--2-(4-{(4S,5R)-4,5-Bis-(4-chloro-phenyl)-2-[2-ethoxy-5-(methoxy-methyl-sulfamoyl)-4-methyl-phenyl]-4,5-dihydro-imidazole-1-carbonyl}-piperazin-1-yl)-N,N-bis-(2-methoxy-ethyl)-acetamide;--

In Column 262, Claim 35, Line 48, delete
"5-{(4S 5R)-4,5-Bis-(4-chloro-phenyl)-1-[4-(3,5-dimethyl-isoxazole-4-carbonyl)-piperazine-1-carbonyl]-4,5-dihydro-1H-imidazol-2-yl}-4-ethoxy-N-methoxy-2,N-dimethyl-benzenesulfonamide;"

and insert
--2-(4-{(4S,5R)-4,5-Bis-(4-chloro-phenyl)-2-[2-ethoxy-5-(methoxy-methyl-sulfamoyl)-4-methyl-phenyl]-4,5-dihydro-imidazole-1-carbonyl}-piperazin-1-yl)-N,N-bis-(2-methoxy-ethyl)-acetamide;--

In Column 263, Claim 35, Line 54, delete
"5-[(4S,5R)-4,5-Bis-(4-chloro-phenyl)-1-(4-ethanesulfonyl-piperazine-1-carbonyl)-4,5-dihydro-1H-imidazol-2-yl]-4-ethoxy-N-methoxy-2,N-d imethyl-benzenesulfonamide;"

and insert
--5-[(4S,5R)-4,5-Bis-(4-chloro-phenyl)-1-(4-ethanesulfonyl-piperazine-1-carbonyl)-4,5-dihydro-1H-imidazol-2-yl]-4-ethoxy-N-methoxy-2,N-dimethyl-benzenesulfonamide;--

In Column 263, Claim 36, Line 23, delete
"2-(4-{(4S 5R)-4,5-Bis-(4-chloro-phenyl)-2-[2-ethoxy-4-methoxy-5-(piperidine-1-sulfonyl)-phenyl]-4,5-dihydro-imidazole-1-carbonyl}-piperazin-1-yl)-N-(2-methoxy-1-methyl-ethyl)-acetamide;"

and insert
--2-(4-{(4S,5R)-4,5-Bis-(4-chloro-phenyl)-2-[2-ethoxy-4-methoxy-5-(piperidine-1-sulfonyl)-phenyl]-4,5-dihydro-imidazole-1-carbonyl}-piperazin-1-yl)-N-(2-methoxy-1-methyl-ethyl)-acetamide;--

In Column 263, Claim 37, Line 58, delete
"2-(4-{(4S 5R)-4,5-Bis-(4-chloro-phenyl)-2-[2-ethoxy-4-methoxy-5-(methoxy-methyl-sulfamoyl)-phenyl]-4,5-dihydro-imidazole-1-carbonyl}-piperazin-1-yl)-acetamide;"

and insert
--2-(4-{(4S,5R)-4,5-Bis-(4-chloro-phenyl)-2-[2-ethoxy-4-methoxy-5-(methoxy-methyl-sulfamoyl)-phenyl]-4,5-dihydro-imidazole-1-carbonyl}-piperazin-1-yl)-acetamide;--

In Column 265, Claim 38, Line 9, delete
"2-{4-[(4S 5R)-2-(5-tert-Butylsulfamoyl-2-ethoxy-phenyl)-4,5-bis-(4-chloro-phenyl)-4,5-dihydro-imidazole-1-carbonyl]-piperazin-1-yl}-N-isopropyl-N-methyl-acetamide."

and insert
--2-{4-[(4S,5R)-2-(5-tert-Butylsulfamoyl-2-ethoxy-phenyl)-4,5-bis-(4-chloro-phenyl)-4,5-dihydro-imidazole-1-carbonyl]-piperazin-1-yl}-N-isopropyl-N-methyl-acetamide.--

In Column 266, Claim 40, Line 21, delete
"{(4S 5R)-4,5-Bis-(4-chloro-phenyl)-2-[2-ethoxy-5-(piperidine-1-sulfonyl)-phenyl]-4,5-dihydro-imidazol-1-yl}-[4-(2-methanesulfonyl-ethyl)-piperazin-1-yl]-methanone;"

and insert
--{(4S,5R)-4,5-Bis-(4-chloro-phenyl)-2-[2-ethoxy-5-(piperidine-1-sulfonyl)-phenyl]-4,5-dihydro-imidazol-1-yl}-[4-(2-methanesulfonyl-ethyl)-piperazin-1-yl]-methanone;--

In Column 266, Claim 40, Line 34, delete
"-2-(4-{(4S,5R)-4,5-Bis-(4-chloro-phenyl)-2-(2-ethoxy-5-(methoxy-methyl-sulfa moyl)-phenyl]-4,5-dihydro-imidazole-1-carbonyl}-piperazin-1-yl)-N-tert-butyl-acetamide and"

and insert
--2-(4-{(4S,5R)-4,5-Bis-(4-chloro-phenyl)-2-[2-ethoxy-5-(methoxy-methyl-sulfamoyl)-phenyl]-4,5-dihydro-imidazole-1-carbonyl}-piperazin-1-yl)-N-tert-butyl-acetamide and--

CERTIFICATE OF CORRECTION (continued)
U.S. Pat. No. 7,579,368 B2

In Column 266, Claim 41, Line 45, delete
"2-(4-{(4S,5R)-4,5-Bis-(4-chloro-phenyl)-2-[2-ethoxy-5-(methoxy-methyl-sulfamoyl)-phenyl]-4,5-dihydro-imidazole-1-carbonyl}-piperazin-1-yl)-N  N-bis-(2-methoxy-ethyl)-acetamide;"

and insert
--2-(4-{(4S,5R)-4,5-Bis-(4-chloro-phenyl)-2-[2-ethoxy-5-(methoxy-methyl-sulfamoyl)-phenyl]-4,5-dihydro-imidazole-1-carbonyl}-piperazin-1-yl)-N,N-bis-(2-methoxy-ethyl)-acetamide;--

In Column 268, Claim 42, Line 1, delete
"{(4S  5R)-4,5-Bis-(4-chloro-phenyl)-2-[4-(3,3-dimethyl-but-1-ynyl)-2-ethoxy-phenyl]-4,5-dihydro-imidazol-1-yl}-[4-(2-methanesulfonyl-ethyl)-piperazin-1-yl]-methanone hydrochloride;"

and insert
--{(4S,5R)-4,5-Bis-(4-chloro-phenyl)-2-[4-(3,3-dimethyl-but-1-ynyl)-2-ethoxy-phenyl]-4,5-dihydro-imidazol-1-yl}-[4-(2-methanesulfonyl-ethyl)-piperazin-1-yl]-methanone hydrochloride;--

In Column 268, Claim 42, Line 12, delete
"2-{4-[(4S  5R)-2-(5-tert-Butylsulfamoyl-2-ethoxy-4-methoxy-phenyl)-4,5-bis-(4-chloro-phenyl)-4,5-dihydro-imidazole-1-carbonyl]-piperazin-1-yl}-N-methoxy-N-methyl-acetamide;"

and insert
--2-{4-[(4S,5R)-2-(5-tert-Butylsulfamoyl-2-ethoxy-4-methoxy-phenyl)-4,5-bis-(4-chloro-phenyl)-4,5-dihydro-imidazole-1-carbonyl]-piperazin-1-yl}-N-methoxy-N-methyl-acetamide;--

Signed and Sealed this

Twentieth Day of April, 2010

David J. Kappos
*Director of the United States Patent and Trademark Office*